United States Patent
Savel et al.

(10) Patent No.: US 10,821,185 B2
(45) Date of Patent: Nov. 3, 2020

(54) TRIGLYCERIDE OTIC FORMULATIONS AND USES THEREOF

(71) Applicant: Otonomy, Inc., San Diego, CA (US)

(72) Inventors: Robert Savel, San Diego, CA (US); Zhanpeng Zhang, San Diego, CA (US); Scott Coleman, San Diego, CA (US); Fabrice Piu, San Diego, CA (US); Hong Qi, San Diego, CA (US)

(73) Assignee: Otonomy Inc., San Diego, CA (US)

( * ) Notice: Subject to any disclaimer, the term of this patent is extended or adjusted under 35 U.S.C. 154(b) by 0 days.

(21) Appl. No.: 15/637,767

(22) Filed: Jun. 29, 2017

(65) Prior Publication Data

US 2018/0000950 A1 Jan. 4, 2018

Related U.S. Application Data

(60) Provisional application No. 62/356,300, filed on Jun. 29, 2016.

(51) Int. Cl.

| | | |
|---|---|---|
| *A61K 47/44* | (2017.01) | |
| *A61K 47/14* | (2017.01) | |
| *A61K 9/00* | (2006.01) | |
| *A61K 31/4535* | (2006.01) | |
| *A61K 47/02* | (2006.01) | |
| *A61K 31/573* | (2006.01) | |
| *A61K 9/08* | (2006.01) | |
| *A61K 47/10* | (2017.01) | |
| *A61K 47/32* | (2006.01) | |

(52) U.S. Cl.
CPC ............ *A61K 47/44* (2013.01); *A61K 9/0046* (2013.01); *A61K 9/08* (2013.01); *A61K 31/4535* (2013.01); *A61K 31/573* (2013.01); *A61K 47/02* (2013.01); *A61K 47/10* (2013.01); *A61K 47/14* (2013.01); *A61K 47/32* (2013.01)

(58) Field of Classification Search
CPC .......... A61K 47/14; A61K 47/44; A61K 9/08; A61K 31/2535; A61K 31/573; A61K 47/02; A61K 47/10; A61K 47/32; A61K 9/0046; A61K 31/4535; A61P 27/16
See application file for complete search history.

(56) References Cited

U.S. PATENT DOCUMENTS

| | | | |
|---|---|---|---|
| 3,737,337 A | 6/1973 | Schnoring et al. | |
| 3,773,919 A | 11/1973 | Boswell et al. | |
| 4,389,330 A | 6/1983 | Tice et al. | |
| 4,474,572 A | 10/1984 | McNaughton et al. | |
| 4,530,840 A | 7/1985 | Tice et al. | |
| 4,675,189 A | 6/1987 | Kent et al. | |
| 4,758,435 A | 7/1988 | Schaaf | |
| 4,900,552 A | 2/1990 | Sanvordeker et al. | |
| 5,033,252 A | 7/1991 | Carter | |
| 5,052,558 A | 10/1991 | Carter | |
| 5,122,377 A * | 6/1992 | Miller | A61K 9/0056 424/439 |
| 5,323,907 A | 6/1994 | Kalvelage | |
| 5,421,818 A | 6/1995 | Arenberg | |
| 5,451,399 A | 9/1995 | Gimbrone, Jr. et al. | |
| 5,474,529 A | 12/1995 | Arenberg | |
| 5,476,446 A | 12/1995 | Arenberg | |
| 5,578,709 A | 11/1996 | Woiszwillo | |
| 5,714,167 A | 2/1998 | Milstein et al. | |
| 5,814,330 A | 9/1998 | Putteman et al. | |
| 5,945,126 A | 8/1999 | Thanoo et al. | |
| 5,981,719 A | 11/1999 | Woiszwillo et al. | |
| 5,985,848 A | 11/1999 | Furneaux et al. | |
| 6,036,978 A | 3/2000 | Gombotz et al. | |
| 6,045,528 A | 4/2000 | Arenberg et al. | |
| 6,066,722 A | 5/2000 | Furneaux et al. | |
| 6,083,534 A | 7/2000 | Wallach et al. | |
| 6,090,925 A | 7/2000 | Woiszwillo et al. | |
| 6,139,870 A | 10/2000 | Verrecchia | |
| 6,221,367 B1 | 4/2001 | Milstein et al. | |
| 6,228,847 B1 | 5/2001 | Furneaux et al. | |
| 6,268,053 B1 | 7/2001 | Woiszwillo et al. | |
| 6,270,802 B1 | 8/2001 | Thanoo et al. | |
| 6,306,789 B1 | 10/2001 | Dettmar et al. | |
| 6,319,513 B1 | 11/2001 | Dobrozsi | |
| 6,348,502 B1 | 2/2002 | Gardiner et al. | |
| 6,361,798 B1 | 3/2002 | Thanoo et al. | |
| 6,458,387 B1 | 10/2002 | Scott et al. | |
| 6,492,347 B2 | 12/2002 | Furneaux et al. | |
| 6,509,028 B2 | 1/2003 | Williams et al. | |

(Continued)

FOREIGN PATENT DOCUMENTS

| | | |
|---|---|---|
| DE | 202012100195 U1 | 3/2012 |
| EP | 0551626 A1 | 7/1993 |

(Continued)

OTHER PUBLICATIONS

Paulson DP et al. A novel controlled local drug delivery system for inner ear disease. Laryngoscope, 118:706-711. (Year: 2008).*

Wenzel et al. Effects of extracochlear gacyclidine perfusion on tinnitus in humans: a case seris. Eur. Arch Otorhinolaryngol. 267, 691-699. (Year: 2010).*

Armour et al. Recombinant human IgG molecules lacking Fcgamma receptor I binding and monocyte triggering activities. Eur J Immunol 29(8):2613-2624 (1999).

(Continued)

*Primary Examiner* — Kimberly Ballard

(74) *Attorney, Agent, or Firm* — Procopio, Cory, Hargreaves & Savitch LLP

(57) ABSTRACT

Disclosed herein are triglyceride based formulations, compositions, and methods for the treatment of otic diseases and conditions. Such triglyceride based formulations and compositions are derived from medium chain triglycerides and allow for the delivery of a variety of therapeutic agents to the outer, middle, and/or inner ear.

30 Claims, 13 Drawing Sheets

Specification includes a Sequence Listing.

(56) References Cited

U.S. PATENT DOCUMENTS

| | | |
|---|---|---|
| 6,562,363 B1 | 5/2003 | Mantelle et al. |
| 6,638,521 B2 | 10/2003 | Dobrozsi |
| 6,803,455 B2 | 10/2004 | Furneaux et al. |
| 7,064,109 B2 * | 6/2006 | Luyckx .............. A61K 9/0048 514/29 |
| 7,151,191 B2 | 12/2006 | Boyd et al. |
| 7,279,499 B2 | 10/2007 | Durst et al. |
| 7,384,632 B2 | 6/2008 | Devaux et al. |
| 8,268,866 B2 | 9/2012 | Guitton et al. |
| 8,461,143 B2 | 6/2013 | Gao et al. |
| 8,507,525 B2 | 8/2013 | Guitton et al. |
| 2001/0019823 A1 | 9/2001 | Schramm et al. |
| 2002/0061898 A1 | 5/2002 | Furneaux et al. |
| 2002/0132783 A1 | 9/2002 | Sauve et al. |
| 2003/0096830 A1 | 5/2003 | Furneaux et al. |
| 2003/0119804 A1 | 6/2003 | Ciszewski |
| 2003/0149261 A1 | 8/2003 | Schramm et al. |
| 2003/0229033 A1 | 12/2003 | Sauve et al. |
| 2004/0053944 A1 | 3/2004 | Furneaux et al. |
| 2004/0101560 A1 | 5/2004 | Sawchuk et al. |
| 2004/0110772 A1 | 6/2004 | Furneaux et al. |
| 2004/0181063 A1 | 9/2004 | Furneaux et al. |
| 2004/0185047 A1 | 9/2004 | Giles-Komar et al. |
| 2004/0247575 A1 | 12/2004 | Caplice et al. |
| 2005/0123541 A1 | 6/2005 | Heavner et al. |
| 2005/0153984 A1 | 7/2005 | Chen et al. |
| 2005/0214338 A1 | 9/2005 | Guitton et al. |
| 2005/0215572 A1 | 9/2005 | Kelly et al. |
| 2005/0227986 A1 | 10/2005 | Bo et al. |
| 2005/0272931 A1 | 12/2005 | Bo et al. |
| 2005/0277631 A1 | 12/2005 | Doherty et al. |
| 2005/0277643 A1 | 12/2005 | Kelly et al. |
| 2005/0277646 A1 | 12/2005 | Doherty et al. |
| 2006/0030618 A1 | 2/2006 | Bo et al. |
| 2006/0063801 A1 * | 3/2006 | Brion .............. C07D 405/14 514/312 |
| 2006/0063802 A1 | 3/2006 | Guitton et al. |
| 2006/0100490 A1 | 5/2006 | Wang et al. |
| 2006/0105967 A1 | 5/2006 | Hsu et al. |
| 2006/0194801 A1 | 8/2006 | Kelly et al. |
| 2006/0205773 A1 | 9/2006 | Kelly et al. |
| 2006/0205789 A1 | 9/2006 | Lobl et al. |
| 2006/0205980 A1 | 9/2006 | Hanazawa et al. |
| 2006/0211741 A1 | 9/2006 | Hanazawa et al. |
| 2006/0270682 A1 | 11/2006 | Inoue et al. |
| 2006/0276393 A1 | 12/2006 | Milburn et al. |
| 2007/0128177 A1 | 6/2007 | Burstein et al. |
| 2007/0167918 A1 | 7/2007 | Reed et al. |
| 2007/0249538 A1 | 10/2007 | Sazani et al. |
| 2008/0015183 A1 | 1/2008 | Bakthavatchalam et al. |
| 2008/0085901 A1 | 4/2008 | Caldwell et al. |
| 2008/0088713 A1 | 4/2008 | Jung et al. |
| 2008/0089883 A1 | 4/2008 | Kandimalla et al. |
| 2008/0153857 A1 | 6/2008 | Bakthavatchalam et al. |
| 2008/0175794 A1 | 7/2008 | Caldwell et al. |
| 2009/0011045 A1 * | 1/2009 | Mertin .............. A61K 9/0046 424/618 |
| 2009/0306225 A1 | 12/2009 | Lichter et al. |
| 2010/0086997 A1 | 4/2010 | Lin et al. |
| 2010/0254907 A1 | 10/2010 | Guitton et al. |
| 2011/0301135 A1 | 12/2011 | Mertin et al. |
| 2014/0004119 A1 | 1/2014 | Saragovi et al. |
| 2014/0017172 A1 | 1/2014 | Guitton et al. |
| 2016/0032240 A1 | 2/2016 | Heller et al. |
| 2017/0216439 A1 * | 8/2017 | Lebel .............. A61K 9/06 |

FOREIGN PATENT DOCUMENTS

| | | |
|---|---|---|
| EP | 2402756 A2 | 1/2012 |
| EP | 2004777 B1 | 8/2016 |
| EP | 2005687 B1 | 6/2017 |
| WO | WO-9803546 A1 | 1/1998 |
| WO | WO-9901441 A1 | 1/1999 |
| WO | WO-0100610 A1 | 1/2001 |
| WO | WO-0130774 A1 | 5/2001 |
| WO | WO-0158890 A1 | 8/2001 |
| WO | WO-0168648 A1 | 9/2001 |
| WO | WO-0224679 A1 | 3/2002 |
| WO | WO-0230353 A2 | 4/2002 |
| WO | WO-0230423 A1 | 4/2002 |
| WO | WO-0241843 A2 | 5/2002 |
| WO | WO-0244153 A1 | 6/2002 |
| WO | WO-0246171 A2 | 6/2002 |
| WO | WO-02056890 A1 | 7/2002 |
| WO | WO-02060386 A2 | 8/2002 |
| WO | WO-02094265 A1 | 11/2002 |
| WO | WO-02094322 A2 | 11/2002 |
| WO | WO-03010163 A1 | 2/2003 |
| WO | WO-03024935 A2 | 3/2003 |
| WO | WO-03024936 A1 | 3/2003 |
| WO | WO-03029242 A1 | 4/2003 |
| WO | WO-03076447 A1 | 9/2003 |
| WO | WO-2004058754 A1 | 7/2004 |
| WO | WO-2005009987 A1 | 2/2005 |
| WO | WO-2005113544 A1 | 12/2005 |
| WO | WO-2006076318 A1 | 7/2006 |
| WO | WO-2007091970 A1 | 8/2007 |
| WO | WO-2008039472 A2 * | 4/2008 ........... A61K 9/0095 |
| WO | WO-2009100438 A2 | 8/2009 |
| WO | WO-2012047706 A2 | 4/2012 |
| WO | WO-2013054330 A1 | 4/2013 |
| WO | WO-2013124416 A1 | 8/2013 |
| WO | WO-2013173803 A2 | 11/2013 |
| WO | WO-2013178763 A1 | 12/2013 |
| WO | WO-2013182711 A1 | 12/2013 |
| WO | WO-2014039781 A1 | 3/2014 |
| WO | WO-2015044434 A2 | 4/2015 |
| WO | WO-2015168149 A2 | 11/2015 |
| WO | 2016019000 A1 | 2/2016 |
| WO | WO-2016016518 A2 | 2/2016 |
| WO | WO-2016020408 A2 | 2/2016 |
| WO | WO-2016022776 A2 | 2/2016 |
| WO | 2016124408 A1 | 8/2016 |
| WO | WO-2016128438 A1 | 8/2016 |
| WO | WO-2017007702 A1 | 1/2017 |

OTHER PUBLICATIONS

Bai et al. In glaucoma the upregulated truncated TrkC. T1 receptor isoform in Glia causes increased TNF—a production, leading to retinal ganglion cell death. Inv. Ophthalm. & Visual Sci. 51(12): 6639-6651 (2010).

Bartfai et al. A low molecular weight mimic of the Toll/IL-1 receptor/resistance domain inhibits IL-1 receptor-mediated responses. PNAS 100(13):7971-7976 (2003).

Beitz et al. Aquaporin-Mediated Fluid Regulation in the Inner Ear. Cellular and Molecular Neurobiology 23(3):315-329 (2003).

Brahimi et al. A peptidomimetic of NT-3 acts as a TrkC antagonist. Peptides 30(10):1833-1839 (2009).

Brahimi et al. Combinatorial assembly of small molecules into bivalent antagonists of TrkC or TrkA receptors. PLOS One 9(3):e89617 (2014).

Caggiano. Way-VNA-932: Treatment of Central Diabetes Inspidus Treatment of Nocturnal Enuresis Treatment of Nocturia Vasopressin V2 Agonist. Drugs Gut 27(3):248-253 (2002).

Car et al. Society of Toxicology, 46th Annual Meeting, Charlotte, North Carolina. Mar. 25-29, 2007 (496 pgs).

Carfrae et al. 3 Tesla delayed contrast magnetic resonance imaging evaluation of Ménière's disease. Laryngoscope 118:501-505 (Mar. 2008).

Chai et al. Wnt signaling induces proliferation of sensory precursors in the postnatal mouse cochlea. PNAS USA 109(21):8167-8172 (2012).

Chen et al. Estrogen-related receptor beta/NR3B2 controls epithelial cell fate and endolymph production by the stria vascularis. Dev Cell 13(3):325-337 (2007).

Chi et al. The quantification of endolymphatic hydrops in an experimental animal model with guinea pigs. J Oto-Rhino-Larynol 66:56-61 (2004).

Chothia et al. Canonical structures for the hypervariable regions of immunoglobulins. J Mol Biol. 196(4):901-917 (1987).

(56) References Cited

OTHER PUBLICATIONS

Conway et al. Inhibition of tumor necrosis factor-alpha (TNF-alpha) production and arthritis in the rat by GW3333, a dual inhibitor of TNF-alpha-converting enzyme and matrix metalloproteinases. J. Pharmacol. Exp. Ther. 298:900 (2001).
Dechristopher et al. "Picolog," a synthetically-available bryostatin analog, inhibits growth of MYC-induced lymphoma in vivo. Oncotarget. 3(1):58-66 (2012).
Gloddek et al. Role of Lymphokines in the Immune response of the Inner Ear. Acta Otolaryngol. 108:68-75 (1989).
Gross et al. The treatment of hyponatraemia using vasopressin antagonists. Exp. Physiol. 85:Spec No 253S-257S (2000).
Hansen et al. Determination of the Regime of Rapid Reacting Systems in Stopped- and Steady-Flow Investigations by the Velocity Probe Method. J Phys Chem 92:2189-2196 (1988).
Harris et al. Autoimmune inner ear disease. Otolaryngol. Head Neck Surgery 91:18-32 (1983).
Ibanez et al. An extended surface of binding to Trk tyrosine kinase receptors in NGF and BDNF allows the engineering of a multifunctional pan-neurotrophin. EMBO J 12(6):2281-2293 (1993).
Ibanez et al. Chimeric molecules with multiple neurotrophic activities reveal structural elements determining the specificities of NGF and BDNF. EMBO J 10(8):2105-2110 (1991).
Ilag et al. Pan-neurotrophin 1: a genetically engineered neurotrophic factor displaying multiple specificities in peripheral neurons in vitro and in vivo. PNAS USA 92:607-611 (1995).
Inoue et al. Therapeutic and diagnostic potential of a vasopressin-2 antagonist for impaired water handling in cirrhosis. Clin Pharm Therap 63(5):561-570 (1998).
Kabat et al. Sequences of proteins of immunological interest. NIH Publ. No. 91-3242 1:647-669 (1991).
Karin et al. The IKK NF-kappa B system: a treasure trove for drug development. Nature Reviews Drug Discovery 3:17-26 (2004).
Karin. How NF-kappaB is activated: the role of the IkappaB kinase (IKK) complex. Oncogene 18:6867-6874 (1999).
Karin. The beginning of the end: IkappaB kinase (IKK) and NF-kappaB activation. J. Biol. Chem 274:27339-27342 (1999).
Kitano et al. Vasopressin and oxytocin receptor mRNAs are expressed in the rat inner ear. Neuroreport 8:2289-2292 (1997).
Kondo et al. Novel design of nonpeptide AVP V(2) receptor agonists: structural requirements for an agonist having 1-(4-aminobenzoyl)-2,3,4, 5-tetrahydro-1H-1-benzazepine as a template. J Med Chem 43:4388-4397 (2000).
Lee et al. Novel therapy for hearing loss: delivery of insulin-like growth factor 1 to the cochlea using gelatin hydrogel. Otol Neurotol 28(7):976-981 (2007).
Li et al. Notch inhibition induces mitotically generated hair cells in mammalian cochleae via activating the Wnt pathway. PNAS USA 112(1):166-171 (2015).
Liu et al. Bivalent diketopiperazine-based tropomysin receptor kinase C (TrkC) antagonists. J. Med. Chem. 53(13):5044-5048 (2010).
Liu et al. Calcineurin is a common target of cyclophilin-cyclosporin A and FKBP-FK506 complexes. Cell66:807-815 (1991).
Luzzi. Microencapsulation. Pharm Psy 59:1367-1376 (1970).
Majithiya et al. Thermoreversible-mucoadhesive Gel for Nasal Delivery of Sumatriptan. AAPS PharmSciTech 7(3):E1-E7 (2006).
Martin et al. Selective V2-receptor vasopressin antagonism decreases urinary aquaporin-2 excretion in patients with chronic heart failure. J. Am. Soc. Nephrol. 10(10):2165-2170 (1999).
Martini et al. An animal model based on the Sprague Dawley rat for the evaluation of ototoxicity. Ann. N.Y. Acad. Sci. 884:85-98 (1999).
Mercurio et al. IKK-1 and IKK-2: cytokine-activated IkappaB kinases essential for NF-kappaB activation. Science 278:860-866 (1997).
Morin et al. The D136A mutation of the V2 vasopressin receptor induces a constitutive activity which permits discrimination between antagonists with partial agonist and inverse agonist activities. FEBS Letters 441(3):470-475 (1998).
Musso et al. N-hydroxyformamide peptidomimetics as TACE/matrix metalloprotease inhibitors: oral activity via P1' isobutyl substitution. Bioorg. Med. Chem. Lett. 11:2147-2151 (2001).
Naha et al. Improved bioavailability of orally delivered insulin using Eudragit-L30D coated PLGA microparticles. Journal of Microencapsulation 25(4):248-256 (online publication).
Nakamura et al. Antidiuretic effects of a nonpeptide vasopressin V(2)-receptor agonist, OPC-51803, administered orally to rats. J Pharmacal Exp Ther 295(3):1005-1011 (2000).
Nakamura et al. Characterization of a novel nonpeptide vasopressin V(2)-agonist, OPC-51803, in cells transfected human vasopressin receptor subtypes. Br J Pharmacal 129(8):1700-1706 (2000).
Norman et al. Conivaptan Hydrochloride: Treatment of Heart Failure, Treatment of Hyponatremia, Vasopressin V1a/V2 Antagonist. Drugs Fut 25(11):1121-1130 (2000).
O'Brien et al. A family of highly selective allosteric modulators of the metabotropic glutamate receptor subtype 5. Mol. Pharmacol. 64(3):731-740 (2003).
Palm et al. V2-vasopressin receptor antagonists-mechanism of effect and clinical implications in hyponatraemia. Nephrol Dial Transplant 14:2559-2562 (1999).
Park et al. Mechanisms of Mucoadhesion of Poly(acrylic Acid) Hydrogels. Pharm. Res. 4(6):457-464 (1987).
Parker et al. Triazolo-tetrahydrofluorenones as selective estrogen receptor beta agonsits. Bioorg & Med. Chem. Ltrs,16:4652-4656 (2006).
Queille-Roussel et al. The new topical ascomycin derivative SDZ ASM 981 does not induce skin atrophy when applied to normal skin for 4 weeks: a randomized, double-blind controlled study. Br. J. Dermatol.144:507-513 (2001).
Richard et al. Effects of sterilizing-grade filters on the physicochemical properties of onion-like vesicles. Int J Pharm 312(1-2):144-150 (2006).
Rothwarf et al. IKK-gamma is an essential regulatory subunit of the IkappaB kinase complex. Nature 395:297-300 (1998).
Ryden et al. Functional analysis of mutant neurotrophins deficient in low-affinity binding reveals a role for p75LNGFR in NT-4 signalling. EMBO J 14(9):1979-1990 (1995).
Sanghi et al. Vasopressin antagonism: a future treatment option in heart failure. Eur. Heart J. 26:538-543 (2005).
Satoh et al. Proinflammatory cytokine expression in the endolymphatic sac during inner ear inflammation. J Assoc. Res. Otolaryngol.4:139-147 (2003).
Schreiber et al. The mechanism of action of cyclosporin A and FK506. Immunol. Today 13:136-142 (1992).
Skotnicki et al. Chapter 16: TNF-α Converting Enzyme (TACE) as a Therapeutic Target. Annual Reports in Medicinal Chemistry 38:153-162 (2003).
Stuetz et al. Discovery of topical calcineurin inhibitors and pharmacological profile of pimecrolimus. Int. Arch. Allergy Immunol. (141:199-212 (2006).
Sun et al. Bryostatin-1: Pharmacology and Therapeutic Potential as a CNS Drug. CNS Drug Reviews 12:1-8 (2006).
Taguchi et al. Expressions of aquaporin-2. vasopressin type 2 receptor. transient receptor potential channel vanilloid (TRPV)1. and TRPV4 in the human endolymphatic sac. Laryngoscope 117(4):695-698 (2007).
Takeda et al. A comparison of dehydration effects of V2-antagonist (OPC-31260) on the inner ear between systemic and round window applications. Hearing Res 218:89-97 (2006).
Takeda et al. Endolymphatic hydrops induced by chronic administration of vasopressin. Hear Res 140:1-6 (2000).
Takeda et al. The effects of V2 antagonist (OPC-31260) on endolymphatic hydrops. Hear Res 182(1-2):9-18. (2003).
Taktak et al. Assay of Pyrogens by Interleukin-6 Release from Monocytic Cell Lines. J. Pharm. Pharmacol. 43:578-582 (1991).
The U. S. Food and Drug Administration has provided regulatory guidance in the publication: Guidance for Industry: Sterile Drug Products Produced by Aseptic Processing. available at: http://www.fda.gov/cder/guidance/5882fn1.htm (Aug. 2003) (63 pgs.).
Urfer et al. The binding epitopes of neurotrophin-3 to its receptors trkC and gp75 and the design of a multifunctional human neurotrophin. EMBO J 13(24):5896-5909 (1994).

(56) References Cited

OTHER PUBLICATIONS

Wang et al. Spontaneous Activity of Cochlear Hair Cells Triggered by Fluid Secretion Mechanism in Adjacent Support Cells. Cell 163:1348-1359 (2015).
Wong et al. Sphincter of Oddi Manometry: Comparison of Post-Procedure Abdominal Pain and Post-Procedure Pancreatitis SGW. Gastroent 118(4 Suppl. 2, Part 1) (2000).
Woronicz et al. IkappaB kinase-beta: NF-kappaB activation and complex formation with IkappaB kinase-alpha and NIK. Science 278:866-869 (1997).
Yin et al. Pretreatment with soluble ST2 reduces warm hepatic ischemia/reperfusion injury. Biochem Biophys Res 351(4):940-946 (2006).
Zandi et al. The IkappaB kinase complex (IKK) contains two kinase subunits, IKKalpha and IKKbeta, necessary for IkappaB phosphorylation and NF-kappaB activation. Cell 91:243-252 (1997).
Zapata et al. Engineering linear F(ab')2 fragments for efficient production in *Escherichia coli* and enhanced antiproliferative activity. Protein Eng. 8(10):1057-1062 (1995).
Zou et al. Distribution of Lipid Nanocapsules in Different Cochlear Cell Populations After Round Window Membrane Permeation. J Biomed Materials Res pp. 10-18 (Apr. 24, 2008).
PCT/US2017/040055 International Search Report and Written Opinion dated Sep. 20, 2017.
Nippe, et al. "Parenteral oil-based drospirenone microcrystal suspensions—Evaluation of physicochemical stability and influence of stabilising agents," International Journal of Pharmaceutics, 416 (2011), pp. 181-188, 8 pages.
European Office Action in EP Patent Application No. 17821269.2, dated Dec. 17, 2019, 17 pages.
Supplementary European Search Report in EP Patent Application No. 17821269.2, dated Mar. 5, 2020, 15 pages.

* cited by examiner

2Ca

2Cg

2Cl

2Ai

2Cb

3Cb 1a (SK-IK)
TrkC and TrkA antagonist 1b (IR-IK)
TrkC and TrkA antagonist 2c (GT-EK)
TrkC antagonist 2d (RI-TG)
TrkC antagonist 2e (SM-GK)
TrkC antagonist 3f (KS-KI)
TrkC antagonist 6dh

SEQUENCE LISTING

```
<160> NUMBER OF SEQ ID NOS: 120

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
```

```
ggacaataga gatcatctag t                                             21

<210> SEQ ID NO 2
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ccggggacaa tagagatcat ctagtctcga gactagatga tctctattgt cctttttg     58

<210> SEQ ID NO 3
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aattcaaaaa ggacaataga gatcatctag tctcgagact agatgatctc tattgtcc     58

<210> SEQ ID NO 4
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccggggacat ccaagcctc ttaacctcga ggttaagagg cttggaatgt ccttttg       58

<210> SEQ ID NO 5
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aattcaaaaa ggacattcca agcctcttaa cctcgaggtt aagaggcttg gaatgtcc     58

<210> SEQ ID NO 6
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ccggcatggt ttcagagaaa ttatgctcga gcataatttc tctgaaacca tgttttg      58

<210> SEQ ID NO 7
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aattcaaaaa catggtttca gagaaattat gctcgagcat aatttctctg aaaccatg     58
```

-continued

```
<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cctaaggtta agtcgccctc g                                            21

<210> SEQ ID NO 9
<211> LENGTH: 839
<212> TYPE: PRT
<213> ORGANISM: Homo sapiens

<400> SEQUENCE: 9

Met Asp Val Ser Leu Cys Pro Ala Lys Cys Ser Phe Trp Arg Ile Phe
1               5                   10                  15

Leu Leu Gly Ser Val Trp Leu Asp Tyr Val Gly Ser Val Leu Ala Cys
            20                  25                  30

Pro Ala Asn Cys Val Cys Ser Lys Thr Glu Ile Asn Cys Arg Arg Pro
        35                  40                  45

Asp Asp Gly Asn Leu Phe Pro Leu Leu Glu Gly Gln Asp Ser Gly Asn
    50                  55                  60

Ser Asn Gly Asn Ala Ser Ile Asn Ile Thr Asp Ile Ser Arg Asn Ile
65                  70                  75                  80

Thr Ser Ile His Ile Glu Asn Trp Arg Ser Leu His Thr Leu Asn Ala
                85                  90                  95

Val Asp Met Glu Leu Tyr Thr Gly Leu Gln Lys Leu Thr Ile Lys Asn
            100                 105                 110

Ser Gly Leu Arg Ser Ile Gln Pro Arg Ala Phe Ala Lys Asn Pro His
        115                 120                 125

Leu Arg Tyr Ile Asn Leu Ser Ser Asn Arg Leu Thr Thr Leu Ser Trp
    130                 135                 140

Gln Leu Phe Gln Thr Leu Ser Leu Arg Glu Leu Gln Leu Glu Gln Asn
145                 150                 155                 160

Phe Phe Asn Cys Ser Cys Asp Ile Arg Trp Met Gln Leu Trp Gln Glu
                165                 170                 175

Gln Gly Glu Ala Lys Leu Asn Ser Gln Asn Leu Tyr Cys Ile Asn Ala
            180                 185                 190

Asp Gly Ser Gln Leu Pro Leu Phe Arg Met Asn Ile Ser Gln Cys Asp
        195                 200                 205

Leu Pro Glu Ile Ser Val Ser His Val Asn Leu Thr Val Arg Glu Gly
    210                 215                 220

Asp Asn Ala Val Ile Thr Cys Asn Gly Ser Gly Ser Pro Leu Pro Asp
225                 230                 235                 240

Val Asp Trp Ile Val Thr Gly Leu Gln Ser Ile Asn Thr His Gln Thr
                245                 250                 255

Asn Leu Asn Trp Thr Asn Val His Ala Ile Asn Leu Thr Leu Val Asn
            260                 265                 270

Val Thr Ser Glu Asp Asn Gly Phe Thr Leu Thr Cys Ile Ala Glu Asn
        275                 280                 285

Val Val Gly Met Ser Asn Ala Ser Val Ala Leu Thr Val Tyr Tyr Pro
    290                 295                 300
```

```
Pro Arg Val Val Ser Leu Glu Glu Pro Glu Leu Arg Leu Glu His Cys
305                 310                 315                 320

Ile Glu Phe Val Val Arg Gly Asn Pro Pro Thr Leu His Trp Leu
            325                 330                 335

His Asn Gly Gln Pro Leu Arg Glu Ser Lys Ile Ile His Val Glu Tyr
                340                 345                 350

Tyr Gln Glu Gly Glu Ile Ser Glu Gly Cys Leu Leu Phe Asn Lys Pro
            355                 360                 365

Thr His Tyr Asn Asn Gly Asn Tyr Thr Leu Ile Ala Lys Asn Pro Leu
        370                 375                 380

Gly Thr Ala Asn Gln Thr Ile Asn Gly His Phe Leu Lys Glu Pro Phe
385                 390                 395                 400

Pro Glu Ser Thr Asp Asn Phe Ile Leu Phe Asp Glu Val Ser Pro Thr
                405                 410                 415

Pro Pro Ile Thr Val Thr His Lys Pro Glu Glu Asp Thr Phe Gly Val
            420                 425                 430

Ser Ile Ala Val Gly Leu Ala Ala Phe Ala Cys Val Leu Leu Val Val
        435                 440                 445

Leu Phe Val Met Ile Asn Lys Tyr Gly Arg Arg Ser Lys Phe Gly Met
450                 455                 460

Lys Gly Pro Val Ala Val Ile Ser Gly Glu Glu Asp Ser Ala Ser Pro
465                 470                 475                 480

Leu His His Ile Asn His Gly Ile Thr Thr Pro Ser Ser Leu Asp Ala
                485                 490                 495

Gly Pro Asp Thr Val Val Ile Gly Met Thr Arg Ile Pro Val Ile Glu
            500                 505                 510

Asn Pro Gln Tyr Phe Arg Gln Gly His Asn Cys His Lys Pro Asp Thr
        515                 520                 525

Tyr Val Gln His Ile Lys Arg Arg Asp Ile Val Leu Lys Arg Glu Leu
        530                 535                 540

Gly Glu Gly Ala Phe Gly Lys Val Phe Leu Ala Glu Cys Tyr Asn Leu
545                 550                 555                 560

Ser Pro Thr Lys Asp Lys Met Leu Val Ala Val Lys Ala Leu Lys Asp
                565                 570                 575

Pro Thr Leu Ala Ala Arg Lys Asp Phe Gln Arg Glu Ala Glu Leu Leu
            580                 585                 590

Thr Asn Leu Gln His Glu His Ile Val Lys Phe Tyr Gly Val Cys Gly
        595                 600                 605

Asp Gly Asp Pro Leu Ile Met Val Phe Glu Tyr Met Lys His Gly Asp
        610                 615                 620

Leu Asn Lys Phe Leu Arg Ala His Gly Pro Asp Ala Met Ile Leu Val
625                 630                 635                 640

Asp Gly Gln Pro Arg Gln Ala Lys Gly Glu Leu Gly Leu Ser Gln Met
                645                 650                 655

Leu His Ile Ala Ser Gln Ile Ala Ser Gly Met Val Tyr Leu Ala Ser
            660                 665                 670

Gln His Phe Val His Arg Asp Leu Ala Thr Arg Asn Cys Leu Val Gly
        675                 680                 685

Ala Asn Leu Leu Val Lys Ile Gly Asp Phe Gly Met Ser Arg Asp Val
        690                 695                 700

Tyr Ser Thr Asp Tyr Tyr Arg Leu Phe Asn Pro Ser Gly Asn Asp Phe
705                 710                 715                 720

Cys Ile Trp Cys Glu Val Gly Gly His Thr Met Leu Pro Ile Arg Trp
```

```
                     725                 730                 735
Met Pro Pro Glu Ser Ile Met Tyr Arg Lys Phe Thr Thr Glu Ser Asp
                 740                 745                 750

Val Trp Ser Phe Gly Val Ile Leu Trp Glu Ile Phe Thr Tyr Gly Lys
             755                 760                 765

Gln Pro Trp Phe Gln Leu Ser Asn Thr Glu Val Ile Glu Cys Ile Thr
         770                 775                 780

Gln Gly Arg Val Leu Glu Arg Pro Arg Val Cys Pro Lys Glu Val Tyr
785                 790                 795                 800

Asp Val Met Leu Gly Cys Trp Gln Arg Glu Pro Gln Gln Arg Leu Asn
                 805                 810                 815

Ile Lys Glu Ile Tyr Lys Ile Leu His Ala Leu Gly Lys Ala Thr Pro
             820                 825                 830

Ile Tyr Leu Asp Ile Leu Gly
         835

<210> SEQ ID NO 10
<211> LENGTH: 612
<212> TYPE: PRT
<213> ORGANISM: Homo sapiens

<400> SEQUENCE: 10

Met Asp Val Ser Leu Cys Pro Ala Lys Cys Ser Phe Trp Arg Ile Phe
1               5                   10                  15

Leu Leu Gly Ser Val Trp Leu Asp Tyr Val Gly Ser Val Leu Ala Cys
            20                  25                  30

Pro Ala Asn Cys Val Cys Ser Lys Thr Glu Ile Asn Cys Arg Arg Pro
        35                  40                  45

Asp Asp Gly Asn Leu Phe Pro Leu Leu Glu Gly Gln Asp Ser Gly Asn
    50                  55                  60

Ser Asn Gly Asn Ala Asn Ile Asn Ile Thr Asp Ile Ser Arg Asn Ile
65                  70                  75                  80

Thr Ser Ile His Ile Glu Asn Trp Arg Ser Leu His Thr Leu Asn Ala
                85                  90                  95

Val Asp Met Glu Leu Tyr Thr Gly Leu Gln Lys Leu Thr Ile Lys Asn
            100                 105                 110

Ser Gly Leu Arg Ser Ile Gln Pro Arg Ala Phe Ala Lys Asn Pro His
        115                 120                 125

Leu Arg Tyr Ile Asn Leu Ser Ser Asn Arg Leu Thr Thr Leu Ser Trp
    130                 135                 140

Gln Leu Phe Gln Thr Leu Ser Leu Arg Glu Leu Gln Leu Glu Gln Asn
145                 150                 155                 160

Phe Phe Asn Cys Ser Cys Asp Ile Arg Trp Met Gln Leu Trp Gln Glu
                165                 170                 175

Gln Gly Glu Ala Lys Leu Asn Ser Gln Asn Leu Tyr Cys Ile Asn Ala
            180                 185                 190

Asp Gly Ser Gln Leu Pro Leu Phe Arg Met Asn Ile Ser Gln Cys Asp
        195                 200                 205

Leu Pro Glu Ile Ser Val Ser His Val Asn Leu Thr Val Arg Glu Gly
    210                 215                 220

Asp Asn Ala Val Ile Thr Cys Asn Gly Ser Gly Ser Pro Leu Pro Asp
225                 230                 235                 240

Val Asp Trp Ile Val Thr Gly Leu Gln Ser Ile Asn Thr His Gln Thr
                245                 250                 255
```

-continued

```
Asn Leu Asn Trp Thr Asn Val His Ala Ile Asn Leu Thr Leu Val Asn
            260                 265                 270

Val Thr Ser Glu Asp Asn Gly Phe Thr Leu Thr Cys Ile Ala Glu Asn
        275                 280                 285

Val Val Gly Met Ser Asn Ala Ser Val Ala Leu Thr Val Tyr Tyr Pro
    290                 295                 300

Pro Arg Val Val Ser Leu Glu Pro Glu Leu Arg Leu Glu His Cys
305                 310                 315                 320

Ile Glu Phe Val Val Arg Gly Asn Pro Pro Thr Leu His Trp Leu
                325                 330                 335

His Asn Gly Gln Pro Leu Arg Glu Ser Lys Ile Ile His Val Glu Tyr
            340                 345                 350

Tyr Gln Glu Gly Glu Ile Ser Glu Gly Cys Leu Leu Phe Asn Lys Pro
        355                 360                 365

Thr His Tyr Asn Asn Gly Asn Tyr Thr Leu Ile Ala Lys Asn Pro Leu
    370                 375                 380

Gly Thr Ala Asn Gln Thr Ile Asn Gly His Phe Leu Lys Glu Pro Phe
385                 390                 395                 400

Pro Glu Ser Thr Asp Asn Phe Ile Leu Phe Asp Glu Val Ser Pro Thr
                405                 410                 415

Pro Pro Ile Thr Val Thr His Lys Pro Glu Glu Asp Thr Phe Gly Val
            420                 425                 430

Ser Ile Ala Val Gly Leu Ala Ala Phe Ala Cys Val Leu Leu Val Val
        435                 440                 445

Leu Phe Val Met Ile Asn Lys Tyr Gly Arg Arg Ser Lys Phe Gly Met
    450                 455                 460

Lys Gly Pro Val Ala Val Ile Ser Gly Glu Glu Asp Ser Ala Ser Pro
465                 470                 475                 480

Leu His His Ile Asn His Gly Ile Thr Thr Pro Ser Ser Leu Asp Ala
                485                 490                 495

Gly Pro Asp Thr Val Val Ile Gly Met Thr Arg Ile Pro Val Ile Glu
            500                 505                 510

Asn Pro Gln Tyr Phe Arg Gln Gly His Asn Cys His Lys Pro Asp Thr
        515                 520                 525

Trp Val Phe Ser Asn Ile Asp Asn His Gly Ile Leu Asn Leu Lys Asp
    530                 535                 540

Asn Arg Asp His Leu Val Pro Ser Thr His Tyr Ile Tyr Glu Glu Pro
545                 550                 555                 560

Glu Val Gln Ser Gly Glu Val Ser Tyr Pro Arg Ser His Gly Phe Arg
                565                 570                 575

Glu Ile Met Leu Asn Pro Ile Ser Leu Pro Gly His Ser Lys Pro Leu
            580                 585                 590

Asn His Gly Ile Tyr Val Glu Asp Val Asn Val Tyr Phe Ser Lys Gly
        595                 600                 605

Arg His Gly Phe
    610
```

<210> SEQ ID NO 11
<211> LENGTH: 822
<212> TYPE: PRT
<213> ORGANISM: Homo sapiens

<400> SEQUENCE: 11

```
Met Ser Ser Trp Ile Arg Trp His Gly Pro Ala Met Ala Arg Leu Trp
1               5                   10                  15
```

```
Gly Phe Cys Trp Leu Val Val Gly Phe Trp Arg Ala Ala Phe Ala Cys
                20                  25                  30

Pro Thr Ser Cys Lys Cys Ser Ala Ser Arg Ile Trp Cys Ser Asp Pro
            35                  40                  45

Ser Pro Gly Ile Val Ala Phe Pro Arg Leu Glu Pro Asn Ser Val Asp
50                      55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430
```

```
Val Tyr Ala Val Val Ile Ala Ser Val Val Gly Phe Cys Leu Leu
        435                 440                 445

Val Met Leu Phe Leu Leu Lys Leu Ala Arg His Ser Lys Phe Gly Met
450                 455                 460

Lys Gly Pro Ala Ser Val Ile Ser Asn Asp Asp Ser Ala Ser Pro
465                 470                 475                 480

Leu His His Ile Ser Asn Gly Ser Asn Thr Pro Ser Ser Glu Gly
                485                 490                 495

Gly Pro Asp Ala Val Ile Ile Gly Met Thr Lys Ile Pro Val Ile Glu
                500                 505                 510

Asn Pro Gln Tyr Phe Gly Ile Thr Asn Ser Gln Leu Lys Pro Asp Thr
                515                 520                 525

Phe Val Gln His Ile Lys Arg His Asn Ile Val Leu Lys Arg Glu Leu
            530                 535                 540

Gly Glu Gly Ala Phe Gly Lys Val Phe Leu Ala Glu Cys Tyr Asn Leu
545                 550                 555                 560

Cys Pro Glu Gln Asp Lys Ile Leu Val Ala Val Lys Thr Leu Lys Asp
                565                 570                 575

Ala Ser Asp Asn Ala Arg Lys Asp Phe His Arg Glu Ala Glu Leu Leu
            580                 585                 590

Thr Asn Leu Gln His Glu His Ile Val Lys Phe Tyr Gly Val Cys Val
            595                 600                 605

Glu Gly Asp Pro Leu Ile Met Val Phe Glu Tyr Met Lys His Gly Asp
610                 615                 620

Leu Asn Lys Phe Leu Arg Ala His Gly Pro Asp Ala Val Leu Met Ala
625                 630                 635                 640

Glu Gly Asn Pro Pro Thr Glu Leu Thr Gln Ser Gln Met Leu His Ile
                645                 650                 655

Ala Gln Gln Ile Ala Ala Gly Met Val Tyr Leu Ala Ser Gln His Phe
                660                 665                 670

Val His Arg Asp Leu Ala Thr Arg Asn Cys Leu Val Gly Glu Asn Leu
            675                 680                 685

Leu Val Lys Ile Gly Asp Phe Gly Met Ser Arg Asp Val Tyr Ser Thr
690                 695                 700

Asp Tyr Tyr Arg Val Gly Gly His Thr Met Leu Pro Ile Arg Trp Met
705                 710                 715                 720

Pro Pro Glu Ser Ile Met Tyr Arg Lys Phe Thr Thr Glu Ser Asp Val
                725                 730                 735

Trp Ser Leu Gly Val Val Leu Trp Glu Ile Phe Thr Tyr Gly Lys Gln
                740                 745                 750

Pro Trp Tyr Gln Leu Ser Asn Asn Glu Val Ile Glu Cys Ile Thr Gln
                755                 760                 765

Gly Arg Val Leu Gln Arg Pro Arg Thr Cys Pro Gln Glu Val Tyr Glu
770                 775                 780

Leu Met Leu Gly Cys Trp Gln Arg Glu Pro His Met Arg Lys Asn Ile
785                 790                 795                 800

Lys Gly Ile His Thr Leu Leu Gln Asn Leu Ala Lys Ala Ser Pro Val
                805                 810                 815

Tyr Leu Asp Ile Leu Gly
            820

<210> SEQ ID NO 12
<211> LENGTH: 477
<212> TYPE: PRT
```

<213> ORGANISM: Homo sapiens

<400> SEQUENCE: 12

```
Met Ser Ser Trp Ile Arg Trp His Gly Pro Ala Met Ala Arg Leu Trp
 1               5                  10                  15
Gly Phe Cys Trp Leu Val Val Gly Phe Trp Arg Ala Ala Phe Ala Cys
                20                  25                  30
Pro Thr Ser Cys Lys Cys Ser Ala Ser Arg Ile Trp Cys Ser Asp Pro
            35                  40                  45
Ser Pro Gly Ile Val Ala Phe Pro Arg Leu Glu Pro Asn Ser Val Asp
        50                  55                  60
Pro Glu Asn Ile Thr Glu Ile Phe Ile Ala Asn Gln Lys Arg Leu Glu
65                  70                  75                  80
Ile Ile Asn Glu Asp Asp Val Glu Ala Tyr Val Gly Leu Arg Asn Leu
                85                  90                  95
Thr Ile Val Asp Ser Gly Leu Lys Phe Val Ala His Lys Ala Phe Leu
            100                 105                 110
Lys Asn Ser Asn Leu Gln His Ile Asn Phe Thr Arg Asn Lys Leu Thr
        115                 120                 125
Ser Leu Ser Arg Lys His Phe Arg His Leu Asp Leu Ser Glu Leu Ile
130                 135                 140
Leu Val Gly Asn Pro Phe Thr Cys Ser Cys Asp Ile Met Trp Ile Lys
145                 150                 155                 160
Thr Leu Gln Glu Ala Lys Ser Ser Pro Asp Thr Gln Asp Leu Tyr Cys
                165                 170                 175
Leu Asn Glu Ser Ser Lys Asn Ile Pro Leu Ala Asn Leu Gln Ile Pro
            180                 185                 190
Asn Cys Gly Leu Pro Ser Ala Asn Leu Ala Ala Pro Asn Leu Thr Val
        195                 200                 205
Glu Glu Gly Lys Ser Ile Thr Leu Ser Cys Ser Val Ala Gly Asp Pro
210                 215                 220
Val Pro Asn Met Tyr Trp Asp Val Gly Asn Leu Val Ser Lys His Met
225                 230                 235                 240
Asn Glu Thr Ser His Thr Gln Gly Ser Leu Arg Ile Thr Asn Ile Ser
                245                 250                 255
Ser Asp Asp Ser Gly Lys Gln Ile Ser Cys Val Ala Glu Asn Leu Val
            260                 265                 270
Gly Glu Asp Gln Asp Ser Val Asn Leu Thr Val His Phe Ala Pro Thr
        275                 280                 285
Ile Thr Phe Leu Glu Ser Pro Thr Ser Asp His His Trp Cys Ile Pro
290                 295                 300
Phe Thr Val Lys Gly Asn Pro Lys Pro Ala Leu Gln Trp Phe Tyr Asn
305                 310                 315                 320
Gly Ala Ile Leu Asn Glu Ser Lys Tyr Ile Cys Thr Lys Ile His Val
                325                 330                 335
Thr Asn His Thr Glu Tyr His Gly Cys Leu Gln Leu Asp Asn Pro Thr
            340                 345                 350
His Met Asn Asn Gly Asp Tyr Thr Leu Ile Ala Lys Asn Glu Tyr Gly
        355                 360                 365
Lys Asp Glu Lys Gln Ile Ser Ala His Phe Met Gly Trp Pro Gly Ile
370                 375                 380
Asp Asp Gly Ala Asn Pro Asn Tyr Pro Asp Val Ile Tyr Glu Asp Tyr
385                 390                 395                 400
```

```
Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Val Ile Ala Ser Val Val Gly Phe Cys Leu Leu
        435                 440                 445

Val Met Leu Phe Leu Leu Lys Leu Ala Arg His Ser Lys Phe Gly Met
450                 455                 460

Lys Gly Phe Val Leu Phe His Lys Ile Pro Leu Asp Gly
465                 470                 475

<210> SEQ ID NO 13
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
cuauacaacc uacugccuuc cc                                              22

<210> SEQ ID NO 14
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ugagguagua gguugugugg uu                                              22

<210> SEQ ID NO 15
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
uggaauguaa agaaguaugu au                                              22

<210> SEQ ID NO 16
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
acauacuucu uuauaugccc au                                              22

<210> SEQ ID NO 17
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
auaaagcuag auaaccgaaa gu                                              22
```

<210> SEQ ID NO 18
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ucuuugguua ucuagcugua uga                                              23

<210> SEQ ID NO 19
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
caaauucgua ucuagggaa ua                                                22

<210> SEQ ID NO 20
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uacccuguag auccgaauuu gug                                              23

<210> SEQ ID NO 21
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
caggccauau ugugcugccu ca                                               22

<210> SEQ ID NO 22
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uagcagcaca uaaugguuug ug                                               22

<210> SEQ ID NO 23
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ccaguauuaa cugugcugcu ga                                               22

```
<210> SEQ ID NO 24
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ccaauauuac ugugcugcuu ua                                              22

<210> SEQ ID NO 25
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
uagcagcacg uaaauauugg cg                                              22

<210> SEQ ID NO 26
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
acugcaguga aggcacuugu ag                                              22

<210> SEQ ID NO 27
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
caaagugcuu acagugcagg uag                                             23

<210> SEQ ID NO 28
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
acugcccuaa gugcuccuuc ugg                                             23

<210> SEQ ID NO 29
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
uaaggugcau cuagugcaga uag                                             23
```

-continued

```
<210> SEQ ID NO 30
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
acugcauuau gagcacuuaa ag                                              22

<210> SEQ ID NO 31
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
uaaagugcuu auagugcagg uag                                             23

<210> SEQ ID NO 32
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
uggcucaguu cagcaggaac ag                                              22

<210> SEQ ID NO 33
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
ugccuacuga gcugauauca gu                                              22

<210> SEQ ID NO 34
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ugccuacuga gcugaaacac ag                                              22

<210> SEQ ID NO 35
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
cuuucagucg gauguuuaca gc                                              22

<210> SEQ ID NO 36
```

```
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
uguaaacauc cuugacugga ag                                              22

<210> SEQ ID NO 37
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
acugcugagc uagcacuucc cg                                              22

<210> SEQ ID NO 38
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38 caaagucug uucgugcagg uag                                              23

<210> SEQ ID NO 39
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
agcagcauug uacagggcua uga                                             23

<210> SEQ ID NO 40
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
agcuucuuua cagugcugcc uug                                             23

<210> SEQ ID NO 41
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
ucauagcccu guacaaugcu gcu                                             23

<210> SEQ ID NO 42
<211> LENGTH: 22
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
cugcaaugua agcacuucuu ac                                          22

<210> SEQ ID NO 43
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
aaaagugcuu acagugcagg uag                                         23

<210> SEQ ID NO 44
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
ccgcacugug gguacuugcu gc                                          22

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
uaaagugcug acagugcaga u                                           21

<210> SEQ ID NO 46
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
agcagcauug uacagggcua uca                                         23

<210> SEQ ID NO 47
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
acaggugagg uucuugggag cc                                          22

<210> SEQ ID NO 48
<211> LENGTH: 24
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 48
ucccugagac cuuuaaccu guga                                              24

<210> SEQ ID NO 49
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
acggguuagg cucuugggag cu                                               22

<210> SEQ ID NO 50
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ucacaaguca ggcucuuggg ac                                               22

<210> SEQ ID NO 51
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
ucccugagac ccuaacuugu ga                                               22

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
ucacagugaa ccggucucuu u                                                21

<210> SEQ ID NO 53
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
cggggccgua gcacugucug aga                                              23

<210> SEQ ID NO 54
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 54
gggggccgau acacuguacg aga                                              23

<210> SEQ ID NO 55
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
uuuggucccc uucaaccagc ug                                               22

<210> SEQ ID NO 56
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
agcugguaaa auggaaccaa au                                               22

<210> SEQ ID NO 57
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
uuuggucccc uucaaccagc ua                                               22

<210> SEQ ID NO 58
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
uaacacuguc ugguaaagau gg                                               22

<210> SEQ ID NO 59
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
caucuuccag uacaguguug ga                                               22

<210> SEQ ID NO 60
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 60
agggagggac gggggcugug c                                              21

<210> SEQ ID NO 61
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
ucuggcuccg ugucuucacu ccc                                            23

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
ugguucuaga cuugccaacu a                                              21

<210> SEQ ID NO 63
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
uuuggcaaug guagaacuca cacu                                           24

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
cucccacaug caggguuugc a                                              21

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
caucccuugc augguggagg g                                              21

<210> SEQ ID NO 66
<211> LENGTH: 22
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 66
gguccagagg ggagauaggu uc                                              22

<210> SEQ ID NO 67
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
uaacacuguc ugguaacgau gu                                              22

<210> SEQ ID NO 68
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
caucuuaccg gacagugcug ga                                              22

<210> SEQ ID NO 69
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
uaauacugcc ugguaaugau ga                                              22

<210> SEQ ID NO 70
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
caucuuacug ggcagcauug ga                                              22

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
gcugggaagg caaagggacg u                                               21

<210> SEQ ID NO 72
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 72
uucccuuugu cauccuaugc cu                                              22

<210> SEQ ID NO 73
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
uggaauguaa ggaagugugu gg                                              22

<210> SEQ ID NO 74
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
agcuacauug ucugcugggu uuc                                             23

<210> SEQ ID NO 75
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
accuggcaua caauguagau uu                                              22

<210> SEQ ID NO 76
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
gaggguuggg uggaggcucu cc                                              22

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
agggcccccc cucaauccug u                                               21

<210> SEQ ID NO 78
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 78
cgcauccccu agggcauugg ugu                                                        23

<210> SEQ ID NO 79
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
ccucugggcc cuuccuccag                                                            20

<210> SEQ ID NO 80
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
gcaaagcaca cggccugcag aga                                                        23

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
gccccugggc cuauccuaga a                                                          21

<210> SEQ ID NO 82
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
cuagguaugg ucccagggau cc                                                         22

<210> SEQ ID NO 83
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
uccgucucag uuacuuuaua gc                                                         22

<210> SEQ ID NO 84
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84

-continued uuauaaagca augagacuga uu					22

<210> SEQ ID NO 85
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
gcccugaacg aggggucugg ag					22

<210> SEQ ID NO 86
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
gcugacuccu aguccagggc uc					22

<210> SEQ ID NO 87
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
cuuaucagau uguauuguaa uu					22

<210> SEQ ID NO 88
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
uuauaauaca accugauaag ug					22

<210> SEQ ID NO 89
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
cuuagcaggu uguauuauca uu					22

<210> SEQ ID NO 90
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
auauaauaca accugcuaag ug                                                22

<210> SEQ ID NO 91
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
cacuuagcag guuguauuau au                                                22

<210> SEQ ID NO 92
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
auaauacaac cugcuaagug cu                                                22

<210> SEQ ID NO 93
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
auuccuagaa auuguucaua                                                   20

<210> SEQ ID NO 94
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
acuucaccug guccacuagc cgu                                               23

<210> SEQ ID NO 95
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
uggucgacca guuggaaagu aau                                               23

<210> SEQ ID NO 96
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
acuggacuua gggucagaag gc                                                22

```
<210> SEQ ID NO 97
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
uggcagugua uuguuagcug gu                                                  22

<210> SEQ ID NO 98
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
cagccacaac uacccugcca cu                                                  22

<210> SEQ ID NO 99
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
aggcagugua uuguuagcug gc                                                  22

<210> SEQ ID NO 100
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
uugcuaguug cacuccucuc ugu                                                 23

<210> SEQ ID NO 101
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
uaggcagugu auugcuagcg gcugu                                               25

<210> SEQ ID NO 102
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
gucauacacg gcucuccucu cu                                                  22
```

<210> SEQ ID NO 103
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
ugauugguac gucugugggu ag                                               22

<210> SEQ ID NO 104
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
uacugcagac aguggcaauc a                                                21

<210> SEQ ID NO 105
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
uacugcagac guggcaauca ug                                               22

<210> SEQ ID NO 106
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
agacuuccca uuugaaggug gc                                               22

<210> SEQ ID NO 107
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
gacuauagaa cuuuccccu ca                                                22

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108 aggggggaaag uucuauaguc c                                               21

```
<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
uggaggagaa ggaaggugau g                                              21

<210> SEQ ID NO 110
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Glu Ser Thr Asp Asn Phe Ile Leu Phe Asp Glu Val Ser Pro Thr Pro
1               5                   10                  15

Pro Ile

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: R or W
<220> FEATURE:
<221> NAME/KEY: MOD_RES
<222> LOCATION: (9)..(9)
<223> OTHER INFORMATION: I, L, R, or M

<400> SEQUENCE: 111

Gly Tyr Thr Phe Thr Ser Tyr Xaa Xaa His
1               5                   10

<210> SEQ ID NO 112
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: A, T, S, or G
<220> FEATURE:
<221> NAME/KEY: MOD_RES
<222> LOCATION: (16)..(16)
<223> OTHER INFORMATION: K or E

<400> SEQUENCE: 112

Glu Ile Tyr Pro Ser Asn Xaa Arg Thr Asn Tyr Asn Glu Lys Phe Xaa
1               5                   10                  15

Ser

<210> SEQ ID NO 113
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: T or S
<220> FEATURE:
<221> NAME/KEY: MOD_RES
<222> LOCATION: (8)..(8)
<223> OTHER INFORMATION: R, Q, K, S, or Y

<400> SEQUENCE: 113

Lys Tyr Tyr Tyr Gly Asn Xaa Xaa Arg Ser Trp Tyr Phe Asp Val
1               5                   10                  15

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Tyr Thr Phe Thr Ser Tyr Trp Met His
1               5                   10

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Glu Ile Tyr Pro Ser Asn Gly Arg Thr Asn Tyr Asn Glu Lys Phe Lys
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Lys Tyr Tyr Tyr Gly Asn Ser Tyr Arg Ser Trp Tyr Phe Asp Val
1               5                   10                  15

<210> SEQ ID NO 117
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Asp Asn Tyr
            20                  25                  30

Gly Ile Ser Phe Leu Ala Trp Tyr Gln Gln Lys Pro Gly Lys Ala Pro
        35                  40                  45
```

```
Lys Leu Leu Ile Tyr Ala Ala Ser Asn Arg Gly Ser Gly Val Pro Ser
 50                  55                  60

Arg Phe Ser Gly Ser Gly Ser Gly Thr Asp Phe Thr Phe Thr Ile Ser
 65                  70                  75                  80

Ser Leu Gln Pro Glu Asp Ile Ala Thr Tyr Tyr Cys Gln Gln Ser Lys
                 85                  90                  95

Thr Val Pro Arg Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Ala Thr His Gln Gly Leu Ser Ser Pro
        195                 200                 205

Val Thr Lys Ser Phe Asn Arg Gly Glu Cys
210                 215

<210> SEQ ID NO 118
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Arg Ile His Trp Val Arg Gln Ala Pro Gly Gln Gly Leu Glu Trp Met
         35                  40                  45

Gly Glu Ile Tyr Pro Ser Asn Ala Arg Thr Asn Tyr Asn Glu Lys Phe
 50                  55                  60

Lys Ser Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Lys Tyr Tyr Gly Asn Thr Arg Arg Ser Trp Tyr Phe Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190
```

```
Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
        260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Phe Arg
        290                 295                 300

Val Val Ser Val Leu Thr Val Val His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 119
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (10)..(10)
<223> OTHER INFORMATION: L-azetidine-2-carbonyl-Tyr
<220> FEATURE:
<223> OTHER INFORMATION: C-term NH2

<400> SEQUENCE: 119

Phe Glu Trp Thr Pro Gly Trp Tyr Gln Tyr Ala Leu Pro Leu
1               5                   10

<210> SEQ ID NO 120
<211> LENGTH: 10
<212> TYPE: DNA
<213> ORGANISM: Unknown
```

```
<220> FEATURE:
<223> OTHER INFORMATION: Description of Unknown:
      BRN3 binding site sequence

<400> SEQUENCE: 120
atgaattaat                                                          10
```

TRIGLYCERIDE OTIC FORMULATIONS AND USES THEREOF

CROSS REFERENCE

This application claims the benefit of U.S. Provisional Application No. 62/356,300, filed Jun. 29, 2016, the content of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jun. 23, 2017, is named 37173-767.201_SL.txt and is 57,476 bytes in size.

BACKGROUND OF THE DISCLOSURE

Described herein are triglyceride derived otic formulations for drug delivery into the outer, middle and/or inner ear, including the cochlea and vestibular labyrinth.

SUMMARY OF THE DISCLOSURE

Provided in one aspect is an otic pharmaceutical formulation comprising:

a) a therapeutic agent, or pharmaceutically acceptable prodrug or salt thereof; and b) triglycerides comprising medium chain fatty acids; wherein the triglycerides are present in an amount that is sufficient to stabilize the therapeutic agent for injection into the ear, and wherein the otic pharmaceutical formulation comprises at least about 50% by weight of the triglycerides.

In some embodiments, the triglycerides are present in an amount that is sufficient to provide sufficient retention time in the ear. In some embodiments, the triglycerides are present in an amount that is sufficient to provide sustained release of the therapeutic agent. In some embodiments, the triglycerides are present in an amount that is sufficient to allow delivery of the formulation via a narrow gauge needle. In some embodiments, the triglycerides are derived from glycerol and medium chain fatty acids. In some embodiments, the medium chain fatty acids are caproic acid (hexanoic acid), enanthic acid (heptanoic acid), caprylic acid (octanoic acid), pelargonic acid (nonanoic acid), capric acid (decanoic acid), undecylenic acid (undec-10-enoic acid), lauric acid (dodecanoic acid), or a combination thereof. In some embodiments, the otic pharmaceutical formulation comprises between about 50% to about 99.99% by weight of the triglycerides.

In some embodiments, the otic pharmaceutical formulation further comprises at least one viscosity modulating agent. In some embodiments, the at least one viscosity modulating agent is silicon dioxide, povidone, carbomer, poloxamer, or a combination thereof. In some embodiments, the viscosity modulating agent is silicon dioxide. In some embodiments, the viscosity modulating agents are silicon dioxide and povidone. In some embodiments, the otic pharmaceutical formulation comprises between about 0.01% to about 20% by weight of the povidone. In some embodiments, the viscosity modulating agents are silicon dioxide and carbomer. In some embodiments, the otic pharmaceutical formulation comprises between about 0.01% to about 20% by weight of the carbomer. In some embodiments, the viscosity modulating agents are silicon dioxide and poloxamer. In some embodiments, the otic pharmaceutical formulation comprises between about 0.01% to about 20% by weight of the poloxamer. In some embodiments, the otic pharmaceutical formulation comprises between about 0.01% to about 10% by weight of the silicon dioxide.

In some embodiments, the otic pharmaceutical formulation has a viscosity between about 10 cP to about 10,000 cP. In some embodiments, the therapeutic agent is an immunomodulating agent, an aural pressure modulating agent, a corticosteroid, an antimicrobial agent, an otic neurotrophic factor, an antagonist of truncated TrkC or truncated TrkB, a non-natural TrkB or Trk C agonist, or a WNT modulator. In some embodiments, the therapeutic agent is dexamethasone, ciprofloxacin, gacyclidine, or the pharmaceutically acceptable salt thereof. In some embodiments, the otic neurotrophic factor is selected from brain-derived neurotrophic factor (BDNF), ciliary neurotrophic factor (CNTF), glial cell-line derived neurotrophic factor (GDNF), neurotrophin-3, neurotrophin-4, fibroblast growth factor (FGF), insulin-like growth factor (IGF), epidermal growth factor (EGF), platlet-derived growth factor (PGF), and combination thereof. In some embodiments, the otic neurotrophic factor is selected from brain-derived neurotrophic factor (BDNF), neurotrophin-3, and combination thereof.

In some embodiments, the otic pharmaceutical formulation comprises between about 0.01% to about 20% by weight of the therapeutic agent, or pharmaceutically acceptable prodrug or salt thereof. In some embodiments, the retention time of the formulation in the ear is at least 1 day. In some embodiments, the therapeutic agent is released from the formulation for a period of at least 1 day. In some embodiments, the otic pharmaceutical formulation is free or substantially free of water, C1-C6 alcohols or C1-C6 glycols, C1-C4 alcohols or C1-C4 glycols, or any combination thereof. In some embodiments, the otic pharmaceutical formulation further comprises a drug delivery device selected from a needle and syringe, a pump, a microinjection device, a wick, a spongy material and combinations thereof. In some embodiments, the otic formaceutical formulation is for use in the treatment of an otic disease or condition associated with the outer, middle, and/or inner ear. In some embodiments, the otic disease or condition is ceruminosis or ceruminosis associated with an otic disease or condition, ear pruritus, otitis externa, otalgia, tinnitus, vertigo, ear fullness, hearing loss, Meniere's disease, sensorineural hearing loss, noise induced hearing loss, age related hearing loss (presbycusis), auto immune ear disease, tinnitus, ototoxicity, excitotoxicity, endolymphatic hydrops, labyrinthitis, Ramsay Hunt's Syndrome, vestibular neuronitis, or microvascular compression syndrome, hyperacusis, presbystasis, central auditory processing disorder, auditory neuropathy, improvement of cochlea implant performance, or a combination thereof.

Also provided herein is method of treating an otic disease or condition in a subject in need thereof, the method comprising administering to the subject any one of the otic pharmaceutical formulations disclosed herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 2A is adapted from Esteban et al. *J Cell Biol* 2006; 173:291-299. FIG. 2B is adapted from Luberg et al. J. Neurochem. 2010; 113:952-964.

DETAILED DESCRIPTION

Figure 1:
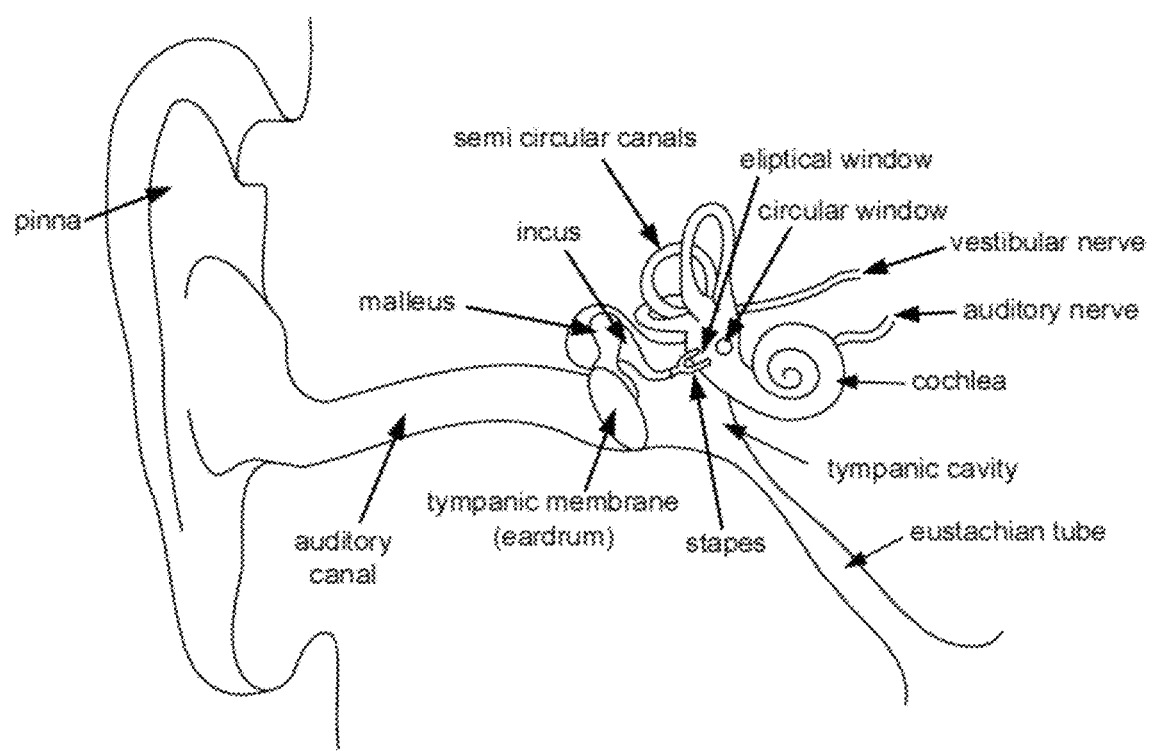
FIG. 1 illustrates the anatomy of the ear.

Systemic administration of active agents is, in some instances, ineffectual in the treatment of diseases that affect inner ear structures. The cochlear canals and the cochlea, for example, are isolated from the circulatory system limiting systemic delivery of active agents to target sites in the inner ear. In some instances, systemic drug administration creates a potential inequality in drug concentration with higher circulating levels in the serum, and lower levels in the target auris interna organ structures. In certain instances, large amounts of drug are required to overcome this inequality in order to deliver sufficient, therapeutically effective quantities of a drug to auditory structures. In some instances, systemic drug administration also increases the likelihood of secondary systemic accumulation and consequent adverse side effects.

Currently available treatment for inner ear diseases also carries the risk of attendant side effects. For example, available methods require multiple daily doses (e.g., intratympanic injection or infusion) of drugs. In certain instances, multiple daily intratympanic injections cause patient discomfort and non-compliance. In certain instances, delivery of active agents to the inner ear via otic drops administered in the ear canal or via intratympanic injection is hindered by the biological barrier presented by the blood-labyrinth-barrier (BLB), the oval window membrane and/or the round window membrane. In some instances, delivery of active agents to the inner ear via otic drops or intratympanic injection causes osmotic imbalance in inner ear structures, introduces infections or other immune disorders as a result of microbial or endotoxin presence, or results in permanent structural damage (e.g. perforation of the tympanic membrane), resulting in hearing loss and the like.

Intratympanic injection of therapeutic agents is the technique of injecting a therapeutic agent behind the tympanic membrane into the auris media and/or auris interna. Some challenges remain with intratympanic injections. For example, access to the round window membrane, the site of drug absorption into the auris interna, is challenging in some instances. In addition, current regimens using intratympanic injections do not address changing the osmolarity and pH of the perilymph and endolymph, and introducing pathogens and endotoxins that directly or indirectly damage inner ear.

Provided herein are otic formulations and compositions that are triglyceride based otic pharmaceutical formulations. Such triglycerides include medium chain triglycerides (MCT). These otic formulations and compositions comprise a therapeutic agent, or a pharmaceutically acceptable prodrug or salt thereof; and triglycerides comprising medium chain fatty acids. In some embodiments, the triglycerides are derived from glycerol and medium chain fatty acids.

In some embodiments, the otic triglyceride based pharmaceutical formulations have triglycerides in an amount that is sufficient to stabilize the therapeutic agent for injection into the ear. In some embodiments, the injection is into the outer ear. In some embodiments, the injection is into the middle ear. In some embodiments, the injection is intratympanic. In some embodiments, the injection is into the inner ear. In some embodiments, the otic triglyceride based pharmaceutical formulations have triglycerides in an amount that is sufficient to provide sufficient retention time in the ear. In some embodiments, the sufficient retention time in the ear is for the middle ear. In some embodiments, the sufficient retention time in the ear is for the inner ear. In some embodiments, the sufficient retention time in the ear is for the outer ear. In some embodiments, the outer ear is the external auditory canal, the outer surface of the tympanic membrane, or a combination thereof. In some embodiments, the outer ear is the external auditory canal. In some embodiments, the otic triglyceride based pharmaceutical formulations have triglycerides in an amount that is sufficient to provide sustained release of the therapeutic agent. In some embodiments, the sustained release of the therapeutic agent is in the outer ear. In some embodiments, the sustained release of the therapeutic agent is in the middle ear. In some embodiments, the sustained release of the therapeutic agent is in the inner ear. In some embodiments, the triglycerides are present in an amount that is sufficient to allow delivery of the formulation via a narrow gauge needle.

These otic triglyercide based pharmaceutical formulations are suitable for drug delivery into the external, middle and/or inner ear. In some instances, these otic pharmaceutical formulations and compositions are suitable for administration to humans. In some instances, the otic formulations and compositions disclosed herein also meet stringent criteria for pH, osmolarity, ionic balance, sterility, endotoxin and/or pyrogen levels. In some instances, the otic formulations and compositions are compatible with the microenvironment of the inner ear (e.g., the perilymph).

Accordingly, provided herein, in certain embodiments, are otic formulations and compositions that are controlled release auris-acceptable formulations and compositions that locally treat auris target structures and provide extended exposure of otic active agents to the target auris structures. In certain embodiments, the otic formulations and compositions described herein are designed for stringent osmolarity and pH ranges that are compatible with auditory structures and/or the endolymph and perilymph. In some embodiments, the otic formulations and compositions described herein are controlled release formulations that provide extended release for a period of at least 3 days and meet stringent sterility requirements. In some instances, otic formulations and compositions described herein contain lower endotoxin levels (e.g. <0.5 EU/mL when compared to typically acceptable endotoxin levels of 0.5 EU/mL. In some instances, the otic formulations and compositions described herein contain low levels of colony forming units (e.g., <50 CFUs) per gram of the formulation or composition. In some instances, the otic formulations or compositions described herein are substantially free of pyrogens and/or microbes. In some instances the otic formulations or compositions described herein are formulated to preserve the ionic balance of the endolymph and/or the perilymph.

In some instances, local administration of the otic formulations and compositions described herein avoids potential adverse side effects as a result of systemic administration of active agents. In some instances, the locally applied otic formulations and compositions described herein are compatible with auris structures. Such compatible auris structures include those associated with the outer, middle, and/or inner ear. In some embodiments, the otic formulations and compositions are administered either directly to the desired auris structure, e.g. the cochlear region, or administered to a structure in direct communication with areas of the auris structure; in the case of the cochlear region, for example, including but not limited to the round window membrane, the crista fenestrae cochleae or the oval window membrane.

In certain instances, the otic formulations and compositions disclosed herein controlled release formulations or compositions that provide a constant rate of release of a drug from the formulation and provide a constant prolonged source of exposure of an otic active agent to the inner ear of an individual or patient suffering from an otic disorder, reducing or eliminating any variabilities associated with other methods of treatment (such as, e.g., otic drops and/or multiple intratympanic injections).

In some embodiments, the otic formulations and compositions described herein provide extended release of the active ingredient(s) into the external ear. In some embodiments, the otic formulations and compositions described herein provide extended release of the active ingredient(s) into the middle and/or inner ear (auris interna), including the cochlea and vestibular labyrinth. In some embodiments, the otic formulations and compositions further comprise an immediate or rapid release component in combination with a controlled release component.

Certain Definitions

The term "auris-acceptable" with respect to a formulation, composition or ingredient, as used herein, includes having no persistent detrimental effect on the auris externa (or external ear or outer ear), auris media (or middle ear) and/or the auris interna (or inner ear) of the subject being treated. By "auris-pharmaceutically acceptable," as used herein, refers to a material, such as a carrier or diluent, which does not abrogate the biological activity or properties of the compound in reference to the auris externa (or external ear or outer ear), auris media (or middle ear) and/or the auris interna (or inner ear), and is relatively or is reduced in toxicity to the auris externa (or external ear or outer ear), auris media (or middle ear) and the auris interna (or inner ear), i.e., the material is administered to an individual without causing undesirable biological effects or interacting in a deleterious manner with any of the components of the composition in which it is contained.

As used herein, amelioration or lessening of the symptoms of a particular otic disease, disorder or condition by administration of a particular compound or pharmaceutical composition refers to any decrease of severity, delay in onset, slowing of progression, or shortening of duration, whether permanent or temporary, lasting or transient that is attributed to or associated with administration of the compound or composition.

As used herein, the terms "immunomodulating agent" or "immunomodulator" or "immunomodulator agent" or "immune-modulating agent" are used as synonyms.

The term "anti-TNF agent" or "anti tumor necrosis factor agent" or "TNF modulator" or "TNF modulating agent" or "TNF-alpha modulator" or "anti-TNF alpha agent" are used as synonyms. The term "anti-TNF agent" and its synonyms generally refer to agents that counteract the biological effect of TNF-α or the biological effect of pro-TNF-α stimulus including agents which bind to and antagonize the molecular target; here, tumor necrosis factor alpha or TNF-alpha (TNF-α), agents which inhibit release of TNF-α, or agents which interfere with TNF-α gene expression due to pro-TNF-α stimulus. Also included are agents that indirectly antagonize the biological activity of TNF-α by modulating targets in the general pathway of TNF-α activation, including but not limited to targets upstream of the pathway of TNF-alpha activation, including but not limited to agents which increase TNF-alpha expression, activity or function.

As used herein, the terms "aural pressure modulating agent" or "aural pressure modulator" are used as synonyms and do not define the degree of efficacy. The aural pressure modulator also includes compounds that modulate the expression or post-transcriptional processing of a fluid homeostasis protein, including vasopressin and estrogen-related receptor beta protein. Additionally, vasopressin receptor or estrogen-related receptor beta modulators include compounds that influence vasopressin receptor or estrogen-related receptor beta signaling or downstream functions under the control of the vasopressin receptor or estrogen-related receptor beta, such as aquaporin function. Vasopressin receptor or estrogen-related receptor beta modulating agents includes compounds that increase and/or decrease vasopressin receptor or estrogen-related receptor beta function, including antagonists, inhibitors, agonists, partial agonists and the like.

"Modulator of neuron and/or hair cells of the auris" and "auris sensory cell modulating agent" are synonyms. They include agents that promote the growth and/or regeneration of neurons and/or the hair cells of the auris.

As used herein, the term "antimicrobial agent" refers to compounds that inhibit the growth, proliferation, or multiplication of microbes, or that kill microbes. Suitable "antimicrobial agents" are antibacterial agents (effective against bacteria), antiviral agents (effective against viruses), antifungal agents (effective against fungi), antiprotozoal (effective against protozoa), and/or antiparasitic to any class of microbial parasites. "Antimicrobial agents" work by any suitable mechanism against the microbes, including by being toxic or cytostatic.

The phrase "antimicrobial small molecule" refers to antimicrobial compounds that are of relatively low molecular weight, e.g., less than 1,000 molecular weight, that are effective for the treatment of otic disorders, particularly otic disorders caused by pathogenic microbes, and are suitable for use in the formulations disclosed herein. Suitable "antimicrobial small molecules" include antibacterial, antiviral, antifungal, antiprotozoal, and antiparasitic small molecules.

"Modulator of free-radicals" and "free-radical modulating agent" are synonyms. They refer to agents that modulate the production of and/or damage caused by free radicals, especially reactive oxygen species.

As used herein, the terms "ion channel modulating agent", "modulator of ion channels" or "ion channel modulator" are used as synonyms and do not define the degree of efficacy. The ion channel modulator also includes compounds that modulate the expression or post-transcriptional processing of a fluid homeostasis protein, including vasopressin and estrogen-related receptor beta protein. Additionally, vasopressin receptor or estrogen-related receptor beta modulators include compounds that influence vasopressin receptor or estrogen-related receptor beta signaling or downstream functions under the control of the vasopressin receptor or estrogen-related receptor beta, such as aquaporin function. Vasopressin receptor or estrogen-related receptor beta modulating agents includes compounds that increase and/or decrease vasopressin receptor or estrogen-related receptor beta function, including antagonists, inhibitors, agonists, partial agonists and the like.

As used herein, the term "otic agent" or "otic structure modulating agent" or "otic therapeutic agent" or "otic active agent" or "active agent" or "therapeutic agent" refers to compounds that are effective for the treatment of otic disorders, e.g., otitis media, otosclerosis, autoimmune diseases of the ear and cancer of the ear, and are suitable for use in the formulations disclosed herein. An "otic agent" or "otic structure modulating agent" or "otic therapeutic agent" or "otic active agent" or "active agent" includes, but is not limited to, compounds that act as an agonist, a partial agonist, an antagonist, a partial antagonist, an inverse agonist, a competitive antagonist, a neutral antagonist, an orthosteric antagonist, an allosteric antagonist, a positive allosteric modulator of an otic structure modulating target, a negative allosteric modulator of an otic structure modulating target or combinations thereof.

"Balance disorder" refers to a disorder, illness, or condition which causes a subject to feel unsteady, or to have a sensation of movement. Included in this definition are dizziness, vertigo, disequilibrium, and pre-syncope. Diseases which are classified as balance disorders include, but are not limited to, Ramsay Hunt's Syndrome, Meniere's Disease, mal de debarquement, benign paroxysmal positional vertigo, labyrinthitis, and presbycusis.

"CNS modulator" and "CNS modulating agent" are synonyms. They refer to agents that decrease, diminish, partially suppress, fully suppress, ameliorate, antagonize, agonize, stimulate or increase the activity of the CNS. For example, in some instances, they increase the activity of GABA by, for example, increasing the sensitivity of the GABA receptors, or they alter the depolarization in neurons.

"Local anesthetic" means a substance which causes a reversible loss of sensation and/or a loss of nociception. Often, these substances function by decreasing the rate of the depolarization and repolarization of excitable membranes (for example, neurons). By way of non-limiting example, local anesthetics include lidocaine, benzocaine, prilocaine, and tetracaine.

"Modulator of the $GABA_A$ receptor," "modulator of the $GABA$ receptor," "$GABA_A$ receptor modulator," and "GABA receptor modulator," are synonyms. They refer to substances which modulate the activity of the GABA neurotransmitter, by, for example, increasing the sensitivity of the GABA receptor to GABA.

As used herein, the term "cytotoxic agent" refers to compounds that are cytotoxic (i.e., toxic to a cell) effective for the treatment of otic disorders, e.g., autoimmune diseases of the ear and cancer of the ear, and are suitable for use in the formulations disclosed herein.

The phrase "cytotoxic small molecule" refers to cytotoxic compounds that are of relatively low molecular weight, e.g., less than 1,000, or less than 600-700, or between 300-700 molecular weight, that are effective for the treatment of otic disorders, e.g., autoimmune diseases of the ear and cancer of the ear, and are suitable for use in the formulations disclosed herein. Suitable "cytotoxic small molecules" include methotrexate, cyclophosphamide, and thalidomide, as well as metabolites, salts, polymorphs, prodrugs, analogues, and derivatives of methotrexate, cyclophosphamide, and thalidomide. In certain embodiments, preferred cytotoxic small molecules are the pharmaceutically active metabolites of cytotoxic agents. For example, in the case of cyclophosphamide, preferred metabolites are pharmaceutically active metabolites of cyclophosphamide, including but not limited to 4-hydroxycyclophosphamide, aldophosphamide, phosphoramide mustard, and combinations thereof.

"Antioxidants" are auris-pharmaceutically acceptable antioxidants, and include, for example, butylated hydroxytoluene (BHT), sodium ascorbate, ascorbic acid, sodium metabisulfite and tocopherol. In certain embodiments, antioxidants enhance chemical stability where required. Antioxidants are also used to counteract the ototoxic effects of certain therapeutic agents, including agents that are used in combination with the otic agents disclosed herein.

"Auris externa" refers to the external (or outer) ear, and includes the pinna and the external auditory canal (EAC).

"Auris interna" refers to the inner ear, including the cochlea and the vestibular labyrinth, and the round window that connects the cochlea with the middle ear.

"Auris-interna bioavailability" or "Auris media bioavailability" refers to the percentage of the administered dose of compounds disclosed herein that becomes available in the inner or middle ear, respectively, of the animal or human being studied.

"Auris media" refers to the middle ear, including the tympanic cavity, auditory ossicles and oval window, which connects the middle ear with the inner ear.

"Blood plasma concentration" refers to the concentration of compounds provided herein in the plasma component of blood of a subject.

"Auris-interna bioavailability" refers to the percentage of the administered dose of compounds disclosed herein that becomes available in the inner ear of the animal or human being studied.

The term "auris-acceptable penetration enhancer" with respect to a formulation, composition or ingredient, as used herein, refers to the property of reducing barrier resistance.

"Carrier materials" are excipients that are compatible with the otic agent, the auris media, the auris interna and the release profile properties of the auris-acceptable pharmaceutical formulations. Such carrier materials include, e.g., binders, suspending agents, disintegration agents, filling agents, surfactants, solubilizers, stabilizers, lubricants, wetting agents, diluents, and the like. "Auris-pharmaceutically compatible carrier materials" include, but are not limited to, acacia, gelatin, colloidal silicon dioxide, calcium glycerophosphate, calcium lactate, maltodextrin, glycerine, magnesium silicate, polyvinylpyrrolidone (PVP), cholesterol, cholesterol esters, sodium caseinate, soy lecithin, taurocholic acid, phosphatidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like.

The term "diluent" are chemical compounds that are used to dilute the otic agent prior to delivery and which are compatible with the auris media and/or auris interna.

"Dispersing agents," and/or "viscosity modulating agents" and/or "thickening agents" are materials that control the diffusion and homogeneity of the otic agent through liquid media. Examples of diffusion facilitators/dispersing agents include but are not limited to hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, HPMC E10M, and HPMC K100M), carboxymethylcellulose, carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), non-crystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenolpolymer with ethylene oxide and formaldehyde (also known as tyloxapol), poloxamers (e.g., Pluronics F68®, F88®, F108®, and F127®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol has a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans, silicon dioxide, and combinations thereof. Plasticizers such as cellulose or triethyl cellulose are also be used as dispersing agents. optional dispersing agents useful in liposomal dispersions and self-emulsifying dispersions of the otic agents disclosed herein are dimyristoyl phosphatidyl choline, natural phosphatidyl choline from eggs, natural phosphatidyl glycerol from eggs, cholesterol and isopropyl myristate. In some embodiments, the "dispersing agent," and/or "viscosity modulating agent" and/or "thickening agent" is not a poloxamer.

"Drug absorption" or "absorption" refers to the process of movement of the otic agent from the localized site of administration, by way of example only, the round window membrane of the inner ear, and across a barrier (the round window membranes, as described below) into the auris interna or inner ear structures. The terms "co-administration" or the like, as used herein, are meant to encompass administration of the otic agent to a single patient, and are intended to include treatment regimens in which the otic agents are administered by the same or different route of administration or at the same or different time.

The terms "effective amount" or "therapeutically effective amount," as used herein, refer to a sufficient amount of the otic agent being administered that would be expected to relieve to some extent one or more of the symptoms of the disease or condition being treated. For example, the result of administration of the otic agents disclosed herein is reduction and/or alleviation of the signs, symptoms, or causes of any one of the diseases or conditions disclosed herein. For example, an "effective amount" for therapeutic uses is the amount of the otic agent, including a formulation as disclosed herein required to provide a decrease or amelioration in disease symptoms without undue adverse side effects. The term "therapeutically effective amount" includes, for example, a prophylactically effective amount. An "effective amount" of a otic agent composition disclosed herein is an amount effective to achieve a desired pharmacologic effect or therapeutic improvement without undue adverse side effects. It is understood that "an effective amount" or "a therapeutically effective amount" varies, in some embodiments, from subject to subject, due to variation in metabolism of the compound administered, age, weight, general condition of the subject, the condition being treated, the severity of the condition being treated, and the judgment of the prescribing physician. In some instances, it is also understood that "an effective amount" in an extended-release dosing format differs from "an effective amount" in an immediate-release dosing format based upon pharmacokinetic and pharmacodynamic considerations.

The terms "enhance" or "enhancing" refers to an increase or prolongation of either the potency or duration of a desired effect of the otic agent, or a diminution of any adverse symptomatology. For example, in reference to enhancing the effect of the otic agents disclosed herein, the term "enhancing" refers to the ability to increase or prolong, either in potency or duration, the effect of other therapeutic agents that are used in combination with the otic agents disclosed herein. An "enhancing-effective amount," as used herein, refers to an amount of an otic agent or other therapeutic agent that is adequate to enhance the effect of another therapeutic agent or otic agent in a desired system. When used in a patient, amounts effective for this use will depend on the severity and course of the disease, disorder or condition, previous therapy, the patient's health status and response to the drugs, and the judgment of the treating physician.

The term "penetration enhancer" refers to an agent that reduces barrier resistance (e.g., barrier resistance of the round window membrane, BLB or the like).

The term "inhibiting" includes preventing, slowing, or reversing the development of a condition, including any one of the conditions described herein, or advancement of a condition in a patient necessitating treatment.

The terms "kit" and "article of manufacture" are used as synonyms.

The term "modulate" includes the interaction with a target, for example, with the TNF-alpha agents disclosed herein, the activity of TNF-alpha, or other direct or indirect targets that alter the activity of TNF-alpha, including, by way of example only, to inhibit the activity of TNF-alpha, or to limit the activity of the TNF-alpha.

"Pharmacodynamics" refers to the factors which determine the biologic response observed relative to the concentration of drug at the desired site within the auris media and/or auris interna.

"Pharmacokinetics" refers to the factors which determine the attainment and maintenance of the appropriate concentration of drug at the desired site within the auris media and/or auris interna.

In prophylactic applications, compositions containing the otic agents described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like.

A "prodrug" refers to the otic agent that is converted into the parent drug in vivo. In certain embodiments, a prodrug is enzymatically metabolized by one or more steps or processes to the biologically, pharmaceutically or therapeuticform of the compound. To produce a prodrug, a pharmaceutically active compound is modified such that the active compound will be regenerated upon in vivo administration. In one embodiment, the prodrug is designed to alter the metabolic stability or the transport characteristics of a drug, to mask side effects or toxicity, or to alter other characteristics or properties of a drug. Compounds provided herein, in some embodiments, are derivatized into suitable prodrugs.

"Solubilizers" refers to auris-acceptable compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, Transcutol®, propylene glycol, and dimethyl isosorbide and the like.

"Stabilizers" refers to compounds such as any antioxidation agents, buffers, acids, preservatives and the like that are compatible with the environment of the auris media and/or auris interna. Stabilizers include but are not limited to agents that will do any of (1) improve the compatibility of excipients with a container, or a delivery system, including a syringe or a glass bottle, (2) improve the stability of a component of the composition, or (3) improve formulation stability.

"Steady state," as used herein, is when the amount of drug administered to the auris media and/or auris interna is equal to the amount of drug eliminated within one dosing interval resulting in a plateau or constant levels of drug exposure within the targeted structure.

As used herein, the term "subject" is used to mean an animal, preferably a mammal, including a human or non-human. The terms patient and subject are used interchangeably.

"Surfactants" refers to compounds that are auris-acceptable, such as sodium lauryl sulfate, sodium docusate, Tween 60 or 80, triacetin, vitamin E TPGS, phospholipids, lecithins, phosphatidyl cholines (c8-c18), phosphatidylethanolamines (c8-c18), phosphatidylglycerols (c8-c18), sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants are included to enhance physical stability or for other purposes.

The terms "treat," "treating" or "treatment," as used herein, include alleviating, abating or ameliorating a disease or condition or the associated symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or controlling or stopping the symptoms of the disease or condition either prophylactically and/or therapeutically.

In any of the aforementioned embodiments, the term "substantially low degradation products" means less than 5% by weight of the active agent are degradation products of the active agent. In further embodiments, the term means less than 3% by weight of the active agent are degradation products of the active agent. In yet further embodiments, the term means less than 2% by weight of the active agent are degradation products of the active agent. In further embodiments, the term means less than 1% by weight of the active agent are degradation products of the active agent.

The term "TrkB or TrkC agonist" include agents that recognize and bind to one or more epitopes on TrkB or TrkC receptor. In some embodiments, the TrkB or TrkC agonist is an antibody. The TrkB or TrkC agonists are agents that promote the growth and/or regeneration of neurons and their processes and connections and/or the hair cells of the auris. In some embodiments, a TrkB or TrkC agonist provides therapeutic benefit (e.g., alleviation of hearing loss) by promoting the growth and/or regeneration and/or phenotypic maintenance of auris sensory cells and their processes and connections (e.g., neurons and/or the hair cells) of the auris. In some embodiments, a TrkB or TrkC agonist provides therapeutic benefit (e.g., alleviation of tinnitus due to acoustic trauma) by treating and/or reversing damage to auris sensory cells (e.g., dysfunction of neurons and/or hair cells of the auris) or reducing or delaying further damage (e.g., cell death) to auris sensory cells (e.g., by exerting an otoprotectant effect or a trophic effect).

TrkB or TrkC agonists include "neurotrophic agent" which means a chemically modified analog of a naturally occurring neurotrophic agent (e.g., BDNF, NT3, NT 4/5, IGF), or a naturally occurring neurotrophic agent with one or more mutations in amino acid residues, that promotes the survival, growth and/or regeneration of auris sensory cells (e.g., neurons and/or the hair cells of the auris). In some embodiments, a neurotrophic agent reduces or inhibits oxidative damage and/or osteoneogenesis and/or degeneration of auris sensory cells. In some embodiments, a neurotrophic agent maintains healthy auris sensory cells (e.g., after a surgical implant of a medical device). In some embodiments, a neurotrophic agent is an immunosuppresant (e.g., an immunosuppresant used during otic surgery). In some embodiments, a neurotrophic agent is a growth factor (e.g., a growth factor used after an implantation procedure to promote growth of auris cells).

As used herein, the term "antibody" means an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Also included are single chain antibodies such as single-chain variable fragment (scFv), diabodies, minibodies, single-domain antibodies (sdAbs) or nanobodies, antibody chimeras, hybrid antibodies, bispecific antibodies, humanized antibodies, and the like), and recombinant peptides comprising the forgoing.

As used herein the term "monoclonal antibody" and "mAb" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method.

Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains.

As used herein, the term "variable" refers to the fact that certain portions of the variable domains differ extensively in sequence among antibodies. Variable regions confer antigen-binding specificity. However, the variability is not evenly distributed throughout the variable domains of antibodies. It is concentrated in three segments called complementarity determining regions (CDRs) or hypervariable regions, both in the light chain and the heavy-chain variable domains. The more highly conserved portions of variable domains are celled in the framework (FR) regions. The variable domains of native heavy and light chains each comprise four FR regions, largely adopting a 13-pleated-sheet configuration, connected by three CDRs, which form loops connecting, and in some cases forming part of, the f3-pleated-sheet structure. The CDRs in each chain are held together in close proximity by the FR regions and, with the CDRs from the other chain, contribute to the formation of the antigen-binding site of antibodies (see, Kabat et al. (1991) NIH PubL. No. 91-3242, Vol. I, pages 647-669). The constant domains are not involved directly in binding an antibody to an antigen, but exhibit various effector functions, such as Fc receptor (FcR) binding, participation of the antibody in antibody-dependent cellular toxicity, initiation of complement dependent cytotoxicity, and mast cell degranulation.

As used herein, the term "hypervariable region," when used herein, refers to the amino acid residues of an antibody that are responsible for antigen-binding. The hypervariable region comprises amino acid residues from a "complementarily determining region" or "CDR" (i.e., residues 24-34 (L1), 50-56 (L2), and 89-97 (L3) in the light-chain variable domain and 31-35 (H1), 50-65 (H2), and 95-102 (H3) in the heavy-chain variable domain; Kabat et al. (1991) Sequences of Proteins of Immunological Interest, 5th Ed. Public Health Service, National Institute of Health, Bethesda, Md.) and/or those residues from a "hypervariable loop" (i.e., residues 26-32 (L1), 50-52 (L2), and 91-96 (L3) in the light-chain variable domain and (H1), 53-55 (H2), and 96-101 (13) in the heavy chain variable domain; Clothia and Lesk, (1987) J. Mol. Biol., 196:901-917). "Framework" or "FR" residues are those variable domain residues other than the hypervariable region residues, as herein deemed.

"Antibody fragments" comprise a portion of an intact antibody. In some embodiments, the portion of an intact antibody is an antigen-binding or variable region of the intact antibody. Examples of antibody fragments include Fab, Fab, F(ab')2, and Fv fragments; diabodies; linear antibodies (Zapata et al. (1995) Protein Eng. 10:1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_{H1}$) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

The "light chains" of antibodies (immunoglobulins) from any vertebrate species assigned to one of two clearly distinct types, called kappa (x) and lambda (X), based on the amino acid sequences of their constant domains.

As used herein the term "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. Human antibodies can be produced using various techniques known in the art. In one embodiment, the human antibody is selected from a phage library, where that phage library expresses human antibodies. Human antibodies can also be made by introducing human immunoglobulin loci into transgenic animals, e.g., mice in which the endogenous immunoglobulin genes have been partially or completely inactivated. Alternatively, the human antibody may be prepared by immortalizing human B lymphocytes that produce an antibody directed against a target antigen (such B lymphocytes may be recovered from an individual or may have been immunized in vitro).

The term "veneered" versions of the antibodies provided herein may also be used in some embodiments. The process of veneering involves selectively replacing FR residues from, e.g., a murine heavy or light chain variable region, with human FR residues in order to provide an antibody that comprises an antigen binding portion which retains substantially all of the native FR protein folding structure. Veneering techniques are based on the understanding that the antigen binding characteristics of an antigen binding portion are determined primarily by the structure and relative disposition of the heavy and light chain CDR sets within the antigen-association surface. Thus, antigen association specificity can be preserved in a humanized antibody only wherein the CDR structures, their interaction with each other and their interaction with the rest of the variable region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface. It should be understood that veneered versions of the antibodies provided herein are encompassed by the present disclosure.

The term "antigen-binding portion" or "antigen-binding fragment" of an antibody (or simply "antibody portion" or "antibody fragment"), as used herein, refers to one or more fragments of an antibody that retain the ability to specifically bind to an antigen (e.g., juxtamembrane region domain of TrkC). It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment, which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules. Such single chain antibodies are also intended to be encompassed within the present disclosure. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites.

It should be understood that the antibodies described herein include fragments, portions, variants or derivatives thereof, such as single-chain antibodies or Fab fragments, that retain the same binding properties (e.g. specificity or affinity) of the full-length antibodies.

The term "otic intervention" means an external insult or trauma to one or more auris structures and includes implants, otic surgery, injections, cannulations, or the like. Implants include auris-interna or auris-media medical devices, examples of which include cochlear implants, hearing sparing devices, hearing-improvement devices, short electrodes, micro-prostheses or piston-like prostheses; needles; stem cell transplants; drug delivery devices; any cell-based therapeutic; or the like. Otic surgery includes middle ear surgery, inner ear surgery, tympanostomy, cochleostomy, labyrinthotomy, mastoidectomy, stapedectomy, stapedotomy, endolymphatic sacculotomy or the like. Injections include intratympanic injections, intracochlear injections, injections across the round window membrane or the like. Cannulations include intratympanic, intracochlear, endolymphatic, perilymphatic or vestibular cannulations or the like.

Pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamineand other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and inorganic salts, such as but not limited to, sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, mesylates, and fumarates. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, aralkyl and cycloalkyl. Pharmaceutically acceptable enol esters include, but are not limited to, derivatives of formula C=C(OC(O)R) where R is hydrogen, alkyl, alkenyl, alkynyl, aryl, aralkyl and cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. As such, one of skill in the art will recognize that administration of a compound in its (R) form is equivalent, for compounds that undergo epimerization in vivo, to administration of the compound in its (S) form.

The instant disclosure is meant to include all such possible isomers, as well as, their racemic and optically pure forms. Optically active (+) and (−), (R)- and (S)-, or (D)- and (L)-isomers are prepared in some instances using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, alkyl, alkenyl and alkynyl carbon chains, if not specified, contain from 1 to 20 carbons, 1 to 16 carbons or 1 to 6 carbons and are straight or branched. In certain embodiments, alkyl, alkenyl and alkynyl carbon chains contain from 1 to 6 carbons. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. The alkenyl carbon chains of 2 to 6 carbons, in certain embodiments, contain 1 to 2 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Alkynyl carbon chains of from 2 to 6 carbons, in certain embodiments, contain 1 to 2 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, vinyl, 1-propenyl, 2-propenyl, isopropenyl, 1-butenyl, 2-butenyl, 3-butenyl, 1,3-butadienyl, ethynyl, 1-propynyl and 2-propynyl. As used herein, lower alkyl, lower alkenyl, and lower alkynyl refer to carbon chains having from about 1 or about 2 carbons up to about 6 carbons.

The term "cycloalkyl" refers to a saturated mono- or multicyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion.

The term "aryl" refers to aromatic monocyclic or multicyclic groups containing from 6 to 19 carbon atoms. Aryl groups include, but are not limited to groups such as fluorenyl, substituted fluorenyl, phenyl, substituted phenyl, naphthyl and substituted naphthyl.

The term "aralkyl" refers to an alkyl group in which one of the hydrogen atoms of the alkyl is replaced by an aryl.

Other objects, features, and advantages of the methods and compositions described herein will become apparent from the following detailed description. It should be understood, however, that the detailed description and the specific examples, while indicating specific embodiments, are given by way of illustration only.

Anatomy of the Ear

The ear serves as both the sense organ that detects sound and the organ that maintains balance and body position. The ear is generally divided into three portions: the outer ear, middle ear and the inner ear (or auris interna). As shown in FIG. 1, the outer ear is the external portion of the organ and is composed of the pinna (auricle), the auditory canal (external auditory meatus) and the outward facing portion of the tympanic membrane, also known as the ear drum. The pinna, which is the fleshy part of the externa ear that is visible on the side of the head, collects sound waves and directs them toward the auditory canal. Thus, the function of the outer ear, in part, is to collect and direct sound waves towards the tympanic membrane and the middle ear.

The middle ear is an air-filled cavity, called the tympanic cavity, behind the tympanic membrane. The tympanic membrane, also known as the ear drum, is a thin membrane that separates the external ear from the middle ear. The middle ear lies within the temporal bone, and includes within this space the three ear bones (auditory ossicles): the malleus, the incus and the stapes. The auditory ossicles are linked together via tiny ligaments, which form a bridge across the space of the tympanic cavity. The malleus, which is attached to the tympanic membrane at one end, is linked to the incus at its anterior end, which in turn is linked to the stapes. The stapes is attached to the oval window, one of two windows located within the tympanic cavity. A fibrous tissue layer, known as the annular ligament connects the stapes to the oval window. Sound waves from the outer ear first cause the tympanic membrane to vibrate. The vibration is transmitted across to the cochlea through the auditory ossicles and oval window, which transfers the motion to the fluids in the auris interna. Thus, the auditory ossicles are arranged to provide a mechanical linkage between the tympanic membrane and the oval window of the fluid-filled auris interna, where sound is transformed and transduced to the auris interna for further processing. Stiffness, rigidity or loss of movement of the auditory ossicles, tympanic membrane or oval window leads to hearing loss, e.g. otosclerosis, or rigidity of the stapes bone.

The tympanic cavity also connects to the throat via the eustachian tube. The eustachian tube provides the ability to equalize the pressure between the outside air and the middle ear cavity. The round window, a component of the auris interna but which is also accessible within the tympanic cavity, opens into the cochlea of the auris interna. The round window is covered by a membrane, which consists of three layers: an external or mucous layer, an intermediate or fibrous layer, and an internal membrane, which communicates directly with the cochlear fluid. The round window, therefore, has direct communication with the auris interna via the internal membrane.

Movements in the oval and round window are interconnected, i.e. as the stapes bone transmits movement from the tympanic membrane to the oval window to move inward against the auris interna fluid, the round window is correspondingly pushed out and away from the cochlear fluid. This movement of the round window allows movement of fluid within the cochlea, which eventually leads in turn to movement of the cochlear inner hair cells, allowing hearing signals to be transduced. Stiffness and rigidity in the round window leads to hearing loss because of the lack of ability of movement in the cochlear fluid. Recent studies have focused on implanting mechanical transducers onto the round window, which bypasses the normal conductive pathway through the oval window and provides amplified input into the cochlear chamber.

Auditory signal transduction takes place in the auris interna. The fluid-filled inner ear, or auris interna, consists of two major components: the cochlear and the vestibular apparatus.

The cochlea is the portion of the auris interna related to hearing. The cochlea is a tapered tube-like structure which is coiled into a shape resembling a snail. The inside of the cochlea is divided into three regions, which is further defined by the position of the vestibular membrane and the basilar membrane. The portion above the vestibular membrane is the scala vestibuli, which extends from the oval window to the apex of the cochlea and contains perilymph fluid, an aqueous liquid low in potassium and high in sodium content. The basilar membrane defines the scala tympani region, which extends from the apex of the cochlea to the round window and also contains perilymph. The basilar membrane contains thousands of stiff fibers, which gradually increase in length from the round window to the apex of the cochlea. The fibers of the basement membrane vibrate when activated by sound. In between the scala vestibuli and the scala tympani is the cochlear duct, which ends as a closed sac at the apex of the cochlea. The cochlear duct contains endolymph fluid, which is similar to cerebrospinal fluid and is high in potassium.

The Organ of Corti, the sensory organ for hearing, is located on the basilar membrane and extends upward into the cochlear duct. The Organ of Corti contains hair cells, which have hairlike projections that extend from their free surface, and contacts a gelatinous surface called the tectorial membrane. Although hair cells have no axons, they are surrounded by sensory nerve fibers that form the cochlear branch of the vestibulocochlear nerve (cranial nerve VIII).

As discussed, the oval window, also known as the elliptical window communicates with the stapes to relay sound waves that vibrate from the tympanic membrane. Vibrations transferred to the oval window increases pressure inside the fluid-filled cochlea via the perilymph and scala vestibuli/ scala tympani, which in turn causes the membrane on the round window to expand in response. The concerted inward pressing of the oval window/outward expansion of the round window allows for the movement of fluid within the cochlea without a change of intra-cochlear pressure. However, as vibrations travel through the perilymph in the scala vestibuli, they create corresponding oscillations in the vestibular membrane. These corresponding oscillations travel through the endolymph of the cochlear duct, and transfer to the basilar membrane. When the basilar membrane oscillates, or moves up and down, the Organ of Corti moves along with it. The hair cell receptors in the Organ of Corti then move against the tectorial membrane, causing a mechanical deformation in the tectorial membrane. This mechanical deformation initiates the nerve impulse which travels via the vestibulocochlear nerve to the central nervous system, mechanically transmitting the sound wave received into signals that are subsequently processed by the central nervous system.

The auris interna is located in part within the osseous or bony labyrinth, an intricate series of passages in the temporal bone of the skull. The vestibular apparatus is the organ of balance and consists of the three semi-circular canals and the vestibule. The three semi-circular canals are arranged relative to each other such that movement of the head along the three orthogonal planes in space is detected by the movement of the fluid and subsequent signal processing by the sensory organs of the semi-circular canals, called the crista amupllaris. The crista ampullaris contains hair cells and supporting cells, and is covered by a dome-shaped gelatinous mass called the cupula. The hairs of the hair cells are embedded in the cupula. The semi-circular canals detect dynamic equilibrium, the equilibrium of rotational or angular movements.

When the head turns rapidly, the semicircular canals move with the head, but endolymph fluid located in the membranous semi-circular canals tends to remain stationary. The endolymph fluid pushes against the cupula, which tilts to one side. As the cupula tilts, it bends some of the hairs on the hair cells of the crista ampullaris, which triggers a sensory impulse. Because each semicircular canal is located in a different plane, the corresponding crista ampullaris of each semi-circular canal responds differently to the same movement of the head. This creates a mosaic of impulses that are transmitted to the central nervous system on the vestibular branch of the vestibulocochlear nerve. The central nervous system interprets this information and initiates the appropriate responses to maintain balance. Of importance in the central nervous system is the cerebellum, which mediates the sense of balance and equilibrium.

The vestibule is the central portion of the auris interna and contains mechanoreceptors bearing hair cells that ascertain static equilibrium, or the position of the head relative to gravity. Static equilibrium plays a role when the head is motionless or moving in a straight line. The membranous labyrinth in the vestibule is divided into two sac-like structures, the utricle and the saccule. Each structure in turn contains a small structure called a macula, which is responsible for maintenance of static equilibrium. The macula consists of sensory hair cells, which are embedded in a gelatinous mass (similar to the cupula) that covers the macula. Grains of calcium carbonate, called otoliths, are embedded on the surface of the gelatinous layer.

When the head is in an upright position, the hairs are straight along the macula. When the head tilts, the gelatinous mass and otoliths tilts correspondingly, bending some of the hairs on the hair cells of the macula. This bending action initiates a signal impulse to the central nervous system, which travels via the vestibular branch of the vestibulocochlear nerve, which in turn relays motor impulses to the appropriate muscles to maintain balance.

In some instances, the otic formulations described herein are placed in the outer ear. In some instances, the otic formulations described herein are placed in the middle or inner ear, including the cochlea and vestibular labyrinth: one option is to use a syringe/needle or pump and inject the formulation across the tympanic membrane (the eardrum). In some instances, for cochlear and vestibular labyrinth delivery, one option is to deliver the active ingredient across the round window membrane or even by microinjection directly into the auris interna also known as cochlear microperfusion.

Diseases or Conditions of the Ear

In some embodiments, the otic formulations and compositions described herein are suitable for the treatment and/or prevention of diseases or conditions associated with the outer, middle, and/or inner ear. In some embodiments, the otic formulations and compositions described herein are suitable for the treatment and/or prevention of diseases or conditions associated with the outer ear. In some embodiments, the otic formulations and compositions described herein are suitable for the treatment and/or prevention of diseases or conditions associated with the middle ear. In some embodiments, the otic formulations and compostions described herein are suitable for the treatment and/or prevention of diseases or conditions associated with the inner ear. In some embodiments, the otic formulations and compositions described herein reduce, reverse and/or ameliorate symptoms of otic diseases or conditions, such as any one of these disclosed herein. These disorders or conditions have many causes, which include but are not limited to, infection, injury, inflammation, tumors and adverse response to drugs or other chemical agents.

In some embodiments, the otic formulations and compositions described herein are used to modulate the production of cerumen. In some embodiments, the otic formulations and compositions described herein are used in the treatment of ceruminosis. In some embodiments, ceruminosis is associated with a disease or condition. In some embodiments, disease or condition is ear pruritus, otitis externa, otalgia, tinnitus, vertigo, ear fullness, hearing loss, or a combination thereof.

In some embodiments, the otic formulations and compositions described herein are used to for the treatment and/or prevention of Meniere's disease, sensorineural hearing loss, noise induced hearing loss, presbycusis (age related hearing loss), auto immune ear disease, tinnitus, ototoxicity, excitotoxicity, endolymphatic hydrops, labyrinthitis, Ramsay Hunt's Syndrome, vestibular neuronitis, microvascular compression syndrome, hyperacusis, presbystasis, central auditory processing disorder, or auditory neuropathy. In some embodiments, the otic formulations and compositions described herein are used for the improvement of cochlea implant performance. In some embodiments, the otic formulations and compositions are used for the treatment and/or prevention of Meniere's disease. In some embodiments, the otic formulations and compositions are used for the treatment and/or prevention of sensorineural hearing loss. In some embodiments, the otic formulations and compositions are used for the treatment and/or prevention of noise induced hearing loss. In some embodiments, the otic formulations and compositions are used for the treatment and/or prevention of presbycusis (age related hearing loss). In some embodiments, the otic formulations and compositions are used for the treatment and/or prevention of auto immune ear disease. In some embodiments, the otic formulations and compositions are used for the treatment and/or prevention of tinnitus. In some embodiments, the otic formulations and compositions are used for the treatment and/or prevention of ototoxicity. In some embodiments, the otic formulations and compositions are used for the treatment and/or prevention of excitotoxicity. In some embodiments, the otic formulations and compositions are used for the treatment and/or prevention of endolymphatic hydrops. In some embodiments, the otic formulations and compositions are used for the treatment and/or prevention of labyrinthitis. In some embodiments, the otic formulations and compositions are used for the treatment and/or prevention of Ramsay Hunt's Syndrome. In some embodiments, the otic formulations and compositions are used for the treatment and/or prevention of vestibular neuronitis. In some embodiments, the otic formulations and compositions are used for the treatment and/or prevention of microvascular compression syndrome. In some embodiments, the otic formulations and compositions are used for the treatment and/or prevention of hyperacusis. In some embodiments, the otic formulations and compositions are used for the treatment and/or prevention of presbystasis. In some embodiments, the otic formulations and compositions are used for the treatment and/or prevention of central auditory processing disorder. In some embodiments, the otic formulations and compositions are used for the treatment and/or prevention of auditory neuropathy. In some embodiments, the otic formulations and compositions are used for the improvement of cochlea implant performance.

Cerumen Production

Disclosed herein are otic formulations and compositions that modulate cerumen production. Cerumen, or earwax, is a waxy secretion found throughout the external ear canal (EAC). Generally, cerumen is stratified into two phenotypes, wet and dry. The wet phenotype has a honey-brown to dark-brown appearance and is characterized by a high concentration of lipid and pigment granules. In some embodiments, the wet cerumen contains about 50% lipid. It is predominantly found in the African and European population. The dry phenotype has a gray to white flaky appearance and is characterized by a low concentration of lipid and pigment granules. In some embodiments, the dry cerumen contains about 20% lipid. It is predominantly found in the Asian and Native American population. Further, these two types of cerumen are genetically distinct, in which a single genetic change in the ATP-binding cassette C11 (ABCC11) gene on chromosome 16 determines the type. Specifically, the allele for the wet phenotype contains a G at 538 of the coding region of ABCC11 whereas for the dry phenotype, an A at 538 is present.

Cerumen lubricates the sensitive ear canal lining from dryness and protects the ear from bacteria, fungi, insects, and foreign particles. Indeed, in several studies, the antimicrobial property of cerumen was demonstrated when the occurrences of ear infections were consistently correlated to absences of cerumen. In some embodiments, cerumen exerts an antimicrobial property against bacteria and fungi. Exemplary bacteria include, but are not limited to, *Haemophilus influenza, Staphylococcus aureus, Pseudomonas aeruginosa*, and *Escherichia coli*. Exemplary fungi include, but are not limited to, *Aspergillus niger*, and *Candida albicans*.

Cerumen is a mixture comprised of over 40 different substances. The primarily component of cerumen is keratin, which comprises about 60% by weight. Additional components include secretions from sebaceous and ceruminous glands, gradular secretions from hairs within the external ear canal (EAC), sloughed epithelial cells, saturated and unsaturated long-chain fatty acids, alcohols, squalene, lanosterol, and cholesterol. The EAC comprise of the pinna (auricle or the fleshy part of the external ear visible on the side of the head), the auditory canal (external auditory meatus) and the outward facing portion of the tympanic membrane, also known as the ear drum. Cerumen is found throughout the EAC.

Sebaceous glands and ceruminous glands (or modified apocrine glands) are two exocrine glands located in the EAC. Sebaceous glands are exocrine glands located in the skin. They secrete sebum, a viscous oily or waxy secretion, which is used to lubricate and waterproof the skin and hair. There are two types of sebaceous glands, those that connect to hair follicles and those that exist independently. When the sebaceous glands are connected to hair follicles, the deposited sebum is secreted onto the base of the hair and then transported onto the surface of the skin via the hair shaft.

Sebaceous glands are known to participate in innate immunity and participate in pro- and anti-inflammatory functions. Sebum, the product of sebaceous glands, has been shown to exert antimicrobial properties as well. Sebum comprises triglycerides, wax esters, squalene, cholesterol esters, cholesterol, and fatty acids such as sapienic acid. Sebum also contains free fatty acids (FFA) which has been shown to exhibit antibacterial activity against a broad range of Gram-positive bacteria in vitro. Further fatty acids such as monoenoic fatty acids (e.g. oleic and palmitoleic acids) have also been shown to exert antibacterial activities. Indeed, administration of palmitoleate was shown to decrease the size of bacterial lesions in wild-type C57BL/6 and mutant flake mice. In a separate study, oleic and palmitoleic acids were shown to be inhibitory against $S.$ $aureus$ and $S.$ $pyogenes$. In addition to fatty acids, sebaceous glands also release antimicrobial peptides (AMPs) such as human β-defensins (hBDs) including hBD-1, hBD-2, and hBD-3, and LL-37, a 37-amino acid long C-terminal portion of cathelicidin antimicrobial peptide 18 (hCAP-18), which further contribute to the antimicrobial properties in cerumen.

Ceruminous glands or modified apocrine sweat glands are specialized sudoriferous glands located subcutaneously in the external auditory canal. The ceruminous glands comprise an inner secretory layer of cells that form into coiled tubular shaped glands and an outer myoepithelial layer of cells. The glands drain into larger ducts which then drain into the guard hairs residing in the external auditory canal. Ceruminous gland secretes a comparatively less-viscous secretion than the sebum.

Abnormal cerumen occurs when there is an imbalance in the production and elimination mechanisms. A build-up of cerumen can lead to from discomfort to serious health complications.

Ceruminosis

Ceruminosis or cerumen impaction occurs when earwax becomes wedged in and blocks the EAC and/or impaction on the eardrum. Ceruminosis occurs in about one in 10 children, one in 20 adults, and more than one-third of the geriatric and developmentally delayed populations. About 12 million people seek medical care annually in the United States. In some embodiments, impaction of cerumen is a complete obstruction of the EAC. In some embodiments, impaction of cerumen is a partial obstruction of the EAC.

The occurrences of ceruminosis can be attributed to a build-up of cerumen in the EAC, normal extrusion such as hearing aides leading to compounded cerumen, or by the use of cotton buds or other ear cleaning devices which compounds cerumen. Disease or conditions associated with ceruminosis include ear pruritus, otalgia, tinnitus, vertigo, ear fullness, and hearing loss.

Treatments for ceruminosis include irrigation, manual removal other than irrigation, cerumenolytic agents for softening cerumen, or a combination thereof. Irrigation includes the use of water or saline solution by ear syringing. Manual removal other than irrigation involves the use of curette, probe, hook, forceps, or suction. Cerumenolytic agents include water-based, oil-based, and non-water-, non-oil based agents. For example, water-based cerumenolytic agents include acetic acid, CERUMENEX® (triethanolamine polypeptide oleate condensate), COLACE® (docusate sodium), MOLCER® (docusate sodium), WAX-SOL1® (docusate sodium, mixed parabens in 2-phenoxyethanol), XERUMENEX® (triethanolamine polypeptide oleate-condensate, propylene glycol, and chlorbutol), hydrogen peroxide, sodium bicarbonate, and sterile saline solution. Oil-based cerumenolytic agents include almond oil, arachis oil, olive oil, a mineral oil/liquid petrolatum combination, CLEANEARS® (a composition of mineral oil, squalene and spiramint oil), CERUMOL® (a compositon of arachis oil, turpentine oil, chlorbutol, and paradichlorobenzene), CIOCTYL-MEDO® (dioctyl sodium sulphosuccinate, maize oil), and EAREX® (archis oil, almond oil, and rectified camphor oil). Non-water-, non-oil-based cerumenolytic agents include AUDAX® (choline salicylate, glycerine), DEBROX® (carbamide peroxide), AURO® (a composition of carbamide peroxide and anhydrous glycerin) and EXTEROL® (carbamide peroxide and anhydrous glycerol).

Sometimes, treatments of ceruminosis result in significant complications. For example, complications such as tympanic membrane perforation, ear canal laceration, infection of the ear, or hearing loss occur at a rate of about one in 1000 ear irrigations. Additional complications include otitis externa, pain, dizziness and syncope or fainting. The present disclosure recognizes the need for otic compositions and treatment methods that reduces or ameliorates the complications associated with cerumen removal.

Ceruminosis Associated Diseases or Conditions

Diseases or conditions associated with ceruminosis include ear pruritus, otitis externa, otalgia, tinnitus, vertigo, ear fullness, and hearing loss. In some embodiments, the otic formulations and compositions disclosed herein modulate the production of cerumen and thereby alleviate the diseases or conditions associated with ceruminosis.

Ear Pruritus

Ear pruritus, or itchy ear canal, is a tickling or irritating sensation that causes a desire or reflex to scratch the affected area. In some cases, redness, swelling, soreness and flaking may develop in the affected area. Ear pruritus is caused by a variety of agents. In some embodiments, ear pruritus occurs due to either primary microbial infection within the ear or as a secondary infection from the body where it is then spread into the ear canal. In some embodiments, skin conditions such as eczema or psoriasis lead to skin irritations within the ear canal. Further, external irritants such as hairspray, shampoo, shower gel, or allergen such as dust, pets, and pollen, can lead to ear pruritus. In some embodiments, ear pruritus serves as an early sign for more serious complications such as otitis externa.

Otalgia

Otalgia, also known as earache or ear pain, is classified into two types, primary otalgia and referred otalgia. Primary otalgia is ear pain which originates from inside of the ear. Referred otalgia is ear pain which originates from the outside of the ear. Although the etiology of referred otalgia can be complex, several well-known culprits include dental disorders, sinusitis, neck problems, tonsillitis, pharyngitis, and sensory branches from the vagus and glossopharyngeal nerves. In some cases, referred otalgia has been associated with head and neck malignancies.

Ear Fullness

Ear fullness or aural fullness is described as a feeling that the ears are clogged, stuffed, or congested. Similar to otalgia, the etiology of ear fullness is diverse with numerous underlying causes. Generally, ear fullness may also be accompanied by tinnitus, otalgia, and impaired hearing.

Hearing Loss

Hearing loss is a partial or total impairment to hearing. Hearing loss is classified into three types, conductive hearing loss, sensorineural hearing loss, and mixed hearing loss. Conductive hearing loss occurs when sound is not conducted efficiently through the external auditory canal to the tympanic membrane or eardrum. In some embodiments, conductive hearing loss involves a reduction in sound level or the ability to hear faint sounds. Treatment involves corrective medical or surgical procedures. Sensorineural hearing loss occurs when there is damage to the cochlea (inner ear), or to the nerve pathways from the cochlea to the brain. This type of hearing loss generally leads to permanent hearing loss. Mixed hearing loss is a combination of conductive hearing loss and sensorineural hearing loss in which damage occurs along both the outer and inner ear regions.

The degree or severity of hearing loss is categorized into seven groups ranging from normal, slight, mild, moderate, moderately severe, severe to pround. In addition, hearing loss is stratified based on frequency in some instances. For example, a hearing loss that only affects the high tones is referred to as a high frequency hearing loss, whereas that which affects the low tones is referred to as a low frequency hearing loss. In some cases, hearing loss affects both high and low frequencies.

Hearing loss is often accompanied by additional causes and symptoms such as ceruminosis, otitis externa, otalgia, tinnitus and vertigo. In some embodiments, it has been shown that ceruminosis can decrease hearing acuity by 40-45 dB. Such impairment, especially in the geriatic population can cause difficulties in communication and even physical immobility.

Vertigo

Vertigo is described as a feeling of spinning or swaying while the body is stationary. There are two types of vertigo. Subjective vertigo is the false sensation of movement of the body. Objective vertigo is the perception that one's surrounding are in motion. It is often accompanied by nausea, vomiting, and difficulty maintaining balance. In some embodiments, otitis externa can induce vertigo.

Meniere's Disease

Meniere's Disease is an idiopathic condition characterized by sudden attacks of vertigo, nausea and vomiting that lasts for 3 to 24 hours, and subside gradually. Progressive hearing loss, tinnitus and a sensation of pressure in the ears accompanies the disease through time. The cause of Meniere's disease is likely related to an imbalance of auris interna fluid homeostasis, including an increase in production or a decrease in resorption of auris interna fluid.

The cause of symptoms associated with Meniere's disease is likely an imbalance of inner ear fluid homeostasis, including an increase in production or a decrease in reabsorption of inner ear fluid.

Although the cause of Meniere's disease is unknown, certain evidence suggests a viral etiology for the disease. Accordingly, in some embodiments, the otic formulations described herein comprise antiviral agents, e.g., ganciclvir, acyclovir, famovir, and valgancyclovir, and are administered to the ear for localized treatment of Meniere's disease.

Recent studies of the vasopressin (VP)-mediated aquaporin 2 (AQP2) system in the auris interna suggest a role for VP in inducing endolymph production, thereby increasing pressure in the vestibular and cochlear structures). VP levels were found to be upregulated in endolymphatic hydrops (Meniere's Disease) cases, and chronic administration of VP in guinea pigs was found to induce endolymphatic hydrops. Treatment with VP antagonists, including infusion of OPC-31260 (a competitive antagonist of $V_2$-R) into the scala tympani resulted in a marked reduction of Meniere's disease symptoms. Other VP antagonists include WAY-140288, CL-385004, tolvaptan, conivaptan, SR 121463A and VPA 985. (Sanghi et al. *Eur. Heart J.* (2005) 26:538-543; Palm et al. *Nephrol. Dial Transplant* (1999) 14:2559-2562).

Other studies suggest a role for estrogen-related receptor 3/NR3B2 (ERR/Nr3b2) in regulating endolymph production, and therefore pressure in the vestibular/cochlear apparatus. Knock-out studies in mice demonstrate the role of the protein product of the Nr3b2 gene in regulating endolymph fluid production. Nr3b2 expression has been localized in the endolymph-secreting strial marginal cells and vestibular dark cells of the cochlea and vestibular apparatus, respectively. Moreover, conditional knockout of the Nr3b2 gene results in deafness and diminished endolymphatic fluid volume. In some instances, treatment with antagonists to ERR/Nr3b2 assist in reducing endolymphatic volume, and thus alter pressure in the auris interna structures.

Other treatments are aimed at dealing with the immediate symptoms and prevention of recurrence. Low-sodium diets, avoidance of caffeine, alcohol, and tobacco have been advocated. Medications that temporarily relieve vertigo attacks include antihistamines (including meclizine (Antivert, Bonine, Dramamine, Driminate) and other antihistamines), and central nervous system agents, including barbiturates and/or benzodiazepines, including lorazepam or diazepam. Other examples of drugs that are useful in relieving symptoms include muscarinic antagonists, including scopolamine. Nausea and vomiting are relieved by suppositories containing antipsychotic agents, including the phenothiazine agent prochlorperazine (Compazine, Buccastem, Stemetil and Phenotil).

Surgical procedures have also been used to relieve symptoms of Meniere's disease, including destruction of vestibular function to relieve vertigo symptoms. These procedures aim to either reduce fluid pressure in the inner ear and/or to destroy inner ear balance function. An endolymphatic shunt procedure, which relieves fluid pressure, are placed in the inner ear to relieve symptoms of vestibular dysfunction. Severing of the vestibular nerve is also employed, which controls vertigo while preserving hearing.

Another approach to destruction of vestibular function for the treatment of severe Meniere's disease is intratympanic application of an agent that destroys sensory hair cell function in the vestibular system, thereby eradicating inner ear balance function. Various antimicrobial agents are used in the procedure, including aminoglycosides such as gentamicin and streptomycin. The agents are injected through the tympanic membrane using a small needle, a tympanostomy tube with or without a wick, or surgical catheters. Various dosing regimens are used to administer the antimicrobial agents, including a low dose method in which less of the agents are administered over longer periods of time (e.g., one month between injections), and high dose methods in which more of the agents are administered over a shorter time frame (e.g., every week). Although the high dose method is typically more effective, it is more risky, as it results in hearing loss in some cases.

In some instances, the otic formulations disclosed herein are also useful for administration of antimicrobial agents, e.g., gentamicin and streptomycin, for disabling the vestibular apparatus to treat Meniere's disease. In some embodiments, the formulations disclosed herein are used to maintain a steady release of the active agents inside the tympanic membrane, thereby avoiding the need for multiple injections or the insertion of a tympanostomy tube. Further, by keeping the active agents localized in the vestibular system, the otic formulations disclosed herein are used to administer higher doses of the antimicrobial agents with a decreased risk of hearing loss in some embodiments.

Meniere's Syndrome

Meniere's Syndrome, which displays similar symptoms as Meniere's disease, is attributed as a secondary affliction to another disease process, e.g. thyroid disease or auris interna inflammation due to syphilis infection. Meniere's syndrome, thus, are secondary effects to various process that interfere with normal production or resportption of endolymph, including endocrine abnormalities, electrolyte imbalance, autoimmune dysfunction, medications, infections (e.g. parasitic infections) or hyperlipidemia. Treatment of patients afflicted with Meniere's Syndrome is similar to Meniere's Disease.

Sensorineural Hearing Loss

Sensorineural hearing loss is a type of hearing loss which results from defects (congenital and acquired) in the vestibulocochlear nerve (also known as cranial nerve VIII), or sensory cells of the inner ear. The majority of defects of the inner ear are defects of otic hair cells.

Aplasia of the cochlea, chromosomal defects, and congenital cholesteatoma are examples of congenital defects which result in sensorineural hearing loss. By way of non-limiting example, inflammatory diseases (e.g. suppurative labyrinthitis, meningitis, mumps, measles, viral syphilis, and autoimmune disorders), Meniere's Disease, exposure to ototoxic drugs (e.g. aminoglycosides, loop diuretics, antimetabolites, salicylates, and cisplatin), physical trauma, presbycusis, and acoustic trauma (prolonged exposure to sound in excess of 90 dB) all result in acquired sensorineural hearing loss.

If the defect resulting in sensorineural hearing loss is a defect in the auditory pathways, the sensorineural hearing loss is called central hearing loss. If the defect resulting in sensorineural hearing loss is a defect in the auditory pathways, the sensorineural hearing loss is called cortical deafness.

In some instances, sensorineural hearing loss occurs when the components of the auris interna or accompanying neural components are affected, and contain a neural, i.e. when the auditory nerve or auditory nerve pathways in the brain are affected, or sensory component. Sensory hearing loss are hereditary, or it are caused by acoustic trauma (i.e. very loud noises), a viral infection, drug-induced or Meniere's disease. In some instances, neural hearing loss occurs as a result of brain tumors, infections, or various brain and nerve disorders, such as stroke. Some hereditary diseases, such as Refsum's disease (defective accumulation of branched fatty acids), also cause neural disorders affecting hearing loss. Auditory nerve pathways are damaged by demyelinating diseases, e.g. idiopathic inflammatory demyelinating disease (including multiple sclerosis), transverse myelitis, Devic's disease, progressive multifocal leukoencephalopathy, Guillain-Barre syndrome, chronic inflammatory demyelinating polyneuropathy and anti-MAG peripheral neuropathy.

The incidence of sudden deafness, or sensorineural hearing loss, occurs in about 1 in 5000 individuals, and are caused by viral or bacterial infections, e.g. mumps, measles, *influenza*, chickenpox, cytomegalovirus, syphilis or infectious mononucleosis, or physical injury to the inner ear organ. In some cases, no cause is identified. In some cases, tinnitus and vertigo accompany sudden deafness, which subsides gradually. Oral corticosteroids are frequently prescribed to treat sensorineural hearing loss. In some cases, surgical intervention is necessary. Other treatments include AM-101 and AM-111, compounds under development for the treatment of auris interna tinnitus and acute sensorineural hearing loss. (Auris Medical AG, Basel, Switzerland).

Noise Induced Hearing Loss

Noise induced hearing loss (NIHL) is caused upon exposure to sounds that are too loud or loud sounds that last a long time. In some instances, hearing loss occurs from prolonged exposure to loud noises, such as loud music, heavy equipment or machinery, airplanes or gunfire. Long or repeated or impulse exposure to sounds at or above 85 decibels cause hearing loss in some cases. NIHL causes damage to the hair cells and/or the auditory nerve. The hair cells are small sensory cells that convert sound energy into electrical signals that travel to the brain. In some cases, impulse sound results in immediate hearing loss that is permanent. This kind of hearing loss are accompanied by tinnitus—a ringing, buzzing, or roaring in the ears or head—which subsides over time in some cases. Hearing loss and tinnitus are experienced in one or both ears, and tinnitus continue constantly or occasionally throughout a lifetime in some instances. Permanent damage to hearing loss is often diagnosed. Continuous exposure to loud noise also damages the structure of hair cells, resulting in hearing loss and tinnitus, although the process occurs more gradually than for impulse noise.

In some embodiments, an otoprotectant reverses, reduces or ameliorates NIHL. Examples of otoprotectants that treat or prevent NIHL include, but are not limited to, D-methionine, L-methionine, ethionine, hydroxyl methionine, methioninol, amifostine, mesna (sodium 2-sulfanylethanesulfonate), a mixture of D and L methionine, normethionine, homomethionine, S-adenosyl-L-methionine), diethyldithiocarbamate, ebselen (2-phenyl-1, 2-benzisoselenazol-3(2H)-one), sodium thiosulfate, AM-111 (a cell permeable JNK inhibitor, (Laboratoires Auris SAS)), leucovorin, leucovorin calcium, dexrazoxane, or combinations thereof.

Presbycusis (Age Related Hearing Loss)

Presbycusis (age related hearing loss (ARHL)) is the progressive bilateral loss of hearing that results from aging. Most hearing loss occurs at higher frequencies (i.e. frequencies above 15 or 16 Hz) making it difficult to hear a female voice (as opposed to male voice), and an inability to differentiate between high-pitched sounds (such as "s" and "th"). It is difficult to filter out background noise. The disorder is most often treated by the implantation of a hearing aid and/or the administration of pharmaceutical agents which prevent the build up of ROS.

The disorder is caused by changes in the physiology of the inner ear, the middle ear, and/or the VIII nerve. Changes in the inner ear resulting in presbycusis include epithelial atrophy with loss of otic hair cells and/or stereocilia, atrophy of nerve cells, atrophy of the stria vascularis, and the thickening/stiffening of the basilar membrane. Additional changes which contribute to presbycusis include the accumulation of defects in the tympanic membrane and the ossicles.

In some instances, changes leading to presbycusis occur due to the accumulation of mutations in DNA, and mutations in mitochondrial DNA; however, the changes are exacerbated by exposure to loud noise, exposure to ototoxic agents, infections, and/or the lessening of blood flow to the ear. The latter is attributable to atherosclerosis, diabetes, hypertension, and smoking.

Presbycusis, or age-related hearing loss, occurs as a part of normal aging, and occurs as a result of degeneration of the receptor cells in the spiral Organ of Corti in the auris interna. Other causes are also attributed to a decrease in a number of nerve fibers in the vestibulocochlear nerve, as well as a loss of flexibility of the basilar membrane in the cochlea. Most commonly, it arises from changes in the inner ear as one ages, but it also results from changes in the middle ear, or from complex changes along the nerve pathways from the ear to the brain. Certain medical conditions and medications also play a role. In some instances, presbycusis results from a gradual loss of spiral ganglion neuron afferent fibers and their synapses with hair cells (ribbon synapses), causing a disconnection between the sensory cells that detect sound and the auditory nerve that transmits this information to the auditory brain. Loss of spiral ganglion neurons and hair cells also occurs. In some cases, prior exposure to loud noise or other otic insults exacerbates this ageing process, leading to an accelerated loss of hearing. Presbycusis also involves "hidden hearing loss", an inability to detect sound against a background noise ("speech-in-noise") despite a lack of marked changes in hearing thresholds. These more subtle decrements in hearing have been associated with a loss of spiral ganglion neuron afferent fibers and their synaptic connections with hair cells (ribbon synapses).

Autoimmune Inner Ear Disease

Autoimmune inner ear disease (AIED) is one of the few reversible causes of sensorineural hearing loss. It is a rare disorder appearing in both adults and children that often involves a bilateral disturbance of the audio and vestibular functions of the auris interna. The origin of AIED is likely autoantibodies and/or immune cells attacking inner ear structures, but are associated with other autoimmune conditions. In many cases, AIED occurs without systemic autoimmune symptoms, but up to one-third of patients also suffer from a systemic autoimmune illness, such as inflammatory bowel disease, rheumatoid arthritis, Ankylosing spondylitis, Systemic Lupus Erythematosus (SLE), Sjögren's Syndrome, Cogan's disease, ulcerative colitis, Wegener's granulomatosis and scleroderma. Behçet's disease, a multisystem disease, also commonly has audiovestibular problems. There is some evidence for food-related allergies as a cause for cochlear and vestibular autoimmunity, but there is presently no agreement as to its importance in the aetiology of the disease. A classification scheme for AIED has been developed (Harris and Keithley, (2002) Autoimmune inner ear disease, in *Otorhinolaryngology Head and Neck Surgery.* 91, 18-32).

The immune system normally performs a crucial role in protecting the auris interna from invasive pathogens such as bacteria and viruses. However, in AIED the immune system itself begins to damage the delicate auris interna tissues. It is well established that the auris interna is fully capable of mounting a localized immune response to foreign antigens. When a foreign antigen enters the auris interna, it is first processed by immunocompetent cells which reside in and around the endolymphatic sac. Once the foreign antigen has been processed by these immunocompetent cells, these cells secrete various cytokines which modulate the immune response of the auris interna. One result of this cytokine release is to facilitate the influx of inflammatory cells which are recruited from the systemic circulation. These systemic inflammatory cells enter the cochlea via diapedesis through the spiral modiolar vein and its tributaries and begin to participate in antigen uptake and deregulation just as it occurs in other parts of the body. Interleukin 1 (IL-1) plays an important role in modulating the innate (nonspecific) immune response and is a known activator of resting T helper cells and B-cells. T helper cells, once activated by IL-1, produce IL-2. IL-2 secretion results in differentiation of pluripotent T-cells into helper, cytotoxic and suppressor T-cell subtypes. IL-2 also assists T helper cells in the activation of B lymphocytes and probably plays a pivotal role in the immunoregulation of the immune response of the auris interna. IL-2 has been identified within the perilymph of the auris interna as early as 6 h after antigen challenge with peak levels at 18 h after antigen challenge. The perilymphatic levels of IL-2 then dissipate, and it is no longer present within the perilymph at 120 hours post antigen challenge (Gloddek, *Acta Otolaryngol.* (1989) 108, 68-75).

Both IL-1β and tumor necrosis factor-α (TNF-α) play a key role in the initiation and amplification of the immune response. IL-1β is expressed by the fibrocytes of the spiral ligament in the presence of trauma such as surgical trauma or acoustic trauma in a nonspecific response. THF-α is expressed either by infiltrating systemic cells or by resident cells contained within the endolymphatic sac in the presence of antigen. THF-α is released as part of the adaptive (specific) immune response in animal models. When antigen is injected into the auris internas of mice, IL-1β and TNF-α are both expressed and a vigorous immune response occurs. However, when antigen is introduced to the auris interna via the cerebral spinal fluid without trauma to the auris interna, only TNF-α is expressed and the immune response in minimal (Satoh, *J. Assoc. Res. Otolaryngol.* (2003), 4, 139-147). Importantly, cochlear trauma in isolation also results in a minimal immune response. These results suggest that both the nonspecific and specific components of the immune response act in concert in the auris interna to achieve a maximal response.

Accordingly, if the cochlea is traumatized and an antigen is injected (or in the case of autoimmune disease, the patient has immune cells directed against auris interna antigens), both the nonspecific and the specific immune responses are activated simultaneously. This results in the concurrent production of IL-1β as well as THF-α which causes a greatly amplified level of inflammation leading to substantial damage to the auris interna. Subsequent experiments in animal models confirm that an important step in immune-mediated damage requires that the auris interna be conditioned by the non-specific innate immune response before the specific adaptive immune response leads to enough inflammation to result in damage. As a result, agents which downregulate or block the specific immune response, and in particular the effect of TNF-α, might be able to prevent the excessive immune response seen when both the specific and nonspecific immune responses are simultaneously activated.

In some instances, the otic formulations described herein are used for the treatment of autoimmune ear disease and comprise anti-TNF agents. Suitable anti-TNF agents include but are not limited to etanercept (ENBREL®), infliximab (REMICADE®) and adalimumab (HUMIRA®). In certain embodiments, formulations disclosed herein comprising antiviral agents are administered for treatment of AIED. In other embodiments, the antimicrobial agent formulations disclosed herein are administered for the treatment of AIED in conjunction with other pharmaceutical agents useful for treating the same conditions or symptoms of the same conditions, including steroids, cytotoxic agents, collagen, gamma globulin infusion, or other immune modulating drugs. Steroids include, e.g., prednisone or decadron. Cytotoxic agents for the treatment of AIED include, e.g., methotrexate, cyclophosphamide, and thalidomide. Plasmapheresis procedures are optionally used. Treatment with oral collagen, gamma globulin infusions, or other immune modulating drugs (e.g. beta-interferon, alpha-interferon or copaxone) is also optionally used in combination with the antimicrobial agent formulations disclosed herein. The additional pharmaceutical agents are optionally administered together with the controlled release formulations disclosed herein, or through other modes of administration, e.g., orally, by injection, topically, nasally or through any other suitable means. The additional pharmaceutical agents are optionally co-administered, or administered at different time periods.

Tinnitus

Tinnitus is defined as the perception of sound in the absence of any external stimuli. In some cases, it occurs in one or both ears, continuously or sporadically, and is most often described as a ringing sound. It is most often used as a diagnostic symptom for other diseases. There are two types of tinnitus: objective and subjective. The former is a sound created in the body which is audible to anyone. The latter is audible only to the affected individual. Studies estimate that over 50 million Americans experience some form of tinnitus. Of those 50 million, about 12 million experience severe tinnitus.

In certain instances, tinnitus results from damage to otic structures (e.g. stereocillia), the dysfunction of one or more molecular receptors, and/or the dysfunction of one or more neural pathways. In certain instances, tinnitus results from excitotoxicity caused by abnormal activity of an NMDA receptor. In certain instances, tinnitus results from by dysfunction of an α9 and/or α10 acetylcholine receptor. In certain instances, tinnitus results from damage to the vestibulocochlear nerve. In certain embodiments, a reduction in neurotransmitter reuptake (e.g. the increase in extracellular neurtotransmitters) treats, and/or ameliorates the symptoms of tinnitus. In certain embodiments, antagonism of an NK1 receptor treats, and/or ameliorates the symptoms of tinnitus. In certain embodiments, a reduction in neurotransmitter reuptake and antagonism of an NK1 receptor treats, and/or ameliorates the symptoms of tinnitus.

There are several treatments for tinnitus. Lidocaine, administered by IV, reduces or eliminates the noise associated with tinnitus in about 60-80% of sufferers. Selective neurotransmitter reuptake inhibitors, such as nortriptyline, sertraline, and paroxetine, have also demonstrated efficacy against tinnitus. Benzodiazepines are also prescribed to treat tinnitus.

Ototoxicity

Ototoxicity refers to hearing loss caused by a toxin. The hearing loss are due to trauma to otic hair cells, the cochlea, and/or the cranial nerve VII. Multiple drugs are known to be ototoxic. Often ototoxicity is dose-dependent. It is permanent or reversible upon withdrawal of the drug.

Known ototoxic drugs include, but are not limited to, the aminoglycoside class of antibiotics (e.g. gentamicin, and amikacin), some members of the macrolide class of antibiotics (e.g erythromycin), some members of the glycopeptide class of antibiotics (e.g. vancomycin), salicylic acid, nicotine, some chemotherapeutic agents (e.g. actinomycin, bleomycin, cisplatin, carboplatin and vincristine), and some members of the loop diuretic family of drugs (e.g. furosemide).

Cisplatin and the aminoglycoside class of antibiotics induce the production of reactive oxygen species ("ROS"). ROS damages cells directly by damaging DNA, polypeptides, and/or lipids. Antioxidants prevent damage of ROS by preventing their formation or scavenging free radicals before they damage the cell. Both cisplatin and the aminoglycoside class of antibiotics are also thought to damage the ear by binding melanin in the stria vascularis of the inner ear.

Salicylic acid is classified as ototoxic as it inhibits the function of the polypeptide prestin. Prestin mediates outer otic hair cell motility by controlling the exchange of chloride and carbonate across the plasma membrane of outer otic hair cells. It is only found in the outer otic hair cells, not the inner otic hair cells. Accordingly, in some embodiments, the use of the controlled release auris-compositions comprising antioxidants prevents, ameliorates or lessens ototoxic effects of chemotherapy, including but not limited to cisplatin treatment, aminoglycoside or salicylic acid administration, or other ototoxic agents.

Excitotoxicity

Excitotoxicity refers to the death or damaging of neurons and/or otic hair cells by glutamate and/or similar substances.

Glutamate is the most abundant excitatory neurotransmitter in the central nervous system. Pre-synaptic neurons release glutamate upon stimulation. It flows across the synapse, binds to receptors located on post-synaptic neurons, and activates these neurons. The glutamate receptors include the NMDA, AMPA, and kainate receptors. Glutamate transporters are tasked with removing extracellular glutamate from the synapse. Certain events (e.g. ischemia or stroke) damage the transporters. This results in excess glutamate accumulating in the synapse. Excess glutamate in synapses results in the over-activation of the glutamate receptors.

The AMPA receptor is activated by the binding of both glutamate and AMPA. Activation of certain isoforms of the AMPA receptor results in the opening of ion channels located in the plasma membrane of the neuron. When the channels open, $Na^+$ and $Ca^{2+}$ ions flow into the neuron and $K^+$ ions flow out of the neuron.

The NMDA receptor is activated by the binding of both glutamate or NMDA together with a co-agonist glycine or D-serine. Activation of the NMDA receptor, results in the opening of ion channels located in the plasma membrane of the neuron. However, these channels are blocked by $Mg^{2+}$ ions. Activation of the AMPA receptor results in the expulsion of $Mg^{2+}$ ions from the ion channels into the synapse. When the ion channels open, and the $Mg^{2+}$ ions evacuate the ion channels, $Na^+$ and $Ca^{2+}$ ions flow into the neuron, and $K^+$ ions flow out of the neuron.

Excitotoxicity occurs when the NMDA receptor and AMPA receptors are over-activated by the binding of excessive amounts of ligands, for example, abnormal amounts of glutamate. The over-activation of these receptors causes excessive opening of the ion channels under their control. This allows abnormally high levels of $Ca^{2+}$ and $Na^+$ to enter the neuron. The influx of these levels of $Ca^{2+}$ and $Na^+$ into the neuron causes the neuron to fire more often, resulting in a rapid buildup of free radicals and inflammatory compounds within the cell. The free radicals eventually damage the mitochondria, depleting the cell's energy stores. Furthermore, excess levels of $Ca^{2+}$ and $Na^+$ ions activate excess levels of enzymes including, but not limited to, phospholipases, endonucleases, and proteases. The over-activation of these enzymes results in damage to the cytoskeleton, plasma membrane, mitochondria, and DNA of the sensory neuron.

Endolymphatic Hydrops

Endolymphatic hydrops refers to an increase in the hydraulic pressure within the endolymphatic system of the inner ear. The endolymph and perilymph are separated by thin membranes which contain multiple nerves. Fluctuation in the pressure stresses the membranes and the nerves they house. If the pressure is great enough, disruptions form in the membranes. This results in a mixing of the fluids which leads to a depolarization blockade and transient loss of function. Changes in the rate of vestibular nerve firing often lead to vertigo. Further, the Organ of Corti are affected in some cases. Distortions of the basilar membrane and the inner and outer hair cells leads to hearing loss and/or tinnitus.

Causes include metabolic disturbances, hormonal imbalances, autoimmune disease, and viral, bacterial, or fungal infections. Symptoms include hearing loss, vertigo, tinnitus, and aural fullness. Nystagmus is also present in some instances. Treatment includes systemic administration of benzodiazepine, diuretics (to decrease the fluid pressure), corticosteroids, and/or anti-bacterial, anti-viral, or anti-fungal agents.

Labyrinthitis

Labyrinthitis is an inflammation of the labyrinths of the ear which contain the vestibular system of the inner ear. Causes include bacterial, viral, and fungal infections. It is also caused by a head injury or allergies in some instances. Symptoms of labyrinthitis include difficulty maintaining balance, dizziness, vertigo, tinnitus, and hearing loss. In some cases, recovery takes one to six weeks; however, chronic symptoms are present for years.

There are several treatments for labyrinthitis. Prochlorperazine is often prescribed as an antiemetic. Serotonin-reuptake inhibitors have been shown to stimulate new neural growth within the inner ear. Additionally, treatment with antibiotics is prescribed if the cause is a bacterial infection, and treatment with corticosteroids and antivirals is recommended if the condition is caused by a viral infection.

Ramsay Hunt's Syndrome (Herpes Zoster Infection)

Ramsay Hunt's syndrome is caused by a herpes zoster infection of the auditory nerve. The infection causes severe ear pain, hearing loss, vertigo, as well as blisters on the outer ear, in the ear canal, as well as on the skin of the face or neck supplied by the nerves. In some cases, facial muscles also become paralyzed if the facial nerves are compressed by the swelling. Hearing loss are temporary or permanent, with vertigo symptoms usually lasting from several days to weeks.

Treatment of Ramsay Hunt's syndrome includes administration of antiviral agents, including acyclovir. Other antiviral agents include famciclovir and valacyclovir. Combination of antiviral and corticosteroid therapy are also employed to ameliorate herpes zoster infection. Analgesics or narcotics are also administered to relieve the pain, and diazepam or other central nervous system agents to suppress vertigo. Capsaicin, lidocaine patches and nerve blocks are also used. Surgery is also performed on compressed facial nerves to relieve facial paralysis.

Vestibular Neuronitis

Vestibular neuronitis, or vestibular neuropathy, is an acute, sustained dysfunction of the peripheral vestibular system. It is theorized that vestibular neuronitis is caused by a disruption of afferent neuronal input from one or both of the vestibular apparatuses. Sources of this disruption include viral infection, and acute localized ischemia of the vestibular nerve and/or labyrinth. Vestibular neuronitis is characterized by sudden vertigo attacks, which manifests as a single attack of vertigo, a series of attacks, or a persistent condition which diminishes over a matter of weeks. Symptoms typically include nausea, vomiting, and previous upper respiratory tract infections, although there are generally no auditory symptoms. The first attack of vertigo is usually severe, leading to nystagmus, a condition characterized by flickering of the eyes involuntarily toward the affected side. Hearing loss does not usually occur.

In some instances, vestibular neuronitis is caused by inflammation of the vestibular nerve, the nerve that connects the inner ear to the brain, and is likely caused by viral infection. Diagnosis of vestibular neuronitis usually involves tests for nystagmus using electronystamography, a method of electronically recording eye movements. Magnetic resonance imaging is also performed to determine if other causes play a role in the vertigo symptoms.

Treatment of vestibular neuronitis typically involves alleviating the symptoms of the condition, primarily vertigo, until the condition clears on its own. Treatment of vertigo is often identical to Meniere's disease, and optionally includes meclizine, lorazepam, prochlorperazine, or scopolamine. Fluids and electrolytes are intravenously administered if the vomiting is severe. Corticosteroids, such as prednisilone, are also given if the condition is detected early enough.

In some embodiments, the compositions disclosed herein comprising an antiviral agent is administered for the treatment of vestibular neuronitis. Further, in some embodiments, the compositions are administered with other agents that are typically used to treat symptoms of the condition, including anticholinergics, antihistamines, benzodiazepines, or steroids. Treatment of vertigo is identical to Meniere's disease, and include meclizine, lorazepam, prochlorperazine or scopolamine. Fluids and electrolytes are also intravenously administered if the vomiting is severe.

The most significant finding when diagnosing vestibular neuronitis is spontaneous, unidirectional, horizontal nystagmus. It is often accompanied by nausea, vomiting, and vertigo. It is, generally, not accompanied by hearing loss or other auditory symptoms.

There are several treatments for vestibular neuronitis. H1-receptor antagonists, such as dimenhydrinate, diphenhydramine, meclizine, and promethazine, diminish vestibular stimulation and depress labyrinthine function through anticholinergic effects. Benzodiazepines, such as diazepam and lorazepam, are also used to inhibit vestibular responses due to their effects on the $GABA_A$ receptor. Anticholinergics, for example scopolamine, are also prescribed. They function by suppressing conduction in the vestibular cerebellar pathways. Finally, corticosteroids (i.e. prednisone) are prescribed to ameliorate the inflammation of the vestibular nerve and associated apparatus.

Microvascular Compression Syndrome

Microvascular compression syndrome (MCS), also called "vascular compression" or "neurovascular compression", is a disorder characterized by vertigo and tinnitus. It is caused by the irritation of Cranial Nerve VIII by a blood vessel. Other symptoms found in subjects with MCS include, but are not limited to, severe motion intolerance, and neuralgic like "quick spins". MCS is treated with carbamazepine, TRILEPTAL®, and baclofen. It is also surgically treated for some cases.

Auditory Nerve Tumors

Auditory nerve tumors, including acoustic neuroma, acoustic neurinoma, vestibular schwannoma and eighth nerve tumor) are tumors that originate in Schwann cells, cells that wrap around a nerve. Auditory nerve tumors account for approximately 7-8% of all tumors originating in the skull, and are often associated with the diagnosis of neurofibromatosis in a patient. Depending upon the location of the tumor, some symptoms include hearing loss, tinnitus, dizziness and loss of balance. In some cases, other more serious symptoms develop as the tumor becomes larger, which compresses against the facial or trigemminal nerve, which affect connections between the brain and the mouth, eye or jaw. Smaller tumors are removed by microsurgery, or sterotactic radio surgical techniques, including fractionated sterotactic radiotherapy. Malignant Schwannomas are treated with chemotherapeutic agents, including vincristine, adriamycin, cyclophosphamide and imidazole carboxamide.

Auditory Neuropathy

Auditory neuropathy (AN) is also known as auditory neuropathy/auditory dys-synchrony (AN/AD) or auditory neuropathy spectrum disorder (ANSD). Auditory neuropathy describes hearing loss in which the outer hair cells within the cochlea are present and functional, but auditory information is not properly transmitted to the auditory nerve and brain.

Benign Paroxysmal Positional Vertigo

Benign paroxysmal positional vertigo is caused by the movement of free floating calcium carbonate crystals (otoliths) from the utricle to one of the semicircular canals, most often the posterior semicircular canal. Movement of the head results in the movement of the otoliths causing abnormal endolymph displacement and a resultant sensation of vertigo. The episodes of vertigo usually last for about a minute and are rarely accompanied by other auditory symptoms.

Cancer of the Ear

Although the cause is unknown, cancer of the ear is often associated with long-term and untreated otitis, suggesting a link between chronic inflammation and development of the cancer, at least in some cases. In some instances, tumors in the ear are benign or malignant, and they exist in the external, middle, or inner ear. Symptoms of ear cancer include otorrhea, otalgia, hearing loss, facial palsy, tinnitus, and vertigo. Treatment options are limited, and include surgery, radiotherapy, chemotherapy, and combinations thereof. Also, additional pharmaceutical agents are used to treat symptoms or conditions associated with the cancer, including corticosteroids in the case of facial palsy, and antimicrobial agents when otitis is present.

Systemic administration of conventional cytotoxic agents have been used to treat cancer of the ear, including systemic administration of cyclophosphamide (in CHOP chemotherapy) in combination with radiotherapy and methotrexate, and perfusion of methotrexate through the external carotid artery. However, such treatments requiring systemic administration of the active agents suffer from the same drawbacks discussed herein. Namely, relatively high doses of the agents are required to achieve the necessary therapeutic doses in the ear, which result in an increase of undesired, adverse side effects. Accordingly, in some embodiments, the local administration of the cytotoxic agents in the compositions and formulations disclosed herein results in treatment of cancer of the ear with lower effective doses, and with a decrease in the incidence and/or severity of side effects. Typical side effects of systemic administration of cytotoxic agents, e.g., methotrexate, cyclophosphamide, and thalidomide, for the treatment of cancer of the ear include anemia, neutropenia, bruising, nausea, dermatitis, hepatitis, pulmonary fibrosis, teratogenicity, peripheral neuropathy, fatigue, constipation, deep vein thrombosis, pulmonary edema, atelectasis, aspiration pneumonia, hypotension, bone marrow suppression, diarrhea, darkening of skin and nails, alopecia, changes in hair color and texture, lethargy, hemorrhagic cystitis, carcinoma, mouth sores, and decreased immunity.

In certain embodiments, the cytotoxic agents are methotrexate (RHEUMATREX®, Amethopterin) cyclophosphamide (CYTOXAN®), and thalidomide (THALIDOMID®). In some embodiments, the compounds have anti-inflammatory properties and are used in the formulations and compositions disclosed herein for the treatment of inflammatory disorders of the ear, including AIED.

Although systemic administration of methotrexate, cyclophosphamide, and thalidomide is currently used to treat or is being investigated for the treatment of otic disorders, such as inflammatory otic disorders, including AIED, Meniere's disease, and Behçet's disease, as well as cancer of the ear, the cytotoxic agents are not without the potential for serious adverse side effects. Moreover, cytotoxic agents which demonstrate efficacy but are otherwise not approvable because of safety considerations is also contemplated within the embodiments disclosed herein. In some embodiments, the localized application of the cytotoxic agents to the target otic structures for treatment of autoimmune and/or inflammatory disorders, as well as cancer of the ear, results in the reduction or elimination of adverse side effects experienced with systemic treatment. In some embodiments, the localized treatment with the cytotoxic agents contemplated herein reduce the amount of agent needed for effective treatment of the targeted disorder due, for example, to increased retention of the active agents in the auris interna and/or media, to the existence of the biological blood barrier in the auris interna, or to the lack of sufficient systemic access to the auris media.

In some embodiments, cytotoxic agents used in the compositions, formulations, and methods disclosed herein are metabolites, salts, polymorphs, prodrugs, analogues, and derivatives of cytotoxic agents, including methotrexate, cyclophosphamide, and thalidomide. Particularly preferred are metabolites, salts, polymorphs, prodrugs, analogues, and derivatives of cytotoxic agents, e.g., methotrexate, cyclophosphamide, and thalidomide that retain at least partially the cytotoxicity and anti-inflammatory properties of the parent compounds. In certain embodiments, analogues of thalidomide used in the formulations and compositions disclosed herein are lenalidomide (REVLIMID®) and CC-4047 (ACTIMID®).

Cyclophosphamide is a prodrug that undergoes in vivo metabolism when administered systemically. The oxidized metabolite 4-hydroxycyclophosphamide exists in equilibrium with aldophosphamide, and the two compounds serve as the transport forms of the active agent phosphoramide mustard and the degradation byproduct acrolein. In some embodiments, preferred cyclophosphamide metabolites for incorporation into the formulations and compositions disclosed herein are 4-hydroxycyclophosphamide, aldophosphamide, phosphoramide mustard, and combinations thereof.

Other cytotoxic agents used in the compositions, formulations, and methods disclosed herein, particularly for the treatment of cancer of the ear, are any conventional chemotherapeutic agents, including acridine carboxamide, actinomycin, 17-N-allylamino-17-demethoxygeldanamycin, aminopterin, amsacrine, anthracycline, antineoplastic, antineoplaston, 5-azacytidine, azathioprine, BL22, bendamustine, biricodar, bleomycin, bortezomib, bryostatin, busulfan, calyculin, camptothecin, capecitabine, carboplatin, chlorambucil, cisplatin, cladribine, clofarabine, cytarabine, dacarbazine, dasatinib, daunorubicin, decitabine, dichloroacetic acid, discodermolide, docetaxel, doxorubicin, epirubicin, epothilone, eribulin, estramustine, etoposide, exatecan, exisulind, ferruginol, floxuridine, fludarabine, fluorouracil, fosfestrol, fotemustine, gemcitabine, hydroxyurea, IT-101, idarubicin, ifosfamide, imiquimod, irinotecan, irofulven, ixabepilone, laniquidar, lapatinib, lenalidomide, lomustine, lurtotecan, mafosfamide, masoprocol, mechlorethamine, melphalan, mercaptopurine, mitomycin, mitotane, mitoxantrone, nelarabine, nilotinib, oblimersen, oxaliplatin, PAC-1, paclitaxel, pemetrexed, pentostatin, pipobroman, pixantrone, plicamycin, procarbazine, proteasome inhibitors (e.g., bortezomib), raltitrexed, rebeccamycin, rubitecan, SN-38, salinosporamide A, satraplatin, streptozotocin, swainsonine, tariquidar, taxane, tegafur-uracil, temozolomide, testolactone, thioTEPA, tioguanine, topotecan, trabectedin, tretinoin, triplatin tetranitrate, tris(2-chloroethyl)amine, troxacitabine, uracil mustard, valrubicin, vinblastine, vincristine, vinorelbine, vorinostat, and zosuquidar.

Central Auditory Processing Disorder

Central auditory processing disorder (CAPD), also referred as auditory processing disorder (APD), is a general term for describing a variety of disorders that affect the way the brain processes auditory information. Individuals with CAPD usually have normal structure and function of the outer, middle and inner ear (peripheral hearing). However, these individuals are unable to process the auditory information, which leads to difficulties in recognizing and interpreting sounds, especially the sounds from speech. Central auditory processing disorder is either developmental or acquired and is believed to arise from dysfunction in the central nervous system.

Cholesteatoma

A cholesteatoma is a hyperproliferative cyst often found in the middle ear. Cholesteatoma are classified as congenital or acquired. Acquired cholesteatomas result from retraction of the ear drum (primary) and/or a tear in the ear drum (secondary).

The most common primary cholesteatoma results from the pars flaccida retracting into the epitympanum. As the pars flaccida continues to retract, the lateral wall of the epitympanum slowly erodes. This produces a defect in the lateral wall of the epitympanum that slowly expands. A less common type of primary acquired cholesteatoma results from the retraction of the posterior quadrant of the tympanic membrane retracts into the posterior middle ear. As the tympanic membrane retracts, squamous epithelium envelops the stapes and retracts into the sinus tympani. Secondary cholesteatomas result from injury to the tympanic membrane (e.g. a perforation resulting from otitis media; trauma; or a surgically-induced injury).

Complications associated with a growing cholesteatoma include injury to the osteoclasts and, in some cases, deterioration of the thin bone layer separating the top of the ear from the brain. Damage to the osteoclasts results from the persistent application of pressure to the bones resulting from the expansion of the cholesteatoma. Additionally, the presence of multiple cytokines (e.g. TNF-α, TGF-β1, TGF-β2, Il-1, and IL-6) in the epithelium of the cholesteatoma results in further degradation of the surrounding bones.

Patients with a cholesteatoma often present with earache, hearing loss, mucopurulent discharge, and/or dizziness. Physical examination confirms the presence of a cholesteatoma. Symptoms that are identified upon physical examination include damage to the ossicles, and a canal filled with mucopus and granulation tissue.

There is currently no effective medical therapy for cholesteatomas. As a cholesteatoma has no blood supply, it cannot be treated with systemic antibiotics. Topical administration of antibiotics often fails to treat a cholesteatoma.

Drug-Induced Inner Ear Damage

Damage from the administration of drugs, including certain antibiotics, diuretics (e.g. ethacrynic acid and furosemide), aspirin, aspirin-like substances (e.g. salicylates) and quinine. Deterioration of the auris interna organ are hastened by impaired kidney function, which results in decreased clearance of the affecting drugs and their metabolites. In some instances, these drugs affect both hearing and equilibrium, but likely affects hearing to a greater extent.

For example, neomycin, kanamycin, amikacin have a greater effect on hearing than on balance. The antibiotics viomycin, gentamicin and tobramycin affect both hearing and equilibrium. Streptomycin, another commonly administered antibiotic, induces vertigo more than loss of hearing, and leads to Dandy's syndrome, where walking in the dark becomes difficult and induces a sensation of the environment moving with each step. Aspirin, when taken in very high doses, also leads to temporary hearing loss and tinnitus, a condition where sound is perceived in the absence of external sound. Similarly, quinine, ethacryinic acid and furosemide result in temporary or permanent hearing loss in some instances.

Hereditary Disorders

Hereditary disorders, including Scheibe, Mondini-Michelle, Waardenburg's, Michel, Alexander's ear deformity, hypertelorism, Jervell-Lange Nielson, Refsum's and Usher syndromes, are found in approximately 20% of patients with sensorineural hearing loss. In some instances, congenital ear malformations result from defects in the development of the membranous labyrinthine, the osseous labyrinthine, or both. Along with profound hearing loss and vestibular function abnormalities, hereditary deformities are associated with other dysfunctions, including development of recurring meningitis, cerebral spinal fluid (CSF) leaks, as well as perilymphatic fistulas. Treatment of chronic infections is necessitated in hereditary disorder patients.

Hyperacusis

Hyperacusis is a condition characterized by an increased sensitivity to certain frequency and volume ranges of sound (a collapsed tolerance to usual environmental sound). In some cases, hyperacusis occur gradually and in other cases, hyperacusis appears suddenly. A person with severe hyperacusis has difficulty tolerating everyday sounds, wherein some of these sounds seem unpleasantly or painfully loud to the afflicted person but not to others.

Inflammatory Disorders of the Auris Media

Otitis media (OM), which includes acute otitis media (AOM), otitis media with effusion (OME) and chronic otitis media as examples, is a condition affecting both adults and children. OM susceptibility is multifactorial and complex, including environmental, microbial and host factors. Bacterial infection accounts for a large percentage of OM cases, with more than 40% of cases attributed to *Streptococcus pneumoniae* infection. However, viral causes, as well as other microbial agents, also account for OM conditions in some cases.

Regardless of the causative agent, increases in cytokine production, including interleukins and TNF, have been observed in the effluent media of individuals afflicted with OM. IL-1β, IL-6 and TNF-α are acute-phase cytokines that promote acute inflammatory response after infection with viruses and bacteria. Genetic studies support this link between cytokines and OM by demonstrating a correlation in the occurrence of TNF-α SNP (single-nucleotide polymorphisms) and an increased susceptibility for OM in pediatric patients suffering from AOM and with a subsequent need for placement of tympanostomy tubes. In animal models of OM induced with pneumococci inoculations, TNF-α and interleukins levels were found to increase in early developmental phase of OM, with TNF-α levels steadily increasing 72 hours after inoculation. Moreover, higher TNF-α levels have been associated with a history of multiple tympanostomy tube placements, indicating a role for TNF-α in chronic OM cases. Finally, direct injection of TNF-α and interleukins has been shown to induce middle ear inflammation in a guinea pig model. These studies support the role that cytokines play in the origin and maintenance of OM in the auris media.

In some instances, because OM is caused by a virus, bacteria or both, it is often difficult to identify the exact cause and thus the most appropriate treatment. Treatment options of OM in the auris media include treatment with antibiotics, such as amoxicillin, clavulanate acid, trimethoprim-sulfamethoxazole, cefuroxime, clarithromycin and azithromycin and other cephalosporins, macrolides, penicillins or sulfonamides. Surgical intervention is also available, including a myringotomy, an operation to insert a tympanostomy tube through the tympanic membrane and into the patient's middle ear to drain the fluid and balance the pressure between the outer and middle ear. In some instances, antipyretics and analgesics, including benzocaine, ibuprofen and acetaminophen, are also prescribed to treat accompanying fever or pain effects. Pre-treatment with TNF-α inhibitors in experimental lipopolysaccharide (LPS)-induced OM animal models has been shown to suppress development of OM, suggesting a role in the treatment of OM or OME. In addition, treatment of such conditions include use of TNF-α inhibitors in combination with other inflammatory response mediators, including platelet activating factor antagonists, nitric oxide synthase inhibitors and histamine antagonists.

As discussed above, methotrexate, cyclophosphamide, and thalidomide are all cytotoxic small molecule agents that are systemically administered to treat AIED. In some embodiments, the compounds are useful in the compositions and formulations disclosed herein for the treatment of inflammatory disorders of the auris media, including OM, by having a direct anti-inflammatory effect, particularly by interfering with TNF activity. In other embodiments, metabolites, salts, polymorphs, prodrugs, analogues, and derivatives of methotrexate, cyclophosphamide, and thalidomide that retain the ability of the parent cytotoxic agents to treat inflammatory disorders of the auris media, including OM, are useful in the formulations disclosed herein for the treatment of inflammatory disorders of the auris media, including OM. In certain embodiments, preferred metabolites of cyclophosphamide for incorporation into the compositions and formulations disclosed herein include 4-hydroxycyclophosphamide, aldophosphamide, phosphoramide mustard, or combinations thereof.

In addition, other otic disorders have inflammatory response aspects or are tangentially related to autoimmune conditions, including Meniere's disease and non-sudden hearing loss or noise induced hearing loss. These disorders are also explicitly contemplated as benefiting from the cytotoxic agent formulations disclosed herein, and therefore are within the scope of the embodiments disclosed.

Inflammatory Disorders of the Auris Externa

Otitis externa (OE), also referred to as swimmer's ear, is an inflammation and/or infection of the external ear. OE is often caused by bacteria in the outer ear, which establish infection following damage to the skin of the ear canal. Primary bacterial pathogens that cause OE are *Pseudomonas aeruginosa* and *Staphylococcus aureus*, but the condition is associated with the presence of many other strains of gram positive and negative bacteria. OE is also sometimes caused by fungal infection in the outer ear, including *Candida albicans* and *Aspergillus*. Symptoms of OE include otalgia, swelling, and otorrhea. If the condition progresses significantly, OE causes temporary conductive hearing loss as a result of the swelling and discharge.

Treatment of OE involves eliminating the aggravating pathogen from the ear canal and reducing inflammation, which is usually accomplished by administering combinations of antimicrobial agents, e.g., antibacterial and antifungal agents, with anti-inflammatory agents, e.g., steroids. Typical antibacterial agents for the treatment of OE include aminoglycosides (e.g., neomycin, gentamycin, and tobramycin), polymyxins (e.g., polymyxin B), fluoroquinolone (e.g., ofloxacin and ciprofloxacin), cephalosporins (e.g., cefuroxime, ceflacor, cefprozil, loracarbef, cefindir, cefixime, cefpodoxime proxetil, cefibuten, and ceftriaxone), penicillins (e.g., amoxicillin, amoxicillin-clavulanate, and penicillinase-resistant penicillins), and combinations thereof. Typical antifungal agents for the treatment of OE include clotrimazole, thimerasol, M-cresyl acetate, tolnaftate, itraconazole, and combinations thereof. Acetic acid is also administered to the ear, alone and in combination with other agents, to treat bacterial and fungal infections. Ear drops are often used as the vehicle for administration of the active agents. In the case that ear swelling has progressed substantially and ear drops do not penetrate significantly into the ear canal, a wick is inserted into the ear canal to facilitate penetration of the treatment solutions. Oral antibiotics are also administered in the case of extensive soft tissue swelling that extends to the face and neck. When the pain of OE is extremely severe such that it interferes with normal activity, e.g., sleeping, pain relievers such as topical analgesics or oral narcotics are given until the underlying inflammation and infection are alleviated.

Notably, some types of topical ear drops, such as ear drops containing neomycin, are safe and effective for use in the ear canal, but are irritating and even ototoxic to the auris media, prompting concern that such topical preparations should not be used unless the tympanic membrane is known to be intact. In some embodiments, the utilization of the formulations disclosed herein for the treatment of OE allows for use of active agents that are potentially damaging to the auris media, even when the tympanic membrane is not intact. Specifically, the controlled release formulations disclosed herein, in some instances, is applied locally in the external ear with improved retention time, thus eliminating concern that the active agents will leak out of the ear canal into the auris media. Furthermore, otoprotectants are optionally added when ototoxic agents, such as neomycin, are used.

In some embodiments, treatment of severe OE with the compositions disclosed herein, particularly highly viscous and/or mucoadhesive formulations, also obviates the need for extended use of an ear wick. Specifically, in some embodiments, the compositions disclosed herein have increased retention time in the ear canal as a result of the formulation technology, thus eliminating the need for a device to maintain their presence in the outer ear. In some embodiments, the formulations are applied in the outer ear with a needle or an ear dropper, and the active agents are maintained at the site of inflammation without the aid of an ear wick.

In some embodiments, the treatment of OE with antimicrobial formulations disclosed herein encompasses the treatment of granular myringitis, a specific form of OE characterized by chronic inflammation of the pars tensa of the tympanic membrane. The outer epithelial and underlying fibrous layers of the tympanic membrane are replaced by a proliferating granulation tissue. The predominant symptom is foul-smelling otorrhea. A variety of bacteria and fungi cause the condition, including *Proteus* and *Psuedomonas* species. Accordingly, antimicrobial agent formulations disclosed herein comprising antibacterial or antifungal agents are useful for the treatment of granular myringitis in some embodiments.

In some embodiments, the treatment of OE with antimicrobial formulations disclosed herein encompasses the treatment of chronic stenosing otitis externa. Chronic stenosing otitis externa is characterized by repeated infections, typically caused by bacteria or fungi. The primary symptoms are pruritus in the ear canal, otorrhea, and chronic swelling. Antimicrobial agent formulations disclosed herein comprising antibacterial or antifungal agents are useful for the treatment of chronic stenosing otitis externa.

In some embodiments, the treatment of OE with antimicrobial formulations disclosed herein encompasses the treatment of malignant or necrotizing external otitis, an infection involving the temporal and adjacent bones. Malignant external otitis is typically a complication of external otitis. It occurs primarily in persons with compromised immunity, especially in older persons with diabetes mellitus. Malignant external otitis is often caused by the bacteria *Pseudomonas aeruginosa*. Treatment typically involves correction of immunosuppression when possible, in conjunction with antibacterial therapy and pain relievers. Accordingly, in some embodiments, the antimicrobial agent formulations disclosed herein are useful for the treatment of malignant or necrotizing external otitis.

Otitis media (OM), which includes acute otitis media (AOM), chronic otitis media, otitis media with effusion (OME), secretory otitis media, and chronic secretory otitis media as examples, is a condition affecting both adults and children. OM susceptibility is multifactorial and complex, including environmental, microbial and host factors. Bacterial infection accounts for a large percentage of OM cases, with more than 40% of cases attributed to *Streptococcus pneumoniae* infection. However, viruses, as well as other microbes, also account for OM conditions in some cases.

In some instances, because OM is caused by a virus, bacteria or both, it is often difficult to identify the exact cause and thus the most appropriate treatment. Treatment options for OM include antibiotics, such as penicillins (e.g., amoxicillin and amoxicillin-clavulanate), clavulanate acid, trimethoprim-sulfamethoxazole, cephalosporins (e.g., cefuroxime, ceflacor, cefprozil, loracarbef, cefindir, cefixime, cefpodoxime proxetil, cefibuten, and ceftriaxone), macrolides and azalides (e.g., erythromycin, clarithromycin, and azithromycin), sulfonamides, and combinations thereof. Surgical intervention is also available, including myringotomy, an operation to insert a tympanostomy tube through the tympanic membrane and into the patient's middle ear to drain the fluid and balance the pressure between the outer and middle ear. Antipyretics and analgesics, including benzocaine, ibuprofen and acetaminophen, are also prescribed to treat accompanying fever or pain effects.

Regardless of the causative agent, increases in cytokine production, including interleukins and TNF, have been observed in the effluent media of individuals afflicted with OM. IL-1β, IL-6 and TNF-α are acute-phase cytokines that promote acute inflammatory response after infection with viruses and bacteria. Moreover, higher TNF-α levels have been associated with a history of multiple tympanostomy tube placements, indicating a role for TNF-α in chronic OM cases. Finally, direct injection of TNF-α and interleukins has been shown to induce middle ear inflammation in a guinea pig model. These studies support the role that cytokines play in the origin and maintenance of OM in the auris media. Thus, treatment of OM includes the use of antimicrobial agents in conjunction with anti-inflammatory agents to eliminate the pathogen and treat the symptoms of inflammation. Such treatments include use of steroids, TNF-α inhibitors, platelet activating factor antagonists, nitric oxide synthase inhibitors, histamine antagonists, and combinations thereof in conjunction with the antimicrobial formulations disclosed herein in some embodiments.

Mastoiditis is an infection of the mastoid process, which is the portion of the temporal bone behind the ear. It is typically caused by untreated acute otitis media. Madtoiditis are acute or chronic. Symptoms include pain, swelling, and tenderness in the mastoid region, as well as otalgia, erythematous, and otorrhea. Mastoiditis typically occurs as bacteria spread from the middle ear to the mastoid air cells, where the inflammation causes damage to the bony structures. The most common bacterial pathogens are *Streptococcus pneumoniae, Streptococcus pyogenes, Staphylococcus aureus*, and gram-negative bacilli. Accordingly, in some embodiments, the antimicrobial agent formulations disclosed herein comprising antibacterial agents effective against the bacteria are useful for the treatment of mastoiditis, including acute mastoiditis and chronic mastoiditis.

Bullous myringitis is an infection of the tympanic membrane, caused by a variety of bacteria and viruses, including *Mycoplasma* bacteria. The infection leads to inflammation of the tympanic membrane and nearby canal, and causes the formation of blisters on the ear drum. The primary symptom of Bullous myringitis is pain, which are relieved through the administration of analgesics. In some embodiments, the antimicrobial formulations disclosed herein comprising antibacterial and antiviral agents are useful for the treatment of Bullous myringitis.

Eustachian tubal catarrh, or Eustachian salpingitis, is caused from inflammation and swelling of the Eustachian tubes, resulting in a build-up of catarrh. In some embodiments, the antimicrobial formulations disclosed herein are useful for the treatment of Eustachian salpingitis.

Labyrinthitis, e.g., serous labyrinthitis, is an inflammation of the inner ear that involves one or more labyrinths housing the vestibular system. The primary symptom is vertigo, but the condition is also characterized by hearing loss, tinnitus, and nystagmus. Labrynthitis maybe acute, lasting for one to six weeks and being accompanied by severe vertigo and vomiting, or chronic, with symptoms lasting for months or even years. Labyrinthitis is typically caused by viral or bacterial infection. In some embodiments, the antimicrobial formulations disclosed herein comprising antibacterial and antiviral agents are useful for the treatment of labyrinthitis.

Facial nerve neuritis is a form of neuritis, an inflammation of the peripheral nervous system, afflicting the facial nerve. The primary symptoms of the condition are a tingling and burning sensation, and stabbing pains in the affected nerves. In severe cases, there are numbness, loss of sensation, and paralysis of the nearby muscles. The condition is typically caused by herpes zoster or herpes simplex viral infection, but has also been associated with bacterial infection, e.g., leprosy. In some embodiments, the antimicrobial formulations disclosed herein comprising antibacterial and antiviral agents are useful for the treatment of facial nerve neuritis.

In some embodiments, antimicrobial formulations disclosed herein are also useful for the treatment of temporal bone osteoradionecrosis.

Kinetosis

Kinetosis, also known as motion sickness, is a condition in which there is a disconnection between visually perceived movement and the vestibular system's sense of movement. Dizziness, fatigue, and nausea are the most common symptoms of kinetosis. Dimenhydrinate, cinnarizine, and meclizine are all systemic treatments for kinetosis. Additionally, benzodiazepines and antihistamines have demonstrated efficacy in treating kinetosis.

Mal De Debarquement

Mal de debarquement is a condition which usually occurs subsequent to a sustained motion event, for example, a cruise, car trip, or airplane ride. It is characterized by a persistent sense of motion, difficulty maintaining balance, fatigue, and cognitive impairment. Symptoms also include dizziness, headaches, hyperacusis, and/or tinnitus. Symptoms often last in excess of a month. Treatment includes benzodiazepines, diuretics, sodium channel blockers, and tricyclic antidepressants.

Other Microbial Infections Causing Cochleovestibular Disorders

Other microbial infections are known to cause cochleovestibular disorders, including hearing loss. Such infections include rubella, cytomegalovirus, mononucleosis, varicella zoster (chicken pox), pneumonia, *Borrelia* species of bacteria (Lyme disease), and certain fungal infections. Accordingly, in some embodiments, the controlled release antimicrobial agent formulations disclosed herein are also used for localized treatment of these infections in the ear.

Otic Disorders Caused by Free Radicals

Free radicals are highly reactive atoms, molecules, or ions the reactivity of which results from the presence of unpaired electrons. Reactive oxygen species ("ROS") form as a result of sequential reduction of molecular oxygen. Examples of reactive oxygen species of interest ("ROS") include, but are not limited to, superoxide, hydrogen peroxide, and hydroxyl radicals. ROS are naturally produced as a by-product of the production of ATP. In some cases, ROS also results from the use of cisplatin, and aminoglycosides. Further, stress to stereocila caused by acoustic trauma results in otic hair cells producing ROS.

In some instances, ROS damages cells directly by damaging nuclear DNA and mitochondrial DNA. Damage to the former leads to mutations which impair the functioning of auditory cells and/or apoptosis. Damage to the latter often results in decreased energy production and increased ROS production both of which leads to impaired cellular functioning or apoptosis. Further, ROS also damages or kills cells by oxidizing the polydesaturated fatty acids which comprise lipids, oxidizing the amino acids which comprise proteins, and oxidizing co-factors necessary for the activity of enzymes. Antioxidants ameliorate damage by caused by ROS by preventing their formation, or scavenging the ROS before they damage the cell.

Damage to mitochondria by ROS is often seen in hearing loss, especially hearing loss due to aging. The loss of ATP correlates to a loss in neural functioning in the inner ear. It also leads to physiological changes in the inner ear. Further, damage to mitochondria often results in an increased rate of cellular degradation and apoptosis of inner ear cells. The cells of the stria vascularis are the most metabolically active due to the vast energy requirements needed to maintain the ionic balance of fluids in the inner ear. Thus, the cells of the stria vascularis are most often damaged or killed due to damage of the mitochondria.

Otosclerosis

Otosclerosis is an abnormal growth of bone in the middle ear, which prevents structures within the ear from transducing vibration, which causes hearing loss. Otoscelorosis usually affects the ossicles, in particular the stapes, which rests in the entrance to the cochlea in the oval window. The abnormal bone growth fixates the stapes onto the oval window, preventing sound passing waves from traveling to the cochlea. Otoscelorosis causes a sensorineural hearing loss, i.e. damaged nerve fibers or hearing hair cells, or conductive hearing loss.

In some cases, treatment of otoscelrosis include surgery to remove the fixated stapes bone, called a stapedectomy. In some cases, fluoride treatment is also be used, which will not reverse the hearing loss but slows the development of otoscelorosis.

Presbystasis

Presbystasis, also known as disequilibrium of aging, is a disorder wherein affected individuals have generalized imbalance, but without spinning vertigo. The generalized imbalance is typically noticed during walking.

Postural Vertigo

Postural vertigo, otherwise known as positional vertigo, is characterized by sudden violent vertigo that is triggered by certain head positions. This condition is caused by damaged semicircular canals caused by physical injury to the auris interna, otitis media, ear surgery or blockage of the artery to the auris interna.

Vertigo onset in patients with postural vertigo usually develops when a person lies on one ear or tilts the head back to look up. Vertigo is accompanied by nystagmus. In severe cases of postural vertigo, the vestibular nerve is severed to the affected semicircular canal. Treatment of vertigo is often identical to Meniere's disease, and includes meclizine, lorazepam, prochlorperazine or scopolamine. Fluids and electrolytes are intravenously administered if the vomiting is severe.

Recurrent Vestibulopathy

Recurrent vestibulopathy is a condition wherein the subject experiences multiple episodes of severe vertigo. The episodes of vertigo last for minutes or hours. Unlike Meniere's Disease, it is not accompanied by hearing loss. In some cases it develops into Meniere's Disease or Benign Paroxysmal Positional Vertigo. Treatment is similar to that of Meniere's Disease.

Syphilis Infection

Syphilis infection also leads to congenital prenatal hearing loss, affecting approximately 11.2 per 100,000 live births in the United States, as well as sudden hearing loss in adults. Syphilis is a venereal disease, caused by the spirochete *Treponema pallidum*, which in its secondary and tertiary stages results in auditory and vestibular disorders due to membranous labyrinthis, and secondarily include meningitis.

Both acquired and congenital syphilis cause otic disorders. Symptoms of cochleovestibular disorders resulting from syphilis are often similar to those of other otic disorders, such as AIED and Meniere's disease, and include tinnitus, deafness, vertigo, malaise, sore throat, headaches, and skin rashes. In some instances, syphilis infection leads to congenital prenatal hearing loss, affecting approximately 11.2 per 100,000 live births in the United States, as well as sudden hearing loss in adults.

Treatment with steroids and antibiotics, including penicillins (e.g. benzathine penicillin G (BICILLIN LA®), are effective in eradicating the spirochete organism. However, Treponemas remains in the cochlear and vestibular endolymph even after eradication from other sites in the body. Accordingly, long term treatment with penicillins are warranted to achieve complete eradication of the spirochete organism from the endolymph fluid.

Treatment of otosyphilis (syphilis presenting otic symptoms) typically includes a combination of steroids (e.g., prednisilone) and antibacterial agents (e.g., benzathine penicillin G (BICILLIN LA®), penicillin G procaine, doxycycline, tetracycline, ceftriaxone, azithromycin). Such treatments are effective in eradicating the spirochete organism. However, Treponemas remains in the cochlear and vestibular endolymph even after eradication from other sites in the body. Accordingly, long term treatment with penicillins are required to achieve complete eradication of the spirochete organism from the endolymph fluid. Also, in the case of a severe or advanced case of syphilis, a uricosuric drug, such as probenecid, are administered in conjunction with the antibacterial agent to increase its efficacy.

Temporal Bone Fractures

The temporal bone, which contains part of the ear canal, the middle ear and the auris interna, is subject to fractures from blows to the skull or other injuries. Bleeding from the ear or patchy bruising is symptomatic of a fracture to the temporal bone, and requires a computed tomography (CT) scan for accurate diagnosis. Temporal bone fractures rupture the eardrum, causing facial paralysis and sensorineural hearing loss.

Treatment of detected temporal bone fractures includes an antibiotic regimen to prevent meningitis, or an infection of brain tissue. In addition, surgery is performed to relieve any subsequent pressure on the facial nerve due to swelling or infection.

Temporomandibular Joint Disease

Some evidence exists for a relationship between temporomandibular joint disease (TMD) and auris interna disorders. Anatomical studies demonstrate the possible involvement of the trigeminal nerve, where trigemminal innervation of the vascular system has been shown to control cochlear and vestibular labyrinth function. Additionally, in some cases, projections of ophthalmic fibers of the trigeminal Gasser ganglion to the cochlea through the basilar and anterior inferior cerebellar arteries play an important role in the vascular tone in quick vsaodilatatory response to metabolic stresses, e.g. intense noise. Auris interna diseases and symptoms, such as sudden hearing loss, vertigo and tinnitus, originate from reduction of the cochlear blood flow due to the presence of abnormal activity in the trigeminal ganglion, for example from migraine or by the central excitatory effect originated in chronic or deep pain produced by TMD.

Similarly, other researchers have found that the trigeminal ganglion also innervates the ventral cochlear nucleus and the superior olivary complex, which interfere with auditory pathways leading to the auditory cortex where constant peripheral somatic signals from the ophthalmic and mandibular trigenimal peripheral innervation occurs in TMD cases. These somatosensory and auditory system interactions via the central nervous system explain otic symptoms in the absence of existing disease in the ear, nose or throat.

Accordingly, forceful muscle contractions in TMD elicit modulations in the neurological and auditory and equilibrium function. For example, the auditory and vestibular modulations occur as a result of hypertonicity and muscular spasm, which in turn irritates nerves and blood vessels that affect auris interna function by muscular trapping. Relief of the affected nerve or muscular contractions act to relieve auditory or vestibular symptoms. Medications, including barbiturates or diazepam, thus relieve auditory or vestibular dysfunction in TMD patients.

Utricular Dysfunction

The utricle is one of the two otolith organs found in the vestibular labyrinth. It is responsive to both gravity and linear acceleration along the horizontal plane. Utricular dysfunction is a disorder caused by damage to the utricle. It is often characterized by a subject's perception of tilting or imbalance.

Vertigo

Vertigo is described as a feeling of spinning or swaying while the body is stationary. There are two types of vertigo. Subjective vertigo is the false sensation of movement of the body. Objective vertigo is the perception that one's surrounding are in motion. It is often accompanied by nausea, vomiting, and difficulty maintaining balance.

While not wishing to be bound by any one theory, it is hypothesized that vertigo is caused by an over-accumulation of fluid in the endolymph. This fluid imbalance results in increased pressure on the cells of the inner ear which leads to the sensation of movement. The most common cause of vertigo is benign paroxysmal positional vertigo, or BPPV. In some cases, it is brought on by a head injury, or a sudden change of blood pressure. It is a diagnostic symptom of several diseases including superior canal dehiscence syndrome.

Local Otic Administration

Also provided herein are methods, formulations, and compositions for local delivery of therapeutic agents (otic agents) to auris externa, auris media, and/or auris interna structures. In some embodiments, local delivery of the therapeutic agent (otic agent) overcomes the toxic and attendant side effects of systemic delivery. In some embodiments, access to the vestibular and cochlear apparatus is through the auris media and includes the round window membrane, the oval window/stapes footplate, the annular ligament and through the otic capsule/temporal bone.

Provided herein, in certain embodiments, are otic formulations and compositions that remain in contact with the target auditory surfaces (e.g., the round window) for extended periods of time. In some embodiments, the otic formulations and compositions further comprise mucoadhesives that allow the otic formulations to adhere to otic mucosal surfaces. In some instances, the formulations and compositions described herein avoid attenuation of therapeutic benefit due to drainage or leakage of active agents via the eustachian tube.

In some embodiments, the localized treatment of the auris externa, auris media and/or auris interna affords the use of previously undesired therapeutic agents, including agents with poor PK profiles, poor uptake, low systemic release and/or toxicity issues. In some embodiments, localized targeting of the otic agent formulations and compositions reduces the risk of adverse effects with previously characterized toxic or ineffective therapeutic agents (otic active agents), (e.g., immunomodulatory agents such as anti-TNF agents). Accordingly, also contemplated within the scope of the embodiments described herein is the use of active agents and/or agents that have been previously rejected by practitioners because of adverse effects or ineffectiveness of the therapeutic agent (otic agent).

In some embodiments, specifically targeting the auris externa, auris media and/or auris interna structures avoids the adverse side effects usually associated with systemic treatment. In some embodiments, the otic formulations and compositions described herein are controlled release therapeutic agent formulations (e.g., immunomodulating agent or auris pressure modulator formulation) and compositions that treat otic disorders by providing a constant, variable and/or extended source of a therapeutic agent (otic agent) to the individual or patient suffering from an otic disorder, thereby reducing or eliminating the variability of treatment. Accordingly, one embodiment disclosed herein is to provide a formulation or composition that enables at least one therapeutic agent (otic agent) to be released in therapeutically effective doses either at variable or constant rates such as to ensure a continuous release of the at least one therapeutic agent (otic agent). In some embodiments, the therapeutic agents (otic agents) disclosed herein are administered as an immediate release formulation or composition. In other embodiments, the therapeutic agents (otic agents) are administered as a controlled release formulation, released either continuously or in a pulsatile manner, or variants of both. In still other embodiments, the therapeutic agent (otic agent) formulation or composition is administered as both an immediate release and controlled release formulation or composition, released either continuously or in a pulsatile manner, or variants of both. The release is optionally dependent on environmental or physiological conditions, for example, the external ionic environment (see, e.g. Oros® release system, Johnson & Johnson).

Also included within the embodiments disclosed herein is the use of additional therapeutic agents (otic agents), such as auris externa, auris media and/or auris interna agents, in combination with the otic formulations and compositions disclosed herein comprising therapeutic agents. When used, such additional therapeutic agents (otic agents) assist in the treatment of hearing or equilibrium loss or dysfunction as a result of an autoimmune disorder, including vertigo, tinnitus, hearing loss, balance disorders, infections, inflammatory response or combinations thereof. Accordingly, additional therapeutic agents (otic agents) that ameliorate or reduce the effects of vertigo, tinnitus, hearing loss, balance disorders, infections, inflammatory response or combinations thereof are also contemplated to be used in combination with the therapeutic agents (otic agents) described herein. Additional therapeutic agents (otic agents) include but are not limited to steroids, anti-emetic agents, local anesthetic agents, corticosteroids, chemotherapeutic agents, including cytoxan, azathiaprine or methotrexate; treatment with collagen, gamma globulin, interferons, copaxone, central nervous system agents, antibiotics, platelet-activating factor antagonists, nitric oxide synthase inhibitors and combinations thereof.

In addition, the otic compositions or formulations included herein also optionally include carriers, adjuvants, such as preserving, stabilizing, wetting or emulsifying agents, solution promoters, salts for regulating the osmotic pressure, and/or buffers. Such carriers, adjuvants, and other excipients are compatible with the environment in the auris externa, auris media and/or auris interna. Accordingly, specifically contemplated are carriers, adjuvants and excipients that lack ototoxicity or are minimally ototoxic in order to allow effective treatment of the otic disorders contemplated herein with minimal side effects in the targeted regions or areas. To prevent ototoxicity, otic compositions or formulations disclosed herein are optionally targeted to distinct regions of the auris externa, auris media and/or auris interna, including but not limited to the tympanic cavity, vestibular bony and membranous labyrinths, cochlear bony and membranous labyrinths and other anatomical or physiological structures located within the auris interna.

Treatment

Provided herein are otic formulations and compositions suitable for the treatment of any otic condition, disease or disorder (e.g., outer, middle and/or inner ear disorders) described herein, comprising administration of a therapeutic agent (otic agent) described herein to an individual or patient in need thereof. The formulations and compositions described herein are suitable for the treatment of any disease described herein. In some instances, the treatment is long-term treatment for chronic recurring disease. In some instances, the treatment is prophylactic administration of an otic formulation described herein for the treatment of any otic disease or disorder described herein. In some instances, prophylactic administration avoids occurrence of disease in individuals suspected of having a disease or in individuals genetically predisposed to an otic disease or disorder. In some instances the treatment is preventive maintenance therapy. In some instances, preventive maintenance therapy avoids recurrence of a disease.

In some instances, because of their otic compatibility and improved sterility, the otic formulations and compositions described herein are safe for long-term administration. In some embodiments, the otic formulations and compositions described herein have very low ototoxicity.

In some embodiments, the otic formulations and compositions described herein provide a steady sustained release of a therapeutic agent (otic agent) for a period of at least one day, three days, five days, one week, two weeks, three weeks, a month, two months, three months, four months, five months, six months, or a year. In some embodiments, the otic formulations and compositions described herein provide a steady sustained release of a therapeutic agent (otic agent) for a period of at least three days. In some embodiments, the otic formulations and compositions described herein provide a steady sustained release of a therapeutic agent (otic agent) for a period of at least five days. In some embodiments, the otic formulations and compositions described herein provide a steady sustained release of a therapeutic agent (otic agent) for a period of at least one week. In some embodiments, the otic formulations and compositions described herein provide a steady sustained release of a therapeutic agent (otic agent) for a period of at least two weeks. In some embodiments, the otic formulations and compositions described herein provide a steady sustained release of a therapeutic agent (otic agent) for a period of at least three weeks. In some embodiments, the otic formulations and compositions described herein provide a steady sustained release of a therapeutic agent (otic agent) for a period of at least a month. In some embodiments, the otic formulations and compositions described herein provide a steady sustained release of a therapeutic agent (otic agent) for a period of at least two months. In some embodiments, the otic formulations and compositions described herein provide a steady sustained release of a therapeutic agent (otic agent) for a period of at least three months. In some embodiments, the otic formulations and compositions described herein provide a steady sustained release of a therapeutic agent (otic agent) for a period of at least four months. In some embodiments, the otic formulations and compositions described herein provide a steady sustained release of a therapeutic agent (otic agent) for a period of at least five months. In some embodiments, the otic formulations and compositions described herein provide a steady sustained release of a therapeutic agent (otic agent) for a period of at least six months. In some embodiments, the otic formulations and compositions described herein provide a steady sustained release of a therapeutic agent (otic agent) for a period of at least a year.

In some embodiments, the otic formulations and compositions described herein provide a steady sustained release of a therapeutic agent (otic agent) for a period of about a day, three days, five days, one week, two weeks, three weeks, a month, two months, three months, four months, five months, six months, or a year. In some embodiments, the otic formulations and compositions described herein provide a steady sustained release of a therapeutic agent (otic agent) for a period of about three days. In some embodiments, the otic formulations and compositions described herein provide a steady sustained release of a therapeutic agent (otic agent) for a period of about five days. In some embodiments, the otic formulations and compositions described herein provide a steady sustained release of a therapeutic agent (otic agent) for a period of about one week. In some embodiments, the otic formulations and compositions described herein provide a steady sustained release of a therapeutic agent for a period of about two weeks. In some embodiments, the otic formulations and compositions described herein provide a steady sustained release of a therapeutic agent (otic agent) for a period of about three weeks. In some embodiments, the otic formulations and compositions described herein provide a steady sustained release of a therapeutic agent (otic agent) for a period of about a month. In some embodiments, the otic formulations and compositions described herein provide a steady sustained release of a therapeutic agent (otic agent) for a period of about two months. In some embodiments, the otic formulations and compositions described herein provide a steady sustained release of a therapeutic agent (otic agent) for a period of about three months. In some embodiments, the otic formulations and compositions described herein provide a steady sustained release of a therapeutic agent (otic agent) for a period of about four months. In some embodiments, the otic formulations and compositions described herein provide a steady sustained release of a therapeutic agent (otic agent) for a period of about five months. In some embodiments, the otic formulations and compositions described herein provide a steady sustained release of a therapeutic agent (otic agent) for a period of about six months. In some embodiments, the otic formulations and compositions described herein provide a steady sustained release of a therapeutic agent (otic agent) for a period of about a year.

In one aspect, provided herein are controlled release compositions and formulations to treat and/or prevent diseases or conditions associated with the ear. In some instances, these diseases or conditions associated with the ear include the outer, the middle ear and/or inner ear.

Such otic diseases or conditions include ceruminosis or ceruminosis is associated with a disease or condition. In some embodiments, disease or condition is ear pruritus, otitis externa, otalgia, tinnitus, vertigo, ear fullness, hearing loss, or a combination thereof.

Other otic diseases or conditions include autoimmune inner ear disorder (AIED), Ménière's disease, endolymphatic hydrops, noise induced hearing loss (NIHL), sensorineural hearing loss (SNL), tinnnitus, otosclerosis, balance disorders, vertigo and the like. In some embodiments, the disease or condition associated with the ear is Meniere's disease, sensorineural hearing loss, noise induced hearing loss, presbycusis (age related hearing loss), auto immune ear disease, tinnitus, ototoxicity, excitotoxicity, endolymphatic hydrops, labyrinthitis, Ramsay Hunt's Syndrome, vestibular neuronitis, microvascular compression syndrome, hyperacusis, presbystasis, central auditory processing disorder, auditory neuropathy, or improvement of cochlea implant performance.

The etiology of several ear diseases or disorders consists of a syndrome of progressive hearing loss, including noise induced hearing loss and age-related hearing loss, dizziness, nausea, nystagmus, vertigo, tinnitus, inflammation, swelling, infection and/or congestion. These disorders have many causes, such as infection, exposure to noise, injury, inflammation, tumors and/or adverse response to drugs or other chemical agents. Several causes of hearing and/or equilibrium impairment are attributed to inflammation and/or an autoimmune disorder and/or a cytokine-mediated inflammatory response.

Provided herein are immunomodulator compositions and formulations to treat otic diseases or conditions. In some embodiments, these compositions and formulations are controlled release. In some instances, the otic diseases or conditions are inflammation or infection of the auris media, including otitis media. Immunomodulators include but are not limited anti-TNF agents, calcineurin inhibitors, IKK inhibitors, an interleukin inhibitors, TNF-α converting enzymes (TACE) inhibitors, or toll-like receptor inhibitors.

Provided herein are aural pressure modulating compositions and formulations to treat of otic diseases or conditions. In some embodiments, these compositions and formulations are controlled release. In some instances, otic diseases or conditions are fluid homeostasis disorder of the inner ear, which include Meniere's Disease, endolymphatic hydrops, progressive hearing loss, noise induced hearing loss, age-related hearing loss, dizziness, vertigo, tinnitus and similar conditions. Examples of aural pressure modulating agents include but are not limited to modulators of aquaporin, estrogen related receptor beta modulators, gap junction protein modulators, NMDA receptor modulators, including NMDA receptor antagonists, osmotic diuretics, progesterone receptor modulators, prostaglandin modulators, or vasopressin receptor modulators.

In some embodiments, the formulations and compositions provided herein are CNS modulating compositions and formulations to treat tinnitus, progressive hearing loss, including noise induced hearing loss and age-related hearing loss, and balance disorders. Balance disorders include benign paroxysmal positions vertigo, dizziness, endolymphatic hydrops, kinetosis, labyrinthitis, Mal de debarquement, Meniere's Disease, Meniere's Syndrome, myringitis, otitis media, Ramsay Hunt's Syndrome, recurrent vestibulopathy, tinnitus, vertigo, microvascular compression syndrome, utricular dysfunction, and vestibular neuronitis. A few therapeutic products are available for the treatment of balance disorders, including $GABA_A$ receptor modulators and local anesthetics.

In some embodiments, the formulations and compositions provided herein are cytotoxic agent compositions and formulations for the treatment of autoimmune diseases of the ear, including autoimmune inner ear disease (AIED). Also provided herein are controlled release cytotoxic agent compositions for the treatment of disorders of the auris media, including otitis media. The compositions disclosed herein are also useful for the treatment of cancer, particularly cancer of the ear. A few therapeutic products are available for the treatment of AIED, including certain cytotoxic agents. Particularly, the cytotoxic agents methotrexate and cyclophosphamide have been tested and are used for systemic treatment of AIED. Also, thalidomide, while not currently administered for the treatment of AIED, has been used to treat Behçet's disease, which is often associated with AIED.

In some embodiments, the formulations and compositions provided herein comprise auris sensory cell modulators for treating or ameliorating hearing loss or reduction resulting from destroyed, stunted, malfunctioning, damaged, fragile or missing hairs in the inner ear. Further disclosed herein are controlled release auris sensory cell modulating agent compositions and formulations to treat ototoxicity, excitotoxicity, sensorineural hearing loss, Meniere's Disease/Syndrome, endolymphatic hydrops, labyrinthitis, Ramsay Hunt's Syndrome, vestibular neuronitis and microvascular compression syndrome.

In some embodiments, the formulations and compositions provided herein are corticosteroid compositions and formulations to treat of otic diseases or conditions. In some embodiments, these compositions are controlled release.

In some embodiments, the formulations and compositions provided herein are antimicrobial agent compositions and formulations to treat of otic diseases or conditions. Otic diseases or conditions include but are not limited to otitis externa, otitis media, Ramsay Hunt syndrome, otosyphilis, AIED, Meniere's disease, and vestibular neuronitis. In some embodiments, these compositions are controlled release.

In some embodiments, the formulations and compositions provided herein prevent, relieve, reverse or ameliorate the degeneration of neurons and/or hair cells of the auris due to free radicals and/or the dysfunction of the mitochondria.

Also provided herein are ion channel modulating compositions and formulations to treat fluid homeostasis disorders of the inner ear, including Meniere's Disease, endolymphatic hydrops, progressive hearing loss, including noise induced hearing loss and age-related hearing loss, dizziness, vertigo, tinnitus and similar conditions. In some embodiments, these compositions and formulations are controlled release. Systemic routes via oral, intravenous or intramuscular routes are currently used to deliver ion channel modulating therapeutic agents.

Provided herein are truncated TrkC or truncated TrkB antagonist compositions and formulations to treat otic diseases and conditions. In some embodiments, these compositions and formulations are controlled release.

Provided herein are non-natural TrkC or TrkB agonist compositions and formulations to treat otic diseases and conditions. In some embodiments, these compositions and formulations are controlled release.

Triglycerides

Provided herein are otic formulations and compositions comprising triglycerides. Triglycerides are esters derived from glycerol and three fatty acids. In some instances, these fatty acids are saturated fatty acids, unsaturated fatty acids, or a combination thereof. Provided herein in one aspect, is an otic formulation or a composition comprising a therapeutic agent, or pharmaceutically acceptable prodrug or salt thereof; and triglycerides comprising medium chain fatty acids; wherein the triglycerides are present in an amount that is sufficient to stabilize the therapeutic agent for injection into the ear, and wherein the otic pharmaceutical formulation or composition comprises at least about 50% by weight of the triglycerides.

In some instances, these triglycerides are medium chain triglycerides (MCTs). In some embodiments, these triglycerides comprise medium chain fatty acids.

In some embodiments, the triglycerides are derived from glycerol and medium chain fatty acids. In some embodiments, each medium chain fatty acid independently comprises 6 to 12 carbon atoms in the carbon chain. In some embodiments, each medium chain fatty acid independently comprises 8 to 12 carbon atoms in the carbon chain. In some embodiments, each medium chain fatty acid independently comprises 6, 7, 8, 9, 10, 11, or 12 carbon atoms in the carbon chain. In some embodiments, each medium chain fatty acid independently comprises 8 or 10 carbon atoms in the carbon chain. In some embodiments, the medium chain fatty acids are caproic acid (hexanoic acid), enanthic acid (heptanoic acid), caprylic acid (octanoic acid), pelargonic acid (nonanoic acid), capric acid (decanoic acid), undecylenic acid (undec-10-enoic acid), lauric acid (dodecanoic acid), or a combination thereof. In some embodiments, the medium chain fatty acids are caprylic acid (octanoic acid), capric acid (decanoic acid), or a combination thereof.

In some embodiments, the triglycerides comprising medium chain fatty acids are balassee oil, coconut oil, cohune oil, palm kernel oil, tucum oil, or combinations thereof. In some embodiments, the triglycerides comprising medium chain fatty acids are balassee oil. In some embodiments, the triglycerides comprising medium chain fatty acids are coconut oil. In some embodiments, the triglycerides comprising medium chain fatty acids are cohune oil. In some embodiments, the triglycerides comprising medium chain fatty acids are palm kernel oil. In some embodiments, the triglycerides comprising medium chain fatty acids are tucum oil.

In some embodiments, the otic pharmaceutical formulation has triglycerides in an amount that is sufficient to stabilize the therapeutic agent for injection into the ear. In some embodiments, the otic pharmaceutical formulation has triglycerides in an amount that is sufficient to provide sufficient retention time in the ear. In some embodiments, the ear is the outer ear, middle ear, or inner ear. In some embodiments, the otic pharmaceutical formulation has triglycerides in an amount that is sufficient to provide sustained release of the therapeutic agent. In some embodiments, the triglycerides are present in an amount that is sufficient to allow delivery of the formulation via a narrow gauge needle.

In some embodiments, the otic pharmaceutical formulation comprises between about 50% to about 99.9% by weight of the triglycerides. In some embodiments, the otic pharmaceutical formulation comprises between about 55% to about 99.9% by weight of the triglycerides. In some embodiments, the otic pharmaceutical formulation comprises between about 60% to about 99.9% by weight of the triglycerides. In some embodiments, the otic pharmaceutical formulation comprises between about 65% to about 99.9% by weight of the triglycerides. In some embodiments, the otic pharmaceutical formulation comprises between about 70% to about 99.9% by weight of the triglycerides. In some embodiments, the otic pharmaceutical formulation comprises between about 75% to about 99.9% by weight of the triglycerides. In some embodiments, the otic pharmaceutical formulation comprises between about 80% to about 99.9% by the weight of the triglycerides. In some embodiments, the otic pharmaceutical formulation comprises between about 85% to about 99.9% by the weight of the triglycerides. In some embodiments, the otic pharmaceutical formulation comprises between about 90% to about 99.9% by the weight of the triglycerides. In some embodiments, the otic pharmaceutical formulation comprises between about 95% to about 99.9% by the weight of the triglycerides.

In some embodiments, the otic pharmaceutical formulation comprises between about 50% to about 99.99% by weight of the triglycerides. In some embodiments, the otic pharmaceutical formulation comprises between about 55% to about 99.99% by weight of the triglycerides. In some embodiments, the otic pharmaceutical formulation comprises between about 60% to about 99.99% by weight of the triglycerides. In some embodiments, the otic pharmaceutical formulation comprises between about 65% to about 99.99% by weight of the triglycerides. In some embodiments, the otic pharmaceutical formulation comprises between about 70% to about 99.99% by weight of the triglycerides. In some embodiments, the otic pharmaceutical formulation comprises between about 75% to about 99.99% by weight of the triglycerides. In some embodiments, the otic pharmaceutical formulation comprises between about 80% to about 99.99% by weight of the triglycerides. In some embodiments, the otic pharmaceutical formulation comprises between about 85% to about 99.99% by weight of the triglycerides. In some embodiments, the otic pharmaceutical formulation comprises between about 90% to about 99.99% by weight of the triglycerides. In some embodiments, the otic pharmaceutical formulation comprises between about 95% to about 99.99% by weight of the triglycerides.

In some embodiments, the otic pharmaceutical formulation comprises between about 50% to about 95% by weight of the triglycerides. In some embodiments, the otic pharmaceutical formulation comprises between about 55% to about 95% by weight of the triglycerides. In some embodiments, the otic pharmaceutical formulation comprises between about 60% to about 95% by weight of the triglycerides. In some embodiments, the otic pharmaceutical formulation comprises between about 65% to about 95% by weight of the triglycerides. In some embodiments, the otic pharmaceutical formulation comprises between about 70% to about 95% by weight of the triglycerides. In some embodiments, the otic pharmaceutical formulation comprises between about 75% to about 95% by weight of the triglycerides. In some embodiments, the otic pharmaceutical formulation comprises between about 80% to about 95% by weight of the triglycerides. In some embodiments, the otic pharmaceutical formulation comprises between about 85% to about 95% by weight of the triglycerides. In some embodiments, the otic pharmaceutical formulation comprises between about 90% to about 95% by weight of the triglycerides.

In some embodiments, the otic pharmaceutical formulation comprises between about 50% to about 55% by weight of the triglycerides. In some embodiments, the otic pharmaceutical formulation comprises between about 55% to about 60% by weight of the triglycerides. In some embodiments, the otic pharmaceutical formulation comprises between about 60% to about 65% by weight of the triglycerides. In some embodiments, the otic pharmaceutical formulation comprises between about 65% to about 70% by weight of the triglycerides. In some embodiments, the otic pharmaceutical formulation comprises between about 70% to about 75% by weight of the triglycerides. In some embodiments, the otic pharmaceutical formulation comprises between about 75% to about 80% by weight of the triglycerides. In some embodiments, the otic pharmaceutical formulation comprises between about 80% to about 85% by weight of the triglycerides. In some embodiments, the otic pharmaceutical formulation comprises between about 85% to about 90% by weight of the triglycerides. In some embodiments, the otic pharmaceutical formulation comprises between about 90% to about 95% by weight of the triglycerides. In some embodiments, the otic pharmaceutical formulation comprises between about 95% to about 99% by weight of the triglycerides. In some embodiments, the otic pharmaceutical formulation comprises between about 95% to about 99.9% by weight of the triglycerides. In some embodiments, the otic pharmaceutical formulation comprises between about 95% to about 99.99% by weight of the triglycerides.

In some embodiments, the otic pharmaceutical formulation comprises between about 50% to about 60% by weight of the triglycerides. In some embodiments, the otic pharmaceutical formulation comprises between about 60% to about 70% by weight of the triglycerides. In some embodiments, the otic pharmaceutical formulation comprises between about 70% to about 80% by weight of the triglycerides. In some embodiments, the otic pharmaceutical formulation comprises between about 80% to about 90% by weight of the triglycerides. In some embodiments, the otic pharmaceutical formulation comprises between about 90% to about 99% by weight of the triglycerides. In some embodiments, the otic pharmaceutical formulation comprises between about 90% to about 99.9% by weight of the triglycerides. In some embodiments, the otic pharmaceutical formulation comprises between about 90% to about 99.99% by weight of the triglycerides.

In some embodiments, the otic pharmaceutical formulation comprises about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% by weight of the triglycerides.

In some embodiments, the otic pharmaceutical formulation comprises about 50% by weight of the triglycerides. In some embodiments, the otic pharmaceutical formulation comprises about 51% by weight of the triglycerides. In some embodiments, the otic pharmaceutical formulation comprises about 52% by weight of the triglycerides. In some embodiments, the otic pharmaceutical formulation comprises about 53% by weight of the triglycerides. In some embodiments, the otic pharmaceutical formulation comprises about 54% by weight of the triglycerides. In some embodiments, the otic pharmaceutical formulation comprises about 55% by weight of the triglycerides. In some embodiments, the otic pharmaceutical formulation comprises about 56% by weight of the triglycerides. In some embodiments, the otic pharmaceutical formulation comprises about 57% by weight of the triglycerides. In some embodiments, the otic pharmaceutical formulation comprises about 58% by weight of the triglycerides. In some embodiments, the otic pharmaceutical formulation comprises about 59% by weight of the triglycerides. In some embodiments, the otic pharmaceutical formulation comprises about 60% by weight of the triglycerides. In some embodiments, the otic pharmaceutical formulation comprises about 61% by weight of the triglycerides. In some embodiments, the otic pharmaceutical formulation comprises about 62% by weight of the triglycerides. In some embodiments, the otic pharmaceutical formulation comprises about 63% by weight of the triglycerides. In some embodiments, the otic pharmaceutical formulation comprises about 64% by weight of the triglycerides. In some embodiments, the otic pharmaceutical formulation comprises about 65% by weight of the triglycerides. In some embodiments, the otic pharmaceutical formulation comprises about 66% by weight of the triglycerides. In some embodiments, the otic pharmaceutical formulation comprises about 67% by weight of the triglycerides. In some embodiments, the otic pharmaceutical formulation comprises about 68% by weight of the triglycerides. In some embodiments, the otic pharmaceutical formulation comprises about 69% by weight of the triglycerides. In some embodiments, the otic pharmaceutical formulation comprises about 70% by weight of the triglycerides. In some embodiments, the otic pharmaceutical formulation comprises about 71% by weight of the triglycerides. In some embodiments, the otic pharmaceutical formulation comprises about 72% by weight of the triglycerides. In some embodiments, the otic pharmaceutical formulation comprises about 73% by weight of the triglycerides. In some embodiments, the otic pharmaceutical formulation comprises about 74% by weight of the triglycerides. In some embodiments, the otic pharmaceutical formulation comprises about 75% by weight of the triglycerides. In some embodiments, the otic pharmaceutical formulation comprises about 76% by weight of the triglycerides. In some embodiments, the otic pharmaceutical formulation comprises about 77% by weight of the triglycerides. In some embodiments, the otic pharmaceutical formulation comprises about 78% by weight of the triglycerides. In some embodiments, the otic pharmaceutical formulation comprises about 79% by weight of the triglycerides. In some embodiments, the otic pharmaceutical formulation comprises about 80% by weight of the triglycerides. In some embodiments, the otic pharmaceutical formulation comprises about 81% by weight of the triglycerides. In some embodiments, the otic pharmaceutical formulation comprises about 82% by weight of the triglycerides. In some embodiments, the otic pharmaceutical formulation comprises about 83% by weight of the triglycerides. In some embodiments, the otic pharmaceutical formulation comprises about 84% by weight of the triglycerides. In some embodiments, the otic pharmaceutical formulation comprises about 85% by weight of the triglycerides. In some embodiments, the otic pharmaceutical formulation comprises about 86% by weight of the triglycerides. In some embodiments, the otic pharmaceutical formulation comprises about 87% by weight of the triglycerides. In some embodiments, the otic pharmaceutical formulation comprises about 88% by weight of the triglycerides. In some embodiments, the otic pharmaceutical formulation comprises about 89% by weight of the triglycerides. In some embodiments, the otic pharmaceutical formulation comprises about 90% by weight of the triglycerides. In some embodiments, the otic pharmaceutical formulation comprises about 91% by weight of the triglycerides. In some embodiments, the otic pharmaceutical formulation comprises about 92% by weight of the triglycerides. In some embodiments, the otic pharmaceutical formulation comprises about 93% by weight of the triglycerides. In some embodiments, the otic pharmaceutical formulation comprises about 94% by weight of the triglycerides. In some embodiments, the otic pharmaceutical formulation comprises about 95% by weight of the triglycerides. In some embodiments, the otic pharmaceutical formulation comprises about 96% by weight of the triglycerides. In some embodiments, the otic pharmaceutical formulation comprises about 97% by weight of the triglycerides. In some embodiments, the otic pharmaceutical formulation comprises about 98% by weight of the triglycerides. In some embodiments, the otic pharmaceutical formulation comprises about 99% by weight of the triglycerides.

In some embodiments, the triglycerides in any one of the otic formulations and compositions described herein are replaced with at least one of the following components in the corresponding amounts of triglyceride in the formulation or composition disclosed herein: mineral oil or any corresponding higher alkanes; Vaseline (petroleum jelly); silicone oil (polydimethylsiloxane) in different molecular weights; beeswax dissolved in any of the oils disclosed herein.

In some embodiments, the otic formulation or composition further comprises at least one viscosity modulating agent. In some embodiments, the at least one viscosity modulating agent is silicon dioxide, povidone, carbomer, poloxamer, or a combination thereof. In some embodiments, the viscosity modulating agent is silicon dioxide. In some embodiments, the viscosity modulating agent is povidone. In some embodiments, the viscosity modulating agent is carbomer. In some embodiments, the viscosity modulating agent is poloxamer. In some embodiments, the viscosity modulating agents are silicon dioxide and povidone. In some embodiments, the viscosity modulating agents are silicon dioxide and carbomer. In some embodiments, the viscosity modulating agents are silicon dioxide and poloxamer. In some embodiments, the poloxamer is P407.

In some embodiments, the otic formulation or composition comprises between about 0.01% to about 40% by weight of the povidone. In some embodiments, the otic formulation or composition comprises between about 0.01% to about 35% by weight of the povidone. In some embodiments, the otic formulation or composition comprises between about 0.01% to about 30% by weight of the povidone. In some embodiments, the otic formulation or composition comprises between about 0.01% to about 25% by weight of the povidone. In some embodiments, the otic formulation or composition comprises between about 0.01% to about 20% by weight of the povidone. In some embodiments, the otic formulation or composition comprises between about 0.01% to about 15% by weight of the povidone. In some embodiments, the otic formulation or composition comprises between about 0.01% to about 10% by weight of the povidone. In some embodiments, the otic formulation or composition comprises about 0.01% to about 7% by weight of the povidone. In some embodiments, the otic formulation or composition comprises comprises between about 0.01% to about 5% by weight of the povidone. In some embodiments, the otic formulation or composition comprises between about 0.01% to about 3% by weight of the povidone. In some embodiments, the otic formulation or composition comprises comprises between about 0.01% to about 2% by weight of the povidone. In some embodiments, the otic formulation or composition comprises about 0.01% to about 1% by weight of the povidone.

In some embodiments, the otic formulation or composition comprises about 0.01% by weight of the povidone. In some embodiments, the otic formulation or composition comprises about 0.02% by weight of the povidone. In some embodiments, the otic formulation or composition comprises about 0.03% by weight of the povidone. In some embodiments, the otic formulation or composition comprises about 0.04% by weight of the povidone. In some embodiments, the otic formulation or composition comprises about 0.05% by weight of the povidone. In some embodiments, the otic formulation or composition comprises about 0.06% by weight of the povidone. In some embodiments, the otic formulation or composition comprises about 0.07% by weight of the povidone. In some embodiments, the otic formulation or composition comprises about 0.08% by weight of the povidone. In some embodiments, the otic formulation or composition comprises about 0.09% by weight of the povidone. In some embodiments, the otic formulation or composition comprises about 0.1% by weight of the povidone. In some embodiments, the otic formulation or composition comprises about 0.2% by weight of the povidone. In some embodiments, the otic formulation or composition comprises about 0.3% by weight of the povidone. In some embodiments, the otic formulation or composition comprises about 0.4% by weight of the povidone. In some embodiments, the otic formulation or composition comprises about 0.5% by weight of the povidone. In some embodiments, the otic formulation or composition comprises about 0.6% by weight of the povidone. In some embodiments, the otic formulation or composition comprises about 0.7% by weight of the povidone. In some embodiments, the otic formulation or composition comprises about 0.8% by weight of the povidone. In some embodiments, the otic formulation or composition comprises about 0.9% by weight of the povidone. In some embodiments, the otic formulation or composition comprises about 1% by weight of the povidone. In some embodiments, the otic formulation or composition comprises about 2% by weight of the povidone. In some embodiments, the otic formulation or composition comprises about 3% by weight of the povidone. In some embodiments, the otic formulation or composition comprises about 4% by weight of the povidone. In some embodiments, the otic formulation or composition comprises about 5% by weight of the povidone. In some embodiments, the otic formulation or composition comprises about 6% by weight of the povidone. In some embodiments, the otic formulation or composition comprises about 7% by weight of the povidone. In some embodiments, the otic formulation or composition comprises about 8% by weight of the povidone. In some embodiments, the otic formulation or composition comprises about 9% by weight of the povidone. In some embodiments, the otic formulation or composition comprises about 10% by weight of the povidone. In some embodiments, the otic formulation or composition comprises about 11% by weight of the povidone. In some embodiments, the otic formulation or composition comprises about 12% by weight of the povidone. In some embodiments, the otic formulation or composition comprises about 13% by weight of the povidone. In some embodiments, the otic formulation or composition comprises about 14% by weight of the povidone. In some embodiments, the otic formulation or composition comprises about 15% by weight of the povidone. In some embodiments, the otic formulation or composition comprises about 16% by weight of the povidone. In some embodiments, the otic formulation or composition comprises about 17% by weight of the povidone. In some embodiments, the otic formulation or composition comprises about 18% by weight of the povidone. In some embodiments, the otic formulation or composition comprises about 19% by weight of the povidone. In some embodiments, the otic formulation or composition comprises about 20% by weight of the povidone. In some embodiments, the otic formulation or composition comprises about 25% by weight of the povidone. In some embodiments, the otic formulation or composition comprises about 30% by weight of the povidone. In some embodiments, the otic formulation or composition comprises about 35% by weight of the povidone. In some embodiments, the otic formulation or composition comprises about 40% by weight of the povidone.

In some embodiments, the otic formulation or composition comprises between about 0.01% to about 40% by weight of the carbomer. In some embodiments, the otic formulation or composition comprises between about 0.01% to about 35% by weight of the carbomer. In some embodiments, the otic formulation or composition comprises between about 0.01% to about 30% by weight of the carbomer. In some embodiments, the otic formulation or composition comprises between about 0.01% to about 25% by weight of the carbomer. In some embodiments, the otic formulation or composition comprises between about 0.01% to about 20% by weight of the carbomer. In some embodiments, the otic formulation or composition comprises between about 0.01% to about 15% by weight of the carbomer. In some embodiments, the otic formulation or composition comprises between about 0.01% to about 10% by weight of the carbomer. In some embodiments, the otic formulation or composition comprises about 0.01% to about 7% by weight of the carbomer. In some embodiments, the otic formulation or composition comprises between about 0.01% to about 5% by weight of the carbomer. In some embodiments, the otic formulation or composition comprises between about 0.01% to about 3% by weight of the carbomer. In some embodiments, the otic formulation or composition comprises between about 0.01% to about 2% by weight of the carbomer. In some embodiments, the otic formulation or composition comprises about 0.01% to about 1% by weight of the carbomer.

In some embodiments, the otic formulation or composition comprises about 0.01% by weight of the carbomer. In some embodiments, the otic formulation or composition comprises about 0.02% by weight of the carbomer. In some embodiments, the otic formulation or composition comprises about 0.03% by weight of the carbomer. In some embodiments, the otic formulation or composition comprises about 0.04% by weight of the carbomer. In some embodiments, the otic formulation or composition comprises about 0.05% by weight of the carbomer. In some embodiments, the otic formulation or composition comprises about 0.06% by weight of the carbomer. In some embodiments, the otic formulation or composition comprises about 0.07% by weight of the carbomer. In some embodiments, the otic formulation or composition comprises about 0.08% by weight of the carbomer. In some embodiments, the otic formulation or composition comprises about 0.09% by weight of the carbomer. In some embodiments, the otic formulation or composition comprises about 0.1% by weight of the carbomer. In some embodiments, the otic formulation or composition comprises about 0.2% by weight of the carbomer. In some embodiments, the otic formulation or composition comprises about 0.3% by weight of the carbomer. In some embodiments, the otic formulation or composition comprises about 0.4% by weight of the carbomer. In some embodiments, the otic formulation or composition comprises about 0.5% by weight of the carbomer. In some embodiments, the otic formulation or composition comprises about 0.6% by weight of the carbomer. In some embodiments, the otic formulation or composition comprises about 0.7% by weight of the carbomer. In some embodiments, the otic formulation or composition comprises about 0.8% by weight of the carbomer. In some embodiments, the otic formulation or composition comprises about 0.9% by weight of the carbomer. In some embodiments, the otic formulation or composition comprises about 1% by weight of the carbomer. In some embodiments, the otic formulation or composition comprises about 2% by weight of the carbomer. In some embodiments, the otic formulation or composition comprises about 3% by weight of the carbomer. In some embodiments, the otic formulation or composition comprises about 4% by weight of the carbomer. In some embodiments, the otic formulation or composition comprises about 5% by weight of the carbomer. In some embodiments, the otic formulation or composition comprises about 6% by weight of the carbomer. In some embodiments, the otic formulation or composition comprises about 7% by weight of the carbomer. In some embodiments, the otic formulation or composition comprises about 8% by weight of the carbomer. In some embodiments, the otic formulation or composition comprises about 9% by weight of the carbomer. In some embodiments, the otic formulation or composition comprises about 10% by weight of the carbomer. In some embodiments, the otic formulation or composition comprises about 11% by weight of the carbomer. In some embodiments, the otic formulation or composition comprises about 12% by weight of the carbomer. In some embodiments, the otic formulation or composition comprises about 13% by weight of the carbomer. In some embodiments, the otic formulation or composition comprises about 14% by weight of the carbomer. In some embodiments, the otic formulation or composition comprises about 15% by weight of the carbomer. In some embodiments, the otic formulation or composition comprises about 16% by weight of the carbomer. In some embodiments, the otic formulation or composition comprises about 17% by weight of the carbomer. In some embodiments, the otic formulation or composition comprises about 18% by weight of the carbomer. In some embodiments, the otic formulation or composition comprises about 19% by weight of the carbomer. In some embodiments, the otic formulation or composition comprises about 20% by weight of the carbomer. In some embodiments, the otic formulation or composition comprises about 25% by weight of the carbomer. In some embodiments, the otic formulation or composition comprises about 30% by weight of the carbomer. In some embodiments, the otic formulation or composition comprises about 35% by weight of the carbomer. In some embodiments, the otic formulation or composition comprises about 40% by weight of the carbomer.

In some embodiments, the otic formulation or composition comprises between about 0.01% to about 40% by weight of the poloxamer. In some embodiments, the otic formulation or composition comprises between about 0.01% to about 35% by weight of the poloxamer. In some embodiments, the otic formulation or composition comprises between about 0.01% to about 30% by weight of the poloxamer. In some embodiments, the otic formulation or composition comprises between about 0.01% to about 25% by weight of the poloxamer. In some embodiments, the otic formulation or composition comprises between about 0.01% to about 20% by weight of the poloxamer. In some embodiments, the otic formulation or composition comprises between about 0.01% to about 15% by weight of the poloxamer. In some embodiments, the otic formulation or composition comprises between about 0.01% to about 10% by weight of the poloxamer. In some embodiments, the otic formulation or composition comprises about 0.01% to about 7% by weight of the poloxamer. In some embodiments, the otic formulation or composition comprises between about 0.01% to about 5% by weight of the poloxamer. In some embodiments, the otic formulation or composition comprises between about 0.01% to about 3% by weight of the poloxamer. In some embodiments, the otic formulation or composition comprises between about 0.01% to about 2% by weight of the poloxamer. In some embodiments, the otic formulation or composition comprises about 0.01% to about 1% by weight of the poloxamer.

In some embodiments, the otic formulation or composition comprises about 0.01% by weight of the poloxamer. In some embodiments, the otic formulation or composition comprises about 0.02% by weight of the poloxamer. In some embodiments, the otic formulation or composition comprises about 0.03% by weight of the poloxamer. In some embodiments, the otic formulation or composition comprises about 0.04% by weight of the poloxamer. In some embodiments, the otic formulation or composition comprises about 0.05% by weight of the poloxamer. In some embodiments, the otic formulation or composition comprises about 0.06% by weight of the poloxamer. In some embodiments, the otic formulation or composition comprises about 0.07% by weight of the poloxamer. In some embodiments, the otic formulation or composition comprises about 0.08% by weight of the poloxamer. In some embodiments, the otic formulation or composition comprises about 0.09% by weight of the poloxamer. In some embodiments, the otic formulation or composition comprises about 0.1% by weight of the poloxamer. In some embodiments, the otic formulation or composition comprises about 0.2% by weight of the poloxamer. In some embodiments, the otic formulation or composition comprises about 0.3% by weight of the poloxamer. In some embodiments, the otic formulation or composition comprises about 0.4% by weight of the poloxamer. In some embodiments, the otic formulation or composition comprises about 0.5% by weight of the poloxamer. In some embodiments, the otic formulation or composition comprises about 0.6% by weight of the poloxamer. In some embodiments, the otic formulation or composition comprises about 0.7% by weight of the poloxamer. In some embodiments, the otic formulation or composition comprises about 0.8% by weight of the poloxamer. In some embodiments, the otic formulation or composition comprises about 0.9% by weight of the poloxamer. In some embodiments, the otic formulation or composition comprises about 1% by weight of the poloxamer. In some embodiments, the otic formulation or composition comprises about 2% by weight of the poloxamer. In some embodiments, the otic formulation or composition comprises about 3% by weight of the poloxamer. In some embodiments, the otic formulation or composition comprises about 4% by weight of the poloxamer. In some embodiments, the otic formulation or composition comprises about 5% by weight of the poloxamer. In some embodiments, the otic formulation or composition comprises about 6% by weight of the poloxamer. In some embodiments, the otic formulation or composition comprises about 7% by weight of the poloxamer. In some embodiments, the otic formulation or composition comprises about 8% by weight of the poloxamer. In some embodiments, the otic formulation or composition comprises about 9% by weight of the poloxamer. In some embodiments, the otic formulation or composition comprises about 10% by weight of the poloxamer. In some embodiments, the otic formulation or composition comprises about 11% by weight of the poloxamer. In some embodiments, the otic formulation or composition comprises about 12% by weight of the poloxamer. In some embodiments, the otic formulation or composition comprises about 13% by weight of the poloxamer. In some embodiments, the otic formulation or composition comprises about 14% by weight of the poloxamer. In some embodiments, the otic formulation or composition comprises about 15% by weight of the poloxamer. In some embodiments, the otic formulation or composition comprises about 16% by weight of the poloxamer. In some embodiments, the otic formulation or composition comprises about 17% by weight of the poloxamer. In some embodiments, the otic formulation or composition comprises about 18% by weight of the poloxamer. In some embodiments, the otic formulation or composition comprises about 19% by weight of the poloxamer. In some embodiments, the otic formulation or composition comprises about 20% by weight of the poloxamer. In some embodiments, the otic formulation or composition comprises about 25% by weight of the poloxamer. In some embodiments, the otic formulation or composition comprises about 30% by weight of the poloxamer. In some embodiments, the otic formulation or composition comprises about 35% by weight of the poloxamer. In some embodiments, the otic formulation or composition comprises about 40% by weight of the poloxamer.

In some embodiments, the otic formulation or composition comprises between about 0.01% to about 20% by weight of the silicon dioxide. In some embodiments, the otic formulation or composition comprises between about 0.01% to about 15% by weight of the silicon dioxide. In some embodiments, the otic formulation or composition comprises between about 0.01% to about 10% by weight of the silicon dioxide. In some embodiments, the otic formulation or composition comprises about 0.01% to about 7% by weight of the silicon dioxide. In some embodiments, the otic formulation or composition comprises between about 0.01% to about 5% by weight of the silicon dioxide. In some embodiments, the otic formulation or composition comprises between about 0.01% to about 3% by weight of the silicon dioxide. In some embodiments, the otic formulation or composition comprises between about 0.01% to about 2% by weight of the silicon dioxide. In some embodiments, the otic formulation or composition comprises about 0.01% to about 1% by weight of the silicon dioxide.

In some embodiments, the otic formulation or composition comprises about 0.01% by weight of the silicon dioxide. In some embodiments, the otic formulation or composition comprises about 0.02% by weight of the silicon dioxide. In some embodiments, the otic formulation or composition comprises about 0.03% by weight of the silicon dioxide. In some embodiments, the otic formulation or composition comprises about 0.04% by weight of the silicon dioxide. In some embodiments, the otic formulation or composition comprises about 0.05% by weight of the silicon dioxide. In some embodiments, the otic formulation or composition comprises about 0.06% by weight of the silicon dioxide. In some embodiments, the otic formulation or composition comprises about 0.07% by weight of the silicon dioxide. In some embodiments, the otic formulation or composition comprises about 0.08% by weight of the silicon dioxide. In some embodiments, the otic formulation or composition comprises about 0.09% by weight of the silicon dioxide. In some embodiments, the otic formulation or composition comprises about 0.1% by weight of the silicon dioxide. In some embodiments, the otic formulation or composition comprises about 0.2% by weight of the silicon dioxide. In some embodiments, the otic formulation or composition comprises about 0.3% by weight of the silicon dioxide. In some embodiments, the otic formulation or composition comprises about 0.4% by weight of the silicon dioxide. In some embodiments, the otic formulation or composition comprises about 0.5% by weight of the silicon dioxide. In some embodiments, the otic formulation or composition comprises about 0.6% by weight of the silicon dioxide. In some embodiments, the otic formulation or composition comprises about 0.7% by weight of the silicon dioxide. In some embodiments, the otic formulation or composition comprises about 0.8% by weight of the silicon dioxide. In some embodiments, the otic formulation or composition comprises about 0.9% by weight of the silicon dioxide. In some embodiments, the otic formulation or composition comprises about 1% by weight of the silicon dioxide. In some embodiments, the otic formulation or composition comprises about 2% by weight of the silicon dioxide. In some embodiments, the otic formulation or composition comprises about 3% by weight of the silicon dioxide. In some embodiments, the otic formulation or composition comprises about 4% by weight of the silicon dioxide. In some embodiments, the otic formulation or composition comprises about 5% by weight of the silicon dioxide. In some embodiments, the otic formulation or composition comprises about 6% by weight of the silicon dioxide. In some embodiments, the otic formulation or composition comprises about 7% by weight of the silicon dioxide. In some embodiments, the otic formulation or composition comprises about 8% by weight of the silicon dioxide. In some embodiments, the otic formulation or composition comprises about 9% by weight of the silicon dioxide. In some embodiments, the otic formulation or composition comprises about 10% by weight of the silicon dioxide. In some embodiments, the otic formulation or composition comprises about 11% by weight of the silicon dioxide. In some embodiments, the otic formulation or composition comprises about 12% by weight of the silicon dioxide. In some embodiments, the otic formulation or composition comprises about 13% by weight of the silicon dioxide. In some embodiments, the otic formulation or composition comprises about 14% by weight of the silicon dioxide. In some embodiments, the otic formulation or composition comprises about 15% by weight of the silicon dioxide. In some embodiments, the otic formulation or composition comprises about 16% by weight of the silicon dioxide. In some embodiments, the otic formulation or composition comprises about 17% by weight of the silicon dioxide. In some embodiments, the otic formulation or composition comprises about 18% by weight of the silicon dioxide. In some embodiments, the otic formulation or composition comprises about 19% by weight of the silicon dioxide. In some embodiments, the otic formulation or composition comprises about 20% by weight of the silicon dioxide.

In some embodiments, the viscosity modulating agent is silicon dioxide. In some embodiments, the viscosity modulating agent is a polymer, such as povidone, carbomer, or poloxamer. In some embodiments, the viscosity modulating agent is a polysaccharide, such as dextran or alginate. In some embodiments, the viscosity modulating agent is cellulose-based, such as hydroxypropyl cellulose, hydroxypropyl methylcellulose, carboxymethylcellulose, carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), and noncrystalline cellulose. In some embodiments, the viscosity modulating agent is polyvinyl alcohol (PVA). In some embodiments, the viscosity modulating agent is polyethylene glycol (PEG) based.

In some embodiments, the otic formulation or composition comprises between about 0.01% to about 40% by weight of the viscosity modulating agent(s). In some embodiments, the otic formulation or composition comprises between about 0.01% to about 35% by weight of the viscosity modulating agent(s). In some embodiments, the otic formulation or composition comprises between about 0.01% to about 30% by weight of the viscosity modulating agent(s). In some embodiments, the otic formulation or composition comprises between about 0.01% to about 25% by weight of the viscosity modulating agent(s). In some embodiments, the otic formulation or composition comprises between about 0.01% to about 20% by weight of the viscosity modulating agent(s). In some embodiments, the otic formulation or composition comprises between about 0.01% to about 15% by weight of the viscosity modulating agent(s). In some embodiments, the otic formulation or composition comprises between about 0.01% to about 10% by weight of the viscosity modulating agent(s). In some embodiments, the otic formulation or composition comprises about 0.01% to about 7% by weight of the viscosity modulating agent(s). In some embodiments, the otic formulation or composition comprises comprises between about 0.01% to about 5% by weight of the viscosity modulating agent(s). In some embodiments, the otic formulation or composition comprises between about 0.01% to about 3% by weight of the viscosity modulating agent(s). In some embodiments, the otic formulation or composition comprises between about 0.01% to about 2% by weight of the viscosity modulating agent(s). In some embodiments, the otic formulation or composition comprises about 0.01% to about 1% by weight of the viscosity modulating agent(s).

In some embodiments, the otic formulation or composition comprises about 0.01% by weight of the viscosity modulating agent(s). In some embodiments, the otic formulation or composition comprises about 0.02% by weight of the viscosity modulating agent(s). In some embodiments, the otic formulation or composition comprises about 0.03% by weight of the viscosity modulating agent(s). In some embodiments, the otic formulation or composition comprises about 0.04% by weight of the viscosity modulating agent(s). In some embodiments, the otic formulation or composition comprises about 0.05% by weight of the viscosity modulating agent(s). In some embodiments, the otic formulation or composition comprises about 0.06% by weight of the viscosity modulating agent(s). In some embodiments, the otic formulation or composition comprises about 0.07% by weight of the viscosity modulating agent(s). In some embodiments, the otic formulation or composition comprises about 0.08% by weight of the viscosity modulating agent(s). In some embodiments, the otic formulation or composition comprises about 0.09% by weight of the viscosity modulating agent(s). In some embodiments, the otic formulation or composition comprises about 0.1% by weight of the viscosity modulating agent(s). In some embodiments, the otic formulation or composition comprises about 0.2% by weight of the viscosity modulating agent(s). In some embodiments, the otic formulation or composition comprises about 0.3% by weight of the viscosity modulating agent(s). In some embodiments, the otic formulation or composition comprises about 0.4% by weight of the viscosity modulating agent(s). In some embodiments, the otic formulation or composition comprises about 0.5% by weight of the viscosity modulating agent(s). In some embodiments, the otic formulation or composition comprises about 0.6% by weight of the viscosity modulating agent(s). In some embodiments, the otic formulation or composition comprises about 0.7% by weight of the viscosity modulating agent(s). In some embodiments, the otic formulation or composition comprises about 0.8% by weight of the viscosity modulating agent(s). In some embodiments, the otic formulation or composition comprises about 0.9% by weight of the viscosity modulating agent(s). In some embodiments, the otic formulation or composition comprises about 1% by weight of the viscosity modulating agent(s). In some embodiments, the otic formulation or composition comprises about 2% by weight of the viscosity modulating agent(s). In some embodiments, the otic formulation or composition comprises about 3% by weight of the viscosity modulating agent(s). In some embodiments, the otic formulation or composition comprises about 4% by weight of the viscosity modulating agent(s). In some embodiments, the otic formulation or composition comprises about 5% by weight of the viscosity modulating agent(s). In some embodiments, the otic formulation or composition comprises about 6% by weight of the viscosity modulating agent(s). In some embodiments, the otic formulation or composition comprises about 7% by weight of the viscosity modulating agent(s). In some embodiments, the otic formulation or composition comprises about 8% by weight of the viscosity modulating agent(s). In some embodiments, the otic formulation or composition comprises about 9% by weight of the viscosity modulating agent(s). In some embodiments, the otic formulation or composition comprises about 10% by weight of the viscosity modulating agent(s). In some embodiments, the otic formulation or composition comprises about 11% by weight of the viscosity modulating agent(s). In some embodiments, the otic formulation or composition comprises about 12% by weight of the viscosity modulating agent(s). In some embodiments, the otic formulation or composition comprises about 13% by weight of the viscosity modulating agent(s). In some embodiments, the otic formulation or composition comprises about 14% by weight of the viscosity modulating agent(s). In some embodiments, the otic formulation or composition comprises about 15% by weight of the viscosity modulating agent(s). In some embodiments, the otic formulation or composition comprises about 16% by weight of the viscosity modulating agent(s). In some embodiments, the otic formulation or composition comprises about 17% by weight of the viscosity modulating agent(s). In some embodiments, the otic formulation or composition comprises about 18% by weight of the viscosity modulating agent(s). In some embodiments, the otic formulation or composition comprises about 19% by weight of the viscosity modulating agent(s). In some embodiments, the otic formulation or composition comprises about 20% by weight of the viscosity modulating agent(s). In some embodiments, the otic formulation or composition comprises about 25% by weight of the viscosity modulating agent(s). In some embodiments, the otic formulation or composition comprises about 30% by weight of the viscosity modulating agent(s). In some embodiments, the otic formulation or composition comprises about 35% by weight of the viscosity modulating agent(s). In some embodiments, the otic formulation or composition comprises about 40% by weight of the viscosity modulating agent(s).

Therapeutic Agents

In some embodiments, the otic formulations and compositions described herein have pH and osmolarity that are auris-acceptable. In some embodiments, the otic formulations and compositions described herein meet the stringent sterility requirements described herein and are compatible with the endolymph and/or the perilymph. Pharmaceutical agents that are used in conjunction with the formulations and compositions disclosed herein include agents that ameliorate or lessen otic disorders, including auris interna disorders, and their attendant symptoms, which include but are not limited to hearing loss, nystagmus, vertigo, tinnitus, inflammation, swelling, infection and congestion. Otic disorders have many causes and include infection, injury, inflammation, tumors and adverse response to drugs or other chemical agents that are responsive to the pharmaceutical agents disclosed herein. In some embodiments, pharmaceutically active metabolites, salts, polymorphs, prodrugs, analogues, and derivatives of the otic agents disclosed herein are used in the formulations.

Active ingredients or therapeutic agents (also known as otic agents) include, but are not limited to, immunomodulating agents, aural pressure modulating agents, corticosteroids, antimicrobial agents, antagonists of truncated TrkC or truncated TrkB, or non-natural TrkB or TrkC agonists, or a WNT modulator. In some embodiments, the therapeutic agent is an immunomodulating agent. In some embodiments, the therapeutic agent is an aural pressure modulating agent. In some embodiments, the therapeutic agent is a corticosteroid. In some embodiments, the therapeutic agent is an antimicrobial agent. In some embodiments, the therapeutic agent is an antagonist of truncated TrkC or truncated TrkB. In some embodiments, the therapeutic agent is a non-natural TrkB or Trk C agonist. In some embodiments, the therapeutic agent is a corticosteroid, an antimicrobial agent, or a NMDA receptor antagonist. In some embodiments, the therapeutic agent is dexamethasone, ciprofloxacin, or gacyclidine. In some embodiments, therapeutic agent is a WNT modulator.

In some embodiments, the therapeutic agent is an anti-TNF agent, a calcineurin inhibitor, an IKK inhibitor, an interleukin inhibitor, a TNF-α converting enzyme (TACE) inhibitor, or a toll-like receptor inhibitor. In some embodiments, the therapeutic agent is a modulator of aquaporin, an estrogen related receptor beta modulator, a gap junction protein modulator, an NMDA receptor antagonist, an osmotic diuretic, a progesterone receptor modulator, a prostaglandin modulator, or a vasopressin receptor modulator. In some embodiments, the therapeutic agent is 1-aminoadamantane, dextromethorphan, dextrorphan, ibogaine, ketamine, esketamine (AM-101), nitrous oxide, phencyclidine, riluzole, tiletamine, memantine, dizocilpine, aptiganel, remacimide, 7-chlorokynurenate, DCKA (5,7-dichlorokynurenic acid), kynurenic acid, 1-aminocyclopropanecarboxylic acid (ACPC), AP7 (2-amino-7-phosphonoheptanoic acid), APV (R-2-amino-5-phosphonopentanoate), CPPene (3-[(R)-2-carboxypiperazin-4-yl]-prop-2-enyl-1-phosphonic acid); (+)-(1S,2S)-1-(4-hydroxy-phenyl)-2-(4-hydroxy-4-phenylpiperidino)-1-pro-panol; (1S,2S)-1-(4-hydroxy-3-methoxyphenyl)-2-(4-hydroxy-4-phenylpiperi-dino)-1-propanol; (3R,4S)-3-(4-(4-fluorophenyl)-4-hydroxypiperidin-1-yl-)-chroman-4,7-diol; (1R*,2R*)-1-(4-hydroxy-3-methylphenyl)-2-(4-(4-fluoro-phenyl)-4-hydroxypiperidin-1-yl)-propan-1-ol-mesylate; or gacyclidine (1-[(1R,2S)-2-methyl-1-thiophen-2-ylcyclohexyl]piperidine). In some embodiments, the therapeutic agent is gacyclidine or the pharmaceutically acceptable salt thereof.

Other therapeutic agents contemplated for use include but are not limited to anti-inflammatory agents, anti-oxidants, neuroprotective agents, glutamate modulators, TNF-alpha modulators, interleukin 1 beta modulators, retinaldehyde modulators, notch modulators, gamma-secretase modulators, thalidomide, ion and/or fluid (e.g., water) homeostasis modulators, vasopressin inhibitors, inhibitors of the vasopressin-mediated AQP2 (aquaporin 2) system, transcriptional regulators of the inner-ear transcriptional regulatory network (including, e.g., transcriptional regulators of estrogen-related receptor beta), inner ear hair cell growth factors, including BDNF (brain derived neurotrophic factor) and neurotrophin-3, and other therapeutic modalities.

Therapeutic agents explicitly include an agonist of an otic target, a partial agonist of an otic target, an antagonist of an otic target, a partial agonist of an otic target, an inverse agonist of an otic target, a competitive antagonist of an otic target, a neutral antagonist of an otic target, an orthosteric antagonist of an otic target, an allosteric antagonist of an otic target a positive allosteric modulator of an otic target, a negative allosteric modulator of an otic target, or combinations thereof.

For some embodiments, wherein the formulation or composition is designed such that the active ingredient has limited or no systemic release, therapeutic agents that produce systemic toxicities (e.g., liver toxicity) or have poor PK characteristics (e.g. short half-life) are also optionally used. Thus, in some embodiments, therapeutic agents that have been previously shown to be toxic, harmful or non-effective during systemic application, for example through toxic metabolites formed after hepatic processing, toxicity of the drug in particular organs, tissues or systems, through high levels needed to achieve efficacy, through the inability to be released through systemic pathways or through poor PK characteristics, are useful. The formulations and compositions disclosed herein are contemplated to be targeted directly to otic structures where treatment is needed; for example, one embodiment contemplated is the direct application of the otic formulations disclosed herein onto the round window membrane or the crista fenestrae cochlea of the auris interna, allowing direct access and treatment of the auris interna, or inner ear components. In other embodiments, the otic formulations and compositions disclosed herein are applied directly to the oval window. In yet other embodiments, direct access is obtained through microinjection directly into the auris interna, for example, through cochlear microperfusion. Such embodiments also optionally comprise a drug delivery device, wherein the drug delivery device delivers the aural pressure modulating formulations through use of a needle and syringe, a pump, a microinjection device, a spongy material or any combination thereof.

In still other embodiments, application of any otic formulation or composition described herein is targeted to the auris media through piercing of the intratympanic membrane and applying the otic agent formulation directly to the auris media structures affected, including the walls of the tympanic cavity or auditory ossicles. In some embodiments, the auris active agent formulations and compositions disclosed herein are confined to the targeted auris media structure, and will not be lost, for example, through diffusion or leakage through the eustachian tube or pierced tympanic membrane. In some embodiments, the otic formulations and compositions disclosed herein are delivered to the auris externa in any suitable manner, including by cotton swab, injection or ear drops. Also, in other embodiments, the otic formulations and compositions described herein are targeted to specific regions of the auris externa by application with a needle and syringe, a pump, a microinjection device, a spongy material or any combination thereof. For example, in the case of treatment of otitis externa, antimicrobial agent formulations disclosed herein are delivered directly to the ear canal, where they are retained, thereby reducing loss of the active agents from the target ear structure by drainage or leakage.

In some embodiments, agents that have been previously rejected as, for example, an antimicrobial agent, find use herein because of the targeted nature of the embodiments which bypass systemic effects, including toxicity and harmful side effects. By way of example only, onercept, a previously rejected anti-TNF agent due to toxicity and safety issues, is useful as an anti-TNF agent in some of the embodiments disclosed herein. Also contemplated within the scope of embodiments described herein is the administration of higher doses of pharmaceutical agents, for example agents that have dose limiting toxicities, compared to currently approved doses for such pharmaceutical agents Some pharmaceutical agents, either alone or in combination, are ototoxic. For example, some chemotherapeutic agents, including actinomycin, bleomycin, cisplatin, carboplatin and vincristine; and antibiotics, including erythromycin, gentamicin, streptomycin, dihydrostreptomycin, tobramycin, netilmicin, amikacin, neomycin, kanamycin, etiomycin, vancomycin, metronidizole, capreomycin, are mildly to very toxic, and affect the vestibular and cochlear structures differentially in some instances. However, in some embodiments, the combination of an ototoxic drug, for example cisplatin, in combination with an antioxidant is protective and lessen the ototoxic effects of the drug. Moreover, the localized application of the potentially ototoxic drug lessens the toxic effects that might otherwise occur through systemic application through the use of lower amounts with maintained efficacy, or the use of targeted amounts for a shorter period of time. Accordingly, a skilled practitioner choosing a course of therapy for targeted otic disorder will have the knowledge to avoid or combine an ototoxic compound, or to vary the amount or course of treatment to avoid or lessen ototoxic effects.

In certain instances, pharmaceutical excipients, diluents or carriers are potentially ototoxic. For example, benzalkonium chloride, a common preservative, is ototoxic and therefore potentially harmful if introduced into the vestibular or cochlear structures. In formulating a controlled release otic formulation, it is advised to avoid or combine the appropriate excipients, diluents or carriers to lessen or eliminate potential ototoxic components from the formulation, or to decrease the amount of such excipients, diluents or carriers. In some instances, the ototoxicity of the pharmaceutical agents, excipients, diluents, carriers, or formulations and compositions disclosed herein is ascertained using an accepted animal model. See, e.g., Maritini, A., et al. *Ann. N.Y. Acad. Sci.* (1999) 884:85-98. Optionally, a controlled release otic formulation or composition includes otoprotective agents, such as antioxidants, alpha lipoic acid, calicum, fosfomycin or iron chelators, to counteract potential ototoxic effects that arise from the use of specific therapeutic agents or excipients, diluents or carriers.

Other agents that are used in the embodiments disclosed herein, either alone or in combination with other auris interna agents, include anti-apoptotic agents, including caspases, JNK inhibitors (by way of example only CEP/KT-7515, AS601245, SPC9766 and SP600125), antioxidants, NSAIDs, neuroprotectants, glutamate modulators, interleukin 1 modulators, interleukin-1 antagonists, including tumor necrosis factor-α converting enzyme (TACE) and caspases, retinaldehyde modulator, notch modulator, gamma secretase modulator, thalidomide, latanoprost (Xalatan®) for reducing internal pressure and combinations thereof.

Immunomodulating Agents
Anti-TNF Agents

Contemplated for use with the formulations and compositions disclosed herein are agents which reduce or ameliorate symptoms or effects as a result of an autoimmune disease and/or inflammatory disorder, including AIED or OM. Accordingly, some embodiments incorporate the use of agents which block the effects of TNF-α, including anti-TNF agents. By way of example only, anti-TNF agents include protein-based therapeutics, such as etanercept (ENBREL®), infliximab (REMICADE®), adalimumab (HU-MIRA®) and golimumab (CNTO 148), and small molecule therapeutics, such as TACE inhibitors, IKK inhibitors or calcineurin inhibitors or combinations thereof.

Infliximab and adalimumab are anti-TNF monoclonal antibodies, and etanercept is a fusion protein designed to bind specifically to the TNF protein. All are currently approved for use in the treatment of rheumatoid arthritis. Golimumab, which is currently in Phase 3 clinical trials for rheumatoid arthritis, psoriatic arthritis and ankylosing spondylitis, is a fully-humanized anti-TNF-alpha IgG1 monoclonal antibody that targets and neutralizes both the soluble and the membrane-bound form of TNF-α. Other antagonists to TNF, by way of example only, include TNF receptors (pegylated soluble TNF receptor type 1; Amgen); TNF binding factors (Onercept; Serono); TNF antibodies (US Patent App. No. 2005/0123541; US Patent App. No. 2004/0185047); single domain antibodies against the p55 TNF receptor (US Patent App. No. 2008/00088713); soluble TNF receptors (US Patent App. No. 2007/0249538); fusion polypeptides binding to TNF (US Patent App. No. 2007/0128177); and flavone derivatives (US Patent App. No. 2006/0105967), all of which are incorporated by reference for such disclosure. The use of onercept, a soluble TNF p55 receptor, was discontinued in 2005. Three phase-III clinical trials reported patients diagnosed with fatal sepsis. A risk to benefit analysis was subsequently performed, resulting in the discontinuation of the clinical trials. As discussed above, the embodiments herein specifically contemplate the use of anti-TNF agents which have been previously shown to have limited or no systemic release, systemic toxicity, poor PK characteristics of combinations thereof.

Although etanercept, infliximab and adalimumab are currently approved systemic therapies for use in rheumatoid arthritis, these anti-TNF agents are not without serious adverse side effects. It is contemplated that in some embodiments that the localized application of the anti-TNF agents to the target otic structures for treatment of autoimmune and/or inflammatory disorders results in the reduction or elimination of these adverse side effects experienced with systemic treatment. Moreover, in some embodiments, localized treatment with the anti-TNF agents contemplated herein reduces the amount of agent needed for effective treatment of the targeted disorder due, for example, to the existence of the biological blood barrier in the auris interna or to the lack of sufficient systemic access to the auris media.

Etanercept is a dimeric fusion protein consisting of the extracellular ligand-binding portion of the human 75 kilodalton (p'75) tumor necrosis factor receptor (TNFR) linked to the Fc portion of human IgG1. The Fc component of etanercept contains the $C_H2$ domain, the $C_H3$ domain and hinge region, but not the $C_H1$ domain of IgG1. Etanercept is a recombinant protein consisting of 934 amino acids, with an apparent molecular weight of approximately 150 kilodaltons. Etanercept binds specifically to tumor necrosis factor (TNF), and acts by inhibiting the interaction of TNF with cell surface TNF receptors. Serious side effects with etanercept have been reported with systemic administration, including serious infections and sepsis that resulted in fatalities. Other side effects observed upon intravenous administration of etanercept include contraction of tuberculosis; onset or exacerbation of central nervous system disorders, including mental status changes, transverse myelitis, optic neuritis, multiple sclerosis and seizures resulting in permanent disability; adverse hematologic events, including pancytopenia, aplastic anemia with fatal outcomes, blood dyscrasias, persistent fever, bruising, bleeding and pallor, neutropenia and cellulitis. Treatment with etanercept, in some cases, also results in the formation of autoantibodies, which develops into a lupus-like syndrome, as well as development of malignant disorders. Moreover, over one-third of patients systemically treated with etanercept experience injection site reactions including mild to moderate erythema and/or itching, pain and/or swelling. Injection site bleeding and bruising has also been observed. Other side effects from the systemic administration of etanercept include headache, nausea, rhinitis, dizziness, pharyngitis, cough, asthenia, abdominal pain, rash, peripheral edema, respiratory disorder, dyspepsia, sinusitis, vomiting, mouth ulcer, alopecia and pneumon itis. Infrequent side effects include heart failure, myocardial infarction, myocardial ischemia, hypertension, hypotension, deep vein thrombosis, thrombophlebitis, cholecystitis, pancreatitis, gastrointestinal hemorrhage, bursitis, polymyositis, cerebral ischemia, depression, dyspnea, pulmonary embolism, and membranous glomerulonephropathy in rheuma toid arthritis patients. Varicella infections, gastroenteritis, depression/personality disorder, cutaneous ulcer, esophagitis/gastritis, group A streptococcal septic shock, type I diabetes mellitus, and soft tissue and post-operative wound infection was also seen in juvenile rheumatoid arthritis patients.

Infliximab is a chimeric human-mouse IgG1K monoclonal antibody with an approximate molecular weight of 149 kilodaltons. Infliximab binds specifically to TNFα with an association constant of $10^{10}$ $M^{-1}$. Infliximab is produced by a recombinant cell line cultured by continuous perfusion. Infliximab acts to neutralize the binding activity of TNFα by inhibiting binding of TNF to its cell surface receptors. Serious side effects as a result of systemic intravenous infusions or injections have been reported with the use of infliximab, including fatal sepsis and serious infections. Cases of histoplasmosis, listeriosis, pneumocystosis and tuberculosis have also been observed. Hypersensitivity, including urticaria, dyspnea and hypotension have occurred upon treatment with infliximab. Infusion reactions include cardiopulmonary reactions (primarily chest pain, hypotension, hypertension or dyspnea), pruritus, and combined reactions. Other hypersensitivity symptoms include fever, rash, headache, sore throat, myalgias, polyarthraligias, hand and facial edema and/or dysphagia, anaphylaxis, convulsions, erythematous rash, laryngeal/pharyngeal edema and severe bronchospasm. Neurologic adverse events include optic neuritis, seizure and new onset or exacerbation and/or radiographic evidence of central nervous system demyelinating disorders, including multiple sclerosis. The formation of autoantibodies have also been observed, including symptoms suggestive of a lupus-like syndrome following treatment. Other serious adverse events include worsening rheumatoid arthritis, rheumatoid nodules, abdominal hernia, asthenia, chest pain, diaphragmatic hernia, pancytopenia, splenic infarction, splenomegaly, syncope, cerebral hypoxia, convulsions, dizziness, encephalopathy, hemiparesis, spinal stenosis, upper motor neuron lesion, ceruminosis, endophthalmitis, and other infrequent-occurring side effects.

Adalimumab is a recombinant human IgG1 monoclonal antibody specific for human TNF. Adalimumab was created using phage display technology resulting in an antibody with human derived heavy and light chain variable regions and human IgG1:κ constant regions, and consists of 1330 amino acids with a molecular weight of approximately 148 kilodaltons. Adalimumab binds specifically to TNF-α and blocks its interaction with both the p55 and p75 TNF cell surface receptors. Adalimumab also lyses TNF expressing cells in vitro in the presence of complement. Adalimumab does not bind or inactivate lymphotoxin (TNF-β). Serious side effects from systemic administration have been reported with the intravenous administration or injection of adalimumab, including fatal sepsis and serious infections, including upper respiratory infections, bronchitis, urinary tract infections, pneumonia, septic arthritis, prosthetic and post-surgical infections, erysipelas cellulitis, diverticulitis, pyelonephritis, tuberculosis, and invasive opportunistic infections caused by histoplasma, *aspergillus* and nocardia. Other serious adverse reactions were neurologic events, including confusion, multiple sclerosis, paresthesia, subdural hematoma, and tremor, and the development of malignancies, including lymphoma development. The formation of autoantibodies has also been observed, including symptoms suggestive of a lupus-like syndrome following treatment. The most common adverse reaction was injection site reactions, with 20% of patients developing erythema and/or itching, hemorrhage, pain and/or swelling. Other adverse events as a result of systemic administration of adalimumab include clinical flare reaction, rash and pneumonia. Other adverse events included sinusitis, flu syndrome, nausea, abdominal pain, hypercholesterolemia, hyperlipidemia, hematuria, increased alkaline phosphatase levels, back pain, hypertension, as well as more infrequent serious adverse events, including pain, pelvic pain, thorax pain, arrthythmia, atrial fibrillation, cardiovascular disorder, congestive heart failure, coronary artery disorder, heart arrest, hypertensive encelphalopathy, myocardial infact, palpitation, pericardial effusion, pericarditis, syncope, tachycardia, vascular disorders, and other disorders.

Calcineurin Inhibitors

Calcineurin inhibitors are a group of structurally diverse small molecule immunomodulators which function through the inhibition of calcineurin function. Calcineurin is a calcium-activated protein phosphatase which catalyses the dephosphorylation of cytoplasmic NFAT. Upon dephosphorylation, NFAT migrates to the nucleus and forms a regulatory complex involved in the transcription of cytokines, such as TNF-α, IL-2, IL-3 and IL-4. Inhibition of calcineurin function blocks the dephosphorylation event and subsequent cytokine transcription. An unusual aspect of calcineurin inhibition is that cyclosporine, tacrolimus and pimecrolimus are required to form a complex with an immunophilin for the inhibitory properties to be realized (Schreiber et al, Immunol. Today (1992), 13:136-42; Liu et al, Cell (1991), 66:807-15). For cyclosporine the immunophilin is cyclophilin; tacrolimus and pimecrolimus bind to the FK506-binding protein (FKBP).

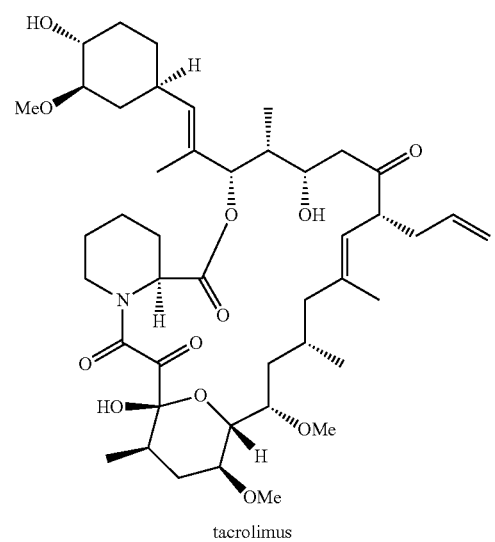

tacrolimus

-continued

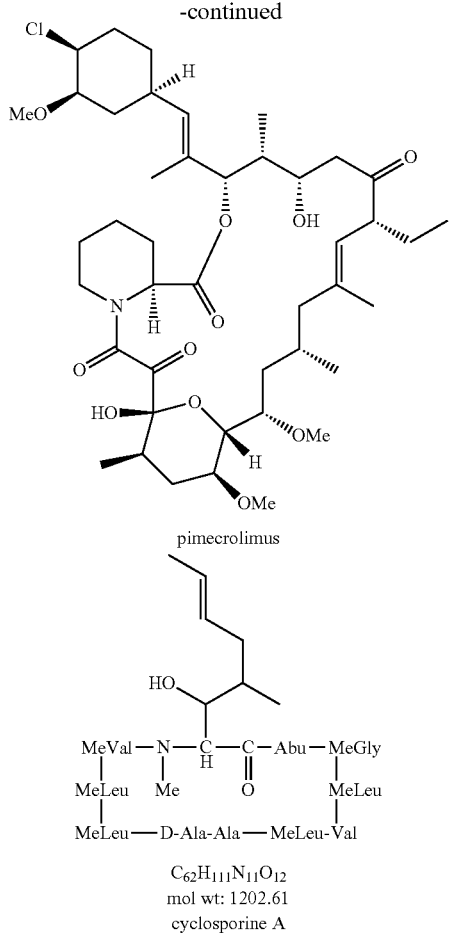

pimecrolimus

MeVal—N—C—C—Abu—MeGly
|       |   H   ||        |
MeLeu  Me      O        MeLeu
|                         |
MeLeu—D-Ala-Ala—MeLeu-Val $C_{62}H_{111}N_{11}O_{12}$
mol wt: 1202.61
cyclosporine A Cyclosporine is an 11-residue cyclic peptide produced as a metabolite of the fungus *Beauveria nivea* and has the chemical name cyclo[RE)-(2S,3R,4R)-3-hydroxy-4-methyl-2-(methylamino)-6-octenoyl]-L-2-aminobutyryl-N-methyl-glycyl-N-methyl-L-leucyl-L-valyl-N-methyl-L-leucyl-L-alanyl-D-alanyl-N-methyl-L-leucyl-N-methyl-L-leucyl-N-methyl-L-valyl. It is provided in several formulations for both systemic or local administration. Sandimmune® provides cyclosporine in three different formulations: soft gelatin capsules, an oral solution or a formulation for injection. Sandimmune® is indicated for prevention of organ rejection in kidney, liver or heart transplants. Neoral® and Gengraf® provide cyclosporine in two formulations: soft gelatin capsules and an oral solution. They are indicated for prevention of organ rejection in kidney, liver or heart transplants, for treatment of patients with severe active, rheumatoid arthritis, or for treatment of severe psoriasis. Compared to Sandimmune®, Neoral® and Gengraf® provide increased bioavailability of cyclosporine. Restasis® provides cyclosporine in an ophthalmic emulsion formulation. It is indicated to increase tear production in patients with reduced tear production due to ocular inflammation associated with keratoconjunctivitis sicca.

Tacrolimus, also known as FK-506 or fujimycin, is a 23-membered macrolide natural product produced by *Streptomyces tsukubaensis* and has the chemical name [3S-[3R*[E(1S*,3S*,4S*)], 4S*,5R*,8S*,9E,12R*,14R*,15S*,16R*,18S*,19S*,26aR*]]-5,6,8,11,12,13,14,15,16,17,18,19,24,25,26,26a-hexadecahydro-5,19-dihydroxy-3-[2-(4-hydroxy-3-methoxycyclohexyl)-1-methylethenyl]-14,16-dimethoxy-4,10,12,18-tetramethyl-8-(2-propenyl)-15,19-epoxy-3H-pyrido[2,1-39c][1,4]oxaazacyclotricosine-1,7,20,21(4H,23H)-tetrone monohydrate. It is provided in formulations suitable for systemic or topical administration. For systemic administration, the Prograf® formulation provides an oral capsule or a sterile solution for injection. Prograf® is indicated for prevention of organ rejection in liver, kidney or heart transplants. For topical administration, the Protopic® formulation is indicated for the treatment of moderate-to-severe atopic dermatitis.

Pimecrolimus is a semi-synthetic analog of tacrolimus and has the chemical name (1R,9S,12S,13R,14S,17R,18E,21S,23S,24R,25S,27R)-12-[(1E)-2-{(1R,3R,4S)-4-chloro-3-methoxycyclohexyl}-1-methylvinyl]-17-ethyl-1,14-dihydroxy-23,25-dimethoxy-13,19,21,27-tetramethyl-11,28-dioxa-4-aza-tricyclo[22.3.1.04,9]octacos-18-ene-2,3,10,16-tetraone. It is provided in a formulation suitable for topical application and is indicated for the treatment of mild-to-moderate atopic dermatitis.

Studies have shown that tacrolimus and pimecrolimus do not suppress Langerhans' cells or dermal connective tissue and therefore do not cause atrophy of the skin, unlike corticosteroids (Stuetz et al, Int. Arch. Allergy Immunol. (2006), 141:199-212; Queille-Roussel et al, Br. J. Dermatol. (2001), 144:507-13). Because of the importance of calcineurin, systemic administration of calcineurin inhibitors leads to significant side effects. Systemic side effects are related to dose, exposure levels and duration of therapy. Prolonged elevated blood levels result in hypertension, nephrotoxicity, psychiatric disorders, hyperlipidemia, and profound immunosuppression. Topical application of tacrolimus or pimecrolimus has shown to afford very little, if any, systemic exposure, with tacrolimus having demonstrated less than 0.5% bioavailability after topical application.

In one embodiment, the otic formulation or composition comprises a calcineurin inhibitor. In another embodiment, the otic formulation or composition comprises cyclosporine. In another embodiment, the otic formulation or composition comprises tacrolimus. In another embodiment, the otic formulation or composition comprises pimecrolimus. In another embodiment, the otic formulation or composition comprises a calcineurin inhibitor which induces toxicity upon systemic administration.

Other pharmaceutical agents that are optionally used in combination with immunomodulating-α agents for the treatment of autoimmune and/or inflammatory disorders include other agents that have been used to treat autoimmune and inflammatory disorders, including corticosteroids, local anesthetic agents, chemotherapeutic agents, including cytoxan, azathiaprine or methotrexate; treatment with collagen, gamma globulin, interferons, copaxone, or combinations thereof. Accordingly, also contemplated within the scope of the embodiments herein is the use of other therapeutic agents in combination with the immunomodulating compositions and formulations disclosed in the treatment of autoimmune otic disorders. In addition, other therapeutically agents are optionally used to treat attendant symptoms of AIED or other autoimmune disorder, including vomiting, dizziness and general malaise.

IKK Inhibitors

The transcription of TNF-α is dependent on the transcription factor NF-κB. In unstimulated cells, NF-κB is in the cytoplasm as part of a protein complex with the protein inhibitor of NF-κB, also known as IκB. Activation of NF-κB depends on phosphorylation-induced ubiquitination of the IκB. Once poly-ubiquitinated, the IκB undergoes a rapid degradation through the 26S proteasome and the free NF-κB migrates to the nucleus to activate pro-inflammatory gene transcription. The phosphorylation event which releases NF-κB is mediated by the IκB kinase (IKK) complex, composed of IKK kinases. Two IKK enzymes, generally referred to as IKK-α and IKK-β (Woronicz et al. Science (1997), 278:866; Zandi et al. Cell (1997), 91:243) or IKK-1 and IKK-2 (Mercurio et al. Science (1997), 278:860) have been discovered. In some instances, both forms of IKK exist as homodimers and as IKK-α/IKK-β heterodimers. Another component of the IκB kinase complex is a regulatory protein, known as IKK-γ or NEMO (NF-κB-Essential Modulator) (Rothwarf et al. Nature (1998), 395:297). NEMO does not contain a catalytic domain, and thus it appears to have no direct kinase activity and it probably serves a regulatory function. Existing data suggests that the predominant form of IKK in cells is an IKK-α/IKK-β heterodimer associated with either a dimer or a trimer of NEMO (Rothwarf et al. Nature (1998) 395:297). Biochemical and molecular biology experiments have identified IKK-α and IKK-β as the most likely mediators of TNF-α-induced IκB phosphorylation and degradation, which results in NF-κB activation and upregulation of families of genes involved in inflammatory processes (Woronicz et al. Science (1997); Karin, Oncogene (1999) 18:6867; Karin, J. Biol. Chem. (1999) 274:27339).

Many IKK-β inhibitors have been identified. SPC-839 has been extensively studied. It inhibits IKK-β with an $IC_{50}$ of 62 nM and reduces paw edema in a rat arthritis model at 30 mg/kg. Carboline PS-1145 inhibits the IKK complex with an $IC_{50}$ of 150 nM and reduces the production of TNF-α in LPS-challenged mice. BMS-345541, an allosteric inhibitor, inhibits IKK-β with an $IC_{50}$ of 0.3 μM. In the mouse collagen-induced arthritis model it significantly reduced the severity of disease at a 30 mg/kg dose. A scientific review of IKK inhibitors has been published (Karin et al., Nature Reviews Drug Discovery (2004), 3, 17-26), incorporated herein by reference for the disclosure of IKK inhibitors.

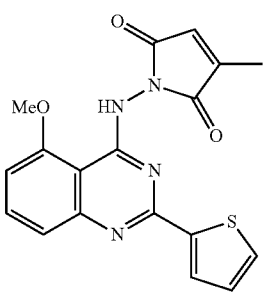

SPC-839

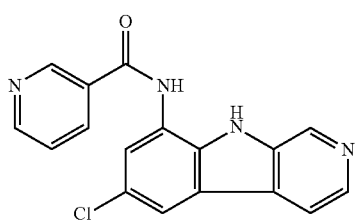

PS-1145

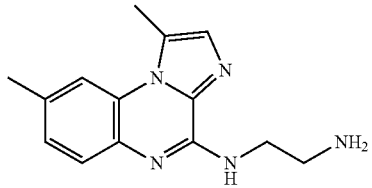

BMS-345541

In one embodiment, the otic formulation or composition comprises an IKK inhibitor. In a further embodiment, the otic formulation or composition comprises a IKK-β inhibitor. In another embodiment, the otic formulation or composition comprises a IKK inhibitor which induces toxicity upon systemic administration. In an additional embodiment, the otic formulation or composition comprises a IKK inhibitor which is not orally absorbed. In an additional embodiment, the otic formulation or composition comprises an IKK inhibitor selected from SPC-839, PS-1145, BMS-345541, and SC-514. In an additional embodiment, the otic formulation or composition comprises an IKK inhibitor selected from compounds disclosed in the following group of patent publications: WO199901441, WO2001068648, WO2002060386, WO2002030353, WO2003029242, WO2003010163, WO2001058890, WO2002044153, WO2002024679, WO2002046171, WO2003076447, WO2001030774, WO2001000610, WO2003024936, WO2003024935, WO2002041843, WO200230423, WO2002094265, WO2002094322, WO2005113544 and WO2006076318, all of which are incorporated by reference herein for the disclosure of IKK inhibitors.

Interleukin Inhibitors

Interleukins are a class of cytokines. In certain instances, they are signaling molecules secreted by leukocytes having encountered a pathogen. In certain instances, the secretion of interleukins activates and recruits additional leukocytes to the site of infection. In certain instances, the recruitment of additional leukocytes to the site of infection results in inflammation (due to the increase in leukocyte containing lymph). IL-1α, IL-1β, IL-2, and IL-8 are found in middle ear effusions. In certain instances, IL-1α and IL-1β are also found in the epithelium of cholesteatomas.

Il-1 is a class of interleukins comprised of IL-1α, and IL-1β. IL-1 is made by macrophages, B cells, monocytes, and dendritic cells (DC). It binds to receptors IL1R1/CD121a and IL1R2/CD121b. The binding of IL-1 to its receptors results in an increase in cell-surface adhesion factors. This enables the migration of leukocytes to the site of infection.

IL-2 is made by TH-1 cells and binds to the receptors CD25/IL2Ra, CD122IL2Rb, and CD132/IL2Rg. 11-2 secretion is stimulated by the binding of an antigen to a TH-1 cell. The binding of IL-2 to a receptor stimulates the growth, and differentiation of memory T cells.

IL-8 is made by macrophages, lymphocytes, epithelial cells, and endothelial cells. It binds to CXCR1/IL8Ra and CXCR2/IL8Ra/CD128. Secretion of IL-8 initiates neutrophil chemotaxis to the site of infection.

In some embodiments, a subject in need thereof is administered an inhibitor of a pro-inflammatory interleukin. In some embodiments, the pro-inflammatory interleukin is IL-1α, IL-1β, IL-2, or IL-8. In some embodiments, the inhibitor of a pro-inflammatory interleukin is a WS-4 (an antibody against IL-8); [Ser IL-8]$_{72}$; or [Ala IL-8]$_{77}$ (See U.S. Pat. No. 5,451,399 which is hereby incorporated by reference for disclosures relating to these peptides); IL-1RA; SB 265610 (N-(2-Bromophenyl)-N'-(7-cyano-1H-benzotriazol-4-yl)urea); SB 225002 (N-(2-Bromophenyl)-N'-(2-hydroxy-4-nitrophenyl)urea); SB203580 (4-(4-Fluorophenyl)-2-(4-methylsulfinyl phenyl)-5-(4-pyridyl) 1H-imidazole); SB272844 (GlaxoSmithKline); SB517785 (GlaxoSmithKline); SB656933 (GlaxoSmithKline); Sch527123 (2-hydroxy-N,N-dimethyl-3-{12-[[(R)-1-(5-methyl-furan-2-yl)-propyl]amino]-3,4-dioxo-cyclobut-1-enylamino}-benzamide); PD98059(2-(2-amino-3-methoxyphenyl)-4H-1-Benzopyran-4-one); reparixin; N-[4-chloro-2-hydroxy-3-(piperazine-1-sulfonyl)phenyl]-N'-(2-chloro-3-fluorophenyl)urea p-toluenesulfonate (See WO/2007/150016 which is hereby incorporated by reference for disclosures relating to this compound); sivelestat; bG31P (CXCL8((3-74))K11R/G31P); basiliximab; cyclosporin A; SDZ RAD (40-O-(2-hydroxyethyl)-rapamycin); FR235222 (Astellas Pharma); daclizumab; anakinra; AF12198 (Ac-Phe-Glu-Trp-Thr-Pro-Gly-Trp-Tyr-Gln-L-azetidine-2-carbonyl-Tyr-Ala-Leu-Pro-Leu-NH2) (SEQ ID NO: 119); or combinations thereof.

Platelet Activating Factor Antagonists

Platelet activating factor antagonists are contemplated for use in combination with the immunomodulating formulations disclosed herein. Platelet activating factor antagonists include, by way of example only, kadsurenone, phomactin G, ginsenosides, apafant (4-(2-chlorophenyl)-9-methyl-2[3 (4-morpholinyl)-3-propanol-1-yl[6H-thieno[3.2-f[[1.2.4]triazolo]4,3-1]]1.4]diazepine), A-85783, BN-52063, BN-52021, BN-50730 (tetrahedra-4,7,8,10 methyl-1 (chloro-1 phenyl)-6 (methoxy-4 phenyl-carbamoyl)-9 pyrido [4',3'-4,5] thieno [3,2-f] triazolo-1,2,4 [4,3-a] diazepine-1,4), BN 50739, SM-12502, RP-55778, Ro 24-4736, SR27417A, CV-6209, WEB 2086, WEB 2170, 14-deoxyandrographolide, CL 184005, CV-3988, TCV-309, PMS-601, TCV-309 and combinations thereof.

TNF-α Converting Enzyme (TACE) Inhibitors

TNF-α is initially expressed on the cell surface as a 26 kDa, 233-amino acid, membrane-bound precursor protein. Proteolytic cleavage of the membrane-bound TNF-α by the matrix metalloproteinase TNF-α converting enzyme occurs between Ala-76 and Val-77 and results in a 17 kDa mature TNF-α which exists as a soluble trimer. Inhibition of the proteolytic cleavage could provide an alternative to the use of protein-based therapeutics in anti-inflammatory therapy. One potential complication, however, is that TACE is thought to be involved in the processing of other proteins in addition to TNF-α. For example, in a phase II clinical trial, indications of toxic effects in the liver occurred as a result of TACE inhibition. (Car et al, Society of Toxicology, 46th Annual Meeting, Charlotte, N.C., Mar. 25-29, 2007). The hypothesis for this mechanism-based toxicity is that TACE also acts on other membrane bound proteins, such as TNFRI and TNFRII.

While toxicities following oral administration are problematic for a drug administered systemically, local delivery to the site of action overcomes this problem. Inhibitor GW3333 has a TACE IC$_{50}$ of 40 nM and an IC$_{50}$ of 0.97 µM for inhibiting TNF-α production in the LPS-induced human PBMC cells (Conway et al, J. Pharmacol. Exp. Ther. (2001), 298:900). Nitroarginine analog A has an IC$_{50}$ TACE IC$_{50}$ of 4 nM and an IC$_{50}$ of 0.034 µM for inhibiting TNF-α production in the LPS-induced MonoMac-6 cells (Musso et al, Bioorg. Med. Chem. Lett. (2001), 11:2147), but lacks oral activity. A scientific review of TNF-α converting enzyme inhibitors has been published (Skotnicki et al., Annual Reports in Medicinal Chemistry (2003), 38, 153-162), incorporated by reference herein for such disclosure.

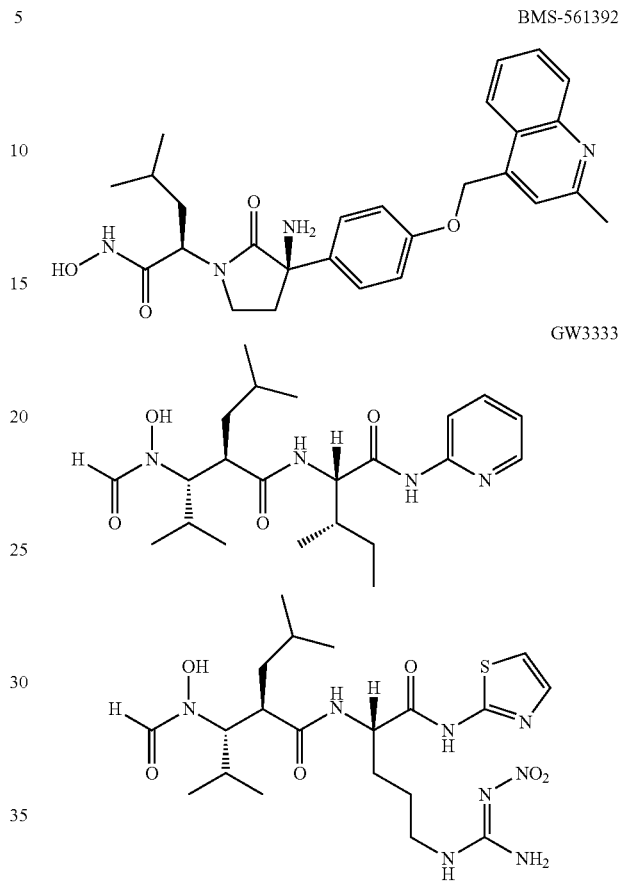

Accordingly, in one embodiment, the otic formulation or composition comprises a TACE inhibitor. In another embodiment, the otic formulation or composition comprises a TACE inhibitor which induces toxicity upon systemic administration. In additional embodiments, the otic formulation or composition comprises a TACE inhibitor which is not orally absorbed. In another embodiment, the otic formulation comprises a TACE inhibitor selected from Nitroarginine analog A, GW3333, TMI-1, BMS-561392, DPC-3333, TMI-2, BMS-566394, TMI-005, apratastat, GW4459, W-3646, IK-682, GI-5402, GI-245402, BB-2983, DPC-A38088, DPH-067517, R-618, and CH-138.

Toll-Like Receptor Inhibitors

Toll-like receptors (TLR) are a family of at least 12 pattern recognition cell-surface and intracellular receptors. The family is defined by the presence of two domains: a ligand-binding domain with multiple leucine-rich repeats, and a short Toll/Il-1 receptor domain; the latter controlling the initiation of downstream-signaling cascades. In certain instances, the receptors are activated by the binding of structurally conserved molecules (i.e. the "patterns") found on pathogens. Each receptor recognizes and binds to specific conserved molecules found on pathogens (e.g. TLR2—lipopeptides; TLR3—viral dsRNA; TLR4—LPS; TLR5—flagellin; TLR9—CpG DNA). In certain instances, the binding of a TLR to a pathogen, initiates the TLR signaling cascade which ultimately leads to the activation of various cytokines, chemokines, and antigen-specific and non-specific immune responses. In certain instances, the expression of TLR2 and/or TLR4 is up-regulated upon exposure to nontypeable *Hemophilus influenzae* (NTHi). Infection by NTHi is a common cause of otitis media.

Toll-like receptors belong to a class of single membrane-spanning non-catalytic receptors that recognize structurally conserved molecules derived from breached microbes are believed to play a key role in the innate immune system. Toll-like receptors thus recognize molecules that are broadly shared by pathogens, but are distinguishable from the host molecules. These receptors form a superfamily with Interleukin-1 receptors, and have in common a Toll-like receptor domain. Toll-like receptor agonists, such as CQ-07001, stimulate Toll-like receptor 3 function, triggering anti-inflammatory and tissue regeneration activity. Toll-like receptor modulators, thus, have implication for use in both auris interna disorders, including AIED, and auris media diseases, including otitis media. In some embodiments, toll-like receptor modulators include toll-like receptor antagonist, partial agonist, inverse agonist, neutral or competitive antagonist, allosteric antagonist, and/or orthosteric antagonist. Other toll-like receptor modulators include but are not limited to polyinosinic-polycytidylic acid [poly(I:C)], polyAU, other nucleic acid molecules, including dsRNA agonists (such as AMPLIGEN®, Hemispherx, Inc., Rockville Md.; and POLYADENUR®, Ipsen), and are also contemplated within the scope of the embodiments disclosed herein.

In some embodiments, the TLR inhibitor is an ST2 antibody; sST2-Fc (functional murine soluble ST2-human IgG1 Fc fusion protein; see Biochemical and Biophysical Research Communications, 29 Dec. 2006, vol. 351, no. 4, 940-946 which is herein incorporated by reference for disclosures related to sST2-Fc); CRX-526 (Corixa); lipid IV$_A$; RSLA (*Rhodobacter sphaeroides* lipid A); E5531 ((6-O-12-deoxy-6-O-methyl-4-O-phosphono-3-O—[(R)-3-Z-dodec-5-endoyloxydecl]-2-[3-oxo-tetradecanoylamino]-β-O-phosphono-α-D-glucopyranose tetrasodium salt); E5564 (α-D-Glucopyranose,3-O-decyl-2-deoxy-6-O-[2-deoxy-3-O-[(3R)-3-methoxydecyl]-6-O-methyl-2-[[(11Z)-1-oxo-11-octadecenyl]amino]-4-O-phosphono-β-D-glucopyranosyl]-2-[(1,3-dioxotetradecyl)amino]-1-(dihydrogen phosphate), tetrasodium salt); compound 4a (hydrocinnamoyl-L-valyl pyrrolidine; see PNAS, Jun. 24, 2003, vol. 100, no. 13, 7971-7976 which is herein incorporated by reference for disclosures related to compound 4a); CPG 52364 (Coley Pharmaceutical Group); LY294002 (2-(4-Morpholinyl)-8-phenyl-4H-1-benzopyran-4-one); PD98059 (2-(2-amino-3-methoxyphenyl)-4H-1-Benzopyran-4-one); chloroquine; and an immune regulatory oligonucleotide (for disclosures relating to IROs see U.S. Patent Application Publication No. 2008/0089883).

Auto-Immune Agents

Also contemplated for use with the formulations and compositions disclosed herein are agents which reduce or ameliorate symptoms or effects as a result of autoimmune disease, including autoimmune inner ear disease (AIED). Accordingly, some embodiments optionally incorporate the use of agents which block the effects of TNF-α, including but not limited to anti-TNF agents. By way of example only, some anti-TNF agents include etanercept (ENBREL®), infliximab (REMICADE®) and adalimumab (HUMIRA®), or combinations thereof. Other pharmaceutical agents to treat autoimmune disorders include chemotherapeutic agents, including cytoxan, azathiaprine or methotrexate; treatment with collagen, gamma globulin, interferons, copaxone, or combinations thereof.

IL-1 Modulators

Interleukin-1 (IL-1) is a pleiotropic cytokine that plays a role in the modulation of local as well as systemic inflammation, immune regulation and hemopoiesis. IL-1β, a member of the IL-1 family, has been implicated in angiogenesis processes, including tumor angiogenesis. In addition, IL-1 has been shown to stimulate the synthesis of inflammatory eicosanoids in macrophages, fibroblasts, synovial cells and chondrocytes, and is believed to contribute to leukocyte activation and tissue destruction in arthritic models. Interfering with IL-1 activity, therefore, is an approach for developing a disease modifying therapy for chronic inflammatory diseases, such as AIED and otitis media. In some embodiments, IL-1 modulators include an IL-1 antagonist, partial agonist, inverse agonist, neutral or competitive antagonist, allosteric antagonist, and/or orthosteric antagonist. In some embodiments, IL-1 modulators include but are not limited to antibodies that specifically recognize IL-1 subunits or its receptors, proteins, peptides, nucleic acids, and small molecule therapeutics. In some embodiments, ILL-1 modulators are IL-1 antagonists, including, for example, AF12198, IL-1 natural antagonists, inactive receptor fragments that bind to IL-1 molecule, and antisense molecules or factors that block expression of IL-1 cytokine proteins. In some embodiments, IL-1 antagonists are IL-1 antibodies including, by way of example, anakinra (Kinaret®) and ACZ885 (Canakinumab®). In some embodiments, modulators of IL-1 are antibodies that modulate cytokines and/or growth factors that affect the release and/or expression of IL-1, including, by way of example, ranibizumab, tefibazumab, and bevacizumab. In some embodiments, IL-1 modulators are IL-1 traps that attach to IL-1 and neutralize IL-1 before it binds to cell surface receptors and include, but are not limited to, rilonocept (Arcalyst®).

RNAi

In some embodiments, where inhibition or down-regulation of a target is desired (e.g. genes encoding one or more calcineurins, IKKs, TACEs, TLRs, or cytokines), RNA interference are utilized. In some embodiments, the agent that inhibits or down-regulates the target is an siRNA molecule. In certain instances, the siRNA molecule inhibits the transcription of a target by RNA interference (RNAi). In some embodiments, a double stranded RNA (dsRNA) molecule with sequences complementary to a target is generated (e.g. by PCR). In some embodiments, a 20-25 bp siRNA molecule with sequences complementary to a target is generated. In some embodiments, the 20-25 bp siRNA molecule has 2-5 bp overhangs on the 3' end of each strand, and a 5' phosphate terminus and a 3' hydroxyl terminus. In some embodiments, the 20-25 bp siRNA molecule has blunt ends. For techniques for generating RNA sequences see Molecular Cloning: A Laboratory Manual, second edition (Sambrook et al., 1989) and Molecular Cloning: A Laboratory Manual, third edition (Sambrook and Russel, 2001), jointly referred to herein as "Sambrook"); Current Protocols in Molecular Biology (F. M. Ausubel et al., eds., 1987, including supplements through 2001); Current Protocols in Nucleic Acid Chemistry John Wiley & Sons, Inc., New York, 2000) which are hereby incorporated by reference for such disclosure.

In some embodiments, the dsRNA or siRNA molecule is incorporated into the otic formulations or compositions described herein. In some embodiments, the otic formulation or composition is injected into the inner ear. In some embodiments, the otic formulation or composition is injected through the round window membrane. In some embodiments, the otic formulation or composition is injected into the cochlea, the Organ of Corti, the vestibular labyrinth, or a combination thereof.

In certain instances, after administration of the dsRNA or siRNA molecule, cells at the site of administration (e.g. the cells of cochlea, Organ of Corti, and/or the vestibular labyrinth) are transformed with the dsRNA or siRNA molecule. In certain instances following transformation, the dsRNA molecule is cleaved into multiple fragments of about 20-25 bp to yield siRNA molecules. In certain instances, the fragments have about 2 bp overhangs on the 3' end of each strand.

In certain instances, an siRNA molecule is divided into two strands (the guide strand and the anti-guide strand) by an RNA-induced Silencing Complex (RISC). In certain instances, the guide strand is incorporated into the catalytic component of the RISC (i.e. argonaute). In certain instances, the guide strand binds to a complementary target mRNA sequence. In certain instances, the RISC cleaves the target mRNA. In certain instances, the expression of the target gene is down-regulated.

In some embodiments, a sequence complementary to a target is ligated into a vector. In some embodiments, the sequence is placed between two promoters. In some embodiments, the promoters are orientated in opposite directions. In some embodiments, the vector is contacted with a cell. In certain instances, a cell is transformed with the vector. In certain instances following transformation, sense and anti-sense strands of the sequence are generated. In certain instances, the sense and anti-sense strands hybridize to form a dsRNA molecule which is cleaved into siRNA molecules. In certain instances, the strands hybridize to form an siRNA molecule. In some embodiments, the vector is a plasmid (e.g pSUPER; pSUPER.neo; pSUPER.neo+gfp).

In some embodiments, the vector is incorporated into the otic formulation. In some embodiments, the otic formulation is injected into the inner ear. In some embodiments, the otic formulation is injected through the round window membrane. In some embodiments, the otic formulation is injected into the cochlea, the Organ of Corti, the vestibular labyrinth, or a combination thereof.

Aural Pressure Modulators
Aquaporin

Contemplated for use with the formulations and compositions disclosed herein are agents that treat disorders of the auris, and/or modulate the cells and structures of the auris. In certain instances, an aquaporin is involved in fluid homeostasis. In certain instances, AQP2 mRNA is elevated in rats treated with vasopressin above the levels observed in control animals. In certain instances, Aquaporin-1 is expressed in the cochlea and endolymphatic sac. In certain instances, Aquaporin-1 is expressed in the spiral ligament, the Organ of Corti, the scala tympani, and the endolymphatic sac. Aquaporin-3 is expressed in the stria vascularis, the spiral ligament, the Organ of Corti, the spiral ganglion and the endolymphatic sac. In certain instances, aquaporin 2 (AQP2) mRNA is elevated above normal levels in individuals with endolymphatic hydrops.

Accordingly, some embodiments incorporate the use of agents that modulate an aquaporin. In some embodiments, the aquaporin is aquaporin 1, aquaporin 2 and/or aquaporin 3. In some embodiments, the agent that modulates an aquaporin (e.g. aquaporin 1, aquaporin 2 or aquaporin 3) is an aquaporin antagonist, partial agonist, inverse agonist, neutral or competitive antagonist, allosteric antagonist, and/or orthosteric antagonist. In some embodiments, the aquaporin antagonist, partial agonist, inverse agonist, neutral or competitive antagonist, allosteric antagonist, and/or orthosteric antagonist includes, but is not limited to, substance P; RU-486; tetraethylammonium (TEA); an anti-aquaporin antibody; a vasopressin and/or a vasopressin receptor antagonist, partial agonist, inverse agonist, neutral or competitive antagonist, allosteric antagonist, and/or orthosteric antagonist; or combinations thereof.

Estrogen-Related Receptor Beta Modulators

Estrogen-related receptor beta (ERR-beta; also known as Nr3b2), an orphan nuclear receptor, is specifically expressed in and controls the development of the endolymph-producing cells of the inner ear: the strial marginal cells in the cochlea and the vestibular dark cells in the ampulla and utricle. (Chen et al. *Dev. Cell.* (2007) 13:325-337). Nr3b2 expression has been localized in the endolymph-secreting strial marginal cells and vestibular dark cells of the cochlea and vestibular apparatus, respectively. Studies in knockout mice have shown that strial marginal cells in these animals fail to express multiple ion channel and transporter genes, suggesting a role in the development and/or function of endolymph producing epithelia. Moreover, conditional knockout of the Nr3b2 gene results in deafness and diminished endolymphatic fluid volume.

Other studies suggest a role for estrogen-related receptor 3/NR3B2 (ERR/Nr3b2) in regulating endolymph production, and therefore pressure in the vestibular/cochlear apparatus. In some embodiments, treatment with antagonists to ERR/Nr3b2 assists in reducing endolymphatic volume, and thus alter pressure in the auris interna structures. Accordingly, agents which antagonize ERR/Nr3b2 expression, protein production or protein function are contemplated as useful with the formulations disclosed herein.

GAP Junction Proteins

Contemplated for use with the formulations and compositions disclosed herein are agents that treat disorders of the auris, and/or modulate the cells and structures of the auris. Gap junctions are intracellular connections. In certain instances, a gap junction connects the cytoplasm of two cells. In certain instances, a gap junction facilitates the passage of small molecules (e.g. $IP_3$) and ions between the cells. In certain instances, gap junctions are formed of connexins (e.g. six connexins form a connexon and two connexons form a gap junction). There are multiple connexins (e.g. Cx23, Cx25, Cx26, Cx29, Cx30, Cx30.2, Cx30.3, Cx31, Cx31.1, Cx31.9, Cx32, Cx33, Cx36, Cx37, Cx39, Cx40, Cx40.1, Cx43, Cx45, Cx46, Cx47, Cx50, Cx59, and Cx62). In certain instances, of Cx26 and Cx43 are expressed in a spiral limbus, a spiral ligament, a stria vascularis, cells of the Organ of Corti. In certain instances, non-syndromic deafness is associated with mutations in genes (e.g. GJB2) encoding connexins (e.g. Cx26). In certain instances, sensorineural hearing loss is associated with mutations in genes encoding connexins (e.g. Cx26). In certain instances, the expression of Cx26 and Cx43 is upregulated in a cholesteatoma. In certain instances, the expression of Cx26 is upregulated following acoustic trauma. In certain instances, gap junctions facilitate the movement of $K^+$ ions in endolymph.

Accordingly, some embodiments disclosed herein incorporate the use of agents that modulate gap junction proteins. In some embodiments, the gap junction protein is a connexin. In some embodiments, the agent that modulates a connexin is a connexin agonist, partial agonist, and/or positive allosteric modulator of a connexin. In some embodiments, the connexin agonist, partial agonist, and/or positive allosteric modulator includes, but is not limited to, astaxanthin; rotigaptide; adenosine; corticotropin-releasing hormone; or combinations thereof.

Vasopressin and the Vasopressin Receptor

Vasopressin (VP) is a hormone that plays an important part in circulatory and water homoeostasis. This hormone is synthesized by neurosecretory cells located predominantly in two specific hypothalamic nuclei—the supraoptic nucleus and the paraventricular nucleus. These neurons have axons that terminate in the neural lobe of the posterior pituitary gland (neurohypophysis) in which they release vasopressin. The three vasopressin receptor subtypes (VP1a, VP1b and VP2) all belong to the G-protein coupled receptor family and have differing tissue distributions. The VP1a receptor is predominantly located in the vascular smooth muscle, hepatocytes and blood platelets. The VP1b receptors are found in the anterior pituitary. The VP2 receptors are localized in the collecting duct of the kidney and regulate the presentation of aquaporin-2 channels at the apical cell surface. The effect of modulation of the VP2 subtype provides readily observed changes in urine volume and electrolyte levels to determine the pharmacological effects of anti-diuresis.

Vasopressin regulates systemic osmolality by controlling urinary volume and composition. Vasopressin is secreted in response to increases in plasma tonicity (very sensitive stimulus) or to decreases in plasma volume (less sensitive stimulus). Vasopressin mainly regulates urinary volume by binding to the VP receptor in the collecting duct of the kidney. The VP receptor also exists in the inner ear of rodents, and aquaporin-2 (AQP2), a VP mediated water channel protein, is also expressed (Kitano et al. Neuroreport (1997), 8:2289-92). Water homeostasis of the inner ear fluid was confirmed to be regulated using the VP-AQP2 system (Takeda et al. Hear Res (2000), 140:1-6; Takeda et al. Hear Res. (2003), 182:9-18). A recent study looked at tissue expression of VP2 and AQP2 in human endolymphatic sac by immunohistochemistry and noted that VP2 and AQP2 were located in the epithelial layer of the endolymphatic sac but not in surrounding connective tissue (Taguchi et al, Laryngoscope (2007), 117:695-698). Studies on the systemic administration of vasopressin in the guinea pig showed the development of endolymphatic hydrops (Takeda et al. Hear Res (2000), 140:1-6). Additionally, the aquaporin-4 knockout mouse, while otherwise healthy, is deaf (Beitz et al., Cellular and Molecular Neurobiology (2003) 23(3):315-29). This suggests that transport of water and solutes in a manner similar to that of the kidney play a role in fluid homeostasis of the endolymphatic sac. A mutant human VP2 receptor protein (D136A) has been identified and characterized as constitutively active (Morin et al., FEBS Letters (1998) 441(3):470-5). This hormone-independent activation of the VP2 receptor could play a role in the etiology of conditions such as Meniere's disease.

Contemplated for use with the formulations and compositions disclosed herein are agents that treat disorders of the auris, and/or modulate the cells (e.g., auris sensory cells) and structures of the auris. In certain instances, VP is involved in fluid homeostasis. In certain instances, VP is involved in endolymph and/or perilymph homeostasis. In certain instances, an increase in endolymph volume increases pressure in the vestibular and cochlear structures. In certain instances, plasma levels of VP are elevated above normal levels in endolymphatic hydrops and/or Meniere's Disease.

Vasopressin Receptor Modulators

Vasopressin receptor modulators are differentiated based upon their efficacy relative to the vasopressin peptide hormone. A vasopressin receptor full agonist is a mimic of the native peptide. A vasopressin receptor antagonist blocks the effect of the native peptide. In some embodiments, a partial agonist serves as a mimic of the native peptide and induces a partial response, or in the presence of elevated levels of the native peptide, a partial agonist competes with the native peptide for receptor occupancy and provides a reduction in efficacy, relative to the native peptide alone. For a vasopressin receptor with constitutive activity, an inverse agonist serves to reverse the activity of the receptor.

Accordingly, some embodiments incorporate the use of agents that modulate vasopressin and/or a vasopressin receptor. In some embodiments, the agent that modulates vasopressin and/or a vasopressin receptor is a vasopressin and/or a vasopressin receptor antagonist, partial agonist, inverse agonist, neutral or competitive antagonist, allosteric antagonist, and/or orthosteric antagonist. In some embodiments, the vasopressin and/or a vasopressin receptor antagonist, partial agonist, inverse agonist, neutral or competitive antagonist, allosteric antagonist, and/or orthosteric antagonist includes, but is not limited to, an anti-vasopressin antibody; an anti-vasopressin receptor antibody; lithium; OPC-31260 ((±)-5-dimethylamino-1-(4-[2-methylbenzoylamino]benzoyl)-2,3,4,5-tetrahydro-1H-benzazepin hydrochloride); WAY-140288 (N-[4-[3-(Dimethylaminomethyl)-10,11-dihydro-5H-pyrrolo[2,1-c][1,4]benzodiazepin-10-ylcarbonyl]-2-methoxyphenyl]biphenyl-2-carboxamide); CL-385004 (5-Fluoro-2-methyl-N-[5-(5H-pyrrolo[2,1-c][1,4]benzodiazepine-10(11H)-ylcarbonyl)-2-pyridinyl]benzamide); relcovaptan, lixivaptan (VPA-985); tolvaptan; conivaptan; SR 121463A (1-(4-(N-tert-butylcarbamoyl)-2-methoxybenzenesulfonyl)-5-ethoxy-3-spiro-(4-(2-morpholinoethoxy)cyclohexane)indol-2-one fumarate); SR-49059 ((2S)-1-[[(2R,3S)-5-Chloro-3-(2-chlorophenyl)-1-[(3,4-di methoxyphenyl)sulfonyl]-2,3-dihydro-3-hydroxy-1H-indol-2-yl]carbonyl]-2-pyrrolidinecarboxamide), Lixivaptan (VPA 985); AC-94544 (ACADIA Pharmaceuticals Inc.); AC-88324 (ACADIA Pharmaceuticals Inc.); AC-110484 (ACADIA Pharmaceuticals Inc.); or combinations thereof.

Recent studies have suggested a role for vasopressin in regulating auris interna pressure by regulating endolymph production, therapy mediating the pressure present in vestibular and cochlear structures. (Takeda et al. *Hearing Res.* (2006) 218:89-97). Treatment with vasopressin antagonists, including OPC-31260, resulted in the marked reduction of Meniere's disease symptoms. Accordingly, vasopressin antagonists are contemplated as useful with the formulations disclosed herein. Examples of vasopressin antagonists include, but are not limited to OPC-31260, WAY-140288, CL-385004, tolvaptan, conivaptan, SR 121463A, VPA 985, valium (diazepam), benzodiazepines and combinations thereof. Testing of vasopressin antagonists include testing and calculating hydrops reduction with treatment in a guinea pig animal model. See, e.g., Chi et al. "The quantification of endolymphatic hydrops in an experimental animal model with guinea pigs", *J. Oto-Rhino-Larynol.* (2004) 66:56-61.

Agonists of the VP2 receptor are known, including OPC-51803 and related analogs (Kondo et al., J. Med. Chem. (2000) 43:4388; Nakamura et al., Br. J. Pharmacol. (2000) 129(8):1700; Nakamure et al., J. Pharmacol. Exp. Ther. (2000) 295(3):1005) and WAY-VNA-932 (Caggiano, Drugs Gut (2002) 27(3):248). Antagonists of the VP2 receptor include lixivaptan, tolvaptan, conivaptan, SR-121463 and OPC-31260 (Martin et al., J. Am. Soc. Nephrol. (1999) 10(10):2165; Gross et al., Exp. Physiol. (2000) 85: Spec No 253S; Wong et al., Gastroent April 2000, vol 118, 4 Suppl. 2, Part 1); Norman et al., Drugs Fut. (2000), 25(11):1121;

Inoue et al., Clin. Pharm. Therap. (1998) 63(5):561). In testing against the constitutively activated D136A mutant VP2 receptor, SR-1211463 and OPC-31260 behaved as inverse agonist (Morin et al., FEBS Letters (1998) 441(3): 470-75).
OPC-51803
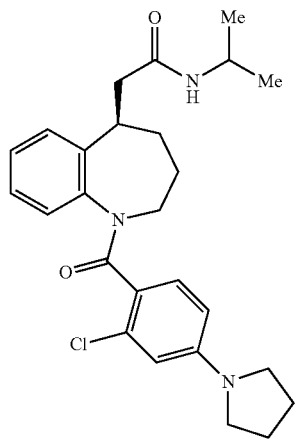
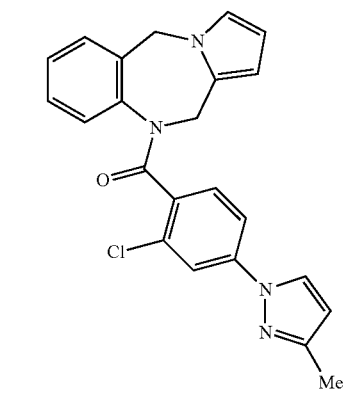
WAY-VNA-932
OPC-31260
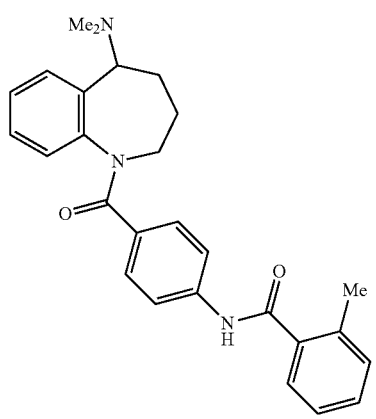
-continued
SR-121463
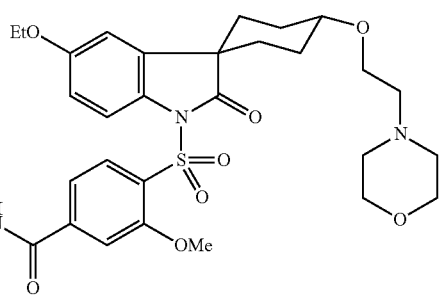
(OPC-41061)
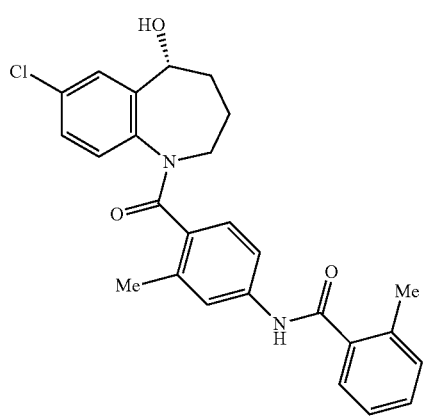
Tolvaptan
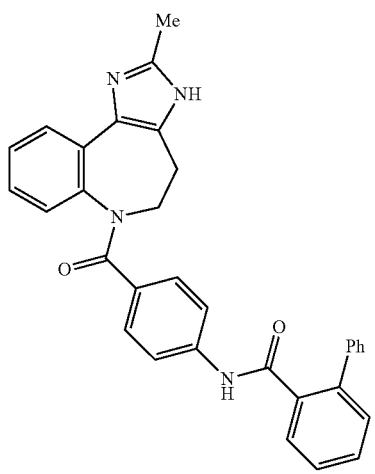
Conivaptan

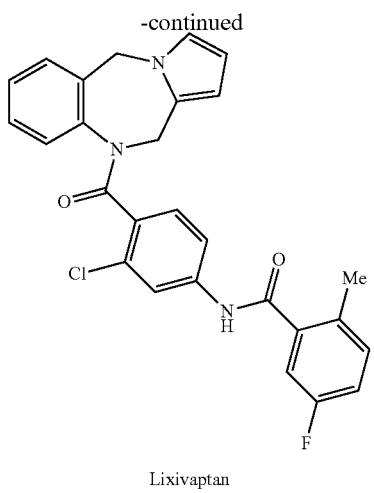

Lixivaptan

NMDA Receptor Modulators

Contemplated for use with the formulations and compositions disclosed herein are agents that modulate the degeneration of neurons and/or hair cells of the auris, and agents for treating or ameliorating hearing disorders such as tinnitus. Accordingly, some embodiments incorporate the use of agents which modulate NMDA receptors.

In certain instances, the over-activation of the NMDA glutamate receptors by the binding of excessive amounts of glutamate, results in the excessive opening of the ion channels under their control. In certain instances, this results in abnormally high levels of $Ca^{2+}$ and $Na^+$ entering the neuron. In certain instances, the influx of $Ca^{2+}$ and $Na^+$ into the neuron activates multiple enzymes including, but not limited to, phospholipases, endonucleases, and proteases. In certain instances, the over-activation of these enzymes results in tinnitus, and/or damage to the cytoskeleton, plasma membrane, mitochondria, and DNA of the neuron. In certain instances, the NMDA receptor modulator neramexane treats, and/or ameliorates the symptoms of tinnitus.

In some embodiments, the agent that modulates the NMDA receptor is an NMDA receptor antagonist. In some embodiments, the agent that modulates an NMDA receptor is an NMDA receptor antagonist, partial agonist, inverse agonist, neutral or competitive antagonist, allosteric antagonist, and/or orthosteric antagonist. In some embodiments, the agent which antagonizes the NMDA receptor includes, but is not limited to, 1-aminoadamantane, dextromethorphan, dextrorphan, ibogaine, ketamine, esketamine (AM-101), nitrous oxide, phencyclidine, riluzole, tiletamine, memantine, neramexane, dizocilpine, aptiganel, remacimide, 7-chlorokynurenate, DCKA (5,7-dichlorokynurenic acid), kynurenic acid, 1-aminocyclopropanecarboxylic acid (ACPC), AP7 (2-amino-7-phosphonoheptanoic acid), APV (R-2-amino-5-phosphonopentanoate), CPPene (3-[(R)-2-carboxypiperazin-4-yl]-prop-2-enyl-1-phosphonic acid); (+)-(1S,2S)-1-(4-hydroxy-phenyl)-2-(4-hydroxy-4-phenylpiperidino)-1-pro-panol; (1S,2S)-1-(4-hydroxy-3-methoxyphenyl)-2-(4-hydroxy-4-phenylpiperi-dino)-1-pro-panol; (3R,4S)-3-(4-(4-fluorophenyl)-4-hydroxypiperidin-1-yl-)-chroman-4,7-diol; or (1R*,2R*)-1-(4-hydroxy-3-methylphenyl)-2-(4-(4-fluoro-phenyl)-4-hydroxypiperidin-1-yl)-propan-1-ol-mesylate; gacyclidine (1-[(1R,2S)-2-methyl-1-thiophen-2-ylcyclohexyl]piperidine); and/or combinations thereof. In some embodiments, the agent which antagonizes the NMDA receptor is gacyclidine (1-[(1R,2S)-2-methyl-1-thiophen-2-ylcyclohexyl]piperidine).

ENaC Receptor Modulators

The epithelial sodium channel (ENaC, sodium channel non-neuronal 1 (SCNN1) or amiloride sensitive sodium channel (ASSC)) is a membrane-bound ion-channel that is permeable for Litions, protons and Nations. The ENaC is located in the apical membrane of polarized epithelial cells and is involved in transepithelial Nation transport. $Na^+/K+$-ATPase is also involved in $Na^+$ transport and ion homeostasis.

ENaC plays a role in the Na+- and K+-ion homeostasis of blood, epithelia and extraepithelial fluids by resorption of Na+-ions. Modulators of the activity of ENaC modulate aural pressure and include, by way of example, the mineralcorticoid aldosterone, triamterene, and amiloride.

Osmotic Diuretics

Contemplated for use with the formulations and compositions disclosed herein, are agents which regulate aural pressure. Accordingly, some embodiments comprise osmotic diuretics. An osmotic diuretic is a substance that produces an osmotic gradient between two spaces. In certain instances, an osmotic diuretic produces an osmotic gradient between the endolymphatic and perilymphatic spaces. In certain instances, an osmotic gradient between the endolymphatic and perilymphatic spaces exerts a dehydrating effect on the endolymphatic space. In certain instances, dehydrating the endolymphatic space decreases aural pressure.

Accordingly, in some embodiments of the compositions and formulations disclosed herein, the aural pressure modulator is an osmotic diuretic. In some embodiments, the osmotic diuretic is erythritol, mannitol, glucose, isosorbide, glycerol; urea; or combinations thereof.

In some instances, contemplated for use in combination with the aural pressure modulating formulations or compositions disclosed herein are diuretic agents. A diuretic agent is a drug that elevates the rate of urination. Such diuretics include triamterene, amiloride, bendroflumethiazide, hydrochlorothiazide, furosemide, torsemide, bumetanide, acetazolamide, dorzolamide and combinations thereof.

Progesterone Receptors

Contemplated for use with the formulations and compositions disclosed herein are therapeutic agents that treat disorders (e.g., inflammation) of the auris, and/or modulate the cells and structures of the auris. Progesterone is a steroidal hormone. In certain instances, progesterone is a ligand for a progesterone receptor. In certain instances, progesterone is found in the brain. In certain instances, progesterone affects synaptic functioning. In certain instances, progesterone is associated with partial or complete loss of hearing. In certain instances, females taking progesterone and estrogen experienced greater hearing loss than females taking estrogen alone (e.g. about 10% to about 30%).

Accordingly, some embodiments incorporate the use of agents that modulate progesterone and/or a progesterone receptor. In some embodiments, the agent that modulates progesterone and/or a progesterone receptor is a progesterone and/or progesterone receptor antagonist, a partial agonist, an inverse agonist, a neutral or competitive antagonist, an allosteric antagonist, and/or an orthosteric antagonist. In other embodiments, the agent that modulates progesterone and/or a progesterone receptor includes, but is not limited to, RU-486 ((11b,17 b)-11-[4-(Dimethylamino)phenyl]-17-hydroxy-17-(1-propynyl)-estra-4,9-dien-3-one); CDB-2914 (17α-acetoxy-11β-[4-N,N-dimethylaminophenyl]-19-nor-pregna-4,9-diene-3,20-dione); CDB-4124 (17α-acetoxy-21-methoxy-11β-[4-N,N-dimethylaminophenyl]-19-nor-pregna-4,9-diene-3,20-dione); CDB-4453 (17α-acetoxy-21- methoxy-11β-[4-N-methylaminophenyl]-19-norpregna-4,9-diene-3,20-dione); RTI 3021-022 (Research Triangle Institute); ZK 230211 (11-(4-acetylphenyl)-17-hydroxy-17-(1,1,2,2,2-pentafluoroethyl)estra-4,9-dien-3-one); ORG 31710 (11-(4-dimethylaminophenyl)-6-methyl-4',5'-dihydro (estra-4,9-diene-17,2'-(3H)-furan)-3-one); ORG 33628 (Organon); onapristone (ZK 98299); asoprisnil; ulipristal; an anti-progesterone antibody; an anti-progesterone receptor antibody; or combinations thereof.

Prostaglandins

Prostaglandins are members of a group of fatty-acid derived compounds and depending upon the subtype, participate in a variety of functions, including control of constriction or dilation in vascular smooth muscle cells, aggregation or disaggregation of platelets, sensitization of spinal neurons to pain, increase or decrease in intraocular pressure, regulation of inflammatory mediation, regulation of calcium movement, control of hormone regulation and control of hormonal regulation. Prostaglandins have both paracrine and autocrine functions, and are a subclass of eicosanoid compounds.

Prostaglandin analogues, such as latanoprost, travoprost, unoprostone, minprostin F2 alpha and bimtoprost, have been shown in reduce intra-ocular pressure in glaucoma patients by enhancing the uveoscleral outflow, possibly through vasodilation mechanisms, in addition to effects on the trabecular meshwork. In sensorineural hearing loss animal models, noise exposure induces 8-isoprostaglandin F2α production in the cochlea, concomitant with an increase in vasoconstriction and reduced blood flow. Treatment with SQ29548, a specific antagonist of 8-isoprostaglandin F2α, prevents these noise-induced changes in cochlear blood flow and vascular conductance. Further, the prostaglandin analogue JB004/A improves hearing, and treats, and/or the symptoms of tinnitus and vertigo in patients suffering from Ménière's disease. Inhibition of prostaglandin F2α function also reduces tinnitus in patients suffering from Meniere's disease, as well as improvements in hearing and vertigo. Finally, prostaglandins have been implicated in chronic inflammation associated with otitis media.

Accordingly, one embodiment disclosed herein is the use of prostaglandin modulators, including latanoprost, travoprost, unoprostone, minprostin F2-alpha, bimtoprost and SQ29548, and JB004/A (Synphora AB) to ameliorate or decrease inner ear and middle ear disorders, including Meniere's disease, tinnitus, vertigo, hearing loss and otitis media.

RNAi

In some embodiments, where inhibition or down-regulation of a target is desired (e.g. genes ERR, and Nr3b2), RNA interference are utilized. In some embodiments, the agent that inhibits or down-regulates the target is an siRNA molecule. In certain instances, the siRNA molecule is as described herein.

Cytotoxic Agents

In some instances, immunomodulators and/or aural pressure modulators are useful in treatment of inflammatory otic disorders.

Any cytotoxic agent useful for the treatment of otic disorders, e.g., inflammatory diseases of the ear or cancer of the ear, is suitable for use in the formulations and methods disclosed herein. In certain embodiments, the cytotoxic agent is an antimetabolite, an antifolate, an alkylating agent, a DNA intercalator, an anti-TNF agent, an anti-angiogenic agent, an anti-inflammatory agent, and/or an immunomodulatory agent. In some embodiments, the cytotoxic agent is a protein, a peptide, an antibody, DNA, a carbohydrate, an inorganic molecule, or an organic molecule. In certain embodiments, the cytotoxic agents are cytotoxic small molecules. Typically, cytotoxic small molecules are of relatively low molecular weight, e.g., less than 1,000, or less than 600-700, or between 300-700 molecular weight. In some embodiments, the cytotoxic small molecules will also have anti-inflammatory properties.

In certain embodiments, the cytotoxic agents are methotrexate (RHEUMATREX®, Amethopterin) cyclophosphamide (CYTOXAN®), and thalidomide (THALIDOMID®). In some embodiments, all of the compounds are used to treat cancer, including cancer of the ear. Further, all of the compounds have anti-inflammatory properties and are used in the formulations and compositions disclosed herein for the treatment of inflammatory disorders of the ear, including AIED, in some instances.

Although systemic administration of methotrexate, cyclophosphamide, and thalidomide is currently used to treat or is being investigated for the treatment of otic disorders, such as inflammatory otic disorders, including AIED, Meniere's disease, and Behçet's disease, as well as cancer of the ear, the cytotoxic agents are not without the potential for serious adverse side effects. Moreover, cytotoxic agents which demonstrate efficacy but are otherwise not approvable because of safety considerations is also contemplated within the embodiments disclosed herein. It is contemplated that localized application of the cytotoxic agents to the target otic structures for treatment of autoimmune and/or inflammatory disorders, as well as cancer of the ear, results in the reduction or elimination of adverse side effects experienced with systemic treatment in some embodiments. Moreover, in some embodiments, localized treatment with the cytotoxic agents contemplated herein also reduce the amount of agent needed for effective treatment of the targeted disorder due, for example, to increased retention of the active agents in the auris interna and/or media, to the existence of the biological blood barrier in the auris interna, or to the lack of sufficient systemic access to the auris media.

In some embodiments, cytotoxic agents used in the compositions, formulations, and methods disclosed herein are metabolites, salts, polymorphs, prodrugs, analogues, and derivatives of cytotoxic agents, including methotrexate, cyclophosphamide, and thalidomide. Particularly preferred are metabolites, salts, polymorphs, prodrugs, analogues, and derivatives of cytotoxic agents, e.g., methotrexate, cyclophosphamide, and thalidomide, that retain at least partially the cytotoxicity and anti-inflammatory properties of the parent compounds. In certain embodiments, analogues of thalidomide used in the formulations and compositions disclosed herein are lenalidomide (REVLIMID®) and CC-4047 (ACTIMID®).

Cyclophosphamide is a prodrug that undergoes in vivo metabolism when administered systemically. The oxidized metabolite 4-hydroxycyclophosphamide exists in equilibrium with aldophosphamide, and the two compounds serve as the transport forms of the active agent phosphoramide mustard and the degradation byproduct acrolein. Thus, in some embodiments, preferred cyclophosphamide metabolites for incorporation into the formulations and compositions disclosed herein are 4-hydroxycyclophosphamide, aldophosphamide, phosphoramide mustard, and combinations thereof.

Other cytotoxic agents used in the compositions, formulations, and methods disclosed herein, particularly for the treatment of cancer of the ear, are any conventional chemotherapeutic agents, including acridine carboxamide, actinomycin, 17-N-allylamino-17-demethoxygeldanamycin, aminopterin, amsacrine, anthracycline, antineoplastic, antineoplaston, 5-azacytidine, azathioprine, BL22, bendamustine, biricodar, bleomycin, bortezomib, bryostatin, busulfan, calyculin, camptothecin, capecitabine, carboplatin, chlorambucil, cisplatin, cladribine, clofarabine, cytarabine, dacarbazine, dasatinib, daunorubicin, decitabine, dichloroacetic acid, discodermolide, docetaxel, doxorubicin, epirubicin, epothilone, eribulin, estramustine, etoposide, exatecan, exisulind, ferruginol, floxuridine, fludarabine, fluorouracil, fosfestrol, fotemustine, gemcitabine, hydroxyurea, IT-101, idarubicin, ifosfamide, imiquimod, irinotecan, irofulven, ixabepilone, laniquidar, lapatinib, lenalidomide, lomustine, lurtotecan, mafosfamide, masoprocol, mechlorethamine, melphalan, mercaptopurine, mitomycin, mitotane, mitoxantrone, nelarabine, nilotinib, oblimersen, oxaliplatin, PAC-1, paclitaxel, pemetrexed, pentostatin, pipobroman, pixantrone, plicamycin, procarbazine, proteasome inhibitors (e.g., bortezomib), raltitrexed, rebeccamycin, rubitecan, SN-38, salinosporamide A, satraplatin, streptozotocin, swainsonine, tariquidar, taxane, tegafur-uracil, temozolomide, testolactone, thioTEPA, tioguanine, topotecan, trabectedin, tretinoin, triplatin tetranitrate, tris(2-chloroethyl)amine, troxacitabine, uracil mustard, valrubicin, vinblastine, vincristine, vinorelbine, vorinostat, and zosuquidar.

Auris Sensory Cell Modulators

In some instances, immunomodulators and/or aural pressure modulators modulate the function of neurons and/or auris sensory cells. Contemplated for use with the formulations and compositions disclosed herein are agents that modulate the degeneration of neurons and/or hair cells of the auris, promote the growth of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of agents which promote the survival of neurons and otic hair cells, and/or the growth of neurons and otic hair cells. In some embodiments, the agent which promotes the survival of otic hair cells is a growth factor. In some embodiments, the growth factor modulator is a growth factor modulator antagonist, partial agonist, inverse agonist, neutral or competitive antagonist, allosteric antagonist, and/or orthosteric antagonist.

Amifostine

Contemplated for use with the formulations and compositions disclosed herein are agents that modulate the degeneration of neurons and/or hair cells of the auris, and agents for treating or ameliorating hearing loss or reduction resulting from destroyed, stunted, malfunctioning, damaged, fragile or missing hair cells in the inner ear. Accordingly, some embodiments incorporate the use of agents which rescue neurons and otic hair cells from cisplatin-induced ototoxicity.

Amifostine (also known as WR-2721, or ETHYOL®) is a cytoprotective agent. In certain instances, it prevents or ameliorates the damage to neuron and otic hair cells caused by cisplatin. In certain instances, doses at or above 40 mg/kg are needed to protect against or ameliorate the ototoxic effects of cisplatin.

Anti-Intercellular Adhesion Molecule-1 Antibody

Contemplated for use with the formulations and compositions disclosed herein are antibodies to anti-intercellular adhesion molecule (ICAM). In some instances, ICAM blocks the cascade of reactive oxygen species associated with exposure to noise. In some instances modulation of the cascade of reactive oxygen species associated with exposure to noise ameliorates or reduces the degeneration of neurons and/or hair cells of the auris. Accordingly, some embodiments incorporate the use of agents that are antibodies to ICAMs (e.g., anti-ICAM-1 Ab, anti-ICAM-2 Ab or the like).

Modulation of Atoh/Math1

Contemplated for use with the formulations and compositions disclosed herein are agents that promote the growth and/or regeneration of neurons and/or otic hair cells. Atoh1 is a transcription factor which binds to an E-box. In certain instances, it is expressed during the development of the hair cells of the vestibular and auditory systems. In certain instances, mice with Atoh1 knocked-out did not develop otic hair cells. In certain instances, adenoviruses expressing Atoh1 stimulate the growth and/or regeneration of otic hair cells in guinea pigs treated with ototoxic antibiotics. Accordingly, some embodiments incorporate modulation of the Atoh1 gene.

In some embodiments, a subject is administered a vector engineered to carry the human Atoh1 gene (the "Atoh1 vector"). For disclosures of techniques for creating the Atoh1 vector see U.S. Pub. No. 2004/02475750, which is hereby incorporated by reference for those disclosures. In some embodiments, the Atoh1 vector is a retrovirus. In some embodiments, the Atoh1 vector is not a retrovirus (e.g. it is an adenovirus; a lentivirus; or a polymeric delivery system such as METAFECTENE, SUPERFECT®, EFFECTENE®, or MIRUS TRANSIT).

In some embodiments, the Atoh1 vector is incorporated into the otic formulation or composition. In some embodiments, the otic formulation or composition is injected into the inner ear. In some embodiments, the otic formulation or composition is injected into the cochlea, the Organ of Corti, the vestibular labyrinth, or a combination thereof.

In certain instances, after administration of the Atoh1 vector, the Atoh1 vector infects the cells at the site of administration (e.g. the cells of cochlea, Organ of Corti, and/or the vestibular labyrinth). In certain instances the Atoh1 sequence is incorporated into the subject's genome (e.g. when the Atoh1 vector is a retrovirus). In certain instances the therapy will need to be periodically re-administered (e.g. when the Atoh1 vector is not a retrovirus). In some embodiments, the therapy is re-administered annually. In some embodiments, the therapy is re-administered semi-annually. In some embodiments, the therapy is re-administered when the subject's hearing loss is moderate (i.e. the subject cannot consistently hear frequencies less than 41 db to 55 dB) to profound (i.e. the subject cannot consistently hear frequencies less than 90 dB).

In some embodiments, a subject is administered the Atoh1 polypeptide. In some embodiments, the Atoh1 polypeptide is incorporated into the otic formulation or composition. In some embodiments, the otic formulation or composition is injected into the inner ear. In some embodiments, the otic formulation or composition is injected into the cochlea, the Organ of Corti, the vestibular labyrinth, or a combination thereof. In some embodiments, the otic formulation or composition is placed in contact with the round window membrane.

In some embodiments, a subject is administered a pharmaceutically acceptable agent which modulates the expression of the Atoh1 gene or activity of the Atoh1 polypeptide. In some embodiments, the expression of the Atoh1 gene or activity of the Atoh1 polypeptide is up-regulated. In some embodiments, the expression of the Atoh1 gene or activity of the Atoh1 polypeptide is down-regulated.

In certain instances, a compound which agonizes or antagonizes Atoh1 is identified (e.g. by use of a high throughput screen). In some embodiments, a construct is designed such that a reporter gene is placed downstream of an E-box sequence. In some embodiments, the reporter gene is luciferase, CAT, GFP, β-lactamase or β-galactosidase. In certain instances, the Atoh1 polypeptide binds to the E-box sequence and initiates transcription and expression of the reporter gene. In certain instances, an agonist of Atoh1 aids or facilitates the binding of Atoh1 to the E-box sequence, thus increasing transcription and expression of the reporter gene relative to a pre-determined baseline expression level. In certain instances, an antagonist of Atoh1 blocks the binding of Atoh1 to the E-box, thus decreasing transcription and expression of the reporter gene relative to a pre-determined baseline expression level.

BRN-3 Modulators

Contemplated for use with the formulations and compositions disclosed herein are agents that promote the growth and/or regeneration of neurons and/or otic hair cells. BRN-3 is a group of transcription factors that include, but are not limited to, BRN-3a, BRN-3b, and BRN-3c. In certain instances, they are expressed in postmitotic hair cells. In certain instances, the hair cells of mice with BRN-3c knocked-out did not develop stereocilia and/or underwent apoptosis. In certain instances, BRN3 genes regulate the differentiation of inner ear supporting cells into inner ear sensory cells. Accordingly, some embodiments incorporate modulation of the BRN3 genes, and/or polypeptides.

In some embodiments, a subject is administered a vector engineered to carry a human BRN-3 gene (the "BRN3 vector"). In some embodiments, the BRN3 vector is a retrovirus. In some embodiments, the BRN3 vector is not a retrovirus (e.g. it is an adenovirus; a lentivirus; or a polymeric delivery system such as METAFECTENE®, SUPERFECT®, EFFECTENE®, or MIRUS' TRANSIT®).

In some embodiments, the subject is administered the BRN3 vector before, during, or after exposure to an ototoxic agent (e.g an aminoglycoside or cisplatin), or a sound of sufficient loudness to induce acoustic trauma.

In some embodiments, the BRN3 vector is incorporated into the otic formulation or composition. In some embodiments, the otic formulation or composition is injected into the inner ear. In some embodiments, the otic formulation or composition is injected into the cochlea, the Organ of Corti, the vestibular labyrinth, or a combination thereof. In some embodiments, the otic formulation or composition is placed in contact with the round window membrane.

In certain instances, after administration of the BRN3 vector, the BRN3 vector infects the cells at the site of administration (e.g. the cells of cochlea, Organ of Corti, and/or the vestibular labyrinth). In certain instances the BRN3 sequence is incorporated into the subject's genome (e.g. when the BRN3 vector is a retrovirus). In certain instances the therapy will need to be periodically re-administered (e.g. when the BRN3 vector is not a retrovirus).

In some embodiments, a subject is administered a BRN3 polypeptide. In some embodiments, the BRN3 polypeptide is incorporated into the otic formulation or composition. In some embodiments, the otic formulation or composition is injected into the inner ear. In some embodiments, otic formulation or composition is injected into the cochlea, the Organ of Corti, the vestibular labyrinth, or a combination thereof. In some embodiments, the otic formulation or composition is placed in contact with the round window membrane.

In some embodiments, a subject is administered a pharmaceutically acceptable agent which modulates the expression of the BRN3 gene or activity of the BRN3 polypeptide. In some embodiments, the expression of the BRN3 gene or activity of the BRN3 polypeptide is up-regulated. In some embodiments, the expression of the BRN3 gene or activity of the BRN3 polypeptide is down-regulated.

In some embodiments, a compound which agonizes or antagonizes BRN3 is identified (e.g. by use of a high throughput screen). In some embodiments, a construct is designed such that a reporter gene is placed downstream of a BRN3 binding site. In some embodiments, the BRN3 binding site has the sequence ATGAATTAAT (SEQ ID NO: 120) (SBNR3). In some embodiments, the reporter gene is luciferase, CAT, GFP, β-lactamase or β-galactosidase. In certain instances, the BRN3 polypeptide binds to the SBNR3 sequence and initiates transcription and expression of the reporter gene. In certain instances, an agonist of BRN3 aids or facilitates the binding of BRN3 to the SBNR3 sequence, thus increasing transcription and expression of the reporter gene relative to a pre-determined baseline expression level. In certain instances, an antagonist of BRN3 blocks the binding of BRN3 to the SBNR3, thus decreasing transcription and expression of the reporter gene relative to a pre-determined baseline expression level.

Carbamates

Contemplated for use with the formulations and compositions disclosed herein are agents that modulate the degeneration of neurons and/or hair cells of the auris, and agents for treating or ameliorating hearing loss or reduction resulting from destroyed, stunted, malfunctioning, damaged, fragile or missing hairs in the inner ear. In certain instances, carbamate compounds protect neurons and otic hair cells from glutamate-induced excitotoxicity. Accordingly, some embodiments incorporate the use of carbamate compounds. In some embodiments, the carbamate compounds are 2-phenyl-1,2-ethanediol monocarbomates and dicarbamates, derivatives thereof, and/or combinations thereof.

Estrogen Receptors

In some embodiments, the agent that promotes the survival of otic hair cells is an Estrogen Receptor agonist. In some embodiments, the estrogen receptor agonist is a partial agonist or inverse agonist.

In certain instances, Estrogen Receptor β(ERβ) is expressed in an outer hair cell, an inner hair cell, a spiral ganglion neuron, or combinations thereof. In certain embodiments, agonism of ERα and/or ERβ ameliorates hearing loss resulting from acoustic trauma. In certain embodiments, agonism of ERα and/or ERβ increases and/or up-regulates the expression of a neurotroph gene and/or the activity of a neurotroph polypeptide (e.g. BDNF). In certain embodiments, antagonism of ERα and/or ERβ increases hearing loss resulting from acoustic trauma. In certain embodiments, antagonism of ERα and/or ERβ down-regulates the expression of a neurotroph gene and/or the activity of a neurotroph polypeptide (e.g. BDNF).

In some embodiments, the ERα agonist is PPT (4,4',4"-(4-Propyl-[1H]-pyrazole-1,3,5-triyl)trisphenol); SKF-82958 (6-chloro-7,8-dihydroxy-3-allyl-1-phenyl-2,3,4,5-tetrahydro-1H-3-benzazepine); estrogen; estradiol; estradiol derivatives, including but not limited to 17-β estradiol, estrone, estriol, synthetic estrogen compositions or combinations thereof. In some embodiments, the ERβ agonist is ERβ-131, phytoestrogen, MK 101 (bioNovo); VG-1010 (bioNovo); DPN (diarylpropiolitrile); ERB-041; WAY-202196; WAY-214156; genistein; estrogen; estradiol; estradiol derivatives, including but not limited to 17-P estradiol, estrone, estriol, synthetic estrogen compositions or combinations thereof. Other ERβ agonists include select benzopyrans and triazolo-tetrahydrofluorenones, disclosed in U.S. Pat. No. 7,279,499, and Parker et al., Bioorg. & Med. Chem.

Ltrs. 16: 4652-4656 (2006), each of which is incorporated herein by reference for such disclosure. In some embodiments, a neurotroph is administered before, after, or simultaneously with an Estrogen Receptor β (ERβ) agonist. In some embodiments, the neurotroph is BDNF, CNTF, GDNF, neurotrophin-3, neurotrophin-4, and/or combinations thereof.

Fatty Acids

Contemplated for use with the formulations and compositions disclosed herein are agents that relieve, prevent, reverse or ameliorate the degeneration of neurons and/or hair cells of the auris. Accordingly, some embodiments incorporate the use of fatty acids. In certain instances, the membrane surrounding auditory neurons and the vestibulocochlear nerve comprise fatty acids. In certain instances, a deficiency in omega-3 fatty acid results in a decreased response to auditory stimuli. In certain instances, maternal deficiency of alpha-linolenic acid (ALA) leads to offspring with hearing deficiency. In some embodiments, the fatty acid includes but is not limited to an omega-3 fatty acid, an omega-6 fatty acid, or combinations thereof. In some embodiments, the omega-3 fatty acid is α-Linolenic acid, Stearidonic acid, Eicosatrienoic acid, Eicosatetraenoic acid, Eicosapentaenoic acid, Docosapentaenoic acid, Clupanodonic acid, Docosahexaenoic acid, Tetracosapentaenoic acid, Tetracosahexaenoic acid (Nisinic acid), or combinations thereof. In some embodiments, the omega-3 fatty acid is α-Linolenic acid, docosahexaenoic acid, eicosapentaenoic acid, or combinations thereof. In some embodiments, the omega-6 fatty acid is Linoleic acid, Gamma-linolenic acid, Eicosadienoic acid, Dihomo-gamma-linolenic acid, Arachidonic acid, Docosadienoic acid, Adrenic acid, Docosapentaenoic acid, Calendic acid, or combinations thereof.

Gamma-Secretase Inhibitors

Contemplated for use with the formulations and compositions disclosed herein are agents that modulate the degeneration of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of agents which inhibit Notch1 signaling. Notch1 is a transmembrane polypeptide which participates in cell development. In some embodiments, the agents which inhibit Notch1 signaling are γ-secretase inhibitors. In certain instances, the inhibition of Notch1 by a γ-secretase inhibitor, following treatment with an ototoxic agent, results in the production of otic hair cells. In some embodiments, the γ-secretase inhibitor is LY450139 (hydroxylvaleryl monobenzocaprolactam), L685458 (1S-benzyl-4R[1-[1-S-carbamoyl-2-phenethylcarbamoyl)-1S-3-methylbutylcarbamoyl]-2R-hydroxy-5-phenylpentyl}carbamic acid tert-butyl ester); LY411575 ($N^2$-[(2S)-2-(3,5-difluorophenyl)-2-hydroxyethanoyl]-$N^1$ [(7S)-5-methyl-6-oxo-6,7-dihydro-5H-dibenzo[bid]azepin-7yl]-L-alaninamide), MK-0752 (Merck), tarenflurbil, and/or BMS-299897 (2-R1R)-1-[[(4-chlorophenyl) sulfony](2,5-difluorophenyl)amino]ethyl]-5-fluorobenzenepropanoic acid).

Glutamate-Receptor Modulators

Contemplated for use with the formulations and compositions disclosed herein are agents that modulate the degeneration of neurons and/or hair cells of the auris, and agents for treating or ameliorating hearing loss or reduction resulting from destroyed, stunted, malfunctioning, damaged, fragile or missing hair cells in the inner ear. Accordingly, some embodiments incorporate the use of agents which modulate glutamate receptors. In some embodiments, the glutamate receptor is the AMPA receptor, the NMDA receptor, kainate receptor, and/or a group I, II or III mGlu receptor.

In some embodiments, the agent that modulates the AMPA receptor is an AMPA receptor antagonist. In some embodiments, the agent which antagonizes the AMPA receptors is CNQX (6-cyano-7-nitroquinoxaline-2,3-dione); NBQX (2,3-dihydroxy-6-nitro-7-sulfamoylbenzo[f]quinoxaline-2,3-dione); DNQX (6,7-dinitroquinoxaline-2,3-dione); kynurenic acid; 2,3-dihydroxy-6-nitro-7-sulfamoyl-benzo-[f]quinoxaline; or combinations thereof.

In some embodiments, the agent that modulates the NMDA receptor is an NMDA receptor antagonist. In some embodiments, the agent which antagonizes the NMDA receptor is 1-aminoadamantane, dextromethorphan, dextrorphan, ibogaine, ketamine, esketamine (AM-101), nitrous oxide, phencyclidine, riluzole, tiletamine, memantine, dizocilpine, aptiganel, remacimide, 7-chlorokynurenate, DCKA (5,7-dichlorokynurenic acid), kynurenic acid, 1-aminocyclopropanecarboxylic acid (ACPC), AP7 (2-amino-7-phosphonoheptanoic acid), APV (R-2-amino-5-phosphonopentanoate), CPPene (3-[(R)-2-carboxypiperazin-4-yl]-prop-2-enyl-1-phosphonic acid); (+)-(1S,2S)-1-(4-hydroxyphenyl)-2-(4-hydroxy-4-phenylpiperidino)-1-pro-panol; (1S,2S)-1-(4-hydroxy-3-methoxyphenyl)-2-(4-hydroxy-4-phenylpiperi-dino)-1-propanol; (3R,4S)-3-(4-(4-fluorophenyl)-4-hydroxypiperidin-1-yl-)-chroman-4,7-diol; or (1R*, 2R*)-1-(4-hydroxy-3-methylphenyl)-2-(4-(4-fluoro-phenyl)-4-hydroxypiperidin-1-yl)-propan-1-ol-mesylate; or gacyclidine (1-[(1R,2S)-2-methyl-1-thiophen-2-ylcyclohexyl]piperidine). In some embodiments, the agent that antagonizes the NMDA receptor is gacyclidine (1-[(1R,2S)-2-methyl-1-thiophen-2-ylcyclohexyl]piperidine).

In certain instances, the over-activation of the AMPA and NMDA glutamate receptors by the binding of excessive amounts of glutamate, results in the excessive opening of the ion channels under their control. In certain instances, this results in abnormally high levels of $Ca^{2+}$ and $Na^+$ entering the neuron. In certain instances, the influx of $Ca^{2+}$ and $Na^+$ into the neuron activates multiple enzymes including, but not limited to, phospholipases, endonucleases, and proteases. In certain instances, the over-activation of these enzymes results in damage to the cytoskeleton, plasma membrane, mitochondria, and DNA of the neuron. Further, in certain instances, the transcription of multiple pro-apoptotic genes and anti-apoptotic genes are controlled by $Ca^{2+}$ levels.

The mGlu receptors, unlike the AMPA and NMDA receptors, do not directly control an ion channel. However, in certain instances, they indirectly control the opening of ion channels by the activation of biochemical cascades. The mGlu receptors are divided into three groups. In certain instances, the members of groups I, II and III reduce or inhibit post-synaptic potentials by preventing or decreasing the formation of cAMP. In certain instances, this causes a reduction in the release of neurotransmitters, especially glutamate. GRM7 is the gene which encodes the mGlu7 receptor, a group III receptor. In certain instances, the agonism of mGlu7 results in a decrease in synaptic concentrations of glutamate. This ameliorates glutamate excitotoxicity.

In some embodiments, the glutamate receptor is a group II mGlu receptor. In some embodiments, the agent which modulates the group II mGlu receptor is a group II mGlu receptor agonist. In some embodiments, the group II mGlu receptor agonist is LY389795 ((−)-2-thia-4-aminobicyclo-hexane-4,6-dicarboxylate); LY379268 ((−)-2-oxa-4-amino-bicyclo-hexane-4,6-dicarboxylate); LY354740 ((+)-2- aminobicyclo-hexane-2,6dicarboxylate); DCG-IV ((2S,2'R, 3'R)-2-(2',3'-dicarboxycyclopropyl)glycine); 2R,4R-APDC (2R,4R-4-aminopyrrolidine-2,4-dicarboxylate), (S)-3C4HPG ((S)-3-carboxy-4-hydroxyphenylglycine); (S)-4C3HPG ((S)-4-carboxy-3-hydroxyphenylglycine); L-CCG-I ((2S,1'S,2'S)-2-(carboxycyclopropyl)glycine); and/or combinations thereof.

In some embodiments, the mGlu receptor is a group III mGlu receptor. In some embodiments, the group III mGlu receptor is mGlu7. In some embodiments, the agent which modulates the group III mGlu receptor is a group III mGlu receptor agonist. In some embodiments, the group III mGlu receptor agonist is ACPT-I ((1S,3R,4S)-1-aminocyclopentane-1,3,4-tricarboxylic acid); L-AP4 (L-(+)-2-Amino-4-phosphonobutyric acid); (S)-3,4-DCPG ((S)-3,4-dicarboxyphenylglycine); (RS)-3,4-DCPG ((RS)-3,4-dicarboxyphenylglycine); (RS)-4-pho sphonophenylglycine ((RS)PPG); AMN082 (,N'-bis(diphenylmethyl)-1,2-ethanediamine dihydrochloride); DCG-IV ((2S,2'R,3'R)-2-(2',3'-dicarboxycyclopropyl)glycine); and/or combinations thereof. In some embodiments, the mGlu receptor is mGlu7. In some embodiments, the agonist of mGlu7 is AMN082. In some embodiments, the mGlu receptor modulator is 3,5-Dimethyl pyrrole-2,4-dicarboxylic acid 2-propyl ester 4-(1, 2,2-trimethyl-propyl) ester (3,5-dimethyl PPP); 3,3'-difluorobenzaldazine (DFB), 3,3'-dimlethoxybenzaldazine (DMeOB), 3,3'-dichlorobenzaldazine (DCB) and other allosteric modulators of mGluR$_5$ disclosed in Mol. Pharmacol. 2003, 64, 731-740; (E)-6-methyl-2-(phenyldiazenyl) pyridin-3-ol (SIB 1757); (E)-2-methyl-6-styrylpyridine (SIB 1893); 2-methyl-6-(phenylethynyl)pyridine (MPEP), 2-methyl-4-((6-methylpyridin-2-yl)ethynyl)thiazole (MTEP); 7-(Hydroxyimino)cyclopropa[b]chromen-1α-carboxylate ethyl ester (CPCCOEt), N-cyclohexyl-3-methylbenzo[d]thiazolo[3,2-a]imidazole-2-carboxamide (YM-298198), tricyclo[3.3.3.1]nonanyl quinoxaline-2-carboxamide (NPS 2390); 6-methoxy-N-(4-methoxyphenyl) quinazolin-4-amine (LY 456239); mGluR1 antagonists disclosed in WO2004/058754 and WO2005/009987; 2-(4-(2,3-dihydro-1H-inden-2-ylamino)-5,6,7,8-tetrahydroquinazolin-2-ylthio)ethanol; 3-(5-(pyridin-2-yl)-2H-tetrazol-2-yl)benzonitrile, 2-(2-methoxy-4-(4-(pyridin-2-yl)oxazol-2-yl)phenyl)acetonitrile; 2-(4-(benzo[d]oxazol-2-yl)-2-methoxyphenyl)acetonitrile; 6-(3-methoxy-4-(pyridin-2-yl) phenyl)imidazo[2,1-b]thiazole; (S)-(4-fluorophenyl)(3-(3-(4-fluorophenyl)-1,2,4-oxadiazol-5-yl)piperidin-1-yl) methanone (ADX47273) and/or combinations thereof. In some embodiments, the mGlu receptor modulator is a positive allosteric modulator of mGlu receptors. In some embodiments, the mGlu receptor modulator is a negative allosteric modulator of mGlu receptors.

In some embodiments, a glutamate receptor modulator is a nootropic agent. Contemplated for use with the formulations and compositions disclosed herein are nootropic agents that modulate neuronal signalling by activating glutamate receptors. In some instances, nootropic agents treat or ameliorate hearing loss (e.g, NIHL) or tinnitus. Accordingly, some embodiments incorporate the use of nootropic agents including, and not limited to, piracetam, Oxiracetam, Aniracetam, Pramiracetam, Phenylpiracetam (Carphedon), Etiracetam, Levetiracetam, Nefiracetam, Nicoracetam, Rolziracetam, Nebracetam, Fasoracetam, Coluracetam, Dimiracetam, Brivaracetam, Seletracetam, and/or Rolipram for the treatment of NIHL or tinnitus.

Growth Factors

Contemplated for use with the formulations and compositions disclosed herein are agents that modulate the degeneration of neurons and/or hair cells of the auris, promote the survival and/or growth of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of agents which promote the survival of neurons and otic hair cells, and/or the growth of neurons and otic hair cells. In some embodiments, the agent which promotes the survival of otic hair cells is a growth factor. In some embodiments, the growth factor is a neurotroph. In certain instances, neurotrophs are growth factors which prevent cells from initiating apoptosis, repair damaged neurons and otic hair cells, and/or induce differentiation in progenitor cells. In some embodiments, the neurotroph is brain-derived neurotrophic factor (BDNF), ciliary neurotrophic factor (CNTF), glial cell-line derived neurotrophic factor (GDNF), neurotrophin-3, neurotrophin-4, and/or combinations thereof. In some embodiments, the neurotroph is brain-derived neurotrophic factor (BDNF), ciliary neurotrophic factor (CNTF), glial cell-line derived neurotrophic factor (GDNF), neurotrophin-3, neurotrophin-4, fibroblast growth factor (FGF), insulin-like growth factor (IGF), epidermal growth factor (EGF), platelet-derived growth factor (PGF), and/or combinations thereof. In some embodiments, the neurotroph is brain-derived neurotrophic factor (BDNF), neurotrophin-3, and/or combinations thereof.

In some embodiments, the growth factor is a fibroblast growth factor (FGF), an insulin-like growth factor (IGF), an epidermal growth factor (EGF), a platelet-derived growth factor (PGF) and/or agonists thereof. In some embodiments, the growth factor is an agonist of the fibroblast growth factor (FGF) receptor, the insulin-like growth factor (IGF) receptor, the epidermal growth factor (EGF) receptor, and/or the platelet-derived growth factor. In some embodiments, the growth factor is hepatocyte growth factor.

In some embodiments, the growth factor is glial cell-line derived neurotrophic factor (GDNF). In some embodiments, the growth factor is a GDNF mimetic. In some embodiments, the growth factor is a GDNF receptor agonist. In some instances, the GDNF mimetic or GDNF receptor agonist activates tyrosine receptor kinase RET and/or neural cell adhesion molecule (NCAM).

In some embodiments, the growth factor is an epidermal growth factor (EGF). In some embodiments, the EGF is heregulin (HRG). In certain instances, HRG stimulates the proliferation of utricular sensory epithelium. In certain instances, HRG-binding receptors are found in the vestibular and auditory sensory epithelium. In some embodiments, the growth factor is a HGF receptor (c-Met) agonist. In some embodiments, the growth factor is dihexa or other angiotensin IV-derived peptides that enhance HGF function.

In some embodiments, the growth factor is an insulin-like growth factor (IGF). In some embodiments, the IGF is IGF-1. In some embodiments, the IGF-1 is mecasermin. In certain instances, IGF-1 attenuates the damage induced by exposure to an aminoglycoside. In certain instances, IGF-1 stimulates the differentiation and/or maturation of cochlear ganglion cells.

In some embodiments, the FGF receptor agonist is FGF-2. In some embodiments, the IGF receptor agonist is IGF-1. Both the FGF and IGF receptors are found in the cells comprising the utricle epithelium.

In some embodiments, the growth factor is hepatocyte growth factor (HGF). In some instances, HGF protects cochlear hair cells from noise-induced damage and reduces noise-exposure-caused ABR threshold shifts.

Also contemplated for use in the otic formulations and compositions described herein are growth factors including Erythropoietin (EPO), Granulocyte-colony stimulating factor (G-CSF), Granulocyte-macrophage colony stimulating factor (GM-CSF), Growth differentiation factor-9 (GDF9), Insulin-like growth factor (IGF), Myostatin (GDF-8), Platelet-derived growth factor (PDGF), Thrombopoietin (TPO), Transforming growth factor alpha (TGF-α), Transforming growth factor beta (TGF-β), Vascular endothelial growth factor (VEGF) or combinations thereof.

Neurotrophs

In some embodiments, the growth factor is a neurotroph. In certain instances, neurotrophs are growth factors which prevent cells from initiating apoptosis, repair damaged neurons and otic hair cells, and/or induce differentiation in progenitor cells. In some embodiments, the neurotroph is brain-derived neurotrophic factor (BDNF), ciliary neurotrophic factor (CNTF), glial cell-line derived neurotrophic factor (GDNF), neurotrophin-3, neurotrophin-4, and/or combinations thereof.

In some embodiments, the neurotroph is BDNF. In certain instances, BDNF is a neurotroph which promotes the survival of existing neurons (e.g. spiral ganglion neurons), and otic hair cells by repairing damaged cells, inhibiting the production of ROS, and inhibiting the induction of apoptosis. In certain embodiments, it also promotes the differentiation of neural and otic hair cell progenitors. Further, in certain embodiments, it protects the Cranial Nerve VIII from degeneration. In some embodiments, BDNF is administered in conjunction with fibroblast growth factor. In some embodiments, BDNF promotes neuronal growth and/or promotion of synapse formation.

In some embodiments, the neurotroph is neurotrophin-3. In certain embodiments, neurotrophin-3 promotes the survival of existing neurons and otic hair cells, and promotes the differentiation of neural and otic hair cell progenitors. Further, in certain embodiments, it protects the VIII nerve from degeneration. In some embodiments, neurotrophin-3 promotes neuronal growth and/or promotion of synapse formation.

In some embodiments, the neurotroph is CNTF. In certain embodiments, CNTF promotes the synthesis of neurotransmitters and the growth of neurites. In some embodiments, CNTF is administered in conjunction with BDNF.

In some embodiments, the neurotroph is GDNF. In certain embodiments, GDNF expression is increased by treatment with ototoxic agents. Further, in certain embodiments, cells treated with exogenous GDNF have higher survival rates after trauma than untreated cells.

Immune System Cells

Contemplated for use with the formulations and compositions disclosed herein are agents that modulate the degeneration of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of cells which participate in the repair of otic hair cells and neurons. In some embodiments, the cells which participate in the repair of otic hair cells and neurons are macrophages, microglia, and/or microglia-like cells. In certain instances, the concentration of macrophages and microglia increase in ears damaged by treatment with ototoxic agents. In certain instances, microglia-like cells eliminate waste from the Organ of Corti and participate in the structural repair of hair cells following treatment with the ototoxic antibiotic neomycin.

Ototoxic Agents

Contemplated for use with the formulations and compositions disclosed herein are agents that destroy neurons and/or otic hair cells. Accordingly, some embodiments incorporate the use of agents which fatally damage and/or induce apoptosis in the neurons and/or otic hair cells of the auris. In some embodiments, the agents which fatally damage and/or induce apoptosis in the neurons and/or otic hair cells of the auris are the aminoglycoside antibiotics (e.g. gentamicin, and amikacin), the macrolide antibiotics (e.g erythromycin), the glycopeptide antibiotics (e.g. vancomycin), the loop diuretics (e.g. furosemide) salicylic acid, and nicotine.

Retinoblastoma Protein Modulation

Contemplated for use with the formulations and compositions disclosed herein are agents that modulate the degeneration of neurons and/or hair cells of the auris, promote the growth of neurons and/or hair cells of the auris, and agents for treating or ameliorating hearing loss or reduction resulting from destroyed, stunted, malfunctioning, damaged, fragile or missing hairs in the inner ear. Further contemplated herein are agents that destroy neurons and/or otic hair cells. Accordingly, some embodiments incorporate the use of agents that modulate retinoblastoma protein (pRB). pRB is a member of the pocket protein family. It is encoded by the RB1 gene. In certain instances, it inhibits transition from G1 to S phase by binding to and inactivating the E2f family of transcription factors. In certain instances, it also regulates differentiation, and survival of hair cells. In certain instances, pRB knock-out mice demonstrate increased proliferation of hair cells.

In some embodiments, the agent that modulates one or more of the pRB is an agonist of pRB. In some embodiments, the agent that modulates one or more of the pRB is an antagonist of pRB. In certain instances, a compound which agonizes or antagonizes pRB is identified (e.g. by use of a high throughput screen). In some embodiments, a construct is designed such that a reporter gene is placed downstream of an E2F binding sequence. In some embodiments, the binding sequence is TTTCGCGC. In some embodiments, the reporter gene is luciferase, CAT, GFP, β-lactamase or β-galactosidase. In certain instances, E2f binds to the binding sequence causing the transcription and expression of the reporter gene. In certain instances, an agonist of pRB causes an increase in the binding of pRB to E2f. In certain instances, the increase in binding of pRB and E2f results in a decrease in the transcription and expression of the reporter gene. In certain instances, an antagonist of pRB causes a decrease in the binding of pRB to E2f. In certain instances, the decrease in binding of pRB and E2f results in an increase in the transcription and expression of the reporter gene.

In some embodiments, the agent that modulates pRB is an siRNA molecule. In certain instances, the siRNA molecule is as described herein.

Salicylic Acid

Contemplated for use with the formulations and compositions disclosed herein are agents that modulate the degeneration of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of salicylic acid. In certain instances, when administered before treatment with an aminoglycoside, it protects otic hair cells and spiral ganglion neurons from aminoglycoside ototoxicity.

Sodium Channel Blockers

Contemplated for use with the formulations and compositions disclosed herein are agents that modulate the degeneration of neurons and hair cells, and agents for treating or ameliorating hearing loss or reduction resulting from destroyed, stunted, malfunctioning, damaged, fragile or missing hairs in the inner ear. In certain instances, excitotoxicity causes the excessive opening of $Na^+$ channels. In certain instances, this results in excess $Na^+$ ions entering the neuron. In certain instances, the excess influx of $Na^+$ ions into the neuron causes the neuron to fire more often. In certain instances, this increased firing yields a rapid buildup of free radicals and inflammatory compounds. In certain instances, the free radicals damage the mitochondria, depleting the cell's energy stores. Further, in certain instances, excess levels of $Na^+$ ions activate excess levels of enzymes including, but not limited to, phospholipases, endonucleases, and proteases. In certain instances, the over-activation of these enzymes results in damage to the cytoskeleton, plasma membrane, mitochondria, and DNA of the neuron. Accordingly, some embodiments incorporate the use of agents which antagonize the opening of $Na^+$ channels. In some embodiments, sodium channel blockers are as described herein.

Stem Cells and Differentiated Auris Sensory Cells

Contemplated for use with the formulations and compositions disclosed herein are transplants of cells that supplement and/or replace the pre-existing neurons and/or hair cells of the auris. In some embodiments, the agent is a stem cell. In some embodiments, the agent is a partially or fully differentiated auris sensory cell. In some embodiments, the differentiated auris sensory cell is derived from a human donor. In some embodiments, the differentiated auris sensory cell is derived from a stem cell, the differentiation of which was induced under artificial (e.g. laboratory) conditions.

Stem cells are cells that possess the capacity to differentiate into multiple cell types. Totipotent stem cells differentiate into embryonic cells or extraembryonic cells. Pluripotent cells differentiate into cells of any of endoderm, mesoderm, or ectoderm origin. Multipotent cells differentiate into closely related cells (e.g hematopoietic stem cells). Unipotent cells differentiate into only one type of cell, but like other stem cells have the characteristic of self-renewal. In some embodiments, the stem cell is totipotent, pluripotent, multipotent, or unipotent. Further, stem cells undergo mitotic division without themselves differentiating (i.e. self-renewal).

Embryonic stem (ES) cells are stem cells derived from the epiblast tissue of the inner cell mass of a blastocyst or earlier stage embryo. ES cells are pluripotent. In some embodiments, the stem cell is an ES cell. Adult stem cells (also known as somatic cells or germline cells) are cells isolated from a developed organism wherein the cells possess the characteristic of self-renewal, and the ability to differentiate into multiple cell types. Adult stem cells are pluripotent (for example, stem cells found in umbilical cord blood), multipotent or unipotent. In some embodiments, the stem cell is an adult stem cell.

In some embodiments, a stem cell and/or a differentiated auris sensory cell is administered in combination with a differentiation stimulating agent. In some embodiments, the differentiation stimulating agent is a growth factor. In some embodiments, the growth factor is a neurotrophin (e.g. nerve growth factor (NGF), brain-derived neurotrophic factor (BDNF), neurotrophin-3 (NT-3), neurotrophin-4 (NT-4), or novel neurotrophin-1 (NNT1). In some embodiments, the growth factor is FGF, EGF, IGF, PGF, or combinations thereof.

In some embodiments, a stem cell and/or a differentiated auris sensory cell is administered to a subject in need thereof as a controlled release agent. In some embodiments, a stem cell and/or a differentiated auris sensory cell is administered to a subject in need thereof as an immediate release agent (e.g. in a cell suspension) in combination with a controlled release auris sensory cell modulating agent. In some embodiments, a controlled release auris sensory cell modulating agent is a vector comprising an Atoh1 or BRN3 gene, an siRNA sequence targeting RB1, a growth factor, or combinations thereof.

In some embodiments, a stem cell and/or a differentiated auris sensory cell is administered to the cochlea or vestibular labyrinth. In some embodiments, a stem cell and/or a differentiated auris sensory cell is administered by via intratympanic injection, and/or a post-auricular incision. In some embodiments, a stem cell and/or a differentiated auris sensory cell is contacted with the Organ of Corti, vestibulocochlear nerve, and/or crista ampullaris.

Thyroid Hormone Receptor Modulation

Contemplated for use with the formulations and compositions disclosed herein are agents that modulate the degeneration of neurons and/or hair cells of the auris, promote the growth of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of agents that modulate Thyroid Hormone (TH) receptors. The TH receptors are a family of nuclear hormone receptors. The family includes, but is not limited to TRα1 and TRβ. In certain instances, TRβ knock-out mice demonstrate a decreased responsiveness to auditory stimuli, and a decrease in $K^+$ current in hair cells.

In some embodiments, the agent that modulates one or more of the TH receptors is an agonist of the one or more TH receptors. In some embodiments, the agonist of one or more of the TH receptors is $T_3$ (3,5,3'-triiodo-L-thyronine); KB-141 (3,5-dichloro-4-(4-hydroxy-3-isopropylphenoxy) phenylacetic acid); GC-1 (3,5-dimethyl-4-(4'-hydroxy-3'-isopropylbenzyl)-phenoxy acetic acid); GC-24 (3,5-dimethyl-4-(4'-hydroxy-3'-benzyl)benzylphenoxyacetic acid); sobetirome (QRX-431); 4-OH—PCB106 (4-OH-2',3,3',4', 5'-pentachlorobiphenyl); MB07811 ((2R,4S)-4-(3-chlorophenyl)-2-[(3,5-dimethyl-4-(4-hydroxy-3-isopropylbenzyl) phenoxy)methyl]-2-oxido-[1,3,2]-dioxaphosphonane); MB07344 (3,5-dimethyl-4-(4-hydroxy-3-isopropylbenzyl) phenoxy)methylphosphonic acid); and combinations thereof. In certain instances, KB-141; GC-1; sobetirome; and GC-24 are selective for TRβ.

TRPV Modulation

Contemplated for use with the formulations and compositions disclosed herein are agents that modulate the degeneration of neurons and hair cells, and agents for treating or ameliorating hearing loss or reduction resulting from destroyed, stunted, malfunctioning, damaged, fragile or missing hairs in the inner ear. Accordingly, some embodiments incorporate the use of agents that modulate TRPV receptors. The TRPV (Transient Receptor Potential Channel Vanilloid) receptors are a family of non-selective ion channels permeable to calcium, amongst other ions. There are six members of the family: TRPV1-6. In certain instances, following treatment with kanamycin, TRPV 1 is upregulated. Additionally, in certain instances, antagonism of the TRPV 4 receptor makes mice vulnerable to acoustic trauma. Further, in certain instances, capsaicin, an agonist of TRPV 1, prevents hyperlocomotion following an ischemic event.

In some embodiments, the agent that modulates one or more of the TRPV receptors is an agonist of the one or more TRPV receptors. In some embodiments, the agonist of one or more of the TRPV receptors is capsaicin, resiniferatoxin, or combinations thereof. In some embodiments, TRPV modulating include the TRPV modulators disclosed in US application publications 2005/0277643, 2005/0215572, 2006/0194801, 2006/0205773, 2006/0194801, 2008/0175794, 2008/0153857, 2008/0085901, 20080015183, 2006/0030618, 2005/0277646, 2005/0277631, 2005/0272931, 2005/0227986, 2005/0153984, 2006/0270682, 2006/0211741, 2006/0205980, and 2006/0100490, and/or combinations thereof.

Sensory Hair Cell Restorative Agents

In some instances, immunomodulators and/or aural pressure modulators modulate the function of neurons and/or auris sensory cells. Therapeutic agents which assist in restoring sensory hair cell presence or function are also contemplated herein. These therapeutic agents assist in the treatment of hearing loss in patients, including sensorineural hearing loss, presbycusis and hearing loss from excessive noise. Recent studies have demonstrated the use of insulin-like growth factor 1 (IGF-1) in the restoration of auditory function for noise-induced hearing loss patients. (Lee et al. *Otol. Neurotol.* (2007) 28:976-981). Accordingly, agents IGF-1, IGF-1 agonists or agents which upregulate the expression, production or function of IGF-1 are optionally included with the formulations described herein.

Adenosine Modulators

Adenosine is comprised of adenine attached to ribofuranose via a β-N9-glycosidic bond. In certain instances, adenosine is an inhibitory neurotransmitter. In certain instances, it functions as a ligand for four GPCRs—adenosine receptor $A_1$, adenosine receptor $A_{2A}$, adenosine receptor $A_{2B}$, and adenosine receptor $A_3$. In certain instances, the binding of adenosine to an adenosine receptor results in (either partially or fully) an anti-inflammatory effect. In certain instances, the binding of adenosine to an adenosine receptor results in (either partially or fully) vasodialation. In certain instances, it is produced in response to cellular damage (e.g., hypoxia, and ischemia). For example, depolarization and asphyxia in the ear induce the release of adenosine into perilymph where it exerts a protective effect.

Accordingly, in some embodiment adensoine modulators are used in the treatment of cochlear and vestibular disorders. In some embodiments, the adenosine modulator is ATL313 (4-(3-(6-amino-9-(5-cyclopropylcarbamoyl-3,4-dihydroxytetrahydrofuran-2-yl)-9H-purin-2-yl)prop-2-ynyl) piperidine-1-carboxylic acid methyl ester); GW328267X ((2R,3R,4S,5R)-2-{16-amino-2-[(1-benzyl-2-hydroxyethyl) amino]-9H-purin-9-yl}-5-(2-ethyl-2H-tetrazol-5-yl)tetrahydrofuran-3,4-diol); CGS 21680 hydrochloride (4-[2-[[6-Amino-9-(N-ethyl-b-D-ribofuranuronamidosyl)-9H-purin-2-yl]amino]ethyl]benzenepropanoic acid hydrochloride); CV 1808 (2-Phenylaminoadenosine); p-DITC-APEC (2-[4-[2-[2-[(4-Isothiocyanatophenyl)thiocarbonylamino]e thylaminocarbonyl]ethyl]phenethylamino]-5'-N-ethylcarbo xamidadenosine); SDZ WAG994 (N-Cyclohexyl-2'-O-methyladenosine); CVT-3146 (regadenoson; 1-(9-(3,4-dihydroxy-5-(hydroxymethyl)oxolan-2-yl)-6-aminopurin-2-yl) pyrazol-4-yl)-N-methylcarboxamide); ATL-146e (4-{3-[6-Amino-9-(5-ethylcarbamoyl-3,4-dihydroxy-tetrahydrofuran-2-yl)-9H-purin-2-yl]-prop-2-ynyl}-cyclohexanecarboxylic acid methyl ester); 5'-n-Ethyl-carboxamidoadenosine; tecadenoson; CVT-510 (N-(3(R)-tetrahydrofuranyl)-6-aminopurine riboside); CCPA (2-Chloro-N6-cyclopentyladenosine); CPA (N6-Cyclopentyladeno sine); GR 79236 (N-[(1S,2S)-2-Hydroxycyclopentyl]adenosine); 2'-MeCCPA; PD 81723 ((2-Amino-4,5-dimethyl-3-thienyl)-[3-(trifluoromethyl)phenyl]methanone); PSB 36 (1-Butyl-8-(hexahydro-2,5-methanopentalen-3a (1H)-yl)-3,7-dihydro-3-(3-hydroxypropyl)-1H-purine-2,6-dione); ribavirin; CHA (N6-cyclohexyladenosine); GW493838 (GSK); (−)-N6-(2-phenylisopropyl) adenosine; GW684067 ((2R,3R,4S,5R)-5-ethynyl-2-[6-tetrahydro-2H-pyran-4-ylamino)-9H-purin-9-yl]tetrahydrofuran-3,4-diol); CVT-3619 (2-(6-(((2-hydroxycyclopentyl)amino)purin-9-yl)-5-((2-fluorophenylthio)methyl)oxolane-3,4-diol); 2-C1-IB-MEGA (CF102; 2-chloro-$N^6$-(3-iodobenzyl)-5'-N-methylcarbamoyladenosine); HEMADO; IB-MECA (CF101; $N^6$-(3-iodobenzyl)-5'-N-methylcarbamoyladenosine); CP-532903 ($N^6$-(2,5-Dichlorobenzyl)-3'-aminoadenosine-5'-N-methylcarboxamide); CF502 (Can-Fite BioPharma); LJ-529 (2-chloro-N(6)-(3-iodobenzyl)-5'-N-methylcarbamoyl-4'-thioadenosine); BAA (8-butylaminoadeno sine); 6-Amino-2-chloropurine riboside; 2-Chloroadenosine; NECA (5'-N-ethylcarboxamidoadeno sine); APNEA (N6-2-(4-aminophenyl)ethyladenosine); or combinations thereof.

Modulators of Atoh 1

An additional sensory hair cell restorative agents are directed towards modulators to the products of the Atoh1 (atonal; ATOH), Neurod1 and Neurog1 genes. Atoh1 belongs to a family of basic Helix-Loop-Helix (bHLH) genes that are involved in cell fate determination across phyla and systems, typically being expressed in proliferating precursors. In mammals, at least three bHLH transcription factors are essential for sensory neuron development, including hair cells and sensory neurons of the ear: Atoh1, Neurod1 and Neurog1. Atoh1, in particular, is essential for hair cell differentiation, and plays a role as a differentiation factor of postmitotic hair cells. Studies have also shown that expression of Atoh1, in combination with Bdnf, form afferent and efferent innervation in undifferentiated cells of epithelial origin.

Treatment of with ATOH protein supports the role of Atoh1 in sensory hair cell development, inducing the formation of new sensory hair cells in cochlear structures, and restoring hearing and balance function. Gene therapy using vectors inserted with the Atoh1 gene further supports ATOH's role in promoting and maintaining sensory hair cell function. Accordingly, one embodiment disclosed herein is the use of ATOH proteins or manipulation of Atoh1 expression to induce sensory hair cell development in hearing and balance disorders.

In additional embodiments, a neurotrophic growth factor is administered to the auris interna via the formulations and compositions described herein to stimulate inner ear hair cell neurotrophic growth factors. The damage caused to spiral ganglion neurons removes not only neural activity, but also neurotrophin support that is normally supplied by hair cells, the absence of which leads to cell death via apoptosis.

In one embodiment, neurotrophic growth factor includes but is not limited to brain-derived neurotrophic fact, neurotrophin-3, glial-derived neurotrophic factor, neurotrophin-4/5, nerve growth factor, chlorphenylthio-cAMP (cptcAMP; a permeant cAMP analog), ciliary derived neurotrophic factor (CNTF) or combinations thereof. In another example, the sensory cell restorative agent is a brain-derived neutrophic factor (BDNF). In yet another example, the neurotrophic growth factor is neurotrophin-3 (NT-3). In other examples, the neurotrophic growth factor is glial-derived neurotrophic factor (GDNF). In some examples, the neurotrophic growth factor is a peptide or protein. In other embodiments, the neurotrophic growth factor stimulates or enhances spiral ganglion neuron survival.

ERR/NR3B2 Antagonists

Studies have also suggested a role for the orphan receptor estrogen related receptor 3/Nr3b2 in regulating endolymph production, thereby possibly playing a role in mediating cochlear and vestibular pressure in the endolymph fluid. (Chen et al. *Dev. Cell.* (2007) 13:325-337). Accordingly, agents which antagonize ERR/Nr3b2 expression, protein production or protein function are contemplated as useful with the formulations disclosed herein.

KCNQ Modulators

Modulators of KCNQ are also contemplated within the scope of the embodiments disclosed herein. KCNQ proteins form potassium channels, which play a role by preventing accumulation of potassium in hair cells. Potassium concentrations are high in the endolymph, giving the endocochlear fluid a high positive potential, which in turn provides a large drive force for potassium entry into the hair cell. KCNQ function is correlated with outer hair cell (OHC) survival; inhibition of KCNQ alters potassium homeostasis, resulting eventually in OHC degeneration. Accordingly, treatment of the auris interna with KCNQ modulators, in some cases activators, is contemplated within the scope of the embodiments disclosed herein as useful in the maintenance of sensory hair cell function in both vestibular and cochlear structures.

Activators of KCNQ2/3 channels have been shown to reduce tinnitus and include retigabine and retigabine analogs (Kumar et al, Mol Pharm 89:667-677, 2016) as KCNQ2/3 activators. Accordingly, activators of KCNQ2/3 channels are comtemplated as useful agents with the formulations disclosed herein.

P2X Modulators

Modulators of P2X channel function are also contemplated within the scope of the embodiments, for use, for example, in auris interna disorders, such as cochlear inflammation and noise-induced hearing loss. P2X channels, which are gated by adenosine triphosphate, are present in a broad distribution of tissues, and are thought to play a role in peripheral and central neuronal transmission, smooth muscle contraction and inflammation. Purine nucleotides are thought to play a role in cochlear disease, where ATP plays a cytotoxic role via both apoptosis and necrosis due to the activation of P2X receptors. For example, chronic perfusion of the perilymphatic space with ATP causes the proliferation of fibrous tissue and neoosterogenesis in the scala tympani. Moreover, noise exposure and hypoxia cause a significant elevation of ATP concentration in the endolymphatic and perilymphatic compartments, which represent an adaptive response of the cells to injury in some cases.

Accordingly, one embodiment is the use of modulators of P2X in the treatment of cochlear and vestibular disorders, including hearing and balance disorders. Antagonists and agonists to P2X channels include BzATP, TNP-ATP, α,β-meATP, A-317491, PPADS, NF279, meSuramin, Reactive Blue II, RO-1, Adamantane amides, RO-3 and 4,5-diarylimidazolines.

In another embodiment, P2Y receptor modulators and antagonists are contemplated for use with the formulations described herein, such as those based described in Wang et al Cell: 163:1348-1359, 2015).

CNS Modulating Agents

In some instances, immunomodulators and/or aural pressure modulators modulate central nervous system activity.

Anticholinergics

Contemplated for use with the formulations and compositions disclosed herein are agents which ameliorate otic disorders, including vestibular disorders and/or tinnitus, through local modulation of central nervous system (CNS) activity. Accordingly, some embodiments incorporate the use of agents which inhibit the release of the neurotransmitter acetylcholine in the CNS. Anticholinergic agents are substances which block acetylcholine in the central and the peripheral nervous system. They treat balance disorders by suppressing conduction in vestibular cerebellar pathways, thus increasing motion tolerance.

In some embodiments, the anticholinergic is glycopyrrolate, homatropine, scopolamine or atropine. In some embodiments, the anticholinergic is glycopyrrolate. In some embodiments, the anticholinergic is homatropine. In some embodiments, the anticholinergic is scopolamine. In some embodiments, the anticholinergic is atropine. In some embodiments, the anticholinergic is an acetylcholinesterase inhibitor that reduces acetylcholine degredation and facilitates cholinergic function of cochlear efferents to protect hair cell degeneration and improves hair cell function. Examples of such compounds include but are not limited to tacrine, galantamine, donezepil, rivastigmine, physostigmine, neostigmine, ambenonium, demacarium, huperzine A.

Antihistamines

Contemplated for use with the formulations and compositions disclosed herein are agents which ameliorate otic disorders, including vestibular disorders and/or tinnitus, through local modulation of central nervous system (CNS) activity. Accordingly, some embodiments incorporate the use of agents which block the action of neurotransmitters in the CNS. Histamine is a neurotransmitter in the CNS. Accordingly, some embodiments incorporate the use of agents which modulate histamine receptors (e.g. the $H_1$ receptor, $H_2$ receptor, $H_3$ receptor and/or the $H_4$ receptor). In some embodiments, anithistamines are as described herein.

Calcium Channel Blockers

Contemplated for use with the formulations and compositions disclosed herein are agents which ameliorate otic disorders, including vestibular disorders and/or tinnitus, through local modulation of central nervous system (CNS) activity. Accordingly, some embodiments incorporate the use of agents which block or antagonize Ca+ channels. Calcium channels are channels formed in the plasma membrane of neurons (amongst other cells) by integral membrane proteins. These channels conduct $Ca^+$ through a cell's plasma membrane. In neurons, the flow of $Ca^{2+}$ is partly responsible for creating and propagating action potentials in neurons. It is also responsible for the release of certain neurotransmitters in some instances.

In some embodiments, the calcium channel antagonist is cinnarizine, flunarizine, or nimodipine. In some embodiments, the calcium channel antagonist is cinnarizine. In some embodiments, the calcium channel antagonist is flunarizine. In some embodiments, the calcium channel antagonist is nimodipine. Other calcium channel blockers include verapamil, diltiazem, omega-conotoxin, GVIA, amlodipine, felodipine, lacidipine, mibefradil, NPPB (5-Nitro-2-(3-phenylpropylamino)benzoic Acid), flunarizine, and/or combinations thereof GABA Receptor Modulators Contemplated for use with the formulations and compositions disclosed herein are agents which ameliorate otic disorders, including vestibular disorders and/or tinnitus, through local modulation of central nervous system (CNS) activity. Accordingly, some embodiments incorporate the use of agents which modulate the action of GABA receptors in the CNS. GABA, or γ-aminobutyric acid, is an inhibitory neurotransmitter in the CNS. It acts at inhibitory synapses of both pre- and postsynaptic neuronal processes. The binding of GABA to its receptors (the $GABA_A$ receptor, the $GABA_B$ receptor, and the $GABA_C$ receptor) results in the opening of ion channels, and the flow of Cl⁻ into the cell and/or K⁺ out of the neuron. The result is hyperpolarization of the neuron. Accordingly, some embodiments incorporate the use of agents which increase or decrease the sensitivity of the GABA receptors, or activate the GABA receptors by mimicking GABA.

The benzodiazepine class of therapeutic agents are agonists of the $GABA_A$ receptor. When a benzodiazepine binds to the $GABA_A$ receptor it induces a conformational change which increases the affinity of GABA for its receptor. The result of the increase in the binding of GABA is an increase in the frequency with which the CF channels in the neurons open. This causes hyperpolarization of the neural membrane. In some embodiments, the benzodiazepine is selected from the group consisting of: alprazolam, bromazepam, brotizolam, chlordiazepoxide, clonazepam, clorazepate, diazepam, estazolam, flunitrazepam, flurazepam, loprazolam, lorazepam, lormetazepam, idazolam, nimetazepam, nitrazepam, oxazepam, prazepam, temazepam, triazolam or combinations thereof. In some embodiments, the benzodiazepine is clonazepam, diazepam, lorazepam, or combinations thereof. In some embodiments, the benzodiazepine is diazepam.

Non-benzodiazepine $GABA_A$ modulators are also contemplated for use in the formulations described herein. Examples of non-benzodiazepine $GABA_A$ modulators include but are not limited to olpidem, alpidem, zaleplon, indiplon, zopiclone, pagoclone, L-655,708, alphaxolone, and ganaxolone.

In some embodiments, the GABA receptor modulator is a loop diuretic. In some embodiments, the loop diuretic is furosemide, bumetanide, or ethacrynic acid. In some embodiments, the loop diuretic is furosemide. In some embodiments, the loop diuretic is bumetanide. In some embodiments, the loop diuretic is ethacrynic acid. Furosemide, for example, binds to the $GABA_A$ receptor and reversibly antagonizes GABA-evoked currents of the α6, β2, and γ2 receptors. By way of example only, useful loop diuretics include, but are not limited to, furosemide, bumetanide, and ethacrynic acid.

In some embodiments, the modulator of a GABA receptor is a GABA analogue. GABA analogues mimic GABA. Thus, when they bind to a GABA receptor, the receptor acts as though GABA is binding to it and the receptor is activated. In some embodiments, the GABA analog is gabapentin, pregabalin, muscimol, or baclofen. In some embodiments, the GABA analog is gabapentin. In some embodiments, the GABA analog is pregabalin. In some embodiments, the GABA analog is muscimol. In some embodiments, the GABA analogue is baclofen. Baclofen is an analogue of GABA which binds to and activates the $GABA_B$ receptor. Muscimol is also an analogue of GABA. It agonizes the $GABA_A$ receptor.

Neurotransmitter Reuptake Inhibitors

Contemplated for use with the formulations and compositions disclosed herein are agents which ameliorate otic disorders, including vestibular disorders and/or tinnitus, through local modulation of central nervous system (CNS) activity. Accordingly, some embodiments incorporate the use of agents which inhibit the reuptake of neurotransmitters in the CNS. In some embodiments, the neurotransmitter reuptake modulator is an antagonist of a neurotransmitter reuptake target, partial agonist, inverse agonist, neutral or competitive antagonist, allosteric antagonist, and/or orthosteric antagonist. Neurotransmitter reuptake inhibitors inhibit the reuptake of neurotransmitters into presynaptic cells of the CNS. This increases the concentration of neurotransmitter available to stimulate post-synaptic cells of the CNS.

In some embodiments, the neurotransmitter reuptake inhibitors are tricyclic antidepressants. Tricyclic antidepressants work by inhibiting the re-uptake of the neurotransmitters norepinephrine and serotonin by pre-synaptic cells. This increases the level of serotonin and/or norepinephrine available to bind to the postsynaptic receptor. In some embodiments, the tricyclic antidepressant is amitriptyline, nortriptyline, or trimipramine. In some embodiments, the tricyclic antidepressant is amitriptyline. In some embodiments, the tricyclic antidepressant is nortriptyline. In some embodiments, the tricyclic antidepressant is trimipramine.

In some embodiments, the neurotransmitter reuptake inhibitor is a selective serotonin reuptake inhibitor. By inhibiting the reuptake of serotonin into the presynaptic cells, SSRIs increase the extracellular level of serotonin. This increases the level of serotonin available to bind to the postsynaptic receptor. SSRIs are hypothesized to stimulate new neural growth within the inner ear. In some embodiments, the selective serotonin reuptake inhibitor is fluoxetine, paroxetine, or sertraline. In some embodiments, the selective serotonin reuptake inhibitor is fluoxetine. In some embodiments, the selective serotonin reuptake inhibitor is paroxetine. In some embodiments, the selective serotonin reuptake inhibitor is sertraline. In some embodiments, the neurotransmitter reuptake inhibitor is a selective nor-epinephrine reuptake inhibitor, such as reboxetine, or a dual serotonin/nor-epiniphrine reuptake inhibitor, such as milnacipran, bicifadine, venlafaxine, and duloxetine.

Contemplated for use with the formulations and compositions disclosed herein are agents that ameliorate otic disorders, including vestibular disorders and/or tinnitus, through local modulation of central nervous system (CNS) activity. Accordingly, some embodiments incorporate the use of agents that antagonize neurokinin receptors. There are at least three neurokinin receptors: NK1, NK2 and NK3. In certain embodiments, the binding of a ligand (e.g. a tachykinin peptide, substance P, neurokinin A, and neurokinin B) to a neurokinin receptor induces the activation of phospholipase C. The activation of phospholipase C produces inositol triphosphate. In some embodiments, the neurokinin receptor is the NK1 receptor, the NK2 receptor, the NK3 receptor, or combinations thereof. In some embodiments, the neurokinin receptor is the NK1 receptor. In some embodiments, the antagonist of the NK1 receptor is vestipitant.

In some embodiments, the SSRI inhibitor is administered in combination with a neurokinin receptor antagonist. In some embodiments, the SSRI is paroxetine and the neurokinin receptor is NK1. In some embodiments, the NK1 receptor antagonist is vestipitant. In certain embodiments, the co-administration of paroxetine and vestipitant treats, and/or the symptoms of tinnitus.

Local Anesthetics

Contemplated for use with the formulations and compositions disclosed herein are agents which ameliorate otic disorders, including vestibular disorders and/or tinnitus, through local modulation of central nervous system (CNS) activity. Accordingly, some embodiments incorporate the use of agents which decrease the rate of the depolarization and repolarization of neurons by, for example, blocking the Na+ channels in cell membranes.

In some embodiments, the CNS modulator is a local anesthetic. In some embodiments, the local anesthetic is selected from the group consisting of: benzocaine, carticaine, cinchocaine, cyclomethycaine, lidocaine, prilocaine, propxycaine, proparacaine, tetracaine, tocainide, and trimecaine. In some embodiments, the local anesthetic is lidocaine. In some embodiments, the local anesthetic is tocainide.

Sodium Channel Blockers

Contemplated for use with the formulations and compositions disclosed herein are agents which ameliorate otic disorders, including vestibular disorders and/or tinnitus, through local modulation of central nervous system (CNS) activity. Accordingly, some embodiments incorporate the use of agents which block or antagonize Na+ channels. Sodium channels are channels formed in the plasma membrane of neurons (amongst other cells) by integral membrane proteins. These channels conduct Na+ through a cell's plasma membrane. In neurons, the flow of Na+ is partly responsible for creating and propagating action potentials in the neurons.

In some embodiments, the sodium channel blocker is carbamazepine, oxcarbazepine, phenytein, valproic acid, or sodium valproate. In some embodiments, the sodium channel blocker is carbamazepine. In some embodiments, the sodium channel blocker is oxcarbazepine.

In some embodiments, the sodium channel blocker is phenytein. In some embodiments, the sodium channel blocker is valproic acid. In some embodiments, the sodium channel blocker is sodium valproate.

In some embodiments, the Na+ channel blocker is vinpocetine ((3a,16a)-Eburnamenine-14-carboxylic acid ethyl ester); sipatrigine (2-(4-Methylpiperazin-1-yl)-5-(2,3,5-trichlorophenyl)-pyrimidin-4-amine); amiloride (3,5-diamino-N-(aminoiminomethyl)-6-chloropyrazinecarbox amide hydrochloride); carbamazepine (5H-dibenzo[b,f] azepine-5-carboxamide); TTX (octahydro-12-(hydroxymethyl)-2-imino-5,9:7,10a-dimethan o-10aH-[1,3]dioxocino[6,5-d]pyrimidine-4,7,10,11,12-pen tol); RS100642 (1-(2,6-dimethyl-phenoxy)-2-ethylaminopropane hydrochloride); mexiletine ((1-(2,6-dimethylphenoxy)-2-aminopropane hydrochloride)); QX-314 (N-(2,6-Dimethylphenylcarbamoylmethyl)triethylammonium bromide); phenytoin (5,5-diphenylimidazolidine-2,4-dione); lamotrigine (6-(2,3-dichlorophenyl)-1,2,4-triazine-3,5-diamine); 4030W92 (2,4-diamino-5-(2,3-dichlorophenyl)-6-fluoromethylpyrimidine); BW1003C87 (5-(2,3,5-trichlorophenyl) pyrimidine-2,4-1.1 ethanesulphonate); QX-222 (2-[(2,6-dimethylphenyl)amino]-N,N,N-trimethyl-2-oxoetha niminium chloride); ambroxol (trans-4-[[(2-Amino-3,5-dibromophenyl)methyl]amino]cyclo hexanol hydrochloride); R56865 (N-[1-(4-(4-fluorophenoxy)butyl]-4-piperidinyl-N-methyl-2-benzo-thiazolamine); lubeluzole; ajmaline ((17R,21alpha)-ajmalan-17,21-diol); procainamide (4-amno-N-(2-diethylaminoethyl)benzamide hydrochloride); flecainide; riluzoleor; or combinations thereof.

In some embodiments, agents which decrease the rate of the depolarization and repolarization of neurons by, for example, blocking the Na+ channels in cell membranes include local anesthetics. In some embodiments, the local anesthetic is selected from the group consisting of: benzocaine, carticaine, cinchocaine, cyclomethycaine, lidocaine, prilocaine, propxycaine, proparacaine, tetracaine, tocainide, and trimecaine. In some embodiments, the local anesthetic is lidocaine. In some embodiments, the local anesthetic is tocainide.

Thyrotropin-Releasing Hormone

Contemplated for use with the formulations and compositions disclosed herein are agents which ameliorate otic disorders, including vestibular disorders and/or tinnitus, through local modulation of central nervous system (CNS) activity. Accordingly, some embodiments incorporate the use of agents which modulate neurotransmitters. Thyrotropin-releasing hormone is a neurotransmitter which inhibits glutamate-induced excitation of neurons. In some embodiments, the CNS modulator is thyrotropin-releasing hormone.

Antimicrobial Agents

Any antimicrobial agent useful for the treatment of otic disorders, e.g., inflammatory diseases of the ear or cancer of the ear, is suitable for use in the formulations, compositions, and methods disclosed herein. In some embodiments, the antimicrobial agent is an antibacterial agent, an antifungal agent, an antiviral agent, an antiprotozoal agent, and/or an antiparasitic agent. Antimicrobial agents include agents that act to inhibit or eradicate microbes, including bacteria, fungi, viruses, protozoa, and/or parasites. Specific antimicrobial agents are used to combat specific microbes. Accordingly, a skilled practitioner would know which antimicrobial agent would be relevant or useful depending on the microbe identified, or the symptoms displayed.

In some embodiments, the antimicrobial agent is a protein, a peptide, an antibody, DNA, a carbohydrate, an inorganic molecule, or an organic molecule. In certain embodiments, the antimicrobial agents are antimicrobial small molecules. Typically, antimicrobial small molecules are of relatively low molecular weight, e.g., less than 1,000, or less than 600-700, or between 300-700 molecular weight.

Antibacterial agents include amikacin, gentamicin, kanamycin, neomycin, netilmicin, streptomycin, tobramycin, paromomycin, geldanmycin, herbimycin, loracarbef, ertapenem, doripenem, imipenem, cilastatin, meropenem, cefadroxil, cefazolin, cefalotin, cefalexin, cefaclor, cefamandole, cefoxitin, defprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillan, bacitracin, colistin, polymyxin B, ciprofloxacin, enoxacin, gatifloxacin, levofloxacin, lomefloxacin, moxifloxacin, norfloxacin, ofloxacin, trovfloxacin, mafenide, prontosil, sulfacetamide, sulfamethizole, sulfanimilimde, sulfsalazine, sulfsioxazole, trimethoprim, demeclocycline, doxycycline, minocycline, oxtetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinuspristin/dalfopristin, rifampin, tinidazole, AL-15469A (Alcon Research), AL-38905 (Alcon Research) and combinations thereof. In some embodiments, the antibacterial agent is ciprofloxacin.

Antiviral agents include acyclovir, famciclovir and valacyclovir. Other antiviral agents include abacavir, aciclovir, adfovir, amantadine, amprenavir, arbidol, atazanavir, artipla, brivudine, cidofovir, combivir, edoxudine, efavirenz, emtricitabine, enfuvirtide, entecavir, fomvirsen, fosamprenavir, foscarnet, fosfonet, ganciclovir, gardasil, ibacitabine, imunovir, idoxuridine, imiquimod, indinavir, inosine, integrase inhibitors, interferons, including interferon type III, interferon type II, interferon type I, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, tenofovir, tenofovir disoproxil, tipranavir, trifluridine, trizivir, tromantadine, truvada, valganciclovir, vicriviroc, vidarabine, viramidine, zalcitabine, zanamivir, zidovudine, and combinations thereof.

Antifungal agents include amrolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, clioquinol, and combinations thereof.

Antiparasitic agents include amitraz, amoscanate, avermectin, carbadox, diethylcarbamizine, dimetridazole, diminazene, ivermectin, macrofilaricide, malathion, mitaban, oxamniquine, permethrin, praziquantel, prantel pamoate, selamectin, sodium stibogluconate, thiabendazole, and combinations thereof.

In some embodiments, pharmaceutically active metabolites, salts, polymorphs, prodrugs, analogues, and derivatives of the antimicrobial agents discussed above that retain the ability of the parent antimicrobial agents to treat otic disorders of the ear are also useful in the formulations disclosed herein.

In some embodiments, the therapeutic agent is an antimicrobial agent. In some embodiments, the therapeutic agent is an antibacterial agent. In some embodiments, the therapeutic agent is an antiviral agent. In some embodiments, the therapeutic agent is an antifungal agent. In some embodiments, the therapeutic agent is an antiparasitic agent.

Free Radical Modulators

In some instances, immunomodulators and/or aural pressure modulators relieve, prevent, reverse or ameliorate the degeneration of neurons and/or hair cells of the auris due to free radicals or the dysfunction of the mitochondria.

Antioxidants

Contemplated for use with the formulations and compositions disclosed herein are agents that relieve, prevent, reverse or ameliorate the degeneration of neurons and/or hair cells of the auris due to free radicals or the dysfunction of the mitochondria. Accordingly, some embodiments incorporate the use of agents which prevent and/or ameliorate the damage caused by free radicals. In some embodiments, the agents which prevent and/or ameliorate the damage caused by free radicals is an antioxidant.

Antioxidants, as disclosed herein, are also useful as protectants against ototoxic agents through the prevention of reactive oxygen species, neutralization of toxic products or blockage of the apoptosis pathway. Resveratrol (3,5,4'-Trihydroxystilbene), a representative example of an antioxidant, exerts its effects through a variety of pathways, including the inhibition of MnSOD, which reduces superoxide to $H_2O_2$, which inhibits free radical chain reactions, reducing superoxide levels in the cell. Moreover, resveratrol has been implicated in preventing neuronal cell dysfunction and cell death. Other antioxidants include but are not limited to vitamin E (tocopherol), vitamin C (ascorbic acid), glutathione, lipoic acid, alpha lipoic acid, uric acid, carotenes, ubiquinol, melatonin, tocotrienols, selenium, flavonoids, polyphenols, lycopene, lutein, lignan, butyl hydroxytoluene, coenzyme Q10, salicylate, or combinations thereof.

In certain embodiments, nitrones act synergistically with antioxidants. In certain embodiments, nitrones trap free radicals. In some embodiments, a nitrone (e.g. alpha-phenyl-tert-butylnitrone (PBN), allpurinol) is co-administered with an antioxidant. In certain embodiments, a nitrone co-administered with an antioxidant treats acute acoustic noise-induced hearing loss.

In some embodiments, the antioxidant is N-acetylcysteine; vitamin E (tocopherols and tocotrienols); vitamin C; vitamin A; lutein; selenium glutathione; melatonin; a polyphenol; a carotenoid (e.g. lycopene, carotenes); coenzyme Q-10; Ebselen (2-phenyl-1, 2-benzisoselenazol-3(2H)-one (also called PZ 51 or DR3305); L-methionine; azulenyl nitrones (e.g. stilbazulenyl nitrone); L-(+)-Ergothioneine ((S)-a-Carboxy-2,3-dihydro-N,N,N-trimethyl-2-thioxo-1H-imidazole4-ethanaminium inner salt); Caffeic Acid Phenyl Ester (CAPE); dimethylthiourea; dimethylsulfoxide; disufenton sodium (NXY-059; disodium 4-[(Z)-(tert-butyl-oxidoazaniumylidene)methyl]benzene-1,3-disulfonate); pentoxifylline; MCI-186 (3-Methyl-1-phenyl-2-pyrazolin-5-one); Ambroxol (trans-4-(2-Amino-3,5-dibromobenzylamino)cyclohexane-HCl; U-83836E ((−)-2-((4-(2,6-di-1-Pyrrolidinyl-4-pyrimidinyl)-1-piperzainyl) methyl)-3,4-dihydro-2,5,7,8-tetramethyl-2H-1-benzopyran-6-ol.2HCl); MITOQ (mitoquinone mesylate, Antipodean Pharmaceuticals); Idebenone (2-(10-hydroxydecyl)-5,6-dimethoxy-3-methyl-cyclohexa-2,5-diene-1,4-dione); (+)-cyanidanol-3; or combinations thereof.

Glutamate-Receptor Modulators

Contemplated for use with the formulations and compositions disclosed herein are agents that modulate the production of free-radicals and/or inhibit damage to the mitochondria. Accordingly, some embodiments incorporate the use of agents which modulate glutamate receptors. In some embodiments, the glutamate receptor is the AMPA receptor, the NMDA receptor, kainate receptor, and/or a group I, II or III mGlu receptor. In some embodiments, a glutamate receptor modulator is as described herein.

Iron Chelators

Contemplated for use with the formulations and compositions disclosed herein are agents that relieve, prevent, reverse or ameliorate the degeneration of neurons and/or hair cells of the auris due to free radicals or the dysfunction of the mitochondria. Accordingly, some embodiments incorporate the use of agents which prevent and/or ameliorate the damage caused by free radicals. In some embodiments, the agents which prevent and/or ameliorate the damage caused by free radicals is an iron chelator. The iron chelator, deferoxamine, prevents ototoxic damage to the ear resulting from treatment with neomycin when it is co-administered with neomycin.

In some embodiments, the iron chelator is desferrioxamine (DFO); hydroxybenzyl ethylene diamine; fullerenol-1, pyrrolidine dithiocarbamate; desferal; Vk-28 (5-[4-(2-hydroxyethyl) piperazine-1-ylmethyl]-quinoline-8-ol); clioquinol; echinochrome; PIH (pyridoxal isonicotinoyl hydrazone); deferasirox; HBED (N,N'-bis (2-hydroxybenzyl) ethylenediamine-N,N'-diacetic acid); SIH (salicylaldehyde isonicotinoyl hydrazone); deferiprone; L1 (1,2-dimethyl-3-hydroxy-4-pyridone); Kojic acid (5-hydroxy-2-hydroxymethyl-4-pyrone); deferoxamine; 2,3-dihydroxybenzoate; or combinations thereof.

Mitochondrial Modulators

Contemplated for use with the formulations and compositions disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents that modulate the activity of the mitochondria. In some embodiments, the agent which modulates the activity of the mitochondria is acetylcarnitine; lipoic acid; or combinations thereof.

Nitric Oxide Synthase Modulators

Contemplated for use with the formulations and compositions disclosed herein are agents for treating or ameliorating hearing loss or reduction resulting from destroyed, stunted, malfunctioning, damaged, fragile or missing hairs in the inner ear. Nitric oxide (NO) is a neurotransmitter. It is synthesized by multiple nitric oxide synthases (NOS) from arginine and oxygen. It is also derived from the reduction of inorganic nitrate. In certain instances, it induces vasodilation; thus, increasing blood flow. In certain instances, it increases cochlear blood flow. In certain instances, NO damages blood vessel walls. In certain instances, NO ameliorates vascular protein leakage in the cochlea. In certain instances, NO increases the sensitivity of hair cells. In certain instances, NO reacts with super-oxide to form the free radical peroxynitrite. Accordingly, some embodiments incorporate the use of agents that modulate nitric oxide and/or nitric oxide synthase (NOS).

In some embodiments, the agent that modulates NO and/or NOS is an antagonist of NO or NOS. In some embodiments, the antagonist of NO and/or NOS is aminoguanidine; 1-Amino-2-hydroxyguanidine p-toluensulfate; GED (guanidinoethyldisulfide); bromocriptine mesylate; dexamethasone; SDMA (symmetric $N^G,N^G$-Dimethyl-L-arginine); ADMA (asymmetric $N^G,N^G$-Dimethyl-L-arginine); L-NMMA ($N^G$-monomethyl-L-arginine); L-NMEA ($N^G$-monoethyl-L-arginine); D-MMA ($N^G$-monomethyl-D-arginine); L-NIL ($N^6$-(1-Iminoethyl)-L-lysine hydrochloride); L-NNA ($N^G$-nitro-L-arginine); L-NPA ($N^G$-propyl-L-arginine); L-NAME ($N^G$-nitro-L-arginine methyl ester dihydrochloride); L-VNIO ($N^5$-(1-imino-3-butenyl)-1-ornithine); diphenyleneiodonium chloride; 2-ethyl-2-thiopseudourea; haloperidol; L-NIO (L-$N^5$-(1-iminoethyl)ornithine); MEG (methylecgonidine); SMT (S-methylisothiourea sulfate); SMTC (S-methyl-L-thiocitrulline); 7-Ni (7-nitroindazole); nNOS inhibitor I ((4S)—N-(4-Amino-5[aminoethyl]amino-pentyl)-N'-nitroguanidine); 1,3-PBITU (S,S'-1,3-Phenylene-bis(1,2-ethanediyl)-bis-isothiourea); L-thiocitrulline; TRIM (1-(2-trifluoromethylphenyl) imidazole); MTR-105 (S-ethylisothiuronium diethylphosphate); BBS-1; BBS-2; ONO-1714 ((1S,5S,6R,7R)-7chloro-3-amino-5methyl-2-azabicyclo[4.1.0]heptane hydrochloride); GW273629 (3-[[2-[(1-iminoethyl)amino]ethyl]sulphonyl]-L-alanine); GW 274150 ((S)-2-amino-(1-iminoethylamino)-5-thioheptanoic acid); PPA250 (3-(2,4-difluorophenyl)-6-{2-[4-(1H-imidazol-1-ylmethyl) phenoxy]ethoxy}-2-phenylpyridine); AR-R17477 ([N-(4-(2((3-chlorophenylmethyl) amino) ethyl) phenyl)-2-thiophecarboxamidine dihydrochloride); AR-R18512 (N(2-methyl-1,2,3,4-tetrahydroisoquinoline-7-yl)-2-thiophenecarboximidamide); spiroquinazolone; 1400W (N-[[3-(aminomethyl)phenyl]methyl]-ethanimidamide dihydrochloride); or combinations thereof.

In some embodiments, the agent that modulates NO and/or NOS is an agonist of NO and/or NOS, or a donor of NO. In some embodiments, the agonist of NO and/or NOS, or donor of NO, is S—NC (S-nitrosocysteine); NTG (nitroglycerine); SNP (sodium nitroprusside); thapsigargin; vascular endothelial growth factor (VEGF); bradykinin; ATP; sphingosine-1-phosphate; estrogen; angiopoietin; acetylcholine; SIN-1 (3-morpholinosydnonimine); GEA 3162 (1,2,3, 4-oxatriazolium, 5-amino-3-(3,4-dichlorophenyl)-,chloride); GEA 3175 (3-(3-chloro-2-methylphenyl)-5-[[4-methylphenyl)sulphonyl]amino]-)hydroxide); GEA 5024 (1,2,3,4-oxatriazolium, 5-amino-3-(30chloro-2-methyl-phenyl)chloride); GEA 5538 (,2,3,4-Oxatriazolium, 3-(3-chloro-2-methylphenyl)-5-[[[cyanomethylamino]carbonyl] amino]-hydroxide inner salt); SNAP (S-nitroso-N-acetylpenicillamine); molsidomine; CNO-4 (1-[(4',5'-Bis (carboxymethoxy)-2'-nitrophenyl)methoxy]-2-oxo-3,3, diethyl-1-triazene dipotassium salt); CNO-5 ([1-(4',5'-Bis (carboymethoxy)-2'-nitrophenyl)methoxy]-2-oxo-3,3-diethyl-1-triazine diacetoxymethyl ester); DEA/NO, IPA/NO, SPER/NO, SULFI/NO, OXI/NO, DETA/NO; or combinations thereof.

Sirtuin Modulators

The sirtuins (or Sir2 proteins) comprise class III of the histone deacetylases (HDACs). While they are classified as protein deacetylases some also function as mono-ADP-ribosyltransferases. Each sirtuin protein has a homologous core sequence of 250 amino acids. This sequence is highly conserved over multiple species. Further, in order to catalyze the deacetylation of a protein, each sirtuin requires $NAD^+$ as a cofactor. There are seven members of the family: Sirt1, Sirt2, Sirt3, Sirt4, Sirt5, Sirt6, and Sirt7. Sirt1 and Sirt3 are protein deacetylases. Sirt2 is involved in mitosis.

Agonism of Sirt1 yields multiple benefits which have previously been identified in subjects undergoing caloric restriction. These benefits include, but are not limited to, decreased glucose levels and improved insulin sensitivity, increased mitochondrial activity, and decreased adiposity (due to the Sirt1 mediated repression of PPAR-γ). Decreases in glucose levels and adiposity contribute to the amelioration of presbycusis as diabetes and atherosclerosis are both factors which contribute to the development and progression of presbycusis.

Sirt1 prevents apoptosis by deacetylating the pro-apoptotic genes p53 and Ku-70. Additional substrates for Sirt1 include, but are not limited to, the transcription factors NFκB, Fox01, Fox03a, Fox04, Fox05; the transcription repressor Hic1; and Pgc-1α, which regulates, among other cellular functions, adaptive thermogenesis, glucose metabolism, and triglyceride metabolism. Agonism of Sirt3 results in increased cellular respiration and a decrease in the production of reactive oxygen species (ROS).

The catalysis of deacetylation by sirtuins is NAD (nicotinamide adenine dinucleotide) dependent. Upon binding to an acetylated protein, the sirtuin hydrolyzes NAD by breaking the glycosidic bond between nicotinamide and ADP-ribose. The acetyl group of the acetylated protein is then transferred to ADP-ribose. At the completion of the reaction nicotinamide, the deacetylated protein, and 2'-O-acetyl-ADP-ribose are released.

Multiple compounds modulate the sirtuin catalyzed deacetylation of proteins. Administration of certain polyphenols such as, but not limited to, stilbenes, chalcones, flavones, isoflavones, flavanones, anthocyanidins, catechins, results in the decrease of the $K_m$ of the deacetylation reaction. Further, as free nicotinamide antagonizes the deacetylation reaction, compounds which inhibit the binding of nicotinamide to sirtuins will also agonize the activity of sirtuins.

Administration of the sirtuin agonizing agent resveratrol (trans-3,5,4'-trihydroxystilbene) decreases apoptosis. It also increases glutamate uptake and thus ameliorates excitotoxicity. Further, administration of resveratrol results in lower levels of reactive oxygen species (ROS) and thus ameliorates damage caused by ischemia, excitotoxicity, ototoxicity caused by cisplatin and aminoglycosides, acoustic trauma and presbycusis.

Contemplated for use with the formulations and compositions disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents the modulate sirtuin catalyzed deacetylation reactions. In some embodiments, the agent which modulates sirtuin catalyzed deacetylation reactions is a stilbene. In some embodiments, the stilbene is trans-stilbene, cis-stilbene, resveratrol, piceatannol, rhapontin, deoxyrhapontin, butein, or combinations thereof.

In some embodiments, the stilbene is resveratrol. In some embodiments, the stilbene is an analog of resveratrol. In some embodiments, the analog of resveratrol is SRT-501 (RM-1821). For additional analogs of resveratrol see U.S. Patent App. Pub. No. 2006/0276393, which is hereby incorporated by reference for this disclosure.

Contemplated for use with the formulations and compositions disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents the modulate sirtuin catalyzed deacetylation reactions. In some embodiments, the agent which modulates sirtuin catalyzed deacetylation reactions is a chalcone. In some embodiments, the chalcone is chalcon; isoliquirtigen; butein; 4,2',4'-trihydroxychalcone; 3,4,2',4',6'-pentahydroxychalcone; or combinations thereof.

Contemplated for use with the formulations and compositions disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents the modulate sirtuin catalyzed deacetylation reactions. In some embodiments, the agent which modulates sirtuin catalyzed deacetylation reactions is a flavone. In some embodiments, the flavone is flavone, morin, fisetin; luteolin; quercetin; kaempferol; apigenin; gossypetin; myricetin; 6-hydroxyapigenin; 5-hydroxyflavone; 5,7,3',4',5'-pentahydroxyflavone; 3,7,3',4',5'-pentahydroxyflavone; 3,6,3',4'-tetrahydroxyflavone; 7,3',4',5'-tetrahydroxyflavone; 3,6,2',4'-tetrahydroxyflavone; 7,4'-dihydroxyflavone; 7,8,3',4'-tetrahydroxyflavone; 3,6,2',3'-tetrahydroxyflavone; 4'-hydroxyflavone; 5-hydroxyflavone; 5,4'-dihydroxyflavone; 5,7-dihydroxyflavone; or combinations thereof.

Contemplated for use with the formulations and compositions disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents the modulate sirtuin catalyzed deacetylation reactions. In some embodiments, the agent which modulates sirtuin catalyzed deacetylation reactions is an isoflavone. In some embodiments, the isoflavone is daidzein, genistein, or combinations thereof.

Contemplated for use with the formulations and compositions disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents the modulate sirtuin catalyzed deacetylation reactions. In some embodiments, the agent which modulates sirtuin catalyzed deacetylation reactions is a flavanone. In some embodiments, the flavanone is naringenin; flavanone; 3,5,7,3',4'-pentahydroxyflavanone; or combinations thereof.

Contemplated for use with the formulations and compositions disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents the modulate sirtuin catalyzed deacetylation reactions. In some embodiments, the agent which modulates sirtuin catalyzed deacetylation reactions is an anthocyanidin. In some embodiments, the anthocyanidin is pelargonidin chloride, cyanidin chloride, delphinidin chloride, or combinations thereof.

Contemplated for use with the formulations and compositions disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents the modulate sirtuin catalyzed deacetylation reactions. In some embodiments, the agent which modulates sirtuin catalyzed deacetylation reactions is a catechin. In some embodiments, the catechin is (−)-epicatechin (Hydroxy Sites: 3,5,7,3',4'); (−)-catechin (Hydroxy Sites: 3,5,7,3',4'); (−)-gallocatechin (Hydroxy Sites: 3,5,7,3',4',5') (+)-catechin (Hydroxy Sites: 3,5,7,3',4'); (+)-epicatechin (Hydroxy Sites: 3,5,7,3',4'); or combinations thereof.

Contemplated for use with the formulations and compositions disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents that modulate the catalytic rate of sirtuin catalyzed deacetylation reactions. In some embodiments, the agent which modulates the catalytic rate of sirtuin catalyzed deacetylation reactions is dipyridamole, ZM 336372 (3-(dimethylamino)-N-[3-[(4-hydroxybenzoyl)-amino]-4-methylphenyl]benzamide), camptothecin, coumestrol, nordihydroguaiaretic acid, esculetin, SRT-1720 (Sirtris), SRT-1460 (Sirtris), SRT-2183 (Sirtris), or combinations thereof.

Contemplated for use with the formulations and compositions disclosed herein are agents that relieve, prevent, reverse or ameliorate the degeneration of neurons and/or hair cells of the auris due to free radicals or the dysfunction of the mitochondria. Accordingly, some embodiments incorporate the use of one or more agents the modulate sirtuin catalyzed deacetylation reactions. In some embodiments, the agent that modulates sirtuin catalyzed deacetylation reactions is a nicotinamide binding antagonist. In some embodiments, the nicotinamide binding antagonist is isonicotinamide or an analog of isonicotinamide. In some embodiments, the analog of isonicotinamide is β-1'-5-methyl-nicotinamide-2'-deoxyribose; (3-D-1'-5-methyl-nico-tinamide-2'-deoxyribofuranoside; β-1'-4,5-dimethyl-nicotinamide-2'-deoxyribose; or β-D-1'-4,5-dimethyl-nicotinamide-2'-deoxyribofuranoside. For additional analogs of isonicotinamide see U.S. Pat. Nos. 5,985,848; 6,066,722; 6,228,847; 6,492,347; 6,803,455; and U.S. Patent Publication Nos. 2001/0019823; 2002/0061898; 2002/0132783; 2003/0149261; 2003/0229033; 2003/0096830; 2004/0053944; 2004/0110772; and 2004/0181063, which are hereby incorporated by reference for that disclosure.

Ion Channel Modulators

Potassium Ion Channel Modulators

Contemplated for use with the formulations and compounds disclosed herein are agents for treating or ameliorating hearing loss or reduction resulting from destroyed, stunted, malfunctioning, damaged, fragile or missing hairs and neurons in the inner ear. Accordingly, some embodiments incorporate the use of agents that modulate potassium ion concentrations. In some embodiments, the agents that modulate potassium ion concentrations are agonists or antagonists of potassium ion channels. Potassium ion channels are channels that regulate the flow of potassium ions into and out of cells. In the cochlea the transduction current through the sensory cells is carried by potassium ions and depends on the high concentration of potassium ions in the endolymph. Mutations in the genes encoding potassium channel protein result in both acquired and congenital hearing loss.

The KCNQ family of potassium channels is a family of delayed rectifier voltage-gated potassium channels found in the cochlea. KCNQ1 subunits form potassium channels in vestibular dark cells and marginal cells of the stria vascularis. These channels regulate the level of potassium in endolymph. KCNQ4 subunits form channels hair cells. Mice with genes encoding KCNQ subunits knocked-out display a hearing loss during development, starting at four weeks of postnatal life.

In some embodiments, the agent that modulates a potassium channel is an agonist of a potassium channel (e.g. a potassium channel opener). In some embodiments, the agonist of a potassium channel is nicorandil; minoxidil; levcromakalim; lemakalim; cromakalim; L-735,334 (14-hydroxy CAF-603 oleate); retigabine; flupirtine; BMS-204352 (3S)-(+)-(5-Chloro-2-methoxyphenyl)-1,3-dihydro-3-fluoro-6-(trifluoromethyl)-2H-indole-2-one); DMP-543 (10,10-bis((2-fluoro-4-pyridinyl)methyl)-9(10H)-anthracenone); or combinations thereof.

In some embodiments, the agent that modulates a potassium channel is an antagonist of a potassium channel (e.g. a potassium channel blocker). In some embodiments, the antagonist of a potassium channel is linopirdine; XE991 (10,10-bis(4-pyridinylmethyl)-9(10H)-anthracenone); 4-AP (4-aminopyridine); 3,4-DAP (3,4-Diaminopyridine); E-4031 (4'-[[1-[2-(6-methyl-2-pyridyl)ethyl]-4-piperidinyl]carbonyl]-methanesulfonanilide); DIDS (4,4'-diisothiocyano stilbene-2,2'-disulfonic acid); Way 123,398 (N-methyl-N-(2-(methyl(1-methyl-1H-benzimidazol-2-yl)amino)ethyl)-4-((methylsulfonyl)amino) benzenesulfonamide HCl); CGS-12066A (7-Trifluoromethyl-4-(4-methyl-1-piperazinyl)pyrrolo-[1,2-a]quinoxaline); dofetilide; sotalol; apamin; amiodarone; azimilide; bretylium; clofilium; tedisamil; ibutilide; sematilide; nifekalant; tamulustoxin and combinations thereof.

Purigenic Receptor Modulators

Contemplated for use with the formulations and compositions disclosed herein are agents for modulating ion channels. Accordingly, some embodiments incorporate the use of agents that modulate the concentration of ions. In some embodiments, the agents that modulate the concentration of ions are agonists or antagonist of purigenic receptors.

Purigenic receptors are a family of plasma membrane-bound receptors. The family includes the P2X, P2Y, and P1 receptors. The P2X receptors comprise ion channels. When ATP binds to the receptor the channel opens. The P2Y receptors comprise G-coupled protein receptors. The ligands for these receptors are ATP, ADP, UTP, UDP, UDP-glucose. The P1 receptors comprise G-coupled protein receptors. The ligand for these receptors is adenosine. Purigenic receptors regulate ion homeostasis in the ear. Endolymph, for example, requires high potassium ($K^+$), low sodium ($Na^+$), and low calcium ($Ca^{2+}$) ion levels for normal auditory transduction.

In some embodiments, the agonist of a purigenic receptor is ATP; ADP; UTP; UDP; UDP-glucose; adenosine; 2-MeSATP; 2-MeSADP; αβmeATP; dATPαS; ATPγS; Bz-ATP; MRS2703 (2-MeSADP with the beta-phosphate group blocked by a 1-(3,4-dimethyloxyphenyl)eth-1-ylphosphoester)); denufosoltetrasodium; MRS2365 ([[(1R,2R,3S,4R,5S)-4-[6-amino-2-(methylthio)-9H-purin-9-yl]-2,3-dihydroxybicyclo[3.1.0]hex-1-yl]methyl] diphosphoric acid mono ester trisodium salt); MRS 2690 (diphosphoric acid 1-a-D-glucopyranosyl ester 2-[(4'-methylthio)uridin-5''-yl] ester disodium salt); PSB 0474 (3-(2-Oxo-2-phenylethyl)-uridine-5'-diphosphate disodium salt); or combinations thereof.

In some embodiments, the antagonist of a purigenic receptor is A-317491 ((5-([(3-Phenoxybenzyl)[(1S)-1,2,3,4-tetrahydro-1-naphthalenyl]amino]carbonyl)-1,2,4-benzenetricarboxylic acid)); RO-3 (Roche); suramin; PPADS (pyridoxalphosphate-6-azophenyl-2',4'-disulfonic acid); PPNDS (Pyridoxal-5'-phosphate-6-(2'-naphthylazo-6'-nitro-4',8'-disulfonate) tetrasodium salt); DIDS; pyridoxal-5-phosphate; 5-(3-bromophenyl)-1,3-dihydro-2H-benzofuro-[3,2-e]-1,4-diazepin-2-one; cibacron blue; basilen blue; ivermectin; A-438079 (3-[[5-(2,3-Dichlorophenyl)-1H-tetrazol-1-yl]methyl]pyri dine hydrochloride); A-740003 ((N-(1-{[(cyanoimino)(5-quinolinylamino) methyl]amino}-2,2-dimethylpropyl)-2-(3,4-dimethoxyphenyl)acetamide); NF449 (4,4',4'',4'''-(carbonylbis(imino-5,1,3-benzenetriyl-bis(carbonylimino)))tetrakis-benzene-1,3-disulfonic acid); NF110 (para-4,4',4'',4'''-(carbonylbis(imino-5,1,3-benzenetriylbis carbonylimino)))tetrakis-benzenesulfonic acid); MRS 2179 (2'-Deoxy-N6-methyladenosine 3',5'-bisphosphate tetrasodium salt); MRS 2211 (2-[(2-chloro-5-nitrophenyl)azo]-5-hydroxy-6-methyl-3-[(phosphonooxy) methyl]-4-pyridinecarboxaldehyde disodium salt); MRS 2279 ((1R,2S,4S,5S)-4-[2-chloro-6-(methylamino)-9H-purin-9-yl]-2-(phosphonooxy)bicyclo[3.1.0]hexane-1-methanol dihydrogen phosphate ester diammonium salt); MRS 2500 tetrasodium salt ((1R,2S,4S,5S)-4-[2-Iodo-6-(methylamino)-9H-purin-9-yl]-2-(phosphonooxy)bicyclo[3.1.0] hexane-1-methanol dihydrogen phosphate ester tetraammonium salt); NF157 (8,8'-[carbonylbis[imino-3,1-phenylenecarbonylimino(4-fluoro-3,1-phenylene) carbonylimino]]bis-1,3,5-naphthalene trisulfonic acid hexasodium salt); TNP-ATP; tetramethylpyrazine; Ip$_5$I; βγ-carboxymethylene ATP; βγ-chlorophosphomethylene ATP; KN-62 (4-[(2S)-2-[(5-isoquinolinylsulfonyl)methylamino]-3-oxo-3-(4-phenyl-1-piperazinyl)propyl]phenyl isoquinolinesulfonic acid ester); NF023 (8,8'-[carbonylbis (imino-3,1-phenylenecarbonylimino)]bis-1,3,5-naphthalene-trisulphonic acid, hexasodium salt); NF279 (8,8'-[Carbonylbis(imino-4,1-phenylenecarbonylimino-4,1-phenylenecarbonylimino)]bis-1,3,5-naphthalenetrisulfonic acid hexasodium salt); spinorphin; or combinations thereof.

RNAi

In some embodiments, where inhibition or down-regulation of a target is desired (e.g. genes encoding a component of a potassium channel, genes encoding a purigenic receptor), RNA interference is optionally utilized. In some embodiments, the agent that inhibits or down-regulates the target is an siRNA molecule. In certain instances, the siRNA molecule is as described herein.

Corticosteroids

Contemplated for use with the otic formulations and compositions described herein are corticosteroid agents, which reduce or ameliorate symptoms or effects as a result of an autoimmune disease and/or inflammatory disorder, including AIED. Such autoimmune responses are a contributing factor to otic disorders such as Meniere's disease. In some embodiments, corticosteroids modulate the degeneration of neurons and/or hair cells of the auris, and agents for treating or ameliorating hearing loss or reduction resulting from destroyed, stunted, malfunctioning, damaged, fragile or missing hairs in the inner ear. Accordingly, some embodiments incorporate the use of agents which protect otic hair cells from ototoxins. In some embodiments, the agent which protects otic hair cells from ototoxins is a corticosteroid.

Examples of suitable corticosteroids include but are not limited to prednisolone, dexamethasone, dexamethasone phosphate, beclomethasone, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide and combinations thereof. In some embodiments, the corticosteroid is triamicinolone actenoide or a suitable derivative thereof. In some embodiments, the corticosteroid is dexamethasone or a suitable derivative thereof.

In certain instances, triamcinolone actenoide and dexamethasone protect otic hair cells from damage caused by the naturally occurring toxin 4-hydroxy-2,3-nonenal (HNE), which is produced in the inner ear in response to oxidative stress.

Truncated TrkC or Truncated TrkB Antagonists

Contemplated for use with the otic formulations and compositions described herein are antagonists of a truncated TrkC or a truncated TrkB. In some embodiments, the antagonist induces a decrease in the truncated TrkC or truncated TrkB expression level or activity or impedes the truncated TrkC or truncated TrkB interaction with a truncated TrkC or truncated TrkB binding partner. In some embodiments, the antagonist of truncated TrkC or truncated TrkB expression level or activity is a nucleic acid polymer, a polypeptide or a small molecule.

Neurotrophins are dimeric polypeptide growth factors that regulate the peripheral and central nervous systems and other tissues and promote functions such as neuronal survival and regulation of synaptic plasticity. In some instances, the family of neurotrophins includes nerve growth factor (NGF), brain-derived neurotrophic factor (BDNF), neurotrophin-3 (NT-3), and neurotrophin-4 (NT-4). In some instances, neurotrophins mediate their effects through interaction with either the Trk family of receptors or with the p75 neurotrophin receptor which belongs to the tumor necrosis factor receptor superfamily. In some cases, interaction with the Trk family of receptors activates several signaling cascades, such as the phosphatidylinositol-3-kinase, phospholipase C, SN T, and Ras/mitogen-activated protein kinase pathways, which mediate growth and survival responses of the neurotrophins.

The Trk family of receptors comprises three homologs, TrkA (NTRK1), TrkB (NTRK2), and TrkC (NTRK3). Tropomyosin receptor kinase C (TrkC), also known as NT-3 growth factor receptor, neurotrophic tyrosine kinase receptor type 3, or TrkC tyrosine kinase, is the receptor for neurotrophin-3 (NT-3). Tropomyosin receptor kinase B (TrkB), also known as Tyrosine receptor kinase B, BDNF/NT-3 growth factors receptor, or neurotrophic tyrosine kinase receptor type 2, is the receptor for BDNF, NT-4, and in some instances, to NT-3 but at a reduced affinity.

Truncated TrkC and Truncated TrkB Isoforms

Figure 2A:
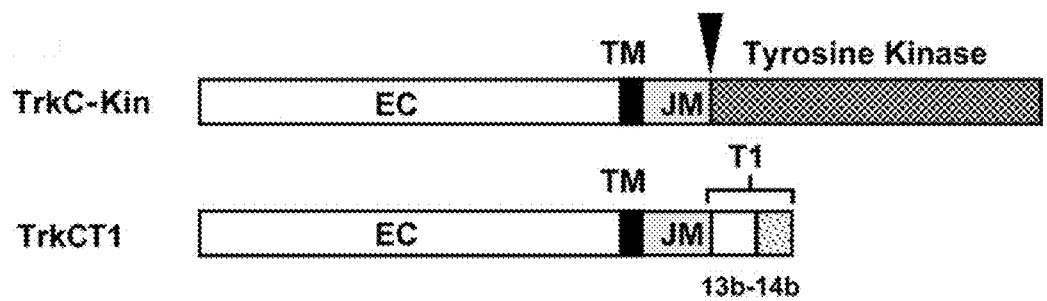
FIG. 2A and FIG. 2B illustrate the full length TrkC and TrkB and their respective isoforms.

In some embodiments, TrkC comprises about 20 exons. In some instances, a truncated TrkC isoform lacks one or more of the 20 exons or comprises one or more altered exons. In some embodiments, the truncated TrkC is a non-catalytic truncated TrkC. In some embodiments, the truncated TrkC protein comprises at least 80%, 85%, 90%, 95%, or 99% sequence identity to the amino acid sequence of SEQ ID NO: 10. In some instances, the truncated TrkC protein consists of the amino acid sequence of SEQ ID NO: 10. In some cases, the truncated TrkC is TrkC.T1. In some instances, the truncated TrkC is a truncated TrkC as illustrated in FIG. 2A.

Figure 2B:
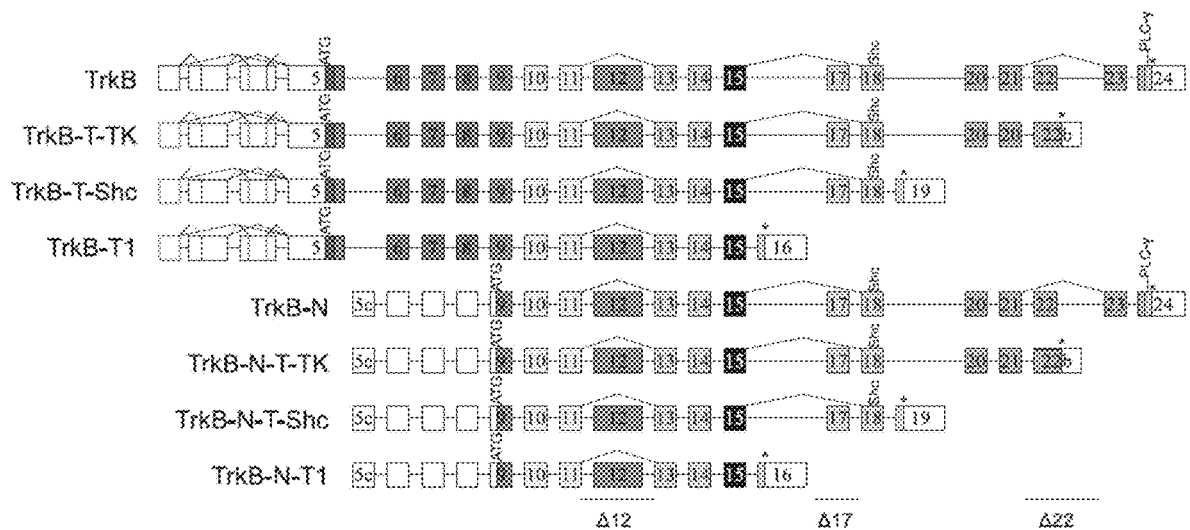

In some instances, TrkB comprises about 24 exons. In some instances, a truncated TrkB isoform lacks one or more of the 24 exons or comprises one or more altered exons. In some instances, truncated TrkB comprises TrkB-T-TK, TrkB-T Shc, TrkB.T1 (or TrkB-T1), TrkB.T2 (or TrkB-T2), TrkB-N, TrkB-N-T-TK, TrkB-N-T-Shc, or TrkB-N-T1. In some embodiments, truncated TrkB is a truncated TrkB as illustrated in FIG. 2B.

In some embodiments, the truncated TrkB is a non-catalytic truncated TrkB. In some instances, the truncated TrkB protein comprises at least 80%, 85%, 90%, 95%, or 99% sequence identity to the amino acid sequence of SEQ ID NO: 12. In some cases, the truncated TrkB protein consists of the amino acid sequence of SEQ ID NO: 12. In some cases, the truncated TrkB is TrkB.T1 (or TrkB-T1).

Nucleic Acid Polymer Antagonists

In some embodiments, the antagonist that induces a decrease in the truncated TrkC or truncated TrkB expression level or activity is a nucleic acid polymer. In some embodiments, the nucleic acid polymer that comprises at least 80% sequence identity to a nucleic acid sequence selected from SEQ ID NOs: 1-5, and wherein the nucleic acid polymer is at most 100 nucleotides in length; and a pharmaceutically acceptable excipient and/or a delivery vehicle. In some instances, the nucleic acid polymer comprises at least 81%, 82%, 83%, 84%, 85%, 86%, 87%, 88%, 89%, 90%, 91%, 92%, 93%, 94%, 95%, 96%, 97%, 98%, or 99% sequence identity to a nucleic acid sequence selected from SEQ ID NOs: 1-5. In some instances, the nucleic acid polymer comprises 100% sequence identity to a nucleic acid sequence selected from SEQ ID NOs: 1-5. In some instances, the nucleic acid polymer consists of a nucleic acid sequence selected from SEQ ID NOs: 1-5.

In some cases, the nucleic acid polymer hybridizes to a target sequence of the truncated TrkC or truncated TrkB mRNA. In some cases, the nucleic acid polymer induces a decrease in a truncated TrkC or truncated TrkB expression level. In some cases, the nucleic acid polymer comprising at least 81%, 82%, 83%, 84%, 85%, 86%, 87%, 88%, 89%, 90%, 91%, 92%, 93%, 94%, 95%, 96%, 97%, 98%, or 99% sequence identity to a nucleic acid sequence selected from SEQ ID NOs: 1-5 hybridizes to a target sequence of the truncated TrkC. In some cases, the nucleic acid polymer comprising 100% sequence identity to a nucleic acid sequence selected from SEQ ID NOs: 1-5 hybridizes to a target sequence of the truncated TrkC. In some cases, the nucleic acid polymer consisting of a nucleic acid sequence selected from SEQ ID NOs: 1-5 hybridizes to a target sequence of the truncated TrkC.

In some instances, the nucleic acid polymer comprising at least 81%, 82%, 83%, 84%, 85%, 86%, 87%, 88%, 89%, 90%, 91%, 92%, 93%, 94%, 95%, 96%, 97%, 98%, or 99% sequence identity to a nucleic acid sequence that hybridizes to a target sequence of the truncated TrkB. In some instances, the nucleic acid polymer comprising 100% sequence identity to a nucleic acid sequence that hybridizes to a target sequence of the truncated TrkB. In some cases, the nucleic acid polymer consisting of a nucleic acid sequence that hybridizes to a target sequence of the truncated TrkB.

In some instances, the nucleic acid polymer hybridizes to a target sequence comprising a binding motif selected from CCAAUC, CUCCAA, or ACUGUG, wherein the binding motif is located in a sequence encoding a truncated TrkC. In some instances, the nucleic acid polymer hybridizes to a target sequence that is located at the 3'UTR region of the truncated TrkC mRNA. In some cases, the nucleic acid polymer comprises a short hairpin RNA (shRNA) molecule, a microRNA (miRNA) molecule, a siRNA molecule, or a double stranded RNA molecule. In some cases, the nucleic acid polymer is a shRNA molecule.

In some embodiments, the nucleic acid polymer that hybridizes to a target sequence on truncated TrkC or truncated TrkB that is recognized by a microRNA (miRNA). In some instances, the miRNA comprises let-7b-3p (SEQ ID NO: 13), let-7b-5p (SEQ ID NO: 14), miR-1-3p (SEQ ID NO: 15), miR-1-5p (SEQ ID NO: 16), miR-9-3p (SEQ ID NO: 17), miR-9-5p (SEQ ID NO: 18), miR-10a-3p (SEQ ID NO: 19), miR-10a-5p (SEQ ID NO: 20), miR-15a-3p (SEQ ID NO: 21), miR-15a-5p (SEQ ID NO: 22), miR-16-1-3p (SEQ ID NO: 23), miR-16-2-3p (SEQ ID NO: 24), miR-16-5p (SEQ ID NO: 25), miR-17-3p (SEQ ID NO: 26), miR-17-5p (SEQ ID NO: 27), miR-18a-3p (SEQ ID NO: 28), miR-18a-5p (SEQ ID NO: 29), miR-20a-3p (SEQ ID NO: 30), miR-20a-5p (SEQ ID NO: 31), miR-24-3p (SEQ ID NO: 32), miR-24-1-5p (SEQ ID NO: 33), miR-24-2-5p (SEQ ID NO: 34), miR-30e-3p (SEQ ID NO: 35), miR-30e-5p (SEQ ID NO: 36), miR-93-3p (SEQ ID NO: 37), miR-93-5p (SEQ ID NO: 38), miR-103a-3p (SEQ ID NO: 39), miR-103a-2-5p (SEQ ID NO: 40), miR-103b (SEQ ID NO: 41), miR-106a-3p (SEQ ID NO: 42), miR-106a-5p (SEQ ID NO: 43), miR-106b-3p (SEQ ID NO: 44), miR-106b-5p (SEQ ID NO: 45), miR-107 (SEQ ID NO: 46), miR-125a-3p (SEQ ID NO: 47), miR-125a-5p (SEQ ID NO: 48), miR-125b-1-3p (SEQ ID NO: 49), miR-125b-2-3p (SEQ ID NO: 50), miR-125b-5p (SEQ ID NO: 51), miR-128-3p (SEQ ID NO: 52), miR-128-1-5p (SEQ ID NO: 53), miR-128-2-5p (SEQ ID NO: 54), miR-133a-3p (SEQ ID NO: 55), miR-133a-5p (SEQ ID NO: 56), miR-133b (SEQ ID NO: 57), miR-141-3p (SEQ ID NO: 58), miR-141-5p (SEQ ID NO: 59), miR-149-3p (SEQ ID NO: 60), miR-149-5p (SEQ ID NO: 61), miR-182-3p (SEQ ID NO: 62), miR-182-5p (SEQ ID NO: 63), miR-188-3p (SEQ ID NO: 64), miR-188-5p (SEQ ID NO: 65), miR-198 (SEQ ID NO: 66), miR-200a-3p (SEQ ID NO: 67), miR-200a-5p (SEQ ID NO: 68), miR-200b-3p (SEQ ID NO: 69), miR-200b-5p (SEQ ID NO: 70), miR-204-3p (SEQ ID NO: 71), miR-204-5p (SEQ ID NO: 72), miR-206 (SEQ ID NO: 73), miR-221-3p (SEQ ID NO: 74), miR-221-5p (SEQ ID NO: 75), miR-296-3p (SEQ ID NO: 76), miR-296-5p (SEQ ID NO: 77), miR-324-5p (SEQ ID NO: 78), miR-326 (SEQ ID NO: 79), miR-330-3p (SEQ ID NO: 80), miR-331-3p (SEQ ID NO: 81), miR-331-5p (SEQ ID NO: 82), miR-340-3p (SEQ ID NO: 83), miR-340-5p (SEQ ID NO: 84), miR-345-3p (SEQ ID NO: 85), miR-345-5p (SEQ ID NO: 86), miR-374a-3p (SEQ ID NO: 87), miR-374a-5p (SEQ ID NO: 88), miR-374b-3p (SEQ ID NO: 89), miR-374b-5p (SEQ ID NO: 90), miR-374c-3p (SEQ ID NO: 91), miR-374c-5p (SEQ ID NO: 92), miR-384 (SEQ ID NO: 93), miR-412-3p (SEQ ID NO: 94), miR-412-5p (SEQ ID NO: 95), miR-422a (SEQ ID NO: 96), miR-449a (SEQ ID NO: 97), miR-449b-3p (SEQ ID NO: 98), miR-449b-5p (SEQ ID NO: 99), miR-449c-3p (SEQ ID NO: 100), miR-449c-5p (SEQ ID NO: 101), miR-485-3p (SEQ ID NO: 102), miR-509-3p (SEQ ID NO: 103), miR-509-5p (SEQ ID NO: 104), miR-509-3-5p (SEQ ID NO: 105), miR-617 (SEQ ID NO: 106), miR-625-3p (SEQ ID NO: 107), miR-625-5p (SEQ ID NO: 108), miR-765 (SEQ ID NO: 109), or miR-768-5p. In some cases, the nucleic acid polymer hybridizes to a target sequence on truncated TrkC or truncated TrkB that is recognized by let-7b-3p (SEQ ID NO: 13), let-7b-5p (SEQ ID NO: 14), miR-1-3p (SEQ ID NO: 15), miR-1-5p (SEQ ID NO: 16), miR-9-3p (SEQ ID NO: 17), miR-9-5p (SEQ ID NO: 18), miR-10a-3p (SEQ ID NO: 19), miR-10a-5p (SEQ ID NO: 20), miR-15a-3p (SEQ ID NO: 21), miR-15a-5p (SEQ ID NO: 22), miR-16-1-3p (SEQ ID NO: 23), miR-16-2-3p (SEQ ID NO: 24), miR-16-5p (SEQ ID NO: 25), miR-17-3p (SEQ ID NO: 26), miR-17-5p (SEQ ID NO: 27), miR-18a-3p (SEQ ID NO: 28), miR-18a-5p (SEQ ID NO: 29), miR-20a-3p (SEQ ID NO: 30), miR-20a-5p (SEQ ID NO: 31), miR-24-3p (SEQ ID NO: 32), miR-24-1-5p (SEQ ID NO: 33), miR-24-2-5p (SEQ ID NO: 34), miR-30e-3p (SEQ ID NO: 35), miR-30e-5p (SEQ ID NO: 36), miR-93-3p (SEQ ID NO: 37), miR-93-5p (SEQ ID NO: 38), miR-103a-3p (SEQ ID NO: 39), miR-103a-2-5p (SEQ ID NO: 40), miR-103b (SEQ ID NO: 41), miR-106a-3p (SEQ ID NO: 42), miR-106a-5p (SEQ ID NO: 43), miR-106b-3p (SEQ ID NO: 44), miR-106b-5p (SEQ ID NO: 45), miR-107 (SEQ ID NO: 46), miR-125a-3p (SEQ ID NO: 47), miR-125a-5p (SEQ ID NO: 48), miR-125b-1-3p (SEQ ID NO: 49), miR-125b-2-3p (SEQ ID NO: 50), miR-125b-5p (SEQ ID NO: 51), miR-128-3p (SEQ ID NO: 52), miR-128-1-5p (SEQ ID NO: 53), miR-128-2-5p (SEQ ID NO: 54), miR-133a-3p (SEQ ID NO: 55), miR-133a-5p (SEQ ID NO: 56), miR-133b (SEQ ID NO: 57), miR-141-3p (SEQ ID NO: 58), miR-141-5p (SEQ ID NO: 59), miR-149-3p (SEQ ID NO: 60), miR-149-5p (SEQ ID NO: 61), miR-182-3p (SEQ ID NO: 62), miR-182-5p (SEQ ID NO: 63), miR-188-3p (SEQ ID NO: 64), miR-188-5p (SEQ ID NO: 65), miR-198 (SEQ ID NO: 66), miR-200a-3p (SEQ ID NO: 67), miR-200a-5p (SEQ ID NO: 68), miR-200b-3p (SEQ ID NO: 69), miR-200b-5p (SEQ ID NO: 70), miR-204-3p (SEQ ID NO: 71), miR-204-5p (SEQ ID NO: 72), miR-206 (SEQ ID NO: 73), miR-221-3p (SEQ ID NO: 74), miR-221-5p (SEQ ID NO: 75), miR-296-3p (SEQ ID NO: 76), miR-296-5p (SEQ ID NO: 77), miR-324-5p (SEQ ID NO: 78), miR-326 (SEQ ID NO: 79), miR-330-3p (SEQ ID NO: 80), miR-331-3p (SEQ ID NO: 81), miR-331-5p (SEQ ID NO: 82), miR-340-3p (SEQ ID NO: 83), miR-340-5p (SEQ ID NO: 84), miR-345-3p (SEQ ID NO: 85), miR-345-5p (SEQ ID NO: 86), miR-374a-3p (SEQ ID NO: 87), miR-374a-5p (SEQ ID NO: 88), miR-374b-3p (SEQ ID NO: 89), miR-374b-5p (SEQ ID NO: 90), miR-374c-3p (SEQ ID NO: 91), miR-374c-5p (SEQ ID NO: 92), miR-384 (SEQ ID NO: 93), miR-412-3p (SEQ ID NO: 94), miR- 412-5p (SEQ ID NO: 95), miR-422a (SEQ ID NO: 96), miR-449a (SEQ ID NO: 97), miR-449b-3p (SEQ ID NO: 98), miR-449b-5p (SEQ ID NO: 99), miR-449c-3p (SEQ ID NO: 100), miR-449c-5p (SEQ ID NO: 101), miR-485-3p (SEQ ID NO: 102), miR-509-3p (SEQ ID NO: 103), miR-509-5p (SEQ ID NO: 104), miR-509-3-5p (SEQ ID NO: 105), miR-617 (SEQ ID NO: 106), miR-625-3p (SEQ ID NO: 107), miR-625-5p (SEQ ID NO: 108), miR-765 (SEQ ID NO: 109), or miR-768-5p. In some cases, the nucleic acid polymer hybridizes to a target sequence on truncated TrkC or truncated TrkB that is recognized by miR-128-3p (SEQ ID NO: 52), miR-128-1-5p (SEQ ID NO: 53), miR-128-2-5p (SEQ ID NO: 54), miR-509-3p (SEQ ID NO: 103), miR-509-5p (SEQ ID NO: 104), miR-509-3-5p (SEQ ID NO: 105), or miR-768-5p. In some cases, the nucleic acid polymer hybridizes to a target sequence on truncated TrkC or truncated TrkB that is recognized by miR-128-3p (SEQ ID NO: 52), miR-128-1-5p (SEQ ID NO: 53), miR-128-2-5p (SEQ ID NO: 54). In some cases, the nucleic acid polymer hybridizes to a target sequence on truncated TrkC or truncated TrkB that is recognized by miR-509-3p (SEQ ID NO: 103), miR-509-5p (SEQ ID NO: 104), miR-509-3-5p (SEQ ID NO: 105). In some cases, the nucleic acid polymer hybridizes to a target sequence on truncated TrkC or truncated TrkB that is recognized by miR-768-5p.

In some embodiments, the nucleic acid polymer is at most 100 nucleotides in length. In some embodiments, the nucleic acid polymer is at most 5, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 70, 80, 90, or 100 nucleotides in length. In some embodiments, the nucleic acid polymer is about 10 nucleotides in length. In some embodiments, the nucleic acid polymer is about 11 nucleotides in length. In some embodiments, the nucleic acid polymer is about 12 nucleotides in length. In some embodiments, the nucleic acid polymer is about 13 nucleotides in length. In some embodiments, the nucleic acid polymer is about 14 nucleotides in length. In some embodiments, the nucleic acid polymer is about 15 nucleotides in length. In some embodiments, the nucleic acid polymer is about 16 nucleotides in length. In some embodiments, the nucleic acid polymer is about 17 nucleotides in length. In some embodiments, the nucleic acid polymer is about 18 nucleotides in length. In some embodiments, the nucleic acid polymer is about 19 nucleotides in length. In some embodiments, the nucleic acid polymer is about 20 nucleotides in length. In some embodiments, the nucleic acid polymer is about 21 nucleotides in length. In some embodiments, the nucleic acid polymer is about 22 nucleotides in length. In some embodiments, the nucleic acid polymer is about 23 nucleotides in length. In some embodiments, the nucleic acid polymer is about 24 nucleotides in length. In some embodiments, the nucleic acid polymer is about 25 nucleotides in length. In some embodiments, the nucleic acid polymer is about 26 nucleotides in length. In some embodiments, the nucleic acid polymer is about 27 nucleotides in length. In some embodiments, the nucleic acid polymer is about 28 nucleotides in length. In some embodiments, the nucleic acid polymer is about 29 nucleotides in length. In some embodiments, the nucleic acid polymer is about 30 nucleotides in length. In some embodiments, the nucleic acid polymer is about 31 nucleotides in length. In some embodiments, the nucleic acid polymer is about 32 nucleotides in length. In some embodiments, the nucleic acid polymer is about 33 nucleotides in length. In some embodiments, the nucleic acid polymer is about 34 nucleotides in length. In some embodiments, the nucleic acid polymer is about 35 nucleotides in length. In some embodiments, the nucleic acid polymer is about 36 nucleotides in length. In some embodiments, the nucleic acid polymer is about 37 nucleotides in length. In some embodiments, the nucleic acid polymer is about 38 nucleotides in length. In some embodiments, the nucleic acid polymer is about 39 nucleotides in length. In some embodiments, the nucleic acid polymer is about 40 nucleotides in length. In some embodiments, the nucleic acid polymer is about 45 nucleotides in length. In some embodiments, the nucleic acid polymer is about 50 nucleotides in length. In some embodiments, the nucleic acid polymer is about 55 nucleotides in length. In some embodiments, the nucleic acid polymer is about 60 nucleotides in length. In some embodiments, the nucleic acid polymer is about 70 nucleotides in length. In some embodiments, the nucleic acid polymer is about 80 nucleotides in length.

In some embodiments, the nucleic acid polymer is between about 10 and about 80 nucleotides in length. In some embodiments, the nucleic acid polymer is between about 10 and about 70 nucleotides in length. In some embodiments, the nucleic acid polymer is between about 10 and about 60 nucleotides in length. In some embodiments, the nucleic acid polymer is between about 10 and about 55 nucleotides in length. In some embodiments, the nucleic acid polymer is between about 10 and about 50 nucleotides in length. In some embodiments, the nucleic acid polymer is between about 10 and about 45 nucleotides in length. In some embodiments, the nucleic acid polymer is between about 10 and about 40 nucleotides in length. In some embodiments, the nucleic acid polymer is between about 10 and about 35 nucleotides in length. In some embodiments, the nucleic acid polymer is between about 10 and about 30 nucleotides in length. In some embodiments, the nucleic acid polymer is between about 10 and about 25 nucleotides in length. In some embodiments, the nucleic acid polymer is between about 10 and about 20 nucleotides in length.

In some embodiments, the nucleic acid polymer comprises a short hairpin RNA (shRNA) molecule, a microRNA (miRNA) molecule, or a siRNA molecule. In some embodiments, the nucleic acid polymer further comprises a complement nucleic acid polymer to form a double stranded RNA molecule.

In some embodiments, the nucleic acid polymer is a shRNA molecule. In some embodiments, the shRNA molecule comprises at least 80% sequence identity to a nucleic acid sequence selected from SEQ ID NOs: 1-5. In some instances, the shRNA molecule comprises at least 85%, 90%, 95%, or 99% sequence identity to a nucleic acid sequence selected from SEQ ID NOs: 1-5. In some instances, the shRNA molecule comprises 100% sequence identity to a nucleic acid sequence selected from SEQ ID NOs: 1-5. In some instances, the shRNA molecule consists of a nucleic acid sequence selected from SEQ ID NOs: 1-5.

In some embodiments, the shRNA molecule hybridizes to a target sequence comprising a binding motif selected from CCAAUC, CUCCAA, or ACUGUG, wherein the binding motif is located in a sequence encoding a truncated TrkC. In some instances, the target sequence is located at the 3'UTR region of the truncated TrkC mRNA.

In some instances, the shRNA molecule is at most 100 nucleotides in length. In some embodiments, the shRNA molecule is at most 5, 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 70, 80, 90, or 100 nucleotides in length. In some embodiments, the shRNA molecule is between about 10 and about 80 nucleotides in length. In some embodiments, the shRNA molecule is between about 10 and about 70 nucleotides in length. In some embodiments, the shRNA molecule is between about 10 and about 60 nucleotides in length. In some embodiments, the shRNA molecule is between about 10 and about 55 nucleotides in length. In some embodiments, the shRNA molecule is between about 10 and about 50 nucleotides in length. In some embodiments, the shRNA molecule is between about 10 and about 45 nucleotides in length. In some embodiments, the shRNA molecule is between about 10 and about 40 nucleotides in length. In some embodiments, the shRNA molecule is between about 10 and about 35 nucleotides in length. In some embodiments, the shRNA molecule is between about 10 and about 30 nucleotides in length. In some embodiments, the shRNA molecule is between about 10 and about 25 nucleotides in length. In some embodiments, the shRNA molecule is between about 10 and about 20 nucleotides in length.

In some embodiments, the nucleic acid polymer described herein comprises RNA, DNA or a combination thereof. In some instances, the nucleic acid polymer is a RNA polymer. In some instances, the nucleic acid polymer is further modified at the nucleoside moiety, at the phosphate moiety, or a combination thereof. In some cases, the nucleic acid polymer further comprises one or more artificial nucleotide bases.

In some instances, the one or more artificial nucleotide bases comprises 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, locked nucleic acid (LNA), ethylene nucleic acid (ENA), peptide nucleic acid (PNA), 1', 5'-anhydrohexitol nucleic acids (HNA), morpholino, methylphosphonate nucleotides, thiolphosphonate nucleotides, or 2'-fluoro N3-P5'-phosphoramidites.

In some embodiments, the nucleic acid polymer comprises a modification at the nucleoside moiety. In some instances, the modification is at the 2' hydroxyl group of the ribose moiety. In some instances, the modification is a 2'-O-methyl modification or a 2'-O-methoxyethyl (2'-O-MOE) modification. In some instances, the 2'-O-methyl modification adds a methyl group to the 2' hydroxyl group of the ribose moiety whereas the 2'O-methoxyethyl modification add a methoxyethyl group to the 2' hydroxyl group of the ribose moiety. Exemplary chemical structures of a 2'-O-methyl modification of an adenosine molecule and 2'O-methoxyethyl modification of a uridine are illustrated below.

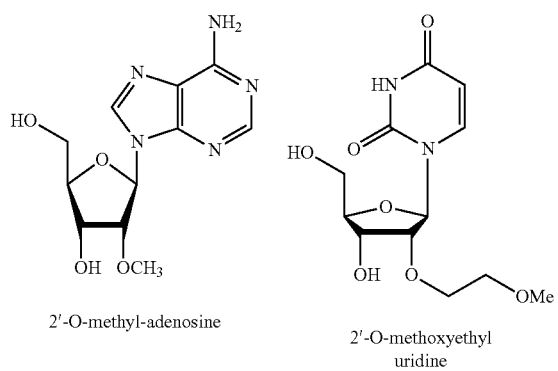

2'-O-methyl-adenosine

2'-O-methoxyethyl uridine

In some embodiments, an additional modification at the 2' hydroxyl group includes a 2'-O-aminopropyl sugar conformation which involves an extended amine group comprising a propyl linker that binds the amine group to the 2' oxygen. In some instances, this modification neutralizes the phosphate derived overall negative charge of the oligonucleotide molecule by introducing one positive charge from the amine group per sugar and thereby improve cellular uptake properties due to its zwitterionic properties. An exemplary chemical structure of a 2'-O-aminopropyl nucleoside phosphoramidite is illustrated below.

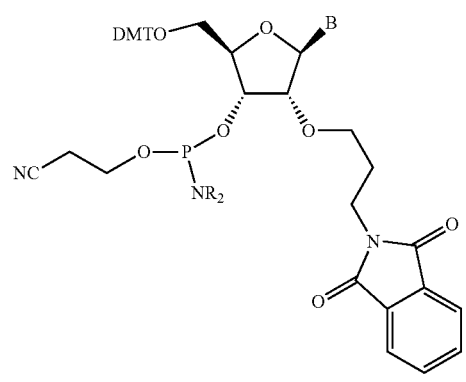

2'-O-aminopropyl nucleoside phosphoramidite

In some embodiments, the modification at the 2' hydroxyl group includes a locked or bridged ribose conformation (e.g., locked nucleic acid or LNA) where the 4' ribose position is also involved. In some embodiments, the oxygen molecule bound at the 2' carbon is linked to the 4' carbon by a methylene group, thus forming a 2'-C,4'-C-oxy-methylene-linked bicyclic ribonucleotide monomer. Exemplary representations of the chemical structure of LNA are illustrated below. The representation shown to the left highlights the chemical connectivities of an LNA monomer. The representation shown to the right highlights the locked 3'-endo ($^3$E) conformation of the furanose ring of an LNA monomer.

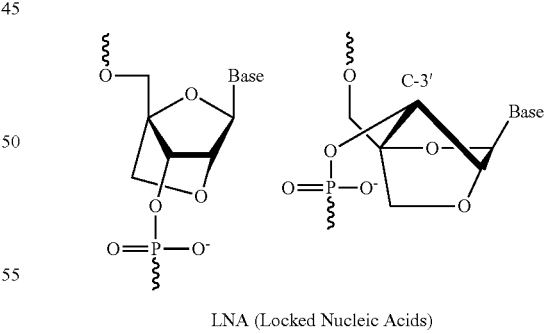

LNA (Locked Nucleic Acids)

In some embodiments, a further modification at the 2' hydroxyl group comprises ethylene nucleic acids (ENA) such as for example 2'-4'-ethylene-bridged nucleic acid, which locks the sugar conformation into a $C_3$'-endo sugar puckering conformation. In some instances, ENAs are part of the bridged nucleic acids class of modified nucleic acids that also comprises LNA. Exemplary chemical structures of the ENA and bridged nucleic acids are illustrated below.

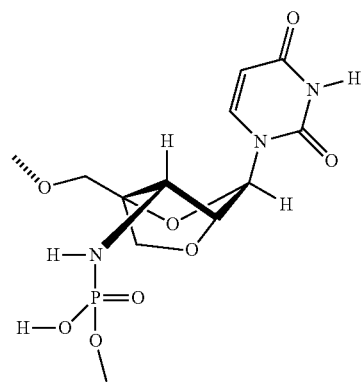

3'-amino-2',4'-BNA

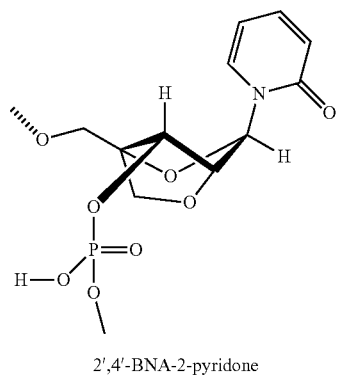

2',4'-BNA-2-pyridone

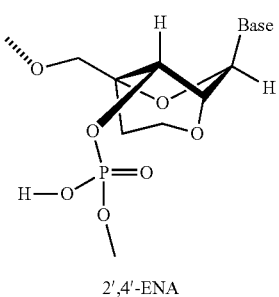

2',4'-ENA

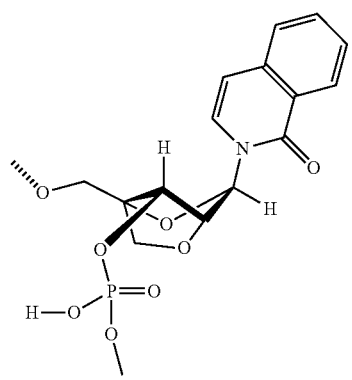

2',4'-BNA-1-isoquinolone

In some embodiments, still other modifications at the 2' hydroxyl group include 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA).

In some embodiments, nucleotide analogues further comprise Morpholinos, peptide nucleic acids (PNAs), methylphosphonate nucleotides, thiolphosphonate nucleotides, 2'-fluoro N3-P5'-phosphoramidites, 1', 5'-anhydrohexitol nucleic acids (HNAs), or a combination thereof. In some instances, morpholino or phosphorodiamidate morpholino oligo (PMO) comprises synthetic molecules whose structure mimics natural nucleic acid structure by deviates from the normal sugar and phosphate structures. Instead, the five member ribose ring in some instances is substituted with a six member morpholino ring containing four carbons, one nitrogen and one oxygen. In some cases, the ribose monomers are linked by a phosphordiamidate group instead of a phosphate group. In some cases, these backbone alterations remove all positive and negative charges making morpholinos neutral molecules that cross cellular membranes without the aid of cellular delivery agents such as those used by charged oligonucleotides.

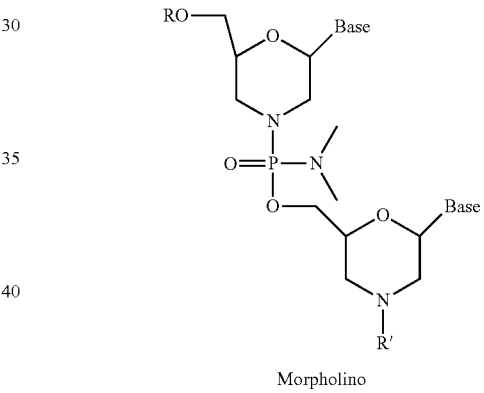

Morpholino

In some embodiments, peptide nucleic acid (PNA) does not contain sugar ring or phosphate linkage. Instead, the bases in some instances are attached and appropriately spaced by oligoglycine-like molecules, therefore, eliminating a backbone charge.

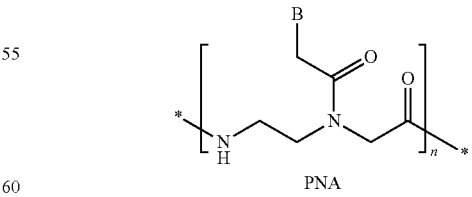

PNA

In some embodiments, modification of the phosphate backbone also comprise methyl or thiol modifications such as thiolphosphonate and methylphosphonate nucleotide. Exemplary thiolphosphonate nucleotide (left) and methylphosphonate nucleotide (right) are illustrated below.

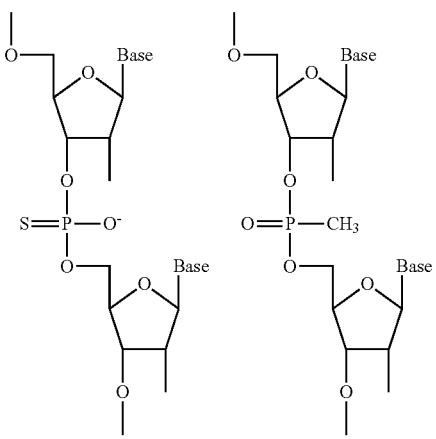

Furthermore, exemplary 2'-fluoro N3-P5'-phosphoramidites is illustrated as:

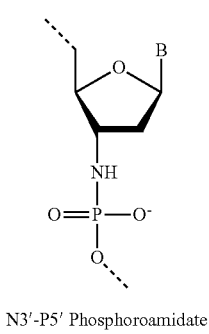

N3'-P5' Phosphoroamidate

And exemplary hexitol nucleic acid (or 1', 5'-anhydrohexitol nucleic acids (HNA)) is illustrated as:

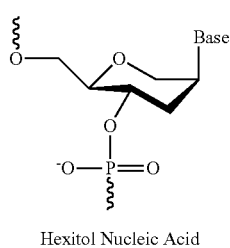

Hexitol Nucleic Acid

Small Molecule Antagonists

In some embodiments, the antagonist that induces a decrease in the truncated TrkC or truncated TrkB expression level or activity is a small molecule. In some embodiments, the small molecule antagonist impedes the truncated TrkC or truncated TrkB interaction with a truncated TrkC or truncated TrkB binding partner.

Figure 3:
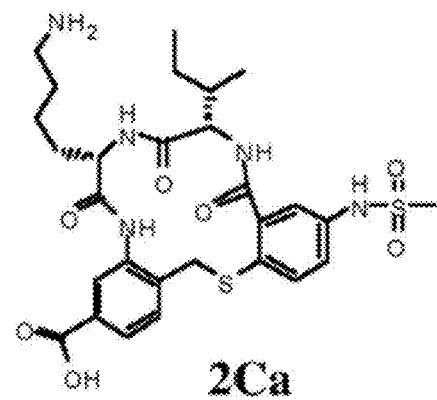
FIG. 3 illustrates exemplary small molecule antagonists of truncated TrkC.
Figure 3:
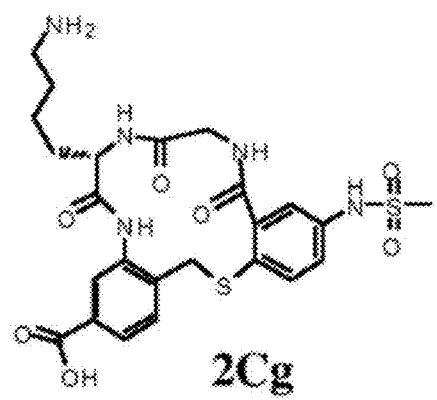
Figure 3:
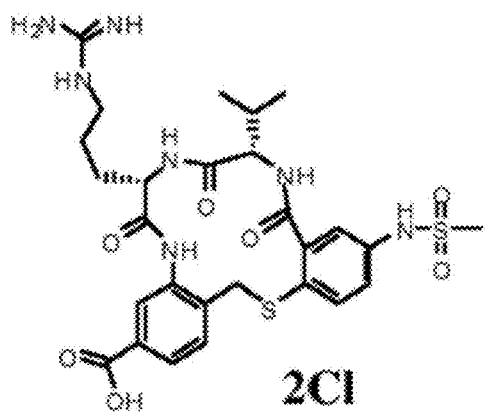
Figure 3:
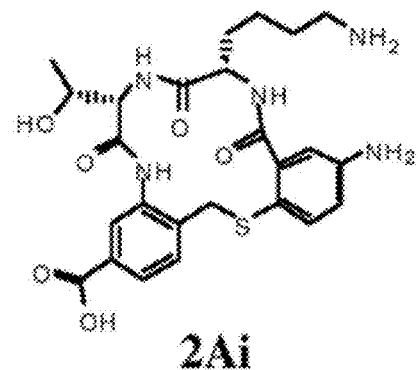
Figure 3:
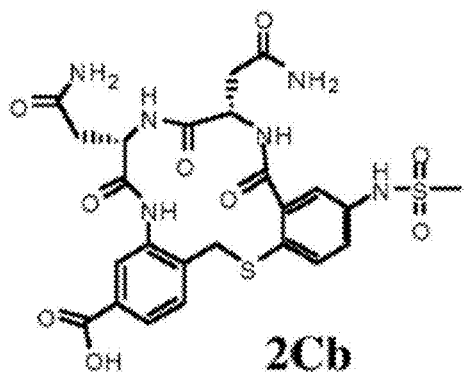
Figure 3:
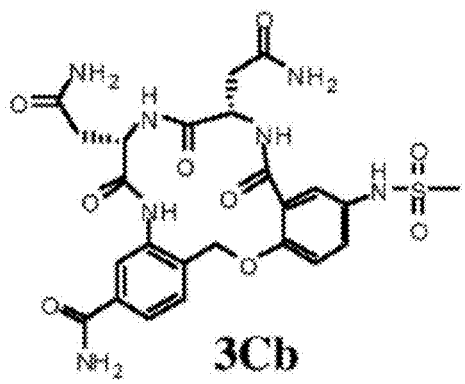
Figure 3:
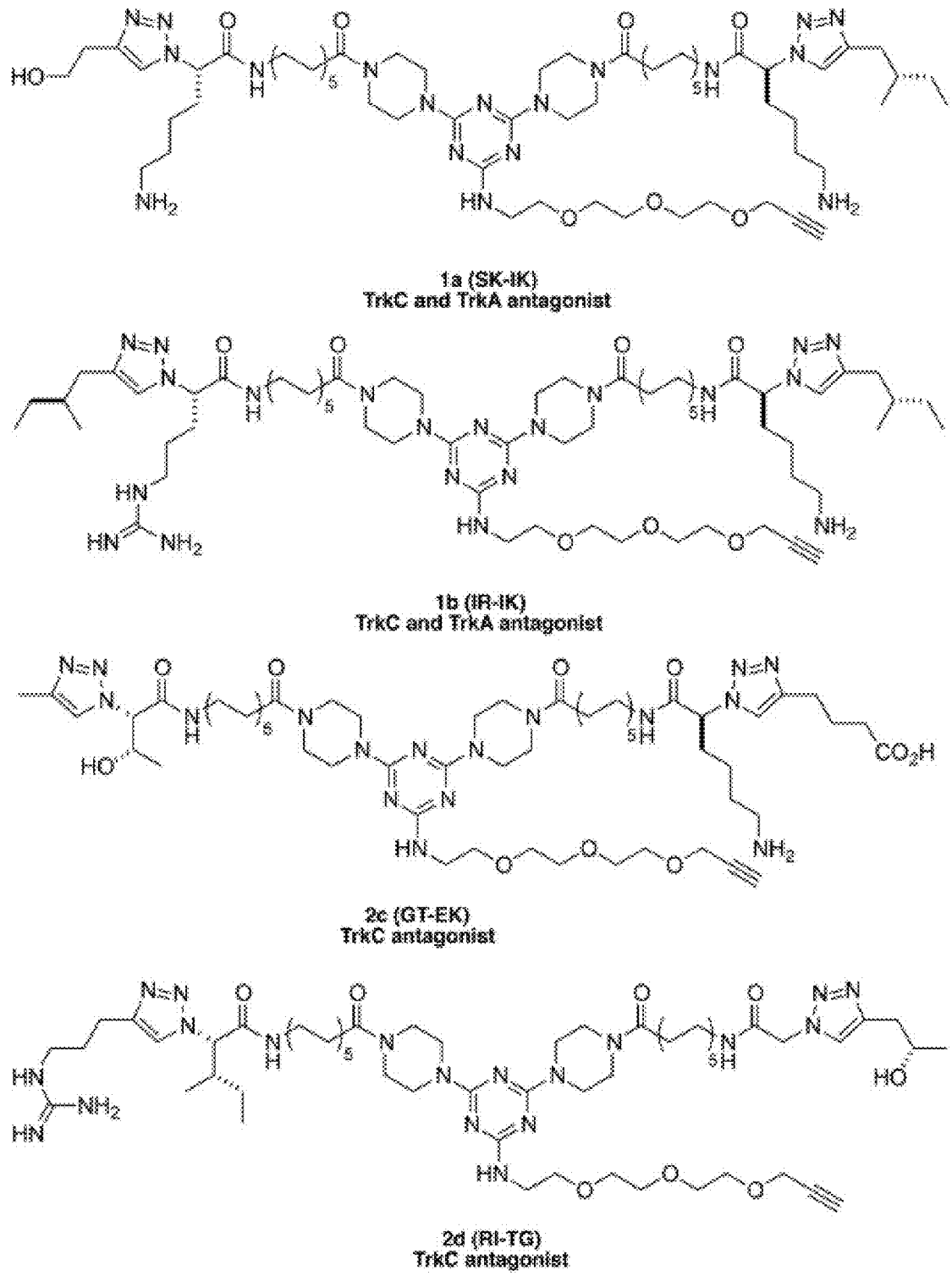
Figure 3:
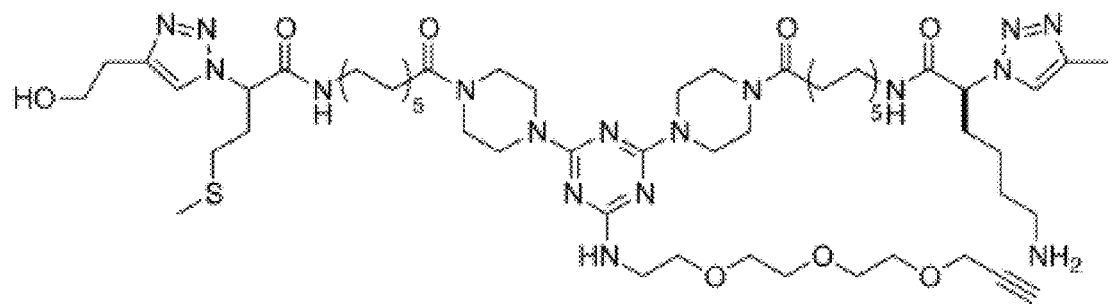
Figure 3:
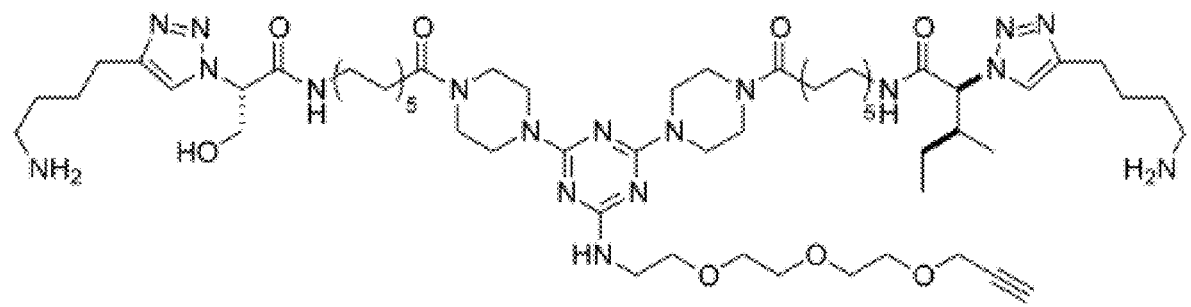
Figure 3:
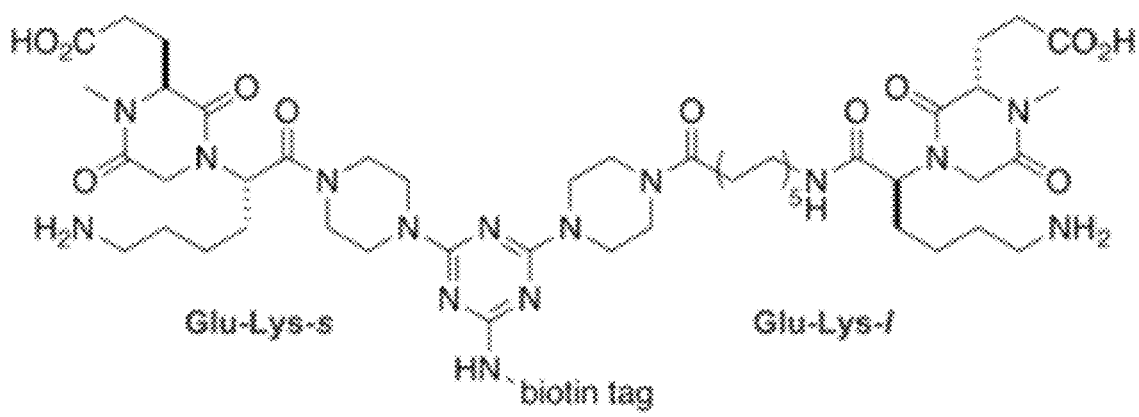

In some instances, the small molecule is a peptidomimetic. In some cases, the small molecule is a small molecule as illustrated in FIG. 3. In some embodiments, the small molecule is a small molecule antagonist described in: Brahimi et al., "A peptidomimetic of NT-3 acts as a TrkC antagonist," Peptides 30(10):1833-1839 (2009); Liu et al., "Bivalent diketopiperazine-based tropomysin receptor kinase C (TrkC) antagonists," J. Med. Chem. 53(13): 5044-5048 (2010); Bai et al., "In glaucoma the upregulated truncated TrkC.T1 receptor isoform in Glia causes increased TNF-α production, leading to retinal ganglion cell death," Inv. Ophthalm. & Visual Sci. 51(12): 6639-6651 (2010); or Brahimi et al., "Combinatorial assembly of small molecules into bivalent antagonists of TrkC or TrkA receptors," PLOS One 9(3): e89617 (2014).

In some embodiments, the small molecule antagonist is a truncated TrkC antagonist. In some embodiments, the truncated TrkC antagonist is a small molecule as illustrated in FIG. 3. In some embodiments, the truncated TrkC antagonists is a small molecule as described in: Brahimi et al., "A peptidomimetic of NT-3 acts as a TrkC antagonist," Peptides 30(10):1833-1839 (2009); Liu et al., "Bivalent diketopiperazine-based tropomysin receptor kinase C (TrkC) antagonists," J. Med. Chem. 53(13): 5044-5048 (2010); Bai et al., "In glaucoma the upregulated truncated TrkC.T1 receptor isoform in Glia causes increased TNF-α production, leading to retinal ganglion cell death," Inv. Ophthalm. & Visual Sci. 51(12): 6639-6651 (2010); or Brahimi et al., "Combinatorial assembly of small molecules into bivalent antagonists of TrkC or TrkA receptors," PLOS One 9(3): e89617 (2014).

In some instances, the truncated TrkC is a non-catalytic truncated TrkC. As described elsewhere herein, the non-catalytic truncated TrkC protein comprises at least 80%, 85%, 90%, 95%, or 99% sequence identity to the amino acid sequence of SEQ ID NO: 10. In some instances, the truncated TrkC protein consists of the amino acid sequence of SEQ ID NO: 10. In some instances, the truncated TrkC is TrkC.T1.

In some embodiments, the truncated TrkB is a non-catalytic truncated TrkB. As described elsewhere herein, the non-catalytic truncated TrkB protein comprises at least 80%, 85%, 90%, 95%, or 99% sequence identity to the amino acid sequence of SEQ ID NO: 12. In some instances, the truncated TrkB protein consists of the amino acid sequence of SEQ ID NO: 12. In some instances, the truncated TrkB is TrkB.T1.

In some embodiments, the truncated TrkC binding partner comprises a neurotropic factor or a microRNA molecule. In some embodiments, the neurotropic factor is neurotrophin-3 (NT-3). In some embodiments, the microRNA molecule comprises miR-128, miR-509, or miR-768-5p. In some embodiments, the truncated TrkB binding partner comprises a neurotropic factor. In some embodiments, the neurotropic factor is brain derived neurotrophic factor (BDNF), neurotrophin-3 (NT-3), or neurotrophin-4 (NT-4).

Polypeptide Antagonists

In some embodiments, the antagonist that induces a decrease in the truncated TrkC or truncated TrkB expression level or activity is a polypeptide. In some embodiments, the polypeptide antagonist is an antibody or binding fragment thereof. In some instances, the antibody or binding fragment thereof comprises a humanized antibody or binding fragment thereof, chimeric antibody or binding fragment thereof, monoclonal antibody or binding fragment thereof, a linear antibody, a single-chain antibody, a bi-specific antibody, a multispecific antibody formed from antibody fragments, a tandem antibody, a veneered antibody, monovalent Fab', divalent Fab2, single-chain variable fragment (scFv), diabody, minibody, single-domain antibody (sdAb), a rIgG fragment, or camelid antibody or binding fragment thereof.

In some embodiments, the antibody or binding fragment thereof recognizes one or more of the epitopes of the truncated TrkC or truncated TrkB. In some embodiments, the epitopes on the truncated TrkC comprise a region within the ectodomain of the truncated TrkC. In some instances, the ectodomain of the truncated TrkC comprises the leucine-rich repeat regions and the Ig-like domain that is involved in ligand interaction. In some instances, the epitope region within the ectodomain of the truncated TrkC comprises one or more cysteine residues. In some instances, the epitope region within the ectodomain of the truncated TrkC comprises one or more cysteine residues that is capable of forming disulfide bond. In some embodiments, the antibody or binding fragment thereof recognizes one or more of the epitopes that comprises one or more of the cysteine residues.

In some embodiments, the epitopes on the truncated TrkB comprise a region within the ectodomain of the truncated TrkB. In some instances, the ectodomain of the truncated TrkB comprises the leucine-rich repeat regions and the Ig-like domain that is involved in ligand interaction. In some instances, the epitope region within the ectodomain of the truncated TrkB comprises one or more cysteine residues. In some instances, the epitope region within the ectodomain of the truncated TrkB comprises one or more cysteine residues that is capable of forming disulfide bond. In some embodiments, the antibody or binding fragment thereof recognizes one or more of the epitopes that comprises one or more of the cysteine residues.

In some embodiments, the polypeptide antagonist comprises an antibody or binding fragment thereof that recognizes one or more of the epitopes of the truncated TrkC or truncated TrkB. In some instances, the polypeptide antagonist comprises an antibody or binding fragment thereof that recognizes one or more of the epitopes from the ectodomain of either truncated TrkC or truncated TrkB that comprises one or more of the cysteine residues.

In some embodiments, the polypeptide antagonist comprises an antibody or binding fragment thereof that recognizes one or more of the epitopes of the truncated TrkC or truncated TrkB but not one or more of the epitopes of the full-length TrkC or full-length TrkB. In some embodiments, the polypeptide antagonist comprises an antibody or binding fragment thereof that recognizes one or more of the epitopes from the ectodomain of the truncated TrkC or truncated TrkB but not one or more of the epitopes from the ectodomain of the full-length TrkC or full-length TrkB.

In some instances, the truncated TrkC is a non-catalytic truncated TrkC. As described elsewhere herein, the non-catalytic truncated TrkC protein comprises at least 80%, 85%, 90%, 95%, or 99% sequence identity to the amino acid sequence of SEQ ID NO: 10. In some instances, the truncated TrkC protein consists of the amino acid sequence of SEQ ID NO: 10. In some instances, the truncated TrkC is TrkC.T1.

In some embodiments, the truncated TrkB is a non-catalytic truncated TrkB. As described elsewhere herein, the non-catalytic truncated TrkB protein comprises at least 80%, 85%, 90%, 95%, or 99% sequence identity to the amino acid sequence of SEQ ID NO: 12. In some instances, the truncated TrkB protein consists of the amino acid sequence of SEQ ID NO: 12. In some instances, the truncated TrkB is TrkB.T1.

Truncated TrkC or Truncated TrkB Antagonist Delivery

In some embodiments, the truncated TrkC or truncated TrkB antagonist pharmaceutical composition or formulation comprises a vector in which the vector comprises one or more of the nucleic acid polymer described herein or comprise nucleic acid sequence that encodes a polypeptide described herein. In some embodiments, the nucleic acid polymer comprises at least 80%, 85%, 90%, 95%, or 99% sequence identity to a nucleic acid sequence selected from SEQ ID NOs: 1-5. In some embodiments, the polypeptide is an antibody or binding fragment thereof. In some embodiments, the antibody or binding fragment thereof comprises a humanized antibody or binding fragment thereof, chimeric antibody or binding fragment thereof, monoclonal antibody or binding fragment thereof, monovalent Fab', divalent Fab2, single-chain variable fragment (scFv), diabody, minibody, single-domain antibody (sdAb), or camelid antibody or binding fragment thereof. In some embodiments, the vector is a viral vector.

In some embodiments, the viral vector is obtained from any virus, such as a DNA or an RNA virus. In some embodiments, a DNA virus is a single-stranded (ss) DNA virus, a double-stranded (ds) DNA virus, or a DNA virus that contains both ss and ds DNA regions. In some embodiments, an RNA virus is a single-stranded (ss) RNA virus or a double-stranded (ds) RNA virus. In some embodiments, a ssRNA virus is further classified into a positive-sense RNA virus or a negative-sense RNA virus.

In some instances, the viral vector is obtained from a dsDNA virus of the family: Myoviridae, Podoviridae, Siphoviridae, Alloherpesviridae, Herpesviridae, Malacoherpesviridae, Lipothrixviridae, Rudiviridae, Adenoviridae, Ampullaviridae, Ascoviridae, Asfaviridae, Baculoviridae, Bicaudaviridae, Clavaviridae, Corticoviridae, Fuselloviridae, Globuloviridae, Guttaviridae, Hytrosaviridae, Iridoviridae, Marseilleviridae, Mimiviridae, Nimaviridae, Pandoraviridae, Papillomaviridae, Phycodnaviridae, Plasmaviridae, Polydnaviruses, Polyomaviridae, Poxviridae, Sphaerolipoviridae, and Tectiviridae.

In some cases, the viral vector is obtained from a ssDNA virus of the family: Anelloviridae, Bacillariodnaviridae, Bidnaviridae, Circoviridae, Geminiviridae, Inoviridae, Microviridae, Nanoviridae, Parvoviridae, and Spiraviridae.

In some embodiments, the viral vector is obtained from a DNA virus that contains both ss and ds DNA regions. In some cases, the DNA virus is from the group pleolipoviruses. In some cases, the pleolipoviruses include Haloarcula hispanica pleomorphic virus 1, Halogeometricum pleomorphic virus 1, Halorubrum pleomorphic virus 1, Halorubrum pleomorphic virus 2, Halorubrum pleomorphic virus 3, and Halorubrum pleomorphic virus 6.

In some cases, the viral vector is obtained from a dsRNA virus of the family: Birnaviridae, Chrysoviridae, Cystoviridae, Endornaviridae, Hypoviridae, Megavirnaviridae, Partitiviridae, Picobirnaviridae, Reoviridae, Rotavirus and Totiviridae.

In some instances, the viral vector is obtained from a positive-sense ssRNA virus of the family: Alphaflexiviridae, Alphatetraviridae, Alvernaviridae, Arteriviridae, Astroviridae, Barnaviridae, Betaflexiviridae, Bromoviridae, Caliciviridae, Carmotetraviridae, Closteroviridae, Coronaviridae, Dicistroviridae, Flaviviridae, Gammaflexiviridae, Iflaviridae, Leviviridae, Luteoviridae, Marnaviridae, Mesoniviridae, Narnaviridae, Nodaviridae, Permutotetraviridae, Picornaviridae, Potyviridae, Roniviridae, Secoviridae, Togaviridae, Tombusviridae, Tymoviridae, and Virgaviridae.

In some cases, the viral vector is obtained from a negative-sense ssRNA virus of the family: Bornaviridae, Filoviridae, Paramyxoviridae, Rhabdoviridae, Nyamiviridae, Arenaviridae, Bunyaviridae, Ophioviridae, and Orthomyxoviridae.

In some instances, the viral vector is obtained from oncolytic DNA viruses that comprise capsid symmetry that is isocahedral or complex. In some cases, icosahedral oncolytic DNA viruses are naked or comprise an envelope. Exemplary families of oncolytic DNA viruses include the Adenoviridae (for example, Adenovirus, having a genome size of 36-38 kb), Herpesviridae (for example, HSV1, having a genome size of 120-200 kb) and Poxviridae (for example, Vaccinia virus and myxoma virus, having a genome size of 130-280 kb).

In some cases, the viral vector is obtained from oncolytic RNA viruses include those having icosahedral or helical capsid symmetry. In some cases, icosahedral oncolytic viruses are naked without envelope and include Reoviridae (for example, Reovirus, having a genome of 22-27 kb) and Picornaviridae (for example, Poliovirus, having a genome size of 7.2-8.4 kb). In other cases, helical oncolytic RNA viruses are enveloped and include Rhabdoviridae (for example, VSV, having genome size of 13-16 kb) and Paramyxoviridae (for example MV and NDV, having genome sizes of 16-20 kb).

Exemplary viral vectors include, but are not limited to, retroviral vectors, lentiviral vectors, adenoviral vectors, adeno-associated viral vectors, alphaviral vectors, herpes simplex virus vectors, vaccinia viral vectors, or chimeric viral vectors. In some embodiments, the viral vector is a lentiviral vector. In some embodiments, the lentiviral vector is pLKO.1 vector.

In some instances, a virus comprising one or more of the nucleic acid polymers or polypeptides described herein are generated using methods well known in the art. In some instances, the methods involve one or more transfection steps and one or more infection steps. In some instances, a cell line such as a mammalian cell line, an insect cell line, or a plant cell line is infected with a virus to produce one or more viruses. Exemplary mammalian cell lines include: 293A cell line, 293FT cell line, 293F cells, 293H cells, CHO DG44 cells, CHOS cells, CHO-K1 cells, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-InTm-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, T-REx™-HeLa cell line, 3T6, A549, A9, AtT-20, BALB/3T3, BHK-21, BHL-100, BT, Caco-2, Chang, Clone 9, Clone M-3, COS-1, COS-3, COS-7, CRFK, CV-1, D-17, Daudi, GH1, GH3, H9, HaK, HCT-15, HEp-2, HL-60, HT-1080, HT-29, HUVEC, I-10, IM-9, JEG-2, Jensen, K-562, KB, KG-1, L2, LLC-WRC 256, McCoy, MCF7, VERO, WI-38, WISH, XC, or Y-1. Exemplary insect cell lines include *Drosophila* S2 cells, Sf9 cells, Sf21 cells, High Five™ cells, or expresSF+® cells. Exemplary plant cell lines include algae cells such as for example *Phaeocystis pouchetii*.

In some embodiments, the vector comprising one or more of the nucleic acid polymer or polypeptide described herein is delivered through electroporation, chemical method, microinjection, gene gun, impalefection, hydrodynamics-based delivery, continuous infusion, or sonication. In some embodiments, the chemical method is lipofection.

In some embodiments, electroporation is a technique in which an electric field is applied to cells to increase the permeability of the cell membrane, allowing for the introduction of chemicals, drugs, or DNA into the cell.

In some embodiments, chemical method is a method of transfection that uses carrier molecules to overcome the cell-membrane barrier. In some instances, the chemical method is lipofection whereby genetic material is injected into a cell using liposomes.

In some embodiments, microinjection is the injection of genetic material into animal cells, tissues or embryos via a needle.

In some embodiments, gene gun is a device that injects cells with genetic information by shooting them with elemental particle of a heavy metal coated with plasmid DNA.

In some embodiments, impalefection is a method of gene delivery using nanomaterials.

In some embodiments, hydrodynamics-based delivery is the rapid injection of a relatively large volume of solution into a blood vessel to enhance the permeability to allow for the delivery of substance into cells. In some instances, the solution contains proteins, oligo nucleotides, DNA, RNA, or small molecules.

In some embodiments, continuous infusion is the uninterrupted administration of drugs, fluids or nutrients into a blood vessel.

In some embodiments, sonication is applying sound energy to agitate particles in a sample for purposes such as but not limited to disrupting or deactivating a biological material or fragmenting molecules of DNA.

In some embodiments, the nucleic acid polymer is delivered as an injection, such as an intramuscular, intratympanic, intravenous or subcutaneous injection, without the need of a viral delivery method or non-viral delivery methods such as electroporation, chemical method, microinjection, gene gun, impalefection, hydrodynamics-based delivery, continuous infusion, or sonication. In some instances, the vector as described above is delivered as an injection, such as an intramuscular, intratympanic, intravenous or subcutaneous injection, without the need of a viral delivery method or non-viral delivery methods such as electroporation, chemical method, microinjection, gene gun, impalefection, hydrodynamics-based delivery, continuous infusion, or sonication.

In some embodiments, the nucleic acid polymer and/or the vector described above further comprises a delivery vehicle. In some instances, the delivery vehicle comprises a lipid-based nanoparticle; a cationic cell penetrating peptide (CPP); or a linear or branched cationic polymer; or a bioconjugate, such as cholesterol, bile acid, lipid, peptide, polymer, protein, or an aptamer, which is conjugated to the nucleic acid polymer or polypeptide described herein for intracellular delivery. In some instances, additional delivery vehicles comprise glycopolymer, carbohydrate polymer, or lipid polymers such as cationic lipids or cationic lipid polymers.

Non-Natural TrkB or Trk C Agonists

Contemplated for use with the otic formulations and compositions described herein are non-natural agonists for TrkB or TrkC receptors. In some embodiments, suitable non-natural agonists for TrkB or TrkC receptors include antibodies, binding fragments, variants, and derivatives, thereof. In some embodiments, suitable non-natural agonists for TrkB or TrkC receptors include chemically modified analogs of neurotrophic agents. In some embodiments, suitable non-natural agonists for TrkB or TrkC receptors include chimeras of antibodies and naturally occurring neurotrophic agents. In some embodiments, suitable non-natural agonists for TrkB or TrkC receptors include chimeras of antibodies and chemically modified analogs of neurotrophic agents.

TrkB Receptor Agonist Antibody

TrkB is one of the most widely distributed neurotrophin receptors in the brain, whose expression is high in such areas as the neocortex, hippocampus, striatum, and brainstem. It is a multidomain transmembrane protein that consists of an extracellular ligand binding domain, a transmembrane region, and an intracellular tyrosine kinase domain. BDNF binding to TrkB induces autophosphorylation of TrkB, and, subsequently, phosphorylation of several mediator kinases, including extracellular signal regulated kinase [mitogen-activated protein kinase (MAPK)], phosphatidylinositol 3-kinase/Akt, phospholipase C-γ, and their downstream targets.

In some embodiments, the otic composition comprises a non-natural TrkB agonist. In some embodiments, non-natural TrkB agonists include agonist antibodies, fragments, variants, and derivatives, thereof. In some embodiments, suitable agonist antibodies are selective for TrkB and bind with affinities similar to or greater than naturally-occurring NT4 and BDNF polypeptides. In some embodiments, the non-natural TrkB agonist is antibody 1D7, TAM-163, 7F5, 11E1, 17D11, 19E12, 36D1, 38B8, 37D12, 19H8(1), 1F8, 23B8, 18H6, or 29D7. In some embodiments, the non-natural TrkB agonist is antibody 7F5, 17D11, or 11E1. In some embodiments, the non-natural TrkB agonist binds to domain 1 and domain 4 of the TrkB receptor. In some embodiments, the non-natural TrkB agonist is antibody 1D7. In some embodiments, the antibody 1D7 binds to TrkB receptor but does not bind to neurotrophic receptor p75$^{NTR}$. In some embodiments, the binding epitope of antibody 1D7 is located in domain 1 and domain 4 of TrkB receptor. In some embodiments, the antibody 1D7 recognizes a TrkB epitope on the TrkB receptor which does not overlap with the epitope recognized by naturally occurring neurotrophic agent BDNF.

In some embodiments, the non-natural TrkB agonist is antibody 29D7. In some embodiments, the non-natural TrkB agonist is antibody TAM-163. In some embodiments, the non-natural TrkB agonist is antibody 38B8. In some embodiments, the 38B8 antibody is produced by the hybridoma strain deposited under ATCC Deposit Number PTA-8766, as described in U.S. patent publication number 20100086997 (application Ser. No. 12/519,743). In some embodiments, the non-natural TrkB agonist is an antibody fragment comprising the complementarity determining regions (CDRs) of the agonist antibody 38B8. In some embodiments, the non-natural TrkB agonist is an antibody fragment comprising the complementarity determining regions (CDRs) of the antibody produced by the hybridoma strain deposited under ATCC Deposit Number PTA-8766.

In some embodiments, the non-natural TrkB agonist is an antibody that selectively binds to TrkB receptor. In some embodiments, the non-natural TrkB agonist is an antibody that does not bind to TrkA or TrkC receptors. In some embodiments, the non-natural TrkB agonist is an antibody that does not bind to the neurotrophic receptor p75$^{NTR}$.

In some embodiments, binding of a non-natural TrkB agonist to TrkB receptor results in increased levels of phosphorylated TrkB, phosphorylated MAPK, phosphorylated Akt, phosphorylated ERK1/2, and phosphorylated phospholipase C-γ. In some embodiments, binding of a non-natural TrkB agonist to TrkB receptor leads to improved neuronal survival. In some embodiments, administration of an otic composition comprising a non-natural TrkB agonist that binds to TrkB receptor leads to improved neuronal survival and treats or prevents an otic condition. In some embodiments, administration of an otic composition comprising a non-natural TrkB agonist that binds to TrkB receptor leads to improved neuronal survival and treats or prevents an otic condition that requires reconnection of afferent sensory fibers and repair of ribbon synapses. In some embodiments, administration of an otic composition comprising a non-natural TrkB agonist that binds to TrkB receptor treats or prevents presbycusis (age related hearing loss). In some embodiments, administration of an otic composition comprising a non-natural TrkB agonist that binds to TrkB receptor leads to improved neuronal survival and treats sensorineural hearing loss.

TrkB Receptor Agonist Compounds

In some embodiments, the otic formulation or composition comprises a TrkB agonist compound.

In some embodiments, the TrkB agonist is a compound selected from a group consisting of 7,8-Dihydroxyflavone, 7,8,3'-Trihydroxyflavone, 4'-Dimethylamino-7,8-dihydroxyflavone, Deoxygedunin, LM-22A4, TDP6, 3,7-Dihydroxyflavone, 3,7,8,2'-Tetrahydroxyflavone, 4'-Dimethylamino-7,8-dihydroxyflavone, 5,7,8-Trihydroxyflavone, 7,3'-Dihydroxyflavone, 7,8,2'-Trihydroxyflavone, N,N',N"Tris (2-hydroxyethyl)-1,3,5-benzenetricarboxamide, N-[2-(5-Hydroxy-1H-indol-3-yl)ethyl]-2-oxo-3-piperidinecarboxamide, N-acetylserotonin, and Amitryptiline. In some embodiments, administration of an otic formulation or composition comprising a TrkB agonist compound that binds to TrkB receptor leads to improved neuronal survival and treats or prevents an otic condition. In some embodiments, administration of an otic formulation or composition comprising a TrkB agonist compound that binds to TrkB receptor leads to improved neuronal survival and treats or prevents an otic condition that requires repair of ribbon synapses. In some embodiments, administration of an otic formulation or composition comprising a TrkB agonist compound that binds to TrkB receptor treats or prevents presbycusis (age related hearing loss). In some embodiments, administration of an otic formulation or composition comprising a TrkB agonist compound that binds to TrkB receptor leads to improved neuronal survival and treats sensorineural hearing loss.

TrkC Receptor Agonist Antibody

TrkC is a transmembrane receptor with intrinsic tyrosine kinase catalytic activity that triggers "positive" signaling cascades that activate mediators phospho-AKT, phospho-Erk, and phospho-PLC-γ. In the inner ear, activation of TrkC receptors promotes growth of sensory neurons and their afferent fibers during development and helps to establish appropriate connections with hair cells through ribbon synapses that are important for inner ear function. Following noise trauma in the adult, TrkC receptor activation restores afferent fiber growth and reestablishment of ribbon synapses.

In some embodiments, the otic formulation or composition comprises non-natural TrkC agonists. In some embodiments, non-natural TrkC agonists include agonist antibodies, fragments, variants, and derivatives, thereof. In some embodiments, suitable agonist antibodies are selective for TrkC and bind with affinities similar to or greater than naturally-occurring neurotrophic agent NT3. In some embodiments, the non-natural TrkC agonist is an antibody that selectively binds to TrkC receptor. In some embodiments, the non-natural TrkC agonist is an antibody that does not bind to TrkA or TrkB receptors. In some embodiments, the non-natural TrkC agonist is an antibody that does not bind to the neurotrophic receptor p75$^{NTR}$. In some embodiments, the non-natural TrkC agonist binds to the full length TrkC receptor. In some instances, the non-natural TrkC agonist does not bind to the truncated TrkC receptor, TrkC.T1. In some embodiments, the non-natural TrkC agonist is a small molecule. In some embodiments, the non-natural TrkC agonist is a small molecule that does not bind to the truncated TrkC receptor, TrkC.T1. In some embodiments, the non-natural TrkC agonist is a small molecule that binds only to the full length TrkC receptor.

In some embodiments, the non-natural TrkC agonist is antibody 2B7, A5, 6.1.2, 6.4.1, 2345, 2349, 2.5.1, 2344, 2248, 2250, 2253, or 2256. In some embodiments, the non-natural TrkC agonist is antibody A5, or antibody 2B7.

In some embodiments, the non-natural TrkC agonist is antibody 2B7, as described in U.S. patent publication number 20140004119 (application Ser. No. 13/820,715). In some embodiments, the 2B7 antibody binds to full length TrkC. In some embodiments, the 2B7 antibody does not bind to the truncated TrkC receptor, TrkC.T1. In some embodiments, the 2B7 antibody binds to one or more specific epitopes near the juxtamembrane region of human TrkC. In some embodiments, the 2B7 antibody binds specifically to the region between the transmembrane domain and the D5 domain of human, rat or mouse TrkC. In some embodiments, the binding epitope for the 2B7 antibody is the sequence ESTDNFILFDEVSPTPPI (SEQ ID NO. 110), of TrkC. In some embodiments, the 2B7 antibody does not bind to TrkA, TrkB, or $p75^{NTR}$. In some embodiments, the antibody 2B7 is produced by the hybridoma having ATCC patent deposit designation 090310-02, said fragments, portions, variants or derivatives binding specifically to the same epitope as the monoclonal antibody. In some embodiments, the 2B7 antibody comprises complementarity-determining regions (CDRs) and/or hypervariable domains of an antibody produced by a hybridoma having ATCC patent deposit designation 090310-02. In some embodiments, the monoclonal antibody produced by the hybridoma having ATCC patent deposit designation 090310-02 or antigen-binding fragments, portions, variants or derivatives thereof is humanized, veneered, or chimeric.

In some embodiments, the non-natural TrkC agonist is A5 antibody. The antibody A5 corresponds to the antibody A5 described in European patent publication no. EP2402756 (application serial number EP 11183081.6). In some embodiments, the A5 antibody binds to the TrkC receptor. In some embodiments, the A5 antibody binds to one or more binding epitopes of the TrkC receptor. In some embodiments, the A5 antibody comprises a light chain that is encoded by a polynucleotide that is produced by a host cell with a deposit number of ATCC No. PTA-5682. In some embodiments, the A5 antibody comprises a heavy chain that is encoded by a polynucleotide that is produced by a host cell with a deposit number of ATCC No. PTA-5683. In some embodiments the A5 antibody comprises, (a) antibody A5; (b) a fragment or a region of the antibody A5; (c) a light chain of the antibody A5 (SEQ ID NO. 8); (d) a heavy chain of the antibody A5 (SEQ ID NO. 9); (d) one or more variable region(s) from a light chain and/or a heavy chain of the antibody A5; (e) one or more CDR(s) (one, two, three, four, five or six CDRs) of antibody A5 and (f) an antibody comprising any one of (b) through (e). In some embodiments, the A5 antibody is of any one or more of (a) through (e). In some embodiments, A5 antibody further comprises the human heavy chain IgG2a constant region containing the following mutations: A330P331 to S330S331 (amino acid numbering with reference to the wildtype IgG2a sequence; see Eur. J. Immunol. (1999) 29:2613-2624); and the human light chain kappa constant region.

In some embodiments, the non-natural TrkC agonist is a human antibody selected from the group consisting of 6.1.2 (PTA-2148), 6.4.1 (PTA-2150), 2345 (PTA-2146), 2349 (PTA-2153), 2.5.1 (PTA-2151) and 2344 (PTA-2144). In some embodiments, the non-natural TrkC agonist is a murine antibody selected from a group consisting of 2248 (PTA-2147), 2250 (PTA-2149), 2253 (PTA-2145) and 2256 (PTA-2152). The antibodies 6.1.2 (PTA-2148), 6.4.1 (PTA-2150), 2345 (PTA-2146), 2349 (PTA-2153), 2.5.1 (PTA-2151), 2344 (PTA-2144), of 2248 (PTA-2147), 2250 (PTA-2149), 2253 (PTA-2145), and 2256 (PTA-2152) correspond to the antibodies 6.1.2 (PTA-2148), 6.4.1 (PTA-2150), 2345 (PTA-2146), 2349 (PTA-2153), 2.5.1 (PTA-2151), 2344 (PTA-2144), of 2248 (PTA-2147), 2250 (PTA-2149), 2253 (PTA-2145), and 2256 (PTA-2152) described in U.S. Pat. No. 7,384,632, which is incorporated by reference herein in its entirety. In some embodiments, the non-natural TrkC agonist is a human or murine antibody selected from the group consisting of 6.1.2 (PTA-2148), 6.4.1 (PTA-2150), 2345 (PTA-2146), 2349 (PTA-2153), 2.5.1 (PTA-2151), 2344 (PTA-2144), of 2248 (PTA-2147), 2250 (PTA-2149), 2253 (PTA-2145), and 2256 (PTA-2152), which recognizes and binds to an epitope on the D5 domain of TrkC receptor. In some embodiments, the non-natural TrkC agonist is a human or murine antibody selected from the group consisting of 6.1.2 (PTA-2148), 6.4.1 (PTA-2150), 2345 (PTA-2146), 2349 (PTA-2153), 2.5.1 (PTA-2151), 2344 (PTA-2144), of 2248 (PTA-2147), 2250 (PTA-2149), 2253 (PTA-2145), and 2256 (PTA-2152), which does not recognize or bind to any epitope on the TrkA or TrkB receptors. In some embodiments, the non-natural TrkC agonist is a human or murine antibody selected from the group consisting of 6.1.2 (PTA-2148), 6.4.1 (PTA-2150), 2345 (PTA-2146), 2349 (PTA-2153), 2.5.1 (PTA-2151), 2344 (PTA-2144), of 2248 (PTA-2147), 2250 (PTA-2149), 2253 (PTA-2145), and 2256 (PTA-2152), which recognizes and binds epitopes on the D5 and D4 domains of TrkC receptor.

In some embodiments, the antibodies described herein are produced by hybridoma strains as outlined in Table 1.

TABLE 1

Hybridoma strains for producing TrkB or TrkC agonists

| Antibody | Antibody ATCC Deposit Number |
|---|---|
| 38B8 | PTA-8766 |
| 2B7 | 090310-02 |
| A5, light chain | PTA-5682 |
| A5, heavy chain | PTA-5683 |
| 6.1.2 | PTA-2148 |
| 6.4.1 | PTA-2150 |
| 2345 | PTA-2146 |
| 2349 | PTA-2153 |
| 2.5.1 | PTA-2151 |
| 2344 | PTA-2144 |
| 2248 | PTA-2147 |
| 2250 | PTA-2149 |
| 2253 | PTA-2145 |
| 2256 | PTA-2152 |

In some embodiments, the antibodies described herein have amino acid sequences as listed in Table 2

TABLE 2

SEQ ID NOs. corresponding to TrkB or TrkC agonist antibodies and their binding fragments thereof

| SEQ ID NO. | Description |
|---|---|
| 110 | ESTDNFILFDEVSPTPPI, binding epitope for antibody 2B7, on TrkC receptor |
| 111 | a CDR1 of antibody A5 of the formula GYTFTSYXaaXaaH, wherein Xaa at position 8 is R or W, and Xaa at position 9 is I, L, R, or M |
| 112 | a CDR2 of antibody A5 of the formula EIYPSNXaaRTNYNEKFXaaS, wherein Xaa at position 7 is A, T, S, or G; and Xaa at position 16 is K or E |
| 113 | a CDR3 of antibody A5 of the formula KYYYGNXaaXaaRSWYFDV, wherein Xaa at position 7 is T or S; wherein Xaa at position 8 is R, Q, K, S, or Y |
| 114 | GYTFTSYWMH, a CDR of antibody A5 |
| 115 | EIYPSNGRTNYNEKFK, a CDR of antibody A5 |
| 116 | KYYYGNSYRSWYFDV, a CDR of antibody A5 |
| 117 | Light chain of antibody A5<br>DIQMTQSPSSLSASVGDRVTITCRASESIDNYGISFLAWYQQKPGKAPKLLIYAASNRGSGVPSRFSGSGSGTDFT<br>FTISSLQPEDIATYYCQQSKTVPRTFGQGTKLEIKRTVAAPSVFIFPPSDEQLKSGTASVVCLLNNFYPREAKVQW<br>KVDNALQSGNSQESVTEQDSKDSTYSLSSTLTLSKADYEKHKVYACEATHQGLSSPVTKSFNRGEC |
| 118 | Heavy chain of antibody A5<br>QVQLVQSGAEVKKPGASVKVSCKASGYTFTSYRIHWVRQAPGQGLEWMGETYPSNARTNYNEKFKSRVTMTRDTST<br>STVYMELSSLRSEDTAVYYCARKYYYGNTRRSWYFDVWGQGTTVTVSSASTKGPSVFPLAPCSRSTSESTAALGCL<br>VKDYFPEPVTVSWNSGALTSGVHTFPAVLQSSGLYSLSSVVTVPSSNFGTQTYTCNVDHKPSNTKVDKTVERKCCV<br>ECPPCPAPPVAGPSVFLFPPKPKDTLMISRTPEVTCVVVDVSHEDPEVQFNWYVDGVEVHNAKTKPREEQFNSTFR<br>VVSVLTVVHQDWLNGKEYKCKVSNKGLPSSIEKTISKTKGQPREPQVYTLPPSREEMTKNQVSLTCLVKGFYPSDI<br>AVEWESNGQPENNYKTTPPMLDSDGSFFLYSKLTVDKSRWQQGNVFSCSVMHEALHNHYTQKSLSLSPGK |

Neurotrophic Agents

In some embodiments, the TrkB or TrkC agonist is a neurotrophic agent. In some embodiments, the TrkB or TrkC agonist is a neurotrophic agent that selectively binds to TrkB receptor. In some embodiments, the TrkB or TrkC agonist is a neurotrophic agent that does not bind to TrkA or TrkC receptors. In some embodiments, the TrkB or TrkC agonist is a neurotrophic agent that does not bind to the neurotrophic receptor p75$^{NTR}$. In some embodiments, the TrkB agonist is a neurotrophic agent that does not bind to the neurotrophic receptor p75NTR In some embodiments, a neurotrophic agent is an agent that promotes the growth of tissue and/or neurons and their processes and connections and/or hair cells of the auris. In some embodiments, a neurotrophic agent is an agent that promotes the survival of neurons and their processes and connections and otic hair cells, and/or the growth of neurons and their processes and connections and otic hair cells. In some embodiments, the neurotrophic agent which promotes the survival of otic hair cells is a growth factor. In some embodiments, the growth factor is a neurotroph. In certain instances, neurotrophs are growth factors which prevent cell death, prevent cell damage, repair damaged neurons and their processes and connections and otic hair cells, and/or induce differentiation in progenitor cells. In some embodiments, the neurotroph is brain-derived neurotrophic factor (BDNF), ciliary neurotrophic factor (CNTF), glial cell-line derived neurotrophic factor (GDNF), neurotrophin-3, neurotrophin-4, and/or combinations thereof. In some embodiments, the growth factor is a fibroblast growth factor (FGF), an insulin-like growth factor (IGF), an epidermal growth factor (EGF), a platlet-derived growth factor (PGF) and/or agonists thereof. In some embodiments, the growth factor is an agonist of the fibroblast growth factor (FGF) receptor, the insulin-like growth factor (IGF) receptor, the epidermal growth factor (EGF) receptor, and/or the platlet-derived growth factor. In some embodiments, the growth factor is hepatocyte growth factor.

In some embodiments, the neurotrophic agent is BDNF. In some embodiments, the neurotrophic agent is GDNF. In certain instances, BDNF and GDNF are neurotrophic agents that promote the survival of existing neurons and their processes and connections (e.g. spiral ganglion neurons), and otic hair cells by repairing damaged cells, inhibiting the production of ROS, and/or inhibiting cell death. In some embodiments, the neurotrophic agent also promotes the differentiation of neural and otic hair cell progenitors. Further, in some embodiments, the neurotrophic agent protects the Cranial Nerve VIII from degeneration. In some embodiments, the neurotrophic agent BDNF is administered in conjunction with fibroblast growth factor.

In some embodiments, the neurotrophic agent is neurotrophin-3. In some embodiments, neurotrophin-3 promotes the survival of existing neurons and their processes and connections and otic hair cells, and promotes the differentiation of neural and otic hair cell progenitors. Further, in some embodiments, neurotrophin-3 protects the VIII nerve from degeneration.

In some embodiments, the neurotrophic agent is CNTF. In some embodiments, CNTF promotes the synthesis of neurotransmitters and the growth of neuritis. In some embodiments, CNTF is administered in conjunction with BDNF.

In some embodiments, the neurotrophic agent is GDNF. Further, in some embodiments, cells treated with exogenous GDNF have higher survival rates after trauma than untreated cells.

In some embodiments, the neurotrophic agent is an epidermal growth factor (EGF). In some embodiments, the EGF is heregulin (HRG). In some embodiments, HRG stimulates the proliferation of utricular sensory epithelium. In some embodiments, HRG-binding receptors are found in the vestibular and auditory sensory epithelium.

In some embodiments, the neurotrophic agent is an insulin-like growth factor (IGF). In some embodiments, the IGF is IGF-1. In some embodiments, the IGF-1 is mecasermin. In some embodiments, IGF-1 attenuates the damage induced by exposure to an aminoglycoside. In some embodiments, IGF-1 stimulates the differentiation and/or maturation of cochlear ganglion cells.

In some embodiments, the FGF receptor agonist is FGF-2. In some embodiments, the IGF receptor agonist is IGF-1. Both the FGF and IGF receptors are found in the cells comprising the utricle epithelium.

In some embodiments, the neurotrophic agent is hepatocyte growth factor (HGF). In some embodiments, HGF protects cochlear hair cells from noise-induced damage and reduces noise-exposure-caused ABR threshold shifts.

In some embodiments, the neurotrophic agents are selected from Erythropoietin (EPO), Granulocyte-colony stimulating factor (G-CSF), Granulocyte-macrophage colony stimulating factor (GM-CSF), Growth differentiation factor-9 (GDF9), Insulin-like growth factor (IGF), Myostatin (GDF-8), Platelet-derived growth factor (PDGF), Thrombopoietin (TPO), Transforming growth factor alpha (TGF-α), Transforming growth factor beta (TGF-β), Vascular endothelial growth factor (VEGF) or combinations thereof.

In some embodiments, the neurotrophic agents described herein are chemically modified analogs of naturally occurring neurotrophic agents. Exemplary chemical modifications include, but are not limited to, phosphorylation or sulfurylation at serine, threonine, or tyrosine residues, by incorporating unnatural amino acids, by incorporating heavy amino acids, by incorporating D-amino acids, by biotinylation, by cyclisations, by acylation, by dimethylation, by amidation, by derivatization, by conjugation to carrier proteins, or by branching of peptide.

Neurotrophin Mutants

In some embodiments, the otic formulation or composition comprises a non-natural Trk receptor agonist, wherein the agonist is a non-natural neurotrophic agent comprising an amino acid modification. In some embodiments, the non-natural neurotrophic agent is derived from nerve growth factor (NGF), neurotrophin-3 (NT-3), neurotrophin-4 (NT-4), neurotrophin-5 (NT-5), brain-derived neurotrophic factor (BDNF), a pan-neurotrophin, or a chimeric neurotrophin. In some embodiments, the non-natural neurotrophic agent comprises at most 1 amino acid modification, at most 2 amino acid modifications, at most 3 amino acid modifications, at most 4 amino acid modifications, at most 5 amino acid modifications, at most 6 amino acid modifications, at most 7 amino acid modifications, at most 8 amino acid modifications, at most 9 amino acid modifications, at most 10 amino acid modifications, or another suitable number of modifications.

In some embodiments, a non-natural neurotrophic agent described herein is derived from NGF. In some embodiments, the non-natural neurotrophic agent is derived from a pro-form of NGF. In some instances, the non-natural neurotrophic agent is derived from a mature form of NGF. In additional instances, the non-natural neurotrophic agent is derived from an isoform of NGF. In some embodiments, the non-natural neurotrophic agent further comprises at most 1 amino acid modification, at most 2 amino acid modifications, at most 3 amino acid modifications, at most 4 amino acid modifications, at most 5 amino acid modifications, at most 6 amino acid modifications, at most 7 amino acid modifications, at most 8 amino acid modifications, at most 9 amino acid modifications, at most 10 amino acid modifications, or another suitable number of modifications. In some instances, the modification is a mutation. For example, the mutation is a mutation to at least one of a non-polar residue, a polar residue, and a charged residue. In some cases, the mutation is a conservative mutation, a semi-conservative mutation, or a non-conservative mutation.

In some embodiments, a non-natural neurotrophic agent described herein is derived from neurotrophin-3 (NT-3). In some embodiments, the non-natural neurotrophic agent is derived from a pro-form of NT-3. In some instances, the non-natural neurotrophic agent is derived from a mature form of NT-3. In other instances, the non-natural neurotrophic agent is derived from an isoform of NT-3. In some embodiments, the non-natural neurotrophic agent further comprises at most 1 amino acid modification, at most 2 amino acid modifications, at most 3 amino acid modifications, at most 4 amino acid modifications, at most 5 amino acid modifications, at most 6 amino acid modifications, at most 7 amino acid modifications, at most 8 amino acid modifications, at most 9 amino acid modifications, at most 10 amino acid modifications, or another suitable number of modifications. In some instances, the modification is a mutation. For example, the mutation is a mutation to at least one of a non-polar residue, a polar residue, and a charged residue. In some cases, the mutation is a conservative mutation, a semi-conservative mutation, or a non-conservative mutation.

In some embodiments, the non-natural neurotrophic agent comprises a naturally occurring neurotrophin-3 with one or more mutations which comprises NT-$3_{(1-119)}$ or NT-$3_{(1-117)}$ as described in PCT Pub. No. WO9803546.

In some embodiments, the non-natural neurotrophic agent comprises a naturally occurring neurotrophin-3 with one or more mutations that comprises a NT-3 mutant described in Urfer, et al., "The binding epitopes of neurotrophin-3 to its receptors TrkC and gp75 and the design of a multifunctional human neurotrophin," EMBO 13(24): 5896-5909 (1994).

In some embodiments, a non-natural neurotrophic agent described herein is derived from neurotrophin-4 (NT-4). In some embodiments, the non-natural neurotrophic agent is derived from a pro-form of NT-4. In some instances, the non-natural neurotrophic agent is derived from a mature form of NT-4. In other instances, the non-natural neurotrophic agent is derived from an isoform of NT-4. In some embodiments, the non-natural neurotrophic agent further comprises at most 1 amino acid modification, at most 2 amino acid modifications, at most 3 amino acid modifications, at most 4 amino acid modifications, at most 5 amino acid modifications, at most 6 amino acid modifications, at most 7 amino acid modifications, at most 8 amino acid modifications, at most 9 amino acid modifications, at most 10 amino acid modifications, or another suitable number of modifications. In some instances, the modification is a mutation. For example, the mutation is a mutation to at least one of a non-polar residue, a polar residue, and a charged residue. In some cases, the mutation is a conservative mutation, a semi-conservative mutation, or a non-conservative mutation.

In some embodiments, a non-natural neurotrophic agent described herein is derived from a neurotrophin-5 (NT-5). In some embodiments, the non-natural neurotrophic agent is derived from a pro-form of NT-5. In some instances, the non-natural neurotrophic agent is derived from a mature form of NT-5. In other instances, the non-natural neurotrophic agent is derived from an isoform of NT-5. In some embodiments, the non-natural neurotrophic agent further comprises at most 1 amino acid modification, at most 2 amino acid modifications, at most 3 amino acid modifications, at most 4 amino acid modifications, at most 5 amino acid modifications, at most 6 amino acid modifications, at most 7 amino acid modifications, at most 8 amino acid modifications, at most 9 amino acid modifications, at most 10 amino acid modifications, or another suitable number of modifications. In some instances, the modification is a mutation. For example, the mutation is a mutation to at least one of a non-polar residue, a polar residue, and a charged residue. In some cases, the mutation is a conservative mutation, a semi-conservative mutation, or a non-conservative mutation.

In some embodiments, a non-natural neurotrophic agent described herein is derived from BDNF. In some embodiments, the non-natural neurotrophic agent is derived from a pro-form of BDNF. In some instances, the non-natural neurotrophic agent is derived from a mature form of BDNF. In other instances, the non-natural neurotrophic agent is derived from an isoform of BDNF. In some embodiments, the non-natural neurotrophic agent further comprises at most 1 amino acid modification, at most 2 amino acid modifications, at most 3 amino acid modifications, at most 4 amino acid modifications, at most 5 amino acid modifications, at most 6 amino acid modifications, at most 7 amino acid modifications, at most 8 amino acid modifications, at most 9 amino acid modifications, at most 10 amino acid modifications, or another suitable number of modifications. In some instances, the modification is a mutation. For example, the mutation is a mutation to at least one of a non-polar residue, a polar residue, and a charged residue. In some cases, the mutation is a conservative mutation, a semi-conservative mutation, or a non-conservative mutation.

In some embodiments, a non-natural neurotrophic agent described herein is a pan-neurotrophin (PNT). In some instances, a pan-neurotrophin is a synthetic trophic factor engineered by combining one or more domains of nerve growth factor (NGF), brain-derived neurotrophic factor (BDNF), and/or neurotrophin 3 (NT-3). In some instances, a pan-neurotrophin recognizes or binds to TrkA, TrkB, and TrkC receptors. In some instances, a pan-neurotrophin is pan-neurotrophin 1 (PNT-1), described in Ilag, et al., "Pan-neurotrophin 1: A genetically engineered neurotrophic factor displaying multiple specificities in peripheral neurons in vitro and in vivo," PNAS 92: 607-611 (1995). In some cases, a pan-neurotrophin is a pan-neurotrophin described in Ibanez, et al, "An extended surface of binding to Trk tyrosine kinase receptors in NGF and BDNF allows the engineering of a multifunctional pan-neurotrophin," EMBO 12(6): 2281-2293 (1993).

In some embodiments, the non-natural neurotrophic agent comprises PNT. In some embodiments, the non-natural neurotrophic agent further comprises at most 1 amino acid modification, at most 2 amino acid modifications, at most 3 amino acid modifications, at most 4 amino acid modifications, at most 5 amino acid modifications, at most 6 amino acid modifications, at most 7 amino acid modifications, at most 8 amino acid modifications, at most 9 amino acid modifications, at most 10 amino acid modifications, or another suitable number of modifications. In some instances, the modification is a mutation. For example, the mutation is a mutation to at least one of a non-polar residue, a polar residue, and a charged residue. In some cases, the mutation is a conservative mutation, a semi-conservative mutation, or a non-conservative mutation.

In some instances, a non-natural neurotrophic agent described herein is a chimeric neurotrophin. In some instances, the chimeric neurotrophin recognizes two or more Trk receptors. In some embodiments, the non-natural neurotrophic agent is a chimera of NGF and BDNF. In some cases, a chimeric neurotrophic agent comprises, for example, one or more domains of nerve growth factor (NGF) and one or more domains of brain-derived neurotrophic factor (BDNF). In some instances, the non-natural neurotrophic agent is a chimera of NGF and BDNF described in Ibáñez, et al., "Chimeric molecules with multiple neurotrophic activities reveal structural elements determining the specificities of NGF and BDNF," EMBO 10(8): 2105-2110, 1991; Ryden, et al., "Functional analysis of mutant neurotrophins deficient in low-affinity binding reveals a role for p75LNGFR in NT-4 signalling," EMBO 14(9): 1979-1990, 1995; and/or Ibáñez, et al., "An extended surface of binding to Trk tyrosine kinase receptors in NGF and BDNF allows the engineering of a multifunctional pan-neurotrophin," EMBO 12(6): 2281-2293, 1993.

In some embodiments, a chimeric neurotrophin described herein is a neurotrophin that binds to two or more Trk receptors. In some embodiments, the chimeric neurotrophin binds to two or more Trk receptors and further has a reduced binding affinity to $p75^{NTR}$. In some embodiments, the chimeric neurotrophin binds to two or more Trk receptors but does not bind to $p75^{NTR}$.

In some embodiments, the chimeric neurotrophin is further characterized with an improved neural or non-neural survival, differentiation, growth, regeneration compared to a non-chimeric neurotrophin, or a combination thereof, relative to a non-chimeric neurotrophin. In some embodiments, the chimeric neurotrophin has an increased binding affinity, efficacy, potency, or a combination thereof, relative to a non-chimeric neurotrophin.

In some embodiments, the non-natural neutrophic agent is a chimera of NGF and BDNF. In some embodiments, the non-natural neurotrophic agent further comprises at most 1 amino acid modification, at most 2 amino acid modifications, at most 3 amino acid modifications, at most 4 amino acid modifications, at most 5 amino acid modifications, at most 6 amino acid modifications, at most 7 amino acid modifications, at most 8 amino acid modifications, at most 9 amino acid modifications, at most 10 amino acid modifications, or another suitable number of modifications. In some embodiments, the non-natural neurotrophic agent further comprises at least 1 amino acid modification, at least 2 amino acid modifications, at least 3 amino acid modifications, at least 4 amino acid modifications, at least 5 amino acid modifications, at least 6 amino acid modifications, at least 7 amino acid modifications, at least 8 amino acid modifications, at least 9 amino acid modifications, at least 10 amino acid modifications, or another suitable number of modifications. In some instances, the modification is a mutation. For example, the mutation is a mutation to at least one of a non-polar residue, a polar residue, and a charged residue. In some cases, the mutation is a conservative mutation, a semi-conservative mutation, or a non-conservative mutation.

In some embodiments, a modification disclosed herein comprises a mutation to a natural or unnatural amino acid residue. For example, in some cases, the modification comprises a mutation of an amino acid residue to an alternative natural amino acid residue, for example a mutation of an arginine to an alanine. In some instances, the modification comprises a mutation of an amino acid residue to an unnatural amino acid residue, for example, a mutation of a cysteine to a seleno-L-cystine.

As used herein, an amino acid residue is a molecule containing both an amino group and a carboxyl group. Suitable amino acids for use in a non-natural neurotrophic agent described herein include, without limitation, both the D- and L-isomers of the naturally-occurring amino acids, as well as non-naturally occurring amino acids prepared by organic synthesis or other metabolic routes. In some instances, an amino acid is an α-amino acid, β-amino acid, natural amino acid, non-natural amino acid, or amino acid analog. A naturally occurring amino acid comprises any one of the twenty amino acids commonly found in peptides synthesized in nature, and known by the one letter abbreviations A, R, N, C, D, Q, E, G, H, I, L, K, M, F, P, S, T, W, Y, and V.

In some instances, unnatural amino acid residues comprise a racemic mixture of amino acid analogs. For example, in some instances, the D isomer of the amino acid analog is used. In some cases, the L isomer of the amino acid analog is used. In some instances, the amino acid analog comprises chiral centers that are in the R or S configuration. Sometimes, the amino group(s) of a β-amino acid analog is substituted with a protecting group, e.g., tert-butyloxycarbonyl (BOC group), 9-fluorenylmethyloxycarbonyl (FMOC), tosyl, and the like. Sometimes, the carboxylic acid functional group of a β-amino acid analog is protected, e.g., as its ester derivative. In some cases, the salt of the amino acid analog is used.

In some instances, the modification comprises a mutation to a hydrophobic or nonpolar amino acid residue. In some cases, a hydrophobic or nonpolar amino acid includes small hydrophobic amino acids and large hydrophobic amino acids. Exemplary small hydrophobic amino acids include glycine, alanine, proline, and analogs thereof. Exemplary large hydrophobic amino acids include valine, leucine, isoleucine, phenylalanine, methionine, tryptophan, and analogs thereof. In some instances, a non-natural neurotrophic agent described herein comprises a mutation to a small hydrophobic amino acid (e.g., a mutation to glycine, alanine, proline, and analogs thereof). In some instances, a non-natural neurotrophic agent described herein comprises a mutation to a large hydrophobic amino acid (e.g., a mutation to valine, leucine, isoleucine, phenylalanine, methionine, tryptophan, and analogs thereof).

In some instances, the modification comprises a mutation to a polar amino acid residue. In some cases, the polar amino acid comprises serine, threonine, asparagine, glutamine, cysteine, tyrosine, and analogs thereof. In some instances, a non-natural neurotrophic agent described herein comprises a mutation to a polar amino acid residue (e.g., a mutation to serine, threonine, asparagine, glutamine, cysteine, tyrosine, and analogs thereof).

In additional instances, the modification comprises a mutation to a charged amino acid residue. In some cases, charged amino acids include lysine, arginine, histidine, aspartate, glutamate, or analog thereof. In some instances, a non-natural neurotrophic agent described herein comprises a mutation to a charged amino acid residue (e.g., a mutation to lysine, arginine, histidine, aspartate, glutamate, or analog thereof).

In some embodiments, a non-natural neurotrophic agent described herein comprise a modification to a non-essential amino acid. In some instances, a non-essential amino acid residue is a residue that is altered from the wild-type sequence of a polypeptide without abolishing or substantially altering its essential biological or biochemical activity (e.g., receptor binding or activation). In some cases, a non-natural neurotrophic agent provided herein comprises an essential amino acid. In some cases, an essential amino acid residue is a residue that, when altered from the wild-type sequence of the polypeptide, results in abolishing or substantially abolishing the polypeptide's essential biological or biochemical activity.

In some embodiments, a non-natural neurotrophic agent described herein comprises a conservative amino acid substitution. In some cases, a conservative amino acid substitution is one in which the amino acid residue is replaced with an amino acid residue having a similar side chain. Families of amino acid residues having similar side chains have been defined in the art. These families include, for example, amino acids with basic side chains (e.g., K, R, H), acidic side chains (e.g., D, E), uncharged polar side chains (e.g., G, N, Q, S, T, Y, C), nonpolar side chains (e.g., A, V, L, I, P, F, M, W), beta-branched side chains (e.g., T, V, I) and aromatic side chains (e.g., Y, F, W, H). Thus, a predicted nonessential amino acid residue in a polypeptide, for example, is replaced with another amino acid residue from the same side chain family. Other examples of acceptable substitutions include substitutions based on isosteric considerations (e.g., norleucine for methionine) or other properties (e.g., 2-thienylalanine for phenylalanine or 6-Cl-tryptophan for tryptophan).

In some embodiments, a non-natural neurotrophic agent described herein comprises a semi-conservative amino acid substitution. In some embodiments, the semi-conservative amino acid substitution involves substitution between amino acids within a same side chain family or amino acids in which the side chains share similar steric confirmations.

In some embodiments, a non-natural neurotrophic agent described herein comprises a non-conservative amino acid substitution. In some embodiments, the non-conservative amino acid substitution involves substitution between amino acids within a different side chain family.

In some embodiments, a non-natural neurotrophic agent described herein comprises a modification that is introduced by mutagenesis. In some embodiments, the mutagenesis is random. In some embodiments, mutagenesis is non-random. An example of non-random mutagenesis is site-directed mutagenesis. In some embodiments, the site-directed mutagenesis utilizes cassette mutagenesis, PCR-site-directed mutagenesis, whole plasmid mutagenesis, Kunkel's method, or in vivo site-directed mutagenesis method. In some instances, the mutagenesis is alanine screening mutagenesis.

In some embodiments, the non-natural neurotrophic agents described herein are chemically modified analogs of naturally occurring neurotrophic agents. Exemplary chemical modifications include, but are not limited to, phosphorylation or sulfurylation at serine, threonine, or tyrosine residues; by incorporating unnatural amino acids; by incorporating heavy amino acids; by incorporating D-amino acids; by biotinylation; by cyclisations; by acylation; by dimethylation; by amidation; by derivatization; by conjugation to carrier proteins; or by branching of peptide.

WNT Modulators

In some embodiments, active agents compatible with the formulations described herein include agents that modulate re-growth of damaged auris sensory hair cells. In some instances, modulation of the WNT pathway promotes morphogenesis and/or re-growth of damaged auris sensory hair cells. WNT signalling proteins include protein products encoded by genes such as WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11, or WNT16. In some embodiments, the therapeutic agent is a modulator of WNT. Modulators of the WNT pathway include, and are not limited to, 2-amino-4-[3,4-(methylenedioxy)benzyl-amino]-6-(3-methoxyphenyl) pyrimidine, the signalling molecule Cerberus, or the like. In some embodiments, the therapeutic agent is 2 amino-4-[3,4-(methylenedioxy)benzyl-amino]-6-(3-methoxyphenyl)pyrimidine, the signalling molecule Cerberus, or the like.

Protein Kinase C Beta Modulators

In some embodiments, the otic formulations or compositions described herein further comprise a protein kinase C modulator. In some embodiments, the protein kinase C modulator is a protein kinase C activator. In some embodiments, the protein kinase C activator is a protein kinase C beta activator. Examples of protein kinase C activators include but are not limited to byrostatins, such as byrostatin-1, and bryostatin analogs, such as picolog. In some embodiments, the protein kinase C activator is a byrostatin or a brystostatin analog. In some instances, a bryostatin or a bryostatin analog is any one of the compounds described in DeChristopher, et al., Oncotarget. (2012) Jan.; 3(1):58-66 and Sun, M.-K. and Alkon, D. L. CNS Drug Reviews, (2006) 12: 1-8. In some instances, any one of the neurotrophins described herein is used in combination with the protein kinase C activator. Examples of suitable neurotrophins contemplated for use include but are not limited to BDNF and NT-3.

Other Therapeutic Agents

In some embodiments, the otic formulations or compositions described herein further comprise a SK2 channel (calcium-activated potassium channel) activator. In some embodiments, the otic formulations or compositions described herein further comprise a SK2 channel (calcium-activated potassium channel) inhibitor. In some embodiments, the otic formulations or compositions described herein further comprise a BK channel (calcium-activated potassium channel) activator. In some embodiments, the otic formulations or compositions described herein further comprise a BK channel (calcium-activated potassium channel) inhibitor. In some embodiments, the otic formulations or compositions described herein further comprise a dopamine receptor agonist. In some embodiments, the otic formulations or compositions described herein further comprise a sphingosine-1-phosphate receptor modulator.

In some embodiments, the otic formulations or compositions described herein further comprise a stemness driver and a differentiation inhibitor. In some embodiments, the stemness driver is a Wnt agonist, or a Wnt agonist derivative. In some embodiments, the stemness driver is BML-284 or SKL2001. In some embodiments, the differentiation inhibitor is a notch agonist, notch agonist derivative, a histone deacetylase (HDAC) inhibitor, or an HDAC inhibitor derivative. In some embodiments, the differentiation inhibitor is valproic acid, suberoylanilide hydroxamic acid (SAHA), or Tubastatin A. In some embodiments, the otic formulations or compositions further comprising a stemness driver and a differentiation inhibitor are used for the treatment of chronic hearing loss.

In some embodiments, the otic formulations or compositions described herein further comprise Keyzilen® (AM-101). In some embodiments, the otic formulations or compositions described herein further comprise (S)-Ketamine hydrochloride. In some embodiments, the otic formulations or compositions described herein further comprise an N-Methyl-D-Aspartate (NMDA) receptor antagonist. In some embodiments, the otic formulations or compositions described herein further comprise AM-111. In some embodiments, the otic formulations or compositions described herein further comprise Brimapitide. In some embodiments, the otic formulations or compositions described herein further comprise D-JNKI-1 (D-stereoisomer of c-Jun N-Terminal Kinase Inhibitor 1), an inhibitor of the JNK stress kinase coupled to an intracellular transporter. In some embodiments, the otic formulations or compositions described herein further comprise AM-125. In some embodiments, the otic formulations or compositions described herein further comprise Betahistine. In some embodiments, the otic formulations or compositions further comprising Keyzilen® (AM-101) are used for the treatment of tinnitus. In some embodiments, the otic formulations or compositions further comprising AM-111 are used for the treatment of acute inner ear (sensorineural) hearing loss. In some embodiments, the otic formulations or compositions further comprising AM-125 are used for the treatment of Ménière's disease. Examples of additional compounds that are used therapeutic agents in some embodiments include but are not limited to those disclosed in U.S. Pat. Nos. 8,268,866, 8,507,525, and U.S. Patent Application Publication Nos. 2005214338, 2006063802, 2010254907, and 20140017172, which are incorporated by reference.

In some embodiments, the otic formulations or compositions described herein further comprise a repulsive guidance molecule a (RGMa) inhibitor or an inhibitor of neogenin. RGMa is a glycosylphosphatidylinositol-anchored protein that induces growth cone collapse and plays a role in axonal pathfinding. Neogenin is a cell surface protein that is a member of the immunoglobulin superfamily and is the receptor for RGMa. In some embodiments, the otic formulations or compositions described herein further comprise a histone deacetylase (HDAC) inhibitor. In some embodiments, the histone deacetylase (HDAC) inhibitor is sodium butyrate, trichostatin A, a hydroxamic acid, a cyclic tetrapeptide, trapoxin B, a depsipeptide, a benzamide, an electrophilic ketone, ROMIDEPSIN, an aliphatic acid compounds, phenylbutyrate, valproic acid, hydroxamic acids, vorinostat (SAHA), belinostat (PXD101), LAQ824, panobinostat (LBH589), entinostat (MS275), C1994, and mocetinostat (MGCD0103). In some embodiments, the otic formulations or compositions described herein further comprise a histone methyltransferase (HMT) inhibitor. In some embodiments, the otic formulations or compositions described herein further comprise a DNA methyltransferase (DNMT) inhibitor. In some embodiments, the DNA methyltransferase (DNMT) inhibitor is azacytidine, decitabine, zebularine (1-(-D-ribofuranosyl)-1,2-dihydropyrimidin-2-one), procainamide, procaine, (−)-epigallocatechin-3-gallate, MG98, hydralazine, RG108, or chlorogenic acid. In some embodiments, the otic formulations or compositions described herein further comprise a proteasome inhibitor. In some embodiments, a proteasome inhibitor is bortezomib, carfilzomib, NPI-0052, MLN9708, CEP-18770, or ONX0912. In some embodiments, the otic formulations or compositions described herein further comprise an EZH2/HMT inhibitor. In some embodiments, the EZH2/HMT inhibitor is deazaneplanocin A; GSK J1; GSK126; EPZ005687; E7438; Ell; EPZ-6438; GSK343; BIX-01294, UNC0638, BRD4770, EPZ004777, AZ505 or PDB 4e47. In some embodiments, the otic formulations or compositions described herein further comprise a compound to increase Atoh-1 expression. In some embodiments, the compound to increase Atoh-1 expression is a compound disclosed in PCT/US2009/033569. In some embodiments, the compound to increase Atoh-1 expression is a compound of the following formula:

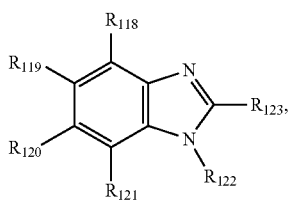

wherein the substituents are those as described in PCT/US2009/033569. Examples of additional compounds are used therapeutic agents in some embodiments include but are not limited to those disclosed in PCT/US2015/028035, PCT/US2011/053868, and PCT/US2015/043976, which are incorporated by reference. In some embodiments, the otic formulations or compositions are used for the treatment of drug-induced ototoxicity, tinnitus, noise-induced hearing loss, genetic hearing loss, or presbycusis.

In some embodiments, the otic formulations or compositions described herein further comprise a notch inhibitor. In some embodiments, the notch inhibitor is 4,4,4-trifluoro—((2S)-1-((9-methoxy-3,3-dimethyl-5-oxo-2,3,5,6-tetrahydro-1H-berizo[fjpyrrolo[1,2-a]azepm-6-yl)arnmo)-1-oxopropan-2-yl)butanamide. In some embodiments, the otic formulations or compositions described herein further comprise a gamma secretase inhibitor. In some embodiments, the gamma secretase inhibitor is LY411575 (N-2((2S)-2-(3,5-difluorophenyl)-2-hydroxyethanoyl)-N 1-((7S)-5-methyl-6-0X0-6, 7-dihydro-5H-dibenzo[b,d]azepin-7-yl)-1-alaninamide; R04929097; DAPT (N-[(3,5-Difluorophenyl)acetyl]-L-alanyl-2-phenyl]glycine-1, 1-dimethylethyl ester); L-685458 ((5S)-(t-Butoxycarbonylamino)-6-phenyl-(4R) hydroxy-(2R)benzylhexanoyl)-L-leu-L-phe-amide); BMS-708163 (Avagacestat); BMS-299897 (2-[(1R)-1-[[(4-Chlorophenyl)sulfonyl](2,5-difluorophenyl)amino]ethyl-5-fluorobenzenebutanoic acid); M-0752; YO-01027; MDL28170 (Sigma); LY41 1575 (N-2((2S)-2-(3,5-difluorophenyl)-2-hydroxyethanoyl)-N 1-((7S)-5-methyl-6-oxo-6,7-dihydro-5H-dibenzo[b,d]azepin-7-yl)-1-alaninamide); ELN-46719 (2-hydroxy-valeric acid amide analog of LY41 1575; PF-03084014 ((S)-2-((S)-5,7-difluoro-1,2,3,4-tetrahydronaphthalen-3-ylamino)-N-(1-(2-methyl-1-(neopentylamino)propan-2-yl)-1H-imidazol-4-yl)pentanamide); Compound E ((2S)-2-{[(3,5-Difluorophenyl)acetyl]amino}-N-[(3S)-1-methyl-2-oxo-5-phenyl-2,3-dihydro-1H-1,4-benzodiazepin-3-yl]propanamide; or Semagacestat (LY450139; (2S)-2-hydroxy-3-methyl-N-((1 S)-1-methyl-2-{[(1 S)-3-methyl-2-oxo-2,3,4,5-tetrahydro-1H-3-benzazepin-1-yl] amino}-2-oxoethyl)butanamide). In some embodiments, the gamma secretase inhibitor is LY41 1575 (N-2((2S)-2-(3,5-difluorophenyl)-2-hydroxyethanoyl)-N 1-((7S)-5-methyl-6-0X0-6, 7-dihydro-5H-dibenzo[b,d]azepin-7-yl)-1-alaninamide. Examples of additional compounds that are used therapeutic agents in some embodiments include but are not limited to those disclosed in PCT/US2016/040612 and PCT/US2013/058446, which are incorporated by reference. In some embodiments, the otic formulations or compositions are used for the treatment of hearing loss.

In some embodiments, the otic formulations or compositions described herein further comprise CGF166, an adenovirus delivering an atonal 1 gene (Atoh1) to induce the differentiation of sensory cells in the inner ear. In some embodiments, the adenovirus uses a GV11 gene delivery system, featuring an E1-, E3-, E4-deleted human adenovector serotype 5 (Ad5) backbone. In some embodiments, the otic formulations or compositions are used for the treatment of hearing loss and vestibular dysfunction.

In some embodiments, the otic formulations or compositions described herein further comprise ebselen. Ebselen is a small molecule mimic and inducer of glutathione peroxidase (GPx), which is the dominant catalytic antioxidant enzyme in the cochlea. In some embodiments, the otic formulations or compositions described herein further comprise SPI-1005, an oral formulation of ebselen. In some embodiments, the otic formulations or compositions described herein further comprise ebselen and allopurinol. In some embodiments, the otic formulations or compositions described herein further comprise SPI-3005, an oral formulation of ebselen and allopurinol. In some embodiments, the otic formulations or compositions described herein further comprise siRNA inhibiting p27Kip1. In some embodiments, the otic formulations or compositions described herein further comprise SPI-5557, which contains a siRNA inhibiting p27Kip1. In some embodiments, the otic formulations or compositions further comprising ebselen are used for the treatment of noise-induced hearing loss (NIHL), mild to moderate hearing loss, or Meniere's disease. In some embodiments, the otic formulations or compositions further comprising ebselen and allopurinol are used for the treatment of chemotherapy-induced ototoxicity or aminoglycoside-induced ototoxicity. In some embodiments, the otic formulations or compositions further comprising siRNA inhibiting p27Kip1 are used for the treatment of severe to profound hearing loss.

In some embodiments, the otic formulations or compositions described herein further comprise AF243 (dendrogenin). AF243 (dendrogenin) is small molecule sterol derivative that induces neuron survival and neuronal differentiation of the following formula shown below:

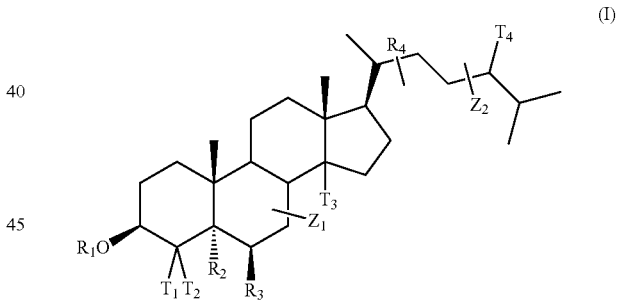

(I)

with the substituents as defined in PCT/FR2015/000164. In some embodiments, the otic formulations or compositions described herein further comprise a small molecule sterol derivative with the formula shown above with the substituents as defined in PCT/FR2015/000164. In some embodiments, the otic formulations or compositions described herein further comprise 6β-[3-(4-aminobutylamino) propylamino]-cholestane-1,5a-diol). In some embodiments, the otic formulations or compositions described herein further comprise 6β-[2-(1H-imidazol-4-yl)-ethylamino]-cholestane-33,5a-diol. In some embodiments, the otic formulations or compositions described herein further comprise 6β-[3-(4-aminobutylamino) propylamino]-cholestane-3,5-diol. In some embodiments, the otic formulations or compositions described herein further comprise 6β-[2-(1-imidazol-4-yl)-ethylamino]-cholestane-5,5-diol. Examples of additional compounds are used therapeutic agents in some embodiments include but are not limited to those disclosed in PCT/FR2015/000164, which is incorporated by reference. In some embodiments, the otic formulations or compositions further comprising AF243 (dendrogenin) or small molecule sterol derivatives are used for the treatment of hearing loss.

In some embodiments, the otic formulations or compositions described herein further comprise latanoprost. In some embodiments, the otic formulations or compositions described herein further comprise a FP prostanoid receptor agonist. In some embodiments, the otic formulations or compositions described herein further comprise a prostaglandin PGF2α analogue. In some embodiments, the otic formulations or compositions further comprising latanoprost or a prostaglandin PGF2α analogue are used for the treatment of Meniere's disease and noise-induced tinnitus. Examples of additional compounds that are used as therapeutic agents in some embodiments include but are not limited to those disclosed in PCT/SE2007/050075 and PCT/SE2002/000062, which are incorporated by reference.

In some embodiments, the otic formulations or compositions described herein further comprise a β-carboline, such as AC-102. In some embodiments, the otic formulations or compositions described herein further comprise 9-methyl-β-carboline. In some embodiments, the otic formulations or compositions further comprising a β-carboline are used for the treatment of acute hearing loss, tinnitus, ototoxicity, age-related hearing loss. Examples of additional β-carbolines include but are not limited to those disclosed in PCT/EP2014/070840, which is incorporated by reference.

In some embodiments, the otic formulations or compositions described herein further comprise a peroxisome proliferator-activated receptor-gamma (PPARγ) agonist. In some embodiments, the otic formulations or compositions described herein further comprise pioglitazone (STR001). In some embodiments, the otic formulations or compositions further comprising pioglitazone are used for the treatment of sensorineural hearing loss (SSHL) caused by cochlear implantation surgery or noise-induced hearing loss. Examples of additional peroxisome proliferator-activated receptor-gamma (PPARγ) agonists include but are not limited to those disclosed in PCT/EP2016/052787, which is incorporated by reference.

In some embodiments, the otic formulations or compositions described herein further comprise a Wnt agonist and a notch inhibitor. In some embodiments, the otic formulations or compositions further comprising a Wnt agonist and a notch inhibitor are used for the treatment of hearing loss. Examples of Wnt agonists and notch inhibitors include but are not limited to those disclosed in Proc Natl Acad Sci USA. 2012 May 22; 109(21):8167-72, and Proc Natl Acad Sci USA. 2015 Jan. 6; 112(1):166-71, which are incorporated by reference.

In some embodiments, the otic formulations or compositions described herein further comprise an α-amino-3-hydroxy-5-methyl-4-isoxazolepropionic acid (AMPA) glutamate-positive allosteric modulator, such as PF-04958242. In some embodiments, the otic formulations or compositions further comprising an α-amino-3-hydroxy-5-methyl-4-isoxazolepropionic acid glutamate-positive allosteric modulator are used for the treatment of age-related sensorineural hearing loss.

In some embodiments, the otic formulations or compositions described herein further comprise a Wnt inhibitor and a TGFβ inhibitor. In some embodiments, the Wnt inhibitor is DKK1. In some embodiments, the TGFβ inhibitor is selective inhibitor of Smad3 (SIS3). In some embodiments, the otic formulations or compositions further comprising a Wnt inhibitor and a TGFβ inhibitor are used for the treatment of hearing loss and balance problems. Examples of Wnt inhibitors and TGFβ inhibitor include but are not limited to those disclosed in US20160032240.

In some embodiments, the otic formulations or compositions described herein further comprise sodium thiosulphate. In some embodiments, the otic formulations or compositions described herein further comprise a chemical reducing agent. In some embodiments, the otic formulations or compositions further comprising sodium thiosulphate are used for the treatment of chemotherapy-induced ototoxicity.

In some embodiments, the otic formulations or compositions described herein further comprise ancrod. Ancrod is a fibrinogenase; lowers fibrinogen in blood, reducing blood viscosity. In some embodiments, the otic formulations or compositions described herein further comprise a biologically active substance from the venom of the Malayan Pit Viper (Calloselasma rhodostoma). In some embodiments, the otic formulations or compositions further comprising ancrod are used for the treatment of sudden sensorineural hearing loss (SSHL) and tinnitus. Examples of uses of ancrod include but are not limited to those disclosed in DE201220100195, which is incorporated by reference.

In some embodiments, the otic formulations or compositions described herein further comprise D-methionine. D-methionine is micronutrient with direct and indirect anti-oxidant effects. In some embodiments, the otic formulations or compositions further comprising D-methionine are used for the treatment of noise-induced hearing loss.

In some embodiments, the otic formulations or compositions described herein further comprise a combination of HPN-07 and N-acetylcysteine (NAC) or NHPN-1010. In some embodiments, HPN-07 is a structural analog of 4-OHPBN, disodium 2,4-disulfophenyl-N-tert-butylnitrone. In some embodiments, NAC is a thiol-containing amino acid derivative that acts as a ROS scavenger and a substrate for glutathione (GSH), the major endogenous antioxidant produced by cells. In some embodiments, the otic formulations or compositions further comprising a combination of HPN-07 and N-acetylcysteine (NAC) are used for the treatment of noise-induced hearing loss or cisplatin-induced hearing loss.

In some embodiments, the otic formulations or compositions described herein further comprise an antagonist of histamine type 4 receptors (H4R). In some embodiments, the antagonist of histamine type 4 receptors (H4R) is SENS-111. In some embodiments, the otic formulations or compositions described herein further comprise a 5-HT3 antagonist. In some embodiments, the 5-HT3 antagonist is setron (SENS-218). In some embodiments, the otic formulations or compositions described herein further comprise a small molecule to reduce accumulation of cisplatin. In some embodiments, the small molecule to reduce accumulation of cisplatin is SENS-300. In some embodiments, the small molecule to reduce accumulation of cisplatin is a compound of the following formula:

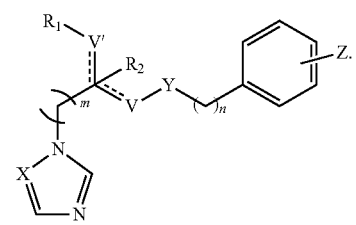

with the substituents as defined in PCT/EP2015/067999. In some embodiments, the otic formulations or compositions described herein further comprise R-azasetron besylate. In some embodiments, the otic formulations or compositions further comprising an antagonist of histamine type 4 receptors (H4R), such as SENS-111, are used for the treatment of vertigo. In some embodiments, the otic formulations or compositions further comprising a 5-HT3 antagonist, such as SENS-218, are used for the treatment of vestibular lesions. In some embodiments, the otic formulations or compositions further comprising a small molecule to reduce accumulation of cisplatin, such as SENS-300, are used for the treatment of drug-induced ototoxicity. In some embodiments, the otic formulations or compositions further comprising R-azasetron besylate are used for the treatment of sudden sensorineural hearing loss. Examples of similar compounds include but are not limited to those disclosed in PCT/EP2015/067999, PCT/EP2013/061205, PCT/EP2013/053557, and PCT/EP2013/061936, which are incorporated by reference.

In some embodiments, the otic formulations or compositions described herein further comprise a Kv3 potassium channel modulator. In some embodiments, the Kv3 potassium channel modulator is AUT00063. In some embodiments, the Kv3 potassium channel modulator is a hydantoin derivative, a triazole, or an imidazolidinedione derivative. In some embodiments, the otic formulations or compositions further comprising a Kv3 potassium channel modulator are used for the treatment of age-related hearing loss, tinnitus, noise-induced hearing loss, cochlear implant users or schizophrenia Amount of Therapeutic Agent In some embodiments, the otic formulation or composition comprises between about 0.001% to about 40% by weight of the therapeutic agent, or pharmaceutically acceptable prodrug or salt thereof. In some embodiments, the otic formulation or composition comprises between about 0.001% to about 30% by weight of the therapeutic agent, or pharmaceutically acceptable prodrug or salt thereof. In some embodiments, the otic formulation or composition comprises between about 0.001% to about 20% by weight of the therapeutic agent, or pharmaceutically acceptable prodrug or salt thereof. In some embodiments, the otic formulation or composition comprises between about 0.001% to about 15% by weight of the therapeutic agent, or pharmaceutically acceptable prodrug or salt thereof. In some embodiments, the otic formulation or composition comprises between about 0.001% to about 10% by weight of the therapeutic agent, or pharmaceutically acceptable prodrug or salt thereof. In some embodiments, the otic formulation or composition comprises between about 0.001% to about 7% by weight of the therapeutic agent, or pharmaceutically acceptable prodrug or salt thereof. In some embodiments, the otic formulation or composition comprises between about 0.001% to about 5% by weight of the therapeutic agent, or pharmaceutically acceptable prodrug or salt thereof. In some embodiments, the otic formulation or composition comprises between about 0.001% to about 3% by weight of the therapeutic agent, or pharmaceutically acceptable prodrug or salt thereof. In some embodiments, the otic formulation or composition comprises between about 0.001% to about 2% by weight of the therapeutic agent, or pharmaceutically acceptable prodrug or salt thereof. In some embodiments, the otic formulation or composition comprises between about 0.001% to about 1% by weight of the therapeutic agent, or pharmaceutically acceptable prodrug or salt thereof.

In some embodiments, the otic formulation or composition comprises between about 0.01% to about 40% by weight of the therapeutic agent, or pharmaceutically acceptable prodrug or salt thereof. In some embodiments, the otic formulation or composition comprises between about 0.01% to about 30% by weight of the therapeutic agent, or pharmaceutically acceptable prodrug or salt thereof. In some embodiments, the otic formulation or composition comprises between about 0.01% to about 20% by weight of the therapeutic agent, or pharmaceutically acceptable prodrug or salt thereof. In some embodiments, the otic formulation or composition comprises between about 0.01% to about 15% by weight of the therapeutic agent, or pharmaceutically acceptable prodrug or salt thereof. In some embodiments, the otic formulation or composition comprises between about 0.01% to about 10% by weight of the therapeutic agent, or pharmaceutically acceptable prodrug or salt thereof. In some embodiments, the otic formulation or composition comprises between about 0.01% to about 7% by weight of the therapeutic agent, or pharmaceutically acceptable prodrug or salt thereof. In some embodiments, the otic formulation or composition comprises between about 0.01% to about 5% by weight of the therapeutic agent, or pharmaceutically acceptable prodrug or salt thereof. In some embodiments, the otic formulation or composition comprises between about 0.01% to about 3% by weight of the therapeutic agent, or pharmaceutically acceptable prodrug or salt thereof. In some embodiments, the otic formulation or composition comprises between about 0.01% to about 2% by weight of the therapeutic agent, or pharmaceutically acceptable prodrug or salt thereof. In some embodiments, the otic formulation or composition comprises between about 0.01% to about 1% by weight of the therapeutic agent, or pharmaceutically acceptable prodrug or salt thereof.

In some embodiments, the otic formulation or composition comprises between about 0.1% to about 40% by weight of the therapeutic agent, or pharmaceutically acceptable prodrug or salt thereof. In some embodiments, the otic formulation or composition comprises between about 0.1% to about 30% by weight of the therapeutic agent, or pharmaceutically acceptable prodrug or salt thereof. In some embodiments, the otic formulation or composition comprises between about 0.10% to about 20% by weight of the therapeutic agent, or pharmaceutically acceptable prodrug or salt thereof. In some embodiments, the otic formulation or composition comprises between about 0.10% to about 15% by weight of the therapeutic agent, or pharmaceutically acceptable prodrug or salt thereof. In some embodiments, the otic formulation or composition comprises between about 0.10% to about 10% by weight of the therapeutic agent, or pharmaceutically acceptable prodrug or salt thereof. In some embodiments, the otic formulation or composition comprises between about 0.10% to about 7% by weight of the therapeutic agent, or pharmaceutically acceptable prodrug or salt thereof. In some embodiments, the otic formulation or composition comprises between about 0.10% to about 5% by weight of the therapeutic agent, or pharmaceutically acceptable prodrug or salt thereof. In some embodiments, the otic formulation or composition comprises between about 0.10% to about 3% by weight of the therapeutic agent, or pharmaceutically acceptable prodrug or salt thereof. In some embodiments, the otic formulation or composition comprises between about 0.10% to about 2% by weight of the therapeutic agent, or pharmaceutically acceptable prodrug or salt thereof. In some embodiments, the otic formulation or composition comprises between about 0.10% to about 1% by weight of the therapeutic agent, or pharmaceutically acceptable prodrug or salt thereof.

In some embodiments, the otic formulation or composition comprises between about 1% to about 40% by weight of the therapeutic agent, or pharmaceutically acceptable prodrug or salt thereof. In some embodiments, the otic formulation or composition comprises between about 1% to about 30% by weight of the therapeutic agent, or pharmaceutically acceptable prodrug or salt thereof. In some embodiments, the otic formulation or composition comprises between about 1% to about 20% by weight of the therapeutic agent, or pharmaceutically acceptable prodrug or salt thereof. In some embodiments, the otic formulation or composition comprises between about 1% to about 15% by weight of the therapeutic agent, or pharmaceutically acceptable prodrug or salt thereof. In some embodiments, the otic formulation or composition comprises between about 1% to about 10% by weight of the therapeutic agent, or pharmaceutically acceptable prodrug or salt thereof. In some embodiments, the otic formulation or composition comprises between about 1% to about 7% by weight of the therapeutic agent, or pharmaceutically acceptable prodrug or salt thereof. In some embodiments, the otic formulation or composition comprises between about 1% to about 5% by weight of the therapeutic agent, or pharmaceutically acceptable prodrug or salt thereof. In some embodiments, the otic formulation or composition comprises between about 1% to about 3% by weight of the therapeutic agent, or pharmaceutically acceptable prodrug or salt thereof. In some embodiments, the otic formulation or composition comprises between about 1% to about 2% by weight of the therapeutic agent, or pharmaceutically acceptable prodrug or salt thereof.

In some embodiments, the otic formulation or composition comprises about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2% about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, or about 40% by weight of the therapeutic agent, or pharmaceutically acceptable prodrug or salt thereof. In some embodiments, the otic formulation or composition comprises about 0.01% by weight of the therapeutic agent, or pharmaceutically acceptable prodrug or salt thereof. In some embodiments, the otic formulation or composition comprises about 0.02% by weight of the therapeutic agent, or pharmaceutically acceptable prodrug or salt thereof. In some embodiments, the otic formulation or composition comprises about 0.03% by weight of the therapeutic agent, or pharmaceutically acceptable prodrug or salt thereof. In some embodiments, the otic formulation or composition comprises about 0.04% by weight of the therapeutic agent, or pharmaceutically acceptable prodrug or salt thereof. In some embodiments, the otic formulation or composition comprises about 0.05% by weight of the therapeutic agent, or pharmaceutically acceptable prodrug or salt thereof. In some embodiments, the otic formulation or composition comprises about 0.06% by weight of the therapeutic agent, or pharmaceutically acceptable prodrug or salt thereof. In some embodiments, the otic formulation or composition comprises about 0.07% by weight of the therapeutic agent, or pharmaceutically acceptable prodrug or salt thereof. In some embodiments, the otic formulation or composition comprises about 0.08% by weight of the therapeutic agent, or pharmaceutically acceptable prodrug or salt thereof. In some embodiments, the otic formulation or composition comprises about 0.09% by weight of the therapeutic agent, or pharmaceutically acceptable prodrug or salt thereof. In some embodiments, the otic formulation or composition comprises about 0.1% by weight of the therapeutic agent, or pharmaceutically acceptable prodrug or salt thereof. In some embodiments, the otic formulation or composition comprises about 0.2% by weight of the therapeutic agent, or pharmaceutically acceptable prodrug or salt thereof. In some embodiments, the otic formulation or composition comprises about 0.3% by weight of the therapeutic agent, or pharmaceutically acceptable prodrug or salt thereof. In some embodiments, the otic formulation or composition comprises about 0.4% by weight of the therapeutic agent, or pharmaceutically acceptable prodrug or salt thereof. In some embodiments, the otic formulation or composition comprises about 0.5% by weight of the therapeutic agent, or pharmaceutically acceptable prodrug or salt thereof. In some embodiments, the otic formulation or composition comprises about 0.6% by weight of the therapeutic agent, or pharmaceutically acceptable prodrug or salt thereof. In some embodiments, the otic formulation or composition comprises about 0.7% by weight of the therapeutic agent, or pharmaceutically acceptable prodrug or salt thereof. In some embodiments, the otic formulation or composition comprises about 0.8% by weight of the therapeutic agent, or pharmaceutically acceptable prodrug or salt thereof. In some embodiments, the otic formulation or composition comprises about 0.9% by weight of the therapeutic agent, or pharmaceutically acceptable prodrug or salt thereof. In some embodiments, the otic formulation or composition comprises about 1% by weight of the therapeutic agent, or pharmaceutically acceptable prodrug or salt thereof. In some embodiments, the otic formulation or composition comprises about 2% by weight of the therapeutic agent, or pharmaceutically acceptable prodrug or salt thereof. In some embodiments, the otic formulation or composition comprises about 3% by weight of the therapeutic agent, or pharmaceutically acceptable prodrug or salt thereof. In some embodiments, the otic formulation or composition comprises about 4% by weight of the therapeutic agent, or pharmaceutically acceptable prodrug or salt thereof. In some embodiments, the otic formulation or composition comprises about 5% by weight of the therapeutic agent, or pharmaceutically acceptable prodrug or salt thereof. In some embodiments, the otic formulation or composition comprises about 6% by weight of the therapeutic agent, or pharmaceutically acceptable prodrug or salt thereof. In some embodiments, the otic formulation or composition comprises about 7% by weight of the therapeutic agent, or pharmaceutically acceptable prodrug or salt thereof. In some embodiments, the otic formulation or composition comprises about 8% by weight of the therapeutic agent, or pharmaceutically acceptable prodrug or salt thereof. In some embodiments, the otic formulation or composition comprises about 9% by weight of the therapeutic agent, or pharmaceutically acceptable prodrug or salt thereof. In some embodiments, the otic formulation or composition comprises about 10% by weight of the therapeutic agent, or pharmaceutically acceptable prodrug or salt thereof. In some embodiments, the otic formulation or composition comprises about 11% by weight of the therapeutic agent, or pharmaceutically acceptable prodrug or salt thereof. In some embodiments, the otic formulation or composition comprises about 12% by weight of the therapeutic agent, or pharmaceutically acceptable prodrug or salt thereof. In some embodiments, the otic formulation or composition comprises about 13% by weight of the therapeutic agent, or pharmaceutically acceptable prodrug or salt thereof. In some embodiments, the otic formulation or composition comprises about 14% by weight of the therapeutic agent, or pharmaceutically acceptable prodrug or salt thereof. In some embodiments, the otic formulation or composition comprises about 15% by weight of the therapeutic agent, or pharmaceutically acceptable prodrug or salt thereof. In some embodiments, the otic formulation or composition comprises about 16% by weight of the therapeutic agent, or pharmaceutically acceptable prodrug or salt thereof. In some embodiments, the otic formulation or composition comprises about 17% by weight of the therapeutic agent, or pharmaceutically acceptable prodrug or salt thereof. In some embodiments, the otic formulation or composition comprises about 18% by weight of the therapeutic agent, or pharmaceutically acceptable prodrug or salt thereof. In some embodiments, the otic formulation or composition comprises about 19% by weight of the therapeutic agent, or pharmaceutically acceptable prodrug or salt thereof. In some embodiments, the otic formulation or composition comprises about 20% by weight of the therapeutic agent, or pharmaceutically acceptable prodrug or salt thereof.

Combination Therapy

In certain embodiments, any therapeutic agent, or otic agent (e.g., an immunomodulator or an auris pressure modulator), is administered in combination with one or more of any other otic active agent described herein. In some embodiments, a therapeutic agent (otic agent) is administered with an anti-emetic agent (e.g., when a balance disorder is accompanied by nausea). In some embodiments, a therapeutic agent (otic agent) is administered in combination with one or more otoprotectant (e.g., when the administration of a cytotoxic agent is accompanied by ototoxicity). In certain embodiments, a therapeutic agent (otic agent) is administered in combination with, for example, an anti-emetic, an antimicrobial agent, a nitric oxide synthase inhibitor, an antioxidant, a neurotransmitter reuptake inhibitor, an otoprotectant, a homeostasis modulator (e.g., ion/fluid (e.g., water) homeostasis modulator) or the like.

EAC Protectant

In some instances, an external auditory canal (EAC) protectant is used in combination with the otic formulations and compositions described herein. In some embodiments, the EAC protectant is an exocrine gland secreted agent or an antimicrobial agent.

Exocrine Gland Secreted Agents

Exocrine gland secretions and exocrine gland secreted agents are contemplated for use with the formulations disclosed herein. Accordingly, some embodiments incorporate the use of secreted agents that mimic the natural cerumen composition and/or exert antimicrobial properties.

Exocrine gland is classified into three categories, holocrine glands, merocrine (or eccrine) glands, and apocrine glands. Holocrine glands accumulate their secretions into each cell's cytoplasm and release the whole cell into the duct. Sebaceous gland is an example of a holocrine gland. Apocrine glands are sweat glands, with ceruminous gland as an example.

Sebum is the product secreted from the sebaceous gland. In some embodiments, sebum comprises triglycerides, wax esters, squalene, cholesterol esters, cholesterol, and fatty acids. In some embodiments, sebum comprises squalene, lanosterol and cholesterol. Squalene which is secreted as part of sebum serves as a precursor for all animal steroids including lanosterol and cholesterol. Squalene is produced via the mevalonate pathway which is responsible for the production of cholesterol and other isoprenoids. HMG-CoA (or 3-hydroxy-3-methylglutaryl-coenzyme A) reductase is the rate-controlling enzyme in the mevalonate pathway.

In some embodiments, the exocrine gland secreted agents comprise at least one of triglycerides, wax esters, squalene, cholesterol esters, cholesterol, and fatty acids. In some embodiments, the exocrine gland secreted agents comprise at least one of squalene, lanosterol and cholesterol.

Antimicrobial EAC Protectants

In some embodiments, the EAC protectant has antimicrobial properties. In some embodiments, the antimicrobial EAC protectants include lipids, proteins, and antimicrobial peptides (AMPs). In some embodiments, lipids include fatty acids, cholesterol, waxes, sterols, monoglycerides, diglycerides, triglycerides, and phospholipids. In some embodiments, fatty acids include free fatty acids (FFAs) and unsaturated fatty acids such as oleic acids and palmitoleic acids. In some embodiments, AMPs include hBD-1, hBD-2, hBD-3, and LL-37.

Anti-Emetic Agents/Central Nervous System Agents

Anti-Emetic agents are optionally used in combination with any otic formulations and compositions disclosed herein. Anti-emetic agents include antihistamines and central nervous agents, including anti-psychotic agents, barbiturates, benzodiazepines and phenothiazines. Other anti-emetic agents include the serotonin receptor antagonists, which include dolasetron, granisetron, ondansetron, tropisetron, palonosetron, and combinations thereof; dopamine antagonists, including domperidone, properidol, haloperidol, chlorpromazine, promethazine, prochlorperazine and combinations thereof; cannabinoids, including dronabinol, nabilone, sativex, and combinations thereof; anticholinergics, including scopolamine; and steroids, including dexamethasone, trimethobenzamine, emetrol, propofol, muscimol, and combinations thereof.

Optionally, central Nervous System agents and barbiturates are useful in the treatment of nausea and vomiting symptoms that accompany an autoimmune otic disorder. When used, an appropriate barbiturate and/or central nervous system agent is selected to relieve or ameliorate specific symptoms without possible side effects, including ototoxicity. Moreover, as discussed above, targeting of the drugs to the round window membrane of the auris interna reduces possible side effects and toxicity caused by systemic administration of these drugs. Barbiturates, which act as a central nervous system depressant, include allobarbital, alphenal, amobarbital, aprobarbital, barnexaclone, barbital, brallobarbital, butabarbital, butalbital, butallylonal, butobarbital, corvalol, crotylbarbital, cyclobarbital, cyclopal, ethallobarbital, febarbamate, heptabarbital, hexethal, hexobarbital, metharbital, methohexital, methylphenobarbital, narcobarbital, nealbarbital, pentobarbital, phenobarbital, primidone, probarbital, propallylonal, proxibarbital, reposal, secobarbital, sigmodal, sodium thiopental, talbutal, thialbarbital, thiamylal, thiobarbital, thiobutabarbital, tuinal, valofane, vinbarbital, vinylbital, and combinations thereof.

Other central nervous system agents which are optionally used in conjunction with the otic formulations disclosed herein include benzodiazepines or phenothiazines. Useful benzodiazepines include, but are not limited to diazepam, lorazepam, oxazepam, prazepam, alprazolam, bromazepam, chlordiazepoxide, clonazepam, clorazepate, brotizolam, estazolam, flunitrazepam, flurazepam, loprazolam, lormetazepam, midazolam, nimetazepam, nitrazepam, ternazepam, triazolam, and combinations thereof. Examples of phenothiazines include prochlorperazine, chlorpromazine, promazine, triflupromazine, levopromazine, methotrimepramazine, mesoridazine, thiroridazine, fluphenazine, perphenazine, flupentixol, trifluoperazine, and combinations thereof.

Antihistamines, or histamine antagonists, act to inhibit the release or action of histamine. Antihistamines that target the H1 receptor are useful in the alleviation or reduction of nausea and vomiting symptoms that are associated with AIED, other autoimmune disorders, as well as anti-inflammatory disorders. Accordingly, some embodiments incorporate the use of agents which modulate histamine receptors (e.g. the $H_1$ receptor, $H_2$ receptor, and/or the $H_3$ receptor).

Such antihistamines include, but are not limited to, meclizine, diphenhydramine, loratadine and quetiapine. Other antihistamines include mepyramine, piperoxan, antazoline, carbinoxamine, doxylamine, clemastine, dimenhydrinate, pheniramine, chlorphenamine, chlorpheniramine, dexchlorpheniramine, brompheniramine, triprolidine, cyclizine, chlorcyclizine, hydroxyzine, promethazine, alimemazine, trimeprazine, cyproheptadine, azatadine, ketotifen, oxatomide and combinations thereof.

In some embodiments, the $H_1$ receptor antagonist is meclizine hydrochloride. In some embodiments, the $H_1$ receptor antagonist is promethazine hydrochloride. In some embodiments, the $H_1$ receptor antagonist is dimenhydrinate. In some embodiments, the $H_1$ receptor antagonist is diphenhydramine. In some embodiments, the $H_1$ receptor antagonist is cinnarizine. In some embodiments, the $H_1$ receptor antagonist is hydroxyzine pamoate.

Antihistamines which target the $H_3$ receptor include, but are not limited to betahistine dihydrochloride.

Antimicrobial Agents

Antimicrobial agents are also contemplated as useful with the formulations and compositions disclosed herein. In some embodiments, the antimicrobial agent is as described herein.

Corticosteroids

Corticosteroids are also contemplated as useful with the formulations and compositions disclosed herein. In some embodiments, the corticosteroid is as described herein.

Otoprotectants

In some embodiments, any otic formulation or composition described herein (e.g. auris sensory cell modulating agent formulations disclosed herein) further comprise otoprotectants that reduce, inhibit or ameliorate the ototoxicity of agents such as chemotherapeutic agents and/or antibiotics as described herein, or reduce, inhibit or ameliorate the effects of other environmental factors, including excessive noise and the like. Examples of otoprotectants include, and are not limited to, thiols and/or thiol derivatives and/or pharmaceutically acceptable salts, or derivatives (e.g. prodrugs) thereof (e.g., D-methionine, L-methionine, ethionine, hydroxyl methionine, methioninol, amifostine, mesna (sodium 2-sulfanylethanesulfonate), a mixture of D and L methionine, normethionine, homomethionine, S-adenosyl-L-methionine), diethyldithiocarbamate, ebselen (2-phenyl-1, 2-benzisoselenazol-3(2H)-one), sodium thio sulfate, AM-111 (a cell permeable JNK inhibitor, (Laboratoires Auris SAS)), leucovorin, leucovorin calcium, dexrazoxane, piracetam, Oxiracetam, Aniracetam, Pramiracetam, Phenylpiracetam (Carphedon), Etiracetam, Levetiracetam, Nefiracetam, Nicoracetam, Rolziracetam, Nebracetam, Fasoracetam, Coluracetam, Dimiracetam, Brivaracetam, Seletracetam, Rolipramand or combinations thereof. Otoprotectants allow for the administration of chemotherapeutic agents and/or antibiotics at doses that are higher than maximal toxic doses; the chemotherapeutic agents and/or antibiotics would otherwise be administered at lower doses due to ototoxicity. Otoprotectants, when optionally administered by itself, also allow for the amelioration, reduction or elimination of the effect of environmental factors that contribute to loss of hearing and attendant effects, including but not limited to noise-induced hearing loss and tinnitus.

The amount of otoprotectant in any formulation described herein on a mole:mole basis in relation to the ototoxic chemotherapeutic agent (e.g. cis platin) and/or an ototoxic antibiotic (e.g. gentamicin) is in the range of from about 5:1 to about 200:1, from about 5:1 to about 100:1, or from about 5:1 to about 20:1. The amount of otoprotectant in any formulation described herein on a molar basis in relation to the ototoxic chemotherapeutic agent (e.g. cis platin) and/or an ototoxic antibiotic (e.g. gentamicin) is about 50:1, about 20:1 or about 10:1. Any the auris sensory cell modulating agent formulation described herein comprises from about 10 mg/mL to about 50 mg/mL, from about 20 mg/mL to about 30 mg/mL, or from about 25 mg/mL of otoprotectant.

Chemotherapeutic Agents

Chemotherapeutic agents are also contemplated for use with the formulations and compositions disclosed herein. Chemotherapeutic agents act by killing cancer cells or microorganisms, and include antineoplastic agents that target cancer or malignant cells. Some chemotherapeutic agents, either alone or in combination, are also ototoxic. For example, cisplatin is a known cochleotoxic agent. However, use of cisplatin in combination with antioxidants are protective and lessen the ototoxic effects of the chemotherapeutic agent. In some embodiments, the localized application of the cytotoxic drug lessens the ototoxic effects that might otherwise occur through systemic application through the use of lower amounts with maintained efficacy, or the use of targeted amounts for a shorter period of time. Accordingly, a skilled practitioner choosing a course of therapy for tumor growth will have the knowledge to avoid or combine an ototoxic compound, or to vary the amount or course of treatment to avoid or lessen ototoxic effects.

Chemotherapeutic agents that are used in combination with the formulations and compositions disclosed herein include, for example, but are not limited to adriamycin, imidazole carboxamide, cyclophosphamide, mechlorethamine, chlorambucil, melphalan, daunorubicin, doxorubicin, epirubicin, idarubicin, mitoxanthrone, valrubicin, paclitaxel, docetaxel, etoposide, teniposide, tafluposide, azacitidine, azathioprine, capecitabine, cytarabine, doxifluridine, fluorouracil, gemcitabine, mercaptopurine, methotrexate, tioguanine, bleomycin, carboplatin, cisplatin, oxaliplatin, all-trans retinoic acid, vinblastine, vincristine, vindesine, vinorelbine, and combinations thereof.

Homeostasis Modulators

Homeostasis modulators are contemplated as useful with the formulations and compositions described herein. Homeostasis modulators include ion and fluid (e.g. water) homeostasis modulators. In some instances, homeostasis modulators include Na/K-ATPase modulators, ENaC modulators, vasopressin receptor modulators, diuretics or the like as described herein.

Na/K ATPase Modulators

Na/K-ATPase modulators are contemplated for use with the formulations and compositions disclosed herein. Cochlear homeostasis is dependent on the electrolyte composition of the endolymph, which is regulated by an active exchange of $Na^+$ and $K^+$ via a ATPase. Examples of Na/K-

ATPase modulators include, and are not limited to, nimodipine (a sodium-potassium adenosine triphosphatase stimulator), ouabain, and furosemide.

Devices

Also contemplated herein are the use of devices for the delivery of the pharmaceutical formulations and compositions disclosed herein, or alternatively for the measurement or surveillance of the function of the auris formulations disclosed herein. For example, in one embodiment pumps, osmotic devices or other means of mechanically delivering pharmaceutical formulations and compositions are used for the delivery of the pharmaceutical formulations disclosed herein. Reservoir devices are optionally used with the pharmaceutical drug delivery units, and reside either internally along with the drug delivery unit, or externally of the auris structures.

Other embodiments contemplate the use of mechanical or imaging devices to monitor or survey the hearing, balance or other auris disorder. For example, magnetic resonance imaging (MRI) devices are specifically contemplated within the scope of the embodiments, wherein the MRI devices (for example, 3 Tesla MRI devices) are capable of evaluating Meniere Disease progression and subsequent treatment with the pharmaceutical formulations disclosed herein. See, Carfrae et al. Laryngoscope 118:501-505 (March 2008). Whole body scanners, or alternatively cranial scanners, are contemplated, as well as higher resolution (7 Tesla, 8 Tesla, 9.5 Tesla or 11 Tesla for humans) are optionally used in MRI scanning.

Visualization of Otic Formulations

Also provided herein in some embodiments are otic formulations and compositions that comprise a dye (e.g., a Trypan blue dye, Evans blue dye) or other tracer compound. In some instances, addition of an auris-compatible dye to an otic formulation or composition described herein aids visualization of any administered formulation or composition in an ear (e.g., a rodent ear and/or a human ear). In certain embodiments, an otic formulation or composition comprising a dye or other tracer compound eliminates the need for invasive procedures that are currently used in animal models to monitor the concentrations of drugs in the endolymph and/or perilymph.

In some instances, intratympanic injections require the need of a specialist and the formulation or composition needs to be delivered to a specific site of the ear to maximize efficiency of the medication delivered. In certain instances, a visualization technique for any formulation or composition described herein allows for visualization of a dosing site (e.g., the round window) so that the medication is applied in the proper place. In some instances, a formulation or composition comprising a dye allows visualization of the formulation or composition during administration of the formulation to an ear (e.g., a human ear), ensures that the medication will be delivered at the intended site, and avoids any complications due to incorrect placement of a formulation or composition. The inclusion of a dye to help enhance the visualization of the formulation or composition when applied, and the ability to visually inspect the location of the formulation or composition after administration without further intervention, represents an advance over currently available methods for testing intratympanic therapeutics in animal models and/or human trials. In some embodiments, dyes that are compatible with the otic compositions described herein include Evans blue (e.g., 0.5% of the total weight of an otic formulation), Methylene blue (e.g., 1% of the total weight of an otic formulation), Isosulfan blue (e.g., 1% of the total weight of an otic formulation), Trypan blue (e.g., 0.15% of the total weight of an otic formulation), and/or indocyanine green (e.g., 25 mg/vial). Other common dyes, e.g, FD&C red 40, FD&C red 3, FD&C yellow 5, FD&C yellow 6, FD&C blue 1, FD&C blue2, FD&C green 3, fluorescence dyes (e.g., Fluorescein isothiocyanate, rhodamine, Alexa Fluors, DyLight Fluors) and/or dyes that are visualizable in conjunction with non-invasive imaging techniques such as MRI, CAT scans, PET scans or the like (e.g., Gadolinium-based MRI dyes, iodine-base dyes, barium-based dyes or the like) are also contemplated for use with any otic formulation or composition described herein. Other dyes that are compatible with any formulation or composition described herein are listed in the Sigma-Aldrich catalog under dyes (which is included herein by reference for such disclosure). In some embodiments, concentration of a dye in any otic formulation described herein is less than 2%, less than 1.5%, less than 1%, less than 0.5%, less than 0.25%, less than 0.1%, or less than 100 ppm of the total weight and/or volume of any formulation or composition described herein.

In certain embodiments of such auris-compatible formulations or compositions that comprise a dye, the ability to visualize a controlled release otic formulation or composition comprising a dye in an ear meets a long standing need for suitable testing methods that are applicable to the development of intratympanic otic formulations or compositions suitable for human use. In certain embodiments of such auris-compatible formulations or compositions that comprise a dye, the ability to visualize a controlled release otic formulation or composition comprising a dye allows for testing of any otic formulation described herein in human clinical trials.

General Methods of Sterilization

The environment of the inner ear is an isolated environment. The endolymph and the perilymph are static fluids and are not in contiguous contact with the circulatory system. The blood-labyrinth-barrier (BLB), which includes a blood-endolymph barrier and a blood-perilymph barrier, consists of tight junctions between specialized epithelial cells in the labyrinth spaces (i.e., the vestibular and cochlear spaces). The presence of the BLB limits delivery of active agents (e.g., immunomodulators, aural pressure modulators, antimicrobials) to the isolated microenvironment of the inner ear. Auris hair cells are bathed in endolymphatic or perilymphatic fluids and cochlear recycling of potassium ions is important for hair cell function. When the inner ear is infected, there is an influx of leukocytes and/or immunoglobins (e.g. in response to a microbial infection) into the endolymph and/or the perilymph and the delicate ionic composition of inner ear fluids is upset by the influx of leukocytes and/or immunoglobins. In certain instances, a change in the ionic composition of inner ear fluids results in hearing loss, loss of balance and/or ossification of auditory structures. In certain instances, even trace amounts of pyrogens and/or microbes trigger infections and related physiological changes in the isolated microenvironment of the inner ear.

In one aspect, provided herein are otic formulations or compositions that are sterilized with stringent sterility requirements and are suitable for administration to the middle and/or inner ear. In some embodiments, the otic formulations or compositions described herein are auris compatible compositions. In some embodiment, the otic formulations or compostions are substantially free of pyrogens and/or microbes.

Provided herein are otic formulations or compositions that ameliorate or lessen otic disorders described herein. Further provided herein are methods comprising the administration of said otic formulations or compositions. In some embodiments, the formulations or compositions are sterilized. Included within the embodiments disclosed herein are means and processes for sterilization of a pharmaceutical composition disclosed herein for use in humans. The goal is to provide a safe pharmaceutical product, relatively free of infection causing microorganisms. The U. S. Food and Drug Administration has provided regulatory guidance in the publication "Guidance for Industry: Sterile Drug Products Produced by Aseptic Processing" available at: http://www.fda.gov/cder/guidance/5882fnl.htm, which is incorporated herein by reference in its entirety. No specific guidelines are available for safe pharmaceutical products for treatment of the inner ear.

As used herein, sterilization means a process used to destroy or remove microorganisms that are present in a product or packaging. Any suitable method available for sterilization of objects and formulations or compositions is used. Available methods for the inactivation of microorganisms include, but are not limited to, the application of extreme heat, lethal chemicals, or gamma radiation. In some embodiments is a process for the preparation of an otic therapeutic formulation comprising subjecting the formulation to a sterilization method selected from heat sterilization, chemical sterilization, radiation sterilization or filtration sterilization. The method used depends largely upon the nature of the device or composition to be sterilized. Detailed descriptions of many methods of sterilization are given in Chapter 40 of Remington: The Science and Practice of Pharmacy published by Lippincott, Williams & Wilkins, and is incorporated by reference with respect to this subject matter.

Sterilization by Heat

Many methods are available for sterilization by the application of extreme heat. One method is through the use of a saturated steam autoclave. In this method, saturated steam at a temperature of at least 121° C. is allowed to contact the object to be sterilized. The transfer of heat is either directly to the microorganism, in the case of an object to be sterilized, or indirectly to the microorganism by heating the bulk of an aqueous solution to be sterilized. This method is widely practiced as it allows flexibility, safety and economy in the sterilization process.

Dry heat sterilization is a method which is used to kill microorganisms and perform depyrogenation at elevated temperatures. This process takes place in an apparatus suitable for heating HEPA-filtered microorganism-free air to temperatures of at least 130-180° C. for the sterilization process and to temperatures of at least 230-250° C. for the depyrogenation process. Water to reconstitute concentrated or powdered formulations is also sterilized by autoclave.

Chemical Sterilization

Chemical sterilization methods are an alternative for products that do not withstand the extremes of heat sterilization. In this method, a variety of gases and vapors with germicidal properties, such as ethylene oxide, chlorine dioxide, formaldehyde or ozone are used as the anti-apoptotic agents. The germicidal activity of ethylene oxide, for example, arises from its ability to serve as a reactive alkylating agent. Thus, the sterilization process requires the ethylene oxide vapors to make direct contact with the product to be sterilized.

Radiation Sterilization

One advantage of radiation sterilization is the ability to sterilize many types of products without heat degradation or other damage. The radiation commonly employed is beta radiation or alternatively, gamma radiation from a $^{60}$Co source. The penetrating ability of gamma radiation allows its use in the sterilization of many product types, including solutions, compositions and heterogeneous mixtures. The germicidal effects of irradiation arise from the interaction of gamma radiation with biological macromolecules. This interaction generates charged species and free radicals. Subsequent chemical reactions, such as rearrangements and cross-linking processes, result in the loss of normal function for these biological macromolecules. The formulations described herein are also optionally sterilized using beta irradiation.

Filtration

Filtration sterilization is a method used to remove but not destroy microorganisms from solutions. Membrane filters are used to filter heat-sensitive solutions. Such filters are thin, strong, homogenous polymers of mixed cellulosic esters (MCE), polyvinylidene fluoride (PVF; also known as PVDF), or polytetrafluoroethylene (PTFE) and have pore sizes ranging from 0.1 to 0.22 μm. Solutions of various characteristics are optionally filtered using different filter membranes. For example, PVF and PTFE membranes are well suited to filtering organic solvents while aqueous solutions are filtered through PVF or MCE membranes. Filter apparatus are available for use on many scales ranging from the single point-of-use disposable filter attached to a syringe up to commercial scale filters for use in manufacturing plants. The membrane filters are sterilized by autoclave or chemical sterilization. Validation of membrane filtration systems is performed following standardized protocols (Microbiological Evaluation of Filters for Sterilizing Liquids, Vol 4, No. 3. Washington, D.C: Health Industry Manufacturers Association, 1981) and involve challenging the membrane filter with a known quantity (ca. $10^7/cm^2$) of unusually small microorganisms, such as *Brevundimonas diminuta* (ATCC 19146).

Pharmaceutical formulations or compositions are optionally sterilized by passing through membrane filters. In some embodiments, formulations or compositions comprising nanoparticles (U.S. Pat. No. 6,139,870) or multilamellar vesicles (Richard et al., International Journal of Pharmaceutics (2006), 312(1-2):144-50) are amenable to sterilization by filtration through 0.22 μm filters without destroying their organized structure.

In some embodiments, the methods disclosed herein comprise sterilizing the formulation or compositions (or components thereof) by means of filtration sterilization. In another embodiment the otic formulation or composition comprises a particle wherein the particle formulation or composition is suitable for filtration sterilization. In a further embodiment said particle formulation or composition comprises particles of less than 300 nm in size, of less than 200 nm in size, of less than 100 nm in size. In another embodiment the otic formulation or composition comprises a particle formulation or composition wherein the sterility of the particle is ensured by sterile filtration of the precursor component solutions. In another embodiment the otic formulation or composition comprises a particle formulation or composition wherein the sterility of the particle formulation or composition is ensured by low temperature sterile filtration. In a further embodiment, said low temperature sterile filtration occurs at a temperature between 0 and 30° C., or between 0 and 20° C., or between 0 and 10° C., or between 10 and 20° C., or between 20 and 30° C. In another embodiment is a process for the preparation of an auris-acceptable particle formulation or composition comprising: filtering the aqueous solution containing the particle formulation or composition at low temperature through a sterilization filter; lyophilizing the sterile solution; and reconstituting the particle formulation or composition with sterile water prior to administration.

In another embodiment the otic formulation or composition comprises a nanoparticle formulation or composition wherein the nanoparticle formulation or composition is suitable for filtration sterilization. In a further embodiment the nanoparticle formulation or composition comprises nanoparticles of less than 300 nm in size, of less than 200 nm in size, or of less than 100 nm in size. In another embodiment the otic formulation or composition comprises a microsphere formulation or composition wherein the sterility of the microsphere is ensured by sterile filtration of the precursor organic solution and aqueous solutions. In another embodiment, the sterility of the otic formulation or composition is ensured by low temperature sterile filtration. In a further embodiment, the low temperature sterile filtration occurs at a temperature between 0 and 30° C., or between 0 and 20° C., or between 0 and 10° C., or between 10 and 20° C., or between 20 and 30° C.

In certain embodiments, the active ingredients are dissolved in a suitable vehicle (e.g. a buffer) and sterilized separately (e.g. by heat treatment, filtration, gamma radiation); the remaining excipients are sterilized in a separate step by a suitable method (e.g. filtration and/or irradiation of a cooled mixture of excipients); the two solutions that were separately sterilized are then mixed aseptically to provide a final otic formulation or composition.

In some instances, conventionally used methods of sterilization (e.g., heat treatment (e.g., in an autoclave), gamma irradiation, filtration) lead to irreversible degradation of the therapeutic agent in the formulation or composition.

Microorganisms

Provided herein are otic formulations or compositions that ameliorate or lessen otic disorders described herein. Further provided herein are methods comprising the administration of said otic formulations or compositions. In some embodiments, the formulations or compositions are substantially free of microorganisms. Acceptable sterility levels are based on applicable standards that define therapeutically acceptable otic formulations or compositions, including but not limited to United States Pharmacopeia Chapters <1111> et seq. For example, acceptable sterility levels include 10 colony forming units (cfu) per gram of formulation or composition, 50 cfu per gram of formulation or composition, 100 cfu per gram of formulation or composition, 500 cfu per gram of formulation or composition or 1000 cfu per gram of formulation or composition. In addition, acceptable sterility levels include the exclusion of specified objectionable microbiological agents. By way of example, specified objectionable microbiological agents include but are not limited to *Escherichia coli* (*E. coli*), *Salmonella* sp., *Pseudomonas aeruginosa* (*P. aeruginosa*) and/or other specific microbial agents.

Sterility of the otic formulation is confirmed through a sterility assurance program in accordance with United States Pharmacopeia Chapters <61>, <62> and <71>. A key component of the sterility assurance quality control, quality assurance and validation process is the method of sterility testing. Sterility testing, by way of example only, is performed by two methods. The first is direct inoculation wherein a sample of the formulation to be tested is added to growth medium and incubated for a period of time up to 21 days. Turbidity of the growth medium indicates contamination. Drawbacks to this method include the small sampling size of bulk materials which reduces sensitivity, and detection of microorganism growth based on a visual observation. An alternative method is membrane filtration sterility testing. In this method, a volume of product is passed through a small membrane filter paper. The filter paper is then placed into media to promote the growth of microorganisms. This method has the advantage of greater sensitivity as the entire bulk product is sampled. The commercially available Millipore Steritest sterility testing system is optionally used for determinations by membrane filtration sterility testing. For the filtration testing of creams or ointments Steritest filter system No. TLHVSL210 are used. For the filtration testing of emulsions or viscous products Steritest filter system No. TLAREM210 or TDAREM210 are used. For the filtration testing of pre-filled syringes Steritest filter system No. TTHASY210 are used. For the filtration testing of material dispensed as an aerosol or foam Steritest filter system No. TTHVA210 are used. For the filtration testing of soluble powders in ampoules or vials Steritest filter system No. TTHADA210 or TTHADV210 are used.

Testing for *E. coli* and *Salmonella* includes the use of lactose broths incubated at 30-35° C. for 24-72 hours, incubation in MacConkey and/or EMB agars for 18-24 hours, and/or the use of Rappaport medium. Testing for the detection of *P. aeruginosa* includes the use of NAC agar. United States Pharmacopeia Chapter <62> further enumerates testing procedures for specified objectionable microorganisms.

In certain embodiments, any otic formulation or composition described herein has less than about 60 colony forming units (CFU), less than about 50 colony forming units, less than about 40 colony forming units, or less than about 30 colony forming units of microbial agents per gram of formulation. In certain embodiments, the otic formulations or compositions described herein are formulated to be isotonic with the endolymph and/or the perilymph.

Endotoxins

Provided herein are otic formulations or compositions that ameliorate or lessen otic disorders described herein. Further provided herein are methods comprising the administration of said otic formulations or compositions. In some embodiments, the otic formulations or compositions are substantially free of endotoxins. An additional aspect of the sterilization process is the removal of by-products from the killing of microorganisms (hereinafter, "Product"). The process of depyrogenation removes pyrogens from the sample. Pyrogens are endotoxins or exotoxins which induce an immune response. An example of an endotoxin is the lipopolysaccharide (LPS) molecule found in the cell wall of gram-negative bacteria. While sterilization procedures such as autoclaving or treatment with ethylene oxide kill the bacteria, the LPS residue induces a proinflammatory immune response, such as septic shock. Because the molecular size of endotoxins varies widely, the presence of endotoxins is expressed in "endotoxin units" (EU). One EU is equivalent to 100 picograms of *E. coli* LPS. In some cases, humans develop a response to as little as 5 EU/kg of body weight. The sterility is expressed in any units as recognized in the art. In certain embodiments, otic formulations or compositions described herein contain lower endotoxin levels (e.g. <4 EU/kg of body weight of a subject) when compared to conventionally acceptable endotoxin levels (e.g., 5 EU/kg of body weight of a subject). In some embodiments, the otic formulation or composition has less than about 5 EU/kg of body weight of a subject. In other embodiments, the otic formulation or composition has less than about 4 EU/kg of body weight of a subject. In additional embodiments, the otic formulation or composition has less than about 3 EU/kg of body weight of a subject. In additional embodiments, the otic formulation or composition has less than about 2 EU/kg of body weight of a subject.

In some embodiments, the otic formulation or composition has less than about 5 EU/kg of formulation. In other embodiments, the otic therapeutic formulation or composition has less than about 4 EU/kg of formulation. In additional embodiments, the otic formulation or composition has less than about 3 EU/kg of formulation. In some embodiments, the otic formulation or composition has less than about 5 EU/kg Product. In other embodiments, the otic formulation or composition has less than about 1 EU/kg Product. In additional embodiments, the otic formulation or composition has less than about 0.2 EU/kg Product. In some embodiments, the otic formulation or composition has less than about 5 EU/g of unit or Product. In other embodiments, the otic formulation or composition has less than about 4 EU/g of unit or Product. In additional embodiments, the otic formulation or composition has less than about 3 EU/g of unit or Product. In some embodiments, the otic formulation or composition has less than about 5 EU/mg of unit or Product. In other embodiments, the otic formulation or composition has less than about 4 EU/mg of unit or Product. In additional embodiments, the otic formulation or composition has less than about 3 EU/mg of unit or Product. In certain embodiments, otic formulations or compositions described herein contain from about 1 to about 5 EU/mL of formulation or composition. In certain embodiments, otic formulations or compositions described herein contain from about 2 to about 5 EU/mL of formulation or composition, from about 3 to about 5 EU/mL of formulation or composition, or from about 4 to about 5 EU/mL of formulation or composition.

In certain embodiments, otic formulations or compositions described herein contain lower endotoxin levels (e.g. <0.5 EU/mL of formulation or composition) when compared to conventionally acceptable endotoxin levels (e.g., 0.5 EU/mL of formulation or composition). In some embodiments, the otic formulation or composition has less than about 0.5 EU/mL of formulation or composition. In other embodiments, the otic formulation or composition has less than about 0.4 EU/mL of formulation or composition. In additional embodiments, the otic formulation or composition has less than about 0.2 EU/mL of formulation or composition.

Pyrogen detection, by way of example only, is performed by several methods. Suitable tests for sterility include tests described in United States Pharmacopoeia (USP)<71> Sterility Tests (23rd edition, 1995). The rabbit pyrogen test and the Limulus amebocyte lysate test are both specified in the United States Pharmacopeia Chapters <85> and <151> (USP23/NF 18, Biological Tests, The United States Pharmacopeial Convention, Rockville, Md., 1995). Alternative pyrogen assays have been developed based upon the monocyte activation-cytokine assay. Uniform cell lines suitable for quality control applications have been developed and have demonstrated the ability to detect pyrogenicity in samples that have passed the rabbit pyrogen test and the Limulus amebocyte lysate test (Taktak et al, J. Pharm. Pharmacol. (1990), 43:578-82). In an additional embodiment, the otic formulation or composition is subject to depyrogenation. In a further embodiment, the process for the manufacture of the otic formulation or composition comprises testing the formulation for pyrogenicity. In certain embodiments, the formulations or compositions described herein are substantially free of pyrogens.

pH and Osmolarity

Described herein are otic formulations or compositions with an ionic balance that is compatible with the perilymph and/or the endolymph and does not cause any change in cochlear potential. In specific embodiments, osmolarity/osmolality of the present formulations or compositions is adjusted, for example, by the use of appropriate salt concentrations (e.g., concentration of sodium salts) or the use of tonicity agents which renders the formulations or compositions endolymph-compatible and/or perilymph compatible (i.e. isotonic with the endolymph and/or perilymph). In some instances, the endolymph-compatible and/or perilymph-compatible formulations or compositions described herein cause minimal disturbance to the environment of the inner ear and cause minimum discomfort (e.g, vertigo) to a mammal (e.g., a human) upon administration. In some embodiments, the formulations or compositions described herein are free of preservatives and cause minimal disturbance (e.g., change in pH or osmolarity, irritation) in auditory structures. In some embodiments, the formulations or compositions described herein comprise antioxidants that are non-irritating and/or non-toxic to otic structures.

The main cation present in the endolymph is potassium. In addition the endolymph has a high concentration of positively charged amino acids. The main cation present in the perilymph is sodium. In certain instances, the ionic composition of the endolymph and perilymph regulate the electrochemical impulses of hair cells. In certain instances, any change in the ionic balance of the endolymph or perilymph results in a loss of hearing due to changes in the conduction of electrochemical impulses along otic hair cells. In some embodiments, a composition or formulation disclosed herein does not disrupt the ionic balance of the perilymph. In some embodiments, a composition or formulation disclosed herein has an ionic balance that is the same as or substantially the same as the perilymph. In some embodiments, a composition or formulation disclosed herein does not disrupt the ionic balance of the endolymph. In some embodiments, a composition or formulation disclosed herein has an ionic balance that is the same as or substantially the same as the endolymph. In some embodiments, a composition or formulation described herein is formulated to provide an ionic balance that is compatible with inner ear fluids (i.e., endolymph and/or perilymph).

The endolymph and the perilymph have a pH that is close to the physiological pH of blood. The endolymph has a pH range of about 7.2-7.9; the perilymph has a pH range of about 7.2-7.4. The in situ pH of the proximal endolymph is about 7.4 while the pH of distal endolymph is about 7.9.

In some embodiments, the pH of a formulation or composition described herein is adjusted (e.g., by use of a buffer) to an endolymph-compatible pH range of about 7.0 to 8.0, and a preferred pH range of about 7.2-7.9. In some embodiments, the pH of the formulations or compositions described herein is adjusted (e.g., by use of a buffer) to a perilymph—compatible pH of about 7.0-7.6, and a preferred pH range of about 7.2-7.4.

In some embodiments, useful formulations or compositions also include one or more pH adjusting agents or buffering agents. Suitable pH adjusting agents or buffers include, but are not limited to acetate, bicarbonate, ammonium chloride, citrate, phosphate, pharmaceutically acceptable salts thereof and combinations or mixtures thereof.

In one embodiment, when one or more buffers are utilized in the formulations or compositions of the present disclosure, they are combined, e.g., with a pharmaceutically acceptable vehicle and are present in the final formulation or composition, e.g., in an amount ranging from about 0.1% to about 20%, from about 0.5% to about 10%. In certain embodiments of the present disclosure, the amount of buffer included in the formulations or compositions are an amount such that the pH of the formulation or composition does not interfere with the body's natural buffering system. In some embodiments, from about 5 mM to about 200 mM concentration of a buffer is present in the formulation or composition. In certain embodiments, from about a 20 mM to about a 100 mM concentration of a buffer is present. In other embodiments, the concentration of buffer is such that a pH of the formulation or composition is between 3 and 9, between 5 and 8, or alternatively between 6 and 7. In other embodiments, the pH of the formulation or composition is about 7. In one embodiment is a buffer such as acetate or citrate at slightly acidic pH. In one embodiment the buffer is a sodium acetate buffer having a pH of about 4.5 to about 6.5. In another embodiment the buffer is a sodium acetate buffer having a pH of about 5.5 to about 6.0. In a further embodiment the buffer is a sodium acetate buffer having a pH of about 6.0 to about 6.5. In one embodiment the buffer is a sodium citrate buffer having a pH of about 5.0 to about 8.0. In another embodiment the buffer is a sodium citrate buffer having a pH of about 5.5 to about 7.0. In one embodiment the buffer is a sodium citrate buffer having a pH of about 6.0 to about 6.5.

In some embodiments, the concentration of buffer is such that a pH of the formulation or composition is between 6 and 9, between 6 and 8, between 6 and 7.6, between 7 and 8. In other embodiments, the pH of the formulation or composition is about 6.0, about 6.5, about 7 or about 7.5. In one embodiment is a buffer such as tris(hydroxymethyl)aminomethane, bicarbonate, carbonate or phosphate at slightly basic pH. In one embodiment, the buffer is a sodium bicarbonate buffer having a pH of about 7.5 to about 8.5. In another embodiment the buffer is a sodium bicarbonate buffer having a pH of about 7.0 to about 8.0. In a further embodiment the buffer is a sodium bicarbonate buffer having a pH of about 6.5 to about 7.0. In one embodiment the buffer is a sodium phosphate dibasic buffer having a pH of about 6.0 to about 9.0. In another embodiment the buffer is a sodium phosphate dibasic buffer having a pH of about 7.0 to about 8.5. In one embodiment the buffer is a sodium phosphate dibasic buffer having a pH of about 7.5 to about 8.0.

In one embodiment, diluents are also used to stabilize compounds because they provide a more stable environment. Salts dissolved in buffered solutions (which also provide pH control or maintenance) are utilized as diluents in the art, including, but not limited to a phosphate buffered saline solution.

In a specific embodiment the pH of a formulation or composition described herein is between about 6.0 and about 7.6, between 7 and about 7.8, between about 7.0 and about 7.6, between about 7.2 and about 7.6, or between about 7.2 and about 7.4. In certain embodiments the pH of a formulation or composition described herein is about 6.0, about 6.5, about 7.0, about 7.1, about 7.2, about 7.3, about 7.4, about 7.5, or about 7.6. In some embodiments, the pH of any formulation or composition described herein is designed to be compatible with the targeted otic structure (e.g., endolymph, perilymph or the like).

In some embodiments, any formulation or composition described herein has a pH that allows for sterilization (e.g., by filtration or aseptic mixing or heat treatment and/or autoclaving (e.g., terminal sterilization)) of a formulation or composition without degradation of the therapeutic agent. In order to reduce hydrolysis and/or degradation of the therapeutic agent during sterilization, the buffer pH is designed to maintain pH of the formulation or composition in the 7-8 range during the process of sterilization.

In specific embodiments, any formulation or composition described herein has a pH that allows for terminal sterilization (e.g, by heat treatment and/or autoclaving) of a formulation or composition without degradation of the therapeutic agent. For example, in order to reduce hydrolysis and/or degradation of the therapeutic agent during autoclaving, the buffer pH is designed to maintain pH of the formulation or composition in the 7-8 range at elevated temperatures. Any appropriate buffer is used depending on the therapeutic agent used in the formulation or composition. In some instances, since $pK_a$ of TRIS decreases as temperature increases at approximately −0.03/° C. and $pK_a$ of PBS increases as temperature increases at approximately 0.003/° C., autoclaving at 250° F. (121° C.) results in a significant downward pH shift (i.e. more acidic) in the TRIS buffer whereas a relatively much less upward pH shift in the PBS buffer and therefore much increased hydrolysis and/or degradation of an otic agent in TRIS than in PBS. In some embodiments, degradation of a therapeutic agent is reduced by the use of an appropriate of a buffer as described herein.

In some embodiments, a pH of between about 6.0 and about 7.6, between about 7 and about 7.8, between about 7.0 and about 7.6, between about 7.2 and about 7.6, between about 7.2 and about 7.4 is suitable for sterilization (e.g, by filtration or aseptic mixing or heat treatment and/or autoclaving (e.g., terminal sterilization)) of formulations or compositions described herein. In specific embodiments a formulation or composition pH of about 6.0, about 6.5, about 7.0, about 7.1, about 7.2, about 7.3, about 7.4, about 7.5, or about 7.6 is suitable for sterilization (e.g, by filtration or aseptic mixing or heat treatment and/or autoclaving (e.g., terminal sterilization)) of any formulation or composition described herein.

In some embodiments, the formulations or compositions described herein have a pH between about 3 and about 9, or between about 4 and 8, or between about 5 and 8, or between about 6 and about 7, or between about 6.5 and about 7, or between about 5.5 and about 7.5, or between about 7.1 and about 7.7, and have a concentration of active pharmaceutical ingredient between about 0.1 mM and about 100 mM. In some embodiments, the formulations or compositions described herein have a pH between about 5 and about 8, or between about 6 and about 7, or between about 6.5 and about 7, or between about 5.5 and about 7.5, or between about 7.1 and about 7.7, and have a concentration of active pharmaceutical ingredient between about 1 and about 100 mM. In some embodiments, the formulations or compositions described herein have a pH between about 5 and about 8, or between about 6 and about 7, or between about 6.5 and about 7, or between about 5.5 and about 7.5, or between about 7.1 and about 7.7, and have a concentration of active pharmaceutical ingredient between about 50 and about 80 mM. In some embodiments, the concentration of active pharmaceutical ingredient between about 10 and about 100 mM. In other embodiments, the concentration of active pharmaceutical ingredient between about 20 and about 80 mM. In additional embodiments, the concentration of active pharmaceutical ingredient between about 10 and about 50 mM.

In some embodiments, the formulations or compositions have a pH as described herein, and include a thickening agent (i.e, a viscosity enhancing agent) such as, by way of non-limiting example, a cellulose based thickening agent described herein. In some instances, the addition of a thickening agent and a pH of formulation or compositions as described herein, allows for sterilization of a formulation described herein without any substantial degradation of the therapeutic agent in the otic formulation or composition. In some embodiments, the amount of thickening agent in any formulation or composition described herein is about 1%, 5%, about 10%, or about 15% of the total weight of the formulation or composition. In some embodiments, the amount of thickening agent in any formulation or composition described herein is about 0.5%, about 1%, about 1.5%, about 2%, about 2.5%, about 3%, about 3.5%, about 4%, about 4.5%, or about 5% of the total weight of the formulation or composition.

In some embodiments, the pharmaceutical formulations or compositions described herein are stable with respect to pH over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the formulations or compositions described herein are stable with respect to pH over a period of at least about 1 week. Also described herein are formulations or compositions that are stable with respect to pH over a period of at least about 1 month.

Tonicity Agents

In general, the endolymph has a higher osmolality than the perilymph. For example, the endolymph has an osmolality of about 304 mOsm/kg $H_2O$ while the perilymph has an osmolality of about 294 mOsm/kg $H_2O$. In some embodiments, formulations or compositions described herein are formulated to provide an osmolarity of about 250 to about 320 mM (osmolality of about 250 to about 320 mOsm/kg $H_2O$); and preferably about 270 to about 320 mM (osmolality of about 270 to about 320 mOsm/kg $H_2O$). In specific embodiments, osmolarity/osmolality of the present formulations or compositions is adjusted, for example, by the use of appropriate salt concentrations (e.g., concentration of potassium salts) or the use of tonicity agents which renders the formulations or compositions endolymph-compatible and/or perilymph-compatible (i.e. isotonic with the endolymph and/or perilymph. In some instances, the endolymph-compatible and/or perilymph-compatible formulations or compositions described herein cause minimal disturbance to the environment of the inner ear and cause minimum discomfort (e.g., vertigo and/or nausea) to a mammal upon administration.

In some embodiments, any formulation or composition described herein is isotonic with the perilymph. Isotonic formulations or compositions are provided by the addition of a tonicity agent. Suitable tonicity agents include, but are not limited to any pharmaceutically acceptable sugar, salt or any combinations or mixtures thereof, such as, but not limited to dextrose, glycerin, mannitol, sorbitol, sodium chloride, and other electrolytes.

Useful otic formulations or compositions include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In further embodiments, the tonicity agents are present in an amount as to provide a final osmolality of an otic formulation or composition of about 100 mOsm/kg to about 500 mOsm/kg, from about 200 mOsm/kg to about 400 mOsm/kg, from about 250 mOsm/kg to about 350 mOsm/kg or from about 280 mOsm/kg to about 320 mOsm/kg. In some embodiments, the formulations or compositions described herein have a osmolarity of about 100 mOsm/L to about 500 mOsm/L, about 200 mOsm/L to about 400 mOsm/L, about 250 mOsm/L to about 350 mOsm/L, or about 280 mOsm/L to about 320 mOsm/L. In some embodiments, the osmolarity of any formulation or composition described herein is designed to be isotonic with the targeted otic structure (e.g., endolymph, perilymph or the like).

In some embodiments, the formulations or compositions described herein have a pH and osmolarity as described herein, and have a concentration of active pharmaceutical ingredient between about 1 µM and about 10 µM, between about 1 mM and about 100 mM, between about 0.1 mM and about 100 mM, between about 0.1 mM and about 100 nM. In some embodiments, the formulations or compositions described herein have a pH and osmolarity as described herein, and have a concentration of active pharmaceutical ingredient between about 0.01-about 20%, between about 0.01-about 10%, between about 0.01-about 7%, between about 0.01-5%, between about 0.01-about 3%, between about 0.01-about 2% of the active ingredient by weight of the formulation or composition. In some embodiments, the formulations or composition described herein have a pH and osmolarity as described herein, and have a concentration of active pharmaceutical ingredient between about 0.1-about 70 mg/mL, between about 1 mg-about 70 mg/mL, between about 1 mg-about 50 mg/mL, between about 1 mg/mL and about 20 mg/mL, between about 1 mg/mL to about 10 mg/mL, between about 1 mg/mL to about 5 mg/mL, or between about 0.5 mg/mL to about 5 mg/mL of the active agent by volume of the formulation or composition.

Particle Size

Size reduction is used to increase surface area and/or modulate formulation dissolution properties. It is also used to maintain a consistent average particle size distribution (PSD) (e.g., micrometer-sized particles, nanometer-sized particles or the like) for any formulation or composition described herein. In some embodiments, the formulation or composition comprises micrometer-sized particles. In some embodiments, the formulation or composition comprises nanometer-sized particles. In some instances, any formulation or composition described herein comprises multiparticulates, i.e., a plurality of particle sizes (e.g., micronized particles, nanosized particles, non-sized particles); i.e, the formulation or composition is a multiparticulate formulation or composition. In some embodiments, any formulation or composition described herein comprises one or more multiparticulate (e.g., micronized) therapeutic agents. Micronization is a process of reducing the average diameter of particles of a solid material. Micronized particles are from about micrometer-sized in diameter to about picometer—sized in diameter. In some embodiments, the use of multiparticulates (e.g., micronized particles) of a therapeutic agent, or an otic agent, allows for extended and/or sustained release of the therapeutic agent from any formulation described herein compared to a formulation or composition comprising non-multiparticulate (e.g, non-micronized) therapeutic agent. In some instances, formulations or compositions containing multiparticulate (e.g. micronized) therapeutic agents are ejected from a 1 mL syringe adapted with a 27G needle without any plugging or clogging. In some embodiments, the therapeutic agent is essentially in the form of micronized particles. In some embodiments, the therapeutic agent is essentially in the form of microsized particles. In some embodiments, the therapeutic agent is essentially in the form of nanosized particles.

In some embodiments, the particle size of the formulation or composition described herein increases the retention time of the formulation or composition described herein. In some embodiments, the particle size of the formulation or composition described herein provides slow release of the therapeutic agent. In some embodiments, the particle size of the formulation or composition described herein provides sustained release of the therapeutic agent. In some embodiments, the particle size is less than 450 nm, less than 400 nm, less than 350 nm, less than 300 nm, less than 275 nm, less than 250 nm, less than 225 nm, less than 200 nm in size, less than 175 nn, less than 150 nm, or less than 125 nm, or less than 100 nm. In some embodiments, the particle size is less than 300 nm. In some embodiments, the particle size is less than 250 nm. In some embodiments, the particle size is less than 200 nm.

In some instances, any particle in any formulation or composition described herein is a coated particle (e.g., a coated micronized particle) and/or a microsphere and/or a liposomal particle. Particle size reduction techniques include, by way of example, grinding, milling (e.g., air-attrition milling (jet milling), ball milling), coacervation, high pressure homogenization, spray drying and/or supercritical fluid crystallization. In some instances, particles are sized by mechanical impact (e.g., by hammer mills, ball mill and/or pin mills). In some instances, particles are sized via fluid energy (e.g., by spiral jet mills, loop jet mills, and/or fluidized bed jet mills). In some embodiments formulations described herein comprise crystalline particles. In some embodiments, formulations or compositions described herein comprise amorphous particles. In some embodiments, formulations or compositions described herein comprise therapeutic agent particles wherein the therapeutic agent is a free base, or a salt, or a prodrug of a therapeutic agent, or any combination thereof.

In some instances, a combination of a therapeutic agent and a salt of the therapeutic agent is used to prepare pulsed release otic formulations or compositions using the procedures described herein. In some formulations, a combination of a micronized therapeutic agent (and/or salt or prodrug thereof) and coated particles (e.g., nanoparticles, liposomes, microspheres) is used to prepare pulsed release otic formulations or compositions using any procedure described herein.

In some embodiments, a pulsed release profile is achieved by solubilizing up to 20% of the delivered dose of the therapeutic agent (e.g., micronized therapeutic agent, or free base or salt or prodrug thereof; multiparticulate therapeutic agent, or free base or salt or prodrug thereof) with the aid of cyclodextrins, surfactants (e.g., poloxamers (407, 338, 188), tween (80, 60, 20,81), PEG-hydrogenated castor oil, cosolvents like N-methyl-2-Pyrrolidone or the like and preparing pulsed release formulations or compositions using any procedure described herein.

In some specific embodiments, any otic formulation or composition described herein comprises one or more micronized therapeutic agents. In some of such embodiments, a micronized therapeutic agent comprises micronized particles, coated (e.g., with an extended release coat) micronized particles, or a combination thereof. In some of such embodiments, a micronized therapeutic agent comprising micronized particles, coated micronized particles, or a combination thereof, comprises a therapeutic agent as a free base, a salt, a prodrug or any combination thereof.

Controlled Release Otic Formulations

In certain embodiments, any controlled release otic formulation or composition described herein increases the exposure of a therapeutic agent and increases the Area Under the Curve (AUC) in otic fluids (e.g., endolymph and/or perilymph) by about 30%, about 40%, about 50%, about 60%, about 70%, about 80% or about 90% compared to a formulation or composition that is not a controlled release otic formulation or composition. In certain embodiments, any controlled release otic formulation or composition described herein increases the exposure of a therapeutic agent and decreases the $C_{max}$ in otic fluids (e.g., endolymph and/or perilymph) by about 40%, about 30%, about 20%, or about 10%, compared to a formulation or composition that is not a controlled release otic formulation or composition. In certain embodiments, any controlled release otic formulation or composition described herein alters (e.g. reduces) the ratio of $C_{max}$ to $C_{min}$ compared to a formulation or composition that is not a controlled release otic formulation. In certain embodiments, the ratio of $C_{max}$ to $C_{min}$ is 10:1, 9:1, 8:1, 7:1, 6:1, 5:1, 4:1, 3:1, 2:1 or 1:1. In certain embodiments, any controlled release otic formulation described herein increases the exposure of a therapeutic agent and increases the length of time that the concentration of a therapeutic agent is above $C_{min}$ by about 30%, about 40%, about 50%, about 60%, about 70%, about 80% or about 90% compared to a formulation or composition that is not a controlled release otic formulation or composition. In certain instances, controlled release formulations or compositions described herein delay the time to $C_{max}$. In certain instances, the controlled steady release of a drug prolongs the time the concentration of the drug will stay above the $C_{min}$. In some embodiments, auris formulations or compositions described herein prolong the residence time of a drug in the inner ear. In certain instances, once drug exposure (e.g., concentration in the endolymph or perilymph) of a drug reaches steady state, the concentration of the drug in the endolymph or perilymph stays at or about the therapeutic dose for an extended period of time (e.g., one day, 2 days, 3 days, 4 days, 5 days, 6 days, 1 week, 2 weeks, 3 weeks, a month, two months, three months, six months, or one year).

In some embodiments, the otic formulations or compositions described herein deliver an active agent to the external, middle and/or inner ear, including the cochlea and vestibular labyrinth. In some embodiments, local otic delivery of the auris formulations or compositions described herein allows for controlled release of active agents to auris structures and overcomes the drawbacks associated with systemic administration (e.g, low bioavailability of the drug in the endolymph or perilymph, variability in concentration of the drug in the external, middle and/or internal ear).

Controlled-release options include but are not limited to liposomes, cyclodextrins, biodegradable polymers, dispersible polymers, emulsions, microspheres or microparticles, other viscous media, paints, foams, in spongy materials, liposomes, nanocapsules or nanospheres, and combinations thereof; other options or components include mucoadhesives, penetration enhancers, bioadhesives, antioxidants, surfactants, buffering agents, diluents, salts and preservatives. To the extent viscosity considerations potentially limit the use of a syringe/needle delivery system, thermoreversible gels or post-administration viscosity-enhancing options are also envisioned, as well as alternative delivery systems, including pumps, microinjection devices and the like.

In one embodiment of the otic formulations or compositions described herein, the otic formulation or composition is provided as a thickened liquid formulation composition, also referred to herein as "auris acceptable thickened liquid formulation or composition," "auris thickened liquid formulations or compositions" or variations thereof. All of the components of the thickened liquid formulation or composition must be compatible with the auris interna. Further, the thickened liquid formulation or composition provides controlled release of the therapeutic agent to the desired site within the auris interna for some embodiments. In some embodiments, the thickened liquid formulation or composition also has an immediate or rapid release component for delivery of the therapeutic agent to the desired target site.

In one embodiment of the otic formulations or compositions described herein, the otic formulation or composition is provided as a suspension formulation composition, also referred to herein as "auris acceptable suspension formulation or composition," "auris suspension formulations or compositions" or variations thereof. All of the components of the suspension formulation or composition must be compatible with the auris interna. Further, the suspension formulation or composition provides controlled release of the therapeutic agent to the desired site within the auris interna for some embodiments. In some embodiments, the suspension formulation or composition also has an immediate or rapid release component for delivery of the therapeutic agent to the desired target site.

In one embodiment of the otic formulations or compositions described herein, the otic formulation or composition is provided as a solution formulation composition, also referred to herein as "auris acceptable solution formulation or composition," "auris solution formulations or compositions" or variations thereof. All of the components of the solution formulation or composition must be compatible with the auris interna. Further, the solution formulation or composition provides controlled release of the therapeutic agent to the desired site within the auris interna for some embodiments. In some embodiments, the solution formulation or composition also has an immediate or rapid release component for delivery of the therapeutic agent to the desired target site.

In some embodiments, the formulations or compositions described herein are bimodal formulations or compositions and comprise an immediate release component and an extended release component. In some instances, bimodal formulations allow for a constant rate of release of an immediate release component (multiparticulate agent (e.g., micronized active agent)) and a constant rate of release of an extended release component (e.g., an encapsulated active agent that serves as a depot for extending the release of an active agent). In other embodiments, the otic formulations or compositions described herein are administered as a controlled release formulation or compositions, released either continuously or in a pulsatile manner, or variants of both. In still other embodiments, the active agent formulation or composition is administered as both an immediate release and controlled release formulation or composition, released either continuously or in a pulsatile manner, or variants of both. In certain embodiments, the formulations or compositions comprise an excipient that increases the release rate of the therapeutic agent. In certain embodiments, the formulations or compositions comprise an excipient that decreases the release rate of the therapeutic agent. In certain embodiments, the formulations or compositions comprise penetration enhancers that allow for delivery of the active agents across the oval window or the round window of the ear.

In some embodiments, the otic formulations are biodegradeable. In other embodiments, the otic formulations or compositions include a mucoadhesive excipient to allow adhesion to the external mucous membrane of the round window. In yet other embodiments, the otic formulations or compositions include a penetration enhancer excipient; in further embodiments, the otic formulation or composition contains a viscosity enhancing agent. In other embodiments, the otic pharmaceutical formulations or compositions provide an auris-acceptable microsphere or microparticle; in still other embodiments, the otic pharmaceutical formulations or compositions provide an auris-acceptable liposome, in yet other embodiments, the otic pharmaceutical formulations or compositions provide an auris-acceptable paint or foam. In other embodiments, the otic pharmaceutical formulations or compositions provide an auris-acceptable spongy material.

The formulations or compositions disclosed herein alternatively encompass an otoprotectant agent in addition to the at least one active agent and/or excipients, including but not limited to such as antioxidants, alpha lipoic acid, calicum, fosfomycin or iron chelators, to counteract potential ototoxic effects that arise from the use of specific therapeutic agents or excipients, diluents or carriers.

One aspect of the embodiments disclosed herein is to provide a controlled release composition or formulation for the treatment of fluid homeostasis disorders. The controlled release aspect of the compositions and/or formulations disclosed herein is imparted through a variety of agents, including but not limited to excipients, agents or materials that are acceptable for use in the auris interna or other otic structure. By way of example only, such excipients, agents or materials include an auris-acceptable polymer, an auris-acceptable viscosity enhancing agent, an auris-acceptable microsphere, an auris-acceptable liposome, an auris-acceptable nanocapsule or nanosphere, or combinations thereof.

Thus, provided herein are pharmaceutical formulations or compositions that include at least one auris therapeutic agent and auris-acceptable diluent(s), excipient(s), and/or carrier(s). In some embodiments, the pharmaceutical compositions include other medicinal or pharmaceutical agents, carriers, adjuvants, such as preserving, stabilizing, wetting or emulsifying agents, solution promoters, salts for regulating the osmotic pressure, and/or buffers. In other embodiments, the pharmaceutical formulations or compositions also contain other therapeutic substances.

Auris Acceptable Formulations/Compositions

In some embodiments, the otic formulations or compositions described herein are thickened liquid formulations or compositions. The otic formulations or compositions described herein are suspension formulations or compositions. The otic formulations or compositions described herein are solution formulations or compositions. In some embodiments, the otic formulations or compositions have greater viscosity than an aqueous liquid composition. In some embodiments, the formulation or composition has a viscosity of greater than 1 cP (centipoise). In some embodiments, the formulation or composition has a viscosity of at least about 10 cP, about 20 cP, about 30 cP, about 40 cP, about 50 cP, about 60 cP, about 70 cP, about 80 cP, about 90 cP, about 100 cP, about 200 cP, about 300 cP, about 400 cP, about 500 cP, about 600 cP, about 700 cP, about 800 cP, about 900 cP, about 1,000 cP, about 2,000 cP, about 3,000 cP, about 4,000 cP, about 5,000 cP, about 6,000 cP, about 7,000 cP, about 8,000 cP, about 9,000 cP, about 10,000 cP, about 15,000 cP, or about 20,000 cP. In some embodiments, the formulation or composition has a viscosity of less than about 1,000 cP. In some embodiments, the formulation or composition has a viscosity of less than about 10,000 cP. In some embodiments, the formulation or composition has a viscosity of about 2 cP to about 250,000 cP, about 2 cP to about 100,000 cP, about 2 cP to about 50,000 cP, about 2 cP to about 25,000 cP, about 2 cP to about 10,000 cP, about 2 cP to about 5,000 cP, about 2 cP to about 1,000 cP, about 2 cP to about 500 cP, about 2 cP to about 250 cP, about 2 cP to about 100 cP, about 2 cP to about 90 cP, about 2 cP to about 80 cP, about 2 cP to about 70 cP, about 2 cP to about 60 cP, about 2 cP to about 50 cP, about 2 cP to about 40 cP, about 2 cP to about 30 cP, about 2 cP to about 20 cP, or about 2 cP to about 10 cP. In some embodiments, the liquid formulation or composition has a viscosity of about 2 cP, about 5 cP, about 10 cP, about 20 cP, about 30 cP, about 40 cP, about 50 cP, about 60 cP, about 70 cP, about 80 cP, about 90 cP, about 100 cP, about 200 cP, about 300 cP, about 400 cP, about 500 cP, about 600 cP, about 700 cP, about 800 cP, about 900 cP, about 1,000 cP, about 5,000 cP, about 10,000 cP, about 20,000 cP, about 50,000 cP, about 100,000 cP, or about 250,000 cP.

In some embodiments, the formulation or composition has a viscosity between about 10 cP to about 20,000 cP. In some embodiments, the formulation or composition has a viscosity between about 10 cP to about 10,000 cP. In some embodiments, the formulation or composition has a viscosity between about 10 cP to about 5,000 cP. In some embodiments, the formulation or composition has a viscosity between about 10 cP to about 1,000 cP. In some embodiments, the formulation or composition has a viscosity between about 10 cP to about 500 cP. In some embodiments, the formulation or composition has a viscosity between about 10 cP to about 250 cP. In some embodiments, the formulation or composition has a viscosity between about 10 cP to about 100 cP. In some embodiments, the formulation or composition has a viscosity between about 10 cP to about 50 cP.

In some embodiments, the formulation or composition has a viscosity of about 10 cP. In some embodiments, the formulation or composition has a viscosity of about 20 cP. In some embodiments, the formulation or composition has a viscosity of about 30 cP. In some embodiments, the formulation or composition has a viscosity of about 40 cP. In some embodiments, the formulation or composition has a viscosity of about 50 cP. In some embodiments, the formulation or composition has a viscosity of about 60 cP. In some embodiments, the formulation or composition has a viscosity of about 70 cP. In some embodiments, the formulation or composition has a viscosity of about 80 cP. In some embodiments, the formulation or composition has a viscosity of about 90 cP. In some embodiments, the formulation or composition has a viscosity of about 100 cP. In some embodiments, the formulation or composition has a viscosity of about 150 cP. In some embodiments, the formulation or composition has a viscosity of about 200 cP. In some embodiments, the formulation or composition has a viscosity of about 250 cP. In some embodiments, the formulation or composition has a viscosity of about 300 cP. In some embodiments, the formulation or composition has a viscosity of about 350 cP. In some embodiments, the formulation or composition has a viscosity of about 400 cP. In some embodiments, the formulation or composition has a viscosity of about 450 cP. In some embodiments, the formulation or composition has a viscosity of about 500 cP. In some embodiments, the formulation or composition has a viscosity of about 550 cP. In some embodiments, the formulation or composition has a viscosity of about 600 cP. In some embodiments, the formulation or composition has a viscosity of about 650 cP. In some embodiments, the formulation or composition has a viscosity of about 700 cP. In some embodiments, the formulation or composition has a viscosity of about 750 cP. In some embodiments, the formulation or composition has a viscosity of about 800 cP. In some embodiments, the formulation or composition has a viscosity of about 850 cP. In some embodiments, the formulation or composition has a viscosity of about 900 cP. In some embodiments, the formulation or composition has a viscosity of about 950 cP. In some embodiments, the formulation or composition has a viscosity of about 1,000 cP. In some embodiments, the formulation or composition has a viscosity of about 1,500 cP. In some embodiments, the formulation or composition has a viscosity of about 2,000 cP. In some embodiments, the formulation or composition has a viscosity of about 2,500 cP. In some embodiments, the formulation or composition has a viscosity of about 3,000 cP. In some embodiments, the formulation or composition has a viscosity of about 3,500 cP. In some embodiments, the formulation or composition has a viscosity of about 4,000 cP. In some embodiments, the formulation or composition has a viscosity of about 4,500 cP. In some embodiments, the formulation or composition has a viscosity of about 5,000 cP. In some embodiments, the formulation or composition has a viscosity of about 5,500 cP. In some embodiments, the formulation or composition has a viscosity of about 6,000 cP. In some embodiments, the formulation or composition has a viscosity of about 6,500 cP. In some embodiments, the formulation or composition has a viscosity of about 7,000 cP. In some embodiments, the formulation or composition has a viscosity of about 7,500 cP. In some embodiments, the formulation or composition has a viscosity of about 8,000 cP. In some embodiments, the formulation or composition has a viscosity of about 8,500 cP. In some embodiments, the formulation or composition has a viscosity of about 9,000 cP. In some embodiments, the formulation or composition has a viscosity of about 9,500 cP. In some embodiments, the formulation or composition has a viscosity of about 10,000 cP. In some embodiments, the formulation or composition has a viscosity of about 20,000 cP.

In some embodiments, the otic composition or formulation is free or substantially free of viscosity modulating agent. In some embodiments, the otic formulation or composition contains at least one viscosity modulating agent that provides the otic formulation or composition with a viscosity of at least about 10 cP, about 20 cP, about 30 cP, about 40 cP, about 50 cP, about 60 cP, about 70 cP, about 80 cP, about 90 cP, about 100 cP, about 200 cP, about 300 cP, about 400 cP, about 500 cP, about 600 cP, about 700 cP, about 800 cP, about 900 cP, about 1000 cP, about 2,000 cP, about 3,000 cP, about 4,000 cP, about 5,000 cP, about 6,000 cP, about 7,000 cP, about 8,000 cP, about 9,000 cP, about 10,000 cP, about 15,000 cP, or about 20,000 cP. In some embodiments, the formulation or composition contains at least one viscosity modulating agent that provides the otic formulation or composition with a viscosity of less than about 1,000 cP. In some embodiments, the formulation or composition contains at least one viscosity modulating agent that provides the otic formulation or composition with a viscosity of less than about 10,000 cP. In some embodiments, the otic composition or formulation contains at least one viscosity modulating agent that provides the otic composition or formulation with a viscosity of about 2 cP to about 250,000 cP, about 2 cP to about 100,000 cP, about 2 cP to about 50,000 cP, about 2 cP to about 25,000 cP, about 2 cP to about 10,000 cP, about 2 cP to about 5,000 cP, about 2 cP to about 1,000 cP, about 2 cP to about 500 cP, about 2 cP to about 250 cP, about 2 cP to about 100 cP, about 2 cP to about 90 cP, about 2 cP to about 80 cP, about 2 cP to about 70 cP, about 2 cP to about 60 cP, about 2 cP to about 50 cP, about 2 cP to about 40 cP, about 2 cP to about 30 cP, about 2 cP to about 20 cP, or about 2 cP to about 10 cP. In some embodiments, the otic formulation or composition contains at least one viscosity modulating agent that provides the otic formulation or composition with a viscosity of about 2 cP, about 5 cP, about 10 cP, about 20 cP, about 30 cP, about 40 cP, about 50 cP, about 60 cP, about 70 cP, about 80 cP, about 90 cP, about 100 cP, about 200 cP, about 300 cP, about 400 cP, about 500 cP, about 600 cP, about 700 cP, about 800 cP, about 900 cP, about 1,000 cP, about 5,000 cP, about 10,000 cP, about 20,000 cP, about 50,000 cP, about 100,000 cP, or about 250,000 cP. In some embodiments, the viscosity modulating agent is not a poloxamer. In some embodiments, the viscosity modulating agent is a poloxamer. In some embodiments, the poloxamer is P407. In some embodiments, the viscosity modulating agent is povidone. In some embodiments, the viscosity modulating agent is carbomer. In some embodiments, the viscosity modulating agent is a polymer. In some embodiments, the viscosity modulating agent is silicon dioxide. In some embodiments, the viscosity modulating agent is silicon dioxide, poloxamer, carbomer, povidone, or a combination thereof. In some embodiments, the viscosity modulating agent is a polysaccharide, such as dextran or alginate. In some embodiments, the viscosity modulating agent is cellulose-based, such as hydroxypropyl cellulose, hydroxypropyl methylcellulose, carboxymethylcellulose, carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), and noncrystalline cellulose. In some embodiments, the viscosity modulating agent is polyvinyl alcohol (PVA). In some embodiments, the viscosity modulating agent is polyethylene glycol (PEG) based. In some embodiments, the viscosity modulating agent is silicon dioxide, poloxamer, carbomer, povidone, polysaccharide, cellulose-based, polyvinyl alcohol, polyethylene glycol, or a combination thereof. In some embodiments, the viscosity modulating agent is an oil. In some embodiments, the viscosity modulating agent is beeswax. In some embodiments, the viscosity modulating agent is vaseline. In some embodiments, the viscosity modulating agent is petroleum jelly. In some embodiments, the viscosity modulating agent is 12-hydroxystearic acid. In some embodiments, the formulation or composition comprises between about 0.01% to about 80% by weight of the viscosity modulating agent. In some embodiments, the formulation or composition comprises between about 0.01% to about 50% by weight of the viscosity modulating agent. In some embodiments, the formulation or composition comprises between about 0.01% to about 20% by weight of the viscosity modulating agent. In some embodiments, the formulation or composition comprises between about 0.01% to about 15% by weight of the viscosity modulating agent. In some embodiments, the formulation or composition comprises between about 0.01% to about 10% by weight of the viscosity modulating agent. In some embodiments, the formulation or composition comprises between about 0.01% to about 9% by weight of the viscosity modulating agent. In some embodiments, the formulation or composition comprises between about 0.01% to about 8% by weight of the viscosity modulating agent. In some embodiments, the formulation or composition comprises between about 0.01% to about 7% by weight of the viscosity modulating agent. In some embodiments, the formulation or composition comprises between about 0.01% to about 6% by weight of the viscosity modulating agent. In some embodiments, the formulation or composition comprises between about 0.01% to about 5% by weight of the viscosity modulating agent. In some embodiments, the formulation or composition comprises between about 0.01% to about 4% by weight of the viscosity modulating agent. In some embodiments, the formulation or composition comprises between about 0.01% to about 3% by weight of the viscosity modulating agent. In some embodiments, the formulation or composition comprises between about 0.01% to about 2% by weight of the viscosity modulating agent. In some embodiments, the formulation or composition comprises between about 0.01% to about 1% by weight of the viscosity modulating agent. In some embodiments, the formulation or composition comprises between about 0.1% to about 80% by weight of the viscosity modulating agent. In some embodiments, the formulation or composition comprises between about 0.1% to about 50% by weight of the viscosity modulating agent. In some embodiments, the formulation or composition comprises between about 0.1% to about 20% by weight of the viscosity modulating agent. In some embodiments, the formulation or composition comprises between about 0.1% to about 10% by weight of the viscosity modulating agent. In some embodiments, the formulation or composition comprises between about 0.1% to about 5% by weight of the viscosity modulating agent. In some embodiments, the formulation or composition comprises between about 1% to about 80% by weight of the viscosity modulating agent. In some embodiments, the formulation or composition comprises between about 1% to about 50% by weight of the viscosity modulating agent. In some embodiments, the formulation or composition comprises between about 1% to about 20% by weight of the viscosity modulating agent. In some embodiments, the formulation or composition comprises between about 1% to about 10% by weight of the viscosity modulating agent. In some embodiments, the formulation or composition comprises between about 1% to about 5% by weight of the viscosity modulating agent. In some embodiments, the formulation or composition comprises about 0.01%, about 0.05%, about 0.1%, about 0.2%, about 0.3%, about 0.4%, about 0.5%, about 0.6%, about 0.7%, about 0.8%, about 0.9%, about 1.0%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90% by weight of the viscosity modulating agent. In some embodiments, the formulation or composition comprises greater than about 0.01%, greater than about 0.05%, greater than about 0.1%, greater than about 0.2%, greater than about 0.3%, greater than about 0.4%, greater than about 0.5%, greater than about 0.6%, greater than about 0.7%, greater than about 0.8%, greater than about 0.9%, greater than about 1.0%, greater than about 2%, greater than about 3%, greater than about 4%, greater than about 5%, greater than about 6%, greater than about 7%, greater than about 8%, greater than about 9%, greater than about 10%, greater than about 11%, greater than about 12%, greater than about 13%, greater than about 14%, greater than about 15%, greater than about 16%, greater than about 17%, greater than about 18%, greater than about 19%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90% by weight of the viscosity modulating agent. In some embodiments, the formulation or composition comprises less than about 0.01%, less than about 0.05%, less than about 0.1%, less than about 0.2%, less than about 0.3%, less than about 0.4%, less than about 0.5%, less than about 0.6%, less than about 0.7%, less than about 0.8%, less than about 0.9%, less than about 1.0%, less than about 2%, less than about 3%, less than about 4%, less than about 5%, less than about 6%, less than about 7%, less than about 8%, less than about 9%, less than about 10%, less than about 11%, less than about 12%, less than about 13%, less than about 14%, less than about 15%, less than about 16%, less than about 17%, less than about 18%, less than about 19%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90% by weight of the viscosity modulating agent.

In some embodiments, the otic composition or formulation is free or substantially free of water. In some embodiments, the otic composition or formulation comprises less than 10% by weight of water. In some embodiments, the otic composition or formulation comprises less than 9% by weight of water. In some embodiments, the otic composition or formulation comprises less than 8% by weight of water. In some embodiments, the otic composition or formulation comprises less than 7% by weight of water. In some embodiments, the otic composition or formulation comprises less than 6% by weight of water. In some embodiments, the otic composition or formulation comprises less than 5% by weight of water. In some embodiments, the otic composition or formulation comprises less than 4% by weight of water. In some embodiments, the otic composition or formulation comprises less than 3% by weight of water. In some embodiments, the otic composition or formulation comprises less than 2% by weight of water. In some embodiments, the otic composition or formulation comprises less than 1% by weight of water. In some embodiments, the otic composition or formulation comprises less than 0.5% by weight of water. In some embodiments, the otic composition or formulation comprises less than 0.1% by weight of water. In some embodiments, an otic composition or formulation disclosed herein comprises less than about 50 ppm of water. In some embodiments, an otic composition or formulation disclosed herein comprises less than about 25 ppm of water. In some embodiments, an otic composition or formulation disclosed herein comprises less than about 20 ppm of water. In some embodiments, an otic composition or formulation disclosed herein comprises less than about 10 ppm of water. In some embodiments, an otic composition or formulation disclosed herein comprises less than about 5 ppm of water. In some embodiments, an otic composition or formulation disclosed herein comprises less than about 1 ppm of water.

In some embodiments, the otic composition or formulation is free or substantially free of poloxamer. In some embodiments, the otic composition or formulation is free or substantially free of poloxamer 407.

In some embodiments, the otic composition or formulation is free or substantially free of C1-C6 alcohols or C1-C6 glycols. In some embodiments, the otic composition or formulation is free or substantially free of C1-C6 alcohols. In some embodiments, the otic composition or formulation is free or substantially free of C1-C6 glycols. In some embodiments, the otic composition or formulation comprises less than 10% by weight of C1-C6 alcohols or C1-C6 glycols. In some embodiments, the otic composition or formulation comprises less than 9% by weight of C1-C6 alcohols or C1-C6 glycols. In some embodiments, the otic composition or formulation comprises less than 8% by weight of C1-C6 alcohols or C1-C6 glycols. In some embodiments, the otic composition or formulation comprises less than 7% by weight of C1-C6 alcohols or C1-C6 glycols. In some embodiments, the otic composition or formulation comprises less than 6% by weight of C1-C6 alcohols or C1-C6 glycols. In some embodiments, the otic composition or formulation comprises less than 5% by weight of C1-C6 alcohols or C1-C6 glycols. In some embodiments, the otic composition or formulation comprises less than 4% by weight of C1-C6 alcohols or C1-C6 glycols. In some embodiments, the otic composition or formulation comprises less than 3% by weight of C1-C6 alcohols or C1-C6 glycols. In some embodiments, the otic composition or formulation comprises less than 2% by weight of C1-C6 alcohols or C1-C6 glycols. In some embodiments, the otic composition or formulation comprises less than 1% by weight of C1-C6 alcohols or C1-C6 glycols. In some embodiments, the otic composition or formulation comprises less than 0.5% by weight of C1-C6 alcohols or C1-C6 glycols. In some embodiments, the otic composition or formulation comprises less than 0.1% by weight of C1-C6 alcohols or C1-C6 glycols. In some embodiments, an otic composition or formulation disclosed herein comprises less than about 50 ppm of each of C1-C6 alcohols or C1-C6 glycols. In some embodiments, an otic composition or formulation disclosed herein comprises less than about 25 ppm of each of C1-C6 alcohols or C1-C6 glycols. In some embodiments, an otic composition or formulation disclosed herein comprises less than about 20 ppm of each of C1-C6 alcohols or C1-C6 glycols. In some embodiments, an otic composition or formulation disclosed herein comprises less than about 10 ppm of each of C1-C6 alcohols or C1-C6 glycols. In some embodiments, an otic composition or formulation disclosed herein comprises less than about 5 ppm of each of C1-C6 alcohols or C1-C6 glycols. In some embodiments, an otic composition or formulation disclosed herein comprises less than about 1 ppm of each of C1-C6 alcohols or C1-C6 glycols.

In some embodiments, the otic composition or formulation is free or substantially free of C1-C4 alcohols or C1-C4 glycols. In some embodiments, the otic composition or formulation is free or substantially free of C1-C4 alcohols. In some embodiments, the otic composition or formulation is free or substantially free of C1-C4 glycols. In some embodiments, the otic composition or formulation comprises less than 10% by weight of C1-C4 alcohols or C1-C4 glycols. In some embodiments, the otic composition or formulation comprises less than 9% by weight of C1-C4 alcohols or C1-C4 glycols. In some embodiments, the otic composition or formulation comprises less than 8% by weight of C1-C4 alcohols or C1-C4 glycols. In some embodiments, the otic composition or formulation comprises less than 7% by weight of C1-C4 alcohols or C1-C4 glycols. In some embodiments, the otic composition or formulation comprises less than 6% by weight of C1-C4 alcohols or C1-C4 glycols. In some embodiments, the otic composition or formulation comprises less than 5% by weight of C1-C4 alcohols or C1-C4 glycols. In some embodiments, the otic composition or formulation comprises less than 4% by weight of C1-C4 alcohols or C1-C4 glycols. In some embodiments, the otic composition or formulation comprises less than 3% by weight of C1-C4 alcohols or C1-C4 glycols. In some embodiments, the otic composition or formulation comprises less than 2% by weight of C1-C4 alcohols or C1-C4 glycols. In some embodiments, the otic composition or formulation comprises less than 1% by weight of C1-C4 alcohols or C1-C4 glycols. In some embodiments, the otic composition or formulation comprises less than 0.5% by weight of C1-C4 alcohols or C1-C4 glycols. In some embodiments, the otic composition or formulation comprises less than 0.1% by weight of C1-C4 alcohols or C1-C4 glycols. In some embodiments, an otic composition or formulation disclosed herein comprises less than about 50 ppm of each of C1-C4 alcohols or C1-C4 glycols. In some embodiments, an otic composition or formulation disclosed herein comprises less than about 25 ppm of each of C1-C4 alcohols or C1-C4 glycols. In some embodiments, an otic composition or formulation disclosed herein comprises less than about 20 ppm of each of C1-C4 alcohols or C1-C4 glycols. In some embodiments, an otic composition or formulation disclosed herein comprises less than about 10 ppm of each of C1-C4 alcohols or C1-C4 glycols. In some embodiments, an otic composition or formulation disclosed herein comprises less than about 5 ppm of each of C1-C4 alcohols or C1-C4 glycols. In some embodiments, an otic composition or formulation disclosed herein comprises less than about 1 ppm of each of C1-C4 alcohols or C1-C4 glycols.

By way of non-limiting example, the use of the following commonly used solvents should be limited, reduced or eliminated when formulating agents for administration to the ear: alcohols, propylene glycol, and cyclohexane. Thus, in some embodiments, an otic composition or formulation disclosed herein is free or substantially free of alcohols, propylene glycol, and cyclohexane. In some embodiments, an otic composition or formulation disclosed herein comprises less than about 50 ppm of each of alcohols, propylene glycol, and cyclohexane. In some embodiments, an otic composition or formulation disclosed herein comprises less than about 25 ppm of each of alcohols, propylene glycol, and cyclohexane. In some embodiments, an otic composition or formulation disclosed herein comprises less than about 20 ppm of each of alcohols, propylene glycol, and cyclohexane. In some embodiments, an otic composition or formulation disclosed herein comprises less than about 10 ppm of each of alcohols, propylene glycol, and cyclohexane. In some embodiments, an otic composition or formulation disclosed herein comprises less than about 5 ppm of each of alcohols, propylene glycol, and cyclohexane. In some embodiments, an otic composition or formulation disclosed herein comprises less than about 1 ppm of each of alcohols, propylene glycol, and cyclohexane.

In some embodiments, therapeutic agent, or pharmaceutically acceptable prodrug or salt thereof, is multiparticulate. In some embodiments, the therapeutic agent, or pharmaceutically acceptable prodrug or salt thereof, is essentially in the form of micronized particles. In some embodiments, the therapeutic agent, or pharmaceutically acceptable prodrug or salt thereof, is essentially dissolved in the otic pharmaceutical formulation or composition.

Poloxamers

In some embodiments, the otic formulations or compositions described herein further comprise poloxamer. In some embodiments, the otic formulations or compositions described herein are free or substantially free of poloxamer. An example of a poloxamer includes Poloxamer 407 (PF-127) is a nonionic surfactant composed of polyoxyethylene-polyoxypropylene copolymers. Other commonly used poloxamers also include but are not limited to 188 (F-68 grade), 237 (F-87 grade), 338 (F-108 grade). Aqueous solutions of poloxamers are stable in the presence of acids, alkalis, and metal ions. PF-127 is a commercially available polyoxyethylene-polyoxypropylene triblock copolymer, with an average molar mass of 13,000. It contains approximately 70% ethylene oxide, which accounts for its hydrophilicity. It is one of the series of poloxamer ABA block copolymers, whose members share the chemical formula shown below.

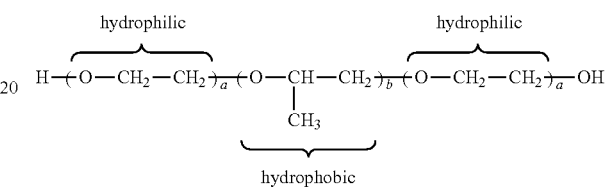

In some embodiments, the otic formulations or compositions disclosed herein comprise PF-127, 188 (F-68 grade), 237 (F-87 grade), or 338 (F-108 grade). In some embodiments, the otic formulations or compositions disclosed herein comprise poloxamer 407.

In some embodiments, the otic formulations or compositions disclosed herein are free or substantially free of PF-127, 188 (F-68 grade), 237 (F-87 grade), or 338 (F-108 grade). In some embodiments, the otic formulations or compositions disclosed here are free or substantially free of poloxamer 407.

In certain embodiments, the thickening agents (i.e., viscosity enhancing agents or viscosity modulating agents) are also utilized in the otic formulations or compositions presented herein. In some embodiments, the thickening agent is a cellulose based thickening agent. In some instances, the addition of a thickening agent introduces a diffusional barrier and reduces the rate of release of the therapeutic agent. In some embodiments, the thickening agent or viscosity enhancer or viscosity modulating agent is not a poloxamer. In some embodiments, the thickening agent or viscosity enhancer or viscosity modulating agent is not poloxamer 407. In some embodiments, the thickening agent or viscosity enhancer or viscosity modulating agent is a poloxamer. In some embodiments, the thickening agent or viscosity enhancer or viscosity modulating agent is poloxamer 407.

In some embodiments, the otic formulations or compositions disclosed herein also contain preservatives, cosolvents, suspending agents, viscosity enhancing agents, ionic-strength and osmolality adjustors and other excipients in addition to buffering agents. Suitable water soluble preservatives which are employed in the drug delivery vehicle are sodium bisulfite, sodium thiosulfate, ascorbate, benzalkonium chloride, chorobutanol, thimerosal, parabens, benzyl alcohol, phenylethanol and others. These agents are present, generally, in amounts of about 0.001% to about 5% by weight and, preferably, in the amount of about 0.01 to about 2% by weight.

Suitable water soluble buffering agents are alkali or alkaline earth metal carbonates, phosphates, bicarbonates, citrates, borates, acetates, succinates and the like, such as sodium phosphate, citrate, borate, acetate, bicarbonate, carbonate and tromethamine (TRIS). These agents are present in amounts sufficient to maintain the pH of the system at 7.4±0.2 and preferably, 7.4. As such, the buffering agent is as much as 5% on a weight basis of the total composition in some instances.

In some embodiments, cosolvents are used to enhance drug solubility; however, some drugs are insoluble.

Mucoadhesive Excipients

In some embodiments, mucoadhesive characteristics are also imparted to otic formulations disclosed herein, by incorporation of mucoadhesive carbomers, such as Carbopol 934P, to the composition (Majithiya et al, AAPS PharmSciTech (2006), 7(3), p. E1; EP0551626).

The term 'mucoadhesion' is commonly used for materials that bind to the mucin layer of a biological membrane. To serve as mucoadhesive polymers, the polymers should possess some general physiochemical features such as predominantly anionic hydrophilicity with numerous hydrogen bond forming groups, suitable surface property for wetting mucus/mucosal tissue surfaces and sufficient flexibility to penetrate the mucus network. In some embodiments, mucoadhesive formulations or compositions described herein adhere to the round window and/or the oval window and/or any inner ear structure.

Mucoadhesive agents including, but not limited to, at least one soluble polyvinylpyrrolidone polymer (PVP); a water-swellable, fibrous, cross-linked carboxy-functional polymer; a crosslinked poly(acrylic acid) (e.g. Carbopol 947P); a carbomer homopolymer; a carbomer copolymer; a hydrophilic polysaccharide gum, maltodextrin, a cross-linked alignate gum gel, a water-dispersible polycarboxylated vinyl polymer, at least two particulate components selected from the group consisting of titanium dioxide, silicon dioxide, and clay, or a mixture thereof. In some embodiments, the mucoadhesive agent is used in combination with a viscosity increasing excipient, or are used alone to increase the interaction of the composition with a mucosal layer. In one non-limiting example, the mucoadhesive agent is maltodextrin and/or an alginate gum. Those of ordinary skill in the art will recognize that the mucoadhesive character imparted to the formulation or composition should be at a level that is sufficient to deliver an effective amount of the composition to, for example, the mucosal membrane of the round window in an amount that coats the mucosal membrane, and thereafter deliver the composition to the affected areas, including by way of example only, the vestibular and/or cochlear structures of the auris interna. Those of ordinary skill in the art are able to determine the mucoadhesive characteristics of the compositions provided herein, and thus determine appropriate ranges. One method for determining sufficient mucoadhesiveness includes monitoring changes in the interaction of the composition with a mucosal layer, including but not limited to measuring changes in residence or retention time of the composition in the absence and presence of the excipient.

Mucoadhesive agents have been described, for example, in U.S. Pat. Nos. 6,638,521, 6,562,363, 6,509,028, 6,348,502, 6,319,513, 6,306,789, 5,814,330, and 4,900,552, each of which is hereby incorporated by reference in its entirety.

In one non-limiting example, the mucoadhesive agent is maltodextrin. Maltodextrin is a carbohydrate produced by the hydrolysis of starch that are derived from corn, potato, wheat or other plant products. Maltodextrin are used either alone or in combination with other mucoadhesive agents to impart mucoadhesive characteristics on the formulations or compositions disclosed herein. In one embodiment, a combination of maltodextrin and a carbopol polymer are used to increase the mucoadhesive characteristics of the formulations or compositions disclosed herein.

In another non-limiting example, a mucoadhesive agent is, for example, at least two particulate components selected from titanium dioxide, silicon dioxide, and clay, wherein the composition is not further diluted with any liquid prior to administration and the level of silicon dioxide, if present, is from about 3% to about 15%, by weight of the composition. Silicon dioxide, if present, are selected from the group consisting of fumed silicon dioxide, precipitated silicon dioxide, coacervated silicon dioxide, gel silicon dioxide, and mixtures thereof. Clay, if present, are kaolin minerals, serpentine minerals, smectites, illite or a mixture thereof. For example, clay is laponite, bentonite, hectorite, saponite, montmorillonites or a mixture thereof.

Stabilizers

In one embodiment, stabilizers are selected from, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some embodiments, amide analogues of stabilizers are also used. In a further embodiment, the chosen stabilizer changes the hydrophobicity of the formulation or composition (e.g., oleic acid, waxes), or improves the mixing of various components in the formulation or composition (e.g., ethanol), controls the moisture level in the formula (e.g., PVP or polyvinyl pyrrolidone), controls the mobility of the phase (substances with melting points higher than room temperature such as long chain fatty acids, alcohols, esters, ethers, amides etc. or mixtures thereof; waxes), and/or improves the compatibility of the formula with encapsulating materials (e.g., oleic acid or wax). In another embodiment some of these stabilizers are used as solvents/co-solvents (e.g., ethanol). In a further embodiment, stabilizers are present in sufficient amount to inhibit the degradation of the active pharmaceutical ingredient. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the stabilizer is silicon dioxide. In some embodiments, the silicon dioxide is stabilizer in suspension formulations. In some embodiments, the silicon dioxide is an anticaking agent (i.e. an agent that prevents the formation of lumps). In some embodiments, the silicon dioxide is an anticaking agent (i.e. an agent that prevents the formation of lumps) that stabilizes suspension formulations. In some embodiments, the stabilizer is an anticaking agent.

In some embodiments, the stabilizer is a carbomer. In some embodiments, the carbomer is a complexing agent for positively charged proteins. In some embodiments, the positively charged protein in the complex has reduced solubility and therefore is released slowly from the formulation.

In some embodiments, the stabilizer is a complexing agent. In some embodiments, stabilizer interacts with the therapeutic agent to form a complex. In some embodiments, the stabilizer is a protein complexing agent. In some embodiments, the protein complexing agent is a polymer with a charge that is opposite to charge of the protein therapeutic agent. In some embodiments, the polymer is carbomer or alginate. In some embodiments, the stabilizer forms a complex with the protein therapeutic agent that reduces the solubilty of the protein therapeutic agent. In some embodiments, the stabilizer forms a complex with the protein therapeutic agent that provides for the slow release of the protein therapeutic agent. In some embodiments, the stabilizer forms a complex with the protein therapeutic agent that provides for the sustained release of the protein therapeutic agent.

In some embodiments, the stabilizer is a neutral polymer. Examples of a neutral polymer include but are not limited to povidone, poloxamer, and HMPC. In some embodiments, the neutral polymer forms a polymer matrix that encapsulates the therapeutic agent and provides for the slow release of the therapeutic agent. In some embodiments, the neutral polymer forms a polymer matrix that encapsulates the therapeutic agent and provides for the sustained release of the therapeutic agent.

Additional useful auris-acceptable formulations or compositions include one or more anti-aggregation additives to enhance stability of otic formulations or compositions by reducing the rate of protein aggregation. The anti-aggregation additive selected depends upon the nature of the conditions to which the therapeutic agents, or otic agents, for example anti-TNF antibodies are exposed. For example, certain formulations or compositions undergoing agitation and thermal stress require a different anti-aggregation additive than a formulation undergoing lyophilization and reconstitution. Useful anti-aggregation additives include, by way of example only, urea, guanidinium chloride, simple amino acids such as glycine or arginine, sugars, polyalcohols, polysorbates, polymers such as polyethylene glycol and dextrans, alkyl saccharides, such as alkyl glycoside, and surfactants.

Other useful formulations or compositions include one or more antioxidants to enhance chemical stability where required. Suitable antioxidants include, by way of example only, ascorbic acid and sodium metabisulfite. In one embodiment, antioxidants are selected from metal chelating agents, thiol containing compounds and other general stabilizing agents.

Still other useful formulations or compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

In some embodiments, the pharmaceutical formulations or compositions described herein are stable with respect to compound degradation over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the formulations or compositions described herein are stable with respect to compound degradation over a period of at least about 1 week. Also described herein are formulations or compositions that are stable with respect to compound degradation over a period of at least about 1 month.

In other embodiments, an additional surfactant (co-surfactant) and/or buffering agent is combined with one or more of the pharmaceutically acceptable vehicles previously described herein so that the surfactant and/or buffering agent maintains the product at an optimal pH for stability. Suitable co-surfactants include, but are not limited to: a) natural and synthetic lipophilic agents, e.g., phospholipids, cholesterol, and cholesterol fatty acid esters and derivatives thereof; b) nonionic surfactants, which include for example, polyoxyethylene fatty alcohol esters, sorbitan fatty acid esters (Spans), polyoxyethylene sorbitan fatty acid esters (e.g., polyoxyethylene (20) sorbitan monooleate (Tween 80), polyoxyethylene (20) sorbitan monostearate (Tween 60), polyoxyethylene (20) sorbitan monolaurate (Tween 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremphor A25, Cremphor A20, Cremophor® EL) and other Cremophors, sulfosuccinates, alkyl sulphates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij® 700, ascorbyl-6-palmitate, stearylamine, sodium lauryl sulfate, polyoxethyleneglycerol triiricinoleate, and any combinations or mixtures thereof; c) anionic surfactants include, but are not limited to, calcium carboxymethylcellulose, sodium carboxymethylcellulose, sodium sulfosuccinate, dioctyl, sodium alginate, alkyl polyoxyethylene sulfates, sodium lauryl sulfate, triethanolamine stearate, potassium laurate, bile salts, and any combinations or mixtures thereof; and d) cationic surfactants such as quarternary ammonium compounds, benzalkonium chloride, cetyltrimethylammonium bromide, and lauryldimethylbenzyl-ammonium chloride.

In a further embodiment, when one or more co-surfactants are utilized in the formulations or compositions of the present disclosure, they are combined, e.g., with a pharmaceutically acceptable vehicle and is present in the final formulation, e.g., in an amount ranging from about 0.1% to about 20%, from about 0.5% to about 10%. In one embodiment, the surfactant has an HLB value of 0 to 20. In additional embodiments, the surfactant has an HLB value of 0 to 3, of 4 to 6, of 7 to 9, of 8 to 18, of 13 to 15, of 10 to 18.

Preservatives

In some embodiments, the otic formulations or compositions described herein is free of preservatives. In some embodiments, a formulation or composition disclosed herein comprises a preservative. Suitable auris-acceptable preservatives for use in a formulation or composition disclosed herein include, but are not limited to benzoic acid, boric acid, p-hydroxybenzoates, benzyl alcohol, lower alkyl alcohols (e.g., ethanol, butanol or the like), quaternary compounds, stabilized chlorine dioxide, mercurials, such as merfen and thiomersal, mixtures of the foregoing and the like. Suitable preservatives for use with a formulation disclosed herein are not ototoxic. In some embodiments, a formulation or composition disclosed herein does not include a preservative that is ototoxic. In some embodiments, a formulation or composition disclosed herein does not include benzalkonium chloride or benzethonium chloride.

In certain embodiments, any otic formulation or composition described herein has an endotoxin level of less than 0.5 EU/kg, less than 0.4 EU/kg or less than 0.3 EU/kg. In certain embodiments, any otic formulation or composition described herein has less than about 60 colony forming units (CFU), has less than about 50 colony forming units, has less than about 40 colony forming units, has less than about 30 colony forming units of microbial agents per gram of formulation or composition. In certain embodiments, any controlled release formulation or composition described herein is substantially free of pyrogens.

In a further embodiment, the preservative is, by way of example only, an antimicrobial agent, within the formulation or composition presented herein. In one embodiment, the formulation or composition includes a preservative such as by way of example only, methyl paraben. In another embodiment, the methyl paraben is at a concentration of about 0.05% to about 1.0%, about 0.1% to about 0.2%. In certain embodiments, the preservative employed in any auris-compatible formulation described herein is an antioxidant (e.g., butyl hydroxytoluene (BHT) or the like, as described herein). In certain embodiments, an antioxidant preservative is non-toxic and/or non-irritating to the inner ear environment.

Carriers

Suitable carriers for use in a formulation or composition described herein include, but are not limited to, any pharmaceutically acceptable solvent. For example, suitable solvents include polyalkylene glycols such as, but not limited to, polyethylene glycol (PEG) and any combinations or mixtures thereof. In other embodiments, the base is a combination of a pharmaceutically acceptable surfactant and solvent.

In some embodiments, other excipients include, sodium stearyl fumarate, diethanolamine cetyl sulfate, isostearate, polyethoxylated castor oil, benzalkonium chloride, nonoxyl 10, octoxynol 9, sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate), lecithins, phospholipids, phosphatidyl cholines (c8-c18), phosphatidylethanolamines (c8-c18), phosphatidylglycerols (c8-c18), pharmaceutical acceptable salts thereof and combinations or mixtures thereof.

In further embodiments, the carrier is polyethylene glycol. Polyethylene glycol is available in many different grades having varying molecular weights. For example, polyethylene glycol is available as PEG 200; PEG 300; PEG 400; PEG 540 (blend); PEG 600; PEG 900; PEG 1000; PEG 1450; PEG 1540; PEG 2000; PEG 3000; PEG 3350; PEG 4000; PEG 4600 and PEG 8000. For purposes of the present disclosure, all grades of polyethylene glycol are contemplated for use in preparation of a formulation described herein. In some embodiments the polyethylene glycol used to prepare a formulation described herein is PEG 300.

In other embodiments, the carrier is a polysorbate. Polysorbates are nonionic surfactants of sorbitan esters. Polysorbates useful in the present disclosure include, but are not limited to polysorbate 20, polysorbate 40, polysorbate 60, polysorbate 80 (Tween 80) and any combinations or mixtures thereof. In further embodiments, polysorbate 80 is utilized as the pharmaceutically acceptable carrier.

In some embodiments, the percentage of active pharmaceutical ingredient is varied between about 0.01% and about 20%, between about 0.01% and about 10%, between about 0.01% and about 5% or more of the weight or volume of the total pharmaceutical formulation or composition. In some embodiments, the amount of the compound(s) in each therapeutically useful formulation or composition is prepared in such a way that a suitable dosage will be obtained in any given unit dose of the compound. Factors such as solubility, bioavailability, biological half-life, route of administration, product shelf life, as well as other pharmacological considerations are contemplated herein and the preparation of such pharmaceutical formulations or compositions is presented herein.

Suspending Agents

In one embodiment is active pharmaceutical ingredient in a pharmaceutically acceptable formulation or composition wherein the formulation or composition comprises at least one suspending agent.

In one embodiment, at least one cytotoxic agent is included in a pharmaceutically acceptable enhanced viscosity formulation or composition wherein the formulation or composition further comprises at least one suspending agent, wherein the suspending agent assists in imparting controlled release characteristics to the formulation or composition. In some embodiments, suspending agents also serve to increase the viscosity of the auris-acceptable cytotoxic agent formulations or compositions.

Suspending agents include by example only, compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol has a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like. In some embodiments, useful aqueous suspensions also contain one or more polymers as suspending agents. Useful polymers include water-soluble polymers such as cellulosic polymers, e.g., hydroxypropyl methylcellulose, and water-insoluble polymers such as cross-linked carboxyl-containing polymers.

In some embodiments, the formulations or compositions include excipients, other medicinal or pharmaceutical agents, carriers, adjuvants, such as preserving, stabilizing, wetting or emulsifying agents, solution promoters, and salts. In some embodiments, the excipients, carriers, adjuvants, are useful in forming a pharmaceutically acceptable formulation or composition. In some embodiments, the formulation or composition comprises a stabilizer. In another embodiment the formulation or composition comprises a solubilizer. In a further embodiment the formulation or composition comprises an antifoaming agent. In yet a further embodiment, the formulation or composition comprises an antioxidant. In yet another embodiment, the formulation or composition comprises a dispersing agent. In one embodiment, the formulation or composition comprises a surfactant. In yet another embodiment, the formulation or composition comprises a wetting agent.

Viscosity Enhancing Agents

In one embodiment is a formulation or composition that is free or substantially free of a viscosity enhancing agent. In one embodiment is a formulation or composition comprising at least one active pharmaceutical ingredient and a viscosity agent. Also described herein are controlled release formulations or compositions that is free or substantially free of a viscosity enhancing agent. Also described herein are controlled release formulations or compositions comprising a therapeutic agent and a viscosity enhancing agent. In some embodiments, suitable viscosity-enhancing agents do not include poloxamers. Suitable viscosity-enhancing agents include by way of example only, thickening agents and suspending agents. In one embodiment, the enhanced viscosity formulation or composition does not include a pharmaceutically acceptable buffer. In other embodiments, the enhanced viscosity formulation or composition includes a pharmaceutically acceptable buffer. Sodium chloride or other tonicity agents are optionally used to adjust tonicity, if necessary.

Described herein are formulations or compositions comprising an active pharmaceutical ingredient and a thickening agent. Suitable thickening agents include by way of example only, suspending agents. In one embodiment, the thickened formulation or composition does not include a pharmaceutically acceptable buffer. In another embodiment, the thickened formulation or composition includes a pharmaceutically acceptable buffer.

By way of example only, the auris-acceptable viscosity agent include hydroxypropyl methylcellulose, hydroxyethyl cellulose, polyvinylpyrrolidone (PVP: povidone), carboxymethyl cellulose, polyvinyl alcohol, sodium chondroitin sulfate, sodium hyaluronate. Other viscosity agents that are used in pharmaceutical compositions described herein include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, polyethylene glycol (e.g. PEG 200-4500), gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly (methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, Splenda® (dextrose, maltodextrin and sucralose) or combinations thereof. In specific embodiments, the viscosity-enhancing excipient is a combination of methylcellulose (MC) and CMC. In another embodiment, the viscosity-enhancing agent is a combination of carboxymethylated chitosan, or chitin, and alginate. The combination of chitin and alginate with the CNS modulators disclosed herein acts as a controlled release formulation, restricting the diffusion of the CNS modulator from the formulation. Moreover, the combination of carboxymethylated chitosan and alginate is optionally used to assist in increasing the permeability of any active agent described herein through the round window membrane.

In further embodiments, the auris formulation or composition contains a viscosity enhancing agent or viscosity modulating agent sufficient to provide a viscosity of between about 10 and 1,000,000 centipoise, between about 100 and 1,000,000 centipoise, between about 500 and 1,000,000 centipoise, between about 750 and 1,000,000 centipoise; between about 1000 and 40,000 centipoise; between about 2000 and 35,000 centipoise; between about 3000 and 30,000 centipoise; between about 4000 and 25,000 centipoise; between about 5000 and 20,000 centipoise; or between about 6000 and 15,000 centipoise.

In further embodiments, the auris formulation or composition contains a viscosity enhancing agent or viscosity modulating agent sufficient to provide a viscosity of about 2 cP to about 250,000 cP, about 2 cP to about 100,000 cP, about 2 cP to about 50,000 cP, about 2 cP to about 25,000 cP, about 2 cP to about 10,000 cP, about 2 cP to about 5,000 cP, about 2 cP to about 1,000 cP, about 2 cP to about 500 cP, about 2 cP to about 250 cP, about 2 cP to about 100 cP, about 2 cP to about 90 cP, about 2 cP to about 80 cP, about 2 cP to about 70 cP, about 2 cP to about 60 cP, about 2 cP to about 50 cP, about 2 cP to about 40 cP, about 2 cP to about 30 cP, about 2 cP to about 20 cP, or about 2 cP to about 10 cP. In some embodiments, the formulation or composition has a viscosity of about 2 cP, about 5 cP, about 10 cP, about 20 cP, about 30 cP, about 40 cP, about 50 cP, about 60 cP, about 70 cP, about 80 cP, about 90 cP, about 100 cP, about 200 cP, about 300 cP, about 400 cP, about 500 cP, about 600 cP, about 700 cP, about 800 cP, about 900 cP, about 1,000 cP, about 5,000 cP, about 10,000 cP, about 20,000 cP, about 50,000 cP, about 100,000 cP, or about 250,000 cP.

In some embodiments, the viscosity of the otic formulations or compositions presented herein are measured by any means described herein. For example, in some embodiments, an LVDV-II+CP Cone Plate Viscometer and a Cone Spindle CPE-40 is used to calculate the viscosity of the formulation described herein. In other embodiments, a Brookfield (spindle and cup) viscometer is used to calculate the viscosity of the formulation or composition described herein. In some embodiments, the viscosity ranges referred to herein are measured at room temperature. In other embodiments, the viscosity ranges referred to herein are measured at body temperature.

Auris-Acceptable Penetration Enhancers

In another embodiment the formulation or composition further comprises one or more penetration enhancers. Penetration into biological membranes is enhanced by the presence of penetration enhancers. Penetration enhancers are chemical entities that facilitate transport of coadministered substances across biological membranes. Penetration enhancers are grouped according to chemical structure. Surfactants, both ionic and non-ionic, such as sodium lauryl sulfate, sodium laurate, polyoxyethylene-20-cetyl ether, laureth-9, sodium dodecylsulfate, dioctyl sodium sulfosuccinate, polyoxyethylene-9-lauryl ether (PLE), Tween 80, nonylphenoxypolyethylene (NP-POE), polysorbates and the like, function as penetration enhancers. Bile salts (such as sodium glycocholate, sodium deoxycholate, sodium taurocholate, sodium taurodihydrofusidate, sodium glycodihydrofusidate and the like), fatty acids and derivatives (such as oleic acid, caprylic acid, mono- and di-glycerides, lauric acids, acylcholines, caprylic acids, acylcarnitines, sodium caprates and the like), chelating agents (such as EDTA, citric acid, salicylates and the like), sulfoxides (such as dimethyl sulfoxide (DMSO), decylmethyl sulfoxide and the like), and alcohols (such as ethanol, isopropanol, propylene glycol, polyethylene glycol, glycerol, propanediol and the like) also function as penetration enhancers. In addition, the peptide-like penetration enhancers described in U.S. Pat. Nos. 7,151, 191, 6,221,367 and 5,714,167, herein incorporated by references for such disclosure, are contemplated as an additional embodiment. These penetration enhancers are amino-acid and peptide derivatives and enable drug absorption by passive transcellular diffusion without affecting the integrity of membranes or intercellular tight junctions. In some embodiments, a penetration enhancer is hyaluronic acid.

In some embodiments, the auris acceptable penetration enhancer is a surfactant. In some embodiments, the auris acceptable penetration enhancer is a surfactant comprising an alkyl-glycoside and/or a saccharide alkyl ester. As used herein, an "alkyl-glycoside" means a compound comprising any hydrophilic saccharide (e.g. glucose, fructose, sucrose, maltose, or glucose) linked to a hydrophobic alkyl. In some embodiments, the auris acceptable penetration enhancer is a surfactant comprising an alkyl-glycoside wherein the alkylglycoside comprises a sugar linked to a hydrophobic alkyl (e.g., an alkyl comprising about 6 to about 25 carbon atoms) by an amide linkage, an amine linkage, a carbamate linkage, an ether linkage, a thioether linkage, an ester linkage, a thioester linkage, a glycosidic linkage, a thioglycosidic linkage, and/or a ureide linkage. In some embodiments, the auris acceptable penetration enhancer is a surfactant comprising hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-maltoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-glucoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-sucroside; hexyl-, heptyl-, octyl-, dodecyl-, tridecyl-, and tetradecyl-β-D-thiomaltoside; heptyl- or octyl-1-thio-α- or β-D-glucopyranoside; alkyl thiosucroses; alkyl maltotriosides; long chain aliphatic carbonic acid amides of sucrose β-aminoalkyl ethers; derivatives of palatinose or isomaltamine linked by an amide linkage to an alkyl chain and derivatives of isomaltamine linked by urea to an alkyl chain; long chain aliphatic carbonic acid ureides of sucrose β-amino-alkyl ethers and long chain aliphatic carbonic acid amides of sucrose β-amino-alkyl ethers. In some embodiments, the auris acceptable penetration enhancer is a surfactant comprising an alkyl-glycoside wherein the alkyl glycoside is maltose, sucrose, glucose, or a combination thereof linked by a glycosidic linkage to an alkyl chain of 9-16 carbon atoms (e.g., nonyl-, decyl-, dodecyl- and tetradecyl sucroside; nonyl-, decyl-, dodecyl- and tetradecyl glucoside; and nonyl-, decyl-, dodecyl- and tetradecyl maltoside). In some embodiments, the auris acceptable penetration enhancer is a surfactant comprising an alkyl-glycoside wherein the alkyl glycoside is dodecylmaltoside, tridecylmaltoside, and tetradecylmaltoside. In some embodiments, the auris acceptable penetration enhancer is a surfactant comprising an alkyl-glycoside wherein the alkyl glycoside is tetradecyl-β-D-maltoside. In some embodiments, the auris acceptable penetration enhancer is a surfactant comprising an alkyl-glycoside wherein the alkyl-glycoside is a disaccharide with at least one glucose. n some embodiments, the auris acceptable penetration enhancer is a surfactant comprising α-D-glucopyranosyl-O-glycopyranoside, n-Dodecyl-4-O-α-D-glucopyranosyl-β-glycopyranoside, and/or n-tetradecyl-4-O-α-D-glucopyranosyl-β-glycopyranoside. In some embodiments, the auris acceptable penetration enhancer is a surfactant comprising an alkyl-glycoside wherein the alkyl-glycoside has a critical micelle concentration (CMC) of less than about 1 mM in pure water or in aqueous solutions. In some embodiments, the auris acceptable penetration enhancer is a surfactant comprising an alkyl-glycoside wherein an oxygen atom within the alkyl-glycoside is substituted with a sulfur atom. In some embodiments, the auris acceptable penetration enhancer is a surfactant comprising an alkyl-glycoside wherein the alkylglycoside is the β anomer. In some embodiments, the auris acceptable penetration enhancer is a surfactant comprising an alkyl-glycoside wherein the alkylglycoside comprises 90%, 91%, 92%, 93%, 94%, 95%, 96%, 97%, 98%, 99%, 99.1%, 99.5%, or 99.9% of the β anomer.

In certain instances, the penetration enhancing agent is a hyaluronidase. In certain instances, a hyaluronidase is a human or bovine hyaluronidase. In some instances, a hyaluronidase is a human hyaluronidase (e.g., hyaluronidase found in human sperm, PH20 (Halozyme), Hyelenex® (Baxter International, Inc.)). In some instances, a hyaluronidase is a bovine hyaluronidase (e.g., bovine testicular hyaluronidase, Amphadase® (Amphastar Pharmaceuticals), Hydase® (PrimaPharm, Inc). In some instances, a hyluronidase is an ovine hyaluronidase, Vitrase® (ISTA Pharmaceuticals). In certain instances, a hyaluronidase described herein is a recombinant hyaluronidase. In some instances, a hyaluronidase described herein is a humanized recombinant hyaluronidase. In some instances, a hyaluronidase described herein is a pegylated hyaluronidase (e.g., PEGPH20 (Halozyme)).

Foams and Paints

In Some Embodiments, the Auris Therapeutic Agents Disclosed Herein are Dispensed as an auris-acceptable paint. As used herein, paints (also known as film formers) are solutions comprised of a solvent, a monomer or polymer, an active agent, and optionally one or more pharmaceutically-acceptable excipients. After application to a tissue, the solvent evaporates leaving behind a thin coating comprised of the monomers or polymers, and the active agent. The coating protects active agents and maintains them in an immobilized state at the site of application. This decreases the amount of active agent which are lost and correspondingly increases the amount delivered to the subject. By way of non-limiting example, paints include collodions (e.g. Flexible Collodion, USP), and solutions comprising saccharide siloxane copolymers and a cross-linking agent. Collodions are ethyl ether/ethanol solutions containing pyroxylin (a nitrocellulose). After application, the ethyl ether/ethanol solution evaporates leaving behind a thin film of pyroxylin. In solutions comprising saccharide siloxane copolymers, the saccharide siloxane copolymers form the coating after evaporation of the solvent initiates the cross-linking of the saccharide siloxane copolymers. For additional disclosures regarding paints, see Remington: The Science and Practice of Pharmacy which is hereby incorporated in its entirety. The paints contemplated for use herein, are flexible such that they do not interfere with the propagation of pressure waves through the ear. Further, the paints are applied as a liquid (i.e. solution, suspension, or emulsion), a semisolid (i.e. a gel, foam, paste, or jelly) or an aerosol.

In some embodiments, the auris therapeutic agents disclosed herein are dispensed as a controlled-release foam. Examples of suitable foamable carriers for use in the compositions disclosed herein include, but are not limited to, alginate and derivatives thereof, carboxymethylcellulose and derivatives thereof, collagen, polysaccharides, including, for example, dextran, dextran derivatives, pectin, starch, modified starches such as starches having additional carboxyl and/or carboxamide groups and/or having hydrophilic side-chains, cellulose and derivatives thereof, agar and derivatives thereof, such as agar stabilized with polyacrylamide, polyethylene oxides, glycol methacrylates, gelatin, gums such as xanthum, guar, karaya, gellan, arabic, tragacanth and locust bean gum, or combinations thereof. Also suitable are the salts of the aforementioned carriers, for example, sodium alginate. The formulation optionally further comprises a foaming agent, which promotes the formation of the foam, including a surfactant or external propellant. Examples of suitable foaming agents include cetrimide, lecithin, soaps, silicones and the like. Commercially available surfactants such as Tween® are also suitable.

Auris-Acceptable Spongy Material

Also contemplated within the scope of the embodiments is the use of a spongy material in the auris interna or auris media. In some embodiments, the spongy material is formed from hyaluronic acid or its derivatives. The spongy material is impregnated with a desired auris therapeutic agent and placed within the auris media so as to provide controlled release of the auris therapeutic agent within the auris media, or in contact with the round window membrane so as to provide controlled release of the auris therapeutic agent into the auris interna. In some embodiments, the spongy material is biodegradable.

Cyclodextrin Formulations/Compositions

In a specific embodiment, the formulation or composition alternatively comprises a cyclodextrin. Cyclodextrins are cyclic oligosaccharides containing 6, 7, or 8 glucopyranose units, referred to as α-cyclodextrin, β-cyclodextrin, or γ-cyclodextrin respectively. Cyclodextrins have been found to be particularly useful in pharmaceutical formulations or compositions. Cyclodextrins have a hydrophilic exterior, which enhances water-soluble, and a hydrophobic interior which forms a cavity. In an aqueous environment, hydrophobic portions of other molecules often enter the hydrophobic cavity of cyclodextrin to form inclusion compounds. Additionally, cyclodextrins are also capable of other types of nonbonding interactions with molecules that are not inside the hydrophobic cavity. Cyclodextrins have three free hydroxyl groups for each glucopyranose unit, or 18 hydroxyl groups on α-cyclodextrin, 21 hydroxyl groups on β-cyclodextrin, and 24 hydroxyl groups on γ-cyclodextrin. One or more of these hydroxyl groups are reacted with any of a number of reagents to form a large variety of cyclodextrin derivatives. Some of the more common derivatives of cyclodextrin are hydroxypropyl ethers, sulfonates, and sulfoalkylethers. Shown below is the structure of β-cyclodextrin and the hydroxypropyl-β-cyclodextrin (HPβCD).

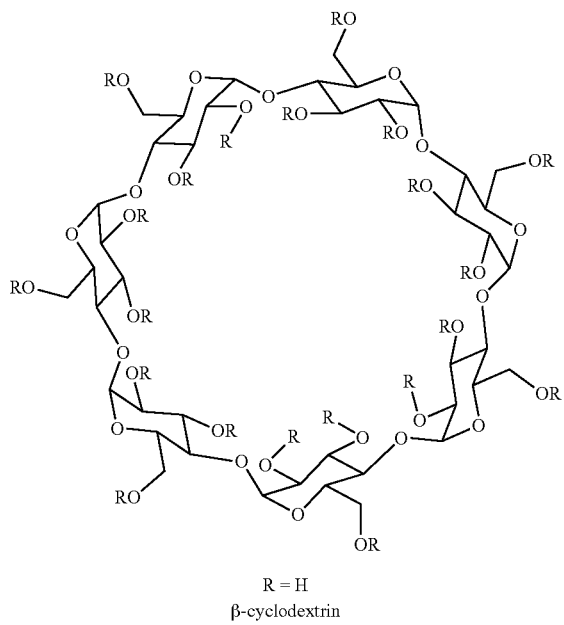

R = H
β-cyclodextrin

R = CH$_2$CH(OH)CH$_3$
hydroxypropyl β-cyclodextrin

The use of cyclodextrins in pharmaceutical formulations or compositions is well known in the art as cyclodextrins and cyclodextrin derivatives are often used to improve the solubility of a drug. Inclusion compounds are involved in many cases of enhanced solubility; however other interactions between cyclodextrins and insoluble compounds improve solubility. Hydroxypropyl-β-cyclodextrin (HPβCD) is commercially available as a pyrogen free product. It is a nonhygroscopic white powder that readily dissolves in water. HPβCD is thermally stable and does not degrade at neutral pH. Thus, cyclodextrins improve the solubility of a therapeutic agent in a composition or formulation. Accordingly, in some embodiments, cyclodextrins are included to increase the solubility of the therapeutic agents, or auris-acceptable otic agents, within the formulations or compositions described herein. In other embodiments, cyclodextrins in addition serve as controlled release excipients within the formulations or compositions described herein.

Preferred cyclodextrin derivatives for use include α-cyclodextrin, β-cyclodextrin, γ-cyclodextrin, hydroxyethyl β-cyclodextrin, hydroxypropyl γ-cyclodextrin, sulfated β-cyclodextrin, sulfated α-cyclodextrin, sulfobutyl ether β-cyclodextrin.

In some embodiments, the concentration of the cyclodextrin used in the formulations or compositions and methods disclosed herein vary according to the physiochemical properties, pharmacokinetic properties, side effect or adverse events, formulation or composition considerations, or other factors associated with the therapeutic agent, or a salt or prodrug thereof. The properties of other excipients in a formulation or composition are also important in some instances. Thus, the concentration or amount of cyclodextrin used in accordance with the formulations, compositions and methods disclosed herein vary in some embodiments.

In certain embodiments, the composition or formulation further comprise a suitable viscosity agent, such as hydroxypropyl methylcellulose, hydroxyethyl cellulose, polyvinylpyrrolilidone, carboxymethyl cellulose, polyvinyl alcohol, sodium chondrointin sulfate, sodium hyaluronate etc. as a dispersant, if necessary. A nonionic surfactant such as polysorbate 80, polysorbate 20, tyloxapol, Cremophor, HCO 40 etc. is optionally used. In certain embodiments, the preparations optionally contain a suitable buffering system, such as phosphate, citrate, borate, tris, etc., and pH regulators such as sodium hydroxide and hydrochloric acid also are optionally used in the formulations of the disclosures. Sodium chloride or other tonicity agents are also used to adjust tonicity, if necessary.

Auris Acceptable Microspheres and Nanospheres

Otic agents and/or other pharmaceutical agents disclosed herein are optionally incorporated within controlled release particles, lipid complexes, liposomes, nanoparticles, microspheres, nanocapsules or other agents which enhance or facilitate the localized delivery of the otic agent. In some embodiments, a single formulation or composition is used, in which at least one active pharmaceutical ingredient is present, while in other embodiments, a pharmaceutical formulation or composition that comprises a mixture of two or more distinct formulations or compositions is used, in which at least one active pharmaceutical ingredient is present. In certain embodiments, the formulations or compositions are cross-linked by one or more agents to alter or improve the properties of the formulation or composition.

Microspheres have been described in the following references, which are incorporated herein by reference: Luzzi, L. A., J. Pharm. Psy. 59:1367 (1970); U.S. Pat. No. 4,530, 840; Lewis, D. H., "Controlled Release of Bioactive Agents from Lactides/Glycolide Polymers" in Biodegradable Polymers as Drug Delivery Systems, Chasin, M. and Langer, R., eds., Marcel Decker (1990); U.S. Pat. No. 4,675,189; Beck et al., "Poly(lactic acid) and Poly(lactic acid-co-glycolic acid) Contraceptive Delivery Systems," in Long Acting Steroid Contraception, Mishell, D. R., ed., Raven Press (1983); U.S. Pat. Nos. 4,758,435; 3,773,919; 4,474,572; G. Johns et al. "Broad Applicability of a Continuous Formation Process," Drug Delivery Technology vol. 4 (January/February 2004), each of which is hereby incorporated by reference for such disclosure. Examples of protein therapeutics formulated as microspheres include: U.S. Pat. Nos. 6,458,387; 6,268,053; 6,090,925; 5,981,719; and 5,578,709, and are herein incorporated by reference for such disclosure.

Microspheres usually have a spherical shape, although irregularly-shaped microparticles are possible. The microspheres vary in size, ranging from submicron to 1000 micron diameters. Preferably, submicron to 250 micron diameter microspheres, are desirable, allowing administration by injection with a standard gauge needle. The microspheres are thus prepared by any method which produces microspheres in a size range acceptable for use in an injectable formulation or composition. Injections are accomplished with standard gauge needles used for administering liquid formulation or compositions.

Suitable examples of polymeric matrix materials include poly(glycolic acid), poly-d,l-lactic acid, poly-l-lactic acid, copolymers of the foregoing, poly(aliphatic carboxylic acids), copolyoxalates, polycaprolactone, polydioxonene, poly(orthocarbonates), poly(acetals), poly(lactic acid-caprolactone), polyorthoesters, poly(glycolic acid-caprolactone), polydioxonene, polyanhydrides, polyphosphazines, and natural polymers including albumin, casein, and some waxes, such as, glycerol mono- and distearate, and the like. Various commercially available poly(lactide-co-glycolide) materials (PLGA) are used in the method disclosed herein. For example, poly (d,l-lactic-co-glycolic acid) is commercially available from Boehringer-Ingelheim as RESOMER RG 503 H. This product has a mole percent composition of 50% lactide and 50% glycolide. These copolymers are available in a wide range of molecular weights and ratios of lactic acid to glycolic acid. A preferred polymer for use is poly(d,l-lactide-co-glycolide). It is preferred that the molar ratio of lactide to glycolide in such a copolymer be in the range of from about 95:5 to about 50:50. In other embodiments, PLGA copolymers with polyethylene glycol (PEG) are suitable polymeric matrices for the formulations disclosed herein. For example, PEG-PLGA-PEG block polymers are biodegradable matrices that provide high mechanical stability of the resulting formulation. Mechanical stabilities of formulations using PEG-PLGA-PEG block polymers have been maintained for more than one month in vitro. In some embodiments, PEG-PLGA-PEG block polymers are used to control the release rate of cytotoxic agents with different physical properties. Particularly, in some embodiments, hydrophilic cytotoxic agents are released more quickly, e.g., approximately 50% of drug release after 24 hours, the remainder released over approximately 5 days, whereas hydrophobic agents are released more slowly, e.g., approximately 80% after 8 weeks.

The molecular weight of the polymeric matrix material is of some importance. The molecular weight should be high enough so that it forms satisfactory polymer coatings, i.e., the polymer should be a good film former. Usually, a satisfactory molecular weight is in the range of 5,000 to 500,000 daltons. The molecular weight of a polymer is also important from the point of view that molecular weight influences the biodegradation rate of the polymer. For a diffusional mechanism of drug release, the polymer should remain intact until all of the drug is released from the microparticles and then degrade. The drug is also released from the microparticles as the polymeric excipient bioerodes. By an appropriate selection of polymeric materials a microsphere formulation are made such that the resulting microspheres exhibit both diffusional release and biodegradation release properties. This is useful in affording multiphasic release patterns.

A variety of methods are known by which compounds are encapsulated in microspheres. In these methods, the active pharmaceutical ingredient is generally dispersed or emulsified, using stirrers, agitators, or other dynamic mixing techniques, in a solvent containing a wall-forming material. Solvent is then removed from the microspheres, and thereafter the microsphere product is obtained.

In one embodiment, controlled release formulations or compositions are made through the incorporation of the otic agents and/or other pharmaceutical agents into ethylene-vinyl acetate copolymer matrices. (See U.S. Pat. No. 6,083,534, incorporated herein for such disclosure). In another embodiment, otic agents are incorporated into poly (lactic-glycolic acid) or poly-L-lactic acid microspheres. In yet another embodiment, the otic agents are encapsulated into alginate microspheres. (See U.S. Pat. No. 6,036,978, incorporated herein for such disclosure). Biocompatible methacrylate-based polymers to encapsulate the otic agents or compositions are optionally used in the formulations and methods disclosed herein. A wide range of methacrylate-based polymer systems are commercially available, such as the EUDRAGIT polymers marketed by Evonik. One useful aspect of methacrylate polymers is that the properties of the formulation are varied by incorporating various co-polymers. For example, poly(acrylic acid-co-methylmethacrylate) microparticles exhibit enhanced mucoadhesion properties as the carboxylic acid groups in the poly(acrylic acid) form hydrogen bonds with mucin (Park et al, Pharm. Res. (1987) 4(6):457-464). Variation of the ratio between acrylic acid and methylmethacrylate monomers serves to modulate the properties of the copolymer. Methacrylate-based microparticles have also been used in protein therapeutic formulations (Naha et al, Journal of Microencapsulation 4 Feb. 2008 (online publication)). In one embodiment, the enhanced viscosity auris-acceptable formulations described herein comprise otic agent microspheres wherein the microspheres are formed from a methacrylate polymer or copolymer. In an additional embodiment, the enhanced viscosity formulation described herein comprises otic agent microspheres wherein the microspheres are mucoadhesive. Other controlled release systems, including incorporation or deposit of polymeric materials or matrices onto solid or hollow spheres containing otic agents, are also explicitly contemplated within the embodiments disclosed herein. The types of controlled release systems available without significantly losing activity of the otic agent are determined using the teachings, examples, and principles disclosed herein An example of a conventional microencapsulation process for pharmaceutical preparations is shown in U.S. Pat. No. 3,737,337, incorporated herein by reference. The substances to be encapsulated or embedded are dissolved or dispersed in the organic solution of the polymer (phase A), using conventional mixers, including (in the preparation of dispersion) vibrators and high-speed stirrers, etc. The dispersion of phase (A), containing the core material in solution or in suspension, is carried out in the aqueous phase (B), again using conventional mixers, such as high-speed mixers, vibration mixers, or even spray nozzles, in which case the particle size of the microspheres will be determined not only by the concentration of phase (A), but also by the emulsate or microsphere size. With conventional techniques for the microencapsulation of active pharmaceutical ingredients, the microspheres form when the solvent containing an active agent and a polymer is emulsified or dispersed in an immiscible solution by stirring, agitating, vibrating, or some other dynamic mixing technique, often for a relatively long period of time.

Conventional methods for the construction of microspheres are also described in U.S. Pat. Nos. 4,389,330, and 4,530,840, incorporated herein by reference. The desired agent is dissolved or dispersed in an appropriate solvent. To the agent-containing medium is added the polymeric matrix material in an amount relative to the active ingredient which gives a product of the desired loading of active agent. Optionally, all of the ingredients of the microsphere product are blended in the solvent medium together. Suitable solvents for the agent and the polymeric matrix material include organic solvents such as acetone, halogenated hydrocarbons such as chloroform, methylene chloride and the like, aromatic hydrocarbon compounds, halogenated aromatic hydrocarbon compounds, cyclic ethers, alcohols, ethyl acetate and the like.

In some embodiments, the controlled-release auris-acceptable microspheres are combined in a controlled-release auris-acceptable increased-viscosity formulation or composition.

A suitable controlled-release auris-acceptable microsphere example for use with the auris-acceptable therapeutic agents disclosed herein includes CHRONIJECT™, a PLGA-based controlled release injectable drug delivery system. Chroniject microspheres are useful for both hydrophobic and hydrophilic auris therapeutic agents, with achieved durations of release ranging from as short as 1 week to as long as 1 year. Release profiles for the microspheres are achieved by modifying polymer and/or process conditions, with initial release or burst of the auris therapeutic agent also available. The manufacturing process is adaptable to aseptic conditions, allowing direct therapeutic use of the manufactured product. Chroniject manufacturing processes are described in U.S. Pat. Nos. 5,945,126; 6,270,802 and 6,3361,798, each of which is hereby incorporated by reference for such disclosure.

In some embodiments, the mixture of ingredients in the solvent is emulsified in a continuous-phase processing medium; the continuous-phase medium being such that a dispersion of microdroplets containing the indicated ingredients is formed in the continuous-phase medium. Naturally, the continuous-phase processing medium and the organic solvent must be immiscible, and most commonly is water although nonaqueous media such as xylene and toluene and synthetic oils and natural oils are used. Usually, a surfactant is added to the continuous-phase processing medium to prevent the microparticles from agglomerating and to control the size of the solvent microdroplets in the emulsion. A preferred surfactant-dispersing medium combination is a 1 to 10 wt. % poly vinyl alcohol in water mixture. The dispersion is formed by mechanical agitation of the mixed materials. An emulsion is also formed by adding small drops of the active agent-wall forming material solution to the continuous phase processing medium. The temperature during the formation of the emulsion is not especially critical but in some cases, influences the size and quality of the microspheres and the solubility of the drug in the continuous phase. It is desirable to have as little of the agent in the continuous phase as possible. Moreover, depending on the solvent and continuous-phase processing medium employed, the temperature must not be too low or the solvent and processing medium will solidify or the processing medium will become too viscous for practical purposes, or too high that the processing medium will evaporate, or that the liquid processing medium will not be maintained. Moreover, the temperature of the medium cannot be so high that the stability of the particular agent being incorporated in the microspheres is adversely affected. Accordingly, the dispersion process is conducted at any temperature which maintains stable operating conditions, which preferred temperature being about 30° C. to 60° C., depending upon the drug and excipient selected.

In some embodiments, the dispersion which is formed is a stable emulsion and from this dispersion the organic solvent immiscible fluid is optionally partially removed in the first step of the solvent removal process. The solvent is easily removed by common techniques such as heating, the application of a reduced pressure or a combination of both. The temperature employed to evaporate solvent from the microdroplets is not critical, but should not be that high that it degrades the agent employed in the preparation of a given microparticle, nor should it be so high as to evaporate solvent at such a rapid rate to cause defects in the wall forming material. Generally, from 5 to 75%, of the solvent is removed in the first solvent removal step.

In some embodiments, after the first stage, the dispersed microparticles in the solvent immiscible fluid medium are isolated from the fluid medium by any convenient means of separation. Thus, for example, the fluid is decanted from the microsphere or the microsphere suspension is filtered. Still other, various combinations of separation techniques are used if desired.

In some embodiments, following the isolation of the microspheres from the continuous-phase processing medium, the remainder of the solvent in the microspheres is removed by extraction. In this step, the microspheres are suspended in the same continuous-phase processing medium used in step one, with or without surfactant, or in another liquid. The extraction medium removes the solvent from the microspheres and yet does not dissolve the microspheres. During the extraction, the extraction medium with dissolved solvent is optionally removed and replaced with fresh extraction medium. This is best done on a continual basis. Obviously, the rate of extraction medium replenishment of a given process is a variable which is easily determined at the time the process is performed and, therefore, no precise limits for the rate must be predetermined. After the majority of the solvent has been removed from the microspheres, the microspheres are dried by exposure to air or by other conventional drying techniques such as vacuum drying, drying over a desiccant, or the like. This process is very efficient in encapsulating the agent since core loadings of up to 80 wt. %, preferably up to 60 wt. % are obtained.

In some embodiments, controlled release microspheres containing an active pharmaceutical agent are prepared through the use of static mixers. Static or motionless mixers consist of a conduit or tube in which is received a number of static mixing agents. Static mixers provide homogeneous mixing in a relatively short length of conduit, and in a relatively short period of time. With static mixers, the fluid moves through the mixer, rather than some part of the mixer, such as a blade, moving through the fluid.

In some embodiments, a static mixer is used to create an emulsion. When using a static mixer to form an emulsion, several factors determine emulsion particle size, including the density and viscosity of the various solutions or phases to be mixed, volume ratio of the phases, interfacial tension between the phases, static mixer parameters (conduit diameter; length of mixing element; number of mixing elements), and linear velocity through the static mixer. Temperature is a variable because it affects density, viscosity, and interfacial tension. The controlling variables are linear velocity, sheer rate, and pressure drop per unit length of static mixer.

In order to create microspheres containing an active pharmaceutical agent, an organic phase and an aqueous phase are combined in some embodiments. The organic and aqueous phases are largely or substantially immiscible, with the aqueous phase constituting the continuous phase of the emulsion. The organic phase includes an active pharmaceutical agent as well as a wall-forming polymer or polymeric matrix material. In some embodiments, the organic phase is prepared by dissolving an active pharmaceutical agent in an organic or other suitable solvent, or by forming a dispersion or an emulsion containing the active agent. The organic phase and the aqueous phase are pumped so that the two phases flow simultaneously through a static mixer, thereby forming an emulsion which comprises microspheres containing the active pharmaceutical agent encapsulated in the polymeric matrix material. The organic and aqueous phases are pumped through the static mixer into a large volume of quench liquid to extract or remove the organic solvent. Organic solvent are removed from the microspheres while they are washing or being stirred in the quench liquid. After the microspheres are washed in a quench liquid, they are isolated, as through a sieve, and dried.

In some embodiments, the process whereby microspheres are prepared using a static mixer is optionally carried out for a variety of techniques used to encapsulate active agents. In some embodiments, the process is not limited to the solvent extraction technique discussed above and is used with other encapsulation techniques. For example, the process is used with a phase separation encapsulation technique in some instances. To do so, an organic phase is prepared that comprises an active pharmaceutical agent suspended or dispersed in a polymer solution. The non-solvent second phase is free from solvents for the polymer and active agent. A preferred non-solvent second phase is silicone oil. The organic phase and the non-solvent phase are pumped through a static mixer into a non-solvent quench liquid, such as heptane. The semisolid particles are quenched for complete hardening and washing. The process of microencapsulation also includes spray drying, solvent evaporation, a combination of evaporation and extraction, and melt extrusion.

In another embodiment, the microencapsulation process involves the use of a static mixer with a single solvent. This process is described in detail in U.S. application Ser. No. 08/338,805, herein incorporated by reference. An alternative process involves the use of a static mixer with co-solvents. In this process for preparing biodegradable microspheres comprising a biodegradable polymeric binder and an active pharmaceutical agent, a blend of at least two substantially non-toxic solvents, free of halogenated hydrocarbons, is used to dissolve both the agent and the polymer. The solvent blend containing the dissolved agent and polymer is dispersed in an aqueous solution to form droplets. The resulting emulsion is then added to an aqueous extraction medium preferably containing at least one of the solvents of the blend, whereby the rate of extraction of each solvent is controlled, whereupon the biodegradable microspheres containing the pharmaceutically active agent are formed. The process has the advantage that less extraction medium is required because the solubility of one solvent in water is substantially independent of the other and solvent selection is increased, especially with solvents that are particularly difficult to extract.

Nanoparticles are material structures of about 100 nm or less in size. One use of nanoparticles in pharmaceutical formulations is the formation of suspensions as the interaction of the particle surface with solvent is strong enough to overcome differences in density. Nanoparticle suspensions are sterilized as the nanoparticles are small enough to be subjected to sterilizing filtration (U.S. Pat. No. 6,139,870). Nanoparticles comprise at least one hydrophobic, water-insoluble and water-indispersible polymer or copolymer emulsified in a solution or aqueous dispersion of surfactants, phospholipids or fatty acids. The active pharmaceutical ingredient is introduced with the polymer or the copolymer into the nanoparticles.

Lipid nanocapsules act as controlled release structures, as well for penetrating the round window membrane and reaching auris interna targets, is also contemplated herein. See Zou et al. *J. Biomed. Materials Res.*, online pub. (Apr. 24, 2008). Lipid nanocapsules are formed by emulsifying 1.028 g capric and caprylic acid triglycerides (LABRAFAC WL 1349; avg. mw 512), 0.075 g soybean lecithin (LIPOID S75-3; 69% phosphatidylcholine and other phospholipids), 0.846 g surfactant (SOLUTOL HS15), mixture of polyethylene glycol 660 hydroxystearate and free polyethylene glycol 660; 0.089 g NaCl and 2.962 g water. The mixture is stirred at room temperature to obtain an oil emulsion in water. After progressive heating at a rate of 4° C./min under magnetic stirring, a short interval of transparency should occur close to 70° C., and the inverted phase (water droplets in oil) obtained at 85° C. Three cycles of cooling and heating is then applied between 85° C. and 60° C. at the rate of 4° C./min, and a fast dilution in cold water at a temperature close to 0° C. to produce a suspension of nanocapsules. To encapsulate auris interna active agents, the agent are added just prior to the dilution with cold water.

In some instances, agents are inserted into the lipid nanocapsules by incubation for 90 minutes with an aqueous micellar solution of the auris interna active agent. The suspension is then vortexed every 15 minutes, and then quenched in an ice bath for 1 minute.

Suitable surfactants are, by way of example, cholic acid or taurocholic acid salts. Taurocholic acid, the conjugate formed from cholic acid and taurine, is a fully metabolizable sulfonic acid surfactant. An analog of taurocholic acid, tauroursodeoxycholic acid (TUDCA), is a naturally occurring bile acid and is a conjugate of taurine and ursodeoxycholic acid (UDCA). Other naturally occurring anionic (e.g., galactocerebroside sulfate), neutral (e.g., lactosylceramide) or zwitterionic surfactants (e.g., sphingomyelin, phosphatidyl choline, palmitoyl carnitine) could also be used to prepare nanoparticles.

The phospholipids are chosen, by way of example, from natural, synthetic or semi-synthetic phospholipids; lecithins (phosphatidylcholine) such as, for example, purified egg or soya lecithins (lecithin E100, lecithin E80 and phospholipons, for example phospholipon 90), phosphatidylethanolamine, phosphatidylserine, phosphatidylinositol, phosphatidylglycerol, dipalmitoylphosphatidylcholine, dipalmitoylglycerophosphatidylcholine, dimyristoylphosphatidylcholine, distearoylphosphatidylcholine and phosphatidic acid or mixtures thereof are used more particularly.

The fatty acids are chosen from, by way of example, from lauric acid, mysristic acid, palmitic acid, stearic acid, isostearic acid, arachidic acid, behenic acid, oleic acid, myristoleic acid, palmitoleic acid, linoleic acid, alpha-linoleic acid, arachidonic acid, eicosapentaenoic acid, erucic acid, docosahexaenoic acid, and the like.

Suitable surfactants are preferably selected from known organic and inorganic pharmaceutical excipients. Such excipients include various polymers, low molecular weight oligomers, natural products, and surfactants. Preferred surface modifiers include nonionic and ionic surfactants. Two or more surface modifiers are used in combination for some embodiments.

Representative examples of surfactants include cetyl pyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters; polyethylene glycols, dodecyl trimethyl ammonium bromide, polyoxyethylenestearates, colloidal silicon dioxide, phosphates, sodium dodecylsulfate, carboxymethylcellulose calcium, hydroxypropyl cellulose (HPC, HPC-SL, and HPC-L), hydroxypropyl methylcellulose (HPMC), carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1,1,3,3-tetaamethylbutyl)-phenolpolymer with ethylene oxide and formaldehyde (also known as tyloxapol, superione, and triton), poloxamers, poloxamnines, a charged phospholipid such as dimyristoyl phophatidyl glycerol, dioctylsulfosuccinate (DOSS); Tetronic 1508, dialkylesters of sodium sulfosuccinic acid, Duponol P, Tritons X-200, Crodestas F-110, p-isononylphenoxypoly-(glycidol), Crodestas SL-40® (Croda, Inc.); and SA9OHCO, which is $C_{18}H_{37}CH_2$ $(CONCH_3)$—$CH_2$ $(CHOH)_4$ $(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucarmide; n-octyl-β-D-glucopyranoside; octyl β-D-thioglucopyranoside; and the like.

Most of these surfactants are known pharmaceutical excipients and are described in detail in the Handbook of Pharmaceutical Excipients, published jointly by the American Pharmaceutical Association and The Pharmaceutical Society of Great Britain (The Pharmaceutical Press, 1986), specifically incorporated by reference.

The hydrophobic, water-insoluble and water-indispersible polymer or copolymer are chosen from biocompatible and biodegradable polymers, for example lactic or glycolic acid polymers and copolymers thereof, or polylactic/polyethylene (or polypropylene) oxide copolymers, preferably with molecular weights of between 1000 and 200000, polyhydroxybutyric acid polymers, polylactones of fatty acids containing at least 12 carbon atoms, or polyanhydrides.

In one embodiment, the nanoparticles are suitable for use with hydrophobic active principles. In some embodiments, the active principles are chosen from the major classes of medicaments for use in human or veterinary medicine. In some embodiments, the active principles are chosen from principles for use in the cosmetics or agrifood industry or sports medicine or from diagnostic agents. By way of example, active principles which are of interest in the pharmaceutical industry are chosen, in a non-limiting manner, from antirheumatic, non-steroidal anti-inflammatory (e.g., NSAIDs), analgesic, antitussive and psychotropic agents, steroids, barbiturates, antimicrobial, antiallergenic, antiasthmatic, antispasmodic, antisecretory and cardiovascular agents, cerebral vasodilators, cerebral and hepatic protective agents, therapeutic agents of the gastrointestinal tract, anticancer or antiviral agents, vitamins, contraceptives, vaccines, etc.

The nanoparticles are obtained by the technique of evaporation of solvent, from an aqueous dispersion or solution of phospholipids and of an oleic acid salt into which is added an immiscible organic phase comprising the active principle and the hydrophobic, water-insoluble and water-indispersible polymer or copolymer. The mixture is pre-emulsified and then subjected to homogenization and evaporation of the organic solvent to obtain an aqueous suspension of very small-sized nanoparticles.

A variety of methods are employed to fabricate nanoparticles. These methods include vaporization methods, such as free jet expansion, laser vaporization, spark erosion, electro explosion and chemical vapor deposition; physical methods involving mechanical attrition (e.g., "pearlmilling" technology, Elan Nanosystems), super critical CO2 and interfacial deposition following solvent displacement. In one embodiment, the solvent displacement method is used. The size of nanoparticles produced by this method is sensitive to the concentration of polymer in the organic solvent; the rate of mixing; and to the surfactant employed in the process. Continuous flow mixers provide the necessary turbulence to ensure small particle size. One type of continuous flow mixing device that is used to prepare nanoparticles has been described (Hansen et al. J Phys Chem 92, 2189-96, 1988). In other embodiments, ultrasonic devices, flow through homogenizers or supercritical CO2 devices are used to prepare nanoparticles.

If suitable nanoparticle homogeneity is not obtained on direct synthesis, then size-exclusion chromatography is used to produce highly uniform drug-containing particles that are freed of other components involved in their fabrication. Size-exclusion chromatography (SEC) techniques, such as gel-filtration chromatography, is used to separate particle-bound drug from free drug or to select a suitable size range of drug-containing nanoparticles. Various SEC media, such as Superdex 200, Superose 6, and Sephacryl 1000 are commercially available and are readily employed by persons of skill in the art for the size-based fractionation of mixture. Additionally, nanoparticles are purified by centrifugation, membrane filtration and by use of other molecular sieving devices, crosslinked gels/materials and membranes.

In some embodiments, liposomes or lipid particles are also employed to encapsulate the otic agent formulations or compositions. Phospholipids that are gently dispersed in an aqueous medium form multilayer vesicles with areas of entrapped aqueous media separating the lipid layers. Sonication, or turbulent agitation, of these multilayer vesicles results in the formation of single layer vesicles, commonly referred to as liposomes, with sizes of about 10-1000 nm. These liposomes have many advantages as drug carriers. They are biologically inert, biodegradable, non-toxic and non-antigenic. Liposomes are formed in various sizes and with varying compositions and surface properties. Additionally, they are able to entrap a wide variety of small molecule drugs and release the drug at the site of liposome collapse.

Suitable phospholipids for use in the present compositions are, for example, phosphatidyl cholines, ethanolamines and serines, sphingomyelins, cardiolipins, plasmalogens, phosphatictic acids and cerebrosides, in particular those which are soluble together with piroxicam in non-toxic, pharmaceutically acceptable organic solvents. Preferred phospholipids are, for example, phosphatidyl choline, phosphatidyl ethanolmine, phosphatidyl serine, phosphatidyl inositol, lysophosphatidyl choline, phosphatidyl glycerol and the like, and mixtures thereof especially lecithin, e.g. soya lecithin. The amount of phospholipid used in the present formulation ranges from about 10 to about 30%, preferably from about 15 to about 25% and in particular is about 20%.

Lipophilic additives are employed advantageously to modify selectively the characteristics of the liposomes. Examples of such additives include, for example, stearylamine, phosphatictic acid, tocopherol, cholesterol, cholesterol hemisuccinate and lanolin extracts. The amount of lipophilic additive used ranges from 0.5 to 8%, preferably from 1.5 to 4% and in particular is about 2%. Generally, the ratio of the amount of lipophilic additive to the amount of phospholipid ranges from about 1:8 to about 1:12 and in particular is about 1:10. Said phospholipid, lipophilic additive and the active ingredient piroxicam are employed in conjunction with a non-toxic, pharmaceutically acceptable organic solvent system which dissolves said ingredients. Said solvent system not only must dissolve the active pharmaceutical ingredient completely, but it also has to allow the formulation of stable single bilayered liposomes. The solvent system comprises dimethylisosorbide and tetraglycol (glycofurol, tetrahydrofurfuryl alcohol polyethylene glycol ether) in an amount of about 8 to about 30%. In said solvent system, the ratio of the amount of dimethylisosorbide to the amount of tetraglycol ranges from about 2:1 to about 1:3, in particular from about 1:1 to about 1:2.5 and preferably is about 1:2. The amount of tetraglycol in the final composition thus varies from 5 to 20%, in particular from 5 to 15% and preferably is approximately 10%. The amount of dimethylisosorbide in the final composition thus ranges from 3 to 10%, in particular from 3 to 7% and preferably is approximately 5%.

The term "organic component" as used hereinafter refers to mixtures comprising said phospholipid, lipophilic additives and organic solvents.

The active pharmaceutical ingredient is dissolved in the organic component. It is advantageous to use micronized forms of the active ingredient to facilitate its dissolution. The amount of active ingredient in the final formulation ranges from 0.1 to 5.0%. In addition, other ingredients such as anti-oxidants are added to the organic component. Examples include tocopherol, butylated hydroxyanisole, butylated hydroxytoluene, ascorbyl palmitate, ascorbyl oleate and the like.

In some embodiments, the aqueous component of the present formulation comprises mainly water and optionally contains various additives such as electrolytes, buffer systems, preservatives and the like. Suitable electrolytes include metal salts, in particular alkali metal and earth alkaline metal salts such as, for example, calcium chlorides, sodium chloride, potassium chloride, preferably sodium chloride. In some instances, the concentration of the electrolytes varies over a wide range and depends on the nature and the concentration of each of the ingredients in the final formulation and should be sufficient to stabilize the liposomal membranes. In the present composition the amount of sodium chloride ranges from 0.05 to 0.2%. Buffer systems comprise mixtures of appropriate amounts of an acid such as phosphoric, succinic, or preferably citric acid, and a base, in particular sodium hydroxide. Said buffer systems should maintain the pH of the formulation within the range of 3 to 9, alternatively within the range or 6 to 8 or between the range of 5 to 7. Preservatives which are employed in the present composition to prevent degradation by microorganisms comprise benzoic acid, methylparaben and propylparaben in some embodiments.

Liposomal formulations are optionally prepared by (a) heating the phospholipid and the organic solvent system to about 60-80° C. in a vessel, dissolving the active ingredient, then adding any additional formulating agents, and stirring the mixture until complete dissolution is obtained; (b) heating the aqueous solution to 90-95° C. in a second vessel and dissolving the preservatives therein, allowing the mixture to cool and then adding the remainder of the auxiliary formulating agents and the remainder of the water, and stirring the mixture until complete dissolution is obtained; thus preparing the aqueous component; (c) transferring the organic phase directly into the aqueous component, while homogenizing the combination with a high performance mixing apparatus, in particular a high-shear mixer; and (d) adding a thickener to the resulting mixture while further homogenizing. Preferably, the aqueous component is placed in a suitable vessel which is equipped with a homogenizer and homogenization is effected by creating great turbulence during the injection of the organic component. Any mixing means or homogenizer which exerts high shear forces on the mixture is employed. Generally, a mixer capable of speeds from about 1,500 to 20,000 rpm, in particular from about 3,000 to about 6,000 rpm are employed. Suitable thickening agents for use in process step (d) are for example, xanthan gum, hydroxypropyl cellulose, hydroxypropyl methylcellulose or mixtures thereof, cellulose derivatives being preferred. The amount of thickening agent depends on the nature and the concentration of the other ingredients and in general ranges from about 0.5 to 1.5%, and in particular is approximately 1.5%. In order to prevent degradation of the materials used during the preparation of the liposomal formulation, it is advantageous to purge all solutions with an inert gas such as nitrogen or argon, and to conduct all steps under an inert atmosphere. Liposomes prepared by the above described method usually contain most of the active ingredient bound in the lipid bilayer and separation of the liposomes from unencapsulated material is not required.

Auris-Acceptable Lipid Formulations/Compositions

In some embodiments, the drug delivery formulation or composition is a lipid-based formulation or composition. In some embodiments, the lipid-based drug delivery formulation or composition is a lipid emulsion (e.g., microemulsions and oil-in-water emulsions), a lipid vesicle (e.g., liposomes, micelles and transfersomes) or a combination thereof. In some embodiments, the lipid-based drug delivery formulation or composition is a lipid vesicle wherein the lipid vesicle is a liposome. In some embodiments, the lipid-based drug delivery formulation or composition is a phospholipid-based formulation or composition. In some embodiments, the lipid-based drug delivery formulation or composition is a phospholipid-based formulation or composition wherein the natural or synthetic phospholipid is phosphatidylethanolamine, phosphatidylserine, phosphatidylinositol, phosphatidylglycerol, phosphatidic acid, lysophospholipids, egg or soybean phospholipid, or a combination thereof. The phospholipid is optionally salted or desalted, hydrogenated or partially hydrogenated, natural, synthetic, or semisynthetic. In some embodiments, the lipid-based drug delivery formulation is a phospholipid-based formulation (e.g., hydrogenated or nonhydrogenated phospholipids, lecithins, phosphatidyl cholines (C8-C18), phosphatidylethanolamines (C8-C18), phosphatidylglycerols (C8-C18)) wherein the phospholipid is phospholipon 90H (1,2-diacyl-SN-glycero-3-phosphatidyl choline), egg phospholipids P123, Lipoid E80; Phospholipon 80H®, 80G®, 90H® and 100H®, or combinations thereof.

In some embodiments, the lipid-based drug delivery formulation or composition comprises a water-soluble preservative (i.e., a component that prevents microbes from substantially growing and multiplying). In some embodiments, the lipid-based drug delivery formulation or composition comprises a water-soluble preservative wherein the preservative is a benzethonium salt (e.g., benzethonium chloride), benzoic acid, and/or a benzylkonium salt (e.g., benzylkonium chloride). As used herein, water soluble means that the component has a solubility in water from about 100 μg/mL (0.01%) to about 0.01 mg/mL (0.1%).

In some embodiments, the lipid-based drug delivery formulation or composition comprises a lipid soluble antioxidant. In some embodiments, the lipid-based drug delivery formulation or composition comprises vitamin E.

In some embodiments, the lipid-based drug delivery formulation or composition comprises less than about 2% w/w, less than about 1.5%, less than about 1.0%, less than about 0.5%, or less than about 0.25% of a viscosity enhancing agent.

In some embodiments, the lipid-based drug delivery formulation or composition has a viscosity of at least about 10,000 centipoise, at least about 20,000 centipoise, at least about 30,000 centipoise, at least about 40,000 centipoise, at least about 50,000 centipoise, at least about 60,000 centipoise, or at least about 70,000 centipoise, all at 58° C., without the presence of any methyl-cellulose or other viscosity enhancing agents. In some embodiments, the lipid-based drug delivery formulation or composition comprises oleyl alcohol to enhance the transmembrane penetration.

In some embodiments, the lipid-based drug delivery formulation or composition comprises a penetration enhancer (e.g., a low molecular weight alcohol (e.g., ethanol, oleyl alcohol), alkyl methanol sulphoxides, N-methyl-2-pyrrolidone, fatty amines (e.g., oleylamine), fatty acids (e.g., oleic acid, palmitoleic acid, linoleic acid, myristate acid), gluconic acid (the hexonic acid derived from glucose by oxidation of the aldehyde group at C-1 to a carboxyl group) and its derivatives, such as gluconolactone (especially, glucono-D-lactone, a chelating agent produced by the oxidation of glucose), azone and propylene glycol, singly or in combination). In some embodiments, the lipid-based drug delivery formulation or composition comprises a penetration enhancer wherein the penetration enhancer is propylene glycol, either alone or in up to a 1:1 ratio with another enhancer, such as oleic acid or ethanol. In some embodiments, the lipid-based drug delivery formulation or composition comprises a penetration enhancer wherein the penetration enhancer is gluconolactone (e.g., glucono-D-lactone), either alone or in up to a 1:1 ratio with another enhancer, such as propylene glycol.

In some embodiments, the lipid-based drug delivery formulation or composition comprises about 25% v/v or less of any one or more chemical penetration enhancer(s), most preferably from about 2% to 15% v/v, although the exact formulation or composition will vary depending on the presence and amounts of excipients, preservatives, water, pH modulators, and the like included therein.

In some embodiments, prepared liposomes loaded with the aural pressure modulators herein are gently mixed with viscosity, mucosal adhesives or absorption penetration enhancers. For example, aural pressure modulators loaded into liposomes are mixed with a chitosan-glycerophosphate composition. The liposome size are optionally increased or decreased to modulate the release kinetics of the controlled release particles. In additional aspects, release kinetics is altered by changing the lipid composition of the liposomes as described above.

The formulations or compositions described herein are administered in any suitable form. By way of non-limiting examples, the formulations are administered as otic drops, as intratympanic injections, as foams or as otic paints. The formulations or compositions are administered via cannula and/or injection, via a drop dispenser, as a spray in the ear canal, or as a paint via a cotton tipped stick.

Controlled Release Kinetics

The goal of every drug delivery technique is to deliver the proper amount of drug to the site of action at the right time to obtain a therapeutic benefit. In general, controlled release drug formulations impart control over the release of drug with respect to site of release and time of release within the body. As discussed herein, controlled release refers to any release other than solely immediate release. In some instances, controlled release is delayed release, extended release, sustained release and/or pulsatile release (e.g., a combination of extended release and immediate release) or a combination thereof. Many advantages are offered by controlled release. First, controlled release of a pharmaceutical agent allows less frequent dosing and thus minimizes repeated treatment. Second, controlled release treatment results in more efficient drug utilization and less of the compound remains as a residue. Third, controlled release offers the possibility of localized drug delivery by placement of a delivery device or formulation at the site of disease. Still further, controlled release offers the opportunity to administer and release two or more different drugs, each having a unique release profile, or to release the same drug at different rates or for different durations, by means of a single dosage unit.

In a specific embodiment the formulations or compositions described herein provide a therapeutically effective amount of at least one active pharmaceutical ingredient at the site of disease with no systemic exposure. In an additional embodiment the formulations or compositions described herein provide a therapeutically effective amount of at least one active pharmaceutical ingredient at the site of disease with no detectable systemic exposure.

In certain embodiments, the formulations or compositions comprise an excipient that increases the release rate of the therapeutic agent. In certain embodiments, the formulations or compositions comprise an excipient that decreases the release rate of the therapeutic agent.

The formulation or composition is designed to provide drug delivery over a desired period of time, including periods up to several weeks. As such, the patient will not need repeated administration of the drug, or at the least, fewer and less frequent administration of the drug.

Drugs delivered to the auris interna have commonly been administered systemically via oral, intravenous or intramuscular routes. However, systemic administration for pathologies local to the auris interna increases the likelihood of systemic toxicities and side effects and creates a nonproductive distribution of drug in which high levels drug are found in the serum and correspondingly lower levels are found at the auris interna.

In one embodiment, the formulations or compositions disclosed herein additionally provides an immediate release of the therapeutic agent, or otic agent, from the formulation or composition, or within 1 minute, or within 5 minutes, or within 10 minutes, or within 15 minutes, or within 30 minutes, or within 60 minutes or within 90 minutes. In other embodiments, a therapeutically effective amount of at least one therapeutic agent, or otic agent, is released from the formulation or composition immediately, or within 1 minute, or within 5 minutes, or within 10 minutes, or within 15 minutes, or within 30 minutes, or within 60 minutes or within 90 minutes. Additional embodiments of the formulation or composition also include an agent that enhances the viscosity of the formulations included herein.

An immediate or rapid release option includes use of different viscosity-enhancing polymers, multi-component formulations or compositions and nanospheres (or submicron spheres). In addition, the microspheres are optionally coated with an immediate-release component and a controlled-release component.

In certain embodiments the formulation or composition provides immediate release of at least one active pharmaceutical ingredient. Additional embodiments of the formulation or composition also include a thickener that thickens the formulations or compositions included herein. In other embodiments the thickened comprises a liposomal formulation or composition providing immediate release of at least one active pharmaceutical ingredient. In certain other embodiments the formulation or composition comprises a cyclodextrin-containing formulation or composition providing immediate release of at least one active pharmaceutical ingredient. In additional embodiments the formulation or composition comprises a microsphere formulation or composition providing immediate release of at least one active pharmaceutical ingredient. In additional embodiments the formulation or composition comprises a nanoparticle formulation or composition providing immediate release of at least one active pharmaceutical ingredient.

In other or further embodiments, the formulation or composition provides a controlled release formulation or composition of at least one therapeutic agent, or otic agent. In certain embodiments, diffusion of at least one otic agent from the formulation or composition occurs for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year. In other embodiments, a therapeutically effective amount of at least one otic agent is released from the formulation or composition for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year.

In other embodiments, the formulation or composition provides both an immediate release and an extended release formulation or composition of a therapeutic agent, or an otic agent. In yet other embodiments, the formulation or composition contains a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations or compositions. In a further embodiment the formulation or composition provides an immediate release of a first otic agent and an extended release of a second otic agent or other therapeutic agent. In yet other embodiments, the formulation or composition provides an immediate release and extended release formulation or composition of at least one otic agent, and at least one therapeutic agent. In some embodiments, the formulation or composition provides a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations or compositions of a first otic agent and second therapeutic agent, respectively.

In a specific embodiment the formulation or composition provides a therapeutically effective amount of at least one otic agent at the site of disease with essentially no systemic exposure. In an additional embodiment the formulation or composition provides a therapeutically effective amount of at least one otic agent at the site of disease with essentially no detectable systemic exposure. In other embodiments, the formulation or composition provides a therapeutically effective amount of at least one otic therapeutic agent at the site of disease with little or no detectable systemic exposure.

In some instances, upon administration (e.g., intratympanic injection) of a conventional otic formulation or composition (e.g., DSP in a buffer), the concentration of a drug in the perilymph of an individual will rise sharply ($C_{max}$ at about 1-2 hours) and then taper off to below $C_{min}$. In some instances, administration of an otic formulation or composition described herein lowers the ratio of $C_{max}$ to $C_{min}$ and provides a larger Area Under the Curve (AUC) with a prolonged PK profile based on the $C_{min}$. In certain instances, controlled release formulations or compositions described herein delay the time to $C_{max}$. In certain instances, the controlled steady release of a drug prolongs the time the concentration of the drug will stay above the minimum therapeutic concentration (i.e., $C_{min}$). In some instances, controlled release of an otic agent provided by the formulations or compositions described herein allows for release of an otic agent at concentrations greater than $C_{min}$ for a period of at least 1 day, 3 days, 4 days, 5 days, 6 days, 7 days, 10 days, 14 days, 3 weeks, 1 month, or 6 months. In some embodiments, auris formulations or compositions described herein prolong the residence time of a drug in the inner ear. In certain instances, once drug exposure (e.g., concentration in the perilymph) of a drug reaches steady state, the concentration of the drug in the perilymph stays at or about the therapeutic dose for an extended period of time (e.g., one day, 2 days, 3 days, 4 days, 5 days, 6 days, 1 week, 2 weeks, 1 month, or 6 months). In some embodiments, otic formulations or compositions described herein increase the bioavailability and/or steady state levels of a drug in auris structures (e.g., in inner ear and/or the endolymph and/or the perilymph).

In some instances, upon administration of a controlled release auris formulation or composition described herein (e.g., a formulation comprising an anti-inflammatory agent (e.g., an anti-TNF agent)), drug concentrations relative to the binding constants of one or more otic receptors (e.g., corticoid receptors, NMDA receptors, glutamate receptors or the like, or any combination thereof) are relevant in determining a biologically meaningful PK profile or the minimum concentration of an active agent required for a therapeutic effect. In some instances, upon administration of a controlled release auris formulation or composition described herein, drug concentrations relative to the binding constants of two receptors, such as, by way of example only, mineralcorticoid receptor (MR) and glucocorticoid receptor (GR), are relevant in determining the $C_{min}$ or the biologically most meaningful PK profile. In some instances, for example, a drug saturates a first receptor (e.g. GR) first, then saturates a second receptor (e.g., MR), and there is therapeutic benefit even when the first receptor is saturated and the second receptor is not yet saturated. In some instances, the drug concentration for saturation the second receptor is about the same as the $C_{min}$. In some of such instances, for example, a next dose is administered when drug concentration drops below saturation levels of the second receptor and/or the $C_{min}$ The combination of immediate release, delayed release and/or extended release otic compositions or formulations are combined with other pharmaceutical agents, as well as the excipients, diluents, stabilizers, tonicity agents and other components disclosed herein. As such, depending upon the otic agent used, the thickness or viscosity desired, or the mode of delivery chosen, alternative aspects of the embodiments disclosed herein are combined with the immediate release, delayed release and/or extended release embodiments accordingly.

In certain embodiments, the pharmacokinetics of the otic formulations or compositions described herein are determined by injecting the formulation on or near the round window membrane of a test animal (including by way of example, a guinea pig, a chinchilla, or a rat). At a determined period of time (e.g., 6 hours, 12 hours, 1 day, 2 days, 3 days, 4 days, 5 days, 6 days, 7 days, and 14 days for testing the pharmacokinetics of a formulation or composition over a 1 or 2 week period), the test animal is euthanized and the inner ear removed and tested for the presence of the otic agent. As needed, the level of otic agent is measured in other organs. In addition, the systemic level of the otic agent is measured by withdrawing a blood sample from the test animal. In order to determine whether the formulation or composition impedes hearing, the hearing of the test animal is optionally tested.

Alternatively, an inner ear is provided (as removed from a test animal) and the migration of the otic agent is measured. As yet another alternative, an in vitro model of a round window membrane is provided and the migration of the otic agent is measured.

Retention Time

In some embodiments, the formulation or composition has a retention time in the ear of about 5 minutes, about 15 minutes, about 30 minutes, about 1 hour, about 4 hours, about 6 hours, about 12 hours, about 18 hours, about 1 day, about 2 days, about 3 days, about 4 days, about 5 days, about 6 days, about 7 days, about 10 days, about 12 days, about 14 days, about 18 days, about 21 days, about 25 days, about 30 days, about 45 days, about 2 months, about 3 months, about 4 months, about 5 months, about 6 months, about 9 months or about 1 year. In some embodiments, the formulation or composition has a retention time in the ear of at least 5 minutes, at least 15 minutes, at least 30 minutes, at least 1 hour, at least 4 hours, at least 6 hours, at least 12 hours, at least 18 hours, at least 1 day, at least 2 days, at least 3 days, at least 4 days, at least 5 days, at least 6 days, at least 7 days, at least 10 days, at least 12 days, at least 14 days, at least 18 days, at least 21 days, at least 25 days, at least 30 days, at least 45 days, at least 2 months, at least 3 months, at least 4 months, at least 5 months, at least 6 months, at least 9 months or at least 1 year.

In some embodiments, the ear is the outer ear, middle ear, or inner ear. In some embodiments, the ear is the middle ear. In some embodiments, the ear is the inner ear. In some embodiments, the ear is the outer ear. In some embodiments, the outer ear is the external auditory canal, the outer surface of the tympanic membrane, or a combination thereof.

Modes of Otic Administration

In some embodiments, the auris formulations or compositions described herein are administered into the ear canal, or in the vestibule of the ear. Access to, for example, the vestibular and cochlear apparatus occurs through the auris media including the round window membrane, the oval window/stapes footplate, the annular ligament and through the otic capsule/temporal bone. In some embodiments, otic administration of the formulations or compositions described herein avoids toxicity associated with systemic administration (e.g., hepatotoxicity, cardiotoxicity, gastrointestinal side effects, and renal toxicity) of the active agents. In some instances, localized administration in the ear allows an active agent to reach a target organ (e.g., inner ear) in the absence of systemic accumulation of the active agent. In some instances, local administration to the ear provides a higher therapeutic index for an active agent that would otherwise have dose-limiting systemic toxicity.

Provided herein are modes of treatment for otic formulations or compositions that ameliorate or lessen otic disorders described herein. Drugs delivered to the inner ear have been administered systemically via oral, intravenous or intramuscular routes. However, systemic administration for pathologies local to the inner ear increases the likelihood of systemic toxicities and adverse side effects and creates a non-productive distribution of drug in which high levels of drug are found in the serum and correspondingly lower levels are found at the inner ear.

Provided herein are methods comprising the administration of said auris formulations or compositions on or near the round window membrane via intratympanic injection. In some embodiments, a composition disclosed herein is administered on or near the round window or the crista fenestrae cochleae through entry via a post-auricular incision and surgical manipulation into or near the round window or the crista fenestrae cochleae area. Alternatively, a formulation or composition disclosed herein is applied via syringe and needle, wherein the needle is inserted through the tympanic membrane and guided to the area of the round window or crista fenestrae cochleae. In some embodiments, a formulation or composition disclosed herein is then deposited on or near the round window or crista fenestrae cochleae for localized treatment. In other embodiments, a formulation or composition disclosed herein is applied via microcatheters implanted into the patient, and in yet further embodiments a composition disclosed herein is administered via a pump device onto or near the round window membrane. In still further embodiments, a formulation or composition disclosed herein is applied at or near the round window membrane via a microinjection device. In yet other embodiments, a formulation or composition disclosed herein is applied in the tympanic cavity. In some embodiments, a formulation or composition disclosed herein is applied on the tympanic membrane. In still other embodiments, a formulation or composition disclosed herein is applied onto or in the auditory canal. The formulations or compositions described herein, and modes of administration thereof, are also applicable to methods of direct instillation or perfusion of the inner ear compartments. Thus, the formulations or compositions described herein are useful in surgical procedures including, by way of non-limiting examples, cochleostomy, labyrinthotomy, mastoidectomy, stapedectomy, endolymphatic sacculotomy or the like.

Intratympanic Injections

In some embodiments, a surgical microscope is used to visualize the tympanic membrane. In some embodiments, the tympanic membrane is anesthetized by any suitable method (e.g., use of phenol, lidocaine, and xylocaine). In some embodiments, the anterior-superior and posterior-inferior quadrants of the tympanic membrane are anesthetized.

In some embodiments, a puncture is made in the tympanic membrane to vent any gases behind the tympanic membrane. In some embodiments, a puncture is made in the anterior-superior quadrant of the tympanic membrane to vent any gases behind the tympanic membrane. In some embodiments, the puncture is made with a needle (e.g., a 25 gauge needle). In some embodiments, the puncture is made with a laser (e.g., a $CO_2$ laser). In one embodiment the delivery system is a syringe and needle apparatus that is capable of piercing the tympanic membrane and directly accessing the round window membrane or crista fenestrae cochleae of the auris interna.

In one embodiment, the needle is a hypodermic needle used for instant delivery of the formulation. The hypodermic needle is a single use needle or a disposable needle. In some embodiments, a syringe is used for delivery of the pharmaceutically acceptable otic agent-containing compositions as disclosed herein wherein the syringe has a press-fit (Luer) or twist-on (Luer-lock) fitting. In one embodiment, the syringe is a hypodermic syringe. In another embodiment, the syringe is made of plastic or glass. In yet another embodiment, the hypodermic syringe is a single use syringe. In a further embodiment, the glass syringe is capable of being sterilized. In yet a further embodiment, the sterilization occurs through an autoclave. In another embodiment, the syringe comprises a cylindrical syringe body wherein the formulation is stored before use. In other embodiments, the syringe comprises a cylindrical syringe body wherein the pharmaceutically acceptable otic formulations or compositions as disclosed herein is stored before use which conveniently allows for mixing with a suitable pharmaceutically acceptable buffer. In other embodiments, the syringe contains other excipients, stabilizers, suspending agents, diluents or a combination thereof to stabilize or otherwise stably store the otic agent or other pharmaceutical compounds contained therein.

In some embodiments, the syringe comprises a cylindrical syringe body wherein the body is compartmentalized in that each compartment is able to store at least one component of the auris-acceptable otic formulation. In a further embodiment, the syringe having a compartmentalized body allows for mixing of the components prior to injection into the auris media or auris interna. In other embodiments, the delivery system comprises multiple syringes, each syringe of the multiple syringes contains at least one component of the formulation such that each component is pre-mixed prior to injection or is mixed subsequent to injection. In a further embodiment, the syringes disclosed herein comprise at least one reservoir wherein the at least one reservoir comprises an otic agent, or a pharmaceutically acceptable buffer, or a viscosity enhancing agent, or a combination thereof. Commercially available injection devices are optionally employed in their simplest form as ready-to-use plastic syringes with a syringe barrel, needle assembly with a needle, plunger with a plunger rod, and holding flange, to perform an intratympanic injection.

In some embodiments, a needle is used to deliver the formulations or compositions described herein. In some embodiments, a needle punctures the posterior-inferior quadrant of the tympanic membrane. In some embodiments, the needle is a standard gauge needle. In some embodiments, the needle is a narrow gauge needle. In some embodiments, the needle is wider than an 18 gauge needle. In another embodiment, the needle gauge is from about 18 gauge to about 30 gauge. In some embodiments, the needle gauge is from about 20 gauge to about 30 gauge. In some embodiments, the needle gauge is from about 25 gauge to about 30 gauge. In some embodiments, the needle gauge is about 18 gauge, about 19 gauge, about 20 gauge, about 21 gauge, about 22 gauge, about 23 gauge, about 24 gauge, about 25 gauge, about 26 gauge, about 27 gauge, about 28 gauge, about 29 gauge, or about 30 gauge. In a further embodiment, the needle is a 25 gauge needle. Depending upon the thickness or viscosity of a formulation or composition disclosed herein, the gauge level of the syringe or hypodermic needle is varied accordingly. In some embodiments, the formulations or compositions described herein are liquids and are administered via narrow gauge needles or cannulas (e.g., 22 gauge needle, 25 gauge needle, or cannula), minimizing damage to the tympanic membrane upon administration. The formulations or compositions described herein are administered with minimal discomfort to a patient.

In some embodiments, an otoendoscope (e.g., about 1.7 mm in diameter) is used to visualize the round window membrane. In some embodiments, any obstructions to the round window membrane (e.g., a false round window membrane, a fat plug, fibrous tissue) are removed.

In some embodiments, a formulation or composition disclosed herein is injected onto the round window membrane. In some embodiments, 0.1 to 0.5 cc of a formulation or composition disclosed herein is injected onto the round window membrane.

In some embodiments, the tympanic membrane puncture is left to heal spontaneously. In some embodiments, a paper patch myringoplasty is performed by a trained physician. In some embodiments, a tympanoplasty is performed by a trained physician. In some embodiments, an individual is advised to avoid water. In some embodiments, a cotton ball soaked in petroleum-jelly is utilized as a barrier to water and other environmental agents.

Other Delivery Routes

In some embodiments, a formulation or composition disclosed herein is administered locally to the outer ear, such as the external auditory canal, the outer surface of the tympanic membrane, or a combination thereof. In some embodiments, the formulations or compositions described herein are not administered through the tympanic membrane.

In some embodiments, a formulation or composition disclosed herein is administered to the inner ear. In some embodiments, a formulation or composition disclosed herein is administered to the inner ear via an incision in the stapes footplate. In some embodiments, a formulation or composition disclosed herein is administered to the cochlea via a cochleostomy. In some embodiments, a formulation or composition disclosed herein is administered to the vestibular apparatus (e.g., semicircular canals or vestibule).

In some embodiments, a formulation or composition disclosed herein is applied via syringe and needle. In other embodiments, a formulation or composition disclosed herein is applied via microcatheters implanted into the patient. In some embodiments, a formulation or composition disclosed herein is administered via a pump device. In still further embodiments, a formulation or composition disclosed herein is applied via a microinjection device. In some embodiments, a formulation or composition disclosed herein is administered via a prosthesis, a cochlear implant, a constant infusion pump, or a wick.

In some embodiments, the delivery device is an apparatus designed for administration of therapeutic agents to the middle and/or inner ear. By way of example only: GYRUS Medical GmbH offers micro-otoscopes for visualization of and drug delivery to the round window niche; Arenberg has described a medical treatment device to deliver fluids to inner ear structures in U.S. Pat. Nos. 5,421,818; 5,474,529; and 5,476,446, each of which is incorporated by reference herein for such disclosure. U.S. patent application Ser. No. 08/874,208, which is incorporated herein by reference for such disclosure, describes a surgical method for implanting a fluid transfer conduit to deliver therapeutic agents to the inner ear. U.S. Patent Application Publication 2007/0167918, which is incorporated herein by reference for such disclosure, further describes a combined otic aspirator and medication dispenser for intratympanic fluid sampling and medicament application.

Dosage

In some embodiments, auris formulations or compositions described herein are controlled release formulations, and are administered at reduced dosing frequency compared to the current standard of care. In certain instances, when an auris formulation or composition is administered via intratympanic injection, a reduced frequency of administration alleviates discomfort caused by multiple intratympanic injections in individuals undergoing treatment for a middle and/or inner ear disease, disorder or condition. In certain instances, a reduced frequency of administration of intratympanic injections reduces the risk of permanent damage (e.g., perforation) to the ear drum. In some embodiments, formulations or compositions described herein provide a constant, sustained, extended, delayed or pulsatile rate of release of an active agent into the inner ear environment and thus avoid any variability in drug exposure in treatment of otic disorders.

The formulations or compositions containing the compound(s) described herein are administered for prophylactic and/or therapeutic treatments. In therapeutic applications, the formulations or compositions are administered to a patient already suffering from a disease, condition or disorder, in an amount sufficient to cure or at least partially arrest the symptoms of the disease, disorder or condition. Amounts effective for this use will depend on the severity and course of the disease, disorder or condition, previous therapy, the patient's health status and response to the drugs, and the judgment of the treating physician.

The amount of a given agent that will correspond to such an amount will vary depending upon factors such as the particular compound, disease condition and its severity, but is nevertheless routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-50 mg per administration, preferably 1-15 mg per administration. In some embodiments, the desired dose is conveniently presented in a single dose or as divided doses administered simultaneously (or over a short period of time) or at appropriate intervals.

Frequency of Administration

In the case wherein the patient's condition does not improve, upon the doctor's discretion the administration of the compounds is administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds are given continuously; alternatively, the dose of drug being administered are temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday are from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, the dosage or the frequency of administration, or both, is reduced, as a function of the symptoms, to a level at which the improved disease, disorder or condition is retained. Patients, however, require intermittent treatment on a long-term basis upon any recurrence of symptoms in some embodiments.

In some embodiments, the initial administration is of a particular formulation and the subsequent administration is of a different formulation or active pharmaceutical ingredient.

Otic Surgery and Implants

In some embodiments, the pharmaceutical formulations or compositions described herein are used in combination with (e.g., implantation, short-term use, long-term use, or removal of) implants (e.g., cochlear implants). As used herein, implants include auris-interna or auris-media medical devices, examples of which include cochlear implants, hearing sparing devices, hearing-improvement devices, short electrodes, micro-prostheses or piston-like prostheses; needles; stem cell transplants; drug delivery devices; any cell-based therapeutic; or the like. In some instances, the implants are used in conjunction with a patient experiencing hearing loss. In some instances, the hearing loss is present at birth. In some instances, the hearing loss is associated with conditions such as AIED, bacterial meningitis or the like that lead to osteoneogenesis and/or nerve damage with rapid obliteration of cochlear structures and profound hearing loss.

In some instances, an implant is an immune cell or a stem cell transplant in the ear. In some instances, an implant is a small electronic device that has an external portion placed behind the ear, and a second portion that is surgically placed under the skin that helps provide a sense of sound to a person who is profoundly deaf or severely hard-of-hearing. By way of example, such cochlear medical device implants bypass damaged portions of the ear and directly stimulate the auditory nerve. In some instances cochlear implants are used in single sided deafness. In some instances cochlear implants are used for deafness in both ears.

In some embodiments, administration of a formulation or composition or device described herein in combination with an otic intervention (e.g., an intratympanic injection, a stapedectomy, a medical device implant or a cell-based transplant) delays or prevents collateral damage to auris structures, e.g., irritation, cell damage, cell death, osteoneogeneis and/or further neuronal degeneration, caused by the external otic intervention (e.g., installation of an external device and/or cells in the ear). In some embodiments, administration of a formulation or device described herein in combination with an implant allows for a more effective restoration of hearing loss compared to an implant alone.

In some embodiments, administration of formulation or composition or device described herein reduces damage to cochlear structures caused by underlying conditions (e.g., bacterial meningitis, autoimmune ear disease (AIED)) allowing for successful cochlear device implantation. In some embodiments, administration of a formulation or composition or device described herein, in conjunction with otic surgery, medical device implantation and/or cell transplantation, reduces or prevents cell damage and/or death (e.g., auris sensory hair cell death and/or damage) associated with otic surgery, medical device implantation and/or cell transplantation.

In some embodiments, administration of a formulation or composition or device described herein (e.g., a composition or device comprising a growth factor) in conjunction with a cochlear implant or stem cell transplant has a trophic effect (e.g., promotes healthy growth of cells and/or healing of tissue in the area of an implant or transplant). In some embodiments, a trophic effect is desirable during otic surgery or during intratympanic injection procedures. In some embodiments, a trophic effect is desirable after installation of a medical device or after a cell transplant. In some of such embodiments, the formulations or compositions or devices described herein are administered via direct cochlear injection, through a chochleostomy or via deposition on the round window.

In some embodiments, administration of an anti-inflammatory or immunosuppressant formulations or compositions (e.g., a formulation or composition comprising an immunosuppressant such as a corticosteroid) reduces inflammation and/or infections associated with otic surgery, implantation of a medical device or a cell transplant. In some instances, perfusion of a surgical area with a formulation described herein reduces or eliminates post-surgical and/or post-implantation complications (e.g., inflammation, hair cell damage, neuronal degeneration, osteoneogenesis or the like). In some instances, perfusion of a surgical area with a formulation or composition described herein reduces post-surgery or post-implantation recuperation time. In some embodiments, a medical device is coated with a formulation or composition described herein prior to implantation in the ear.

In one aspect, the formulations or compositions described herein, and modes of administration thereof, are applicable to methods of direct perfusion of the inner ear compartments. Thus, the formulations or compositions described herein are useful in combination with otic interventions. In some embodiments, an otic intervention is an implantation procedure (e.g., implantation of a hearing device in the cochlea). In some embodiments, an otic intervention is a surgical procedure including, by way of non-limiting examples, cochleostomy, labyrinthotomy, mastoidectomy, stapedectomy, stapedotomy, endolymphatic sacculotomy, tympanostomy or the like. In some embodiments, the inner ear compartments are perfused with a formulation or composition described herein prior to otic intervention, during otic intervention, or after otic intervention, or a combination thereof.

In some embodiments, when perfusion is carried out in combination with otic intervention, the formulations or compositions are immediate release compositions. In some of such embodiments, the immediate release formulations described herein are substantially free of extended release components.

Kits and Other Articles of Manufacture

The disclosure also provides kits for preventing, treating or ameliorating the symptoms of a diseases or disorder in a mammal. Such kits generally will comprise one or more of the pharmaceutically acceptable compositions as disclosed herein, and instructions for using the kit. The disclosure also contemplates the use of one or more of the formulations or compositions, in the manufacture of medicaments for treating, abating, reducing, or ameliorating the symptoms of a disease, dysfunction, or disorder in a mammal, such as a human that has, is suspected of having, or at risk for developing an auris interna disorder.

In some embodiments, a kit disclosed herein comprises a needle that penetrates a tympanic membrane and/or a round window. In some embodiments, a kit disclosed herein further comprises a hydrogel with a penetration enhancer (e.g., an alkylglycoside and/or a saccharide alkyl ester).

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Packaging materials for use in packaging pharmaceutical products presented herein. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations or compositions of the compounds and formulations or compositions provided herein are contemplated as are a variety of treatments for any disease, disorder, or condition that would benefit by extended release administration of a therapeutic agent to the auris interna.

In some embodiments, a kit will typically includes one or more additional containers, each with one or more of various materials (such as reagents, optionally in concentrated form, and/or devices) desirable from a commercial and user standpoint for use of a formulation or composition described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

In a further embodiment, a label is on or associated with the container. In yet a further embodiment, a label is on a container when letters, numbers or other characters forming the label are attached, molded or etched into the container itself; a label is associated with a container when it is present within a receptacle or carrier that also holds the container, e.g., as a package insert. In other embodiments a label is used to indicate that the contents are to be used for a specific therapeutic application. In yet another embodiment, a label also indicates directions for use of the contents, such as in the methods described herein.

In certain embodiments, the pharmaceutical formulations or compositions are presented in a pack or dispenser device which contains one or more unit dosage forms containing a compound provided herein. In another embodiment, the pack for example contains metal or plastic foil, such as a blister pack. In a further embodiment, the pack or dispenser device is accompanied by instructions for administration. In yet a further embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. In another embodiment, such notice, for example, is the labeling approved by the U.S. Food and Drug Administration for prescription drugs, or the approved product insert. In yet another embodiment, compositions containing a compound provided herein formulated in a compatible pharmaceutical carrier are also prepared, placed in an appropriate container, and labeled for treatment of an indicated condition.

EXAMPLES

Example A1

Development of Selective Inhibitors of TrkC.T1

A short hairpin RNA (shRNA) specifically targeting a unique 3' sequence of the TrkC.T1 mRNA is designed. The TrkC.T1-targeting shRNA sequence or a scrambled control are cloned into a pLKO.1 lentiviral shRNA-expression vector. pLKO.1$^{scrambled}$ and pLKO.1$^{TrkC-T1}$ lentivirus are purified and tested by infection of HEK293-TrkC.T1 or HEK293-TrkC-FL (cells transfected with TrkC.T1 or TrkC-FL cDNAs). Infection with PLKO.1$^{TrkC.T1}$ reduces TrkC.T1 mRNA without affecting TrkC-FL mRNA, whereas infection with control virus PLKO.1$^{Scrambled}$ has no effect on either TrkC.T1 or TrkC-FL mRNA. The data is verified by studying protein expression in lysates of the same cells. In multiple experiments TrkC.T1 protein expression in culture is reduced by ~80% to 97%. To assess whether reduction of TrkC.T1 has a biological impact, production of TNF-α is used as a functional endpoint for TrkC.T1 activity.

Example A2

Table 3 illustrates shRNA sequences.

TABLE 3

| SEQ ID NOs | |
|---|---|
| 1 | GGACAATAGAGATCATCTAGT |
| 2 | CCGGGGACAATAGAGATCATCTAGTCTCGAGACTAGATGATCTCTATTGTCCTTTTTG |
| 3 | AATTCAAAAAGGACAATAGAGATCATCTAGTCTCGAGACTAGATGATCTCTATTGTCC |
| 4 | CCGGGGACATTCCAAGCCTCTTAACCTCGAGGTTAAGAGGCTTGGAATGTCCTTTTTG |
| 5 | AATTCAAAAAGGACATTCCAAGCCTCTTAACCTCGAGGTTAAGAGGCTTGGAATGTCC |
| 6 | CCGGCATGGTTTCAGAGAAATTATGCTCGAGCATAATTTCTCTGAAACCATGTTTTTG |
| 7 | AATTCAAAAACATGGTTTCAGAGAAATTATGCTCGAGCATAATTTCTCTGAAACCATG |
| 8 (control) | CCTAAGGTTAAGTCGCCCTCG |

Table 4 illustrates sequences of the full-length and truncated isoforms of TrkC and TrkB.

TABLE 4

| | |
|---|---|
| TrkC Full-length GenBank: CAA12029.1 SEQ ID NO: 9 | MDVSLCPAKCSFWRIFLLGSVWLDYVGSVLACPANCVCSKTEIN CRRPDDGNLFPLLEGQDSGNSNGNASINITDISRNITSIHIENWRSL HTLNAVDMELYTGLQKLTIKNSGLRSIQPRAFAKNPHLRYINLSS NRLTTLSWQLFQTLSLRELQLEQNFFNCSCDIRWMQLWQEQGE AKLNSQNLYCINADGSQLPLFRMNISQCDLPEISVSHVNLTVREG DNAVITCNGSGSPLPDVDWIVTGLQSINTHQTNLNWTNVHAINL TLVNVTSEDNGFTLTCIAENVVGMSNASVALTVYYPPRVVSLEE PELRLEHCIEFVVRGNPPPTLHWLHNGQPLRESKIIHVEYYQEGEI SEGCLLFNKPTHYNNGNYTLIAKNPLGTANQTINGHFLKEPFPES TDNFILFDEVSPTPPITVTHKPEEDTFGVSIAVGLAAFACVLLVVL FVMINKYGRRSKFGMKGPVAVISGEEDSASPLHHINHGITTPSSL DAGPDTVVIGMTRIPVIENPQYFRQGHNCHKPDTYVQHIKRRDIV LKRELGEGAFGKVFLAECYNLSPTKDKMLVAVKALKDPTLAAR KDFQREAELLTNLQEHIVKFYGVCGDGDPLIMVFEYMKHGDL NKFLRAHGPDAMILVDGQPRQAKGELGLSQMLHIASQIASGMV YLASQHFVHRDLATRNCLVGANLLVKIGDFGMSRDVYSTDYYR LFNPSGNDFCIWCEVGGHTMLPIRWMPPESIMYRKFTTESDVWS FGVILWEIFTYGKQPWFQLSNTEVIECITQGRVLERPRVCPKEVY DVMLGCWQREPQQRLNIKEIYKILHALGKATPIYLDILG |
| TrkC.T1 GenBank: AAB33112.1 SEQ ID NO: 10 | MDVSLCPAKCSFWRIFLLGSVWLDYVGSVLACPANCVCSKTEIN CRRPDDGNLFPLLEGQDSGNSNGNANINITDISRNITSIHIENWRS LHTLNAVDMELYTGLQKLTIKNSGLRSIQPRAFAKNPHLRYINLS SNRLTTLSWQLFQTLSLRELQLEQNFFNCSCDIRWMQLWQEQGE AKLNSQNLYCINADGSQLPLFRMNISQCDLPEISVSHVNLTVREG DNAVITCNGSGSPLPDVDWIVTGLQSINTHQTNLNWTNVHAINL TLVNVTSEDNGFTLTCIAENVVGMSNASVALTVYYPPRVVSLEE PELRLEHCIEFVVRGNPPPTLHWLHNGQPLRESKIIHVEYYQEGEI SEGCLLFNKPTHYNNGNYTLIAKNPLGTANQTINGHFLKEPFPES TDNFILFDEVSPTPPITVTHKPEEDTFGVSIAVGLAAFACVLLVVL FVMINKYGRRSKFGMKGPVAVISGEEDSASPLHHINHGITTPSSL DAGPDTVVIGMTRIPVIENPQYFRQGHNCHKPDTWVFSNIDNHGI LNLKDNRDHLVPSTHYIYEEPEVQSGEVSYPRSHGFREIMLNPISL PGHSKPLNHGIYVEDVNVYFSKGRHGF |
| TrkB Full-length GenBank: AAB33109.1 SEQ ID NO: 11 | MSSWIRWHGPAMARLWGFCWLVVGFWRAAFACPTSCKCSASR IWCSDPSPGIVAFPRLEPNSVDPENITEIFIANQKRLEIINEDDVEA YVGLRNLTIVDSGLKFVAHKAFLKNSNLQHINFTRNKLTSLSRK HFRHLDLSELILVGNPFTCSCDIMWIKTLQEAKSSPDTQDLYCLN ESSKNIPLANLQIPNCGLPSANLAAPNLTVEEGKSITLSCSVAGDP |

TABLE 4-continued

| | |
|---|---|
| | VPNMYWDVGNLVSKHMNETSHTQGSLRITNISSDDSGKQISCVA<br>ENLVGEDQDSVNLTVHFAPTITFLESPTSDHHWCIPFTVKGNPKP<br>ALQWFYNGAILNESKYICTKIHVTNHTEYHGCLQLDNPTHMNN<br>GDYTLIAKNEYGKDEKQISAHFMGWPGIDDGANPNYPDVIYED<br>YGTAANDIGTTNRSNEIPSTDVTDKTGREHLSVYAVVVIASVV<br>GFCLLVMLFLLKLARHSKFGMKGPASVISNDDDSASPLHHISNGS<br>NTPSSSEGGPDAVIIGMTKIPVIENPQYFGITNSQLKPDTFVQHIKR<br>HNIVLKRELGEGAFGKVFLAECYNLCPEQDKILVAVKTLKDASD<br>NARKDFHREAELLTNLQHEHIVKFYGVCVEGDPLIMVFEYMKH<br>GDLNKFLRAHGPDAVLMAEGNPPTELTQSQMLHIAQQIAAGMV<br>YLASQHFVHRDLATRNCLVGENLLVKIGDFGMSRDVYSTDYYR<br>VGGHTMLPIRWMPPESIMYRKFTTESDVWSLGVVLWEIFTYGK<br>QPWYQLSNNEVIECITQGRVLQRPRTCPQEVYELMLGCWQREPH<br>MRKNIKGIHTLLQNLAKASPVYLDILG |
| TrkB.T1<br>GenBank:<br>AAM77876.1<br>SEQ ID NO: 12 | MSSWIRWHGPAMARLWGFCWLVVGFWRAAFACPTSCKCSASR<br>IWCSDPSPGIVAFPRLEPNSVDPENITEIFIANQKRLEIINEDDVEA<br>YVGLRNLTIVDSGLKFVAHKAFLKNSNLQHINFTRNKLTSLSRK<br>HFRHLDLSELILVGNPFTCSCDIMWIKTLQEAKSSPDTQDLYCLN<br>ESSKNIPLANLQIPNCGLPSANLAAPNLTVEEGKSITLSCSVAGDP<br>VPNMYWDVGNLVSKHMNETSHTQGSLRITNISSDDSGKQISCVA<br>ENLVGEDQDSVNLTVHFAPTITFLESPTSDHHWCIPFTVKGNPKP<br>ALQWFYNGAILNESKYICTKIHVTNHTEYHGCLQLDNPTHMNN<br>GDYTLIAKNEYGKDEKQISAHFMGWPGIDDGANPNYPDVIYED<br>YGTAANDIGTTNRSNEIPSTDVTDKTGREHLSVYAVVVIASVV<br>GFCLLVMLFLLKLARHSKFGMKGFVLFHKIPLDG |

Table 5 illustrates miRNA sequences.

TABLE 5

| | miRNA | Sequence |
|---|---|---|
| SEQ ID NO: 13 | let-7b-3p | CUAUACAACCUACUGCCUUCCC |
| SEQ ID NO: 14 | let-7b-5p | UGAGGUAGUAGGUUGUGUGGUU |
| SEQ ID NO: 15 | miR-1-3p | UGGAAUGUAAAGAAGUAUGUAU |
| SEQ ID NO: 16 | miR-1-5p | ACAUACUUCUUUAUAUGCCCAU |
| SEQ ID NO: 17 | miR-9-3p | AUAAAGCUAGAUAACCGAAAGU |
| SEQ ID NO: 18 | miR-9-5p | UCUUUGGUUAUCUAGCUGUAUGA |
| SEQ ID NO: 19 | miR-10a-3p | CAAAUUCGUAUCUAGGGGAAUA |
| SEQ ID NO: 20 | miR-10a-5p | UACCCUGUAGAUCCGAAUUUGUG |
| SEQ ID NO: 21 | miR-15a-3p | CAGGCCAUAUUGUGCUGCCUCA |
| SEQ ID NO: 22 | miR-15a-5p | UAGCAGCACAUAAUGGUUUGUG |
| SEQ ID NO: 23 | miR-16-1-3p | CCAGUAUUAACUGUGCUGCUGA |
| SEQ ID NO: 24 | miR-16-2-3p | CCAAUAUUACUGUGCUGCUUUA |
| SEQ ID NO: 25 | miR-16-5p | UAGCAGCACGUAAAUAUUGGCG |
| SEQ ID NO: 26 | miR-17-3p | ACUGCAGUGAAGGCACUUGUAG |
| SEQ ID NO: 27 | miR-17-5p | CAAAGUGCUUACAGUGCAGGUAG |
| SEQ ID NO: 28 | miR-18a-3p | ACUGCCCUAAGUGCUCCUUCUGG |
| SEQ ID NO: 29 | miR-18a-5p | UAAGGUGCAUCUAGUGCAGAUAG |
| SEQ ID NO: 30 | miR-20a-3p | ACUGCAUUAUGAGCACUUAAAG |
| SEQ ID NO: 31 | miR-20a-5p | UAAAGUGCUUAUAGUGCAGGUAG |
| SEQ ID NO: 32 | miR-24-3p | UGGCUCAGUUCAGCAGGAACAG |
| SEQ ID NO: 33 | miR-24-1-5p | UGCCUACUGAGCUGAUAUCAGU |
| SEQ ID NO: 34 | miR-24-2-5p | UGCCUACUGAGCUGAAACACAG |
| SEQ ID NO: 35 | miR-30e-3p | CUUUCAGUCGGAUGUUUACAGC |

TABLE 5-continued

| | miRNA | Sequence |
|---|---|---|
| SEQ ID NO: 36 | miR-30e-5p | UGUAAACAUCCUUGACUGGAAG |
| SEQ ID NO: 37 | miR-93-3p | ACUGCUGAGCUAGCACUUCCCG |
| SEQ ID NO: 38 | miR-93-5p | CAAAGUGCUGUUCGUGCAGGUAG |
| SEQ ID NO: 39 | miR-103a-3p | AGCAGCAUUGUACAGGGCUAUGA |
| SEQ ID NO: 40 | miR-103a-2-5p | AGCUUCUUUACAGUGCUGCCUUG |
| SEQ ID NO: 41 | miR-103b | UCAUAGCCCUGUACAAUGCUGCU |
| SEQ ID NO: 42 | miR-106a-3p | CUGCAAUGUAAGCACUUCUUAC |
| SEQ ID NO: 43 | miR-106a-5p | AAAAGUGCUUACAGUGCAGGUAG |
| SEQ ID NO: 44 | miR-106b-3p | CCGCACUGUGGGUACUUGCUGC |
| SEQ ID NO: 45 | miR-106b-5p | UAAAGUGCUGACAGUGCAGAU |
| SEQ ID NO: 46 | miR-107 | AGCAGCAUUGUACAGGGCUAUCA |
| SEQ ID NO: 47 | miR-125a-3p | ACAGGUGAGGUUCUUGGGAGCC |
| SEQ ID NO: 48 | miR-125a-5p | UCCCUGAGACCCUUUAACCUGUGA |
| SEQ ID NO: 49 | miR-125b-1-3p | ACGGGUUAGGCUCUUGGGAGCU |
| SEQ ID NO: 50 | miR-125b-2-3p | UCACAAGUCAGGCUCUUGGGAC |
| SEQ ID NO: 51 | miR-125b-5p | UCCCUGAGACCCUAACUUGUGA |
| SEQ ID NO: 52 | miR-128-3p | UCACAGUGAACCGGUCUCUUU |
| SEQ ID NO: 53 | miR-128-1-5p | CGGGGCCGUAGCACUGUCUGAGA |
| SEQ ID NO: 54 | miR-128-2-5p | GGGGGCCGAUACACUGUACGAGA |
| SEQ ID NO: 55 | miR-133a-3p | UUUGGUCCCCUUCAACCAGCUG |
| SEQ ID NO: 56 | miR-133a-5p | AGCUGGUAAAAUGGAACCAAAU |
| SEQ ID NO: 57 | miR-133b | UUUGGUCCCCUUCAACCAGCUA |
| SEQ ID NO: 58 | miR-141-3p | UAACACUGUCUGGUAAAGAUGG |
| SEQ ID NO: 59 | miR-141-5p | CAUCUUCCAGUACAGUGUUGGA |
| SEQ ID NO: 60 | miR-149-3p | AGGGAGGGACGGGGGCUGUGC |
| SEQ ID NO: 61 | miR-149-5p | UCUGGCUCCGUGUCUUCACUCCC |
| SEQ ID NO: 62 | miR-182-3p | UGGUUCUAGACUUGCCAACUA |
| SEQ ID NO: 63 | miR-182-5p | UUUGGCAAUGGUAGAACUCACACU |
| SEQ ID NO: 64 | miR-188-3p | CUCCCACAUGCAGGGUUUGCA |
| SEQ ID NO: 65 | miR-188-5p | CAUCCCUUGCAUGGUGGAGGG |
| SEQ ID NO: 66 | miR-198 | GGUCCAGAGGGGAGAUAGGUUC |
| SEQ ID NO: 67 | miR-200a-3p | UAACACUGUCUGGUAACGAUGU |
| SEQ ID NO: 68 | miR-200a-5p | CAUCUUACCGGACAGUGCUGGA |
| SEQ ID NO: 69 | miR-200b-3p | UAAUACUGCCUGGUAAUGAUGA |
| SEQ ID NO: 70 | miR-200b-5p | CAUCUUACUGGGCAGCAUUGGA |
| SEQ ID NO: 71 | miR-204-3p | GCUGGGAAGGCAAAGGGACGU |
| SEQ ID NO: 72 | miR-204-5p | UUCCCUUUGUCAUCCUAUGCCU |
| SEQ ID NO: 73 | miR-206 | UGGAAUGUAAGGAAGUGUGUGG |
| SEQ ID NO: 74 | miR-221-3p | AGCUACAUUGUCUGCUGGGUUUC |

TABLE 5-continued

|  | miRNA | Sequence |
|---|---|---|
| SEQ ID NO: 75 | miR-221-5p | ACCUGGCAUACAAUGUAGAUUU |
| SEQ ID NO: 76 | miR-296-3p | GAGGGUUGGGUGGAGGCUCUCC |
| SEQ ID NO: 77 | miR-296-5p | AGGGCCCCCCUCAAUCCUGU |
| SEQ ID NO: 78 | miR-324-5p | CGCAUCCCCUAGGGCAUUGGUGU |
| SEQ ID NO: 79 | miR-326 | CCUCUGGGCCCUUCCUCCAG |
| SEQ ID NO: 80 | miR-330-3p | GCAAAGCACACGGCCUGCAGAGA |
| SEQ ID NO: 81 | miR-331-3p | GCCCCUGGGCCUAUCCUAGAA |
| SEQ ID NO: 82 | miR-331-5p | CUAGGUAUGGUCCCAGGGAUCC |
| SEQ ID NO: 83 | miR-340-3p | UCCGUCUCAGUUACUUUAUAGC |
| SEQ ID NO: 84 | miR-340-5p | UUAUAAAGCAAUGAGACUGAUU |
| SEQ ID NO: 85 | miR-345-3p | GCCCUGAACGAGGGGUCUGGAG |
| SEQ ID NO: 86 | miR-345-5p | GCUGACUCCUAGUCCAGGGCUC |
| SEQ ID NO: 87 | miR-374a-3p | CUUAUCAGAUUGUAUUGUAAUU |
| SEQ ID NO: 88 | miR-374a-5p | UUAUAAUACAACCUGAUAAGUG |
| SEQ ID NO: 89 | miR-374b-3p | CUUAGCAGGUUGUAUUAUCAUU |
| SEQ ID NO: 90 | miR-374b-5p | AUAUAAUACAACCUGCUAAGUG |
| SEQ ID NO: 91 | miR-374c-3p | CACUUAGCAGGUUGUAUUAUAU |
| SEQ ID NO: 92 | miR-374c-5p | AUAAUACAACCUGCUAAGUGCU |
| SEQ ID NO: 93 | miR-384 | AUUCCUAGAAAUUGUUCAUA |
| SEQ ID NO: 94 | miR-412-3p | ACUUCACCUGGUCCACUAGCCGU |
| SEQ ID NO: 95 | miR-412-5p | UGGUCGACCAGUUGGAAAGUAAU |
| SEQ ID NO: 96 | miR-422a | ACUGGACUUAGGGUCAGAAGGC |
| SEQ ID NO: 97 | miR-449a | UGGCAGUGUAUUGUUAGCUGGU |
| SEQ ID NO: 98 | miR-449b-3p | CAGCCACAACUACCCUGCCACU |
| SEQ ID NO: 99 | miR-449b-5p | AGGCAGUGUAUUGUUAGCUGGC |
| SEQ ID NO: 100 | miR-449c-3p | UUGCUAGUUGCACUCCUCUCUGU |
| SEQ ID NO: 101 | miR-449c-5p | UAGGCAGUGUAUUGCUAGCGGCUGU |
| SEQ ID NO: 102 | miR-485-3p | GUCAUACACGGCUCUCCUCUCU |
| SEQ ID NO: 103 | miR-509-3p | UGAUUGGUACGUCUGUGGGUAG |
| SEQ ID NO: 104 | miR-509-5p | UACUGCAGACAGUGGCAAUCA |
| SEQ ID NO: 105 | miR-509-3-5p | UACUGCAGACGUGGCAAUCAUG |
| SEQ ID NO: 106 | miR-617 | AGACUUCCCAUUUGAAGGUGGC |
| SEQ ID NO: 107 | miR-625-3p | GACUAUAGAACUUUCCCCCUCA |
| SEQ ID NO: 108 | miR-625-5p | AGGGGGAAAGUUCUAUAGUCC |
| SEQ ID NO: 109 | miR-765 | UGGAGGAGAAGGAAGGUGAUG |

Example 1—Medium Chain Triglyceride Formulations—Dexamethasone

Dexamethasone in MCTs

6% Dexamethasone (0.4 um) Aseptic formulation was prepared as follows. The heat sterilized dexamethasone powder was dispersed in sterile filtered MCT (CRODAMOL, GTCC-LQ-(MV), PhEur) by gentle mixing. The suspension was then homogenized with a Microfluidizer to reduce the particle size to 0.4 um. Then, either 0.05% or 2% heat sterilized SiO2 powder was added into the suspension. After thorough mixing, a uniform suspension was formed. Dexamethasone was suspended in MCT to reach a concentration of 60 mg/ml (6.0%).

6% Dexamethasone (5 um) Aseptic formulation was prepared as follows. The heat sterilized dexamethasone powder was dispersed in sterile filtered MCT (CRODAMOL, GTCC-LQ-(MV), PhEur) by gentle mixing. Then, either 0.05% or 2% heat sterilized SiO2 powder was added into the suspension. After thorough mixing, a uniform suspension was formed. Dexamethasone was suspended in MCT to reach a concentration of 60 mg/ml (6.0%).

6% Dexamethasone (Sum) Autoclave formulation was prepared as follows. The dexamethasone powder was dispersed in MCT (CRODAMOL, GTCC-LQ-(MV), PhEur) by gentle mixing. Then, either 0.05% or 2% SiO2 powder was added into the suspension. After thorough mixing, a uniform suspension was formed. The suspension was then autoclaved (121C for 20 min) before dosing. Dexamethasone was suspended in MCT to reach a concentration of 60 mg/ml (6.0%).

Pharmacokinetics

The pharmacokinetics of the dexamethasone formulations were determined according to the procedures described in Example 6.

Analytical Method

Determination of dexamethasone concentrations was performed using high-pressure liquid chromatography (HPLC) combined with mass spectrometry detection (MS). Samples were extracted by liquid-liquid extraction using ethyl acetate/acetonitrile (2/3, v/v)), then vortexed and centrifuged. The supernatant was collected and evaporated to dryness then reconstituted with acetonitrile/water (30/70, v/v) containing 0.1% formic acid. Samples were analyzed by reversed phase HPLC (1200 series, Agilent) using a Phenomenex Synergi Polar-RP 100A column (50×2.0 mm, 2.5 μm) at a flow rate of 0.6 ml/min, with an analysis time of two and half minutes. A gradient method was used: mobile phase A consisted of 2 mM ammonium formate in 0.2:100 (formic acid:water, v/v) water and mobile phase B consisted of 2 mM ammonium formate in 0.2:5:95 (formic acid:water:acetonitrile, v/v/v). The gradient initially consisted of 30% B, stepped to 95% B at 1.25 min, then brought back to 30% B to re-equilibrate the column. Dexamethasone-d4 was used as the internal standard (IS). Mass spectrometry was carried out using an AB Sciex API 5500 triple quadripole MS equipped with a Turbo IonSpray source. ESI mass spectra were acquired in positive MRM mode with a mass transition of m/z 393.20 to m/z 373.30 for dexamethasone, and of m/z 397.10 to 377.10 m/z for Dexamethasone-d4. Peak areas of dexamethasone were determined using Analyst 1.5 (Applied Biosystems). The calibration curves were obtained by fitting the peak area ratios of analyte/internal standard (IS) and the standard concentrations using a linear regression analysis (1/concentration$^2$). Sample dexamethasone concentrations were then interpolated using the equations derived from the calibration curves, using the peak area ratios derived from the software Analyst 1.5 (Applied Biosytems).

Figure 4A:
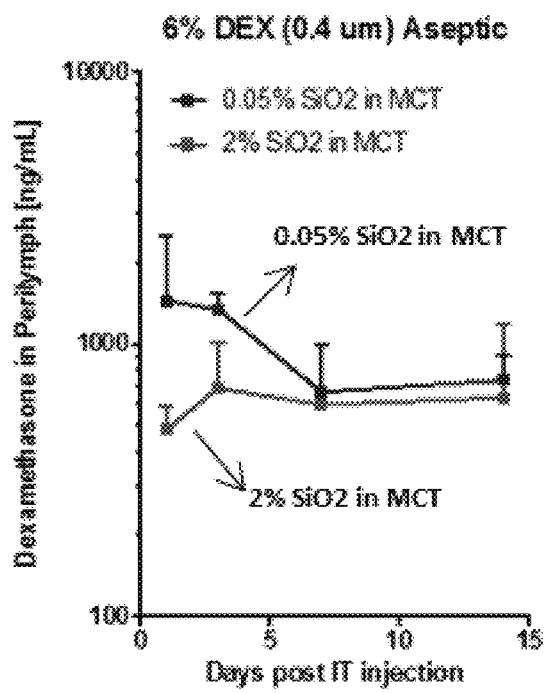
FIG. 4A, FIG. 4B, and FIG. 4C show the concentration of dexamethasone in the perilymph post administration for the 6% dexamethasone (0.4 um) aseptic MCT, 6% dexamethasone (5 um) aseptic MCT and 6% dexamethasone (5 um) autoclaved MCT formulations, respectively.
Figure 4B:
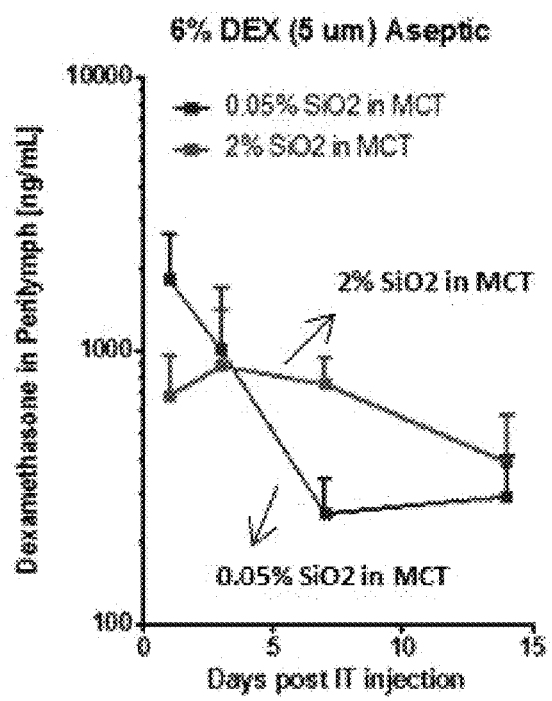
Figure 4C:
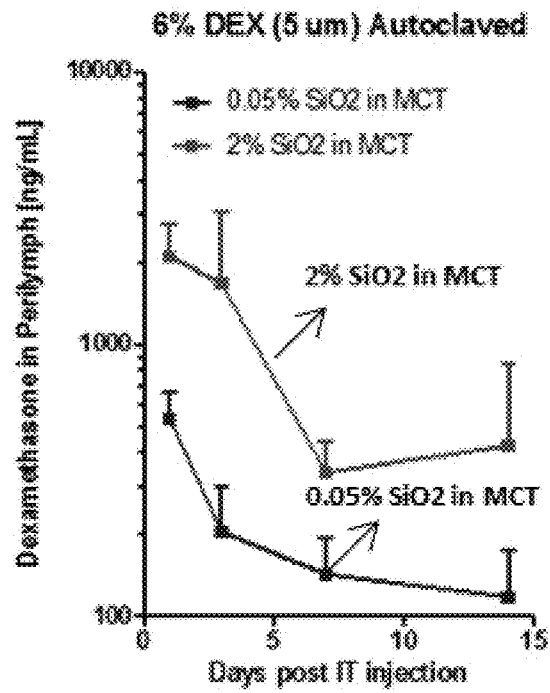

FIG. 4A, FIG. 4B, and FIG. 4C show the concentration of dexamethasone in the perilymph post administration for the 6% dexamethasone (0.4 um) aseptic MCT, 6% dexamethasone (5 um) aseptic MCT and 6% dexamethasone (5 um) autoclaved MCT formulations, respectively.

Example 2—Medium Chain Triglyceride Formulations—Gacyclidine

Gacyclidine in MCTs

MCT—0.3% or 3% GYC formulations were prepared as follows. 0.3% or 3% of gacyclidine (GYC) was dissolved in MCT (CRODAMOL, GTCC-LQ-(MV), PhEur). The solutions were filtered through 0.2 um filter. Gacyclidine was dissolved in MCT to reach concentrations ranging from 3 mg/ml (0.3%) to 30 mg/ml (3%).

MCT—3% GYC HCl formulation was prepared as follows. 3% of gacyclidine HCL (GYC HCl) was dispersed in sterile filtered MCT (CRODAMOL, GTCC-LQ-(MV), PhEur) by shaking. Gacyclidine HCl was suspended in MCT to reach concentration of 30 mg/ml (3%).

Pharmacokinetics

The pharmacokinetics of the gacyclidine formulations were determined according to the procedures described in Example 6.

Analytical Method

Samples were extracted by protein precipitation, then vortexed and centrifuged. The supernatant was collected and diluted with two folds of water. Samples were analyzed by reversed phase HPLC (1200 series, Agilent) using a Water Acquity UPLC BEH C18 column (2.1×50 mm, 1.7 μm) at a flow rate of 0.8 mL/min and column temperature was 55° C., with an analysis time of four and half minutes. A gradient method was used: mobile phase A consisted of 95% water: 5% acetonitrile: 0.1% formic acid (v/v/v) and mobile phase B consisted of 50% acetonitrile: 50% methanol: 0.1% formic acid (v/v/v). The gradient initially consisted of 50% B, stepped to 95% B at 2.30 min, then brought back to 50% B to re-equilibrate the column.

Carbamazepine was used as the internal standard (I.S.) for racemate. Mass spectrometry was carried out using an AB Sciex API 5500 Triple Quad MS equipped with a Turbo IonSpray source. ESI mass spectra were acquired in positive MRM mode with a mass transition of m/z 264.300 to m/z 86.000 for gacyclidine and of m/z 237.100 to m/z 194.100 for carbamazepine. Peak areas of GCY were determined using Analyst 1.5 (Applied Biosystems). The calibration curves were obtained by fitting the peak area ratios of analyte/internal standard (IS) and the standard concentrations using a linear regression analysis (1/concentration$^2$). Sample GCY concentrations were then interpolated using the equations derived from the calibration curves, using the peak area ratios derived from the software.

Figure 5A:
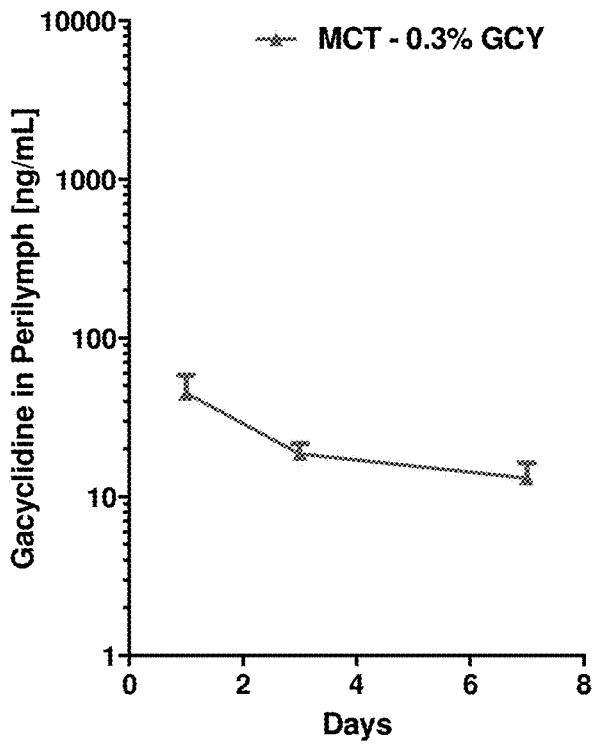
FIG. 5A shows the concentration of gacyclidine in the perilymph post administration for the 0.3% gacyclidine MCT formulation.
Figure 5B:
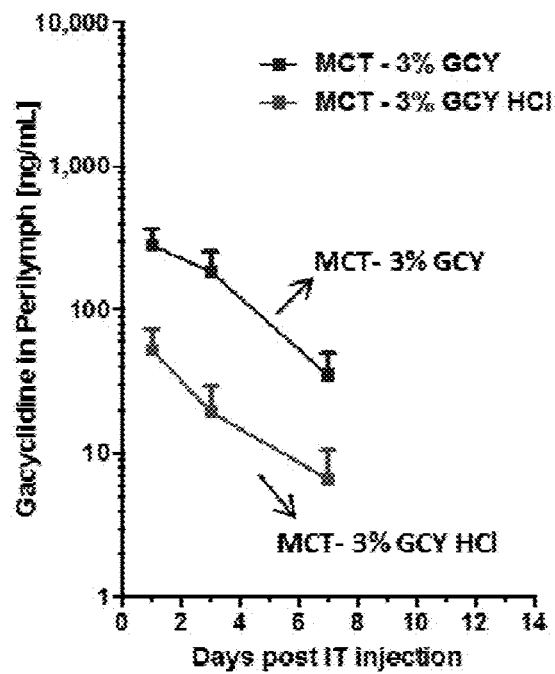
FIG. 5B shows the concentration of gacyclidine in the perilymph post administration for the 3% gacyclidine MCT formulation and 3% gacyclidine HCL MCT formulation.

FIG. 5A shows the concentration of gacyclidine in the perilymph post administration for the 0.3% gacyclidine MCT formulation. FIG. 5B show the concentration of gacyclidine in the perilymph post administration for the 3% gacyclidine MCT formulation and 3% gacyclidine HCL MCT formulation.

Example 3—Medium Chain Triglyceride Formulations—Gacyclidine

Gacyclidine Free Base in MCT

The appropriate amounts of gacyclidine free base were weighed and added to the target amount of MCT (CRODAMOL, GTCC-LQ-(MV), PhEur). The formulations were mixed until complete dissolution was observed. Sterilization of the formulated solution was performed by filtration through a 0.22 um filter and filtered solution was filled into vials.

Gacyclidine HCl Salt/PVP in MCT with SiO2

Gacyclidine HCl salt and PVP (1:4 w/w ratio) were dissolved in water. Sterilization of the formulated solution was performed by filtration through a 0.22 um filter and the filtered solution was transferred into vials. The solutions in the vials were freeze dried and the resultant lyo cake was dispersed into the appropriate amount of sterile filtered MCT (CRODAMOL, GTCC-LQ-(MV), PhEur). The particle size in the mixture was reduced by bead blasting. The target amount of silicon dioxide (3%) was added into the suspension and mixed until uniform.

Gacyclidine Pamoate Salt in MCT with SiO2

The gacyclidine pamoate salt was dispersed into the appropriate amount of sterile filtered MCT (CRODAMOL, GTCC-LQ-(MV). The particle size in the mixture was reduced by bead blasting. The target amount of silicon dioxide (3%) was added into the suspension and mixed until uniform.

The pharmacokinetics of the gacyclidine formulations were determined according to the procedures described in Example 6.

Analytical Method

Samples were extracted by protein precipitation, then vortexed and centrifuged. The supernatant was collected and diluted with two folds of water. Samples were analyzed by reversed phase HPLC (1200 series, Agilent) using a Water Acquity UPLC BEH C18 column (2.1×50 mm, 1.7 µm) at a flow rate of 0.8 mL/min and column temperature was 55° C., with an analysis time of four and half minutes. A gradient method was used: mobile phase A consisted of 95% water: 5% acetonitrile: 0.1% formic acid (v/v/v) and mobile phase B consisted of 50% acetonitrile: 50% methanol: 0.1% formic acid (v/v/v). The gradient initially consisted of 50% B, stepped to 95% B at 2.30 min, then brought back to 50% B to re-equilibrate the column.

Carbamazepine was used as the internal standard (I.S.) for racemate. Mass spectrometry was carried out using an AB Sciex API 5500 Triple Quad MS equipped with a Turbo IonSpray source. ESI mass spectra were acquired in positive MRM mode with a mass transition of m/z 264.300 to m/z 86.000 for gacyclidine and of m/z 237.100 to m/z 194.100 for carbamazepine. Peak areas of GCY were determined using Analyst 1.5 (Applied Biosystems). The calibration curves were obtained by fitting the peak area ratios of analyte/internal standard (IS) and the standard concentrations using a linear regression analysis (1/concentration$^2$). Sample GCY concentrations were then interpolated using the equations derived from the calibration curves, using the peak area ratios derived from the software.

Figure 6:
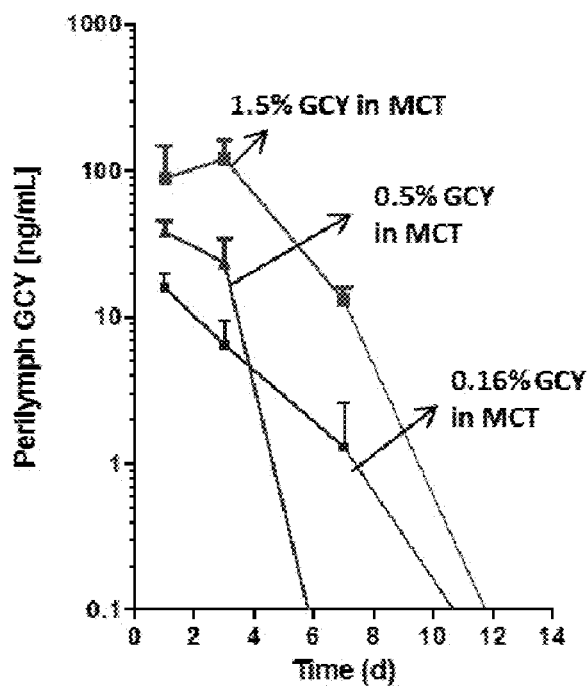
FIG. 6 shows the concentration of gacyclidine in the perilymph post administration for the 0.16% gacyclidine free base MCT formulation, 0.5% gacyclidine free base MCT formulation, and 1.5% gacyclidine free base MCT formulation.
Figure 7:
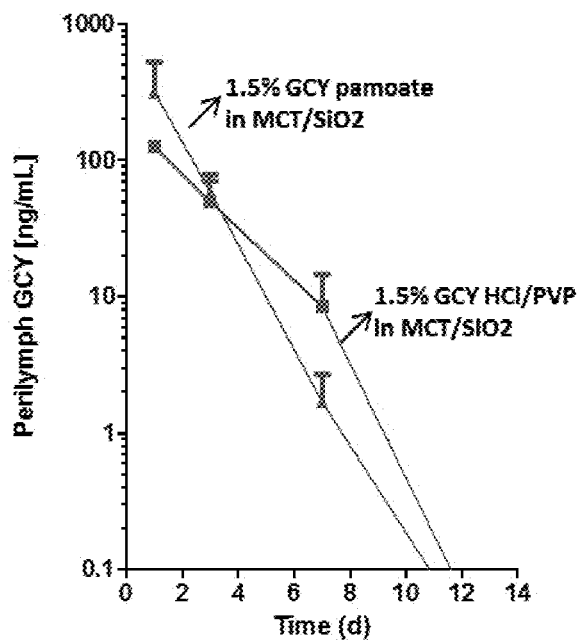
FIG. 7 shows the concentration of gacyclidine in the perilymph post administration for the 1.5% gacyclidine HCl/PVP in MCT/SiO2 formulation and 1.5% gacyclidine pamoate in MCT/SiO2 formulation.

FIG. 6 shows the concentration of gacyclidine in the perilymph post administration for the 0.16% gacyclidine free base MCT formulation, 0.5% gacyclidine free base MCT formulation, and 1.5% gacyclidine free base MCT formulation. FIG. 7 shows the concentration of gacyclidine in the perilymph post administration for the 1.5% gacyclidine HCl/PVP in MCT/SiO2 formulation and 1.5% gacyclidine pamoate in MCT/SiO2 formulation.

Example 4—Medium Chain Triglyceride Formulations—Human IgG

Human IgG in MCT

MCT/SiO2 (0.5% or 3%) formulations were prepared as follows. The lyo cake containing IgG was dispersed in MCT (CRODAMOL, GTCC-LQ-(MV), PhEur) as a suspension by ball milling and then either 0.5% or 3% of SiO2 particles were added to the above suspension. After thorough mixing by shaking, a uniform suspension was obtained. Human IgG concentration in the final suspension was 10 mg/ml (1.0%).

MCT/PVP (2%, 4% or 10%)/SiO2 (0.5% or 3%) formulations were prepared as follows. The lyo cake containing IgG was dissolved in water at 0.2, 0.25 or 0.5% IgG concentration. Then, PVP was added into the IgG solution and dissolved at 0.5 or 2% PVP concentration such that the IgG to PVP ratios (weight by weight) were 1:2, 1:4 or 1:10. The IgG/PVP solution was then lyophilized and the lyo cake was dispersed in MCT (CRODAMOL, GTCC-LQ-(MV), PhEur) as a suspension by ball milling. Either 0.5% or 3% of SiO2 particles were added to the above suspensions. After thorough mixing by shaking, a uniform suspension was obtained. Human IgG concentration in the final suspension was 10 mg/ml (1.0%).

MCT/Carbomer (1% or 2%)/SiO2 (0.5% or 3%) formulations were prepared as follows. The lyo cake containing IgG was dissolved in water at 0.05% IgG concentration. Then, Carbomer was added into the IgG solution and dissolved at 0.05 or 0.1% Carbomer concentration such that the IgG to carbomer ratios (weight by weight) were 1:1 or 1:2. The IgG/Carbomer solution was then lyophilized and the lyo cake was dispersed in MCT (CRODAMOL, GTCC-LQ-(MV), PhEur) as a suspension by ball milling. Either 0.5% or 3% of SiO2 particles were added to the above suspensions. After thorough mixing by shaking, a uniform suspension was obtained. Human IgG concentration in the final suspension was 10 mg/ml (1.0%)

MCT/P407 (4% or 10%)/SiO2 (0.5% or 3%) formulations were prepared as follows. The lyo cake containing IgG was dissolved in water at 0.5% or 1% IgG concentration. Then, P407 was added into the IgG solution and dissolved at 2% or 10% P407 concentration such that the IgG to PVP ratios (weight by weight) were 1:4 or 1:10. The IgG/P407 solution was then lyophilized and the lyo cake was dispersed in MCT (CRODAMOL, GTCC-LQ-(MV), PhEur) as a suspension by ball milling. Either 0.5% or 3% of SiO2 particles were added to the above suspensions. After thorough mixing by shaking, a uniform suspension was obtained. Human IgG concentration in the final suspension was 10 mg/ml (1.0%).

Pharmacokinetics

The pharmacokinetics of the Human IgG formulations were determined according to the procedures described in Example 6.

Analytical Method

Concentrations of IgG in perilymph samples were determined using commercially available ELISA kits.

Figure 8A:
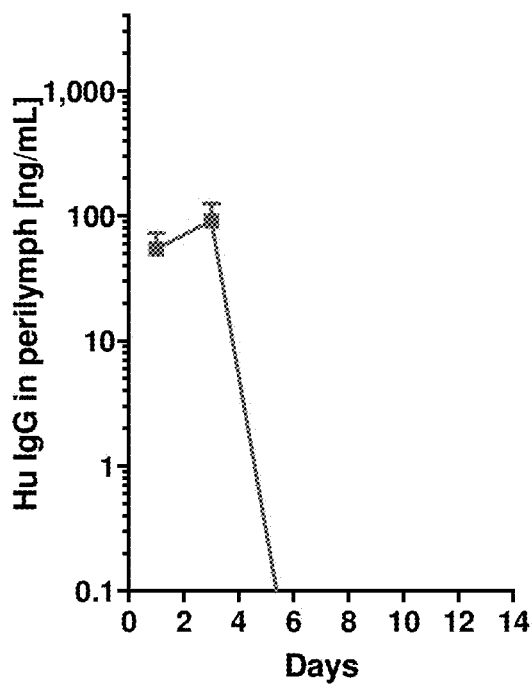
FIG. 8A shows the concentration of Human IgG in the perilymph post administration for the IgG MCT/0.5% SiO2 formulation.
Figure 8B:
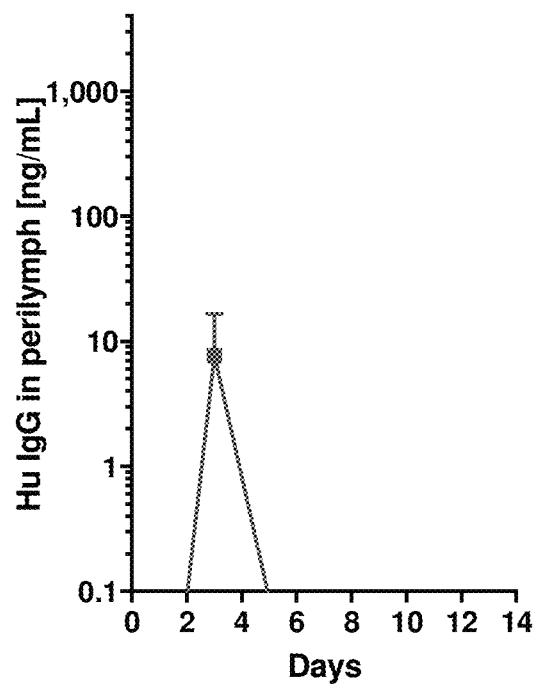
FIG. 8B shows the concentration of Human IgG in the perilymph post administration for the IgG MCT/3% SiO2 formulation.

FIG. 8A shows the concentration of Human IgG in the perilymph post administration for the IgG MCT/0.5% SiO2 formulation. FIG. 8B shows the concentration of Human IgG in the perilymph post administration for the IgG MCT/3% SiO2 formulation.

Figure 9A:
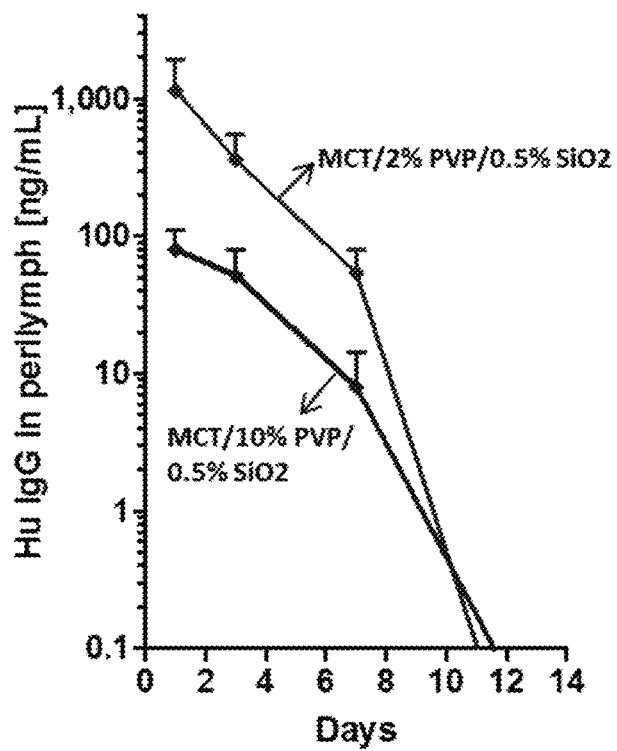
FIG. 9A shows the concentration of Human IgG in the perilymph post administration for the IgG MCT/PVP/0.5% SiO2 formulations.
Figure 9B:
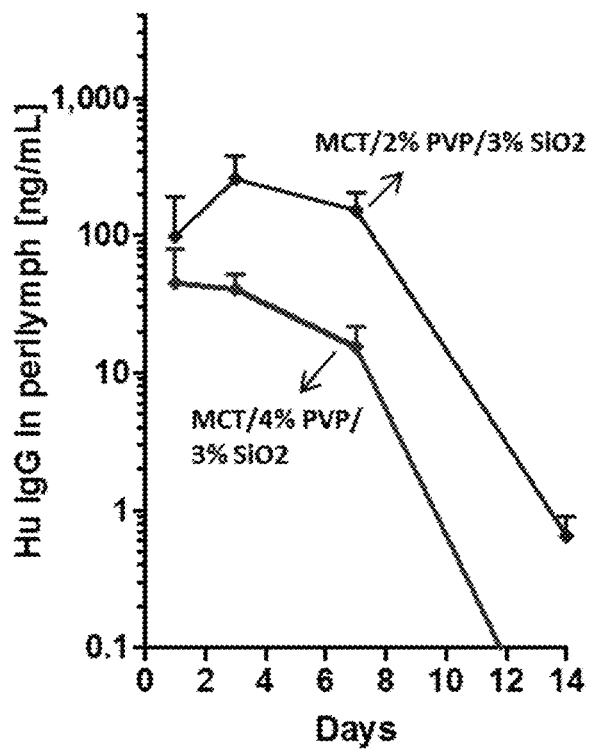
FIG. 9B shows the concentration of Human IgG in the perilymph post administration for the IgG MCT/PVP/3% SiO2 formulations.

FIG. 9A shows the concentration of Human IgG in the perilymph post administration for the IgG MCT/PVP/0.5% SiO2 formulations. FIG. 9B shows the concentration of Human IgG in the perilymph post administration for the IgG MCT/PVP/3% SiO2 formulations.

Figure 10A:
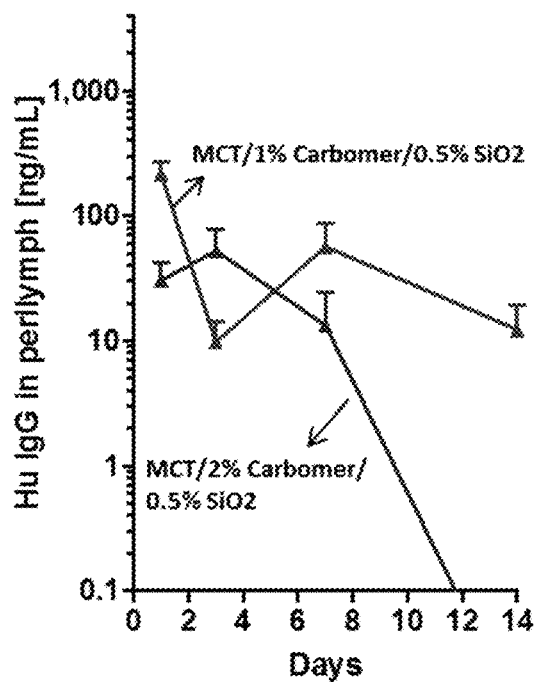
FIG. 10A shows the concentration of Human IgG in the perilymph post administration for the IgG MCT/carbomer/0.5% SiO2 formulations.
Figure 10B:
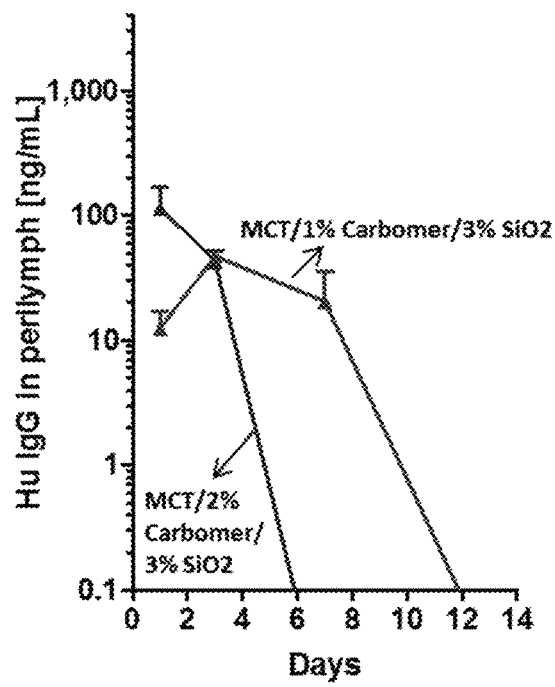
FIG. 10B shows the concentration of Human IgG in the perilymph post administration for the IgG MCT/carbomer/3% SiO2 formulations.

FIG. 10A shows the concentration of Human IgG in the perilymph post administration for the IgG MCT/carbomer/0.5% SiO2 formulations. FIG. 10B shows the concentration of Human IgG in the perilymph post administration for the IgG MCT/carbomer/3% SiO2 formulations.

Figure 11A:
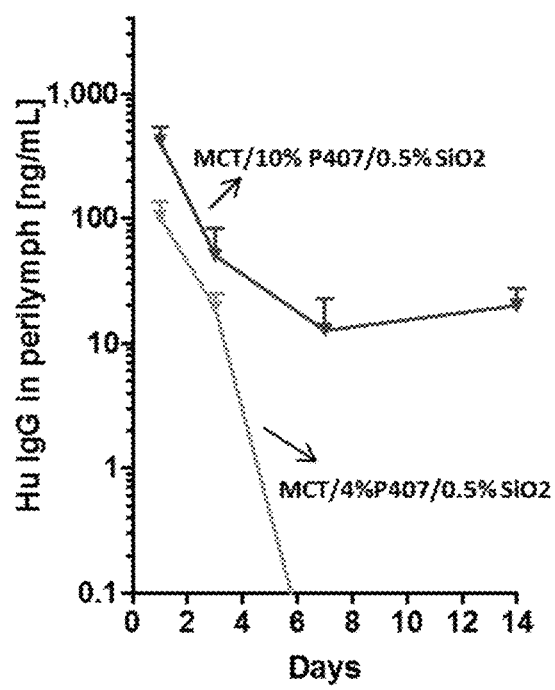
FIG. 11A shows the concentration of Human IgG in the perilymph post administration for the IgG MCT/P407/0.5% SiO2 formulations.
Figure 11B:
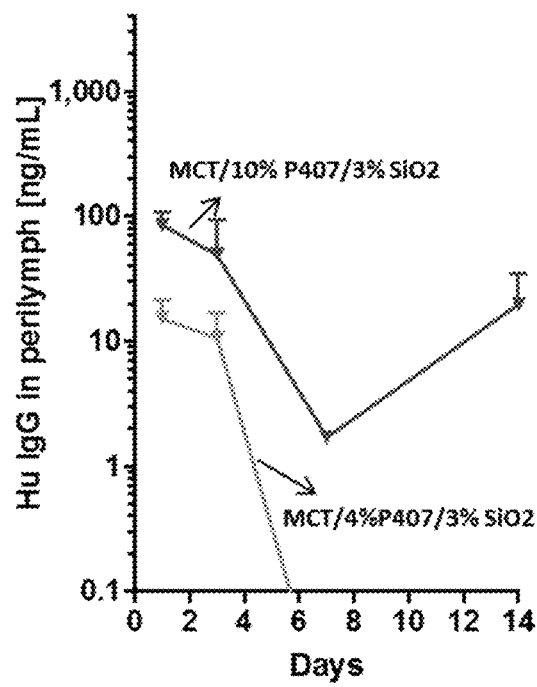
FIG. 11B shows the concentration of Human IgG in the perilymph post administration for the IgG MCT/P407/3% SiO2 formulations.
Figure 12:
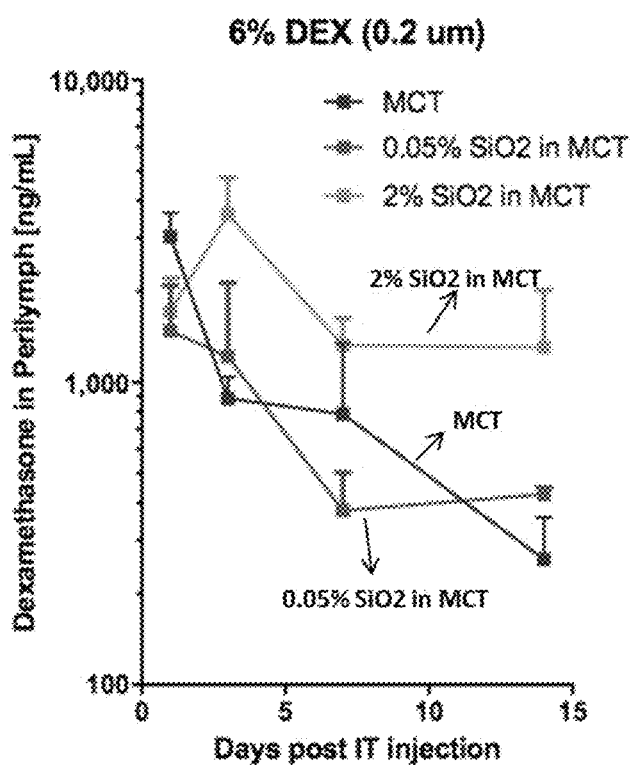
FIG. 12 shows the concentration of dexamethasone in the perilymph post administration for the 6% dexamethasone (0.2 um) MCT, 6% dexamethasone (0.2 um) MCT/0.05% SiO2 and 6% dexamethasone (0.2 um) MCT/2% SiO2 formulations, respectively.

FIG. 11A shows the concentration of Human IgG in the perilymph post administration for the IgG MCT/P407/0.5% SiO2 formulations. FIG. 11B shows the concentration of Human IgG in the perilymph post administration for the IgG MCT/P407/3% SiO2 formulations.

Example 5—Medium Chain Triglyceride Formulations—Dexamethasone

Dexamethasone in MCT with and without SiO2

The appropriate amount of dexamethasone was weighed and added to the target amount of MCT (CRODAMOL, GTCC-LQ-(MV), PhEur). The particle size of dexamethasone was reduced to about 0.2 um (D50) using a high energy ball milling process. Then either MCT was added to bring the formulation to its final volume, or the appropriate amount of SiO2 was added to the formulation before the MCT was used to bring the formulation to the final volume. The formulations were then mixed until homogeneous and the resultant suspensions were filled into vials.

Pharmacokinetics

The pharmacokinetics of the dexamethasone formulations were determined according to the procedures described in Example 6.

Analytical Method

The analytical method used for this experiment is the same as the method described in Example 1.

FIG. 12 shows the concentration of dexamethasone in the perilymph post administration for the 6% dexamethasone (0.2 um) MCT, 6% dexamethasone (0.2 um) MCT/0.05% SiO2 and 6% dexamethasone (0.2 um) MCT/2% SiO2 formulations, respectively.

Example 6—Pharmacokinetics of Medium Chain Triglyceride Formulations

Female rats (Charles River) weighing 200-300 g of approximately 12-16 weeks of age served as subjects (N=4 per group). Prior to any procedures, animals were anesthetized using a combination of xylazine (10 mg/kg) and ketamine (90 mg/kg) for up to an hour via the intraperitoneal route. If needed, an intraoperative booster was administered intraperitoneal representing a one-tenth of the original dose.

Intratympanic Injection—

Each animal was positioned so that the head was tilted at an angle to favor injection towards the round window niche. Briefly, under visualization with an operating microscope, 20 μL, of the formulation was injected using a 25G (Gauge) 11/2 needle through the tympanic membrane into the superior posterior quadrant. Formulations were delivered using a perfusion pump at the rate of 2 μL/sec. Contact with the round window membrane was maintained for 30 minutes by placing the animal in a recumbent position. During the procedure and until recovery, animals were placed on a temperature controlled (40° C.) heating pad until consciousness was regained at which time they were returned to the vivarium.

Perilymph Sampling Procedure—

The skin behind the ear of anesthetized rats was shaved and disinfected with povidone-iodine. An incision was then made behind the ear, and muscles were carefully retracted from over the bulla. A hole was drilled through the bulla using a dental burr so that the middle ear was exposed and accessed. The cochlea and the round window membrane were visualized under a stereo surgical microscope. The basal turn of bulla was cleaned by using small cotton ball. A unique microhole was hand drilled through the bony shell of the cochlea (cochlear capsule) adjacent to the round window. Perilymph (about 2 μL) was then collected using a microcapillary inserted into the cochlear scala tympani. Perilymph samples were added to a vial containing 18 μL of water, stored at −80° C. until analysis.

EMBODIMENTS

Embodiment 1

An otic pharmaceutical formulation comprising:

a) a therapeutic agent, or pharmaceutically acceptable prodrug or salt thereof; and b) triglycerides comprising medium chain fatty acids;

wherein the triglycerides are present in an amount that is sufficient to stabilize the therapeutic agent for injection into the ear, and wherein the otic pharmaceutical formulation comprises at least about 50% by weight of the triglycerides.

Embodiment 2

The otic pharmaceutical formulation of embodiment 1, wherein the triglycerides are present in an amount that is sufficient to provide sufficient retention time in the ear.

Embodiment 3

The otic pharmaceutical formulation of embodiments 1 or 2, wherein the triglycerides are present in an amount that is sufficient to provide sustained release of the therapeutic agent.

Embodiment 4

The otic pharmaceutical formulation of any one of embodiments 1-3, wherein the triglycerides are present in an amount that is sufficient to allow delivery of the formulation via a narrow gauge needle.

Embodiment 5

The otic pharmaceutical formulation of any one of embodiments 1-4, wherein the triglycerides are derived from glycerol and medium chain fatty acids.

Embodiment 6

The otic pharmaceutical formulation of embodiment 5, wherein each medium chain fatty acid independently comprises 6 to 12 carbon atoms in the carbon chain.

Embodiment 7

The otic pharmaceutical formulation of embodiment 5, wherein each medium chain fatty acid independently comprises 8 to 12 carbon atoms in the carbon chain.

Embodiment 8

The otic pharmaceutical formulation of embodiment 5, wherein the medium chain fatty acids are saturated medium chain fatty acids, unsaturated medium chain fatty acids, or a combination thereof.

Embodiment 9

The otic pharmaceutical formulation of embodiment 5, wherein the medium chain fatty acids are caproic acid (hexanoic acid), enanthic acid (heptanoic acid), caprylic acid (octanoic acid), pelargonic acid (nonanoic acid), capric acid (decanoic acid), undecylenic acid (undec-10-enoic acid), lauric acid (dodecanoic acid), or a combination thereof.

Embodiment 10

The otic pharmaceutical formulation of any one of embodiments 1-4, wherein the triglycerides comprising medium chain fatty acids are balassee oil, coconut oil, cohune oil, palm kernel oil, tucum oil, or combinations thereof.

Embodiment 11

The otic pharmaceutical formulation of any one of embodiments 1-10, wherein the otic pharmaceutical formulation comprises between about 50% to about 99.99% by weight of the triglycerides.

Embodiment 12

The otic pharmaceutical formulation of any one of embodiments 1-10, wherein the otic pharmaceutical formulation comprises between about 55% to about 99.99% by weight of the triglycerides.

Embodiment 13

The otic pharmaceutical formulation of any one of embodiments 1-10, wherein the otic pharmaceutical formulation comprises between about 60% to about 99.99% by weight of the triglycerides.

Embodiment 14

The otic pharmaceutical formulation of any one of embodiments 1-10, wherein the otic pharmaceutical formulation comprises between about 65% to about 99.99% by weight of the triglycerides.

Embodiment 15

The otic pharmaceutical formulation of any one of embodiments 1-10, wherein the otic pharmaceutical formulation comprises between about 70% to about 99.99% by weight of the triglycerides.

Embodiment 16

The otic pharmaceutical formulation of any one of embodiments 1-10, wherein the otic pharmaceutical formulation comprises between about 75% to about 99.99% by weight of the triglycerides.

Embodiment 17

The otic pharmaceutical formulation of any one of embodiments 1-10, wherein the otic pharmaceutical formulation comprises between about 80% to about 99.99% by weight of the triglycerides.

Embodiment 18

The otic pharmaceutical formulation of any one of embodiments 1-10, wherein the otic pharmaceutical formulation comprises between about 85% to about 99.99% by weight of the triglycerides.

Embodiment 19

The otic pharmaceutical formulation of any one of embodiments 1-10, wherein the otic pharmaceutical formulation comprises between about 90% to about 99.99% by weight of the triglycerides.

Embodiment 20

The otic pharmaceutical formulation of any one of embodiments 1-10, wherein the otic pharmaceutical formulation comprises between about 95% to about 99.99% by weight of the triglycerides.

Embodiment 21

The otic pharmaceutical formulation of any one of embodiments 1-20, wherein the otic pharmaceutical formulation further comprises at least one viscosity modulating agent.

Embodiment 22

The otic pharmaceutical formulation of any one of embodiments 1-21, wherein the at least one viscosity modulating agent is selected from silicon dioxide, povidone, carbomer, poloxamer, and a combination thereof.

Embodiment 23

The otic pharmaceutical formulation of embodiment 22, wherein the viscosity modulating agent is silicon dioxide.

Embodiment 24

The otic pharmaceutical formulation of embodiment 22, wherein the viscosity modulating agents are silicon dioxide and povidone.

Embodiment 25

The otic pharmaceutical formulation of embodiment 24, wherein the otic pharmaceutical formulation comprises between about 0.01% to about 20% by weight of the povidone.

Embodiment 26

The otic pharmaceutical formulation of embodiment 24, wherein the otic pharmaceutical formulation comprises between about 0.01% to about 15% by weight of the povidone.

Embodiment 27

The otic pharmaceutical formulation of embodiment 24, wherein the otic pharmaceutical formulation comprises between about 0.01% to about 10% by weight of the povidone.

Embodiment 28

The otic pharmaceutical formulation of embodiment 24, wherein the otic pharmaceutical formulation comprises between about 0.01% to about 7% by weight of the povidone.

Embodiment 29

The otic pharmaceutical formulation of embodiment 24, wherein the otic pharmaceutical formulation comprises between about 0.01% to about 5% by weight of the povidone.

Embodiment 30

The otic pharmaceutical formulation of embodiment 24, wherein the otic pharmaceutical formulation comprises between about 0.01% to about 3% by weight of the povidone.

Embodiment 31

The otic pharmaceutical formulation of embodiment 24, wherein the otic pharmaceutical formulation comprises between about 0.01% to about 2% by weight of the povidone.

Embodiment 32

The otic pharmaceutical formulation of embodiment 24, wherein the otic pharmaceutical formulation comprises between about 0.01% to about 1% by weight of the povidone.

Embodiment 33

The otic pharmaceutical formulation of embodiment 22, wherein the viscosity modulating agents are silicon dioxide and carbomer.

Embodiment 34

The otic pharmaceutical formulation of embodiment 33, wherein the otic pharmaceutical formulation comprises between about 0.01% to about 20% by weight of the carbomer.

Embodiment 35

The otic pharmaceutical formulation of embodiment 33, wherein the otic pharmaceutical formulation comprises between about 0.01% to about 15% by weight of the carbomer.

Embodiment 36

The otic pharmaceutical formulation of embodiment 33, wherein the otic pharmaceutical formulation comprises between about 0.01% to about 10% by weight of the carbomer.

Embodiment 37

The otic pharmaceutical formulation of embodiment 33, wherein the otic pharmaceutical formulation comprises between about 0.01% to about 7% by weight of the carbomer.

Embodiment 38

The otic pharmaceutical formulation of embodiment 33, wherein the otic pharmaceutical formulation comprises between about 0.01% to about 5% by weight of the carbomer.

Embodiment 39

The otic pharmaceutical formulation of embodiment 33, wherein the otic pharmaceutical formulation comprises between about 0.01% to about 3% by weight of the carbomer.

Embodiment 40

The otic pharmaceutical formulation of embodiment 33, wherein the otic pharmaceutical formulation comprises between about 0.01% to about 2% by weight of the carbomer.

Embodiment 41

The otic pharmaceutical formulation of embodiment 33, wherein the otic pharmaceutical formulation comprises between about 0.01% to about 1% by weight of the carbomer.

Embodiment 42

The otic pharmaceutical formulation of embodiment 22, wherein the viscosity modulating agents are silicon dioxide and poloxamer.

Embodiment 43

The otic pharmaceutical formulation of embodiment 42, wherein the otic pharmaceutical formulation comprises between about 0.01% to about 20% by weight of the poloxamer.

Embodiment 44

The otic pharmaceutical formulation of embodiment 42, wherein the otic pharmaceutical formulation comprises between about 0.01% to about 15% by weight of the poloxamer.

Embodiment 45

The otic pharmaceutical formulation of embodiment 42, wherein the otic pharmaceutical formulation comprises between about 0.01% to about 10% by weight of the poloxamer.

Embodiment 46

The otic pharmaceutical formulation of embodiment 42, wherein the otic pharmaceutical formulation comprises between about 0.01% to about 7% by weight of the poloxamer.

Embodiment 47

The otic pharmaceutical formulation of embodiment 42, wherein the otic pharmaceutical formulation comprises between about 0.01% to about 5% by weight of the poloxamer.

Embodiment 48

The otic pharmaceutical formulation of embodiment 42, wherein the otic pharmaceutical formulation comprises between about 0.01% to about 3% by weight of the poloxamer.

Embodiment 49

The otic pharmaceutical formulation of embodiment 42, wherein the otic pharmaceutical formulation comprises between about 0.01% to about 2% by weight of the poloxamer.

Embodiment 50

The otic pharmaceutical formulation of embodiment 42, wherein the otic pharmaceutical formulation comprises between about 0.01% to about 1% by weight of the poloxamer.

Embodiment 51

The otic pharmaceutical formulation of any one of embodiments 22-50, wherein the otic pharmaceutical formulation comprises between about 0.01% to about 10% by weight of the silicon dioxide.

Embodiment 52

The otic pharmaceutical formulation of any one of embodiments 22-50, wherein the otic pharmaceutical formulation comprises between about 0.01% to about 7% by weight of the silicon dioxide.

Embodiment 53

The otic pharmaceutical formulation of any one of embodiments 22-50, wherein the otic pharmaceutical formulation comprises between about 0.01% to about 5% by weight of the silicon dioxide.

Embodiment 54

The otic pharmaceutical formulation of any one of embodiments 22-50, wherein the otic pharmaceutical formulation comprises between about 0.01% to about 3% by weight of the silicon dioxide.

Embodiment 55

The otic pharmaceutical formulation of any one of embodiments 22-50, wherein the otic pharmaceutical formulation comprises between about 0.01% to about 2% by weight of the silicon dioxide.

Embodiment 56

The otic pharmaceutical formulation of any one of embodiments 22-50, wherein the otic pharmaceutical formulation comprises between about 0.01% to about 1% by weight of the silicon dioxide.

Embodiment 57

The otic pharmaceutical formulation of any one of embodiments 1-56, wherein the otic pharmaceutical formulation has a viscosity between about 10 cP to about 10,000 cP.

Embodiment 58

The otic pharmaceutical formulation of any one of embodiments 1-56, wherein the otic pharmaceutical formulation has a viscosity between about 10 cP to about 5,000 cP.

Embodiment 59

The otic pharmaceutical formulation of any one of embodiments 1-56, wherein the otic pharmaceutical formulation has a viscosity between about 10 cP to about 1,000 cP.

Embodiment 60

The otic pharmaceutical formulation of any one of embodiments 1-56, wherein the otic pharmaceutical formulation has a viscosity between about 10 cP to about 500 cP.

Embodiment 61

The otic pharmaceutical formulation of any one of embodiments 1-56, wherein the otic pharmaceutical formulation has a viscosity between about 10 cP to about 250 cP.

Embodiment 62

The otic pharmaceutical formulation of any one of embodiments 1-56, wherein the otic pharmaceutical formulation has a viscosity between about 10 cP to about 100 cP.

Embodiment 63

The otic pharmaceutical formulation of any one of embodiments 1-56, wherein the otic pharmaceutical formulation has a viscosity between about 10 cP to about 50 cP.

Embodiment 64

The otic pharmaceutical formulation of any one of embodiments 1-63, wherein the therapeutic agent is an immunomodulating agent, an aural pressure modulating agent, a corticosteroid, an antimicrobial agent, an otic neurotrophic factor, an antagonist of truncated TrkC or truncated TrkB, a non-natural TrkB or Trk C agonist, or a WNT modulator.

Embodiment 65

The otic pharmaceutical formulation of embodiment 64, wherein the immunomodulating agent is an anti-TNF agent, a calcineurin inhibitor, an IKK inhibitor, an interleukin inhibitor, a TNF-α converting enzyme (TACE) inhibitor, or a toll-like receptor inhibitor.

Embodiment 66

The otic pharmaceutical formulation of embodiment 64, wherein the aural pressure modulating agent is a modulator of aquaporin, an estrogen related receptor beta modulator, a gap junction protein modulator, an NMDA receptor antagonist, an osmotic diuretic, a progesterone receptor modulator, a prostaglandin modulator, or a vasopressin receptor modulator

Embodiment 67

The otic pharmaceutical formulation of embodiment 66, wherein the NMDA receptor antagonist is 1-aminoadamantane, dextromethorphan, dextrorphan, ibogaine, ketamine, esketamine (AM-101), nitrous oxide, phencyclidine, riluzole, tiletamine, memantine, dizocilpine, aptiganel, remacimide, 7-chlorokynurenate, DCKA (5,7-dichlorokynurenic acid), kynurenic acid, 1-aminocyclopropanecarboxylic acid (ACPC), AP7 (2-amino-7-pho sphonoheptanoic acid), APV (R-2-amino-5-phosphonopentanoate), CPPene (3-[(R)-2-carboxypiperazin-4-yl]-prop-2-enyl-1-phosphonic acid); (+)-(1S,2S)-1-(4-hydroxy-phenyl)-2-(4-hydroxy-4-phenylpiperidino)-1-pro-panol; (1S,2S)-1-(4-hydroxy-3-methoxyphenyl)-2-(4-hydroxy-4-phenylpiperi-dino)-1-propanol; (3R,4S)-3-(4-(4-fluorophenyl)-4-hydroxypiperidin-1-yl-)-chroman-4,7-diol; or (1R*,2R*)-1-(4-hydroxy-3-methylphenyl)-2-(4-(4-fluoro-phenyl)-4-hydroxypiperidin-1-yl)-propan-1-ol-mesylate, or gacyclidine (1-[(1R,2S)-2-methyl-1-thiophen-2-ylcyclohexyl]piperidine).

Embodiment 68

The otic pharmaceutical formulation of any one of embodiments 64-67, wherein the therapeutic agent is a corticosteroid, an antimicrobial agent, or a NMDA receptor antagonist.

Embodiment 69

The otic pharmaceutical formulation of embodiment 68, wherein the therapeutic agent is dexamethasone, ciprofloxacin, or gacyclidine.

Embodiment 70

The otic pharmaceutical formulation of embodiment 64, wherein the otic neurotrophic factor is selected from brain-derived neurotrophic factor (BDNF), ciliary neurotrophic factor (CNTF), glial cell-line derived neurotrophic factor (GDNF), neurotrophin-3, neurotrophin-4, fibroblast growth factor (FGF), insulin-like growth factor (IGF), epidermal growth factor (EGF), platlet-derived growth factor (PGF), and combination thereof.

Embodiment 71

The otic pharmaceutical formulation of embodiment 70, wherein the otic neurotrophic factor is selected from brain-derived neurotrophic factor (BDNF), neurotrophin-3, and combination thereof.

Embodiment 72

The otic pharmaceutical formulation of embodiment 64, wherein the antagonist of truncated TrkC or truncated TrkB is a nucleic acid polymer comprising 100% sequence identity to a nucleic acid sequence selected from SEQ ID NOs: 1-5.

Embodiment 73

The otic pharmaceutical formulation of embodiment 64, wherein the non-natural TrkC agonist is an antibody selected from the group consisting of 2B7, A5, 6.1.2, 6.4.1, 2345, 2349, 2.5.1, 2344, 2248, 2250, 2253, and 2256.

Embodiment 74

The otic pharmaceutical formulation of embodiment 64, wherein the non-natural TrkB agonist is an antibody selected from the group consisting of 1D7, TAM-163, 7F5, 11E1, 17D11, 19E12, 36D1, 38B8, 37D12, 19H8(1), 1F8, 23B8, 18H6, and 29D7.

Embodiment 75

The otic pharmaceutical formulation of any one of claims 1-74, wherein the otic pharmaceutical formulation comprises between about 0.01% to about 20% by weight of the therapeutic agent, or pharmaceutically acceptable prodrug or salt thereof.

Embodiment 76

The otic pharmaceutical formulation of any one of claims 1-74, wherein the otic pharmaceutical formulation comprises between about 0.01% to about 15% by weight of the therapeutic agent, or pharmaceutically acceptable prodrug or salt thereof.

Embodiment 77

The otic pharmaceutical formulation of any one of claims 1-74, wherein the otic pharmaceutical formulation comprises between about 0.01% to about 10% by weight of the therapeutic agent, or pharmaceutically acceptable prodrug or salt thereof.

Embodiment 78

The otic pharmaceutical formulation of any one of claims 1-74, wherein the otic pharmaceutical formulation comprises between about 0.01% to about 7% by weight of the therapeutic agent, or pharmaceutically acceptable prodrug or salt thereof.

Embodiment 79

The otic pharmaceutical formulation of any one of claims 1-74, wherein the otic pharmaceutical formulation com-

Embodiment 80

The otic pharmaceutical formulation of any one of claims 1-74, wherein the otic pharmaceutical formulation comprises between about 0.01% to about 3% by weight of the therapeutic agent, or pharmaceutically acceptable prodrug or salt thereof.

Embodiment 81

The otic pharmaceutical formulation of any one of claims 1-74, wherein the otic pharmaceutical formulation comprises between about 0.01% to about 2% by weight of the therapeutic agent, or pharmaceutically acceptable prodrug or salt thereof.

Embodiment 82

The otic pharmaceutical formulation of any one of embodiments 1-74, wherein the otic pharmaceutical formulation comprises between about 0.01% to about 1% by weight of the therapeutic agent, or pharmaceutically acceptable prodrug or salt thereof.

Embodiment 83

The otic pharmaceutical formulation of any one of embodiments 1-82, wherein the retention time of the formulation in the ear is at least 1 day.

Embodiment 84

The otic pharmaceutical formulation of any one of embodiments 1-82, wherein the retention time of the formulation in the ear is at least 2 days.

Embodiment 85

The otic pharmaceutical formulation of any one of embodiments 1-82, wherein the retention time of the formulation in the ear is at least 3 days.

Embodiment 86

The otic pharmaceutical formulation of any one of embodiments 1-82, wherein the retention time of the formulation in the ear is at least 4 days.

Embodiment 87

The otic pharmaceutical formulation of any one of embodiments 1-82, wherein the retention time of the formulation in the ear is at least 5 days.

Embodiment 88

The otic pharmaceutical formulation of any one of embodiments 1-82, wherein the retention time of the formulation in the ear is at least 6 days.

Embodiment 89

The otic pharmaceutical formulation of any one of embodiments 1-82, wherein the retention time of the formulation in the ear is at least 7 days.

Embodiment 90

The otic pharmaceutical formulation of any one of embodiments 1-82, wherein the retention time of the formulation in the ear is at least 14 days.

Embodiment 91

The otic pharmaceutical formulation of any one of embodiments 1-82, wherein the therapeutic agent is released from the formulation for a period of at least 1 day.

Embodiment 92

The otic pharmaceutical formulation of any one of embodiments 1-82, wherein the therapeutic agent is released from the formulation for a period of at least 2 days.

Embodiment 93

The otic pharmaceutical formulation of any one of embodiments 1-82, wherein the therapeutic agent is released from the formulation for a period of at least 3 days.

Embodiment 94

The otic pharmaceutical formulation of any one of embodiments 1-82, wherein the therapeutic agent is released from the formulation for a period of at least 4 days.

Embodiment 95

The otic pharmaceutical formulation of any one of embodiments 1-82, wherein the therapeutic agent is released from the formulation for a period of at least 5 days.

Embodiment 96

The otic pharmaceutical formulation of any one of embodiments 1-82, wherein the therapeutic agent is released from the formulation for a period of at least 6 days.

Embodiment 97

The otic pharmaceutical formulation of any one of embodiments 1-82, wherein the therapeutic agent is released from the formulation for a period of at least 7 days.

Embodiment 98

The otic pharmaceutical formulation of any one of embodiments 1-82, wherein the therapeutic agent is released from the formulation for a period of at least 14 days.

Embodiment 99

The otic pharmaceutical formulation of any one of embodiments 1-98, wherein the otic pharmaceutical formulation is a thickened liquid composition.

Embodiment 100

The otic pharmaceutical formulation of any one of embodiments 1-99, wherein the otic pharmaceutical formulation is an auris acceptable formulation.

Embodiment 101

The otic pharmaceutical formulation of any one of embodiments 1-100, wherein the therapeutic agent, or pharmaceutically acceptable prodrug or salt thereof, is multiparticulate.

Embodiment 102

The otic pharmaceutical formulation of any one of embodiments 1-101, wherein the therapeutic agent, or pharmaceutically acceptable prodrug or salt thereof, is essentially in the form of micronized particles.

Embodiment 103

The otic pharmaceutical formulation of any one of embodiments 1-101, wherein the therapeutic agent, or pharmaceutically acceptable prodrug or salt thereof, is essentially in the form of nanosized particles.

Embodiment 104

The otic pharmaceutical formulation of any one of embodiments 1-100, wherein the therapeutic agent, or pharmaceutically acceptable prodrug or salt thereof, is essentially dissolved in the otic pharmaceutical formulation.

Embodiment 105

The otic pharmaceutical formulation of any one of embodiments 1-104, wherein the otic pharmaceutical formulation is free or substantially free of water, C1-C6 alcohols or C1-C6 glycols, C1-C4 alcohols or C1-C4 glycols, or any combination thereof.

Embodiment 106

The otic pharmaceutical formulation of any one of embodiments 1-105, wherein the otic pharmaceutical formulation is free or substantially free of water.

Embodiment 107

The otic pharmaceutical formulation of any one of embodiments 1-105, wherein the otic pharmaceutical formulation is free or substantially free of C1-C6 alcohols or C1-C6 glycols.

Embodiment 108

The otic pharmaceutical formulation of any one of embodiments 1-105, wherein the otic pharmaceutical formulation is free or substantially free of C1-C4 alcohols or C1-C4 glycols.

Embodiment 109

The otic pharmaceutical formulation of any one of embodiments 1-108, further comprising a drug delivery device selected from a needle and syringe, a pump, a microinjection device, a wick, a spongy material and combinations thereof.

Embodiment 110

The otic pharmaceutical formulation of any one of embodiments 1-109, further comprising an antioxidant.

Embodiment 111

The otic pharmaceutical formulation of any one of embodiments 1-110, further comprising a mucoadhesive excipient.

Embodiment 112

The otic pharmaceutical formulation of any one of embodiments 1-111, further comprising a penetration enhancer.

Embodiment 113

The otic pharmaceutical formulation of any one of embodiments 1-112, further comprising a preservative.

Embodiment 114

The otic pharmaceutical formulation of any one of embodiments 1-113, further comprising a chelator.

Embodiment 115

The otic pharmaceutical formulation of any one of embodiments 1-114, further comprising an antimicrobial agent.

Embodiment 116

The otic pharmaceutical formulation of any one of embodiments 1-115, further comprising an excipient that increases the release rate of the therapeutic agent.

Embodiment 117

The otic pharmaceutical formulation of any one of embodiments 1-115, further comprising an excipient that decreases the release rate of the therapeutic agent.

Embodiment 118

The otic pharmaceutical formulation of any one of embodiments 1-117, wherein the otic formulation provides a therapeutically effective amount of the therapeutic agent.

Embodiment 119

The otic pharmaceutical formulation of any one of embodiments 1-118, wherein the injection is into the outer ear.

Embodiment 120

The otic pharmaceutical formulation of any one of embodiments 1-118, wherein the injection is into the middle ear.

Embodiment 121

The otic pharmaceutical formulation of any one of embodiments 1-118, wherein the injection is into the inner ear.

Embodiment 122

The otic pharmaceutical formulation of any one of embodiments 2-121, wherein the sufficient retention time in the ear is for the outer ear.

Embodiment 123

The otic pharmaceutical formulation of any one of embodiments 2-121, wherein the sufficient retention time in the ear is for the middle ear.

Embodiment 124

The otic pharmaceutical formulation of any one of embodiments 2-121, wherein the sufficient retention time in the ear is for the inner ear.

Embodiment 125

The otic pharmaceutical formulation of any one of embodiments 3-124, wherein the sustained release of therapeutic agent is in the outer ear.

Embodiment 126

The otic pharmaceutical formulation of any one of embodiments 3-124, wherein the sustained release of therapeutic agent is in the middle ear.

Embodiment 127

The otic pharmaceutical formulation of any one of embodiments 3-124, wherein the sustained release of therapeutic agent is in the inner ear.

Embodiment 128

The otic pharmaceutical formulation of any one of embodiments 1-127 for use in the treatment of an otic disease or condition associated with the outer, middle, and/or inner ear.

Embodiment 129

The otic pharmaceutical formulation of embodiment 128, wherein the otic disease or condition is ceruminosis or ceruminosis associated with an otic disease or condition, ear pruritus, otitis externa, otalgia, tinnitus, vertigo, ear fullness, hearing loss, Meniere's disease, sensorineural hearing loss, noise induced hearing loss, age related hearing loss (presbycusis), auto immune ear disease, tinnitus, ototoxicity, excitotoxicity, endolymphatic hydrops, labyrinthitis, Ramsay Hunt's Syndrome, vestibular neuronitis, or microvascular compression syndrome, hyperacusis, presbystasis, central auditory processing disorder, auditory neuropathy, improvement of cochlea implant performance, or a combination thereof.

Embodiment 130

The otic pharmaceutical formulation of embodiment 129, wherein the otic disease or condition is ceruminosis or ceruminosis associated with an otic disease or condition.

Embodiment 131

The otic pharmaceutical formulation of embodiment 129, wherein the otic disease or condition is ear pruritus, otitis externa, otalgia, tinnitus, vertigo, ear fullness, hearing loss, or a combination thereof.

Embodiment 132

The otic pharmaceutical formulation of embodiment 129, wherein the otic disease or condition is Meniere's disease, sensorineural hearing loss, noise induced hearing loss, age related hearing loss (presbycusis), auto immune ear disease, tinnitus, ototoxicity, excitotoxicity, endolymphatic hydrops, labyrinthitis, Ramsay Hunt's Syndrome, vestibular neuronitis, microvascular compression syndrome, hyperacusis, presbystasis, central auditory processing disorder, auditory neuropathy, or improvement of cochlea implant performance.

Embodiment 133

A method of treating an otic disease or condition in a subject in need thereof, the method comprising administering to the subject the otic pharmaceutical formulation of any one of embodiments 1-132.

While preferred embodiments of the present disclosure have been shown and described herein, such embodiments are provided by way of example only. Various alternatives to the embodiments described herein are optionally employed. It is intended that the following claims define the scope of the disclosure and that methods and structures within the scope of these claims and their equivalents be covered thereby.

What is claimed is:

1. An otic pharmaceutical formulation comprising:
   a) a therapeutic agent, or pharmaceutically acceptable prodrug or salt thereof; and
   b) triglycerides comprising medium chain fatty acids;
   wherein:
   (i) the otic pharmaceutical formulation comprises at least about 50% by weight of the triglycerides
   (ii) the therapeutic agent is an NMDA receptor antagonist
   (iii) the otic pharmaceutical formulation is essentially free of antibiotics; and
   (iv) the otic pharmaceutical formulation provides sustained release of the therapeutic agent for a period of at least 3 days.

2. The otic pharmaceutical formulation of claim 1, wherein the triglycerides are present in an amount that is sufficient to provide sustained release of the therapeutic agent.

3. The otic pharmaceutical formulation of claim 1, wherein the formulation is capable of being injected via an 18-30 gauge needle.

4. The otic pharmaceutical formulation of claim 1, wherein the triglycerides are derived from glycerol and medium chain fatty acids.

5. The otic pharmaceutical formulation of claim 4, wherein the medium chain fatty acids are caproic acid (hexanoic acid), enanthic acid (heptanoic acid), caprylic acid (octanoic acid), pelargonic acid (nonanoic acid), capric acid (decanoic acid), undecylenic acid (undec-10-enoic acid), lauric acid (dodecanoic acid), or a combination thereof.

6. The otic pharmaceutical formulation of claim 1, wherein the otic pharmaceutical formulation comprises between about 50% to about 99.99% by weight of the triglycerides.

7. The otic pharmaceutical formulation of claim 1, wherein the otic pharmaceutical formulation further comprises at least one viscosity modulating agent.

8. The otic pharmaceutical formulation of claim 7, wherein the at least one viscosity modulating agent is silicon dioxide, povidone, carbomer, poloxamer, or a combination thereof.

9. The otic pharmaceutical formulation of claim 8, wherein the viscosity modulating agent is silicon dioxide.

10. The otic pharmaceutical formulation of claim 1, wherein the therapeutic agent, or pharmaceutically acceptable prodrug or salt thereof is gacyclidine free base.

11. The otic pharmaceutical formulation of claim 1, wherein the otic pharmaceutical formulation comprises between about 60% to about 99.99% by weight of the triglycerides.

12. The otic pharmaceutical formulation of claim 1, wherein the otic pharmaceutical formulation comprises between about 70% to about 99.99% by weight of the triglycerides.

13. The otic pharmaceutical formulation of claim 1, wherein the otic pharmaceutical formulation comprises between about 80% to about 99.99% by weight of the triglycerides.

14. The otic pharmaceutical formulation of claim 1, wherein the otic pharmaceutical formulation comprises between about 85% to about 99.99% by weight of the triglycerides.

15. The otic pharmaceutical formulation of claim 1, wherein the otic pharmaceutical formulation comprises between about 90% to about 99.99% by weight of the triglycerides.

16. The otic pharmaceutical formulation of claim 1, wherein the otic pharmaceutical formulation comprises between about 95% to about 99.99% by weight of the triglycerides.

17. The otic pharmaceutical formulation of claim 1, wherein the otic pharmaceutical formulation has a viscosity between about 10 cP to about 10,000 cP.

18. The otic pharmaceutical formulation of claim 1, wherein the therapeutic agent is gacyclidine.

19. The otic pharmaceutical formulation of claim 1, wherein the otic pharmaceutical formulation comprises between about 0.01% to about 20% by weight of the therapeutic agent, or pharmaceutically acceptable prodrug or salt thereof.

20. The otic pharmaceutical formulation of claim 1, wherein the retention time of the formulation in the inner ear is at least 1 day.

21. The otic pharmaceutical formulation of claim 1, wherein the retention time of the formulation in the inner ear is at least 3 days.

22. The otic pharmaceutical formulation of claim 1, wherein the otic pharmaceutical formulation is free or substantially free of water, C1-C6 alcohols or C1-C6 glycols, C1-C4 alcohols or C1-C4 glycols, or any combination thereof.

23. The otic pharmaceutical formulation of claim 1, further comprising a drug delivery device selected from a needle and syringe, a pump, a microinjection device, a wick, a spongy material and combinations thereof.

24. The otic pharmaceutical formulation of claim 1 for use in the treatment of an otic disease or condition associated with the inner ear.

25. The otic pharmaceutical formulation of claim 1, wherein the otic disease or condition is ceruminosis or ceruminosis associated with an otic disease or condition, ear pruritus, otitis externa, otalgia, tinnitus, vertigo, ear fullness, hearing loss, Meniere's disease, sensorineural hearing loss, noise induced hearing loss, age related hearing loss (presbycusis), auto immune ear disease, ototoxicity, excitotoxicity, endolymphatic hydrops, labyrinthitis, Ramsay Hunt's Syndrome, vestibular neuronitis, or microvascular compression syndrome, hyperacusis, presbystasis, central auditory processing disorder, auditory neuropathy, improvement of cochlea implant performance, or a combination thereof.

26. The otic pharmaceutical formulation of claim 1, wherein the otic pharmaceutical formulation consists essentially of the therapeutic agent and the triglycerides.

27. The otic pharmaceutical formulation of claim 1, wherein the otic pharmaceutical formulation is formulated for intratympanic administration.

28. The otic pharmaceutical formulation of claim 1, wherein the otic pharmaceutical formulation has pH range of about 7.0 to 8.0.

29. The otic pharmaceutical formulation of claim 1, wherein the otic pharmaceutical formulation is essentially free of antimicrobial agents.

30. A method of treating an otic disease or condition in a subject in need thereof, the method comprising administering to the subject the otic pharmaceutical formulation of claim 1.

* * * * *